US012448609B2

(12) United States Patent
Clarke et al.

(10) Patent No.: US 12,448,609 B2
(45) **Date of Patent: *Oct. 21, 2025**

(54) HETEROLOGOUS EXPRESSION OF SHORT-CHAIN MONOOXYGENASES IN MICROORGANISMS

(71) Applicant: INDUSTRIAL MICROBES, INC., Alameda, CA (US)

(72) Inventors: Elizabeth Jane Clarke, San Francisco, CA (US); Baolong Zhu, San Diego, CA (US); Derek Lorin Greenfield, Kensington, CA (US); Stephanie Rhianon Jones, Berkeley, CA (US); Noah Charles Helman, El Cerrito, CA (US)

(73) Assignee: Industrial Microbes, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/217,021

(22) Filed: Jun. 30, 2023

(65) Prior Publication Data

US 2024/0043816 A1 Feb. 8, 2024

Related U.S. Application Data

(63) Continuation of application No. 17/149,394, filed on Jan. 14, 2021, now Pat. No. 11,692,177, which is a continuation of application No. 15/777,158, filed as application No. PCT/US2016/062623 on Nov. 17, 2016, now Pat. No. 10,894,951.

(60) Provisional application No. 62/320,725, filed on Apr. 11, 2016, provisional application No. 62/270,039, filed on Dec. 21, 2015, provisional application No. 62/257,061, filed on Nov. 18, 2015.

(51) Int. Cl.

| | |
|---|---|
| ***C12N 9/02*** | (2006.01) |
| ***C12P 7/04*** | (2006.01) |
| ***C12P 7/06*** | (2006.01) |
| ***C12P 7/22*** | (2006.01) |

(52) U.S. Cl.

CPC ......... *C12N 9/0073* (2013.01); *C12N 9/0071* (2013.01); *C12P 7/04* (2013.01); *C12P 7/06* (2013.01); *C12P 7/22* (2013.01); *C12Y 114/13025* (2013.01)

(58) Field of Classification Search

None

See application file for complete search history.

(56) References Cited

U.S. PATENT DOCUMENTS

| | | | | |
|---|---|---|---|---|
| 9,267,158 | B2 | 2/2016 | Coleman et al. | |
| 9,399,783 | B2 | 7/2016 | Coleman et al. | |
| 9,745,603 | B2 | 8/2017 | Coleman et al. | |
| 10,894,951 | B2 * | 1/2021 | Clarke | C12P 7/22 |
| 11,692,177 | B2 * | 7/2023 | Clarke | C12N 9/0006 435/156 |
| 2005/0176121 | A1 | 8/2005 | Takeshita et al. | |
| 2006/0051782 | A1 | 3/2006 | Wood et al. | |
| 2010/0257778 | A1 | 10/2010 | Gaertner et al. | |
| 2011/0097769 | A1 | 4/2011 | Del Cardayre et al. | |
| 2014/0013658 | A1 | 1/2014 | Silverman et al. | |
| 2014/0162327 | A1 | 6/2014 | Sun et al. | |
| 2014/0273128 | A1 | 9/2014 | Coleman et al. | |
| 2015/0104854 | A1 | 4/2015 | Singh et al. | |
| 2016/0160243 | A1 | 6/2016 | Coleman et al. | |
| 2016/0333359 | A1 | 11/2016 | Song et al. | |
| 2017/0037438 | A1 | 2/2017 | Helman et al. | |
| 2017/0152529 | A1 | 6/2017 | Coleman et al. | |
| 2017/0183638 | A1 | 6/2017 | Jung et al. | |
| 2017/0335351 | A1 | 11/2017 | Coleman et al. | |

FOREIGN PATENT DOCUMENTS

| | | |
|---|---|---|
| EP | 1433856 | 6/2004 |
| WO | WO 2013/110797 | 8/2013 |
| WO | WO 2014/047209 | 3/2014 |
| WO | WO 2015/013295 | 1/2015 |

OTHER PUBLICATIONS

"Information on EC 1.14.13.25—methane monooxygenase (soluble)". BRENDA [online database]. Jan. 2018, [retrieved on Jan. 16, 2019]. Retreived from the Internet: URL <https://www.brenda-enzymes.org/enzyme.php?ecno=1.14.13.25>, 12 pages.

Ali et al., "Development and validation of promoter-probe vectors for the study of methane monooxygenase gene expression in *Methylococcus capsulatus* Bath", Microbiology. Mar. 2009; 155(Pt 3): 761-771.

Altschul et al., "Basic Local Alignment Search Tool", J Mol Biol. Oct. 5, 1990; 215(3): 403-410.

Amann et al., "Tightly regulated tac promoter vectors useful for the expression of unfused and fused proteins in *Escherichia coli*", Gene. Sep. 30, 1988; 69(2): 301-315.

Annaluru et al., "Total Synthesis of a Functional Designer Eukaryotic Chromosome", Science. Apr. 4, 2014; 344(6179): 55-58. Epub Mar. 27, 2014.

Antoine et al., "Cloning and over-expression in *Escherichia coli* of the gene encoding NADPH group III alcohol dehydrogenase from Thermococcus hydrothermalis. Characterization and comparison of the native and the recombinant enzymes", Eur J Biochem. Sep. 1999; 264(3): 880-889.

Araya-Garay et al., "Construction of a novel Pichia pastoris strain for production of xanthophylls", AMB Express. Apr. 25, 2012; 2(1): 24.

Ausubel et al. *Current Protocols in Molecular Biology*. New York, John Wiley & Sons Inc., 2012.

(Continued)

*Primary Examiner* — Christian L Fronda

(74) *Attorney, Agent, or Firm* — Foley & Lardner LLP

(57) ABSTRACT

Methods and compositions for the oxidation of short alkanes by engineered microorganisms expressing enzymes are described, along with methods of use.

13 Claims, 18 Drawing Sheets

Specification includes a Sequence Listing.

(56) References Cited

OTHER PUBLICATIONS

Baik et al., "Mechanistic Studies on the Hydroxylation of Methane by Methane Monooxygenase", Chem Rev. Jun. 2003; 103(6): 2385-2419.
Balasubramanian et al., "Oxidation of methane by a biological dicopper centre", Nature. May 6, 2010; 465(7294): 115-119. Epub Apr. 21, 2010.
Banerjee et al., "Soluble Methane Monooxygenase", Annu Rev Biochem. Jun. 20, 2019; 88: 409-431. Epub Jan. 11, 2019.
Beaucage et al., "Recent Advances in the Chemical Synthesis of RNA", Curr Protoc Nucleic Acid Chem. Sep. 2009; Chapter 2: Unit 2.16.1-31.
Berger et al. *Guide to Molecular Cloning Techniques*, vol. 152, 1st Ed. Academic Press, Inc., 1987.
Bhataya et al., "Metabolic engineering of Pichia pastoris X-33 for lycopene production", Process Biochem. Oct. 2009; 44(10): 1095-1102.
Blazyk, J., "Electron Transfer and Protein Engineering Studies of the Soluble Methane Monooxygenase from Methylococcus capsulatus (Bath)", Doctoral thesis submitted to the Department of Chemistry at the Massachusetts Institute of Technology, Sep. 2003, 312 pages.
Bollinger et al., "Engineering the Diiron Site of *Escherichia coli* Ribonucleotide Reductase Protein R2 to Accumulate an Intermediate Similar to $H_{peroxo}$, the Putative Peroxodiiron(III) Complex from the Methane Monooxygenase Catalytic Cycle", J Am Chem Soc. 1998, 120(5): 1094-1095. Epub Feb. 11, 1998.
Bornscheuer et al., "Survey of Protein Engineering Strategies", Curr Protoc Protein Sci. Nov. 2011; Chapter 26: Unit 26.7.1-14.
Borodina et al., "Mutagenesis of the 'Leucine Gate' to Explore the Basis of Catalytic Versatility in Soluble Methane Monooxygenase", Appl Environ Microbiol. Oct. 2007; 73(20): 6460-6467. Epub Aug. 17, 2007.
Brady, S.F., "Construction of soil environmental DNA cosmid libraries and screening for clones that produce biologically active small molecules", Nat Protoc. 2007; 2(5): 1297-1305.
Brandstetter et al., "Mutational and structural analyses of the regulatory protein B of soluble methane monooxygenase from Methylococcus capsulatus (Bath)", Chem Biol. Jul. 1999; 6(7): 441-449.
Braun et al., "14-3-3 (Bmh) Proteins Regulate Combinatorial Transcription following RNA Polymerase II Recruitment by Binding at Adr1-Dependent Promoters in *Saccharomyces cerevisiae*", Mol Cell Biol. Feb. 2013; 33(4): 712-724. Epub Dec. 3, 2012.
Brouk et al., "Improving Biocatalyst Performance by Integrating Statistical Methods into Protein Engineering", Appl Environ Microbiol. Oct. 2010; 76(19): 6397-6403. Epub Aug. 13, 2010.
Burrows et al., "Substrate Specificities of the Soluble and Particulate Methane Mono-oxygenases of *Methylosinus trichosporium* OB3b", J Gen Microbiol. 1984; 130: 3327-3333.
Callaghan et al., "Residues near the N-terminus of protein B control autocatalytic proteolysis and the activity of soluble methane monooxygenase", Eur J Biochem. Apr. 2002; 269(7): 1835-1843.
Canada et al., "Directed Evolution of Toluene ortho-Monooxygenase for Enhanced 1-Naphthol Synthesis and Chlorinated Ethene Degradation", J Bacteriol. Jan. 2002; 184(2): 344-349.
Carvalho et al., "The remarkable Rhodococcus erythropolis", Appl Microbiol Biotechnol. Jun. 2005; 67(6): 715-726. Epub Feb. 15, 2005.
Cereghino et al., "Heterologous protein expression in the methylotrophic yeast Pichia pastoris", FEMS Microbiol Rev. Jan. 2000; 24(1): 45-66.
Çetinbaş et al., "Catalysis of Protein Folding by Chaperones Accelerates Evolutionary Dynamics in Adapting Cell Populations", Plos Comput Biol. Nov. 2013; 9(11): e1003269. Epub Nov. 7, 2013.
Chistoserdova et al., "A genomic view of methane oxidation by aerobic bacteria and anaerobic archaea", Genome Biol. 2005; 6(2): 208. Epub Feb. 1, 2005.
Cho et al., "Defective Export Of A Periplasmic Enzyme Disrupts Regulation Of Fatty Acid Synthesis", J Biol Chem. Mar. 3, 1995; 270(9): 4216-4219.
Chong et al., "Improving Ethanol Tolerance of *Escherichia coli* by Rewiring Its Global Regulator CAMP Recepter Protein (CRP)", PLoS One. 2013; 8(2):e57628. Epub Feb. 28, 2013.
Clark et al., "*Escherichia coli* mutants with altered control of alcohol dehydrogenase and nitrate reductase", J Bacteriol. Jan. 1980; 141(1): 177-183.
Colby et al., "Some Properties of a Soluble Methane Monooxygenase from *Methylococcus capsulatus* Strain Bath", Biochem J. Aug. 1, 1976; 157(2): 495-497.
Colby et al., "The Soluble Methane Mono-oxygenase of *Methylococcus capsulatus* (Bath). Its ability to oxygenate n-alkanes, n-alkenes, ethers, and alicyclic, aromatic and heterocyclic compounds", Biochem J. Aug. 1, 1977; 165(2): 395-402.
Cole, P.A., "Chaperone-assisted protein expression", Structure. Mar. 15, 1996; 4(3): 239-242.
Coleman et al., "Hydrocarbon monooxygenase in *Mycobacterium*: recombinant expression of a member of the ammonia monooxygenase superfamily", ISME J. Jan. 2012; 6(1): 171-182. Epub Jul. 28, 2011.
Costas et al., "Dioxygen Activation at Mononuclear Nonheme Iron Active Sites: Enzymes, Models, and Intermediates", Chem Rev. Feb. 2004; 104(2): 939-986.
Coufal et al., "Sequencing and analysis of the *Methylococcus capsulatus* (Bath) soluble methane monooxygenase genes", Eur J Biochem. Apr. 2000; 267(8): 2174-2185.
Cregg et al., "Recombinant Protein Expression in Pichia pastoris", Mol Biotechnol. Sep. 2000; 16(1): 23-52.
Crombie et al., "Trace-gas metabolic versatility of the facultative methanotroph *Methylocella silvestris*", Nature. Jun. 5, 2014; 510(7503): 148-151. Epub Apr. 28, 2014.
Crombie, A., "Metabolism of methane and propane and the role of the glyoxylate bypass enzymes in *Methylocella silvestris* BL2", Doctoral thesis submitted to the School of Life Sciences at the University of Warwick, Coventry, UK, Sep. 2011, 315 pages.
Csáki et al., "Genes involved in the copper-dependent regulation of soluble methane monooxygenase of *Methylococcus capsulatus* (Bath): cloning, sequencing and mutational analysis", Microbiology. Jul. 2003; 149(Pt 7): 1785-1795.
Datsenko et al., "One-step inactivation of chromosomal genes in *Escherichia coli* K-12 using PCR Products", Proc Natl Acad Sci USA. Jun. 6, 2000; 97(12): 6640-6645.
De Vries et al., "Cloning, expression, and sequence analysis of the Bacillus methanolicus C1 methanol deydrogenase gene", J Bacteriol. Aug. 1992; 174(16): 5346-5353.
Dedysh et al., "Facultative Methane Oxidizers." in: *Handbook of Hydrocarbon and Lipid Microbiology*, K.N. Timmis (ed.), (Springer-Verlag, Berlin, Heidelberg, 2010), pp. 1968-1976.
Dedysh et al., "*Methylocella* Species Are Facultatively Methanotrophic", J Bacteriol. Jul. 2005; 187(13): 4665-4670.
Duan et al., "High-rate conversion of methane to methanol by *Methylosinus trichosporium* OB3b", Bioresour Technol. Aug. 2011; 102(15): 7349-7353. Epub May 6, 2011.
Duetz et al., "Using proteins in their natural environment: potential and limitations of microbial whole-cell hydroxylations in applied biocatalysis", Curr Opin Biotechnol. Aug. 2001; 12(4): 419-425.
Elango et al., "Crystal structure of the hydroxylase component of methane monooxygenase from *Methylosinus trichosporium* OB3b", Protein Sci. Mar. 1997; 6(3): 556-568.
Engler et al., "Combinatorial DNA assembly using Golden Gate cloning", Methods Mol Biol. 2013; 1073: 141-156. Abstract only.
Erijman et al., "Transfer-PCR (TPCR): A highway for DNA cloning and protein engineering", J Struct Biol. Aug. 2011; 175(2): 171-177. Epub Apr. 15, 2011.
Eroshin et al., "Influence of Amino Acids, Carboxylic Acids and Sugars on the Growth of *Methylococcus capsulatus* on Methane", J Appl Bacteriol. Dec. 1968; 31(4): 560-567.
Foster et al., "A Methane-Dependent Coccus, with Notes on Classification and Nomenclature of Obligate, Methane-Utilizing Bacteria", J Bacteriol. May 1996; 91(5): 1924-1931.
Fox et al., "Evidence for a μ-Oxo-bridged Binuclear Iron Cluster in the Hydroxylase Component of Methane Monooxygenase. Mössbauer and EPR studies", J Biol Chem. Aug. 5, 1988; 263(22): 10553-10556.

(56) References Cited

OTHER PUBLICATIONS

Fox et al., "Methane Monooxygenase from *Methylosinus trichosporium* OB3b", J Biol Chem. Jun. 15, 1989; 264(17): 10023-10033.
Furuya et al., "Reconstitution of Active Mycobacterial Binuclear Iron Monooxygenase Complex in *Escherichia coli*", Appl Environ Microbiol. Oct. 2013; 79(19): 6033-6039. Epub Jul. 26, 2013.
Furuya et al., "The mycobacterial binuclear iron monooxygenases require a specific chaperonin-like protein for functional expression in a heterologous host", FEBS J. Feb. 2013; 280(3): 817-826. Epub Jan. 2, 2013.
Gassner et al., "Component Interactions in the Soluble Methane Monooxygenase System from *Methylococcus capsulatus* (Bath)", Biochemistry. Sep. 28, 1999; 38(39): 12768-12785. Epub Sep. 11, 1999.
Ge et al., "Biological conversion of methane to liquid fuels: Status and opportunities", Biotechnol Adv. Dec. 2014; 32(8): 1460-1475. Epub Oct. 2, 2014.
Gentz et al., "Promoters Recognized by *Escherichia coli* RNA Polymerase Selected by Function: Highly Efficient Promoters from Bacteriophage T5", J Bacteriol. Oct. 1985; 164(1): 70-77.
Gibson et al., "Enzymatic assembly of DNA molecules up to several hundred kilobases", Nat Methods. May 2009; 6(5): 343-345. Epub Apr. 12, 2009.
Glass et al., "Trace metal requirements for microbial enzymes involved in the production and consumption of methane and nitrous oxide", Front Microbiol. Feb. 21, 2012; 3: 61. eCollection 2012.
Gou et al., "Functional expression of the particulate methane mono-oxygenase gene in recombinant Rhodococcus erythropolis", FEMS Microbiol Lett. Oct. 2006; 263(2): 136-141.
Gould et al., "Development of the Yeast Pichia pastoris as a Model Organism for a Genetic and Molecular Analysis of Peroxisome Assembly", Yeast. Aug. 1992; 8(8): 613-628.
Graham et al., "Factors Affecting Competition Between Type I and Type II Methanotrophs in Two-organism, Continuous-flow Reactors", Microb Ecol. Jan. 1993; 25(1): 1-17.
Green et al. *Molecular Cloning: A Laboratory Manual*, 4th ed. Cold Spring Harbor, New York, Cold Spring Harbor Laboratory Press, 2012.
Green et al., "Copper ions as inhibitors of protein C of soluble methane monooxygenase *Methylococcus capsulatus* (Bath)", Eur J Biochem. Nov. 15, 1985; 153(1): 137-144.
Green et al., "Substrate Specificity of Soluble Methane Monooxygenase. Mechanistic Implications", J Biol Chem. Oct. 25, 1989; 264(30): 17698-17703.
Green et al., "The Biosynthesis and Assembly of Protein A of Soluble Methane Monooxygenase of *Methylococcus capsulatus* (Bath)", J Biol Chem. Nov. 25, 1988; 263(33): 17561-17565.
Grosse et al., "Purification and Characterization of the Soluble Methane Monooxygenase of the Type II Methanotrophic Bacterium *Methylocystis* sp. Strain WI 14", Appl Environ Microbiol. Sep. 1999; 65(9): 3929-3935.
Haacke et al., "Chaperone over-expression in *Escherichia coli*: Apparent increased yields of soluble recombinant protein kinases are due mainly to soluble aggregates", Protein Expr Purif. Apr. 2009; 64(2): 185-193. Epub Nov. 11, 2008.
Hakemian et al., "The Biochemistry of Methane Oxidation", Annu Rev Biochem. 2007; 76: 223-241.
Han et al., "Partial Oxidative Conversion of Methane to Methanol Through Selective Inhibition of Methanol Dehydrogenase in Methanotrophic Consortium from Landfill Cover Soil", Appl Biochem Biotechnol. Nov. 2013; 171(6): 1487-1499. Epub Aug. 21, 2013.
Hanson et al., "Methanotrophic bacteria", Microbiol Rev. Jun. 1996; 60(2): 439-471.
Hartl et al., "Mitochondrial protein import", Biochim Biophys Acta. Jan. 18, 1989; 988(1): 1-45.
Hartmann et al. *Handbook of RNA Biochemistry: Second, Completely Revised and Enlarged Edition*. Weinheim, Germany, Wiley-VCH, Verlag GmbH & Co. KGaA, 2014.
Hartner et al., "Regulation of methanol utilisation pathway genes in yeasts", Microb Cell Fact. Dec. 14, 2006; 5: 39.
Haynes et al., "Rethinking biological activation of methane and conversion to liquid fuels", Nat Chem Biol. May 2014; 10(5): 331-339. Epub Apr. 17, 2014.
Henne et al., "Construction of Environmental DNA Libraries in *Escherichia coli* and Screening for the Presence of Genes Conferring Utilization of 4-Hydroxybutyrate", Appl Environ Microbiol. Sep. 1999; 65(9): 3901-3907.
Hoefman et al., "Customized media based on miniaturized screening improve growth rate and cell yield of methane-oxidizing bacteria of the genus *Methylomonas*", Antonie Van Leeuwenhoek. Feb. 2014; 105(2): 353-366. Epub Nov. 24, 2013.
Holmes et al., "Evolutionary ecology and multidisciplinary approaches to prospecting for monooxygenases as biocatalysts", Antonie Van Leeuwenhoek. Jun. 2008; 94(1): 75-84. Epub Feb. 19, 2008.
Hoover et al., "Bacterial production of free fatty acids from freshwater macroalgal cellulose", Appl Microbiol Biotechnol. Jul. 2011; 91(2): 435-446. Epub Jun. 4, 2011.
Hoover et al., "Isolation of Improved Free Fatty Acid Overproducing Strains of *Escherichia coli* via Nile Red Based High-Throughput Screening", Environ Prog Sustain Energy. Apr. 2012; 31(1): 17-23. Epub Nov. 17, 2011.
Huang et al., "Determination of the Carbon Kinetic Isotope Effects on Propane Hydroxylation Mediated by the Methane Monooxygenases from *Methylococcus capsulatus* (Bath) by Using Stable Carbon Isotopic Analysis", Chembiochem. Aug. 2, 2002; 3(8): 760-765.
Huang et al., "DFT study of the mechanism for methane hydroxylation by soluble methane monooxygenase (sMMO): effects of oxidation state, spin state, and coordination number", Dalton Trans. Jan. 28, 2013; 42(4): 1011-1023.
Iguchi et al., "Soluble and particulate methane monooxygenase gene clusters of the type I methanotroph *Methylovulum miyakonense* HT12", FEMS Microbiol Lett. Nov. 2010; 312(1): 71-76. Epub Sep. 15, 2010.
Im et al., "Characterization of a novel facultative *Methylocystis* species capable of growth on methane, acetate and ethanol", Environ Microbiol Rep. Apr. 2011; 3(2): 174-181. Epub Aug. 25, 2010.
Innis, M.A. *PCR Protocols: A Guide to Methods and Applications*. San Diego, CA, Academic Press, 1990. Abstract only.
Jahng et al., "Metal ions and chloramphenicol inhibition of soluble methane monooxygenase from *Methylosinus trichosporium* OB3b", Appl Microbiol Biotechnol. Jul. 1996; 45(6): 744-749.
Jahng et al., "Trichloroethylene and Chloroform Degradation by a Recombinant Pseudomonad Expressing Soluble Methane Monooxygenase from Methylosinus trichosporium OB3b", Appl Environ Microbiol. Jul. 1994; 60(7): 2473-2482.
Jiang et al., "Activation of the hydroxylase of sMMO from *Methylococcus capsulatus* (Bath) by hydrogen peroxide", Biochim Biophys Acta. Apr. 21, 1993; 1163(1): 105-112.
Jiang et al., "Chemical modification of the hydroxylase of soluble methane monooxygenase gives one form of the protein with significantly increased thermostability and another that functions well in organic solvents", Biochim Biophys Acta. Sep. 28, 1994; 1201(1): 76-84.
Jiang et al., "Methanotrophs: Multifunctional bacteria with promising applications in environmental bioengineering", Biochem Eng J. May 15, 2010; 49(3): 277-288.
Kalyuzhnaya et al., "Functional metagenomics of methylotrophs", Methods Enzymol. 2011; 495: 81-98.
Kalyuzhnaya et al., "Characterization of a Novel Methanol Dehydrogenase in Representatives of Burkholderiales: Implications for Environmental Detection of Methylotrophy and Evidence for Convergent Evolution", J Bacteriol. Jun. 2008; 190(11): 3817-3823. Epub Apr. 4, 2008.
Kao et al., "Quantitative Proteomic Analysis of Metabolic Regulation by Copper Ions in *Methylococcus capsulatus* (Bath)", J Biol Chem. Dec. 3, 2004; 279(49): 51554-51560. Epub Sep. 22, 2004.
Kato et al., "The Physiological Role of the Ribulose Monophosphate Pathway in Bacteria and Archaea", Biosci Biotechnol Biochem. Jan. 2006; 70(1): 10-21.
Keel et al., "Large-scale native preparation of in vitro transcribed RNA", Methods Enzymol. 2009; 469: 3-25. Epub Nov. 17, 2009.

(56) References Cited

OTHER PUBLICATIONS

Kim et al., "Optimization of Lab Scale Methanol Production by Methylosinus trichosporium OB3b", Biotechnol Bioprocess Eng. Jun. 2010; 15(3): 476-480.
Leahy et al., "Evolution of the soluble diiron monooxygenases", FEMS Microbiol Rev. Oct. 2003; 27(4): 449-479.
Lee et al., "Control of substrate access to the active site in methane monooxygenase", Nature. Feb. 21, 2013; 494(7437): 380-384. Epub Feb. 10, 2013.
Lee et al., "Transient Intermediates of the Methane Monooxygenase Catalytic Cycle", J Biol Chem. Oct. 15, 1993; 268(29): 21569-21577.
Lidstrom et al., "Methylotrophs: Genetics and Commercial Applications", Annu Rev Microbiol. 1990; 44: 27-58.
Lin-Cereghino et al., "Condensed protocol for competent cell preparation and transformation of the methylotrophic yeast *Pichia pastoris*", Biotechniques. Jan. 2005; 38(1): 44-48.
Lin-Cereghino et al., "Mxr1p, a Key Regulator of the Methanol Utilization Pathway and Peroxisomal Genes in Pichia pastoris", Mol Cell Biol. Feb. 2006; 26(3): 883-897.
Lipscomb, J., "Biochemistry of the Soluble Methane Monooxygenase", Annu Rev Microbiol. 1994; 48: 371-399.
Liu et al., "Kinetic and Spectroscopic Characterization of Intermediates and Component Interactions in Reactions of Methane Monooxygenase from *Methylococcus capsulatus* (Bath)", J Am Chem Soc. 1995; 117(41): 10174-10185.
Liu et al., "Spectroscopic Detection of Intermediates in the Reaction of Dioxygen with the Reduced Methane Monooxygenase Hydroxylase from *Methylococcus capsulatus* (Bath)", J Am Chem Soc. 1994; 116(16): 7465-7466.
Lloyd et al., "Heterologous expression of soluble methane monooxygenase genes in methanotrophs containing only particulate methane monooxygenase", Arch Microbiol. May-Jun. 1999; 171(6): 364-370.
Lloyd et al., "Inactivation of the regulatory protein B of soluble methane monooxygenase from *Methylococcus capsulatus* (Bath) by proteolysis can be overcome by a Gly to Gln modification", Eur J Biochem. Aug. 15, 1997; 248(1): 72-79.
Lloyd, J., "Heterologous Expression and Site-Directed Mutagenesis of Soluble Methane Monooxygenase", Doctoral thesis submitted to the Department of Biological Sciences at the University of Warwick, Nov. 1997, 355 pages.
Lontoh et al., "Methane and Trichloroethylene Degradation by *Methylosinus trichosporium* OB3b Expressing Particulate Methane Monooxygenase", Appl Environ Microbiol. Mar. 1998; 64(3): 1106-1114.
Lüers et al., "The Pichia pastoris Dihydroxyacetone Kinase is a PTS1-containing, but Cytosolic, Protein that is Essential for Growth on Methanol", Yeast. Jun. 15, 1998; 14(8): 759-771.
Lund et al., "Electron transfer reactions in the soluble methane monooxygenase of *Methylococcus capsulatus* (Bath)", Eur J Biochem. Mar. 1, 1985; 147(2): 297-305.
Luo et al., "Improved ethanol tolerance in *Escherichia coli* by changing the cellular fatty acids composition through genetic manipulation", Biotechnol Lett. Dec. 2009; 31(12): 1867-1871. Epub Aug. 15, 2009.
Lynch et al., "Mössbauer and EPR Studies of the Binuclear Iron Center in Ribonucleotide Reductase from *Escherichia coli*. A New Iron-to-Protein Stoichiometry", J Biol Chem. May 15, 1989; 264(14): 8091-8096.
Makhoba et al., "Molecular Chaperone Assisted Expression Systems: Obtaining Pure Soluble and Active Recombinant Proteins for Structural and Therapeutic Purposes", J Proteomics Bioinform. Jan. 2015; 8(9): 212-216.
Martinho et al., "Mossbauer Studies of the Membrane-Associated Methane Monooxygenase from *Methylococcus capsulatus* Bath: Evidence for a Diiron Center", J Am Chem Soc. Dec. 26, 2007; 129(51): 15783-15785. Epub Dec. 5, 2007.
Mcdonald et al., "Diversity of soluble methane monooxygenase-containing methanotrophs isolated from polluted environments", FEMS Microbiol Lett. Feb. 2006; 255(2): 225-232.
Megha et al., "GroEL-GroES assisted folding of multiple recombinant proteins simultaneously over-expressed in *Escherichia coli*", Int J Biochem Cell Biol. Jul. 2015; 64: 277-286. Epub May 6, 2015.
Meinhold et al., "Direct Conversion of Ethane to Ethanol by Engineered Cytochrome", Chembiochem. Oct. 2005; 6(10): 1765-1768.
Membrillo-Hernández et al., "Evolution of the adhE Gene Product of *Escherichia coli* from a Functional Reductase to a Dehydrogenase: Genetic and biochemical studies of the mutant proteins", J Biol Chem. Oct. 27, 2000; 275(43): 33869-33875.
Merkx et al., "Dioxygen Activation and Methane Hydroxylation by Soluble Methane Monooxygenase: A Tale of Two Irons and Three Proteins", Angew Chem Int Ed Engl. Aug. 3, 2001; 40(15): 2782-2807.
Merkx et al., "Why OrfY? Characterization of MMOD, a long overlooked component of the soluble methanemonooxygenase from *Methylococcus capsulatus* (Bath)", J Biol Chem. Feb. 22, 2002; 277(8): 5858-5865. Epub Nov. 14, 2001.
Moon et al., "Metabolic engineering of *Escherichia coli* for the production of malic acid", Biochem Eng J. Jun. 2008; 40(2): 312-320.
Müller et al., "NMR Structure of the [2Fe—2S] Ferredoxin Domain from Soluble Methane Monooxygenase Reductase and Interaction with Its Hydroxylase", Biochemistry. Jan. 8, 2002; 41(1): 42-51.
Murrell et al., "Molecular biology and regulation of methane monooxygenase", Arch Microbiol. May-Jun. 2000; 173(5-6): 325-332.
Nazaries et al., "Methane, microbes and models: fundamental understanding of the soil methane cycle for future predictions", Environ Microbiol. Sep. 2013; 15(9): 2395-2417. Epub May 29, 2013.
Nguyen et al., "Reconstruction of Methanol and Formate Metabolic Pathway in Non-native Host for Biosynthesis of Chemicals and Biofuels", Biotechnol Bioprocess Eng. Aug. 2016; 21(4): 477-482.
Nichol et al., "Controlling the Activities of the Diiron Centre in Bacterial Monooxygenases: Lessons from Mutagenesis and Biodiversity", Eur J Inorg Chem. Jul. 2015; 2015(21): 3419-3431.
Nielsen et al., "Regulation of bacterial methane oxidation: transcription of the soluble methane mono-oxygenase operon of *Methylococcus capsulatus* (Bath) is repressed by copper ions", Microbiology. May 1996; 142(Pt 5): 1289-1296.
Nordlund et al., "The active site structure of methane monooxygenase is closely related to the binuclear iron center of ribonucleotide reductase", FEBS Lett. Aug. 3, 1992; 307(3): 257-262.
Oldenhuis et al., "Kinetics of Chlorinated Hydrocarbon Degradation by Methylosinus trichosporium OB3b and Toxicity of Trichloroethylene", Appl Environ Microbiol. Jan. 1991; 57(1): 7-14.
Orita et al., "Bifunctional enzyme fusion of 3-hexulose-6-phosphate synthase and 6-phospho-3-hexuloisomerase", Appl Microbiol Biotechnol. Aug. 2007; 76(2): 439-445. Epub May 23, 2007.
Orita et al., "The Archaeon Pyrococcus horikoshii Possesses a Bifunctional Enzyme for Formaldehyde Fixation via the Ribulose Monophosphate Pathway", J Bacteriol. Jun. 2005; 187(11): 3636-3642.
Orita et al., "The Ribulose Monophosphate Pathway Substitutes for the Missing Pentose Phosphate Pathway in the Archaeon Thermococcus kodakaraensis", J Bacteriol. Jul. 2006; 188(13): 4698-4704.
Palmer, M., "Optimization of Growth Conditions for Methanol Consumption in *Escherichia coli* Expressing Methylotrophic Genes", Doctoral thesis submitted to the Faculty of the University of Delaware, 2016, 41 pages.
Park et al., "Biological conversion of methane to methanol", Korean J Chem Eng. May 2013; 30(5): 977-987.
Patel et al., "Purification and Properties of the Hydroxylase Component of Methane Monooxygenase", J Bacteriol. May 1987; 169(5): 2313-2317.
Pilkington et al., "Soluble Methane Monooxygenase from *Methylococcus capsulatus* Bath", Methods Enzymol. 1990; 188: 181-190.

(56) References Cited

OTHER PUBLICATIONS

Purich et al. *The Enzyme Reference: A Comprehensive Guidebook to Enzyme Nomenclature, Reactions, and Methods*. Academic Press, 2002. Abstract only.
Ravi et al., "Mechanism of Assembly of the Tyrosyl Radical-Diiron(III) Cofactor of *E. coli* Ribonucleotide Reductase: 1. Mössbauer Characterization of the Diferric Radical Precursor", J Am Chem Soc. 1994; 116(18): 8007-8014.
Redmond et al., "Identification of novel methane-, ethane-, and propane-oxidizing bacteria at marine hydrocarbon seeps by stable isotope probing", Appl Environ Microbiol. Oct. 2010; 76(19): 6412-6422. Epub Jul. 30, 2010.
Rosenzweig et al., "Geometry of the soluble methane monooxygenase catalytic diiron center in two oxidation states", Chem Biol. Jun. 1995; 2(6): 409-418.
Sazinsky et al., "Product Bound Structures of the Soluble Methane Monooxygenase Hydroxylase from *Methylococcus capsulatus* (Bath): Protein Motion in the a-Subunit", J Am Chem Soc. Apr. 27, 2005; 127(16): 5814-5825. Epub Apr. 2, 2005.
Schrader et al., "Methanol-based industrial biotechnology: current status and future perspectives of methylotrophic bacteria", Trends Biotechnol. Feb. 2009; 27(2): 107-115. Epub Dec. 26, 2008.
Senior et al., "The ICI Single Cell Protein Process", Biotechnol Lett. May 1980; 2(5): 205-210.
Sherman, F., "Getting Started with Yeast", Methods Enzymol. 2002; 350: 3-41.
Sirajuddin et al., "Enzymatic Oxidation of Methane", Biochemistry. Apr. 14, 2015; 54(14): 2283-2294. Epub Apr. 1, 2015.
Smith et al., "Improved System for Protein Engineering of the Hydroxylase Component of Soluble Methane Monooxygenase", Appl Environ Microbiol. Nov. 2002; 68(11): 5265-5273.
Smith et al., "Metal reconstitution of particulate methane monooxygenase and heterologous expression of the pmoB subunit", Methods Enzymol. 2011; 495: 195-210.
Smith et al., "Mutagenesis of Soluble Methane Monooxygenase", Methods Enzymol. 2011; 495: 135-147.
Stafford et al., "rpoN, mmoR and mmoG, genes involved in regulating the expression of soluble methane monooxygenase in Methylosinus trichosporium OB3b", Microbiology. Jul. 2003; 149(Pt 7): 1771-1784.
Takeguchi et al., "Optimization of Methanol Biosynthesis by *Methylosinus trichosporium* OB3b: An Approach to Improve Methanol Accumulation", Appl Biochem Biotechnol. Dec. 1997; 68(3): 143-152.
Tamarit et al., "Identification of the Major Oxidatively Damaged Proteins in *Escherichia coli* Cells Exposed to Oxidative Stress", J Biol Chem. Jan. 30, 1998; 273(5): 3027-3032.
Tinberg et al., "Dioxygen Activation in Soluble Methane Monooxygenase", Acc Chem Res. Apr. 19, 2011; 44(4): 280-288. Epub Mar. 10, 2011.
Ulrich et al., "Exponential Megapriming PCR (EMP) Cloning—Seamless DNA Insertion into Any Target Plasmid without Sequence Constraints", PLoS One. 2012; 7(12): e53360. Epub Dec. 31, 2012.
Urlacher et al., "Recent advances in oxygenase-catalyzed biotransformations", Curr Opin Chem Biol. Apr. 2006; 10(2): 156-161. Epub Feb. 20, 2006.
Valentine et al., "Mechanistic Studies of the Reaction of Reduced Methane Monooxygenase Hydroxylase with Dioxygen and Substrates", J Am Chem Soc. 1999; 121(16): 3876-3887. Epub Apr. 9, 1999.
Valentine et al., "Principles of small molecule activation by metalloenzymes as exemplified by the soluble methane monooxygenase from *Methylococcus capsulatus* (Bath)", J Chem Soc., Dalton Trans. 1997; 21: 3925-3931.
Van Der Rest et al., "A heat shock following electroporation induces highly efficient transformation of Corynebacterium glutamicum with xenogeneic plasmid DNA", Appl Microbiol Biotechnol. Oct. 1999; 52(4): 541-545.
Vazquez-Duhalt et al. *Petroleum Biotechnology: Developments and Persepctives*. Elsevier Science, 2004.
Vertès et al., "Manipulating Corynebacteria, from Individual Genes to Chromosomes", Appl Environ Microbiol. Dec. 2005; 71(12): 7633-7642.
Wang et al., "Coupling Oxygen Consumption with Hydrocarbon Oxidation in Bacterial Multicomponent Monooxygenases", Acc Chem Res. Sep. 15, 2015; 48(9): 2632-2639. Epub Aug. 21, 2015.
Wang et al., "Electron Transfer Control in Soluble Methane Monooxygenase", J Am Chem Soc. Jul. 9, 2014; 136(27): 9754-9762. Epub Jun. 24, 2014.
Ward et al., "Genomic Insights into Methanotrophy: The Complete Genome Sequence of Methylococcus capsulatus (Bath)", PLoS Biol. Oct. 2004; 2(10): e303. Epub Sep. 21, 2004.
Werpy et al., "Top Value Added Chemicals from Biomass. Volume I—Results of Screening for Potential Candidates from Sugars and Synthesis Gas", US Department of Energy, Aug. 2004.
West et al., "Functional expression in *Escherichia coli* of proteins B and C from soluble methane monooxygenase of *Methylococcus capsulatus* (Bath)", J Gen Microbiol. Jul. 1992; 138(7): 1301-1307.
Whitaker et al., "Synthetic methylotrophy: engineering the production of biofuels and chemicals based on the biology of aerobic methanol utilization", Curr Opin Biotechnol. Jun. 2015; 33: 165-175. Epub Mar. 19, 2015.
Whittington et al., "Crystal Structures of the Soluble Methane Monooxygenase Hydroxylase from *Methylococcus capsulatus* (Bath) Demonstrating Geometrical Variability at the Dinuclear Iron Active Site", J Am Chem Soc. Feb. 7, 2001; 123(5): 827-838.
Witthoff et al., "Metabolic Engineering of Corynebacterium glutamicum for Methanol Metabolism", Appl Environ Microbiol. Mar. 2015; 81(6): 2215-2225. Epub Jan. 16, 2015.
Wood, T. et al, "Active expression of soluble methane monooxygenase from *Methylosinus trichosporium* OB3b in heterologous hosts", Microbiology. Nov. 2002; 148(Pt 11): 3328-3329.
Woodland et al., "Purification and Characterization of Component A of the Methane Monooxygenase from *Methylococcus capsulatus* (Bath)", J Biol Chem. Jan. 10, 1984; 259(1): 53-59.
Xu et al., "The Heme Monooxygenase Cytochrome $P450_{cam}$ Can Be Engineered to Oxidize Ethane to Ethanol", Angew Chem Int Ed Engl. Jun. 27, 2005; 44(26): 4029-4032.
Yanase et al., "Cloning and sequence analysis of the gene encoding 3-hexulose-6-phosphate synthase from the methylotrophic bacterium, Methylomonas aminofaciens 77a, and its expression in *Escherichia coli*", FEMS Microbiol Lett. Jan. 15, 1996; 135(2-3): 201-205.
Yasueda et al., "Bacillus subtilis yckG and yckF Encode Two Key Enzymes of the Ribulose Monophosphate Pathway Used by Methylotrophs, and yckH Is Required for Their Expression", J Bacteriol. Dec. 1999; 181(23): 7154-7160.
Yoon, S., "Towards Practical Application of Methanotrophic Metabolism in Chlorinated Hydrocarbon Degradation, Greenhouse Gas Removal, and Immobilization of Heavy Metals", Doctoral thesis submitted at the University of Michigan, 2010, 158 pages.
Yuan et al., "Modification of the substrate specificity of an acyl-acyl carrier protein thioesterase by protein engineering", Proc Natl Acad Sci USA. Nov. 7, 1995; 92(23): 10639-10643.
Yurimoto et al., "The ribulose monophosphate pathway operon encoding formaldehyde fixation in a thermotolerant methylotroph, Bacillus brevis S1", FEMS Microbol Lett. Sep. 10, 2002; 214(2): 189-193.
Zelle et al., "Malic Acid Production by *Saccharomyces cerevisiae*: Engineering of Pyruvate Carboxylation, Oxaloacetate Reduction, and Malate Export", Appl Environ Microbiol. May 2008; 74(9): 2766-2777.
Zhang et al., "L-Malate Production by Metabolically Engineered *Escherichia coli*", Appl Environ Microbiol. Jan. 2011; 77(2): 427-434. Epub Nov. 19, 2010.
Zhang et al., "Metabolic evolution of energy-conserving pathways for succinate production in *Escherichia coli*", Proc Natl Acad Sci USA. Dec. 1, 2009; 106(48): 20180-20185. Epub Nov. 16, 2009.
International Search Report and Written Opinion issued Jul. 21, 2015, in International Patent Application No. PCT/US2015/025817, 12 pages.
International Search Report and Written Opinion issued Apr. 3, 2017, in International Patent Application No. PCT/US2016/062623, 13 pages.

(56) References Cited

OTHER PUBLICATIONS

Extended European Search Report issued Nov. 9, 2017, in European Patent Application No. 15780357.8, 9 pages.
Communication pursuant to Rule 164(1) EPC, Partial Supplementary European Search Report issued Mar. 14, 2019, in European Patent Application No. 16867180.8, 16 pages.
Extended European Search Report issued Jun. 25, 2019, in European Patent Application No. 16867180.8, 19 pages.
Chica, R. A., "Semi-Rational Approaches to Engineering Enzyme Activity: Combining the Benefits of Directed Evolution and Rational Design," Science Direct, vol. 16, pp. 378-384 (Jul. 2005).
Kizer, L., et al., "Application of Functional Genomics to Pathway Optimization for Increased Isoprenoid Production," Applied and Environmental Microbiology, pp. 3229-3241 (May 2008).
Prather, K. L., et al., De Novo Biosynthetic Pathways: Rational Design of Mirobial Chemical Factories, Science Direct Biotechnology, vol. 19, pp. 468-474 (Sep. 2008).
Singh, R. K. S., et al., "Protein Engineering Approaches in the Post-Genomic Era," Current Protein and Peptide Science, vol. 18, No. 4, pp. 1-11 (2017).

* cited by examiner

```
TY7           -------------------MSRQSMSKAHKKITELSWEPTFATPAKRFGTDYTFDNAPKK
solimonas     --MAASNLAVKQALKNNPAPSSVDPQEVHKWLQDFTWD--FKEKAGKYPTKYDMDVNT-R
capsulatus    MALSTATKAATDALAANRAPTSVNAQEVHRWLQSFNWD--FKNNRTKYATKYKMANET-K
                                  :  . .:.*: : .:.*:  *     :: *.* :     :

TY7           DPLKQILRSYFPMEEEKDSRVFGAMDGA-IRGNMFRQVQERWMEWQKLFLSIIPFPEISA
solimonas     EQFKLTAKEYARMESAKEERQFGTLLDGLDRLDAGNKVHPRWGEFMKLVANFLETGEYGA
capsulatus    EQFKLIAKEYARMEAVKDERQFGSLQDALTRLNAGVRVHPKWNETMKVVSNFLEVGEYNA
              : :*   :.*  **  *:.* **:: ..  * :   :*: :* *  *:. .::   * .*

TY7           ARAMPMAIDAVPNPEIHNGLAVQMIDEVRHSTIQMNLKRLYMNYYIDPAGFDMTEKA-FA
solimonas     LAGSALLWDTAQSPEQRNGYLAQVIDEVRHVNQCASVSYYYSKHYYDPAGFTNMRQLRAI
capsulatus    IAATGMLWDSAQAAEQKNGYLAQVLDEIRHTHQCAYVNYYFAKNGQDPAGHNDARRTRTI
                .  :  *:.   * :**  .*::**:**      :.  : :   ****.   .:

TY7           NNYAGTIGRQFGEGFITGDAITAANIYLTVVAETAFTNTLFVAMPSEAAANGDYLLPTVF
solimonas     NPLYPGVKRAFGEGFLAGDAVES-SINLQLVAEACFTNPLIVALTEWAAANGDEITPTVF
capsulatus    GPLWKGMKRVFSDGFISGDAVEC-SLNLQLVGEACFTNPLIVAVTEWAAANGDEITPTVF
              .     : * *.:**::***: . .: * :*.*:.*** *:**: . ****** : ****

TY7           HSVQSDESRHISNGYSILLMALSDEDNRQLLERDLRYAWWNNHRVVDAAIGTFIEYGTKD
solimonas     LSIETDELRHMANGYQTIVSIMNNPDTMKYLQTDLDNAFWTQHKFLTPFVGAALEYGSRF
capsulatus    LSIETDELRHMANGYQTVVSIANDPASAKYLNTDLNNAFWTQQKYFTPVLGMLFEYGSKF
               *:::** **:***.  ::   .:  . : *: **  *:*.::: .   :*  :***::

TY7           RRKDRESYAEMWRRWIYDDYYRAYLIPLEKYGLVIPHDLIEESWKQIWEKGYVHEVAQFF
solimonas     ---KVEPWAKSWNRWVYEDWAGIWLGRLQQFGLKSPKCLADAKKDAVWAHH---DLALLA
capsulatus    ---KVEPWVKTWNRWVYEDWGGIWIGRLGKYGVESPRSLKDAKQDAYWAHH---DLYLLA
                 . * :.: *.**:*:*:   ::  * ::*:  *: * : . .  * :    ::  :

TY7           ATGWLANYWRIDSMTDEDFEWFEYKYPGWYDKYGKWWENYNRLSKPNG---HNPIVFE--
solimonas     FALWPLTGIRLELPDRQDMEWFEANYPGWYEHYGKIYEEWRALGFEDPRSGFSGAVWMLQ
capsulatus    YALWPTGFFRLALPDQEEMEWFEANYPGWYDHYGKIYEEWRARGCEDPSSGFIPLMWFIE
               : *     *:     :::**** :*****::*** :*::.  .  :    .   ::

TY7           DVDYVYPAR---CWTCMSPCWSVRTLVTAEVDGQHRTYCHEVCRWTDVRGFPSDVPGRET
solimonas     RGHGIFIDHTSSLPFCPTLGKGALKPSFLEKNGKRFAFSEP-------HGERMWL-----
capsulatus    NNHPIYIDRVSQVPFCPSLAKGASTLRVHEYNGQMHTFSDQ-------WGERMWL-----
                . ::  :      * :   .. .    * :*:  ::..         *    :

TY7           PNMGRLVGKREWETLYHGWNWADVVSDMGFVRDDGKTMTPKPHLDLDPKKMWTLDHMRRC
solimonas     -QEPERYEFQNFFEQFEGWELSDLVKAAGGVRSDGKTLMAQPHLR--STDMWTLDDLKRI
capsulatus    -AEPERYECQNIFEQYEGRELSEVIAELHGLRSDGKTLIAQPHVR--GDKLWTLDDIKRL
                  .    ::    :.* : ::::     :*.****:  :**:     .:****.::*

TY7           PPLQ-SPNVLFNEMSDAERAAYVADYNKQGPAGRPAPQS*
solimonas     NFTVPDPMRILNWQPAH-----------------------
capsulatus    NCVFKNPVKAFN*---------------------------
                   .*   :*
```

FIGURE 18

SEQUENCE LISTING

```
Sequence total quantity: 154
SEQ ID NO: 1            moltype = DNA  length = 54
FEATURE                 Location/Qualifiers
misc_feature            1..54
```

```
                        note = Synthetic primer
source                  1..54
                        mol_type = other DNA
                        organism = synthetic construct
SEQUENCE: 1
gtttgattgg ctgtggtttt atacagtcat acctgtgacg gaagatcact tcgc        54

SEQ ID NO: 2            moltype = DNA  length = 46
FEATURE                 Location/Qualifiers
misc_feature            1..46
                        note = Synthetic primer
source                  1..46
                        mol_type = other DNA
                        organism = synthetic construct
SEQUENCE: 2
gctttttatc gcaactctct actgtttctc ttacgccccg ccctgc                 46

SEQ ID NO: 3            moltype = DNA  length = 29
FEATURE                 Location/Qualifiers
misc_feature            1..29
                        note = Synthetic primer.
source                  1..29
                        mol_type = other DNA
                        organism = synthetic construct
SEQUENCE: 3
tgactgtata aaaccacagc caatcaaac                                    29

SEQ ID NO: 4            moltype = DNA  length = 24
FEATURE                 Location/Qualifiers
misc_feature            1..24
                        note = Synthetic primer.
source                  1..24
                        mol_type = other DNA
                        organism = synthetic construct
SEQUENCE: 4
atgcggtttc agacgggcat taac                                         24

SEQ ID NO: 5            moltype = DNA  length = 30
FEATURE                 Location/Qualifiers
misc_feature            1..30
                        note = Synthetic primer.
source                  1..30
                        mol_type = other DNA
                        organism = synthetic construct
SEQUENCE: 5
gagaaacagt agagagttgc gataaaaagc                                   30

SEQ ID NO: 6            moltype = DNA  length = 24
FEATURE                 Location/Qualifiers
misc_feature            1..24
                        note = Synthetic primer.
source                  1..24
                        mol_type = other DNA
                        organism = synthetic construct
SEQUENCE: 6
tggcgggaac agcaaaatat cacc                                         24

SEQ ID NO: 7            moltype = DNA  length = 426
FEATURE                 Location/Qualifiers
misc_feature            1..426
                        note = Methylococcus capsulatus (Bath)
source                  1..426
                        mol_type = genomic DNA
                        organism = Methylococcus capsulatus
SEQUENCE: 7
atgagcgtaa acagcaacgc atacgacgcc ggcatcatgg gcctgaaagg caaggacttc  60
gccgatcagt tctttgccga cgaaaaccaa gtggtccatg aaagcgacac ggtcgttctg  120
gtcctcaaga agtcggacga gatcaatacc tttatcgagg agatccttct gacggactac  180
aagaagaacg tcaatccgac ggtaaacgtg gaagaccgcg cgggttactg gtggatcaag  240
gccaacggca agatcgaggt cgattgcgac gagatttccg agctgttggg gcggcagttc  300
aacgtctacg acttcctcgt cgacgtttcc tccaccatcg gccgggccta taccctgggc  360
aacaagttca ccattaccag tgagctgatg ggcctggacc gcaagctcga agactatcac  420
gcttaa                                                             426

SEQ ID NO: 8            moltype = AA  length = 141
FEATURE                 Location/Qualifiers
REGION                  1..141
                        note = misc_feature - Methylococcus capsulatus (Bath)
source                  1..141
```

```
                        mol_type = protein
                        organism = Methylococcus capsulatus
SEQUENCE: 8
MSVNSNAYDA GIMGLKGKDF ADQFFADENQ VVHESDTVVL VLKKSDEINT FIEEILLTDY  60
KKNVNPTVNV EDRAGYWWIK ANGKIEVDCD EISELLGRQF NVYDFLVDVS STIGRAYTLG  120
NKFTITSELM GLDRKLEDYH A                                           141

SEQ ID NO: 9            moltype = DNA  length = 1584
FEATURE                 Location/Qualifiers
misc_feature            1..1584
                        note = Methylococcus capsulatus (Bath)
source                  1..1584
                        mol_type = genomic DNA
                        organism = Methylococcus capsulatus
SEQUENCE: 9
atggcactta gcaccgcaac caaggccgcg acggacgcgc tggctgccaa tcgggcaccc  60
accagcgtga atgcacagga agtgcaccgt tggctccaga gcttcaactg ggatttcaag  120
aacaaccgga ccaagtacgc caccaagtac aagatggcga acgagaccaa ggaacagttc  180
aagctgatcg ccaaggaata tgcgcgcatg gaggcagtca aggacgaaag gcagttcggt  240
agcctgcagg atgcgctgac ccgcctcaac gccggtgttc gcgttcatcc gaagtggaac  300
gagaccatga aagtggtttc gaacttcctg gaagtgggcg aatacaacgc catcgccgct  360
accgggatgc tgtgggattc cgcccaggcg gcggaacaga agaacggcta tctggcccag  420
gtgttggatg aaatccgcca cacccaccag tgtgcctacg tcaactacta cttcgcgaag  480
aacggccagg acccggccgg tcacaacgat gctcgccgca cccgtaccat cggtccgctg  540
tggaagggca tgaagcgcgt gttttccgac ggcttcattt ccggcgacgc cgtggaatgc  600
tccctcaacc tgcagctggt gggtgaggcc tgcttcacca atccgctgat cgtcgcagtg  660
accgaatggg ctgccgccaa cggcgatgaa atcaccccga cggtgttcct gtcgatcgag  720
accgacgaac tgcgccacat ggccaacggt taccagaccg tcgtttccat cgccaacgat  780
ccggcttccg ccaagtatct caacacggac ctgaacaacg ccttctggac ccagcagaag  840
tacttcacgc cggtgttggg catgctgttc gagtatggct ccaagttcaa ggtcgagccg  900
tgggtcaaga cgtggaaccg ctgggtgtac gaggactggg gcggcatctg gatcggccgt  960
ctgggcaagt acggggtgga gtcgccgcgc agcctcaagg acgccaagca ggacgcttac  1020
tgggctcacc acgacctgta tctgctggct tatgcgctgt ggccgaccgg cttcttccgt  1080
ctggcgctgc cggatcagga agaaatggag tggttcgagg ccaactaccc cggctggtac  1140
gaccactacg gcaagatcta cgaggaatgg cgcgcccgcg gttgcgagga tccgtcctcg  1200
ggcttcatcc cgctgatgtg gttcatcgaa aacaaccatc ccatctacat cgatcgcgtg  1260
tcgcaagtgc cgttctgccc gagcttggcc aagggcgcca gcaccctgcg cgtgcacgag  1320
tacaacggcc agatgcacac cttcagcgac cagtggggcg agcgcatgtg gctggccgag  1380
ccggagcgct acgagtgcca gaacatcttc gaacagtacg aaggacgcga actgtcggaa  1440
gtgatcgccg aactgcacgg gctgcgcagt gatggcaaga ccctgatcgc ccagccgcat  1500
gtccgtggcg acaagctgtg gacgttggac gatatcaaac gcctgaactg cgtcttcaag  1560
aacccggtga aggcattcaa ttga                                        1584

SEQ ID NO: 10           moltype = AA  length = 527
FEATURE                 Location/Qualifiers
REGION                  1..527
                        note = misc_feature - Methylococcus capsulatus (Bath)
source                  1..527
                        mol_type = protein
                        organism = Methylococcus capsulatus
SEQUENCE: 10
MALSTATKAA TDALAANRAP TSVNAQEVHR WLQSFNWDFK NNRTKYATKY KMANETKEQF  60
KLIAKEYARM EAVKDERQFG SLQDALTRLN AGVRVHPKWN ETMKVVSNFL EVGEYNAIAA  120
TGMLWDSAQA AEQKNGYLAQ VLDEIRHTHQ CAYVNYYFAK NGQDPAGHND ARRTRTIGPL  180
WKGMKRVFSD GFISGDAVEC SLNLQLVGEA CFTNPLIVAV TEWAAANGDE ITPTVFLSIE  240
TDELRHMANG YQTVVSIAND PASAKYLNTD LNNAFWTQQK YFTPVLGMLF EYGSKFKVEP  300
WVKTWNRWVY EDWGGIWIGR LGKYGVESPR SLKDAKQDAY WAHHDLYLLA YALWPTGFFR  360
LALPDQEEME WFEANYPGWY DHYGKIYEEW RARGCEDPSS GFIPLMWFIE NNHPIYIDRV  420
SQVPFCPSLA KGASTLRVHE YNGQMHTFSD QWGERMWLAE PERYECQNIF EQYEGRELSE  480
VIAELHGLRS DGKTLIAQPH VRGDKLWTLD DIKRLNCVFK NPVKAFN                527

SEQ ID NO: 11           moltype = DNA  length = 1170
FEATURE                 Location/Qualifiers
misc_feature            1..1170
                        note = Methylococcus capsulatus (Bath)
source                  1..1170
                        mol_type = genomic DNA
                        organism = Methylococcus capsulatus
SEQUENCE: 11
atgagcatgt taggagaaag acgccgcggt ctgaccgatc cggaaatggc ggccgtcatt  60
ttgaaggcgc ttcctgaagc tccgctggac ggcaacaaca agatgggtta tttcgtcacc  120
ccccgctgga aacgcttgac ggaatatgaa gccctgaccg tttatgcgca gcccaacgcc  180
gactggatcg ccggcggcct ggactggggc gactggaccc agaaattcca cggcggccgc  240
ccttcctggg gcaacgagac cacggagctg cgcaccgtcg actggttcaa gcaccgtgac  300
ccgctccgcc gttggcatgc gccgtacgtc aaggacaagg ccgaggaatg gcgctacacc  360
gaccgcttcc tgcagggtta ctccgccgac ggtcagatcc gggcgatgaa cccgacctgg  420
cgggacgagt tcatcaaccg gtattggggc gccttcctgt tcaacgaata cggattgttc  480
aacgctcatt cgcagggcgc ccgggaggcg ctgtcggacg taacccgcgt cagcctggct  540
ttctggggct tcgacaagat cgacatcgcc cagatgatcc aactcgaacg gggtttcctc  600
```

```
gccaagatcg tacccggttt cgacgagtcc acagcggtgc cgaaggccga atggacgaac  660
ggggaggtct acaagagcgc ccgtctggcc gtggaagggc tgtggcagga ggtgttcgac  720
tggaacgaga gcgctttctc ggtgcacgcc gtctatgacg cgctgttcgg tcagttcgtc  780
cgccgcgagt tctttcagcg gctggctccc cgcttcggcg acaatctgac gccattcttc  840
atcaaccagg cccagacata cttccagatc gccaagcagg gcgtacagga tctgtattac  900
aactgtctgg gtgacgatcc ggagttcagc gattacaacc gtaccgtgat gcgcaactgg  960
accggcaagt ggctggagcc cacgatcgcc gctctgcgcg acttcatggg gctgtttgcg  1020
aagctgccgg cgggcaccac tgacaaggaa gaaatcaccg cgtccctgta ccgggtggtc  1080
gacgactgga tcgaggacta cgccagcagg atcgacttca aggcggaccg cgatcagatc  1140
gttaaagcgg ttctggcagg attgaaataa                                  1170

SEQ ID NO: 12          moltype = AA  length = 389
FEATURE                Location/Qualifiers
REGION                 1..389
                       note = misc_feature - Methylococcus capsulatus (Bath)
source                 1..389
                       mol_type = protein
                       organism = Methylococcus capsulatus
SEQUENCE: 12
MSMLGERRRG LTDPEMAAVI LKALPEAPLD GNNKMGYFVT PRWKRLTEYE ALTVYAQPNA  60
DWIAGGLDWG DWTQKFHGGR PSWGNETTEL RTVDWFKHRD PLRRWHAPYV KDKAEEWRYT  120
DRFLQGYSAD GQIRAMNPTW RDEFINRYWG AFLFNEYGLF NAHSQGAREA LSDVTRVSLA  180
FWGFDKIDIA QMIQLERGFL AKIVPGFDES TAVPKAEWTN GEVYKSARLA VEGLWQEVFD  240
WNESAFSVHA VYDALFGQFV RREFFQRLAP RFGDNLTPFF INQAQTYFQI AKQGVQDLYY  300
NCLGDDPEFS DYNRTVMRNW TGKWLEPTIA ALRDFMGLFA KLPAGTTDKE EITASLYRVV  360
DDWIEDYASR IDFKADRDQI VKAVLAGLK                                   389

SEQ ID NO: 13          moltype = DNA  length = 513
FEATURE                Location/Qualifiers
misc_feature           1..513
                       note = Methylococcus capsulatus (Bath)
source                 1..513
                       mol_type = genomic DNA
                       organism = Methylococcus capsulatus
SEQUENCE: 13
atggcgaaac tgggtataca cagcaacgac acccgcgacg cctgggtgaa caagatcgcg  60
cagctcaaca ccctggaaaa agcggccgag atgctgaagc agttccggat ggaccacacc  120
acgccgttcc gcaacagcta cgaactggac aacgactacc tctggatcga ggccaagctc  180
gaagagaagg tcgccgtcct caaggcacgc gccttcaacg aggtggactt ccgtcataag  240
accgctttcg gcgaggatgc caagtccgtt ctggacggca ccgtcgcgaa gatgaacgcg  300
gccaaggaca agtgggaggc ggagaagatc catatcggtt tccgccaggc ctacaagccg  360
ccgatcatgc cggtgaacta tttcctggac ggcgagcgtc agttggggac ccggctgatg  420
gaactgcgca acctcaacta ctacgacacg ccgctggaag aactgcgcaa acagcgcggt  480
gtgcgggtgg tgcatctgca gtcgccgcac tga                               513

SEQ ID NO: 14          moltype = AA  length = 170
FEATURE                Location/Qualifiers
REGION                 1..170
                       note = misc_feature - Methylococcus capsulatus (Bath)
source                 1..170
                       mol_type = protein
                       organism = Methylococcus capsulatus
SEQUENCE: 14
MAKLGIHSND TRDAWVNKIA QLNTLEKAAE MLKQFRMDHT TPFRNSYELD NDYLWIEAKL  60
EEKVAVLKAR AFNEVDFRHK TAFGEDAKSV LDGTVAKMNA AKDKWEAEKI HIGFRQAYKP  120
PIMPVNYFLD GERQLGTRLM ELRNLNYYDT PLEELRKQRG VRVVHLQSPH             170

SEQ ID NO: 15          moltype = DNA  length = 6372
FEATURE                Location/Qualifiers
misc_feature           1..6372
                       note = Synthetic plasmid.
source                 1..6372
                       mol_type = other DNA
                       organism = synthetic construct
SEQUENCE: 15
gctgcttctg aatcacgtgc gcggtgtctt caaggccgtg gccgtaaccg ctccgggttt  60
tggcgacaaa cgcccgaacc gtttacttga cctggccgcg ttaaccggcg gtcgtgccgt  120
gctcgaagct caaggcgacc gtctggaccg tgttaccctc gcggatctgg gccgtgtgcg  180
ccgtgccgtg gtgtcggcag atgataccgc gctgcttggc atcccgggca ccgaagctag  240
ccgtgcacgc ctcgaaggtc tgcgtttaga agcagagcag taccgtgcgc tgaaaccagg  300
gcagggttct gccaccgggc gcctgcacga acttgaagaa attgaagcgc gcattgtggg  360
tctgtccgga aagagcgccg tttatcgcgt cggaggtgtg accgatgtgg aaatgaaaga  420
gcgcatggtt cgcatcgaaa acgcttaccg ttcggtggta agtgcgctgg aggaaggcgt  480
gctccctggc ggtggtgtcg gctttctggg tagtatgccg gtgcttgcgg aattggaggc  540
ccgcgacgca gatgaagctc gcgggattgg gattgtacgc agcgccttaa cggagcctct  600
tcgtattatc ggcgaaaata gtggcttgag cggtgaagcc gttgttgcca aagtcatgga  660
tcatgccaac ccgggatggg gttacgacca ggagtctggc tctttttgcg acctgcatgc  720
gcgtgggatc tgggatgctg ctaaagtgtt acgtctcgcg ttggagaagg cagcctctgt  780
tgctgggacc tttctgacaa ccgaagctgt tgttctcgaa attccggata cagatgcgtt  840
```

-continued

```
cgcagggttc agtgcagaat gggctgccgc cacgcgcgaa gatccgcgcg tatgagttta  900
aacgcggccg caatttgaac gcacccataa cagatacgga ctttctcaaa ggagagttat  960
caatgaatat tcgtccattg catgatcgcg tgatcgtcaa gcgtaaagaa gttgaaacta  1020
aatctgctgg cggcatcgtt ctgaccggct ctgcagcggc taaatccacc cgcggcgaag  1080
tgctggctgt cggcaatggc cgtatccttg aaaatggcga agtgaagccg ctggatgtga  1140
aagttggcga catcgttatt ttcaacgatg gctacggtgt gaaatctgag aagatcgaca  1200
atgaagaagt gttgatcatg tccgaaagcg acattctggc aattgttgaa gcgtaatccg  1260
cgcacgacac tgaacatacg aatttaagga ataaagataa tggcagctaa agacgtaaaa  1320
ttcggtaacg acgctcgtgt gaaaatgctg cgcggcgtaa acgtactggc agatgcagtg  1380
aaagttaccc tcggtccaaa aggccgtaac gtagttctgg ataaatcttt cggtgcaccg  1440
accatcacca aagatggtgt ttccgttgct cgtgaaatcg aactggaaga caagttcgaa  1500
aatatgggtg cgcagatggt gaaagaagtt gcctctaaag caaacgacgc tgcaggcgac  1560
ggtaccacca ctgcaaccgt actggctcag gctatcatca ctgaaggtct gaaagctgtt  1620
gctgcgggca tgaacccgat ggacctgaaa cgtggtatcg acaaagcggt taccgctgca  1680
gttgaagaac tgaaagcgct gtccgtacca tgctctgact ctaaagcgat tgctcaggtt  1740
ggtaccatct ccgctaactc cgacgaaacc gtaggtaaac tgatcgctga agcgatggac  1800
aaagtcggta aagaaggcgt tatcaccgtt gaagacggta ccggtctgca ggacgaactg  1860
gacgtggttg aaggtatgca gttcgaccgt ggctacctgt ctccttactt catcaacaag  1920
ccggaaactg gcgcagtaga actggaaagc ccgttcatcc tgctggctga caagaaaatc  1980
tccaacatcc gcgaaatgct gccggttctg gaagctgttg ccaaagcagg caaaccgctg  2040
ctgatcatcg ctgaagatgt agaaggcgaa gcgctggcaa ctctggttgt taacaccatg  2100
cgtggcatcg tgaaagtcgc tgcggttaaa gcaccgggct tcggcgatcg tcgtaaagct  2160
atgctgcagg atatcgcaac cctgactggc ggtaccgtga tctctgaaga gatcggtatg  2220
gagctggaaa aagcaaccct ggaagacctg ggtcaggcta aacgtgttgt gatcaacaaa  2280
gacaccacca ctatcatcga tggcgtgggt gaagaagctg caatccaggg ccgtgttgct  2340
cagatccgtc agcagattga agaagcaact tctgactacg accgtgaaaa actgcaggaa  2400
cgcgtagcga aactggcagg cggcgttgca gttatcaaag tgggtgctgc taccgaagtt  2460
gaaatgaaag agaaaaaagc acgcgttgaa gatgccctgc acgcgacccg tgctgcggta  2520
gaagaaggcg tggttgctgg tggtggtgtt gcgctgatcc gcgtagcgtc taaactggct  2580
gacctgcgtg gtcagaacga agaccagaac gtgggtatca aagttgcact gcgtgcaatg  2640
gaagctccgc tgcgtcagat cgtattgaac tgcggcgaag aaccgtctgt tgttgctaac  2700
accgttaaag gcggcgacgg caactacggt tacaacgcag caaccgaaga atacggcaac  2760
atgatcgaca tgggtatcct ggatccaacc aaagtaactc gttctgctct gcagtacgca  2820
gcttctgtgg ctggcctgat gatcaccacc gaatgcatgg ttaccgacct gccgaaaaac  2880
gatgcagctg acttaggcgc tgctggcggt atgggcggca tgggtggcat gggcggcatg  2940
atgtaagttt aaacgcggcc gcaatttgaa cgccagcaca tggactccca gcacatggac  3000
tctcgagtct actagcgcag cttaattaac ctaggctgct gccaccgctg agcaataact  3060
agcataaccc cttggggcct ctaaacgggt cttgaggggt tttttgctga aacctcaggc  3120
atttgagaag cacacggtca cactgcttcc ggtagtcaat aaaccggtaa accagcaata  3180
gacataagcg gctatttaac gaccctgccc tgaaccgacg accgggtcat cgtggccgga  3240
tcttgcggcc cctcggcttg aacgaattgt tagacattat ttgccgacta ccttggtgat  3300
ctcgcctttc acgtagtgga caaattcttc caactgatct gcgcgcgagg ccaagcgatc  3360
ttcttcttgt ccaagataag cctgtctagc ttcaagtatg acgggctgat actgggccgg  3420
caggcgctcc attgcccagt cggcagcgac atccttcggc gcgattttgc cggttactgc  3480
gctgtaccaa atgcgggaca acgtaagcac tacatttcgc tcatcgccag cccagtcggg  3540
cggcgagttc catagcgtta aggtttcatt tagcgcctca aatagatcct gttcaggaac  3600
cggatcaaag agttcctccg ccgctggacc taccaaggca acgctatgtt ctcttgcttt  3660
tgtcagcaag atagccagat caatgtcgat cgtggctggc tcgaagatac ctgcaagaat  3720
gtcattgcgc tgccattctc caaattgcag ttcgcgctta gctggataac gccacggaat  3780
gatgtcgtcg tgcacaacaa tggtgacttc tacagcgcgg agaatctcgc tctctccagg  3840
ggaagccgaa gtttccaaaa ggtcgttgat caaagctcgc cgcgttgttt catcaagcct  3900
tacggtcacc gtaaccagca aatcaatatc actgtgtggc ttcaggccgc catccactgc  3960
ggagccgtac aaatgtacgg ccagcaacgt cggttcgaga tggcgctcga tgacgccaac  4020
tacctctgat agttgagtcg atacttcggc gatcaccgct tccctcatac tcttcctttt  4080
tcaatattat tgaagcattt atcagggtta ttgtctcatg agcggataca tatttgaatg  4140
tatttagaaa aataaacaaa tagctagctc actcggtcgc tacgctccgg gcgtgagact  4200
gcggcgggcg ctgcggacac atacaaagtt acccacagat tccgtggata agcaggggac  4260
taacatgtga ggcaaaacag cagggccgcg ccggtggcgt ttttccatag gctccgccct  4320
cctgccagag ttcacataaa cagacgcttt tccggtgcat ctgtgggagc cgtgaggctc  4380
aaccatgaat ctgacagtac gggcgaaacc cgacaggact taaagatccc caccgtttcc  4440
ggcgggtcgc tccctcttgc gctctcctgt tccgaccctg ccgtttaccg gatacctgtt  4500
ccgcctttct cccttacggg aagtgtggcg ctttctcata gctcacacac tggtatctcg  4560
gctcggtgta ggtcgttcgc tccaagctgg gctgtaagca agaactcccc gttcagcccg  4620
actgctgcgc cttatccggt aactgttcac ttgagtccaa cccggaaaag cacggtaaaa  4680
cgccactggc agcagccatt ggtaactggg agttcgcaga ggatttgttt agctaaacac  4740
gcggttgctc ttgaagtgtg cgccaaagtc cggctacact ggaaggacag atttggttgc  4800
tgtgctctgc gaaagccagt taccacggtt aagcagttcc ccaactgact taaccttcga  4860
tcaaaccacc tccccaggtg gtttttttcgt ttacagggca aaagattacg cgcagaaaaa  4920
aaggatctca agaagatcct ttgatctttt ctactgaacc gctctagatt tcagtgcaat  4980
ttatctcttc aaatgtagca cctgaagtca gccccatacg atataagttg taattctcat  5040
gttagtcatg ccccgcgccc accggaagga gctgactggg ttgaaggctc tcaagggcat  5100
cggtcgagat cccggtgcct aatgagtgag ctaacttttg acggctagct cagtcctagg  5160
gataatgcta gcaccagcct cgagggaaac cacgtaagct ccggcgttta aacacccata  5220
acagatacgg actttctcaa aggagagtta tcagtgaaaa tccgcccgtt acatgaccgt  5280
gtcatcatca aacgcttgga agaagagcgt acctcggcgg gcgggattgt cattccagat  5340
agcgcagctg aaaaaccgat gcgtggtgaa atcctggcag tgggcaatgg aaaagtgctt  5400
gataatggag aggtacgtgc tttacaggtg aaagtgggtg ataaagtgct ctttgggaaa  5460
tacgcgggta cggaggttaa agtagatggg gaagatgttg ttgtcatgcg tgaagatgac  5520
attctggctg tgttagaatc ttaatccgcg cacgacactg aacatacgaa tttaaggaat  5580
```

```
aaagataatg gcgaaagaag ttgtgtatcg tggtagtgcg cgccagcgta tgatgcaggg  5640
tattgaaatt ctcgctcgcg ccgctattcc aacgctgggg gcaaccggcc cgagcgtcat  5700
gattcaacat cgcgccgatg gtctgccacc catttctaca cgcgatggcg ttaccgtagc  5760
gaattctatt gttttaaaag accgtgtcgc gaacctgggt gcccgcctgc tgcgcgacgt  5820
agccggtaca atgagccgtg aagccggcga cggcacgacg actgcgatcg tattggcccg  5880
ccacatcgcc cgtgagatgt ttaaatcgct ggccgtgggt gcagatccga tcgcgctgaa  5940
acgtggtatc gatcgcgccg ttgctcgtgt gtccgaagat attggggcgc gtgcgtggcg  6000
tggcgataaa gaaagcgtga tcctgggtgt cgctgctgtg gcgacgaaag gcgaaccggg  6060
cgttggccgt ctgctgctgg aggctctcga tgcagtgggt gttcacggtg ccgtttctat  6120
cgaactgggc caacgtcgtg aagatctgct ggacgtcgtc gatggctatc gctgggaaaa  6180
aggttattta tctccctact ttgtcacgga ccgtgcccgc gaactcgcgg aactggagga  6240
tgtctacctg ctcatgaccg accgcgaagt ggttgacttc atcgaccttg tacctctgct  6300
ggaggccgtg acggaagcag gaggctccct gctgattgcc gcggatcgtg tgcacgaaaa  6360
ggccttagcg gg                                                      6372
```

```
SEQ ID NO: 16          moltype = DNA  length = 11223
FEATURE                Location/Qualifiers
misc_feature           1..11223
                       note = Synthetic plasmid.
source                 1..11223
                       mol_type = other DNA
                       organism = synthetic construct
SEQUENCE: 16
cgaggacgtc atcaccgccg ccctgcgcca gaacatcttt ctgatgtcgt cctgccggga  60
gggcggctgt gcgacctgca aggccttgtg cagcgaaggg gactacgacc tcaagggctg  120
cagcgttcag gcgctgccgc cggaagagga ggaggaaggg ttggtgttgt tgtgccggac  180
ctacccgaag accgacctgg aaatcgaact gccctatacc cattgccgca tcagttttgg  240
tgaggtcggc agtttcgagg cggaggtcgt cggcctcaac tgggtttcga gcaacaccgt  300
ccagtttctt ttgcagaagc ggcccgacga gtgcggcaac cgtggcgtga aattcgaacc  360
cggtcagttc atggacctga ccatccccgg caccgatgtc tcccgctcct actcgccggc  420
gaaccttcct aatcccgaag gccgcctgga gttcctgatc cgcgtgttac cggagggacg  480
gttttcggac tacctgcgca atgacgcgcg tgtcggacag gtcctctcgg tcaaagggcc  540
actgggcgtg ttcggtctca aggagcgggg catggcgccg cgctatttcg tggccggcgg  600
caccgggttg gcgccggtgg tctcgatggt gcggcagatg caggagtgga ccgcgccgaa  660
cgagacccgc atctatttcg gtgtgaacac cgagccggaa ttgttctaca tcgacgagct  720
caaatccctg gaacgatcga tgcgcaatct caccgtgaag gcctgtgtct ggcacccgag  780
cggggactgg gaaggcgagc agggctcgcc catcgatgcg ttgcgggaag acctggagtc  840
ctccgacgcc aacccggaca tttatttgtg cggtccgccg ggcatgatcg atgccgcctg  900
cgagctggta cgcagccgcg gtatccccgg cgaacaggtc ttcttcgaaa aattcctgcc  960
gtccggggcg gcctgaaccg gggaagtacc gtgaccaccg agcagttccc gccccaattc  1020
ctgcgtgaaa tgatcgagca gctggacgcc agcatccagg agctcgcacg caaggaaaag  1080
ggacttgcgg catccctggg cacgggccgg gtcgccgagc tcaaggaata ctgggaccac  1140
gttgttacaa ccaattaacc aattctgatt agaaaaactc atcgagcatc aaatgaaact  1200
gcaatttatt catatcagga ttatcaatac catatttttg aaaaagccgt ttctgtaatg  1260
aaggagaaaa ctcaccgagg cagttccata ggatggcaag atcctggtat cggtctgcga  1320
ttccgactcg tccaacatca atacaaccta ttaatttccc ctcgtcaaaa ataaggttat  1380
caagtgagaa atcaccatga gtgacgactg aatccggtga gaatggcaaa agcttatgca  1440
tttctttcca gacttgttca acaggccagc cattacgctc gtcatcaaaa tcactcgcat  1500
caaccaaacc gttattcatt cgtgattgcg cctgagcgag acgaaatacg cgatcgctgt  1560
taaaaggaca attacaaaca ggaatcgaat gcaaccggcg caggaacact gccagcgcat  1620
caacaatatt ttcacctgaa tcaggatatt cttctaatac ctggaatgct gttttcccgg  1680
ggatcgcagt ggtgagtaac catgcatcat caggagtacg gataaaatgc ttgatggtcg  1740
gaagaggcat aaattccgtc agccagttta gtctgaccat ctcatctgta acatcattgg  1800
caacgctacc tttgccatgt ttcagaaaca actctggcgc atcgggcttc ccatacaatc  1860
gatagattgt cgcacctgat tgcccgacat tatcgcgagc ccatttatac ccatataaat  1920
cagcatccat gttggaattt aatcgcggcc tcgagcaaga cgtttcccgt tgaatatggc  1980
tcataacacc ccttgtatta ctgtttatgt aagcagacag ttttattgtt catgatgata  2040
tatttttatc ttgtgcaatg taacatcaga gattttgaga cacaacgtgg ctttgttgaa  2100
taaatcgaac ttttgctgag ttgaaggatc agatcacgca tcttcccgac aacgcagacc  2160
gttccgtggc aaagcaaaag ttcaaaatca ccaactggtc cacctacaac aaagctctca  2220
tcaaccgtgg ctccctcact ttctggctgg atgatggggc gattcaggcc tggtatgagt  2280
cagcaacacc ttcttcacga ggcagacctc agcgctagcg gagtgtatac tggcttacta  2340
tgttggcact gatgagggtg tcagtgaagt gcttcatgtg gcaggagaaa aaaggctgca  2400
ccggtgcgtc agcagaatat gtgatacagg atatattccg cttcctcgct cactgactcg  2460
ctacgctcgg tcgttcgact gcggcgagcg gaaatggctt acgaacgggg cggagatttc  2520
ctggaagatg ccaggaagat acttaacagg gaagtgagag ggccgcggca aagccgtttt  2580
tccataggct ccgcccccct gacaagcatc acgaaatctg acgctcaaat cagtggtggc  2640
gaaacccgac aggactataa agataccagg cgtttccccc tggcggctcc ctcgtgcgct  2700
ctcctgttcc tgcctttcgg tttaccggtg tcattccgct gttatggccg cgtttgtctc  2760
attccacgcc tgacactcag ttccgggtag gcagttcgct ccaagctgga ctgtatgcac  2820
gaaccccccg ttcagtccga ccgctgcgcc ttatccggta actatcgtct tgagtccaac  2880
ccggaaagac atgcaaaagc accactggca gcagccactg gtaattgatt tagaggagtt  2940
agtcttgaag tcatgcgccg gttaaggcta aactgaaagg acaagttttg gtgactgcgc  3000
tcctccaagc cagttacctc ggttcaaaga gttggtagct cagagaacct tcgaaaaacc  3060
gccctgcaag gcggtttttt cgttttcaga gcaagagatt acgcgcagac caaaacgatc  3120
tcaagaagat catcttatta aggggtctga cgctcagtgg aacgaaaact cacgttaagg  3180
gattttggtc atgagattat caaaaaggat cttcacctag atccttttaa attaaaaatg  3240
aagttttaaa tcaatctaaa gtatatatga gtaaacttgg tctgacaggt gagctgatac  3300
cgctcgccgc atgcacatgc agtcatgtcg tgctaatgtg taaaacatgt acatgcagat  3360
```

```
tgctgggggt gcagggggcg gagccaccct gtccatgcgg ggtgtggggc ttgccccgcc  3420
ggtacagaca gtgagcaccg gggcacctag tcgcggatac ccccccctagg tatcggacac  3480
gtaaccctcc catgtcgatg caaatcttta acattgagta cgggtaagct ggcacgcata  3540
gccaagctag gcggccacca aacaccacta aaaattaata gtccctagac aagacaaacc  3600
cccgtgcgag ctaccaactc atatgcacgg gggccacata acccgaaggg gtttcaattg  3660
acaaccatag cactagctaa gacaacgggc acaacacccg cacaaactcg cactgcgcaa  3720
ccccgcacaa catcgggtct aggtaacact gaaatagaag tgaacacctc taaggaaccg  3780
caggtcaatg agggttctaa ggtcactcgc gctagggcgt ggcgtaggca aaacgtcatg  3840
tacaagatca ccaatagtaa ggctctggcg gggtgccata ggtggcgcag ggacgaagct  3900
gttgcggtgt cctggtcgtc taacggtgct tcgcagtttg agggtctgca aaactctcac  3960
tctcgctggg ggtcacctct ggctgaattg gaagtcatgg gcgaacgccg cattgagctg  4020
gctattgcta ctaagaatca cttggcggcg ggtggcgcgc tcatgatgtt tgtgggcact  4080
gttcgacaca accgctcaca gtcatttgcg caggttgaag cgggtattaa gactgcgtac  4140
tcttcgatgg tgaaaacatc tcagtggaag aaagaacgtg cacggtacgg ggtggagcac  4200
acctatagtg actatgaggt cacagactct tgggcgaacg gttggcactt gcaccgcaac  4260
atgctgttgt tcttggatcg tccactgtct gacgatgaac tcaaggcgtt tgaggattcc  4320
atgttttccc gctggtctgc tggtgtggtt aaggccggta tggacgcgcc actgcgtgag  4380
cacggggtca aacttgatca ggtgtctacc tggggtggag acgctgcgaa aatggcaacc  4440
tacctcgcta agggcatgtc tcaggaactg actggctccg ctactaaaac cgcgtctaag  4500
gggtcgtaca cgccgtttca gatgttggat atgttggccg atcaaagcga cgcccggcgag  4560
gatatggacg ctgttttggt ggctcggtgg cgtgagtatg aggttggttc taaaaacctg  4620
cgttcgtcct ggtcacgtgg ggctaagcgt gctttgggca ttgattacat agacgctgat  4680
gtacgtcgtg aaatggaaga agaactgtac aagctcgccg gtctggaagc accggaacgg  4740
gtcgaatcaa cccgcgttgc tgttgctttg gtgaagcccg atgattggaa actgattcag  4800
tctgatttcg cggttaggca gtacgttcta gattgcgtgg ataaggctaa ggacgtggcc  4860
gctgcgcaac gtgtcgctaa tgaggtgctg gcaagtctgg gtgtggattc caccccgtgc  4920
atgatcgtta tggatgatgt ggacttggac gcggttctgc ctactcatgg ggacgctact  4980
aagcgtgatc tgaatgcggc ggtgttcgcg ggtaatgagc agactattct tcgcacccac  5040
taaaagcggc ataaaccccg ttcgatattt tgtgcgatga atttatggtc aatgtcgcgg  5100
gggcaaacta tgatgggtct tgttgttgca gccgaacgac ctagcgcagc gagtcagtga  5160
gcgaggaagc ggaagagcgc ctgatgcggt attttctcct tacgcatctg tgcggtattt  5220
cacaccgcat atggtgcact ctcagtacaa tctgctctga tgccgcatag ttaagccagt  5280
atacactccg ctatcgctac gtgactgggt catggctgcg ccccgacacc cgccaacacc  5340
cgctgacgcg ccctgacggg cttgtctgct cccggcatcc gcttacagac aagctgtgac  5400
cgtctccggg agctgcatgt gtcagaggtt ttcaccgtca tcaccgaaac gcgcgaggca  5460
gcagatcaat tcgcgcgcga aggcgaagcg gcatgcataa tgtgcctgtc aaatggacga  5520
agcagggatt ctgcaaaccc tatgctactc cgtcaagccg tcaattgtct gattcgttac  5580
caattatgac aacttgacgg ctacatcatt cactttttct tcacaaccgg cacggaactc  5640
gctcgggctg gccccggtgc atttttttaaa tacccgcgag aaatagagtt gatcgtcaaa  5700
accaacattg cgaccgacgg tggcgatagg catccgggtg gtgctcaaaa gcagcttcgc  5760
ctggctgata cgttggtcct cgcgccagct taagacgcta atccctaact gctggcggaa  5820
aagatgtgac agacgcgacg gcgacaagca aacatgctgt gcgacgctgg cgatatcaaa  5880
attgctgtct gccaggtgat cgctgatgta ctgacaagcc tcgcgtaccc gattatccat  5940
cggtggatgg agcgactcgt taatcgcttc catgcgccgc agtaacaatt gctcaagcag  6000
atttatcgcc agcagctccg aatagcgccc ttccccttgc ccggcgttaa tgatttgccc  6060
aaacaggtcg ctgaaatgcg gctggtgcgc ttcatccggg cgaaagaacc ccgtattggc  6120
aaatattgac ggccagttaa gccattcatg ccagtaggcg cgcggacgaa agtaaaccca  6180
ctggtgatac cattcgcgag cctccggatg acgaccgtag tgatgaatct ctcctggcgg  6240
gaacagcaaa atatcacccg gtcggcaaac aaattctcgt ccctgatttt tcaccacccc  6300
ctgaccgcga atggtgagat tgagaatata acctttcatt cccagcggtc ggtcgataaa  6360
aaaatcgaga taaccgttgg cctcaatcgg cgttaaaccc gccaccagat gggcattaaa  6420
cgagtatccc ggcagcaggg gatcattttg cgcttcagcc atacttttca tactcccgcc  6480
attcagagaa gaaaccaatt gtccatattg catcagacat tgccgtcact gcgtctttta  6540
ctggctcttc tcgctaacca aaccggtaac cccgcttatt aaaagcattc tgtaacaaag  6600
cgggaccaaa gccatgacaa aaacgcgtaa caaaagtgtc tataatcacg gcagaaaagt  6660
ccacattgat tatttgcacg gcgtcacact ttgctatgcc atagcatttt tatccataag  6720
attagcggat cctacctgac gctttttatc gcaactctct actgtttctc catacccgtt  6780
tttttgggcg acctcgtcgg aggttgtatg tccggtgttc cgtgacgtca tcgggcattc  6840
atcattcata gaatgtgtta cggaggaaac aagtaatggc acttagcacc gcaaccaagg  6900
ccgcgacgga cgcgctggct gccaatcggg cacccaccag cgtgaatgca caggaagtgc  6960
accgttggct ccagagcttc aactgggatt tcaagaacaa ccggaccaag tacgccacca  7020
agtacaagat ggcgaacgag accaaggaac agttcaagct gatcgccaag gaatatgcgc  7080
gcatggaggc agtcaaggac gaaaggcagt tcggtagcct gcaggatgcg ctgacccgcc  7140
tcaacgccgg tgttcgcgtt catccgaagt ggaacgagac catgaaagtg gtttcgaact  7200
tcctggaagt gggcgaatac aacgccatcg ccgctaccgg gatgctgtgg gattccgccc  7260
aggcggcgga acagaagaac ggctatctgg cccaggtgtt ggatgaaatc cgccacaccc  7320
accagtgtgc ctacgtcaac tactacttcg cgaagaacgg ccaggacccg gccggtcaca  7380
acgatgctcg ccgcacccgt accatcggtc cgctgtggaa gggcatgaag cgcgtgtttt  7440
ccgacggctt catttccggc gacgccgtgg aatgctccct caacctgcag ctggtgggtg  7500
aggcctgctt caccaatccg ctgatcgtcg cagtgaccga atgggctgcc gccaacggcg  7560
atgaaatcac cccgacggtg ttcctgtcga tcaacaccga cgaactgcgc cacatggcca  7620
acggttacca gaccgtcgtt tccatcgcca acgatccggc ttccgccaag tatctcaaca  7680
cggacctgaa caacgccttc tggacccagc agaagtactt cacgccggtg ttgggcatgc  7740
tgttcgagta tggctccaag ttcaaggtcg agccgtgggt caagacgtgg aaccgctggg  7800
tgtacgagga ctggggcggc atctggatcg gccgtctggg caagtacggg gtggagtcgc  7860
cgcgcagcct caaggacgcc aagcaggacg cttactgggc tcaccacgac ctgtatctgc  7920
tggcttatgc gctgtggccg accggcttct tccgtctggc gctgccggat caggaagaaa  7980
tggagtggtt cgaggccaac taccccggct ggtacgacca ctacggcaag atctacgagg  8040
aatggcgcgc ccgcggttgc gaggatccgt cctcgggctt catcccgctg atgtggttca  8100
```

```
tcgaaaacaa ccatcccatc tacatcgatc gcgtgtcgca agtgccgttc tgcccgagct  8160
tggccaaggg cgccagcacc ctgcgcgtgc acgagtacaa cggccagatg cacaccttca  8220
gcgaccagtg gggcgagcgc atgtggctgg ccgagccgga gcgctacgag tgccagaaca  8280
tcttcgaaca gtacgaagga cgcgaactgt cggaagtgat cgccgaactg cacgggctgc  8340
gcagtgatgg caagaccctg atcgcccagc cgcatgtccg tggcgacaag ctgtggacgt  8400
tggacgatat caaacgcctg aactgcgtct tcaagaaccc ggtgaaggca ttcaattgaa  8460
acgggtgtcg ggctccgtca cagggcgggg cccgacgcac gatcgttcga tcaacctcaa  8520
accaaaaagg aacatcgata tgagcatgtt aggagaaaga cgccgcggtc tgaccgatcc  8580
ggaaatggcg gccgtcattt tgaaggcgct tcctgaagct ccgctggacg gcaacaacaa  8640
gatgggttat ttcgtcaccc cccgctggaa acgcttgacg gaatatgaag ccctgaccgt  8700
ttatgcgcag cccaacgccg actggatcgc cggcggcctg gactggggcg actggaccca  8760
gaaattccac ggcggccgcc cttcctgggg caacgagacc acggagctgc gcaccgtcga  8820
ctggttcaag caccgtgacc cgctccgccg ttggcatgcg ccgtacgtca aggacaaggc  8880
cgaggaatgg cgctacaccg accgcttcct gcagggttac tccgccgacg gtcagatccg  8940
ggcgatgaac ccgacctggc gggacgagtt catcaaccgg tattggggcg ccttcctgtt  9000
caacgaatac ggattgttca acgctcattc gcagggcgcc cgggaggcgc tgtcggacgt  9060
aacccgcgtc agcctggctt tctggggctt cgacaagatc gacatcgccc agatgatcca  9120
actcgaacgg ggtttcctcg ccaagatcgt acccggtttc gacgagtcca cagcggtgcc  9180
gaaggccgaa tggacgaacg gggaggtcta caagagcgcc cgtctggccg tggaagggct  9240
gtggcaggag gtgttcgact ggaacgagag cgctttctcg gtgcacgccg tctatgacgc  9300
gctgttcggt cagttcgtcc gccgcgagtt ctttcagcgg ctggctcccc gcttcggcga  9360
caatctgacg ccattcttca tcaaccaggc ccagacatac ttccagatcg ccaagcaggg  9420
cgtacaggat ctgtattaca actgtctggg tgacgatccg gagttcagcg attacaaccg  9480
taccgtgatg cgcaactgga ccggcaagtg gctggagccc acgatcgccg ctctgcgcga  9540
cttcatgggg ctgtttgcga agctgccggc gggcaccact gacaaggaag aaatcaccgc  9600
gtccctgtac cgggtggtcg acgactggat cgaggactac gccagcagga tcgacttcaa  9660
ggcggaccgc gatcagatcg ttaaagcggt tctggcagga ttgaaataat agaggaacta  9720
ttacgatgag cgtaaacagc aacgcatacg acgccggcat catgggcctg aaaggcaagg  9780
acttcgccga tcagttcttt gccgacgaaa accaagtggt ccatgaaagc gacacggtcg  9840
ttctggtcct caagaagtcg gacgagatca ataccttat cgaggagatc cttctgacgg  9900
actacaagaa gaacgtcaat ccgacggtaa acgtggaaga ccgcgcgggt tactggtgga  9960
tcaaggccaa cggcaagatc gaggtcgatt gcgacgagat ttccgagctg ttggggcggc  10020
agttcaacgt ctacgacttc ctcgtcgacg tttcctccac catcggccgg gcctataccc  10080
tgggcaacaa gttcaccatt accagtgagc tgatgggcct ggaccgcaag ctcgaagact  10140
atcacgctta aggagaatga catggcgaaa ctgggtatac acagcaacga cacccgcgac  10200
gcctgggtga acaagatcgc gcagctcaac accctggaaa aagcggccga gatgctgaag  10260
cagttccgga tggaccacac cacgccgttc cgcaacagct acgaactgga caacgactac  10320
ctctggatcg aggccaagct cgaagagaag gtcgccgtcc tcaaggcacg cgccttcaac  10380
gaggtggact tccgtcataa gaccgctttc ggcgaggatg ccaagtccgt tctggacggc  10440
accgtcgcga agatgaacgc ggccaaggac aagtgggagg cggagaagat ccatatcggt  10500
ttccgccagg cctacaagcc gccgatcatg ccggtgaact atttcctgga cggcgagcgt  10560
cagttgggga cccggctgat ggaactgcgc aacctcaact actacgacac gccgctggaa  10620
gaactgcgca aacagcgcgg tgtgcgggtg gtgcatctgc agtcgccgca ctgaagggag  10680
gaagtctcgc cctggacgcg acggcatcgc cgtgaagtcc agggggcagg gatgccgttc  10740
cgggccggca ggctggcccg gaatctctgg ttttcagggg gcgtgccggt ccacggctcc  10800
cccctccatc tttcgtaagg aaatcaccat ggtcgaatcg gcatttcagc cattttcggg  10860
cgacgcagac gaatggttcg aggaaccacg gccccaggcc ggtttcttcc cttccgcgga  10920
ctggcatctg ctcaaacggg acgagaccta cgcagcctat gccaaggatc tcgatttcat  10980
gtggcggtgg gtcatcgtcc gggaagaaag gatcgtccag gagggttgct cgatcagcct  11040
ggagtcgtcg atccgcgccg tgacgcacgt actgaattat tttggtatga ccgaacaacg  11100
cgccccggca gaggaccgga ccggcggagt tcaacattga acaggtaagt ttatgcagcg  11160
agttcacact atcacggcgg tgacggagga tggcgaatcg ctccgcttcg aatgccgttc  11220
gga                                                                11223
```

```
SEQ ID NO: 17          moltype = DNA  length = 13270
FEATURE                Location/Qualifiers
misc_feature           1..13270
                       note = Synthetic plasmid.
source                 1..13270
                       mol_type = other DNA
                       organism = synthetic construct
SEQUENCE: 17
atatcactgt gtggcttcag gccgccatcc actgcggagc cgtacaaatg tacggccagc  60
aacgtcggtt cgagatggcg ctcgatgacg ccaactacct ctgatagttg agtcgatact  120
tcggcgatca ccgcttccct catactcttc ctttttcaat attattgaag catttatcag  180
ggttattgtc tcatgagcgg atacatattt gaatgtattt agaaaaataa acaaatagct  240
agctcactcg gtcgctacgc tccgggcgtg agactgcggc gggcgctgcg gacacataca  300
aagttaccca cagattccgt ggataagcag gggactaaca tgtgaggcaa aacagcaggg  360
ccgcgccggt ggcgtttttc cataggctcc gccctcctgc cagagttcac ataaacagac  420
gcttttccgg tgcatctgtg ggagccgtga ggctcaacca tgaatctgac agtacgggcg  480
aaacccgaca ggacttaaag atccccaccg tttccggcgg gtcgctccct cttgcgctct  540
cctgttccga ccctgccgtt taccggatac ctgttccgcc tttctccctt acgggaagtg  600
tggcgctttc tcatagctca cacactggta tctcggctcg gtgtaggtcg ttcgctccaa  660
gctgggctgt aagcaagaac tccccgttca gcccgactgc tgcgccttat ccggtaactg  720
ttcacttgag tccaacccgg aaaagcacgg taaaacgcca ctggcagcag ccattggtaa  780
ctgggagttc gcagaggatt tgtttagcta aacacgcggt tgctcttgaa gtgtgcgcca  840
aagtccggct acactggaag gacagatttg gttgctgtgc tctgcgaaag ccagttacca  900
cggttaagca gttccccaac tgacttaacc ttcgatcaaa ccacctcccc aggtggtttt  960
ttcgtttaca gggcaaaaga ttacgcgcag aaaaaaagga tctcaagaag atcctttgat  1020
```

```
cttttctact gaaccgctct agatttcagt gcaatttatc tcttcaaatg tagcacctga  1080
agtcagcccc atacgatata agttgtaatt ctcatgttag tcatgccccg cgcccaccgg  1140
aaggagctga ctgggttgaa ggctctcaag ggcatcggtc gagatcccgg tgcctaatga  1200
gtgagctaac ttttgacggc tagctcagtc ctagggataa tgctagcacc agcctcgagg  1260
gaaaccacgt aagctccggc gtttaaacac ccataacaga tacggacttt ctcaaaggag  1320
agttatcagt gaaaatccgc ccgttacatg accgtgtcat catcaaacgc ttggaagaag  1380
agcgtacctc ggcgggcggg attgtcattc cagatagcgc agctgaaaaa ccgatgcgtg  1440
gtgaaatcct ggcagtgggc aatggaaaag tgcttgataa tggagaggta cgtgctttac  1500
aggtgaaagt gggtgataaa gtgctctttg ggaaatacgc gggtacggag gttaaagtag  1560
atggggaaga tgttgttgtc atgcgtgaag atgacattct ggctgtgtta gaatcttaat  1620
ccgcgcacga cactgaacat acgaatttaa ggaataaaga taatggcgaa agaagttgtg  1680
tatcgtggta gtgcgcgcca gcgtatgatg cagggtattg aaattctcgc tcgcgccgct  1740
attccaacgc tgggggcaac cggcccgagc gtcatgattc aacatcgcgc cgatggtctg  1800
ccacccattt ctacacgcga tggcgttacc gtagcgaatt ctattgtttt aaaagaccgt  1860
gtcgcgaacc tgggtgcccg cctgctgcgc gacgtagccg gtacaatgag ccgtgaagcc  1920
ggcgacggca cgacgactgc gatcgtattg gcccgccaca tcgcccgtga gatgtttaaa  1980
tcgctggccg tgggtgcaga tccgatcgcg ctgaaacgtg gtatcgatcg cgccgttgct  2040
cgtgtgtccg aagatattgg ggcgcgtgcg tggcgtggcg ataaagaaag cgtgatcctg  2100
ggtgtcgctg ctgtggcgac gaaaggcgaa ccgggcgttg gccgtctgct gctggaggct  2160
ctcgatgcag tgggtgttca cggtgccgtt tctatcgaac tgggccaacg tcgtgaagat  2220
ctgctggacg tcgtcgatgg ctatcgctgg gaaaaaggtt atttatctcc ctactttgtc  2280
acggaccgtg cccgcgaact cgcggaactg gaggatgtct acctgctcat gaccgaccgc  2340
gaagtggttg acttcatcga ccttgtacct ctgctggagg ccgtgacgga agcaggaggc  2400
tccctgctga ttgccgcgga tcgtgtgcac gaaaaggcct tagcggggct gcttctgaat  2460
cacgtgcgcg gtgtcttcaa ggccgtggcc gtaaccgctc cgggttttgg cgacaaacgc  2520
ccgaaccgtt tacttgacct ggccgcgtta accggcggtc gtgccgtgct cgaagctcaa  2580
ggcgaccgtc tggaccgtgt taccctcgcg gatctgggcc gtgtgcgccg tgccgtggtg  2640
tcggcagatg ataccgcgct gcttggcatc ccgggcaccg aagctagccg tgcacgcctc  2700
gaaggtctgc gtttagaagc agagcagtac cgtgcgctga aaccagggca gggttctgcc  2760
accgggcgcc tgcacgaact tgaagaaatt gaagcgcgca ttgtgggtct gtccggaaag  2820
agcgccgttt atcgcgtcgg aggtgtgacc gatgtggaaa tgaaagagcg catggttcgc  2880
atcgaaaacg cttaccgttc ggtggtaagt gcgctggagg aaggcgtgct ccctggcggt  2940
ggtgtcggct ttctgggtag tatgccggtg cttgcggaat tggaggcccg cgacgcagat  3000
gaagctcgcg ggattgggat tgtacgcagc gccttaacgg agcctcttcg tattatcggc  3060
gaaaatagtg gcttgagcgg tgaagccgtt gttgccaaag tcatggatca tgccaacccg  3120
ggatggggtt acgaccagga gtctggctct ttttgcgacc tgcatgcgcg tgggatctgg  3180
gatgctgcta aagtgttacg tctcgcgttg gagaaggcag cctctgttgc tgggaccttt  3240
ctgacaaccg aagctgttgt tctcgaaatt ccggatacag atgcgttcgc agggttcagt  3300
gcagaatggg ctgccgccac gcgcgaagat ccgcgcgtat gagtttaaac gcggccgcaa  3360
tttgaacgca cccataacag atacggactt tctcaaagga gagttatcaa tgaatattcg  3420
tccattgcat gatcgcgtga tcgtcaagcg taaagaagtt gaaactaaat ctgctggcgg  3480
catcgttctg accggctctg cagcggctaa atccacccgc ggcgaagtgc tggctgtcgg  3540
caatggccgt atccttgaaa atggcgaagt gaagccgctg gatgtgaaag ttggcgacat  3600
cgttattttc aacgatggct acggtgtgaa atctgagaag atcgacaatg aagaagtgtt  3660
gatcatgtcc gaaagcgaca ttctggcaat tgttgaagcg taatccgcgc acgacactga  3720
acatacgaat ttaaggaata aagataatgg cagctaaaga cgtaaaattc ggtaacgacg  3780
ctcgtgtgaa aatgctgcgc ggcgtaaacg tactggcaga tgcagtgaaa gttaccctcg  3840
gtccaaaagg ccgtaacgta gttctggata aatctttcgg tgcaccgacc atcaccaaag  3900
atggtgtttc cgttgctcgt gaaatcgaac tggaagacaa gttcgaaaat atgggtgcgc  3960
agatggtgaa agaagttgcc tctaaagcaa acgacgctgc aggcgacggt accaccactg  4020
caaccgtact ggctcaggct atcatcactg aaggtctgaa agctgttgct gcgggcatga  4080
acccgatgga cctgaaacgt ggtatcgaca aagcggttac cgctgcagtt gaagaactga  4140
aagcgctgtc cgtaccatgc tctgactcta aagcgattgc tcaggttggt accatctccg  4200
ctaactccga cgaaaccgta ggtaaactga tcgctgaagc gatggacaaa gtcggtaaag  4260
aaggcgttat caccgttgaa gacggtaccg gtctgcagga cgaactggac gtggttgaag  4320
gtatgcagtt cgaccgtggc tacctgtctc cttacttcat caacaagccg gaaactggcg  4380
cagtagaact ggaaagcccg ttcatcctgc tggctgacaa gaaaatctcc aacatccgcg  4440
aaatgctgcc ggttctggaa gctgttgcca aagcaggcaa accgctgctg atcatcgctg  4500
aagatgtaga aggcgaagcg ctggcaactc tggttgttaa caccatgcgt ggcatcgtga  4560
aagtcgctgc ggttaaagca ccgggcttcg gcgatcgtcg taaagctatg ctgcaggata  4620
tcgcaaccct gactggcggt accgtgatct ctgaagagat cggtatggag ctggaaaaag  4680
caaccctgga agacctgggt caggctaaac gtgttgtgat caacaaagac accaccacta  4740
tcatcgatgg cgtgggtgaa gaagctgcaa tccagggccg tgttgctcag atccgtcagc  4800
agattgaaga agcaacttct gactacgacc gtgaaaaact gcaggaacgc gtagcgaaac  4860
tggcaggcgg cgttgcagtt atcaaagtgg gtgctgctac cgaagttgaa atgaaagaga  4920
aaaaagcacg cgttgaagat gccctgcacg cgacccgtgc tgcggtagaa gaaggcgtgg  4980
ttgctggtgg tggtgttgcg ctgatccgcg tagcgtctaa actggctgac ctgcgtggtc  5040
agaacgaaga ccagaacgtg ggtatcaaag ttgcactgcg tgcaatggaa gctccgctgc  5100
gtcagatcgt attgaactgc ggcgaagaac cgtctgttgt tgctaacacc gttaaaggcg  5160
gcgacggcaa ctacggttac aacgcagcaa ccgaagaata cggcaacatg atcgacatgg  5220
gtatcctgga tccaaccaaa gtaactcgtt ctgctctgca gtacgcagct tctgtggctg  5280
gcctgatgat caccaccgaa tgcatggtta ccgacctgcc gaaaaacgat gcagctgact  5340
taggcgctgc tggcggtatg ggcggcatgg gtggcatggg cggcatgatg taagtttaaa  5400
cgcggccgca atttgaacgc cagcacatgg actcccagca catggactct cgagtctact  5460
agcgcagctt aattaaccta ggctgctgcc accgctgagc aataactagc ataacccctt  5520
ggggcctcta aacgggtctt gaggggtttt ttgctgaaac ctcaggcatt tgagaagcac  5580
acggtcacac tgcttccggt agtcaataaa ccggtaaacc agcaatagac ataagcggtg  5640
cataatgtgc ctgtcaaatg gacgaagcag ggattctgca aaccctatgc tactccgtca  5700
agccgtcaat tgtctgattc gttaccaatt atgacaactt gacggctaca tcattcactt  5760
```

```
tttcttcaca accggcacgg aactcgctcg ggctggcccc ggtgcatttt ttaaataccc  5820
gcgagaaata gagttgatcg tcaaaaccaa cattgcgacc gacggtggcg ataggcatcc  5880
gggtggtgct caaaagcagc ttcgcctggc tgatacgttg gtcctcgcgc cagcttaaga  5940
cgctaatccc taactgctgg cggaaaagat gtgacagacg cgacggcgac aagcaaacat  6000
gctgtgcgac gctggcgata tcaaaattgc tgtctgccag gtgatcgctg atgtactgac  6060
aagcctcgcg tacccgatta tccatcggtg gatggagcga ctcgttaatc gcttccatgc  6120
gccgcagtaa caattgctca agcagattta tcgccagcag ctccgaatag cgcccttccc  6180
cttgcccggc gttaatgatt tgcccaaaca ggtcgctgaa atgcggctgg tgcgcttcat  6240
ccgggcgaaa gaaccccgta ttggcaaata ttgacggcca gttaagccat tcatgccagt  6300
aggcgcgcgg acgaaagtaa acccactggt gataccattc gcgagcctcc ggatgacgac  6360
cgtagtgatg aatctctcct ggcgggaaca gcaaaatatc acccggtcgg caaacaaatt  6420
ctcgtccctg atttttcacc acccccctgac cgcgaatggt gagattgaga atataacctt  6480
tcattcccag cggtcggtcg ataaaaaaat cgagataacc gttggcctca atcggcgtta  6540
aacccgccac cagatgggca ttaaacgagt atcccggcag caggggatca ttttgcgctt  6600
cagccatact tttcatactc ccgccattca gagaagaaac caattgtcca tattgcatca  6660
gacattgccg tcactgcgtc ttttactggc tcttctcgct aaccaaaccg gtaaccccgc  6720
ttattaaaag cattctgtaa caaagcggga ccaaagccat gacaaaaacg cgtaacaaaa  6780
gtgtctataa tcacggcaga aaagtccaca ttgattattt gcacggcgtc acactttgct  6840
atgccatagc atttttatcc ataagattag cggatcctac ctgacgcttt ttatcgcaac  6900
tctctactgt ttctccatac ccgttttttt gggcgacctc gtcggaggtt gtatgtccgg  6960
tgttccgtga cgtcatcggg cattcatcat tcatagaatg tgttacggag gaaacaagta  7020
atggcactta gcaccgcaac caaggccgcg acggacgcgc tggctgccaa tcgggcaccc  7080
accagcgtga atgcacagga agtgcaccgt tggctccaga gcttcaactg ggatttcaag  7140
aacaaccgga ccaagtacgc caccaagtac aagatggcga acgagaccaa ggaacagttc  7200
aagctgatcg ccaaggaata tgcgcgcatg gaggcagtca aggacgaaag gcagttcggt  7260
agcctgcagg atgcgctgac ccgcctcaac gccggtgttc gcgttcatcc gaagtggaac  7320
gagaccatga aagtggtttc gaacttcctg gaagtgggcg aatacaacgc catcgccgct  7380
accgggatgc tgtgggattc cgcccaggcg gcggaacaga agaacggcta tctggcccag  7440
gtgttggatg aaatccgcca cacccaccag tgtgcctacg tcaactacta cttcgcgaag  7500
aacggccagg acccggccgg tcacaacgat gctcgccgca cccgtaccat cggtccgctg  7560
tggaagggca tgaagcgcgt gttttccgac ggcttcattt ccggcgacgc cgtggaatgc  7620
tccctcaacc tgcagctggt gggtgaggcc tgcttcacca atccgctgat cgtcgcagtg  7680
accgaatggg ctgccgccaa cggcgatgaa atcaccccga cggtgttcct gtcgatcgag  7740
accgacgaac tgcgccacat ggccaacggt taccagaccg tcgtttccat cgccaacgat  7800
ccggcttccg ccaagtatct caacacggac ctgaacaacg ccttctggac ccagcagaag  7860
tacttcacgc cggtgttggg catgctgttc gagtatggct ccaagttcaa ggtcgagccg  7920
tgggtcaaga cgtggaaccg ctgggtgtac gaggactggg gcggcatctg gatcggccgt  7980
ctgggcaagt acggggtgga gtcgccgcgc agcctcaagg acgccaagca ggacgcttac  8040
tgggctcacc acgacctgta tctgctggct tatgcgctgt ggccgaccgg cttcttccgt  8100
ctggcgctgc cggatcagga agaaatggag tggttcgagg ccaactaccc cggctggtac  8160
gaccactacg gcaagatcta cgaggaatgg cgcgcccgcg gttgcgagga tccgtcctcg  8220
ggcttcatcc cgctgatgtg gttcatcgaa aacaaccatc ccatctacat cgatcgcgtg  8280
tcgcaagtgc cgttctgccc gagcttggcc aagggcgcca gcaccctgcg cgtgcacgag  8340
tacaacggcc agatgcacac cttcagcgac cagtggggcg agcgcatgtg gctggccgag  8400
ccggagcgct acgagtgcca gaacatcttc gaacagtacg aaggacgcga actgtcggaa  8460
gtgatcgccg aactgcacgg gctgcgcagt gatggcaaga ccctgatcgc ccagccgcat  8520
gtccgtggcg acaagctgtg gacgttggac gatatcaaac gcctgaactg cgtcttcaag  8580
aacccggtga aggcattcaa ttgaaacggg tgtcgggctc cgtcacaggg cggggcccga  8640
cgcacgatcg ttcgatcaac ctcaaaccaa aaaggaacat cgatatgagc atgttaggag  8700
aaagacgccg cggtctgacc gatccggaaa tggcggccgt cattttgaag gcgcttcctg  8760
aagctccgct ggacggcaac aacaagatgg gttatttcgt caccccccgc tggaaacgct  8820
tgacggaata tgaagccctg accgtttatg cgcagcccaa cgccgactgg atcgccggcg  8880
gcctggactg gggcgactgg acccagaaat tccacggcgg ccgcccttcc tggggcaacg  8940
agaccacgga gctgcgcacc gtcgactggt tcaagcaccg tgacccgctc cgccgttggc  9000
atgcgccgta cgtcaaggac aaggccgagg aatggcgcta caccgaccgc ttcctgcagg  9060
gttactccgc cgacggtcag atccgggcga tgaacccgac ctggcgggac gagttcatca  9120
accggtattg gggcgccttc ctgttcaacg aatacggatt gttcaacgct cattcgcagg  9180
gcgcccggga ggcgctgtcg gacgtaaccc gcgtcagcct ggctttctgg ggcttcgaca  9240
agatcgacat cgcccagatg atccaactcg aacggggttt cctcgccaag atcgtacccg  9300
gtttcgacga gtccacagcg gtgccgaagg ccgaatggac gaacggggag gtctacaaga  9360
gcgcccgtct ggccgtggaa gggctgtggc aggaggtgtt cgactggaac gagagcgctt  9420
tctcggtgca cgccgtctat gacgcgctgt tcggtcagtt cgtccgccgc gagttctttc  9480
agcggctggc tccccgcttc ggcgacaatc tgacgccatt cttcatcaac caggcccaga  9540
catacttcca gatcgccaag cagggcgtac aggatctgta ttacaactgt ctgggtgacg  9600
atccggagtt cagcgattac aaccgtaccg tgatgcgcaa ctggaccggc aagtggctgg  9660
agcccacgat cgccgctctg cgcgacttca tggggctgtt tgcgaagctg ccggcgggca  9720
ccactgacaa ggaagaaatc accgcgtccc tgtaccgggt ggtcgacgac tggatcgagg  9780
actacgccag caggatcgac ttcaaggcgg accgcgatca gatcgttaaa gcggttctgg  9840
caggattgaa ataatagagg aactattacg atgagcgtaa acagcaacgc atacgacgcc  9900
ggcatcatgg gcctgaaagg caaggacttc gccgatcagt tctttgccga cgaaaaccaa  9960
gtggtccatg aaagcgacac ggtcgttctg gtcctcaaga agtcggacga gatcaatacc  10020
tttatcgagg agatccttct gacggactac aagaagaacg tcaatccgac ggtaaacgtg  10080
gaagaccgcg cgggttactg gtggatcaag gccaacggca agatcgaggt cgattgcgac  10140
gagatttccg agctgttggg gcggcagttc aacgtctacg acttcctcgt cgacgtttcc  10200
tccaccatcg gccgggccta taccctgggc aacaagttca ccattaccag tgagctgatg  10260
ggcctggacc gcaagctcga agactatcac gcttaaggag aatgacatgg cgaaactggg  10320
tatacacagc aacgacaccc gcgacgcctg ggtgaacaag atcgcgcagc tcaacaccct  10380
ggaaaaagcg gccgagatgc tgaagcagtt ccggatggac cacaccacgc cgttccgcaa  10440
cagctacgaa ctggacaacg actacctctg gatcgaggcc aagctcgaag agaaggtcgc  10500
```

```
cgtcctcaag gcacgcgcct tcaacgaggt ggacttccgt cataagaccg ctttcggcga  10560
ggatgccaag tccgttctgg acggcaccgt cgcgaagatg aacgcggcca aggacaagtg  10620
ggaggcggag aagatccata tcggtttccg ccaggcctac aagccgccga tcatgccggt  10680
gaactatttc ctggacggcg agcgtcagtt ggggacccgg ctgatggaac tgcgcaacct  10740
caactactac gacacgccgc tggaagaact gcgcaaacag cgcggtgtgc gggtggtgca  10800
tctgcagtcg ccgcactgaa gggaggaagt ctcgccctgg acgcgacggc atcgccgtga  10860
agtccagggg gcagggatgc cgttccgggc cggcaggctg gcccggaatc tctggttttc  10920
agggggcgtg ccggtccacg gctccccccct ccatctttcg taaggaaatc accatggtcg  10980
aatcggcatt tcagccattt tcgggcgacg cagacgaatg gttcgaggaa ccacggcccc  11040
aggccggttt cttcccttcc gcggactggc atctgctcaa acgggacgag acctacgcag  11100
cctatgccaa ggatctcgat ttcatgtggc ggtgggtcat cgtccgggaa gaaaggatcg  11160
tccaggaggg ttgctcgatc agcctggagt cgtcgatccg cgccgtgacg cacgtactga  11220
attattttgg tatgaccgaa caacgcgccc cggcagagga ccggaccggc ggagttcaac  11280
attgaacagg taagtttatg cagcgagttc acactatcac ggcggtgacg gaggatggcg  11340
aatcgctccg cttcgaatgc cgttcggacg aggacgtcat caccgccgcc ctgcgccaga  11400
acatctttct gatgtcgtcc tgccgggagg gcggctgtgc gacctgcaag gccttgtgca  11460
gcgaagggga ctacgacctc aagggctgca gcgttcaggc gctgccgccg gaagaggagg  11520
aggaagggtt ggtgttgttg tgccggacct acccgaagac cgacctggaa atcgaactgc  11580
cctataccca ttgccgcatc agttttggtg aggtcggcag tttcgaggcg gaggtcgtcg  11640
gcctcaactg ggtttcgagc aacaccgtcc agtttctttt gcagaagcgg cccgacgagt  11700
gcggcaaccg tggcgtgaaa ttcgaacccg gtcagttcat ggacctgacc atccccggca  11760
ccgatgtctc ccgctcctac tcgccggcga accttcctaa tcccgaaggc cgcctggagt  11820
tcctgatccg cgtgttaccg gagggacggt tttcggacta cctgcgcaat gacgcgcgtg  11880
tcggacaggt cctctcggtc aaagggccac tgggcgtgtt cggtctcaag gagcggggca  11940
tggcgccgcg ctatttcgtg gccggcggca ccgggttggc gccggtggtc tcgatggtgc  12000
ggcagatgca ggagtggacc gcgccgaacg agacccgcat ctatttcggt gtgaacaccg  12060
agccggaatt gttctacatc gacgagctca aatccctgga acgatcgatg cgcaatctca  12120
ccgtgaaggc ctgtgtctgg cacccgagcg gggactggga aggcgagcag ggctcgccca  12180
tcgatgcgtt gcgggaagac ctggagtcct ccgacgccaa cccggacatt tatttgtgcg  12240
gtccgccggg catgatcgat gccgcctgcg agctggtacg cagccgcggt atccccggcg  12300
aacaggtctt cttcgaaaaa ttcctgccgt ccggggcggc ctgaaccggg gaagtaccgt  12360
gaccaccgag cagttcccgc cccaattcct gcgtgaaatg atcgagcagc tggacgccag  12420
catccaggag ctcgcacgca aggaaaaggg acttgcggca tccctgggca cgggccgggt  12480
cgccgagctc aaggaatact gggaccacgt tgttacaacc aattaaccaa ttctgactat  12540
ttaacgaccc tgccctgaac cgacgaccgg gtcatcgtgg ccggatcttg cggcccctcg  12600
gcttgaacga attgttagac attatttgcc gactaccttg gtgatctcgc ctttcacgta  12660
gtggacaaat tcttccaact gatctgcgcg cgaggccaag cgatcttctt cttgtccaag  12720
ataagcctgt ctagcttcaa gtatgacggg ctgatactgg gccggcaggc gctccattgc  12780
ccagtcggca gcgacatcct tcggcgcgat tttgccggtt actgcgctgt accaaatgcg  12840
ggacaacgta agcactacat ttcgctcatc gccagcccag tcgggcggcg agttccatag  12900
cgttaaggtt tcatttagcg cctcaaatag atcctgttca ggaaccggat caaagagttc  12960
ctccgccgct ggacctacca aggcaacgct atgttctctt gcttttgtca gcaagatagc  13020
cagatcaatg tcgatcgtgg ctggctcgaa gatacctgca agaatgtcat tgcgctgcca  13080
ttctccaaat tgcagttcgc gcttagctgg ataacgccac ggaatgatgt cgtcgtgcac  13140
aacaatggtg acttctacag cgcggagaat ctcgctctct ccaggggaag ccgaagtttc  13200
caaaaggtcg ttgatcaaag ctcgccgcgt tgtttcatca agccttacgg tcaccgtaac  13260
cagcaaatca                                                        13270
```

```
SEQ ID NO: 18          moltype = DNA  length = 11223
FEATURE                Location/Qualifiers
misc_feature           1..11223
                       note = Synthetic plasmid.
source                 1..11223
                       mol_type = other DNA
                       organism = synthetic construct
SEQUENCE: 18
cgaggacgtc atcaccgccg ccctgcgcca gaacatcttt ctgatgtcgt cctgccggga  60
gggcggctgt gcgacctgca aggccttgtg cagcgaaggg gactacgacc tcaagggctg  120
cagcgttcag gcgctgccgc cggaagagga ggaggaaggg ttggtgttgt tgtgccggac  180
ctacccgaag accgacctgg aaatcgaact gccctatacc cattgccgca tcagttttgg  240
tgaggtcggc agtttcgagg cggaggtcgt cggcctcaac tgggtttcga gcaacaccgt  300
ccagtttctt ttgcagaagc ggcccgacga gtgcggcaac cgtggcgtga aattcgaacc  360
cggtcagttc atggacctga ccatccccgg caccgatgtc tcccgctcct actcgccggc  420
gaaccttcct aatcccgaag gccgcctgga gttcctgatc cgcgtgttac cggagggacg  480
gttttcggac tacctgcgca atgacgcgcg tgtcggacag gtcctctcgg tcaaagggcc  540
actgggcgtg ttcggtctca aggagcgggg catggcgccg cgctatttcg tggccggcgg  600
caccgggttg gcgccggtgg tctcgatggt gcggcagatg caggagtgga ccgcgccgaa  660
cgagacccgc atctatttcg gtgtgaacac cgagccggaa ttgttctaca tcgacgagct  720
caaatccctg gaacgatcga tgcgcaatct caccgtgaag gcctgtgtct ggcacccgag  780
cggggactgg gaaggcgagc agggctcgcc catcgatgcg ttgcgggaag acctggagtc  840
ctccgacgcc aacccggaca tttatttgtg cggtccgccg ggcatgatcg atgccgcctg  900
cgagctggta cgcagccgcg gtatccccgg cgaacaggtc ttcttcgaaa aattcctgcc  960
gtccggggcg gcctgaaccg gggaagtacc gtgaccaccg agcagttccc gccccaattc  1020
ctgcgtgaaa tgatcgagca gctggacgcc agcatccagg agctcgcacg caaggaaaag  1080
ggacttgcgg catccctggg cacgggccgg gtcgccgagc tcaaggaata ctgggaccac  1140
gttgttacaa ccaattaacc aattctgatt agaaaaactc atcgagcatc aaatgaaact  1200
gcaatttatt catatcagga ttatcaatac catatttttg aaaaagccgt ttctgtaatg  1260
aaggagaaaa ctcaccgagg cagttccata ggatggcaag atcctggtat cggtctgcga  1320
ttccgactcg tccaacatca atacaaccta ttaatttccc ctcgtcaaaa ataaggttat  1380
```

```
caagtgagaa atcaccatga gtgacgactg aatccggtga gaatggcaaa agcttatgca  1440
tttctttcca gacttgttca acaggccagc cattacgctc gtcatcaaaa tcactcgcat  1500
caaccaaacc gttattcatt cgtgattgcg cctgagcgag acgaaatacg cgatcgctgt  1560
taaaaggaca attacaaaca ggaatcgaat gcaaccggcg caggaacact gccagcgcat  1620
caacaatatt ttcacctgaa tcaggatatt cttctaatac ctggaatgct gttttcccgg  1680
ggatcgcagt ggtgagtaac catgcatcat caggagtacg gataaaatgc ttgatggtcg  1740
gaagaggcat aaattccgtc agccagttta gtctgaccat ctcatctgta acatcattgg  1800
caacgctacc tttgccatgt ttcagaaaca actctggcgc atcgggcttc ccatacaatc  1860
gatagattgt cgcacctgat tgcccgacat tatcgcgagc ccatttatac ccatataaat  1920
cagcatccat gttggaattt aatcgcggcc tcgagcaaga cgtttcccgt tgaatatggc  1980
tcataacacc ccttgtatta ctgtttatgt aagcagacag ttttattgtt catgatgata  2040
tatttttatc ttgtgcaatg taacatcaga gattttgaga cacaacgtgg ctttgttgaa  2100
taaatcgaac ttttgctgag ttgaaggatc agatcacgca tcttcccgac aacgcagacc  2160
gttccgtggc aaagcaaaag ttcaaaatca ccaactggtc cacctacaac aaagctctca  2220
tcaaccgtgg ctccctcact ttctggctgg atgatggggc gattcaggcc tggtatgagt  2280
cagcaacacc ttcttcacga ggcagacctc agcgctagcg gagtgtatac tggcttacta  2340
tgttggcact gatgagggtg tcagtgaagt gcttcatgtg gcaggagaaa aaaggctgca  2400
ccggtgcgtc agcagaatat gtgatacagg atatattccg cttcctcgct cactgactcg  2460
ctacgctcgg tcgttcgact gcggcgagcg gaaatggctt acgaacgggg cggagatttc  2520
ctggaagatg ccaggaagat acttaacagg gaagtgagag ggccgcggca aagccgtttt  2580
tccataggct ccgcccccct gacaagcatc acgaaatctg acgctcaaat cagtggtggc  2640
gaaacccgac aggactataa agataccagg cgtttccccc tggcggctcc ctcgtgcgct  2700
ctcctgttcc tgcctttcgg tttaccggtg tcattccgct gttatggccg cgtttgtctc  2760
attccacgcc tgacactcag ttccgggtag gcagttcgct ccaagctgga ctgtatgcac  2820
gaaccccccg ttcagtccga ccgctgcgcc ttatccggta actatcgtct tgagtccaac  2880
ccggaaagac atgcaaaagc accactggca gcagccactg gtaattgatt tagaggagtt  2940
agtcttgaag tcatgcgccg gttaaggcta aactgaaagg acaagttttg gtgactgcgc  3000
tcctccaagc cagttacctc ggttcaaaga gttggtagct cagagaacct tcgaaaaacc  3060
gccctgcaag gcggtttttt cgttttcaga gcaagagatt acgcgcagac caaaacgatc  3120
tcaagaagat catcttatta aggggtctga cgctcagtgg aacgaaaact cacgttaagg  3180
gattttggtc atgagattat caaaaaggat cttcacctag atccttttaa attaaaaatg  3240
aagttttaaa tcaatctaaa gtatatatga gtaaacttgg tctgacaggt gagctgatac  3300
cgctcgccgc atgcacatgc agtcatgtcg tgctaatgtg taaaacatgt acatgcagat  3360
tgctgggggt gcagggggcg gagccacccct gtccatgcgg ggtgtggggc ttgccccgcc  3420
ggtacagaca gtgagcaccg gggcacctag tcgcggatac ccccccctagg tatcggacac  3480
gtaaccctcc catgtcgatg caaatcttta acattgagta cgggtaagct ggcacgcata  3540
gccaagctag gcggccacca aacaccacta aaaattaata gtccctagac aagacaaacc  3600
cccgtgcgag ctaccaactc atatgcacgg gggccacata acccgaaggg gtttcaattg  3660
acaaccatag cactagctaa gacaacgggc acaacacccg cacaaactcg cactgcgcaa  3720
ccccgcacaa catcgggtct aggtaacact gaaatagaag tgaacacctc taaggaaccg  3780
caggtcaatg agggttctaa ggtcactcgc gctagggcgt ggcgtaggca aaacgtcatg  3840
tacaagatca ccaatagtaa ggctctggcg gggtgccata ggtggcgcag ggacgaagct  3900
gttgcggtgt cctggtcgtc taacggtgct tcgcagtttg agggtctgca aaactctcac  3960
tctcgctggg ggtcacctct ggctgaattg gaagtcatgg gcgaacgccg cattgagctg  4020
gctattgcta ctaagaatca cttggcggcg ggtggcgcgc tcatgatgtt tgtgggcact  4080
gttcgacaca accgctcaca gtcatttgcg caggttgaag cgggtattaa gactgcgtac  4140
tcttcgatgg tgaaaacatc tcagtggaag aaagaacgtg cacggtacgg ggtggagcac  4200
acctatagtg actatgaggt cacagactct tgggcgaacg gttggcactt gcaccgcaac  4260
atgctgttgt tcttggatcg tccactgtct gacgatgaac tcaaggcgtt tgaggattcc  4320
atgttttccc gctggtctgc tggtgtggtt aaggccggta tggacgcgcc actgcgtgag  4380
cacggggtca aacttgatca ggtgtctacc tggggtggag acgctgcgaa aatggcaacc  4440
tacctcgcta agggcatgtc tcaggaactg actggctccg ctactaaaac cgcgtctaag  4500
gggtcgtaca cgccgtttca gatgttggat atgttggccg atcaaagcga cgccggcgag  4560
gatatggacg ctgttttggt ggctcggtgg cgtgagtatg aggttggttc taaaaacctg  4620
cgttcgtcct ggtcacgtgg ggctaagcgt gctttgggca ttgattacat agacgctgat  4680
gtacgtcgtg aaatggaaga agaactgtac aagctcgccg gtctggaagc accggaacgg  4740
gtcgaatcaa cccgcgttgc tgttgctttg gtgaagcccg atgattggaa actgattcag  4800
tctgatttcg cggttaggca gtacgttcta gattgcgtgg ataaggctaa ggacgtggcc  4860
gctgcgcaac gtgtcgctaa tgaggtgctg gcaagtctgg gtgtggattc caccccgtgc  4920
atgatcgtta tggatgatgt ggacttggac gcggttctgc ctactcatgg ggacgctact  4980
aagcgtgatc tgaatgcggc ggtgttcgcg ggtaatgagc agactattct tcgcacccac  5040
taaaagcggc ataaaccccg ttcgatattt tgtgcgatga atttatggtc aatgtcgcgg  5100
gggcaaacta tgatgggtct tgttgttgca gccgaacgac ctagcgcagc gagtcagtga  5160
gcgaggaagc ggaagagcgc ctgatgcggt attttctcct tacgcatctg tgcggtattt  5220
cacaccgcat atggtgcact ctcagtacaa tctgctctga tgccgcatag ttaagccagt  5280
atacactccg ctatcgctac gtgactgggt catggctgcg ccccgacacc cgccaacacc  5340
cgctgacgcg ccctgacggg cttgtctgct cccggcatcc gcttacagac aagctgtgac  5400
cgtctccggg agctgcatgt gtcagaggtt ttcaccgtca tcaccgaaac gcgcgaggca  5460
gcagatcaat tcgcgcgcga aggcgaagcg gcatgcataa tgtgcctgtc aaatggacga  5520
agcagggatt ctgcaaaccc tatgctactc cgtcaagccg tcaattgtct gattcgttac  5580
caattatgac aacttgacgg ctacatcatt cactttttct tcacaaccgg cacggaactc  5640
gctcgggctg gccccggtgc atttttttaaa tacccgcgag aaatagagtt gatcgtcaaa  5700
accaacattg cgaccgacgg tggcgatagg catccgggtg gtgctcaaaa gcagcttcgc  5760
ctggctgata cgttggtcct cgcgccagct taagacgcta atccctaact gctggcggaa  5820
aagatgtgac agacgcgacg gcgacaagca aacatgctgt gcgacgctgg cgatatcaaa  5880
attgctgtct gccaggtgat cgctgatgta ctgacaagcc tcgcgtaccc gattatccat  5940
cggtggatgg agcgactcgt taatcgcttc catgcgccgc agtaacaatt gctcaagcag  6000
atttatcgcc agcagctccg aatagcgccc ttccccttgc ccggcgttaa tgatttgccc  6060
aaacaggtcg ctgaaatgcg gctggtgcgc ttcatccggg cgaaagaacc ccgtattggc  6120
```

```
aaatattgac ggccagttaa gccattcatg ccagtaggcg cgcggacgaa agtaaaccca  6180
ctggtgatac cattcgcgag cctccggatg acgaccgtag tgatgaatct ctcctggcgg  6240
gaacagcaaa atatcacccg gtcggcaaac aaattctcgt ccctgatttt tcaccacccc  6300
ctgaccgcga atggtgagat tgagaatata acctttcatt cccagcggtc ggtcgataaa  6360
aaaatcgaga taaccgttgg cctcaatcgg cgttaaaccc gccaccagat gggcattaaa  6420
cgagtatccc ggcagcaggg gatcattttg cgcttcagcc atacttttca tactcccgcc  6480
attcagagaa gaaaccaatt gtccatattg catcagacat tgccgtcact gcgtctttta  6540
ctggctcttc tcgctaacca aaccggtaac cccgcttatt aaaagcattc tgtaacaaag  6600
cgggaccaaa gccatgacaa aaacgcgtaa caaaagtgtc tataatcacg gcagaaaagt  6660
ccacattgat tatttgcacg gcgtcacact ttgctatgcc atagcatttt tatccataag  6720
attagcggat cctacctgac gctttttatc gcaactctct actgtttctc catacccgtt  6780
tttttgggcg acctcgtcgg aggttgtatg tccggtgttc cgtgacgtca tcgggcattc  6840
atcattcata gaatgtgtta cggaggaaac aagtaatggc acttagcacc gcaaccaagg  6900
ccgcgacgga cgcgctggct gccaatcggg cacccaccag cgtgaatgca caggaagtgc  6960
accgttggct ccagagcttc aactgggatt tcaagaacaa ccggaccaag tacgccacca  7020
agtacaagat ggcgaacgag accaaggaac agttctcgct gatcgccaag gaatatgcgc  7080
gcatggaggc agtcaaggac gaaaggcagt tcggtagcct gcaggatgcg ctgacccgcc  7140
tcaacgccgg tgttcgcgtt catccgaagt ggaacgagac catgaaagtg gtttcgaact  7200
tcctggaagt gggcgaatac aacgccatcg ccgctaccgg gatgctgtgg gattccgccc  7260
aggcggcgga acagaagaac ggctatctgg cccaggtgtt ggatgaaatc cgccacaccc  7320
accagtgtgc ctacgtcaac tactacttcg cgaagaacgg ccaggacccg gccggtcaca  7380
acgatgctcg ccgcacccgt accatcggtc cgctgtggaa gggcatgaag cgcgtgtttt  7440
ccgacggctt catttccggc gacgccgtgg aatgctccct caacctgcag ctggtgggtg  7500
aggcctgctt caccaatccg ctgatcgtcg cagtgaccga atgggctgcc gccaacggcg  7560
atgaaatcac cccgacggtg ttcctgtcga tcaacaccga cgaactgcgc cacatggcca  7620
acggttacca gaccgtcgtt tccatcgcca acgatccggc ttccgccaag tatctcaaca  7680
cggacctgaa caacgccttc tggacccagc agaagtactt cacgccggtg ttgggcatgc  7740
tgttcgagta tggctccaag ttcaaggtcg agccgtgggt caagacgtgg aaccgctggg  7800
tgtacgagga ctggggcggc atctggatcg gccgtctggg caagtacggg gtggagtcgc  7860
cgcgcagcct caaggacgcc aagcaggacg cttactgggc tcaccacgac ctgtatctgc  7920
tggcttatgc gctgtggccg accggcttct tccgtctggc gctgccggat caggaagaaa  7980
tggagtggtt cgaggccaac taccccggct ggtacgacca ctacggcaag atctacgagg  8040
aatggcgcgc ccgcggttgc gaggatccgt cctcgggctt catcccgctg atgtggttca  8100
tcgaaaacaa ccatcccatc tacatcgatc gcgtgacgca agtgccgttc tgcccgagct  8160
tggccaaggg cgccagcacc ctgcgcgtgc acgagtacaa cggccagatg cacaccttca  8220
gcgaccagtg gggcgagcgc atgtggctgg ccgagccgga gcgctacgag tgccagaaca  8280
tcttcgaaca gtacgaagga cgcgaactgt cggaagtgat cgccgaactg cacgggctgc  8340
gcagtgatgg caagaccctg atcgcccagc cgcatgtccg tggcgacaag ctgtggacgt  8400
tggacgatat caaacgcctg aactgcgtct tcaagaaccc ggtgaaggca ttcaattgaa  8460
acgggtgtcg ggctccgtca cagggcgggg cccgacgcac gatcgttcga tcaacctcaa  8520
accaaaaagg aacatcgata tgagcatgtt aggagaaaga cgccgcggtc tgaccgatcc  8580
ggaaatggcg gccgtcattt tgaaggcgct tcctgaagct ccgctggacg gcaacaacaa  8640
gatgggttat ttcgtcaccc cccgctggaa acgcttgacg gaatatgaag ccctgaccgt  8700
ttatgcgcag cccaacgccg actggatcgc cggcggcatg gactggggcg actggaccca  8760
gaaattccac ggcggccgcc cttcctgggg caacgagacc acggagctgc gcaccgtcga  8820
ctggttcaag caccgtgacc cgctccgccg ttggcatgcg ccgtacgtca aggacaaggc  8880
cgaggaatgg cgctacaccg accgcttcct gcagggttac tccgccgacg gtcagatccg  8940
ggcgatgaac ccgacctggc gggacgagtt catcaaccgg tattggggcg ccttcctgtt  9000
caacgaatac ggattgttca acgctcattc gcagggcgcc cgggaggcgc tgtcggacgt  9060
aacccgcgtc agcctggctt tctggggctt cgacaagatc gacatcgccc agatgatcca  9120
actcgaacgg ggtttcctcg ccaagatcgt acccggtttc gacgagtcca cagcggtgcc  9180
gaaggccgaa tggacgaacg gggaggtcta caagagcgcc cgtctggccg tggaagggct  9240
gtggcaggag gtgttcgact ggaacgagag cgctttctcg gtgcacgccg tctatgacgc  9300
gctgttcggt cagttcgtcc gccgcgagtt ctttcagcgg ctggctcccc gcttcggcga  9360
caatctgacg ccattcttca tcaaccaggc ccagacatac ttccagatcg ccaagcaggg  9420
cgtacaggat ctgtattaca actgtctggg tgacgatccg gagttcagcg attacaaccg  9480
taccgtgatg cgcaactgga ccggcaagtg gctggagccc acgatcgccg ctctgcgcga  9540
cttcatgggg ctgtttgcga agctgccggc gggcaccact gacaaggaag aaatcaccgc  9600
gtccctgtac cgggtggtcg acgactggat cgaggactac gccagcagga tcgacttcaa  9660
ggcggaccgc gatcagatcg ttaaagcggt tctggcagga ttgaaataat agaggaacta  9720
ttacgatgag cgtaaacagc aacgcatacg acgccggcat catgggcctg aaaggcaagg  9780
acttcgccga tcagttcttt gccgacgaaa accaagtggt ccatgaaagc gacacggtcg  9840
ttctggtcct caagaagtcg gacgagatca atacctttat cgaggaggag cttctgacgg  9900
actacaagaa gaacgtcaat ccgacggtaa acgtggaaga ccgcgcgggt tactggtgga  9960
tcaaggccaa cggcaagatc gaggtcgatt gcgacgagat ttccgagctg ttggggcggc  10020
agttcaacgt ctacgacttc ctcgtcgacg tttcctccac catcggccgg gcctataccc  10080
tgggcaacaa gttcaccatt accagtgagc tgatgggcct ggaccgcaag ctcgaagact  10140
atcacgctta aggagaatga catggcgaaa ctgggtatac acagcaacga cacccgcgac  10200
gcctgggtga acaagatcgc gcagctcaac accctggaaa aagcggccga gatgctgaag  10260
cagttccgga tggaccacac cacgccgttc cgcaacagct acgaactgga caacgactac  10320
ctctggatcg aggccaagct cgaagagaag gtcgccgtcc tcaaggcacg cgccttcaac  10380
gaggtggact tccgtcataa gaccgctttc ggcgaggatg ccaagtccgt tctggacggc  10440
accgtcgcga agatgaacgc ggccaaggac aagtgggagg cggagaagat ccatatcggt  10500
ttccgccagg cctacaagcc gccgatcatg ccggtgaact atttcctgga cggcgagcgt  10560
cagttgggga cccggctgat ggaactgcgc aacctcaact actacgacac gccgctggaa  10620
gaactgcgca aacagcgcgg tgtgcgggtg gtgcatctgc agtcgccgca ctgaagggag  10680
gaagtctcgc cctggacgcg acggcatcgc cgtgaagtcc agggggcagg gatgccgttc  10740
cgggccggca ggctggcccg gaatctctgg ttttcagggg gcgtgccggt ccacggctcc  10800
cccctccatc tttcgtaagg aaatcaccat ggtcgaatcg gcatttcagc cattttcggg  10860
```

```
cgacgcagac gaatggttcg aggaaccacg gccccaggcc ggtttcttcc cttccgcgga  10920
ctggcatctg ctcaaacggg acgagaccta cgcagcctat gccaaggatc tcgatttcat  10980
gtggcggtgg gtcatcgtcc gggaagaaag gatcgtccag gagggttgct cgatcagcct  11040
ggagtcgtcg atccgcgccg tgacgcacgt actgaattat tttggtatga ccgaacaacg  11100
cgccccggca gaggaccgga ccggcggagt tcaacattga acaggtaagt ttatgcagcg  11160
agttcacact atcacggcgg tgacggagga tggcgaatcg ctccgcttcg aatgccgttc  11220
gga                                                                11223

SEQ ID NO: 19          moltype = DNA  length = 10075
FEATURE                Location/Qualifiers
misc_feature           1..10075
                       note = Synthetic plasmid.
source                 1..10075
                       mol_type = other DNA
                       organism = synthetic construct
SEQUENCE: 19
ttgacaatta atcatccggc tcgtataatg tgtggaattg tgagcggata acaatttcac  60
acaggaaaca gcgccgctga gaaaaagcga agcggcactg ctctttaaca atttatcaga  120
caatctgtgt gggcactcga ccggaattat cgattaactt tattattaaa aattaaagag  180
gtatatatta atgtatcgat taaataagga ggaataaacc atgatggcac ttagcaccgc  240
aaccaaggcc gcgacggacg cgctggctgc caatcgggca cccaccagcg tgaatgcaca  300
ggaagtgcac cgttggctcc agagcttcaa ctgggatttc aagaacaacc ggaccaagta  360
cgccaccaag tacaagatgg cgaacgagac caaggaacag ttcaagctga tcgccaagga  420
atatgcgcgc atggaggcag tcaaggacga aaggcagttc ggtagcctgc aggatgcgct  480
gacccgcctc aacgccggtg ttcgcgttca tccgaagtgg aacgagacca tgaaagtggt  540
ttcgaacttc ctggaagtgg gcgaatacaa cgccatcgcc gctaccggga tgctgtggga  600
ttccgcccag gcggcggaac agaagaacgg ctatctggcc caggtgttgg atgaaatccg  660
ccacacccac cagtgtgcct acgtcaacta ctacttcgcg aagaacggcc aggacccggc  720
cggtcacaac gatgctcgcc gcacccgtac catcggtccg ctgtggaagg gcatgaagcg  780
cgtgttttcc gacggcttca tttccggcga cgccgtggaa tgctccctca acctgcagct  840
ggtgggtgag gcctgcttca ccaatccgct gatcgtcgca gtgaccgaat gggctgccgc  900
caacggcgat gaaatcaccc cgacggtgtt cctgtcgatc gagaccgacg aactgcgcca  960
catggccaac ggttaccaga ccgtcgtttc catcgccaac gatccggctt ccgccaagta  1020
tctcaacacg gacctgaaca acgccttctg gacccagcag aagtacttca cgccggtgtt  1080
gggcatgctg ttcgagtatg gctccaagtt caaggtcgag ccgtgggtca agacgtggaa  1140
ccgctgggtg tacgaggact ggggcggcat ctggatcggc cgtctgggca agtacggggt  1200
ggagtcgccg cgcagcctca aggacgccaa gcaggacgct tactgggctc accacgacct  1260
gtatctgctg gcttatgcgc tgtggccgac cggcttcttc cgtctggcgc tgccggatca  1320
ggaagaaatg gagtggttcg aggccaacta ccccggctgg tacgaccact acggcaagat  1380
ctacgaggaa tggcgcgccc gcggttgcga ggatccgtcc tcgggcttca tcccgctgat  1440
gtggttcatc gaaaacaacc atcccatcta catcgatcgc gtgtcgcaag tgccgttctg  1500
cccgagcttg gccaagggcg ccagcaccct gcgcgtgcac gagtacaacg gccagatgca  1560
caccttcagc gaccagtggg gcgagcgcat gtggctggcc gagccggagc gctacgagtg  1620
ccagaacatc ttcgaacagt acgaaggacg cgaactgtcg gaagtgatcg ccgaactgca  1680
cgggctgcgc agtgatggca agaccctgat cgcccagccg catgtccgtg gcgacaagct  1740
gtggacgttg gacgatatca aacgcctgaa ctgcgtcttc aagaacccgg tgaaggcatt  1800
caattgaaac gggtgtcggg ctccgtcaca gggcggggcc cgacgcacga tcgttcgatc  1860
aacctcaaac caaaaaggaa catcgatatg agcatgttag gagaaagacg ccgcggtctg  1920
accgatccgg aaatggcggc cgtcattttg aaggcgcttc ctgaagctcc gctggacggc  1980
aacaacaaga tgggttattt cgtcaccccc cgctggaaac gcttgacgga atatgaagcc  2040
ctgaccgttt atgcgcagcc caacgccgac tggatcgccg gcggcctgga ctggggcgac  2100
tggacccaga aattccacgg cggccgccct tcctggggca acgagaccac ggagctgcgc  2160
accgtcgact ggttcaagca ccgtgacccg ctccgccgtt ggcatgcgcc gtacgtcaag  2220
gacaaggccg aggaatggcg ctacaccgac cgcttcctgc agggttactc cgccgacggt  2280
cagatccggg cgatgaaccc gacctggcgg gacgagttca tcaaccggta ttggggcgcc  2340
ttcctgttca acgaatacgg attgttcaac gctcattcgc agggcgcccg ggaggcgctg  2400
tcggacgtaa cccgcgtcag cctggctttc tggggcttcg acaagatcga catcgcccag  2460
atgatccaac tcgaacgggg tttcctcgcc aagatcgtac ccggtttcga cgagtccaca  2520
gcggtgccga aggccgaatg gacgaacggg gaggtctaca agagcgcccg tctggccgtg  2580
gaagggctgt ggcaggaggt gttcgactgg aacgagagcg ctttctcggt gcacgccgtc  2640
tatgacgcgc tgttcggtca gttcgtccgc cgcgagttct ttcagcggct ggctccccgc  2700
ttcggcgaca atctgacgcc attcttcatc aaccaggccc agacatactt ccagatcgcc  2760
aagcagggcg tacaggatct gtattacaac tgtctgggtg acgatccgga gttcagcgat  2820
tacaaccgta ccgtgatgcg caactggacc ggcaagtggc tggagcccac gatcgccgct  2880
ctgcgcgact tcatggggct gtttgcgaag ctgccggcgg gcaccactga caaggaagaa  2940
atcaccgcgt ccctgtaccg ggtggtcgac gactggatcg aggactacgc cagcaggatc  3000
gacttcaagg cggaccgcga tcagatcgtt aaagcggttc tggcaggatt gaaataatag  3060
aggaactatt acgatgagcg taaacagcaa cgcatacgac gccggcatca tgggcctgaa  3120
aggcaaggac ttcgccgatc agttctttgc cgacgaaaac caagtggtcc atgaaagcga  3180
cacggtcgtt ctggtcctca agaagtcgga cgagatcaat acctttatcg aggagatcct  3240
tctgacggac tacaagaaga acgtcaatcc gacggtaaac gtggaagacc gcgcgggtta  3300
ctggtggatc aaggccaacg gcaagatcga ggtcgattgc gacgagattt ccgagctgtt  3360
ggggcggcag ttcaacgtct acgacttcct cgtcgacgtt tcctccacca tcggccgggc  3420
ctataccctg ggcaacaagt tcaccattac cagtgagctg atgggcctgg accgcaagct  3480
cgaagactat cacgcttaag gagaatgaca tggcgaaact gggtatacac agcaacgaca  3540
cccgcgacgc ctgggtgaac aagatcgcgc agctcaacac cctggaaaaa gcggccgaga  3600
tgctgaagca gttccggatg gaccacacca cgccgttccg caacagctac gaactggaca  3660
acgactacct ctggatcgag gccaagctcg aagagaaggt cgccgtcctc aaggcacgcg  3720
ccttcaacga ggtggacttc cgtcataaga ccgctttcgg cgaggatgcc aagtccgttc  3780
```

```
tggacggcac cgtcgcgaag atgaacgcgg ccaaggacaa gtgggaggcg gagaagatcc  3840
atatcggttt ccgccaggcc tacaagccgc cgatcatgcc ggtgaactat ttcctggacg  3900
gcgagcgtca gttggggacc cggctgatgg aactgcgcaa cctcaactac tacgacacgc  3960
cgctggaaga actgcgcaaa cagcgcggtg tgcgggtggt gcatctgcag tcgccgcact  4020
gaagggagga agtctcgccc tggacgcgac ggcatcgccg tgaagtccag gggcaggga  4080
tgccgttccg ggccggcagg ctggcccgga atctctggtt ttcagggggc gtgccggtcc  4140
acggctcccc cctccatctt tcgtaaggaa atcaccatgg tcgaatcggc atttcagcca  4200
ttttcgggcg acgcagacga atggttcgag gaaccacggc cccaggccgg tttcttccct  4260
tccgcggact ggcatctgct caaacgggac gagacctacg cagcctatgc caaggatctc  4320
gatttcatgt ggcggtgggt catcgtccgg gaagaaagga tcgtccagga gggttgctcg  4380
atcagcctgg agtcgtcgat ccgcgccgtg acgcacgtac tgaattattt tggtatgacc  4440
gaacaacgcg ccccggcaga ggaccggacc ggcggagttc aacattgaac aggtaagttt  4500
atgcagcgag ttcacactat cacggcggtg acggaggatg gcgaatcgct ccgcttcgaa  4560
tgccgttcgg acgaggacgt catcaccgcc gccctgcgcc agaacatctt tctgatgtcg  4620
tcctgccggg agggcggctg tgcgacctgc aaggccttgt gcagcgaagg ggactacgac  4680
ctcaagggct gcagcgttca ggcgctgccg ccggaagagg aggaggaagg gttggtgttg  4740
ttgtgccgga cctacccgaa gaccgacctg gaaatcgaac tgccctatac ccattgccgc  4800
atcagttttg gtgaggtcgg cagtttcgag gcggaggtcg tcggcctcaa ctgggtttcg  4860
agcaacaccg tccagtttct tttgcagaag cggcccgacg agtgcggcaa ccgtggcgtg  4920
aaattcgaac ccggtcagtt catggacctg accatccccg gcaccgatgt ctcccgctcc  4980
tactcgccgg cgaaccttcc taatcccgaa ggccgcctgg agttcctgat ccgcgtgtta  5040
ccggagggac ggttttcgga ctacctgcgc aatgacgcgc gtgtcggaca ggtcctctcg  5100
gtcaaagggc cactgggcgt gttcggtctc aaggagcggg gcatggcgcc gcgctatttc  5160
gtggccggcg gcaccgggtt ggcgccggtg gtctcgatgg tgcggcagat gcaggagtgg  5220
accgcgccga acgagacccg catctatttc ggtgtgaaca ccgagccgga attgttctac  5280
atcgacgagc tcaaatccct ggaacgatcg atgcgcaatc tcaccgtgaa ggcctgtgtc  5340
tggcacccga gcggggactg ggaaggcgag cagggctcgc ccatcgatgc gttgcgggaa  5400
gacctggagt cctccgacgc caacccggac atttatttgt gcggtccgcc gggcatgatc  5460
gatgccgcct gcgagctggt acgcagccgc ggtatccccg gcgaacaggt cttcttcgaa  5520
aaattcctgc cgtccggggc ggcctgaacc ggggaagtac cgtgaccacc gagcagttcc  5580
cgccccaatt cctgcgtgaa atgatcgagc agctggacgc cagcatccag gagctcgcac  5640
gcaaggaaaa gggacttgcg gcatccctgg gcacgggccg ggtcgccgag ctcaaggaat  5700
actgggacca cgttctcact cccgaggagg aatgggagct caagcggacc atggacttcc  5760
gcgaccggga actggtgtgg atctggtccc gtctcaggcg ggcccgaacc tcccgcgcca  5820
atgccgggga ggcctatatg cgccacctgt cgccggcggc gcgaaaaaac gaacaatcct  5880
gaaacggagt cgactcaaca tggcaaagga agtggtttac agggggagtg cgcggcagcg  5940
catgatgcaa ggcatcgaga tactcgcgcg ggcggcgata ccgacgctgg gagccaccgg  6000
ccccagcgtc atgatccagc accgcgccga tggcctgccc cccatttcga cgcgggacgg  6060
cgtcacggtg gctaactcca tcgtactcaa ggaccgtgtc gcgaatctcg gtgcccggct  6120
gctgcgggac gtcgccggca ccatgtcccg cgaagcaggg gatggcacca ccaccgccat  6180
cgtgctggcc cgccatatcg cccgggagat gttcaagagc ctcgccgtcg gtgccgatcc  6240
catcgctctc aagcgtggta tcgaccgtgc cgtcgcccgc gtgagcgagg acatcggggc  6300
tcgggcctgg cgcggcgaca aggaatcggt catcctgggg gtggccgcgg tggcgaccaa  6360
gggcgagccg ggcgtgggcc ggctgctgct ggaggcgctg gacgcggtcg gcgtccatgg  6420
cgccgtgtcg atcgaactgg ggcagcggcg cgaggacctg ctcgacgtgg tcgacgggta  6480
tcgttgggaa aaaggttatc tgtcgcccta ttttgtgacc gatcgggctc gcgagctggc  6540
cgaactcgaa gacgtctacc tcttgatgac cgatcgggag gtggtcgatt tcatcgattt  6600
ggtacccctg ctggaggcgg tgaccgaggc tggtggcagc ctcctgatcg ccgccgaccg  6660
tgtccacgag aaggcactgg ccggcctttt gctcaatcac gttcgcggcg tcttcaaggc  6720
cgtcgcggtc accgcgcccg ggttcggcga caagcggccg aaccgccttt tggatctggc  6780
ggcgttgacc ggtgggcggg cggtcctgga agcccagggc gaccgattgg accgggtcac  6840
gctggccgac ctggggcggg tgcggcgggc ggtcgtcagc gctgacgaca ccgcgctgct  6900
cggcataccg ggcaccgaag cctcccgggc ccgcttggag ggtttgcgcc tggaagcgga  6960
gcagtaccgg gcgctcaagc ccggtcaggg atcggcgacg gggcgcttgc acgagctcga  7020
ggaaatcgag gcccggatcg tcggtctgag cggcaagtcc gcggtctacc gcgtgggcgg  7080
cgtgaccgac gtggagatga aggagcggat ggtacggatc gaaaatgcct accgctcggt  7140
ggtgtctgca ctggaggagg gggtgttgcc cggcggcggt gtcgggtttc tgggcagcat  7200
gcccgttttg gccgagctgg aagcgcgcga tgccgacgaa gcacgcggca tcggcatcgt  7260
ccgttccgcg ctgacggagc ccctccggat catcggagaa aattcgggac tgtcagggga  7320
ggccgtcgtc gccaaggtca tggatcacgc caatcccggt tggggttacg atcaggaaag  7380
cggaagtttc tgcgacctcc acgccagggg catttgggat gccgccaagg tgctcaggct  7440
ggccctggaa aaagccgcgt cggtggccgg cacgtttctc accaccgaag ccgtggtact  7500
ggagattccg gacactgacg ctttcgccgg tttcagtgcg gagtgggccg ccgcgacccg  7560
ggaggatccg cgggtctgag cggggggata cgccctcgaa tcctgggata gtcagagacc  7620
ggcatagcgt acgccgttac gcccgttctg cttgacctgg taaagttaca accaattaac  7680
caattctgag agagtaggga actgccaggc atcaaataaa acgaaaggct cagtcgaaag  7740
actgggcctt tcgttttatc tgttgtttgt cggtgaacgc tctcctgagt aggacaaatc  7800
cgccgggagc ggatttgaac gttgcgaagc aacggcccgg agggtggcgg gcaggacgcc  7860
cgcccataaac tgccaggcat caaattaagc agaaggccat cctgacggat ggcctttttg  7920
cgtttctaca aactcttaga aaaactcatc gagcatcaaa tgaaactgca atttattcat  7980
atcaggatta tcaataccat atttttgaaa aagccgtttc tgtaatgaag gagaaaactc  8040
accgaggcag ttccatagga tggcaagatc ctggtatcgg tctgcgattc cgactcgtcc  8100
aacatcaata caacctatta atttcccctc gtcaaaaata aggttatcaa gtgagaaatc  8160
accatgagtg acgactgaat ccggtgagaa tggcaaaagc ttatgcattt ctttccagac  8220
ttgttcaaca ggccagccat tacgctcgtc atcaaaatca ctcgcatcaa ccaaaccgtt  8280
attcattcgt gattgcgcct gagcgagacg aaatacgcga tcgctgttaa aaggacaatt  8340
acaaacagga atcgaatgca accggcgcag gaacactgcc agcgcatcaa caatattttc  8400
acctgaatca ggatattctt ctaatacctg gaatgctgtt ttcccgggga tcgcagtggt  8460
gagtaaccat gcatcatcag gagtacggat aaaatgcttg atggtcggaa gaggcataaa  8520
```

```
ttccgtcagc cagtttagtc tgaccatctc atctgtaaca tcattggcaa cgctaccttt  8580
gccatgtttc agaaacaact ctggcgcatc gggcttccca tacaatcgat agattgtcgc  8640
acctgattgc ccgacattat cgcgagccca tttataccca tataaatcag catccatgtt  8700
ggaatttaat cgcggcctcg agcaagacgt ttcccgttga atatggctca taacacccct  8760
tgtattactg tttatgtaag cagacagttt tattgttcat gatgatatat ttttatcttg  8820
tgcaatgtaa catcagagat tttgagacac aacgtggctt tgttgaataa atcgaacttt  8880
tgctgagttg aaggatcaga tcacgcatct tcccgacaac gcagaccgtt ccgtggcaaa  8940
gcaaaagttc aaaatcacca actggtccac ctacaacaaa gctctcatca accgtggctc  9000
cctcactttc tggctggatg atggggcgat tcaggcctgg tatgagtcag caacaccttc  9060
ttcacgaggc agacctcagc gctagcggag tgtatactgg cttactatgt tggcactgat  9120
gagggtgtca gtgaagtgct tcatgtggca ggagaaaaaa ggctgcaccg gtgcgtcagc  9180
agaatatgtg atacaggata tattccgctt cctcgctcac tgactcgcta cgctcggtcg  9240
ttcgactgcg gcgagcggaa atggcttacg aacggggcgg agatttcctg gaagatgcca  9300
ggaagatact taacagggaa gtgagagggc cgcggcaaag ccgtttttcc ataggctccg  9360
cccccctgac aagcatcacg aaatctgacg ctcaaatcag tggtggcgaa acccgacagg  9420
actataaaga taccaggcgt ttccccctgg cggctccctc gtgcgctctc ctgttcctgc  9480
ctttcggttt accggtgtca ttccgctgtt atggccgcgt ttgtctcatt ccacgcctga  9540
cactcagttc cgggtaggca gttcgctcca agctggactg tatgcacgaa ccccccgttc  9600
agtccgaccg ctgcgcctta tccggtaact atcgtcttga gtccaacccg gaaagacatg  9660
caaaagcacc actggcagca gccactggta attgatttag aggagttagt cttgaagtca  9720
tgcgccggtt aaggctaaac tgaaaggaca agttttggtg actgcgctcc tccaagccag  9780
ttacctcggt tcaaagagtt ggtagctcag agaaccttcg aaaaaccgcc ctgcaaggcg  9840
gttttttcgt tttcagagca agagattacg cgcagaccaa aacgatctca agaagatcat  9900
cttattaagg ggtctgacgc tcagtggaac gaaaactcac gttaagggat tttggtcatg  9960
agattatcaa aaaggatctt cacctagatc cttttaaatt aaaaatgaag ttttaaatca  10020
atctaaagta tatatgagta aacttggtct gacaggtgag ctgataccgc tcgcc       10075

SEQ ID NO: 20          moltype = DNA  length = 3621
FEATURE                Location/Qualifiers
misc_feature           1..3621
                       note = Synthetic plasmid.
source                 1..3621
                       mol_type = other DNA
                       organism = synthetic construct
SEQUENCE: 20
cgacgaccgg gtcatcgtgg ccggatcttg cggcccctcg gcttgaacga attgttagac  60
attatttgcc gactaccttg gtgatctcgc ctttcacgta gtggacaaat tcttccaact  120
gatctgcgcg cgaggccaag cgatcttctt cttgtccaag ataagcctgt ctagcttcaa  180
gtatgacggg ctgatactgg gccggcaggc gctccattgc ccagtcggca gcgacatcct  240
tcggcgcgat tttgccggtt actgcgctgt accaaatgcg ggacaacgta agcactacat  300
ttcgctcatc gccagcccag tcgggcggcg agttccatag cgttaaggtt tcatttagcg  360
cctcaaatag atcctgttca ggaaccggat caaagagttc ctccgccgct ggacctacca  420
aggcaacgct atgttctctt gcttttgtca gcaagatagc cagatcaatg tcgatcgtgg  480
ctggctcgaa gatacctgca agaatgtcat tgcgctgcca ttctccaaat tgcagttcgc  540
gcttagctgg ataacgccac ggaatgatgt cgtcgtgcac aacaatggtg acttctacag  600
cgcggagaat ctcgctctct ccaggggaag ccgaagtttc caaaaggtcg ttgatcaaag  660
ctcgccgcgt tgtttcatca agccttacgg tcaccgtaac cagcaaatca atatcactgt  720
gtggcttcag gccgccatcc actgcggagc cgtacaaatg tacggccagc aacgtcggtt  780
cgagatggcg ctcgatgacg ccaactacct ctgatagttg agtcgatact tcggcgatca  840
ccgcttccct catactcttc ctttttcaat attattgaag catttatcag ggttattgtc  900
tcatgagcgg atacatattt gaatgtattt agaaaaataa acaaataggt agctcactcg  960
gtcgctacgc tccgggcgtg agactgcggc gggcgctgcg gacacataca aagttaccca  1020
cagattccgt ggataagcag gggactaaca tgtgaggcaa aacagcaggg ccgcgccggt  1080
ggcgtttttc cataggctcc gccctcctgc cagagttcac ataaacagac gcttttccgg  1140
tgcatctgtg ggagccgtga ggctcaacca tgaatctgac agtacgggcg aaacccgaca  1200
ggacttaaag atccccaccg tttccggcgg gtcgctccct cttgcgctct cctgttccga  1260
ccctgccgtt taccggatac ctgttccgcc tttctccctt acgggaagtg tggcgctttc  1320
tcatagctca cacactggta tctcggctcg gtgtaggtcg ttcgctccaa gctgggctgt  1380
aagcaagaac tccccgttca gcccgactgc tgcgccttat ccggtaactg ttcacttgag  1440
tccaacccgg aaaagcacgg taaaacgcca ctggcagcag ccattggtaa ctgggagttc  1500
gcagaggatt tgtttagcta aacacgcggt tgctcttgaa gtgtgcgcca aagtccggct  1560
acactggaag gacagatttg gttgctgtgc tctgcgaaag ccagttacca cggttaagca  1620
gttccccaac tgacttaacc ttcgatcaaa ccacctcccc aggtggtttt ttcgtttaca  1680
gggcaaaaga ttacgcgcag aaaaaaagga tctcaagaag atcctttgat cttttctact  1740
gaaccgctct agatttcagt gcaatttatc tcttcaaatg tagcacctga agtcagcccc  1800
atacgatata agttgtaatt ctcatgttag tcatgccccg cgcccaccgg aaggagctga  1860
ctgggttgaa ggctctcaag ggcatcggtc gagatcccgg tgcctaatga gtgagctaac  1920
ttacattaat tgcgttgcgc tcactgcccg ctttccagtc gggaaacctg tcgtgccagc  1980
tgcattaatg aatcggccaa cgcgcgggga gaggcggttt gcgtattggg cgccagggtg  2040
gtttttcttt tcaccagtga gacgggcaac agctgattgc ccttcaccgc ctggccctga  2100
gagagttgca gcaagcggtc cacgctggtt tgccccagca ggcgaaaatc ctgtttgatg  2160
gtggttaacg gcgggatata acatgagctg tcttcggtat cgtcgtatcc cactaccgag  2220
atgtccgcac caacgcgcag cccggactcg gtaatggcgc gcattgcgcc cagcgccatc  2280
tgatcgttgg caaccagcat cgcagtggga acgatgccct cattcagcat ttgcatggtt  2340
tgttgaaaac cggacatggc actccagtcg ccttcccgtt ccgctatcgg ctgaatttga  2400
ttgcgagtga gatatttatg ccagccagcc agacgcagac gcgccgagac agaacttaat  2460
gggcccgcta acagcgcgat ttgctggtga cccaatgcga ccagatgctc cacgcccagt  2520
cgcgtaccgt cttcatggga gaaaataata ctgttgatgg gtgtctggtc agagacatca  2580
agaaataacg ccggaacatt agtgcaggca gcttccacag caatggcatc ctggtcatcc  2640
```

```
agcggatagt taatgatcag cccactgacg cgttgcgcga gaagattgtg caccgccgct  2700
ttacaggctt cgacgccgct tcgttctacc atcgacacca ccacgctggc acccagttga  2760
tcggcgcgag atttaatcgc cgcgacaatt tgcgacggcg cgtgcagggc cagactggag  2820
gtggcaacgc caatcagcaa cgactgtttg cccgccagtt gttgtgccac gcggttggga  2880
atgtaattca gctccgccat cgccgcttcc actttttccc gcgttttcgc agaaacgtgg  2940
ctggcctggt tcaccacgcg ggaaacggtc tgataagaga caccggcata ctctgcgaca  3000
tcgtataacg ttactggttt cacattcacc accctgaatt gactctcttc cgggcgctat  3060
catgccatac cgcgaaaggt tttgcgccat tcgatggtgt ccgggatctc gacgctctcc  3120
cttatgcgac tcctgcatta ggaaattaat acgactcact ataggggaat tgtgagcgga  3180
taacaattcc cctgtagaaa taattttgtt taactttaat aaggagatat accatggcac  3240
atcaccacca ccatcacgtg ggtaccggtt cgaatgatga cgacgacaag agtccggatc  3300
ccaattggga gctcgtgtac acggcgcgcc tgcaggtcga caagcttgcg gccgcactcg  3360
agtctggtaa agaaaccgct gctgcgaaat ttgaacgcca gcacatggac tcgtctacta  3420
gcgcagctta attaacctag gctgctgcca ccgctgagca ataactagca taaccccttg  3480
gggcctctaa acgggtcttg aggggttttt tgctgaaacc tcaggcattt gagaagcaca  3540
cggtcacact gcttccggta gtcaataaac cggtaaacca gcaatagaca taagcggcta  3600
tttaacgacc ctgccctgaa c                                            3621

SEQ ID NO: 21          moltype = DNA  length = 13173
FEATURE                Location/Qualifiers
misc_feature           1..13173
                       note = Synthetic plasmid.
source                 1..13173
                       mol_type = other DNA
                       organism = synthetic construct
SEQUENCE: 21
taatgtgtaa aacatgtaca tgcagattgc tgggggtgca gggggcggag ccaccctgtc  60
catgcggggt gtggggcttg ccccgccggt acagacagtg agcaccgggg cacctagtcg  120
cggataccc ccctaggtat cggacacgta accctcccat gtcgatgcaa atctttaaca  180
ttgagtacgg gtaagctggc acgcatagcc aagctaggcg gccaccaaac accactaaaa  240
attaatagtc cctagacaag acaaaccccc gtgcgagcta ccaactcata tgcacggggg  300
ccacataacc cgaaggggtt tcaattgaca accatagcac tagctaagac aacgggcaca  360
acacccgcac aaactcgcac tgcgcaaccc cgcacaacat cggtctagg taacactgaa  420
atagaagtga acacctctaa ggaaccgcag gtcaatgagg gttctaaggt cactcgcgct  480
agggcgtggc gtaggcaaaa cgtcatgtac aagatcacca atagtaaggc tctggcgggg  540
tgccataggt ggcgcaggga cgaagctgtt gcggtgtcct ggtcgtctaa cggtgcttcg  600
cagtttgagg gtctgcaaaa ctctcactct cgctgggggt cacctctggc tgaattggaa  660
gtcatgggcg aacgccgcat tgagctggct attgctacta agaatcactt ggcggcgggt  720
ggcgcgctca tgatgtttgt gggcactgtt cgacacaacc gctcacagtc atttgcgcag  780
gttgaagcgg gtattaagac tgcgtactct tcgatggtga aaacatctca gtggaagaaa  840
gaacgtgcac ggtacggggt ggagcacacc tatagtgact atgaggtcac agactcttgg  900
gcgaacggtt ggcacttgca ccgcaacatg ctgttgttct tggatcgtcc actgtctgac  960
gatgaactca aggcgtttga ggattccatg ttttcccgct ggtctgctgg tgtggttaag  1020
gccggtatgg acgcgccact gcgtgagcac ggggtcaaac ttgatcaggt gtctacctgg  1080
ggtggagacg ctgcgaaaat ggcaacctac ctcgctaagg gcatgtctca ggaactgact  1140
ggctccgcta ctaaaaccgc gtctaagggg tcgtacacgc cgtttcagat gttggatatg  1200
ttggccgatc aaagcgacgc cggcgaggat atggacgctg ttttggtggc tcggtggcgt  1260
gagtatgagg ttggttctaa aaacctgcgt tcgtcctggt cacgtggggc taagcgtgct  1320
ttgggcattg attacataga cgctgatgta cgtcgtgaaa tggaagaaga actgtacaag  1380
ctcgccggtc tggaagcacc ggaacgggtc gaatcaaccc gcgttgctgt tgctttggtg  1440
aagcccgatg attggaaact gattcagtct gatttcgcgg ttaggcagta cgttctagat  1500
tgcgtggata aggctaagga cgtggccgct gcgcaacgtg tcgctaatga ggtgctggca  1560
agtctgggtg tggattccac cccgtgcatg atcgttatgg atgatgtgga cttggacgcg  1620
gttctgccta ctcatgggga cgctactaag cgtgatctga atgcggcggt gttcgcgggt  1680
aatgagcaga ctattcttcg caccccactaa aagcggcata aaccccgttc gatattttgt  1740
gcgatgaatt tatggtcaat gtcgcggggg caaactatga tgggtcttgt tgttgcagcc  1800
gaacgaccta gcgcagcgag tcagtgagcg aggaagcgga agagcgcctg atgcggtatt  1860
ttctccttac gcatctgtgc ggtatttcac accgcatatg gtgcactctc agtacaatct  1920
gctctgatgc cgcatagtta agccagtata cactccgcta tcgctacgtg actgggtcat  1980
ggctgcgccc cgacacccgc caacacccgc tgacgcgccc tgacgggctt gtctgctccc  2040
ggcatccgct tacagacaag ctgtgaccgt ctccgggagc tgcatgtgtc agaggttttc  2100
accgtcatca ccgaaacgcg cgaggcagca gatcaattcg cgcgcgaagg cgaagcggca  2160
tgcataatgt gcctgtcaaa tggacgaagc agggattctg caaaccctat gctactccgt  2220
caagccgtca attgtctgat tcgttaccaa ttatgacaac ttgacggcta catcattcac  2280
tttttcttca caaccggcac ggaactcgct cgggctggcc ccggtgcatt ttttaaatac  2340
ccgcgagaaa tagagttgat cgtcaaaacc aacattgcga ccgacggtgg cgataggcat  2400
ccgggtggtg ctcaaaagca gcttcgcctg gctgatacgt tggtcctcgc gccagcttaa  2460
gacgctaatc cctaactgct ggcggaaaag atgtgacaga cgcgacggcg acaagcaaac  2520
atgctgtgcg acgctggcga tatcaaaatt gctgtctgcc aggtgatcgc tgatgtactg  2580
acaagcctcg cgtacccgat tatccatcgg tggatggagc gactcgttaa tcgcttccat  2640
gcgccgcagt aacaattgct caagcagatt tatcgccagc agctccgaat agcgcccttc  2700
cccttgcccg gcgttaatga tttgcccaaa caggtcgctg aaatgcggct ggtgcgcttc  2760
atccgggcga aagaaccccg tattggcaaa tattgacggc cagttaagcc attcatgcca  2820
gtaggcgcgc ggacgaaagt aaacccactg gtgataccat tcgcgagcct ccggatgacg  2880
accgtagtga tgaatctctc ctggcgggaa cagcaaaata tcacccggtc ggcaaacaaa  2940
ttctcgtccc tgatttttca ccaccccctg accgcgaatg gtgagattga gaatataacc  3000
tttcattccc agcggtcggt cgataaaaaa atcgagataa ccgttggcct caatcggcgt  3060
taaacccgcc accagatggg cattaaacga gtatcccggc agcaggggat catttgcgc  3120
ttcagccata cttttcatac tcccgccatt cagagaagaa accaattgtc catattgcat  3180
```

```
cagacattgc cgtcactgcg tcttttactg gctcttctcg ctaaccaaac cggtaacccc  3240
gcttattaaa agcattctgt aacaaagcgg gaccaaagcc atgacaaaaa cgcgtaacaa  3300
aagtgtctat aatcacggca gaaaagtcca cattgattat ttgcacggcg tcacactttg  3360
ctatgccata gcatttttat ccataagatt agcggatcct acctgacgct tttatcgca  3420
actctctact gtttctccat acccgttttt ttgggcgacc tcgtcggagg ttgtatgtcc  3480
ggtgttccgt gacgtcatcg ggcattcatc attcatagaa tgtgttacgg aggaaacaag  3540
taatggcact tagcaccgca accaaggccg cgacggacgc gctggctgcc aatcgggcac  3600
ccaccagcgt gaatgcacag gaagtgcacc gttggctcca gagcttcaac tgggatttca  3660
agaacaaccg gaccaagtac gccaccaagt acaagatggc gaacgagacc aaggaacagt  3720
tcaagctgat cgccaaggaa tatgcgcgca tggaggcagt caaggacgaa aggcagttcg  3780
gtagcctgca ggatgcgctg acccgcctca acgccggtgt tcgcgttcat ccgaagtgga  3840
acgagaccat gaaagtggtt tcgaacttcc tggaagtggg cgaatacaac gccatcgccg  3900
ctaccgggat gctgtgggat tccgcccagg cggcggaaca gaagaacggc tatctggccc  3960
aggtgttgga tgaaatccgc cacacccacc agtgtgccta cgtcaactac tacttcgcga  4020
agaacggcca ggacccggcc ggtcacaacg atgctcgccg cacccgtacc atcggtccgc  4080
tgtggaaggg catgaagcgc gtgttttccg acggcttcat ttccggcgac gccgtggaat  4140
gctccctcaa cctgcagctg gtgggtgagg cctgcttcac caatccgctg atcgtcgcag  4200
tgaccgaatg ggctgccgcc aacggcgatg aaatcacccc gacggtgttc ctgtcgatcg  4260
agaccgacga actgcgccac atggccaacg gttaccagac cgtcgtttcc atcgccaacg  4320
atccggcttc cgccaagtat ctcaacacgg acctgaacaa cgccttctgg acccagcaga  4380
agtacttcac gccggtgttg ggcatgctgt tcgagtatgg ctccaagttc aaggtcgagc  4440
cgtgggtcaa gacgtggaac cgctgggtgt acgaggactg gggcggcatc tggatcggcc  4500
gtctgggcaa gtacggggtg gagtcgccgc gcagcctcaa ggacgccaag caggacgctt  4560
actgggctca ccacgacctg tatctgctgg cttatgcgct gtggccgacc ggcttcttcc  4620
gtctggcgct gccggatcag gaagaaatgg agtggttcga ggccaactac cccggctggt  4680
acgaccacta cggcaagatc tacgaggaat ggcgcgcccg cggttgcgag gatccgtcct  4740
cgggcttcat cccgctgatg tggttcatcg aaaacaacca tcccatctac atcgatcgcg  4800
tgtcgcaagt gccgttctgc ccgagcttgg ccaagggcgc cagcaccctg cgcgtgcacg  4860
agtacaacgg ccagatgcac accttcagcg accagtgggg cgagcgcatg tggctggccg  4920
agccggagcg ctacgagtgc cagaacatct tcgaacagta cgaaggacgc gaactgtcgg  4980
aagtgatcgc cgaactgcac gggctgcgca gtgatggcaa gaccctgatc gcccagccgc  5040
atgtccgtgg cgacaagctg tggacgttgg acgatatcaa acgcctgaac tgcgtcttca  5100
agaacccggt gaaggcattc aattgaaacg ggtgtcgggc tccgtcacag ggcggggccc  5160
gacgcacgat cgttcgatca acctcaaacc aaaaaggaac atcgatatga gcatgttagg  5220
agaaagacgc cgcggtctga ccgatccgga aatggcggcc gtcattttga aggcgcttcc  5280
tgaagctccg ctggacggca acaacaagat gggttatttc gtcacccccc gctggaaacg  5340
cttgacggaa tatgaagccc tgaccgttta tgcgcagccc aacgccgact ggatcgccgg  5400
cggcctggac tggggcgact ggacccagaa attccacggc ggccgccctt cctggggcaa  5460
cgagaccacg gagctgcgca ccgtcgactg gttcaagcac cgtgacccgc tccgccgttg  5520
gcatgcgccg tacgtcaagg acaaggccga ggaatggcgc tacaccgacc gcttcctgca  5580
gggttactcc gccgacggtc agatccgggc gatgaacccg acctggcggg acgagttcat  5640
caaccggtat tggggcgcct tcctgttcaa cgaatacgga ttgttcaacg ctcattcgca  5700
gggcgcccgg gaggcgctgt cggacgtaac ccgcgtcagc ctggctttct ggggcttcga  5760
caagatcgac atcgcccaga tgatccaact cgaacggggt ttcctcgcca agatcgtacc  5820
cggtttcgac gagtccacag cggtgccgaa ggccgaatgg acgaacgggg aggtctacaa  5880
gagcgcccgt ctggccgtgg aagggctgtg gcaggaggtg ttcgactgga acgagagcgc  5940
tttctcggtg cacgccgtct atgacgcgct gttcggtcag ttcgtccgcc gcgagttctt  6000
tcagcggctg gctccccgct tcggcgacaa tctgacgcca ttcttcatca accaggccca  6060
gacatacttc cagatcgcca agcagggcgt acaggatctg tattacaact gtctgggtga  6120
cgatccggag ttcagcgatt acaaccgtac cgtgatgcgc aactggaccg gcaagtggct  6180
ggagcccacg atcgccgctc tgcgcgactt catggggctg tttgcgaagc tgccggcggg  6240
caccactgac aaggaagaaa tcaccgcgtc cctgtaccgg gtggtcgacg actggatcga  6300
ggactacgcc agcaggatcg acttcaaggc ggaccgcgat cagatcgtta aagcggttct  6360
ggcaggattg aaataataga ggaactatta cgatgagcgt aaacagcaac gcatacgacg  6420
ccggcatcat gggcctgaaa ggcaaggact tcgccgatca gttctttgcc gacgaaaacc  6480
aagtggtcca tgaaagcgac acggtcgttc tggtcctcaa gaagtcggac gagatcaata  6540
cctttatcga ggagatcctt ctgacggact acaagaagaa cgtcaatccg acggtaaacg  6600
tggaagaccg cgcgggttac tggtggatca aggccaacgg caagatcgag gtcgattgcg  6660
acgagatttc cgagctgttg ggcggcagt tcaacgtcta cgacttcctc gtcgacgttt  6720
cctccaccat cggccgggcc tataccctgg gcaacaagtt caccattacc agtgagctga  6780
tgggcctgga ccgcaagctc gaagactatc acgcttaagg agaatgacat ggcgaaactg  6840
ggtatacaca gcaacgacac ccgcgacgcc tgggtgaaca agatcgcgca gctcaacacc  6900
ctggaaaaag cggccgagat gctgaagcag ttccggatgg accacaccac gccgttccgc  6960
aacagctacg aactggacaa cgactacctc tggatcgagg ccaagctcga agagaaggtc  7020
gccgtcctca aggcacgcgc cttcaacgag gtggacttcc gtcataagac cgctttcggc  7080
gaggatgcca agtccgttct ggacggcacc gtcgcgaaga tgaacgcggc caaggacaag  7140
tgggaggcgg agaagatcca tatcggtttc cgccaggcct acaagccgcc gatcatgccg  7200
gtgaactatt tcctggacgg cgagcgtcag ttggggaccc ggctgatgga actgcgcaac  7260
ctcaactact acgacacgcc gctggaagaa ctgcgcaaac agcgcggtgt gcgggtggtg  7320
catctgcagt cgccgcactg aagggaggaa gtctcgccct ggacgcgacg gcatcgccgt  7380
gaagtccagg gggcagggat gccgttccgg gccggcaggc tggcccggaa tctctggttt  7440
tcagggggcg tgccggtcca cggctccccc ctccatcttt cgtaaggaaa tcaccatggt  7500
cgaatcggca tttcagccat tttcgggcga cgcagacgaa tggttcgagg aaccacggcc  7560
ccaggccggt ttcttccctt ccgcggactg gcatctgctc aaacgggacg agacctacgc  7620
agcctatgcc aaggatctcg atttcatgtg gcggtgggtc atcgtccggg aagaaaggat  7680
cgtccaggag ggttgctcga tcagcctgga gtcgtcgatc cgcgccgtga cgcacgtact  7740
gaattatttt ggtatgaccg aacaacgcgc cccggcagag gaccggaccg gcggagttca  7800
acattgaaca ggtaagttta tgcagcgagt tcacactatc acggcggtga cggaggatgg  7860
cgaatcgctc cgcttcgaat gccgttcgga cgaggacgtc atcaccgccg ccctgcgcca  7920
```

-continued

```
gaacatcttt ctgatgtcgt cctgccggga gggcggctgt gcgacctgca aggccttgtg  7980
cagcgaaggg gactacgacc tcaagggctg cagcgttcag gcgctgccgc cggaagagga  8040
ggaggaaggg ttggtgttgt tgtgccggac ctacccgaag accgacctgg aaatcgaact  8100
gccctatacc cattgccgca tcagttttgg tgaggtcggc agtttcgagg cggaggtcgt  8160
cggcctcaac tgggtttcga gcaacaccgt ccagtttctt ttgcagaagc ggcccgacga  8220
gtgcggcaac cgtggcgtga aattcgaacc cggtcagttc atggacctga ccatccccgg  8280
caccgatgtc tcccgctcct actcgccggc gaaccttcct aatcccgaag gccgcctgga  8340
gttcctgatc cgcgtgttac cggagggacg gttttcggac tacctgcgca atgacgcgcg  8400
tgtcggacag gtcctctcgg tcaaagggcc actgggcgtg ttcggtctca aggagcgggg  8460
catggcgccg cgctatttcg tggccggcgg caccgggttg gcgccggtgg tctcgatggt  8520
gcggcagatg caggagtgga ccgcgccgaa cgagacccgc atctatttcg gtgtgaacac  8580
cgagccggaa ttgttctaca tcgacgagct caaatccctg gaacgatcga tgcgcaatct  8640
caccgtgaag gcctgtgtct ggcacccgag cggggactgg gaaggcgagc agggctcgcc  8700
catcgatgcg ttgcgggaag acctggagtc ctccgacgcc aacccggaca tttatttgtg  8760
cggtccgccg ggcatgatcg atgccgcctg cgagctggta cgcagccgcg gtatccccgg  8820
cgaacaggtc ttcttcgaaa aattcctgcc gtccggggcg gcctgaaccg gggaagtacc  8880
gtgaccaccg agcagttccc gccccaattc ctgcgtgaaa tgatcgagca gctggacgcc  8940
agcatccagg agctcgcacg caaggaaaag ggacttgcgg catccctggg cacgggccgg  9000
gtcgccgagc tcaaggaata ctgggaccac gttctcactc ccgaggagga atgggagctc  9060
aagcggacca tggacttccg cgaccgggaa ctggtgtgga tctggtcccg tctcaggcgg  9120
gcccgaacct cccgcgccaa tgccggggag gcctatatgc gccacctgtc gccggcggcg  9180
cgaaaaaacg aacaatcctg aaacggagtc gactcaacat ggcaaaggaa gtggtttaca  9240
gggggagtgc gcggcagcgc atgatgcaag gcatcgagat actcgcgcgg gcggcgatac  9300
cgacgctggg agccaccggc cccagcgtca tgatccagca ccgcgccgat ggcctgcccc  9360
ccatttcgac gcgggacggc gtcacggtgg ctaactccat cgtactcaag gaccgtgtcg  9420
cgaatctcgg tgcccggctg ctgcgggacg tcgccggcac catgtcccgc gaagcagggg  9480
atggcaccac caccgccatc gtgctggccc gccatatcgc ccgggagatg ttcaagagcc  9540
tcgccgtcgg tgccgatccc atcgctctca agcgtggtat cgaccgtgcc gtcgcccgcg  9600
tgagcgagga catcggggct cgggcctggc gcggcgacaa ggaatcggtc atcctggggg  9660
tggccgcggt ggcgaccaag ggcgagccgg gcgtgggccg gctgctgctg gaggcgctgg  9720
acgcggtcgg cgtccatggc gccgtgtcga tcgaactggg gcagcggcgc gaggacctgc  9780
tcgacgtggt cgacgggtat cgttgggaaa aaggttatct gtcgccctat tttgtgaccg  9840
atcgggctcg cgagctggcc gaactcgaag acgtctacct cttgatgacc gatcgggagg  9900
tggtcgattt catcgatttg gtacccctgc tggaggcggt gaccgaggct ggtggcagcc  9960
tcctgatcgc cgccgaccgt gtccacgaga aggcactggc cggccttttg ctcaatcacg  10020
ttcgcggcgt cttcaaggcc gtcgcggtca ccgcgcccgg gttcggcgac aagcggccga  10080
accgcctttt ggatctggcg gcgttgaccg gtgggcgggc ggtcctggaa gcccagggcg  10140
accgattgga ccgggtcacg ctggccgacc tggggcgggt gcggcgggcg gtcgtcagcg  10200
ctgacgacac cgcgctgctc ggcataccgg gcaccgaagc ctcccgggcc cgcttggagg  10260
gtttgcgcct ggaagcggag cagtaccggg cgctcaagcc cggtcaggga tcggcgacgg  10320
ggcgcttgca cgagctcgag gaaatcgagg cccggatcgt cggtctgagc ggcaagtccg  10380
cggtctaccg cgtgggcggc gtgaccgacg tggagatgaa ggagcggatg gtacggatcg  10440
aaaatgccta ccgctcggtg gtgtctgcac tggaggaggg ggtgttgccc ggcggcggtg  10500
tcgggtttct gggcagcatg cccgttttgg ccgagctgga agcgcgcgat gccgacgaag  10560
cacgcggcat cggcatcgtc cgttccgcgc tgacggagcc cctccggatc atcggagaaa  10620
attcgggact gtcaggggag gccgtcgtcg ccaaggtcat ggatcacgcc aatcccggtt  10680
ggggttacga tcaggaaagc ggaagtttct gcgacctcca cgccaggggc atttgggatg  10740
ccgccaaggt gctcaggctg gccctggaaa aagccgcgtc ggtggccggc acgtttctca  10800
ccaccgaagc cgtggtactg gagattccgg acactgacgc tttcgccggt ttcagtgcgg  10860
agtgggccgc cgcgacccgg gaggatccgc gggtctgagc ggggggatac gccctcgaat  10920
cctgggatag tcagagaccg gcatagcgta cgccgttacg cccgttctgc ttgacctggt  10980
aaagttacaa ccaattaacc aattctgatt agaaaaactc atcgagcatc aaatgaaact  11040
gcaatttatt catatcagga ttatcaatac catatttttg aaaaagccgt ttctgtaatg  11100
aaggagaaaa ctcaccgagg cagttccata ggatggcaag atcctggtat cggtctgcga  11160
ttccgactcg tccaacatca atacaaccta ttaatttccc ctcgtcaaaa ataaggttat  11220
caagtgagaa atcaccatga gtgacgactg aatccggtga gaatggcaaa agcttatgca  11280
tttctttcca gacttgttca acaggccagc cattacgctc gtcatcaaaa tcactcgcat  11340
caaccaaacc gttattcatt cgtgattgcg cctgagcgag acgaaatacg cgatcgctgt  11400
taaaaggaca attacaaaca ggaatcgaat gcaaccggcg caggaacact gccagcgcat  11460
caacaatatt ttcacctgaa tcaggatatt cttctaatac ctggaatgct gttttcccgg  11520
ggatcgcagt ggtgagtaac catgcatcat caggagtacg gataaaatgc ttgatggtcg  11580
gaagaggcat aaattccgtc agccagttta gtctgaccat ctcatctgta acatcattgg  11640
caacgctacc tttgccatgt ttcagaaaca actctggcgc atcgggcttc ccatacaatc  11700
gatagattgt cgcacctgat tgcccgacat tatcgcgagc ccatttatac ccatataaat  11760
cagcatccat gttggaattt aatcgcggcc tcgagcaaga cgtttcccgt tgaatatggc  11820
tcataacacc ccttgtatta ctgtttatgt aagcagacag ttttattgtt catgatgata  11880
tatttttatc ttgtgcaatg taacatcaga gattttgaga cacaacgtgg ctttgttgaa  11940
taaatcgaac ttttgctgag ttgaaggatc agatcacgca tcttcccgac aacgcagacc  12000
gttccgtggc aaagcaaaag ttcaaaatca ccaactggtc cacctacaac aaagctctca  12060
tcaaccgtgg ctccctcact ttctggctgg atgatggggc gattcaggcc tggtatgagt  12120
cagcaacacc ttcttcacga ggcagacctc agcgctagcg gagtgtatac tggcttacta  12180
tgttggcact gatgagggtg tcagtgaagt gcttcatgtg gcaggagaaa aaaggctgca  12240
ccggtgcgtc agcagaatat gtgatacagg atatattccg cttcctcgct cactgactcg  12300
ctacgctcgg tcgttcgact gcggcgagcg gaaatggctt acgaacgggg cggagatttc  12360
ctggaagatg ccaggaagat acttaacagg gaagtgagag ggccgcggca aagccgtttt  12420
tccataggct ccgcccccct gacaagcatc acgaaatctg acgctcaaat cagtggtggc  12480
gaaacccgac aggactataa agataccagg cgtttccccc tggcggctcc ctcgtgcgct  12540
ctcctgttcc tgcctttcgg tttaccggtg tcattccgct gttatggccg cgtttgtctc  12600
attccacgcc tgacactcag ttccgggtag gcagttcgct ccaagctgga ctgtatgcac  12660
```

```
gaacccccg ttcagtccga ccgctgcgcc ttatccggta actatcgtct tgagtccaac  12720
ccggaaagac atgcaaaagc accactggca gcagccactg gtaattgatt tagaggagtt  12780
agtcttgaag tcatgcgccg gttaaggcta aactgaaagg acaagttttg gtgactgcgc  12840
tcctccaagc cagttacctc ggttcaaaga gttggtagct cagagaacct tcgaaaaacc  12900
gccctgcaag gcggtttttt cgttttcaga gcaagagatt acgcgcagac caaaacgatc  12960
tcaagaagat catcttatta aggggtctga cgctcagtgg aacgaaaact cacgttaagg  13020
gattttggtc atgagattat caaaaaggat cttcacctag atccttttaa attaaaaatg  13080
aagttttaaa tcaatctaaa gtatatatga gtaaacttgg tctgacaggt gagctgatac  13140
cgctcgccgc atgcacatgc agtcatgtcg tgc                              13173

SEQ ID NO: 22          moltype = DNA  length = 11223
FEATURE                Location/Qualifiers
misc_feature           1..11223
                       note = Synthetic plasmid.
source                 1..11223
                       mol_type = other DNA
                       organism = synthetic construct
SEQUENCE: 22
taatgtgtaa aacatgtaca tgcagattgc tgggggtgca gggggcggag ccaccctgtc  60
catgcggggt gtggggcttg ccccgccggt acagacagtg agcaccgggg cacctagtcg  120
cggatacccc ccctaggtat cggacacgta accctcccat gtcgatgcaa atctttaaca  180
ttgagtacgg gtaagctggc acgcatagcc aagctaggcg gccaccaaac accactaaaa  240
attaatagtc cctagacaag acaaaccccc gtgcgagcta ccaactcata tgcacggggg  300
ccacataacc cgaaggggtt tcaattgaca accatagcac tagctaagac aacgggcaca  360
acacccgcac aaactcgcac tgcgcaaccc cgcacaacat cgggtctagg taacactgaa  420
atagaagtga acacctctaa ggaaccgcag gtcaatgagg gttctaaggt cactcgcgct  480
agggcgtggc gtaggcaaaa cgtcatgtac aagatcacca atagtaaggc tctggcgggg  540
tgccataggt ggcgcaggga cgaagctgtt gcggtgtcct ggtcgtctaa cggtgcttcg  600
cagtttgagg gtctgcaaaa ctctcactct cgctgggggt cacctctggc tgaattggaa  660
gtcatgggcg aacgccgcat tgagctggct attgctacta agaatcactt ggcggcgggt  720
ggcgcgctca tgatgtttgt gggcactgtt cgacacaacc gctcacagtc atttgcgcag  780
gttgaagcgg gtattaagac tgcgtactct tcgatggtga aaacatctca gtggaagaaa  840
gaacgtgcac ggtacggggt ggagcacacc tatagtgact atgaggtcac agactcttgg  900
gcgaacggtt ggcacttgca ccgcaacatg ctgttgttct tggatcgtcc actgtctgac  960
gatgaactca aggcgtttga ggattccatg ttttcccgct ggtctgctgg tgtggttaag  1020
gccggtatgg acgcgccact gcgtgagcac ggggtcaaac ttgatcaggt gtctacctgg  1080
ggtggagacg ctgcgaaaat ggcaacctac ctcgctaagg gcatgtctca ggaactgact  1140
ggctccgcta ctaaaaccgc gtctaagggg tcgtacacgc cgtttcagat gttggatatg  1200
ttggccgatc aaagcgacgc cggcgaggat atggacgctg ttttggtggc tcggtggcgt  1260
gagtatgagg ttggttctaa aaacctgcgt tcgtcctggt cacgtggggc taagcgtgct  1320
ttgggcattg attacataga cgctgatgta cgtcgtgaaa tggaagaaga actgtacaag  1380
ctcgccggtc tggaagcacc ggaacgggtc gaatcaaccc gcgttgctgt tgctttggtg  1440
aagcccgatg attggaaact gattcagtct gatttcgcgg ttaggcagta cgttctagat  1500
tgcgtggata aggctaagga cgtggccgct gcgcaacgtg tcgctaatga ggtgctggca  1560
agtctgggtg tggattccac cccgtgcatg atcgttatgg atgatgtgga cttggacgcg  1620
gttctgccta ctcatgggga cgctactaag cgtgatctga atgcggcggt gttcgcgggt  1680
aatgagcaga ctattcttcg cacccactaa aagcggcata aaccccgttc gatattttgt  1740
gcgatgaatt tatggtcaat gtcgcggggg caaactatga tgggtcttgt tgttgcagcc  1800
gaacgaccta gcgcagcgag tcagtgagcg aggaagcgga agagcgcctg atgcggtatt  1860
ttctccttac gcatctgtgc ggtatttcac accgcatatg gtgcactctc agtacaatct  1920
gctctgatgc cgcatagtta agccagtata cactccgcta tcgctacgtg actgggtcat  1980
ggctgcgccc cgacacccgc caacacccgc tgacgcgccc tgacgggctt gtctgctccc  2040
ggcatccgct tacagacaag ctgtgaccgt ctccgggagc tgcatgtgtc agaggttttc  2100
accgtcatca ccgaaacgcg cgaggcagca gatcaattcg cgcgcgaagg cgaagcggca  2160
tgcataatgt gcctgtcaaa tggacgaagc agggattctg caaaccctat gctactccgt  2220
caagccgtca attgtctgat tcgttaccaa ttatgacaac ttgacggcta catcattcac  2280
tttttcttca caaccggcac ggaactcgct cgggctggcc ccggtgcatt ttttaaatac  2340
ccgcgagaaa tagagttgat cgtcaaaacc aacattgcga ccgacggtgg cgataggcat  2400
ccgggtggtg ctcaaaagca gcttcgcctg gctgatacgt tggtcctcgc gccagcttaa  2460
gacgctaatc cctaactgct ggcggaaaag atgtgacaga cgcgacggcg acaagcaaac  2520
atgctgtgcg acgctggcga tatcaaaatt gctgtctgcc aggtgatcgc tgatgtactg  2580
acaagcctcg cgtacccgat tatccatcgg tggatggagc gactcgttaa tcgcttccat  2640
gcgccgcagt aacaattgct caagcagatt tatcgccagc agctccgaat agcgcccttc  2700
cccttgcccg gcgttaatga tttgcccaaa caggtcgctg aaatgcggct ggtgcgcttc  2760
atccgggcga aagaaccccg tattggcaaa tattgacggc cagttaagcc attcatgcca  2820
gtaggcgcgc ggacgaaagt aaacccactg gtgataccat tcgcgagcct ccggatgacg  2880
accgtagtga tgaatctctc ctggcgggaa cagcaaaata tcacccggtc ggcaaacaaa  2940
ttctcgtccc tgatttttca ccaccccctg accgcgaatg gtgagattga gaatataacc  3000
tttcattccc agcggtcggt cgataaaaaa atcgagataa ccgttggcct caatcggcgt  3060
taaacccgcc accagatggg cattaaacga gtatcccggc agcaggggat cattttgcgc  3120
ttcagccata cttttcatac tcccgccatt cagagaagaa accaattgtc catattgcat  3180
cagacattgc cgtcactgcg tcttttactg gctcttctcg ctaaccaaac cggtaacccc  3240
gcttattaaa agcattctgt aacaaagcgg gaccaaagcc atgacaaaaa cgcgtaacaa  3300
aagtgtctat aatcacggca gaaaagtcca cattgattat ttgcacggcg tcacactttg  3360
ctatgccata gcatttttat ccataagatt agcggatcct acctgacgct ttttatcgca  3420
actctctact gtttctccat acccgttttt ttgggcgacc tcgtcggagg ttgtatgtcc  3480
ggtgttccgt gacgtcatcg ggcattcatc attcatagaa tgtgttacgg aggaaacaag  3540
taatggcact tagcaccgca accaaggccg cgacggacgc gctggctgcc aatcgggcac  3600
ccaccagcgt gaatgcacag gaagtgcacc gttggctcca gagcttcaac tgggatttca  3660
```

agaacaaccg gaccaagtac gccaccaagt acaagatggc gaacgagacc aaggaacagt 3720
tcaagctgat cgccaaggaa tatgcgcgca tggaggcagt caaggacgaa aggcagttcg 3780
gtagcctgca ggatgcgctg acccgcctca acgccggtgt tcgcgttcat ccgaagtgga 3840
acgagaccat gaaagtggtt tcgaacttcc tggaagtggg cgaatacaac gccatcgccg 3900
ctaccgggat gctgtgggat tccgcccagg cggcggaaca gaagaacggc tatctggccc 3960
aggtgttgga tgaaatccgc cacacccacc agtgtgccta cgtcaactac tacttcgcga 4020
agaacggcca ggacccggcc ggtcacaacg atgctcgccg cacccgtacc atcggtccgc 4080
tgtggaaggg catgaagcgc gtgttttccg acggcttcat ttccggcgac gccgtggaat 4140
gctccctcaa cctgcagctg gtgggtgagg cctgcttcac caatccgctg atcgtcgcag 4200
tgaccgaatg ggctgccgcc aacggcgatg aaatcacccc gacggtgttc ctgtcgatcg 4260
agaccgacga actgcgccac atggccaacg gttaccagac cgtcgtttcc atcgccaacg 4320
atccggcttc cgccaagtat ctcaacacgg acctgaacaa cgccttctgg acccagcaga 4380
agtacttcac gccggtgttg ggcatgctgt tcgagtatgg ctccaagttc aaggtcgagc 4440
cgtgggtcaa gacgtggaac cgctgggtgt acgaggactg gggcggcatc tggatcggcc 4500
gtctgggcaa gtacggggtg gagtcgccgc gcagcctcaa ggacgccaag caggacgctt 4560
actgggctca ccacgacctg tatctgctgg cttatgcgct gtggccgacc ggcttcttcc 4620
gtctggcgct gccggatcag gaagaaatgg agtggttcga ggccaactac cccggctggt 4680
acgaccacta cggcaagatc tacgaggaat ggcgcgcccg cggttgcgag gatccgtcct 4740
cgggcttcat cccgctgatg tggttcatcg aaaacaacca tcccatctac atcgatcgcg 4800
tgtcgcaagt gccgttctgc ccgagcttgg ccaagggcgc cagcaccctg cgcgtgcacg 4860
agtacaacgg ccagatgcac accttcagcg accagtgggg cgagcgcatg tggctggccg 4920
agccggagcg ctacgagtgc cagaacatct tcgaacagta cgaaggacgc gaactgtcgg 4980
aagtgatcgc cgaactgcac gggctgcgca gtgatggcaa gaccctgatc gcccagccgc 5040
atgtccgtgg cgacaagctg tggacgttgg acgatatcaa acgcctgaac tgcgtcttca 5100
agaacccggt gaaggcattc aattgaaacg ggtgtcgggc tccgtcacag ggcggggccc 5160
gacgcacgat cgttcgatca acctcaaacc aaaaaggaac atcgatatga gcatgttagg 5220
agaaagacgc cgcggtctga ccgatccgga aatggcggcc gtcattttga aggcgcttcc 5280
tgaagctccg ctggacggca acaacaagat gggttatttc gtcacccccc gctggaaacg 5340
cttgacggaa tatgaagccc tgaccgttta tgcgcagccc aacgccgact ggatcgccgg 5400
cggcctggac tggggcgact ggacccagaa attccacggc ggccgccctt cctggggcaa 5460
cgagaccacg gagctgcgca ccgtcgactg gttcaagcac cgtgacccgc tccgccgttg 5520
gcatgcgccg tacgtcaagg acaaggccga ggaatggcgc tacaccgacc gcttcctgca 5580
gggttactcc gccgacggtc agatccgggc gatgaacccg acctggcggg acgagttcat 5640
caaccggtat tggggcgcct tcctgttcaa cgaatacgga ttgttcaacg ctcattcgca 5700
gggcgcccgg gaggcgctgt cggacgtaac ccgcgtcagc ctggctttct ggggcttcga 5760
caagatcgac atcgcccaga tgatccaact cgaacggggt ttcctcgcca agatcgtacc 5820
cggtttcgac gagtccacag cggtgccgaa ggccgaatgg acgaacgggg aggtctacaa 5880
gagcgcccgt ctggccgtgg aagggctgtg gcaggaggtg ttcgactgga acgagagcgc 5940
tttctcggtg cacgccgtct atgacgcgct gttcggtcag ttcgtccgcc gcgagttctt 6000
tcagcggctg gctccccgct tcggcgacaa tctgacgcca ttcttcatca accaggccca 6060
gacatacttc cagatcgcca agcagggcgt acaggatctg tattacaact gtctgggtga 6120
cgatccggag ttcagcgatt acaaccgtac cgtgatgcgc aactggaccg gcaagtggct 6180
ggagcccacg atcgccgctc tgcgcgactt catggggctg tttgcgaagc tgccggcggg 6240
caccactgac aaggaagaaa tcaccgcgtc cctgtaccgg gtggtcgacg actggatcga 6300
ggactacgcc agcaggatcg acttcaaggc ggaccgcgat cagatcgtta aagcggttct 6360
ggcaggattg aaataataga ggaactatta cgatgagcgt aaacagcaac gcatacgacg 6420
ccggcatcat gggcctgaaa ggcaaggact tcgccgatca gttctttgcc gacgaaaacc 6480
aagtggtcca tgaaagcgac acggtcgttc tggtcctcaa gaagtcggac gagatcaata 6540
cctttatcga ggagatcctt ctgacggact acaagaagaa cgtcaatccg acggtaaacg 6600
tggaagaccg cgcgggttac tggtggatca aggccaacgg caagatcgag gtcgattgcg 6660
acgagatttc cgagctgttg ggcggcagt tcaacgtcta cgacttcctc gtcgacgttt 6720
cctccaccat cggccgggcc tataccctgg gcaacaagtt caccattacc agtgagctga 6780
tgggcctgga ccgcaagctc gaagactatc acgcttaagg agaatgacat ggcgaaactg 6840
ggtatacaca gcaacgacac ccgcgacgcc tgggtgaaca agatcgcgca gctcaacacc 6900
ctggaaaaag cggccgagat gctgaagcag ttccggatgg accacaccac gccgttccgc 6960
aacagctacg aactggacaa cgactacctc tggatcgagg ccaagctcga agagaaggtc 7020
gccgtcctca aggcacgcgc cttcaacgag gtggacttcc gtcataagac cgctttcggc 7080
gaggatgcca agtccgttct ggacggcacc gtcgcgaaga tgaacgcggc caaggacaag 7140
tgggaggcgg agaagatcca tatcggtttc cgccaggcct acaagccgcc gatcatgccg 7200
gtgaactatt tcctggacgg cgagcgtcag ttggggaccc ggctgatgga actgcgcaac 7260
ctcaactact acgacacgcc gctggaagaa ctgcgcaaac agcgcggtgt gcgggtggtg 7320
catctgcagt cgccgcactg aagggaggaa gtctcgccct ggacgcgacg gcatcgccgt 7380
gaagtccagg gggcagggat gccgttccgg gccggcaggc tggcccggaa tctctggttt 7440
tcaggggcg tgccggtcca cggctccccc ctccatcttt cgtaaggaaa tcaccatggt 7500
cgaatcggca tttcagccat tttcgggcga cgcagacgaa tggttcgagg aaccacggcc 7560
ccaggccggt ttcttccctt ccgcggactg gcatctgctc aaacgggacg agacctacgc 7620
agcctatgcc aaggatctcg atttcatgtg gcggtgggtc atcgtccggg aagaaaggat 7680
cgtccaggag ggttgctcga tcagcctgga gtcgtcgatc cgcgccgtga cgcacgtact 7740
gaattatttt ggtatgaccg aacaacgcgc cccggcagag gaccggaccg gcggagttca 7800
acattgaaca ggtaagttta tgcagcgagt tcacactatc acggcggtga cggaggatgg 7860
cgaatcgctc cgcttcgaat gccgttcgga cgaggacgtc atcaccgccg ccctgcgcca 7920
gaacatcttt ctgatgtcgt cctgccggga gggcggctgt gcgacctgca aggccttgtg 7980
cagcgaaggg gactacgacc tcaagggctg cagcgttcag gcgctgccgc cggaagagga 8040
ggaggaaggg ttggtgttgt tgtgccggac ctacccgaag accgacctgg aaatcgaact 8100
gccctatacc cattgccgca tcagttttgg tgaggtcggc agtttcgagg cggaggtcgt 8160
cggcctcaac tgggtttcga gcaacaccgt ccagtttctt ttgcagaagc ggcccgacga 8220
gtgcggcaac cgtggcgtga aattcgaacc cggtcagttc atggacctga ccatccccgg 8280
caccgatgtc tcccgctcct actcgccggc gaaccttcct aatcccgaag gccgcctgga 8340
gttcctgatc cgcgtgttac cggagggacg gttttcggac tacctgcgca atgacgcgcg 8400

```
tgtcggacag gtcctctcgg tcaaagggcc actgggcgtg ttcggtctca aggagcgggg  8460
catggcgccg cgctatttcg tggccggcgg caccgggttg gcgccggtgg tctcgatggt  8520
gcggcagatg caggagtgga ccgcgccgaa cgagacccgc atctatttcg gtgtgaacac  8580
cgagccggaa ttgttctaca tcgacgagct caaatccctg gaacgatcga tgcgcaatct  8640
caccgtgaag gcctgtgtct ggcacccgag cggggactgg gaaggcgagc agggctcgcc  8700
catcgatgcg ttgcgggaag acctggagtc ctccgacgcc aacccggaca tttatttgtg  8760
cggtccgccg ggcatgatcg atgccgcctg cgagctggta cgcagccgcg gtatccccgg  8820
cgaacaggtc ttcttcgaaa aattcctgcc gtccggggcg gcctgaaccg gggaagtacc  8880
gtgaccaccg agcagttccc gccccaattc ctgcgtgaaa tgatcgagca gctggacgcc  8940
agcatccagg agctcgcacg caaggaaaag ggacttgcgg catccctggg cacgggccgg  9000
gtcgccgagc tcaaggaata ctgggaccac gttgttacaa ccaattaacc aattctgatt  9060
agaaaaactc atcgagcatc aaatgaaact gcaatttatt catatcagga ttatcaatac  9120
catatttttg aaaaagccgt ttctgtaatg aaggagaaaa ctcaccgagg cagttccata  9180
ggatggcaag atcctggtat cggtctgcga ttccgactcg tccaacatca atacaaccta  9240
ttaatttccc ctcgtcaaaa ataaggttat caagtgagaa atcaccatga gtgacgactg  9300
aatccggtga gaatggcaaa agcttatgca tttctttcca gacttgttca acaggccagc  9360
cattacgctc gtcatcaaaa tcactcgcat caaccaaacc gttattcatt cgtgattgcg  9420
cctgagcgag acgaaatacg cgatcgctgt taaaaggaca attacaaaca ggaatcgaat  9480
gcaaccggcg caggaacact gccagcgcat caacaatatt ttcacctgaa tcaggatatt  9540
cttctaatac ctggaatgct gttttcccgg ggatcgcagt ggtgagtaac catgcatcat  9600
caggagtacg gataaaatgc ttgatggtcg gaagaggcat aaattccgtc agccagttta  9660
gtctgaccat ctcatctgta acatcattgg caacgctacc tttgccatgt ttcagaaaca  9720
actctggcgc atcgggcttc ccatacaatc gatagattgt cgcacctgat tgcccgacat  9780
tatcgcgagc ccatttatac ccatataaat cagcatccat gttggaattt aatcgcggcc  9840
tcgagcaaga cgtttcccgt tgaatatggc tcataacacc ccttgtatta ctgtttatgt  9900
aagcagacag ttttattgtt catgatgata tatttttatc ttgtgcaatg taacatcaga  9960
gattttgaga cacaacgtgg ctttgttgaa taaatcgaac ttttgctgag ttgaaggatc  10020
agatcacgca tcttcccgac aacgcagacc gttccgtggc aaagcaaaag ttcaaaatca  10080
ccaactggtc cacctacaac aaagctctca tcaaccgtgg ctccctcact ttctggctgg  10140
atgatggggc gattcaggcc tggtatgagt cagcaacacc ttcttcacga ggcagacctc  10200
agcgctagcg gagtgtatac tggcttacta tgttggcact gatgagggtg tcagtgaagt  10260
gcttcatgtg gcaggagaaa aaaggctgca ccggtgcgtc agcagaatat gtgatacagg  10320
atatattccg cttcctcgct cactgactcg ctacgctcgg tcgttcgact gcggcgagcg  10380
gaaatggctt acgaacgggg cggagatttc ctggaagatg ccaggaagat acttaacagg  10440
gaagtgagag ggccgcggca aagccgtttt tccataggct ccgcccccct gacaagcatc  10500
acgaaatctg acgctcaaat cagtggtggc gaaacccgac aggactataa agataccagg  10560
cgtttccccc tggcggctcc ctcgtgcgct ctcctgttcc tgcctttcgg tttaccggtg  10620
tcattccgct gttatggccg cgtttgtctc attccacgcc tgacactcag ttccgggtag  10680
gcagttcgct ccaagctgga ctgtatgcac gaaccccccg ttcagtccga ccgctgcgcc  10740
ttatccggta actatcgtct tgagtccaac ccggaaagac atgcaaaagc accactggca  10800
gcagccactg gtaattgatt tagaggagtt agtcttgaag tcatgcgccg gttaaggcta  10860
aactgaaagg acaagttttg gtgactgcgc tcctccaagc cagttacctc ggttcaaaga  10920
gttggtagct cagagaacct tcgaaaaacc gccctgcaag gcggtttttt cgttttcaga  10980
gcaagagatt acgcgcagac caaaacgatc tcaagaagat catcttatta aggggtctga  11040
cgctcagtgg aacgaaaact cacgttaagg gattttggtc atgagattat caaaaaggat  11100
cttcacctag atccttttaa attaaaaatg aagttttaaa tcaatctaaa gtatatatga  11160
gtaaacttgg tctgacaggt gagctgatac cgctcgccgc atgcacatgc agtcatgtcg  11220
tgc                                                                11223
```

```
SEQ ID NO: 23           moltype = DNA  length = 6963
FEATURE                 Location/Qualifiers
misc_feature            1..6963
                        note = Synthetic plasmid.
source                  1..6963
                        mol_type = other DNA
                        organism = synthetic construct
SEQUENCE: 23
ccgacaccat cgaatggtgc aaaacctttc gcggtatggc atgatagcgc ccggaagaga  60
gtcaattcag ggtggtgaat gtgaaaccag taacgttata cgatgtcgca gagtatgccg  120
gtgtctctta tcagaccgtt tcccgcgtgg tgaaccaggc cagccacgtt tctgcgaaaa  180
cgcgggaaaa agtggaagcg gcgatggcgg agctgaatta cattcccaac cgcgtggcac  240
aacaactggc gggcaaacag tcgttgctga ttggcgttgc cacctccagt ctggccctgc  300
acgcgccgtc gcaaattgtc gcggcgatta aatctcgcgc cgatcaactg ggtgccagcg  360
tggtggtgtc gatggtagaa cgaagcggcg tcgaagcctg taaagcggcg gtgcacaatc  420
ttctcgcgca acgcgtcagt gggctgatca ttaactatcc gctggatgac caggatgcca  480
ttgctgtgga agctgcctgc actaatgttc cggcgttatt tcttgatgtc tctgaccaga  540
cacccatcaa cagtattatt ttctcccatg aagacggtac gcgactgggc gtggagcatc  600
tggtcgcatt gggtcaccag caaatcgcgc tgttagcggg cccattaagt tctgtctcgg  660
cgcgtctgcg tctggctggc tggcataaat atctcactcg caatcaaatt cagccgatag  720
cggaacggga aggcgactgg agtgccatgt ccggttttca acaaaccatg caaatgctga  780
atgagggcat cgttcccact gcgatgctgg ttgccaacga tcagatggcg ctgggcgcaa  840
tgcgcgccat taccgagtcc gggctgcgcg ttggtgcgga tatttcggta gtgggatacg  900
acgataccga agacagctca tgttatatcc cgccgttaac caccatcaaa caggattttc  960
gcctgctggg gcaaaccagc gtggaccgct tgctgcaact ctctcagggc caggcggtga  1020
agggcaatca gctgttgccc gtctcactgg tgaaaagaaa aaccaccctg gcgcccaata  1080
cgcaaaccgc ctctccccgc gcgttggccg attcattaat gcagctggca cgacaggttt  1140
cccgactgga aagcgggcag tgagcgcaac gcaattaatg taagttagct cactcattag  1200
gcacaattct catgtttgac agcttatcat cgactgcacg gtgcaccaat gcttctggcg  1260
tcaggcagcc atcggaagct gtggtatggc tgtgcaggtc gtaaatcact gcataattcg  1320
```

```
tgtcgctcaa ggcgcactcc cgttctggat aatgtttttt gcgccgacat cataacggtt  1380
ctggcaaata ttctgaaatg agctgttgac aattaatcat cggctcgtat aatgtgtgga  1440
attgtgagcg gataacaatt tcacacagga aacagccagt ccgtttaggt gttttcacga  1500
gcaattgacc aacaaggaca ctaattactg ttaggaggtt gttcatgaaa gccgccgtgg  1560
tcgagcaatt caaaaaacca ctccaggtga aagaggtcga aaaaccgaaa attagttacg  1620
gtgaagtgct ggttcgtatt aaagcttgtg gtgtctgcca caccgatctg catgccgcac  1680
acggcgattg gccggtaaaa ccgaaactgc cgctcatccc cggccatgaa ggcgtaggcg  1740
tcatcgagga agtcggcccg ggtgtgacac accttaaagt tggcgatcgt gtgggcattc  1800
cctggctgta ttcggcgtgt ggccactgtg actattgtct cagcggccag gagactctgt  1860
gcgaacgcca gcagaacgcc ggctacagcg ttgatggtgg ctacgccgag tactgtcgtg  1920
ctgcggcaga ttacgtggtg aagattcctg ataatctttc ctttgaagaa gcggcgccca  1980
ttttatgcgc gggcgttacc acttataaag cgctgaaagt caccggtgcc aaaccaggcg  2040
agtgggtggc catttatgga attgggggcc tcggccatgt ggcagttcag tacgctaaag  2100
caatgggctt aaacgtcgtg gcagtggact tgggagatga aaagctggaa ctggcaaaac  2160
aactgggcgc ggacctggta gtgaatccga aacatgatga tgcagcacaa tggattaaag  2220
aaaaagttgg tggcgtgcat gccacggtgg tgacggcagt tagtaaagcc gcttttgaat  2280
cggcgtataa gtcaatccgc cgcggaggag catgcgtcct tgttggtctg ccaccggagg  2340
aaatccccat tccgattttt gacacagttc tgaacggcgt caaaattatc ggttcaattg  2400
ttggcacccg taaagacctg caggaagccc tccagtttgc tgctgaaggc aaagtgaaaa  2460
ctatcgtgga agttcagccg cttgagaaca ttaacgacgt atttgatcgt atgctgaaag  2520
gacagattaa tggacgtgtg gtcctgaaag tggattgaca tgctaaggtg ctggctgcat  2580
gctaagttga tacgcctgct tcaaagtcta ctaggaggat aagaatggag atcatggata  2640
aggatttaca gagcatccag gaagtacgca cccttatcgc aaaggctaag aaagcacagg  2700
ccgaatttaa gaacttctct caagaggcgg ttaacaaagt cattgagaag atcgcaaaag  2760
ccacggaggt agaggccgtg aagcttgcga agttagctta tgaggataca ggatacggta  2820
aatgggagga caaggtaatt aaaaacaaat ttcctctat cgtagtatac aactatatta  2880
aagaccttaa gacggtaggt attttgaaag aggataaaga aaagaagctt atcgacatcg  2940
cggtaccatt gggggtaatc gcgggcctta ttccaagtac gaaccctact agcaccgcga  3000
ttttcaaggt attaattgca ttgaaggcgg gcaatgccat tgtgttcagc cctcacccaa  3060
cggcggttcg tagcattact gagaccgtca aaatcatgca aaaagcggcg gtcgaagcag  3120
gtgctcctga tggattaatt cagtgcatgt cgattttaac tgtcgaagga accgctgaat  3180
tgatgaagaa caaggatacc gcactgattt tagccaccgg gggcgaggga atggtacgtg  3240
ctgcctacag ttcaggcacg cctgcgatcg gtgtggggcc cggcaatggc ccttgcttta  3300
ttgagcgcac cgctgacatt cctacggctg tccgcaaagt gattggctcg gatacattcg  3360
ataatggtgt gatctgcgca tcggagcaaa gtattatcgc agagacggtt aaaaaggccg  3420
agatcattga agaattcaaa cgtcagaaag gttatttctt gaacgccgaa gaatcagaga  3480
aagtgggaaa gattttattg cgcgccaacg ggacacctaa cccagcgatc gtgggaaagg  3540
atgtccaagc attagccaag ttagcaggta tttcgatccc gagcgacgcg gttatcctgt  3600
tatctgaaca gacggacgta tcgcccaaga atccgtatgc aaaagagaaa ctggcccccgg  3660
tcttagcttt ttacactgtg gaagattggc atgaagcctg tgagaagtca ttggcccttt  3720
tgcataacca aggaagcggg cataccttaa tcattcattc tcagaacgag gaaattatcc  3780
gcgagtttgc gcttaaaaag ccagtaagtc gtatcttggt taacagcccc ggctcacttg  3840
gaggaattgg aggcgctacg aatttagtcc caagcctgac tttagggtgc ggtgcagtcg  3900
gtggttcagc caccagcgat aatgttggtc cggagaattt atttaatatc cgcaaggtgg  3960
cttatggtac gacaaccgtt gaagaaattc gtgaggcctt cggagtgggt gcagccagct  4020
caagtgcgcc cgccgagccg gaggacaatg aagacgttca agcaattgtg aaagcaatca  4080
tggccaagct taatttgtaa gtttgtcggt gaacgctctc ctgagtagga caaatccgcc  4140
gggagcggat ttgaacgttg cgaagcaacg gcccggaggg tggcgggcag gacgcccgcc  4200
ataaactgcc aggcatcaaa ttaagcagaa ggccatcctg acggatggcc tttttgcgtt  4260
tctacaaact ctttcggtcc gttgtttatt tttctaaata cattcaaata tgtatccgct  4320
catgagacaa taaccctgat aaatgcttca ataatattga aaaaggaaga gtatgagtat  4380
tcaacatttc cgtgtcgccc ttattccctt ttttgcggca ttttgccttc ctgtttttgc  4440
tcacccagaa acgctggtga aagtaaaaga tgctgaagat cagttgggtg cacgagtggg  4500
ttacatcgaa ctggatctca acagcggtaa gatccttgag agttttcgcc ccgaagaacg  4560
ttttccaatg atgagcactt ttaaagttct gctatgtggc gcggtattat cccgtgttga  4620
cgccgggcaa gagcaactcg gtcgccgcat acactattct cagaatgact tggttgagta  4680
ctcaccagtc acagaaaagc atcttacgga tggcatgaca gtaagagaat tatgcagtgc  4740
tgccataacc atgagtgata acactgcggc caacttactt ctgacaacga tcggaggacc  4800
gaaggagcta accgcttttt tgcacaacat gggggatcat gtaactcgcc ttgatcgttg  4860
ggaaccggag ctgaatgaag ccataccaaa cgacgagcgt gacaccacga tgcctgtagc  4920
aatggcaaca acgttgcgca aactattaac tggcgaacta cttactctag cttcccggca  4980
acaattaata gactggatgg aggcggataa agttgcagga ccacttctgc gctcggccct  5040
tccggctggc tggtttattg ctgataaatc tggagccggt gagcgtgggt ctcgcggtat  5100
cattgcagca ctggggccag atggtaagcc ctcccgtatc gtagttatct acacgacggg  5160
gagtcaggca actatggatg aacgaaatag acagatcgct gagataggtg cctcactgat  5220
taagcattgg taactgtcag accaagttta ctcatatata ctttagattg atttccttag  5280
gactgagcgt caaccccgta gaaaagatca aaggatcttc ttgagatcct ttttttctgc  5340
gcgtaatctg ctgcttgcaa acaaaaaaac caccgctacc agcggtggtt tgtttgccgg  5400
atcaagagct accaactctt tttccgaagg taactggctt cagcagagcg cagataccaa  5460
atactgtcct tctagtgtag ccgtagttag gccaccactt caagaactct gtagcaccgc  5520
ctacatacct cgctctgcta atcctgttac cagtggctgc tgccagtggc gataagtcgt  5580
gtcttaccgg gttggactca agacgatagt taccggataa ggcgcagcgg tcgggctgaa  5640
cggggggttc gtgcacacag cccagcttgg agcgaacgac ctacaccgaa ctgagatacc  5700
tacagcgtga gctatgagaa agcgccacgc ttcccgaagg gagaaaggcg gacaggtatc  5760
cggtaagcgg cagggtcgga acaggagagc gcacgaggga gcttccaggg ggaaacgcct  5820
ggtatcttta tagtcctgtc gggtttcgcc acctctgact tgagcgtcga tttttgtgat  5880
gctcgtcagg ggggcggagc ctatggaaaa acgccagcaa cgcggccttt ttacggttcc  5940
tggccttttg ctggcctttt gctcacatgt tctttcctgc gttatcccct gattctgtgg  6000
ataaccgtat taccgccttt gagtgagctg ataccgctcg ccgcagccga acgaccgagc  6060
```

```
gcagcgagtc agtgagcgag gaagcggaag agcgcctgat gcggtatttt ctccttacgc  6120
atctgtgcgg tatttcacac cgcatataag gtgcactgtg actgggtcat ggctgcgccc  6180
cgacacccgc caacacccgc tgacgcgccc tgacgggctt gtctgctccc ggcatccgct  6240
tacagacaag ctgtgaccgt ctccgggagc tgcatgtgtc agaggttttc accgtcatca  6300
ccgaaacgcg cgaggcagct gcggtaaagc tcatcagcgt ggtcgtgcag cgattcacag  6360
atgtctgcct gttcatccgc gtccagctcg ttgagtttct ccagaagcgt taatgtctgg  6420
cttctgataa agcgggccat gttaagggcg gttttttcct gtttggtcac tgatgcctcc  6480
gtgtaagggg gatttctgtt catgggggta atgataccga tgaaacgaga gaggatgctc  6540
acgatacggg ttactgatga tgaacatgcc cggttactgg aacgttgtga gggtaaacaa  6600
ctggcggtat ggatgcggcg ggaccagaga aaaatcactc agggtcaatg ccagcgcttc  6660
gttaatacag atgtaggtgt tccacagggt agccagcagc atcctgcgat gcagatccgg  6720
aacataatgg tgcagggcgc tgacttccgc gtttccagac tttacgaaac acggaaaccg  6780
aagaccattc atgttgttgc tcaggtcgca gacgttttgc agcagcagtc gcttcacgtt  6840
cgctcgcgta tcggtgattc attctgctaa ccagtaaggc aaccccgcca gcctagccgg  6900
gtcctcaacg acaggagcac gatcatgcgc acccgtggcc aggacccaac gctgcccgaa  6960
att                                                                6963

SEQ ID NO: 24          moltype = DNA  length = 3826
FEATURE                Location/Qualifiers
misc_feature           1..3826
                       note = Synthetic plasmid.
source                 1..3826
                       mol_type = other DNA
                       organism = synthetic construct
SEQUENCE: 24
ttcgattcct gtttgtaatt gtccttttaa cagcgatcgc gtatttcgtc tcgctcaggc  60
gcaatcacga atgaataacg gtttggttga tgcgagtgat tttgatgacg agcgtaatgg  120
ctggcctgtt gaacaagtct ggaaagaaat gcataagctt ttgccattct caccggattc  180
agtcgtcact catggtgatt tctcacttga taaccttatt tttgacgagg ggaaattaat  240
aggttgtatt gatgttggac gagtcggaat cgcagaccga taccaggatc ttgccatcct  300
atggaactgc ctcggtgagt tttctccttc attacagaaa cggctttttc aaaaatatgg  360
tattgataat cctgatatga ataaattgca gtttcatttg atgctcgatg agtttttcta  420
atcagaattg gttaattggt tgtaacccca aaaaaacggg tatggagaaa cagtagagag  480
ttgcgataaa aagcgtcagg taggatccgc taatcttatg gataaaaatg ctatggcata  540
gcaaagtgtg acgccgtgca aataatcaat gtggactttt ctgccgtgat tatagacact  600
tttgttacgc gtttttgtca tggctttggt cccgctttgt tacagaatgc ttttaataag  660
cggggttacc ggtttggtta gcgagaagag ccagtaaaag acgcagtgac ggcaatgtct  720
gatgcaatat ggacaattgg tttcttctct gaatggcggg agtatgaaaa gtatggctga  780
agcgcaaaat gatcccctgc tgccgggata ctcgtttaat gcccatctgg tggcgggttt  840
aacgccgatt gaggccaacg gttatctcga ttttttatc gaccgaccgc tgggaatgaa  900
aggttatatt ctcaatctca ccattcgcgg tcagggggtg gtgaaaaatc agggacgaga  960
atttgtttgc cgaccgggtg atattttgct gttcccgcca ggagagattc atcactacgg  1020
tcgtcatccg gaggctcgcg aatggtatca ccagtgggtt tactttcgtc cgcgcgccta  1080
ctggcatgaa tggcttaact ggccgtcaat atttgccaat acggggttct ttcgcccgga  1140
tgaagcgcac cagccgcatt tcagcgacct gtttgggcaa atcattaacg ccgggcaagg  1200
ggaagggcgc tattcggagc tgctggcgat aaatctgctt gagcaattgt tactgcggcg  1260
catggaagcg attaacgagt cgctccatcc accgatggat aatcgggtac gcgaggcttg  1320
tcagtacatc agcgatcacc tggcagacag caattttgat atcgccagcg tcgcacagca  1380
tgtttgcttg tcgccgtcgc gtctgtcaca tcttttccgc cagcagttag ggattagcgt  1440
cttaagctgg cgcgaggacc aacgtatcag ccaggcgaag ctgcttttga gcaccacccg  1500
gatgcctatc gccaccgtcg gtcgcaatgt tggttttgac gatcaactct atttctcgcg  1560
ggtatttaaa aaatgcaccg ggccagcccc gagcgagttc cgtgccggtt gtgaagaaaa  1620
agtgaatgat gtagccgtca agttgtcata attggtaacg aatcagacaa ttgacggctt  1680
gacggagtag catagggttt gcagaatccc tgcttcgtcc atttgacagg cacattatgc  1740
atgccgcttc gccttcgcgc gcgaattgat ctgctgcctc gcgcgtttcg gtgatgacgg  1800
tgaaaacctc tgacacatgc agctcccgga gacggtcaca gcttgtctgt aagcggatgc  1860
cgggagcaga caagcccgtc agggcgcgtc agcgggtgtt ggcgggtgtc ggggcgcagc  1920
catgacccag tcacgtagcg atagcggagt gtatactggc ttaactatgc ggcatcagag  1980
cagattgtac tgagagtgca ccatatgcgg tgtgaaatac cgcacagatg cgtaaggaga  2040
aaataccgca tcaggcgctc ttccgcttcc tcgctcactg actcgctgcg ctcggtcgtt  2100
cggctgcggc gagcggtatc agctcactcaaag tcagaccaag tttactcata tatactttag  2160
attgatttaa aacttcattt ttaatttaaa aggatctagg tgaagatcct ttttgataat  2220
ctcatgacca aaatccctta acgtgagttt tcgttccact gagcgtcaga ccccttaata  2280
agatgatctt cttgagatcg ttttggtctg cgcgtaatct cttgctctga aaacgaaaaa  2340
accgccttgc agggcggttt ttcgaaggtt ctctgagcta ccaactcttt gaaccgaggt  2400
aactggcttg gaggagcgca gtcaccaaaa cttgtccttt cagtttagcc ttaaccggcg  2460
catgacttca agactaactc ctctaaatca attaccagtg gctgctgcca gtggtgcttt  2520
tgcatgtctt tccgggttgg actcaagacg atagttaccg gataaggcgc agcggtcgga  2580
ctgaacgggg ggttcgtgca tacagtccag cttggagcga actgcctacc cggaactgag  2640
tgtcaggcgt ggaatgagac aaacgcggcc ataacagcgg aatgacaccg gtaaaccgaa  2700
aggcaggaac aggagagcgc acgagggagc cgccaggggg aaacgcctgg tatctttata  2760
gtcctgtcgg gtttcgccac cactgatttg agcgtcagat ttcgtgatgc ttgtcagggg  2820
ggcggagcct atggaaaaac ggctttgccg cggccctctc acttccctgt taagtatctt  2880
cctggcatct tccaggaaat ctccgccccg ttcgtaagcc atttccgctc gccgcagtcg  2940
aacgaccgag cgtagcgagt cagtgagcga ggaagcggaa tatatcctgt atcacatatt  3000
ctgctgacgc accggtgcag cctttttctt cctgccacat gaagcacttc actgacaccc  3060
tcatcagtgc caacatagta agccagtata cactccgcta gcgctgaggt ctgcctcgtg  3120
aagaaggtgt tgctgactca taccaggcct gaatcgcccc atcatccagc cagaaagtga  3180
gggagccacg gttgatgaga gctttgttgt aggtggacca gttggtgatt ttgaactttt  3240
```

```
gctttgccac ggaacggtct gcgttgtcgg gaagatgcgt gatctgatcc ttcaactcag  3300
caaaagttcg atttattcaa caaagccacg ttgtgtctca aaatctctga tgttacattg  3360
cacaagataa aaatatatca tcatgaacaa taaaactgtc tgcttacata aacagtaata  3420
caaggggtgt tatgagccat attcaacggg aaacgtcttg ctcgaggccg cgattaaatt  3480
ccaacatgga tgctgattta tatgggtata aatgggctcg cgataatgtc gggcaatcag  3540
gtgcgacaat ctatcgattg tatgggaagc ccgatgcgcc agagttgttt ctgaaacatg  3600
gcaaaggtag cgttgccaat gatgttacag atgagatggt cagactaaac tggctgacgg  3660
aatttatgcc tcttccgacc atcaagcatt ttatccgtac tcctgatgat gcatggttac  3720
tcaccactgc gatccccggg aaaacagcat tccaggtatt agaagaatat cctgattcag  3780
gtgaaaatat tgttgatgcg ctggcagtgt tcctgcgccg gttgca               3826

SEQ ID NO: 25          moltype = DNA  length = 13007
FEATURE                Location/Qualifiers
misc_feature           1..13007
                       note = Synthetic plasmid.
source                 1..13007
                       mol_type = other DNA
                       organism = synthetic construct
SEQUENCE: 25
atcatcactg aaggtctgaa agctgttgct gcgggcatga acccgatgga cctgaaacgt  60
ggtatcgaca aagcggttac cgctgcagtt gaagaactga aagcgctgtc cgtaccatgc  120
tctgactcta aagcgattgc tcaggttggt accatctccg ctaactccga cgaaaccgta  180
ggtaaactga tcgctgaagc gatggacaaa gtcggtaaag aaggcgttat caccgttgaa  240
gacggtaccg gtctgcagga cgaactggac gtggttgaag gtatgcagtt cgaccgtggc  300
tacctgtctc cttacttcat caacaagccg gaaactggcg cagtagaact ggaaagcccg  360
ttcatcctgc tggctgacaa gaaaatctcc aacatccgcg aaatgctgcc ggttctggaa  420
gctgttgcca aagcaggcaa accgctgctg atcatcgctg aagatgtaga aggcgaagcg  480
ctggcaactc tggttgttaa caccatgcgt ggcatcgtga aagtcgctgc ggttaaagca  540
ccgggcttcg gcgatcgtcg taaagctatg ctgcaggata tcgcaaccct gactggcggt  600
accgtgatct ctgaagagat cggtatggag ctggaaaaag caaccctgga agacctgggt  660
caggctaaac gtgttgtgat caacaaagac accaccacta tcatcgatgg cgtgggtgaa  720
gaagctgcaa tccagggccg tgttgctcag atccgtcagc agattgaaga agcaacttct  780
gactacgacc gtgaaaaact gcaggaacgc gtagcgaaac tggcaggcgg cgttgcagtt  840
atcaaagtgg gtgctgctac cgaagttgaa atgaaagaga aaaaagcacg cgttgaagat  900
gccctgcacg cgacccgtgc tgcggtagaa gaaggcgtgg ttgctggtgg tggtgttgcg  960
ctgatccgcg tagcgtctaa actggctgac ctgcgtggtc agaacgaaga ccagaacgtg  1020
ggtatcaaag ttgcactgcg tgcaatggaa gctccgctgc gtcagatcgt attgaactgc  1080
ggcgaagaac cgtctgttgt tgctaacacc gttaaaggcg gcgacggcaa ctacggttac  1140
aacgcagcaa ccgaagaata cggcaacatg atcgacatgg gtatcctgga tccaaccaaa  1200
gtaactcgtt ctgctctgca gtacgcagct tctgtggctg gcctgatgat caccaccgaa  1260
tgcatggtta ccgacctgcc gaaaaacgat gcagctgact taggcgctgc tggcggtatg  1320
ggcggcatgg gtggcatggg cggcatgatg taaggtttat tgactaccgg aagcagtgtg  1380
accgtgtgct tctcaaatgc ctgaggtttc agcaaaaaac ccctcaagac ccgtttagag  1440
gccccaaggg gttatgctag ttattgctca gcggtggcag cagagtccac attgattatt  1500
tgcacggcgt cacactttgc tatgccatag catttttatc cataagatta gcggatccta  1560
cctgacgctt tttatcgcaa ctctctactg tttctccata cccgtttttt tgggcgacct  1620
cgtcggaggt tgtatgtccg gtgttccgtg acgtcatcgg gcattcatca ttcatagaat  1680
gtgttacgga ggaaacaagt aatggcactt agcaccgcaa ccaaggccgc gacggacgcg  1740
ctggctgcca atcgggcacc caccagcgtg aatgcacagg aagtgcaccg ttggctccag  1800
agcttcaact gggatttcaa gaacaaccgg accaagtacg ccaccaagta caagatggcg  1860
aacgagacca aggaacagtt caagctgatc gccaaggaat atgcgcgcat ggaggcagtc  1920
aaggacgaaa ggcagttcgg tagcctgcag gatgcgctga cccgcctcaa cgccggtgtt  1980
cgcgttcatc cgaagtggaa cgagaccatg aaagtggttt cgaacttcct ggaagtgggc  2040
gaatacaacg ccatcgccgc taccgggatg ctgtgggatt ccgcccaggc ggcggaacag  2100
aagaacggct atctggccca ggtgttggat gaaatccgcc acacccacca gtgtgcctac  2160
gtcaactact acttcgcgaa gaacggccag gacccggccg gtcacaacga tgctcgccgc  2220
acccgtacca tcggtccgct gtggaagggc atgaagcgcg tgttttccga cggcttcatt  2280
tccggcgacg ccgtggaatg ctccctcaac ctgcagctgg tgggtgaggc ctgcttcacc  2340
aatccgctga tcgtcgcagt gaccgaatgg gctgccgcca acggcgatga aatcaccccg  2400
acggtgttcc tgtcgatcga gaccgacgaa ctgcgccaca tggccaacgg ttaccagacc  2460
gtcgtttcca tcgccaacga tccggcttcc gccaagtatc tcaacacgga cctgaacaac  2520
gccttctgga cccagcagaa gtacttcacg ccggtgttgg gcatgctgtt cgagtatggc  2580
tccaagttca aggtcgagcc gtgggtcaag acgtggaacc gctgggtgta cgaggactgg  2640
ggcggcatct ggatcggccg tctgggcaag tacggggtgg agtcgccgcg cagcctcaag  2700
gacgccaagc aggacgctta ctgggctcac cacgacctgt atctgctggc ttatgcgctg  2760
tggccgaccg gcttcttccg tctggcgctg ccggatcagg aagaaatgga gtggttcgag  2820
gccaactacc ccggctggta cgaccactac ggcaagatct acgaggaatg gcgcgcccgc  2880
ggttgcgagg atccgtcctc gggcttcatc ccgctgatgt ggttcatcga aaacaaccat  2940
cccatctaca tcgatcgcgt gtcgcaagtg ccgttctgcc cgagcttggc caagggcgcc  3000
agcaccctgc gcgtgcacga gtacaacggc cagatgcaca ccttcagcga ccagtggggc  3060
gagcgcatgt ggctggccga gccggagcgc tacgagtgcc agaacatctt cgaacagtac  3120
gaaggacgcg aactgtcgga agtgatcgcc gaactgcacg ggctgcgcag tgatggcaag  3180
accctgatcg cccagccgca tgtccgtggc gacaagctgt ggacgttgga cgatatcaaa  3240
cgcctgaact gcgtcttcaa gaacccggtg aaggcattca attgaaacgg gtgtcgggct  3300
ccgtcacagg gcggggcccg acgcacgatc gttcgatcaa cctcaaacca aaaaggaaca  3360
tcgatatgag catgttagga gaaagacgcc gcggtctgac cgatccggaa atggcggccg  3420
tcattttgaa ggcgcttcct gaagctccgc tggacggcaa caacaagatg ggttatttcg  3480
tcaccccccg ctggaaacgc ttgacggaat atgaagccct gaccgtttat gcgcagccca  3540
acgccgactg gatcgccggc ggcctggact ggggcgactg gacccagaaa ttccacggcg  3600
```

-continued

```
gccgcccttc ctggggcaac gagaccacgg agctgcgcac cgtcgactgg ttcaagcacc  3660
gtgacccgct ccgccgttgg catgcgccgt acgtcaagga caaggccgag gaatggcgct  3720
acaccgaccg cttcctgcag ggttactccg ccgacggtca gatccgggcg atgaacccga  3780
cctggcggga cgagttcatc aaccggtatt ggggcgcctt cctgttcaac gaatacggat  3840
tgttcaacgc tcattcgcag ggcgcccggg aggcgctgtc ggacgtaacc cgcgtcagcc  3900
tggctttctg gggcttcgac aagatcgaca tcgcccagat gatccaactc gaacggggtt  3960
tcctcgccaa gatcgtaccc ggtttcgacg agtccacagc ggtgccgaag gccgaatgga  4020
cgaacgggga ggtctacaag agcgcccgtc tggccgtgga agggctgtgg caggaggtgt  4080
tcgactggaa cgagagcgct ttctcggtgc acgccgtcta tgacgcgctg ttcggtcagt  4140
tcgtccgccg cgagttcttt cagcggctgg ctccccgctt cggcgacaat ctgacgccat  4200
tcttcatcaa ccaggcccag acatacttcc agatcgccaa gcagggcgta caggatctgt  4260
attacaactg tctgggtgac gatccggagt tcagcgatta caaccgtacc gtgatgcgca  4320
actggaccgg caagtggctg gagcccacga tcgccgctct gcgcgacttc atggggctgt  4380
ttgcgaagct gccggcgggc accactgaca aggaagaaat caccgcgtcc ctgtaccggg  4440
tggtcgacga ctggatcgag gactacgcca gcaggatcga cttcaaggcg gaccgcgatc  4500
agatcgttaa agcggttctg gcaggattga aataatagag gaactattac gatgagcgta  4560
aacagcaacg catacgacgc cggcatcatg ggcctgaaag gcaaggactt cgccgatcag  4620
ttctttgccg acgaaaacca agtggtccat gaaagcgaca cggtcgttct ggtcctcaag  4680
aagtcggacg agatcaatac ctttatcgag gagatccttc tgacggacta caagaagaac  4740
gtcaatccga cggtaaacgt ggaagaccgc gcgggttact ggtggatcaa ggccaacggc  4800
aagatcgagg tcgattgcga cgagatttcc gagctgttgg ggcggcagtt caacgtctac  4860
gacttcctcg tcgacgtttc ctccaccatc ggccgggcct ataccctggg caacaagttc  4920
accattacca gtgagctgat gggcctggac cgcaagctcg aagactatca cgcttaagga  4980
gaatgacatg gcgaaactgg gtatacacag caacgacacc cgcgacgcct gggtgaacaa  5040
gatcgcgcag ctcaacaccc tggaaaaagc ggccgagatg ctgaagcagt tccggatgga  5100
ccacaccacg ccgttccgca acagctacga actggacaac gactacctct ggatcgaggc  5160
caagctcgaa gagaaggtcg ccgtcctcaa ggcacgcgcc ttcaacgagg tggacttccg  5220
tcataagacc gctttcggcg aggatgccaa gtccgttctg gacggcaccg tcgcgaagat  5280
gaacgcggcc aaggacaagt gggaggcgga gaagatccat atcggtttcc gccaggccta  5340
caagccgccg atcatgccgg tgaactattt cctggacggc gagcgtcagt tggggacccg  5400
gctgatggaa ctgcgcaacc tcaactacta cgacacgccg ctggaagaac tgcgcaaaca  5460
gcgcggtgtg cgggtggtgc atctgcagtc gccgcactga agggaggaag tctcgccctg  5520
gacgcgacgg catcgccgtg aagtccaggg ggcagggatg ccgttccggg ccggcaggct  5580
ggcccggaat ctctggtttt caggggggcgt gccggtccac ggctccccccc tccatctttc  5640
gtaaggaaat caccatggtc gaatcggcat ttcagccatt ttcgggcgac gcagacgaat  5700
ggttcgagga accacggccc caggccggtt tcttcccttc cgcggactgg catctgctca  5760
aacgggacga gacctacgca gcctatgcca aggatctcga tttcatgtgg cggtgggtca  5820
tcgtccggga agaaaggatc gtccaggagg gttgctcgat cagcctggag tcgtcgatcc  5880
gcgccgtgac gcacgtactg aattattttg gtatgaccga acaacgcgcc ccggcagagg  5940
accggaccgg cggagttcaa cattgaacag gtaagtttat gcagcgagtt cacactatca  6000
cggcggtgac ggaggatggc gaatcgctcc gcttcgaatg ccgttcggac gaggacgtca  6060
tcaccgccgc cctgcgccag aacatctttc tgatgtcgtc ctgccgggag ggcggctgtg  6120
cgacctgcaa ggccttgtgc agcgaagggg actacgacct caagggctgc agcgttcagg  6180
cgctgccgcc ggaagaggag gaggaagggt tggtgttgtt gtgccggacc tacccgaaga  6240
ccgacctgga aatcgaactg ccctataccc attgccgcat cagttttggt gaggtcggca  6300
gtttcgaggc ggaggtcgtc ggcctcaact gggtttcgag caacaccgtc cagtttcttt  6360
tgcagaagcg gcccgacgag tgcggcaacc gtggcgtgaa attcgaaccc ggtcagttca  6420
tggacctgac catccccggc accgatgtct cccgctccta ctcgccggcg aaccttccta  6480
atcccgaagg ccgcctggag ttcctgatcc gcgtgttacc ggagggacgg ttttcggact  6540
acctgcgcaa tgacgcgcgt gtcggacagg tcctctcggt caaagggcca ctgggcgtgt  6600
tcggtctcaa ggagcggggc atggcgccgc gctatttcgt ggccggcggc accgggttgg  6660
cgccggtggt ctcgatggtg cggcagatgc aggagtggac cgcgccgaac gagacccgca  6720
tctatttcgg tgtgaacacc gagccggaat tgttctacat cgacgagctc aaatccctgg  6780
aacgatcgat gcgcaatctc accgtgaagg cctgtgtctg gcacccgagc ggggactggg  6840
aaggcgagca gggctcgccc atcgatgcgt tgcgggaaga cctggagtcc tccgacgcca  6900
acccggacat ttatttgtgc ggtccgccgg gcatgatcga tgccgcctgc gagctggtac  6960
gcagccgcgg tatccccggc gaacaggtct tcttcgaaaa attcctgccg tccggggcgg  7020
cctgaaccgg ggaagtaccg tgaccaccga gcagttcccg ccccaattcc tgcgtgaaat  7080
gatcgagcag ctggacgcca gcatccagga gctcggcacgc aaggaaaagg gacttgcggc  7140
atccctgggc acgggccggg tcgccgagct caaggaatac tgggaccacg ttctcactcc  7200
cgaggaggaa tgggagctca agcggaccat ggacttccgc gaccgggaac tggtgtggat  7260
ctggtcccgt ctcaggcggg cccgaacctc ccgcgccaat gccggggagg cctatatgcg  7320
ccacctgtcg ccggcggcgc gaaaaaacga acaatcctga aacggagtcg actcaacatg  7380
gcaaaggaag tggtttacag ggggagtgcg cggcagcgca tgatgcaagg catcgagata  7440
ctcgcgcggg cggcgatacc gacgctggga gccaccggcc ccagcgtcat gatccagcac  7500
cgcgccgatg gcctgccccc catttcgacg cgggacggcg tcacggtggc taactccatc  7560
gtactcaagg accgtgtcgc gaatctcggt gcccggctgc tgcgggacgt cgccggcacc  7620
atgtcccgcg aagcagggga tggcaccacc accgccatcg tgctggcccg ccatatcgcc  7680
cgggagatgt tcaagagcct cgccgtcggt gccgatccca tcgctctcaa gcgtggtatc  7740
gaccgtgccg tcgcccgcgt gagcgaggac atcggggctc gggcctggcg cggcgacaag  7800
gaatcggtca tcctgggggt ggccgcggtg gcgaccaagg gcgagccggg cgtgggccgg  7860
ctgctgctgg aggcgctgga cgcggtcggc gtccatggcg ccgtgtcgat cgaactgggg  7920
cagcggcgcg aggacctgct cgacgtggtc gacgggtatc gttgggaaaa aggttatctg  7980
tcgccctatt ttgtgaccga tcgggctcgc gagctggccg aactcgaaga cgtctacctc  8040
ttgatgaccg atcgggaggt ggtcgatttc atcgatttgg taccccctgct ggaggcggtg  8100
accgaggctg gtggcagcct cctgatcgcc gccgaccgtg tccacgagaa ggcactggcc  8160
ggccttttgc tcaatcacgt tcgcggcgtc ttcaaggccg tcgcggtcac cgcgcccggg  8220
ttcggcgaca agcggccgaa ccgccttttg gatctggcgg cgttgaccgg tgggcgggcg  8280
gtcctggaag cccagggcga ccgattggac cgggtcacgc tggccgacct ggggcgggtg  8340
```

```
cggcgggcgg tcgtcagcgc tgacgacacc gcgctgctcg gcataccggg caccgaagcc  8400
tcccgggccc gcttggaggg tttgcgcctg gaagcggagc agtaccgggc gctcaagccc  8460
ggtcagggat cggcgacggg gcgcttgcac gagctcgagg aaatcgaggc ccggatcgtc  8520
ggtctgagcg gcaagtccgc ggtctaccgc gtgggcggcg tgaccgacgt ggagatgaag  8580
gagcggatgg tacggatcga aaatgcctac cgctcggtgg tgtctgcact ggaggagggg  8640
gtgttgcccg gcggcggtgt cgggtttctg ggcagcatgc ccgttttggc cgagctggaa  8700
gcgcgcgatg ccgacgaagc acgcggcatc ggcatcgtcc gttccgcgct gacggagccc  8760
ctccggatca tcggagaaaa ttcgggactg tcaggggagg ccgtcgtcgc caaggtcatg  8820
gatcacgcca atcccggttg gggttacgat caggaaagcg gaagtttctg cgacctccac  8880
gccaggggca tttgggatgc cgccaaggtg ctcaggctgg ccctggaaaa agccgcgtcg  8940
gtggccggca cgtttctcac caccgaagcc gtggtactgg agattccgga cactgacgct  9000
ttcgccggtt tcagtgcgga gtgggcgcgc gcgacccggg aggatccgcg ggtctgagcg  9060
gggggatacg ccctcgaatc ctgggatagt cagagaccgg catagcgtac gccgttacgc  9120
ccgttctgct tgacctggta aagttacaac caattaacca attctgatta gaaaaactca  9180
tcgagcatca aatgaaactg caatttattc atatcaggat tatcaatacc atatttttga  9240
aaaagccgtt tctgtaatga aggagaaaac tcaccgaggc agttccatag gatggcaaga  9300
tcctggtatc ggtctgcgat tccgactcgt ccaacatcaa tacaacctat taatttcccc  9360
tcgtcaaaaa taaggttatc aagtgagaaa tcaccatgag tgacgactga atccggtgag  9420
aatggcaaaa gcttatgcat ttctttccag acttgttcaa caggccagcc attacgctcg  9480
tcatcaaaat cactcgcatc aaccaaaccg ttattcattc gtgattgcgc ctgagcgaga  9540
cgaaatacgc gatcgctgtt aaaaggacaa ttacaaacag gaatcgaatg caaccggcgc  9600
aggaacactg ccagcgcatc aacaatattt tcacctgaat caggatattc ttctaatacc  9660
tggaatgctg ttttcccggg gatcgcagtg gtgagtaacc atgcatcatc aggagtacgg  9720
ataaaatgct tgatggtcgg aagaggcata aattccgtca gccagtttag tctgaccatc  9780
tcatctgtaa catcattggc aacgctacct ttgccatgtt tcagaaacaa ctctggcgca  9840
tcgggcttcc catacaatcg atagattgtc gcacctgatt gcccgacatt atcgcgagcc  9900
catttatacc catataaatc agcatccatg ttggaattta atcgcggcct cgagcaagac  9960
gtttcccgtt gaatatggct cataacaccc cttgtattac tgtttatgta agcagacagt  10020
tttattgttc atgatgatat atttttatct tgtgcaatgt aacatcagag attttgagac  10080
acaacgtggc tttgttgaat aaatcgaact tttgctgagt tgaaggatca gatcacgcat  10140
cttcccgaca acgcagaccg ttccgtggca aagcaaaagt tcaaaatcac caactggtcc  10200
acctacaaca aagctctcat caaccgtggc tccctcactt tctggctgga tgatggggcg  10260
attcaggcct ggtatgagtc agcaacacct tcttcacgag gcagacctca gcgcaacgca  10320
attaatgtaa gttagctcac tcattaggca ccgggatctc gaccgatgcc cttgagagcc  10380
ttcaacccag tcagctcctt ccggtgggcg cggggcatga ctaacatgag aattacaact  10440
tatatcgtat ggggctgact tcaggtgcta catttgaaga gataaattgc actgaaatct  10500
agagcggttc agtagaaaag atcaaaggat cttcttgaga tcctttttttt ctgcgcgtaa  10560
tcttttgccc tgtaaacgaa aaaaccacct ggggaggtgg tttgatcgaa ggttaagtca  10620
gttggggaac tgcttaaccg tggtaactgg ctttcgcaga gcacagcaac caaatctgtc  10680
cttccagtgt agccggactt tggcgcacac ttcaagagca accgcgtgtt tagctaaaca  10740
aatcctctgc gaactcccag ttaccaatgg ctgctgccag tggcgtttta ccgtgctttt  10800
ccgggttgga ctcaagtgaa cagttaccgg ataaggcgca gcagtcgggc tgaacgggga  10860
gttcttgctt acagcccagc ttggagcgaa cgacctacac cgagccgaga taccagtgtg  10920
tgagctatga gaaagcgcca cacttcccgt aagggagaaa ggcggaacag gtatccggta  10980
aacggcaggg tcggaacagg agagcgcaag agggagcgac ccgccggaaa cggtggggat  11040
ctttaagtcc tgtcgggttt cgcccgtact gtcagattca tggttgagcc tcacggctcc  11100
cacagatgca ccggaaaagc gtctgtttat gtgaactctg gcaggagggc ggagcctatg  11160
gaaaaacgcc accggcgcgg ccctgctgtt ttgcctcaca tgttagtccc ctgcttatcc  11220
acggaatctg tgggtaactt tgtatgtgtc cgcagcgccc gccgcagtct cacgcccgga  11280
gcgtagcgac cgagtgagct agctatttgt ttatttttct aaatacattc aaatatgtat  11340
ccgctcatga gacaataacc ctgataaatg cttcaataat attgaaaaag gaagagtatg  11400
agggaagcgg tgatcgccga agtatcgact caactatcag aggtagttgg cgtcatcgag  11460
cgccatctcg aaccgacgtt gctggccgta catttgtacg gctccgcagt ggatggcggc  11520
ctgaagccac acagtgatat tgatttgctg gttacggtga ccgtaaggct tgatgaaaca  11580
acgcggcgag ctttgatcaa cgaccttttg gaaacttcgg cttcccctgg agagagcgag  11640
attctccgcg ctgtagaagt caccattgtt gtgcacgacg acatcattcc gtggcgttat  11700
ccagctaagc gcgaactgca atttggagaa tggcagcgca atgacattct tgcaggtatc  11760
ttcgagccag ccacgatcga cattgatctg gctatcttgc tgacaaaagc aagagaacat  11820
agcgttgcct tggtaggtcc agcggcggag gaactctttg atccggttcc tgaacaggat  11880
ctatttgagg cgctaaatga aaccttaacg ctatggaact cgccgcccga ctgggctggc  11940
gatgagcgaa atgtagtgct tacgttgtcc cgcatttggt acagcgcagt aaccggcaaa  12000
atcgcgccga aggatgtcgc tgccgactgg gcaatggagc gcctgccggc ccagtatcag  12060
cccgtcatac ttgaagctag acaggcttat cttggacaag aagaagatcg cttggcctcg  12120
cgcgcagatc agttggaaga atttgtccac tacgtgaaag gcgagatcac caaggtagtc  12180
ggcaaataat gtctaacaat tcgttcaagc cgaggggccg caagatccgg ccacgatgac  12240
ccggtcgtcg gttcagggca gggtcgttaa atagccgctt atgtctattg ctggtttacc  12300
ggctagctca gtcctaggta caatgctagc ggcgtcaccc ataacagata cggactttct  12360
caaaggagag ttatcaatga atattcgtcc attgcatgat cgcgtgatcg tcaagcgtaa  12420
agaagttgaa actaaatctg ctggcggcat cgttctgacc ggctctgcag cggctaaatc  12480
cacccgcggc gaagtgctgg ctgtcggcaa tggccgtatc cttgaaaatg gcgaagtgaa  12540
gccgctggat gtgaaagttg gcgacatcgt tattttcaac gatggctacg gtgtgaaatc  12600
tgagaagatc gacaatgaag aagtgttgat catgtccgaa agcgacattc tggcaattgt  12660
tgaagcgtaa tccgcgcacg acactgaaca tacgaattta aggaataaag ataatggcag  12720
ctaaagacgt aaaattcggt aacgacgctc gtgtgaaaat gctgcgcggc gtaaacgtac  12780
tggcagatgc agtgaaagtt accctcggtc caaaaggccg taacgtagtt ctggataaat  12840
ctttcggtgc accgaccatc accaaagatg gtgtttccgt tgctcgtgaa atcgaactgg  12900
aagacaagtt cgaaaatatg ggtgcgcaga tggtgaaaga agttgcctct aaagcaaacg  12960
acgctgcagg cgacggtacc accactgcaa ccgtactggc tcaggct                13007
```

```
SEQ ID NO: 26          moltype = DNA  length = 9915
FEATURE                Location/Qualifiers
misc_feature           1..9915
                       note = Synthetic plasmid.
source                 1..9915
                       mol_type = other DNA
                       organism = synthetic construct
SEQUENCE: 26
acaagccgcc gatcatgccg gtgaactatt tcctggacgg cgagcgtcag ttggggaccc  60
ggctgatgga actgcgcaac ctcaactact acgacacgcc gctggaagaa ctgcgcaaac  120
agcgcggtgt gcgggtggtg catctgcagt cgccgcactg aagggaggaa gtctcgccct  180
ggacgcgacg gcatcgccgt gaagtccagg gggcagggat gccgttccgg gccggcaggc  240
tggcccggaa tctctggttt tcagggggcg tgccggtcca cggctccccc ctccatcttt  300
cgtaaggaaa tcaccatggt cgaatcggca tttcagccat tttcgggcga cgcagacgaa  360
tggttcgagg aaccacggcc ccaggccggt ttcttccctt ccgcggactg gcatctgctc  420
aaacgggacg agacctacgc agcctatgcc aaggatctcg atttcatgtg gcggtgggtc  480
atcgtccggg aagaaaggat cgtccaggag ggttgctcga tcagcctgga gtcgtcgatc  540
cgcgccgtga cgcacgtact gaattatttt ggtatgaccg aacaacgcgc cccggcagag  600
gaccggaccg gcggagttca acattgaaca ggtaagttta tgcagcgagt tcacactatc  660
acggcggtga cggaggatgg cgaatcgctc cgcttcgaat gccgttcgga cgaggacgtc  720
atcaccgccg ccctgcgcca gaacatcttt ctgatgtcgt cctgccggga gggcggctgt  780
gcgacctgca aggccttgtg cagcgaaggg gactacgacc tcaagggctg cagcgttcag  840
gcgctgccgc cggaagagga ggaggaaggg ttggtgttgt tgtgccggac ctacccgaag  900
accgacctgg aaatcgaact gccctatacc cattgccgca tcagttttgg tgaggtcggc  960
agtttcgagg cggaggtcgt cggcctcaac tgggtttcga gcaacaccgt ccagtttctt  1020
ttgcagaagc ggcccgacga gtgcggcaac cgtggcgtga aattcgaacc cggtcagttc  1080
atggacctga ccatccccgg caccgatgtc tcccgctcct actcgccggc gaaccttcct  1140
aatcccgaag gccgcctgga gttcctgatc cgcgtgttac cggagggacg gttttcggac  1200
tacctgcgca atgacgcgcg tgtcggacag gtcctctcgg tcaaagggcc actgggcgtg  1260
ttcggtctca aggagcgggg catggcgccg cgctatttcg tggccggcgg caccgggttg  1320
gcgccggtgg tctcgatggt gcggcagatg caggagtgga ccgcgccgaa cgagacccgc  1380
atctatttcg gtgtgaacac cgagccggaa ttgttctaca tcgacgagct caaatccctg  1440
gaacgatcga tgcgcaatct caccgtgaag gcctgtgtct ggcacccgag cggggactgg  1500
gaaggcgagc agggctcgcc catcgatgcg ttgcgggaag acctggagtc ctccgacgcc  1560
aacccggaca tttatttgtg cggtccgccg ggcatgatcg atgccgcctg cgagctggta  1620
cgcagccgcg gtatccccgg cgaacaggtc ttcttcgaaa aattcctgcc gtccggggcg  1680
gcctgaaccg gggaagtacc gtgaccaccg agcagttccc gccccaattc ctgcgtgaaa  1740
tgatcgagca gctggacgcc agcatccagg agctcgcacg caaggaaaag ggacttgcgg  1800
catccctggg cacgggccgg gtcgccgagc tcaaggaata ctgggaccac gttctcactc  1860
ccgaggagga atgggagctc aagcggacca tggacttccg cgaccgggaa ctggtgtgga  1920
tctggtcccg tctcaggcgg gcccgaacct cccgcgccaa tgccggggag gcctatatgc  1980
gccacctgtc gccggcggcg cgaaaaaacg aacaatcctg aaacggagtc gactcaacat  2040
ggcaaaggaa gtggtttaca gggggagtgc gcggcagcgc atgatgcaag gcatcgagat  2100
actcgcgcgg gcggcgatac cgacgctggg agccaccggc cccagcgtca tgatccagca  2160
ccgcgccgat ggcctgcccc ccatttcgac gcgggacggc gtcacggtgg ctaactccat  2220
cgtactcaag gaccgtgtcg cgaatctcgg tgcccggctg ctgcgggacg tcgccggcac  2280
catgtcccgc gaagcagggg atggcaccac caccgccatc gtgctggccc gccatatcgc  2340
ccgggagatg ttcaagagcc tcgccgtcgg tgccgatccc atcgctctca agcgtggtat  2400
cgaccgtgcc gtcgcccgcg tgagcgagga catcggggct cggcctggc gcggcgacaa  2460
ggaatcggtc atcctggggg tggccgcggt ggcgaccaag ggcgagccgg gcgtgggccg  2520
gctgctgctg gaggcgctgg acgcggtcgg cgtccatggc gccgtgtcga tcgaactggg  2580
gcagcggcgc gaggacctgc tcgacgtggt cgacgggtat cgttgggaaa aggttatct  2640
gtcgccctat tttgtgaccg atcgggctcg cgagctggcc gaactcgaag acgtctacct  2700
cttgatgacc gatcgggagg tggtcgattt catcgatttg gtacccctgc tggaggcggt  2760
gaccgaggct ggtggcagcc tcctgatcgc cgccgaccgt gtccacgaga aggcactggc  2820
cggccttttg ctcaatcacg ttcgcggcgt cttcaaggcc gtcgcggtca ccgcgcccgg  2880
gttcggcgac aagcggccga accgcctttt ggatctggcg gcgttgaccg gtgggcgggc  2940
ggtcctggaa gcccagggcg accgattgga ccgggtcacg ctggccgacc tggggcgggt  3000
gcggcgggcg gtcgtcagcg ctgacgacac cgcgctgctc ggcataccgg gcaccgaagc  3060
ctcccgggcc cgcttggagg gtttgcgcct ggaagcggag cagtaccggg cgctcaagcc  3120
cggtcaggga tcggcgacgg ggcgcttgca cgagctcgag gaaatcgagg cccggatcgt  3180
cggtctgagc ggcaagtccg cggtctaccg cgtgggcggc gtgaccgacg tggagatgaa  3240
ggagcggatg gtacggatcg aaaatgccta ccgctcggtg gtgtctgcac tggaggaggg  3300
ggtgttgccc ggcggcggtg tcgggtttct gggcagcatg cccgttttgg ccgagctgga  3360
agcgcgcgat gccgacgaag cacgcggcat cggcatcgtc cgttccgcgc tgacggagcc  3420
cctccggatc atcggagaaa attcgggact gtcaggggag gccgtcgtcg ccaaggtcat  3480
ggatcacgcc aatcccggtt ggggttacga tcaggaaagc ggaagtttct gcgacctcca  3540
cgccagggc atttgggatg ccgccaaggt gctcaggctg gccctggaaa aagccgcgtc  3600
ggtggccggc acgtttctca ccaccgaagc cgtggtactg gagattccgg acactgacgc  3660
tttcgccggt ttcagtgcgg agtgggccgc cgcgacccgg gaggatccgc gggtctgagc  3720
ggggggatac gccctcgaat cctgggatag tcagagaccg gcatagcgta cgccgttacg  3780
cccgttctgc ttgacctggt aaagttacaa ccaattaacc aattctgatt agaaaaactc  3840
atcgagcatc aaatgaaact gcaatttatt catatcagga ttatcaatac catatttttg  3900
aaaaagccgt ttctgtaatg aaggagaaaa ctcaccgagg cagttccata ggatggcaag  3960
atcctggtat cggtctgcga ttccgactcg tccaacatca atacaaccta ttaatttccc  4020
ctcgtcaaaa ataaggttat caagtgagaa atcaccatga gtgacgactg aatccggtga  4080
gaatggcaaa agcttatgca tttctttcca gacttgttca acaggccagc cattacgctc  4140
gtcatcaaaa tcactcgcat caaccaaacc gttattcatt cgtgattgcg cctgagcgag  4200
acgaaatacg cgatcgctgt taaaaggaca attacaaaca ggaatcgaat gcaaccggcg  4260
```

```
caggaacact gccagcgcat caacaatatt ttcacctgaa tcaggatatt cttctaatac  4320
ctggaatgct gttttcccgg ggatcgcagt ggtgagtaac catgcatcat caggagtacg  4380
gataaaatgc ttgatggtcg gaagaggcat aaattccgtc agccagttta gtctgaccat  4440
ctcatctgta acatcattgg caacgctacc tttgccatgt ttcagaaaca actctggcgc  4500
atcgggcttc ccatacaatc gatagattgt cgcacctgat tgcccgacat tatcgcgagc  4560
ccatttatac ccatataaat cagcatccat gttggaattt aatcgcggcc tcgagcaaga  4620
cgtttcccgt tgaatatggc tcataacacc ccttgtatta ctgtttatgt aagcagacag  4680
ttttattgtt catgatgata tatttttatc ttgtgcaatg taacatcaga gattttgaga  4740
cacaacgtgg ctttgttgaa taaatcgaac ttttgctgag ttgaaggatc agatcacgca  4800
tcttcccgac aacgcagacc gttccgtggc aaagcaaaag ttcaaaatca ccaactggtc  4860
cacctacaac aaagctctca tcaaccgtgg ctccctcact ttctggctgg atgatggggc  4920
gattcaggcc tggtatgagt cagcaacacc ttcttcacga ggcagacctc aggtaagccc  4980
tcccgtatcg tagttatcta cacgacgggg agtcaggcaa ctatggatga acgaaataga  5040
cagatcgctg agataggtgc ctcactgatt aagcattggt aactgtcaga ccaagtttac  5100
tcatatatac tttagattga tttaaaactt catttttaat ttaaaaggat ctaggtgaag  5160
atcctttttg ataatctcat gaccaaaatc ccttaacgtg agttttcgtt ccactgagcg  5220
tcagaccccct taataagatg atcttcttga gatcgttttg gtctgcgcgt aatctcttgc  5280
tctgaaaacg aaaaaaccgc cttgcagggc ggtttttcga aggttctctg agctaccaac  5340
tctttgaacc gaggtaactg gcttggagga gcgcagtcac caaaacttgt cctttcagtt  5400
tagccttaac cggcgcatga cttcaagact aactcctcta aatcaattac cagtggctgc  5460
tgccagtggt gcttttgcat gtctttccgg gttggactca agacgatagt taccggataa  5520
ggcgcagcgg tcggactgaa cggggggttc gtgcatacag tccagcttgg agcgaactgc  5580
ctacccggaa ctgagtgtca ggcgtggaat gagacaaacg cggccataac agcggaatga  5640
caccggtaaa ccgaaaggca ggaacaggag agcgcacgag ggagccgcca gggggaaacg  5700
cctggtatct ttatagtcct gtcgggtttc gccaccactg atttgagcgt cagatttcgt  5760
gatgcttgtc aggggggcgg agcctatgga aaaacggctt tgccgcggcc ctctcacttc  5820
cctgttaagt atcttcctgg catcttccag gaaatctccg ccccgttcgt aagccatttc  5880
cgctcgccgc agtcgaacga ccgagcgtag cgagtcagtg agcgaggaag cggaatatat  5940
cctgtatcac atattctgct gacgcaccgg tgcagccttt tttctcctgc cacatgaagc  6000
acttcactga caccctcatc agtgccaaca tagtaagcca gtatacactc cgctagcgca  6060
gtccacattg attatttgca cggcgtcaca ctttgctatg ccatagcatt tttatccata  6120
agattagcgg atcctacctg acgcttttta tcgcaactct ctactgtttc tccatacccg  6180
tttttttggg cgacctcgtc ggaggttgta tgtccggtgt tccgtgacgt catcgggcat  6240
tcatcattca tagaatgtgt tacggaggaa acaagtaatg gcacttagca ccgcaaccaa  6300
ggccgcgacg gacgcgctgg ctgccaatcg ggcacccacc agcgtgaatg cacaggaagt  6360
gcaccgttgg ctccagagct tcaactggga tttcaagaac aaccggacca agtacgccac  6420
caagtacaag atggcgaacg agaccaagga acagttcaag ctgatcgcca aggaatatgc  6480
gcgcatggag gcagtcaagg acgaaaggca gttcggtagc ctgcaggatg cgctgacccg  6540
cctcaacgcc ggtgttcgcg ttcatccgaa gtggaacgag accatgaaag tggtttcgaa  6600
cttcctggaa gtgggcgaat acaacgccat cgccgctacc gggatgctgt gggattccgc  6660
ccaggcggcg gaacagaaga acggctatct ggcccaggtg ttggatgaaa tccgccacac  6720
ccaccagtgt gcctacgtca actactactt cgcgaagaac ggccaggacc cggccggtca  6780
caacgatgct cgccgcaccc gtaccatcgg tccgctgtgg aagggcatga agcgcgtgtt  6840
ttccgacggc ttcatttccg gcgacgccgt ggaatgctcc ctcaacctgc agctggtggg  6900
tgaggcctgc ttcaccaatc cgctgatcgt cgcagtgacc gaatgggctg ccgccaacgg  6960
cgatgaaatc accccgacgg tgttcctgtc gatcgagacc gacgaactgc gccacatggc  7020
caacggttac cagaccgtcg tttccatcgc caacgatccg gcttccgcca agtatctcaa  7080
cacggacctg aacaacgcct tctggaccca gcagaagtac ttcacgccgg tgttgggcat  7140
gctgttcgag tatggctcca agttcaaggt cgagccgtgg gtcaagacgt ggaaccgctg  7200
ggtgtacgag gactggggcg gcatctggat cggccgtctg ggcaagtacg gggtggagtc  7260
gccgcgcagc ctcaaggacg ccaagcagga cgcttactgg gctcaccacg acctgtatct  7320
gctggcttat gcgctgtggc cgaccggctt cttccgtctg gcgctgccgg atcaggaaga  7380
aatggagtgg ttcgaggcca actaccccgg ctggtacgac cactacggca agatctacga  7440
ggaatggcgc gcccgcggtt gcgaggatcc gtcctcgggc ttcatcccgc tgatgtggtt  7500
catcgaaaac aaccatccca tctacatcga tcgcgtgtcg caagtgccgt tctgcccgag  7560
cttggccaag ggcgccagca ccctgcgcgt gcacgagtac aacggccaga tgcacacctt  7620
cagcgaccag tggggcgagc gcatgtggct ggccgagccg gagcgctacg agtgccagaa  7680
catcttcgaa cagtacgaag gacgcgaact gtcggaagtg atcgccgaac tgcacgggct  7740
gcgcagtgat ggcaagaccc tgatcgccca gccgcatgtc cgtggcgaca agctgtggac  7800
gttggacgat atcaaacgcc tgaactgcgt cttcaagaac ccggtgaagg cattcaattg  7860
aaacgggtgt cgggctccgt cacagggcgg ggcccgacgc acgatcgttc gatcaacctc  7920
aaaccaaaaa ggaacatcga tatgagcatg ttaggagaaa gacgccgcgg tctgaccgat  7980
ccggaaatgg cggccgtcat tttgaaggcg cttcctgaag ctccgctgga cggcaacaac  8040
aagatgggtt atttcgtcac cccccgctgg aaacgcttga cggaatatga agccctgacc  8100
gtttatgcgc agcccaacgc cgactggatc gccggcggcc tggactgggg cgactggacc  8160
cagaaattcc acggcggccg cccttcctgg ggcaacgaga ccacggagct gcgcaccgtc  8220
gactggttca agcaccgtga cccgctccgc cgttggcatg cgccgtacgt caaggacaag  8280
gccgaggaat ggcgctacac cgaccgcttc ctgcagggtt actccgccga cggtcagatc  8340
cgggcgatga acccgacctg gcgggacgag ttcatcaacc ggtattgggg cgccttcctg  8400
ttcaacgaat acggattgtt caacgctcat tcgcagggcg cccgggaggc gctgtcggac  8460
gtaacccgcg tcagcctggc tttctggggc ttcgacaaga tcgacatcgc ccagatgatc  8520
caactcgaac ggggtttcct cgccaagatc gtacccggtt tcgacgagtc cacagcggtg  8580
ccgaaggccg aatggacgaa cggggaggtc tacaagagcg cccgtctggc cgtggaaggg  8640
ctgtggcagg aggtgttcga ctggaacgag agcgctttct cggtgcacgc cgtctatgac  8700
gcgctgttcg gtcagttcgt ccgccgcgag ttctttcagc ggctggctcc ccgcttcggc  8760
gacaatctga cgccattctt catcaaccag gcccagacat acttccagat cgccaagcag  8820
ggcgtacagg atctgtatta caactgtctg ggtgacgatc cggagttcag cgattacaac  8880
cgtaccgtga tgcgcaactg gaccggcaag tggctggagc ccacgatcgc cgctctgcgc  8940
gacttcatgg ggctgtttgc gaagctgccg gcgggcacca ctgacaagga agaaatcacc  9000
```

```
gcgtccctgt accgggtggt cgacgactgg atcgaggact acgccagcag gatcgacttc  9060
aaggcggacc gcgatcagat cgttaaagcg gttctggcag gattgaaata atagaggaac  9120
tattacgatg agcgtaaaca gcaacgcata cgacgccggc atcatgggcc tgaaaggcaa  9180
ggacttcgcc gatcagttct ttgccgacga aaaccaagtg gtccatgaaa gcgacacggt  9240
cgttctggtc ctcaagaagt cggacgagat caatacettt atcgaggaga tccttctgac  9300
ggactacaag aagaacgtca atccgacggt aaacgtggaa gaccgcgcgg gttactggtg  9360
gatcaaggcc aacggcaaga tcgaggtcga ttgcgacgag atttccgagc tgttggggcg  9420
gcagttcaac gtctacgact tcctcgtcga cgtttcctcc accatcggcc gggcctatac  9480
cctgggcaac aagttcacca ttaccagtga gctgatgggc ctggaccgca agctcgaaga  9540
ctatcacgct taaggagaat gacatggcga aactgggtat acacagcaac gacacccgcg  9600
acgcctgggt gaacaagatc gcgcagctca acaccctgga aaaagcggcc gagatgctga  9660
agcagttccg gatggaccac accacgccgt tccgcaacag ctacgaactg gacaacgact  9720
acctctggat cgaggccaag ctcgaagaga aggtcgccgt cctcaaggca cgcgccttca  9780
acgaggtgga cttccgtcat aagaccgctt tcggcgagga tgccaagtcc gttctggacg  9840
gcaccgtcgc gaagatgaac gcggccaagg acaagtggga ggcggagaag atccatatcg  9900
gtttccgcca ggcct                                                   9915
```

```
SEQ ID NO: 27          moltype = DNA  length = 6963
FEATURE                Location/Qualifiers
misc_feature           1..6963
                       note = Synthetic plasmid.
source                 1..6963
                       mol_type = other DNA
                       organism = synthetic construct
SEQUENCE: 27
ccgacaccat cgaatggtgc aaaacctttc gcggtatggc atgatagcgc ccggaagaga  60
gtcaattcag ggtggtgaat gtgaaaccag taacgttata cgatgtcgca gagtatgccg  120
gtgtctctta tcagaccgtt tcccgcgtgg tgaaccaggc cagccacgtt tctgcgaaaa  180
cgcgggaaaa agtggaagcg gcgatggcgg agctgaatta cattcccaac cgcgtggcac  240
aacaactggc gggcaaacag tcgttgctga ttggcgttgc cacctccagt ctggccctgc  300
acgcgccgtc gcaaattgtc gcggcgatta aatctcgcgc cgatcaactg ggtgccagcg  360
tggtggtgtc gatggtagaa cgaagcggcg tcgaagcctg taaagcggcg gtgcacaatc  420
ttctcgcgca acgcgtcagt gggctgatca ttaactatcc gctggatgac caggatgcca  480
ttgctgtgga agctgcctgc actaatgttc cggcgttatt tcttgatgtc tctgaccaga  540
cacccatcaa cagtattatt ttctcccatg aagacggtac gcgactgggc gtggagcatc  600
tggtcgcatt gggtcaccag caaatcgcgc tgttagcggg cccattaagt tctgtctcgg  660
cgcgtctgcg tctggctggc tggcataaat atctcactcg caatcaaatt cagccgatag  720
cggaacggga aggcgactgg agtgccatgt ccggttttca acaaaccatg caaatgctga  780
atgagggcat cgttcccact gcgatgctgg ttgccaacga tcagatggcg ctgggcgcaa  840
tgcgcgccat taccgagtcc gggctgcgcg ttggtgcgga tatttcggta gtgggatacg  900
acgataccga agacagctca tgttatatcc cgccgttaac caccatcaaa caggattttc  960
gcctgctggg gcaaaccagc gtggaccgct tgctgcaact ctctcagggc caggcggtga  1020
agggcaatca gctgttgccc gtctcactgg tgaaaagaaa aaccaccctg gcgcccaata  1080
cgcaaaccgc ctctccccgc gcgttggccg attcattaat gcagctggca cgacaggttt  1140
cccgactgga aagcgggcag tgagcgcaac gcaattaatg taagttagct cactcattag  1200
gcacaattct catgtttgac agcttatcat cgactgcacg gtgcaccaat gcttctggcg  1260
tcaggcagcc atcggaagct gtggtatggc tgtgcaggtc gtaaatcact gcataattcg  1320
tgtcgctcaa ggcgcactcc cgttctggat aatgtttttt gcgccgacat cataacggtt  1380
ctggcaaata ttctgaaatg agctgttgac aattaatcat cggctcgtat aatgtgtgga  1440
attgtgagcg gataacaatt tcacacagga aacagccagt ccgtttaggt gttttcacga  1500
gcaattgacc aacaaggacg tcaatagagt taaggaggga ggggatgaaa gccgccgtgg  1560
tcgagcaatt caaaaaacca ctccaggtga aagaggtcga aaaaccgaaa attagttacg  1620
gtgaagtgct ggttcgtatt aaagcttgtg gtgtctgcca caccgatctg catgccgcac  1680
acggcgattg gccggtaaaa ccgaaactgc cgctcatccc cggccatgaa ggcgtaggcg  1740
tcatcgagga agtcggcccg ggtgtgacac accttaaagt tggcgatcgt gtgggcattc  1800
cctggctgta ttcggcgtgt ggccactgtg actattgtct cagcggccag gagactctgt  1860
gcgaacgcca gcagaacgcc ggctacagcg ttgatggtgg ctacgccgag tactgtcgtg  1920
ctgcggcaga ttacgtggtg aagattcctg ataatctttc ctttgaagaa gcggcgccca  1980
ttttatgcgc gggcgttacc acttataaag cgctgaaagt caccggtgcc aaaccaggcg  2040
agtgggtggc catttatgga attgggggcc tcggccatgt ggcagttcag tacgctaaag  2100
caatgggctt aaacgtcgtg gcagtggact tgggagatga aaagctggaa ctggcaaaac  2160
aactgggcgc ggacctggta gtgaatccga aacatgatga tgcagcacaa tggattaaag  2220
aaaaagttgg tggcgtgcat gccacggtgg tgacggcagt tagtaaagcc gcttttgaat  2280
cggcgtataa gtcaatccgc cgcggaggag catgcgtcct tgttggtctg ccaccggagg  2340
aaatccccat tccgattttt gacacagttc tgaacggcgt caaaattatc ggttcaattg  2400
ttggcacccg taaagacctg caggaagccc tccagtttgc tgctgaaggc aaagtgaaaa  2460
ctatcgtgga agttcagccg cttgagaaca ttaacgacgt atttgatcgt atgctgaaag  2520
gacagattaa tggacgtgtg gtcctgaaag tggattgaca tgctaaggtg ctggctgcat  2580
gctaagttga tacgcctgcg acaaattttt ctaggagcgt tagtatggag aacatggata  2640
aggatttaca gagcatccag gaagtacgca cccttatcgc aaaggctaag aaagcacagg  2700
ccgaatttaa gaacttctct caagaggcgg ttaacaaagt cattgagaag atcgcaaaag  2760
ccacggaggt agaggccgtg aagcttgcga agttagctta tgaggataca ggatacggta  2820
aatgggagga caaggtaatt aaaaacaaat tttcctctat cgtagtatac aactatatta  2880
aagaccttaa gacggtaggt attttgaaag aggataaaga aaagaagctt atcgacatcg  2940
cggtaccatt gggggtaatc gcgggcctta ttccaagtac gaaccctact agcaccgcga  3000
ttttcaaggt attaattgca ttgaaggcgg gcaatgccat tgtgttcagc cctcacccaa  3060
cggcggttcg tagcattact gagaccgtca aaatcatgca aaaagcggcg gtcgaagcag  3120
gtgctcctga tggattaatt cagtgcatgt cgattttaac tgtcgaagga accgctgaat  3180
tgatgaagaa caaggatacc gcactgattt tagccaccgg gggcgaggga atggtacgtg  3240
```

-continued

```
ctgcctacag ttcaggcacg cctgcgatcg gtgtggggcc cggcaatggc ccttgcttta  3300
ttgagcgcac cgctgacatt cctacggctg tccgcaaagt gattggctcg gatacattcg  3360
ataatggtgt gatctgcgca tcggagcaaa gtattatcgc agagacggtt aaaaaggccg  3420
agatcattga agaattcaaa cgtcagaaag gttatttctt gaacgccgaa gaatcagaga  3480
aagtgggaaa gattttattg cgcgccaacg ggacacctaa cccagcgatc gtgggaaagg  3540
atgtccaagc attagccaag ttagcaggta tttcgatccc gagcgacgcg gttatcctgt  3600
tatctgaaca gacggacgta tcgcccaaga atccgtatgc aaaagagaaa ctggccccgg  3660
tcttagcttt ttacactgtg gaagattggc atgaagcctg tgagaagtca ttggcccttt  3720
tgcataacca aggaagcggg catacottaa tcattcattc tcagaacgag gaaattatcc  3780
gcgagtttgc gcttaaaaag ccagtaagtc gtatcttggt taacagcccc ggctcacttg  3840
gaggaattgg aggcgctacg aatttagtcc caagcctgac tttagggtgc ggtgcagtcg  3900
gtggttcagc caccagcgat aatgttggtc cggagaattt atttaatatc cgcaaggtgg  3960
cttatggtac gacaaccgtt gaagaaattc gtgaggcctt cggagtgggt gcagccagct  4020
caagtgcgcc cgccgagccg gaggacaatg aagacgttca agcaattgtg aaagcaatca  4080
tggccaagct taatttgtaa gtttgtcggt gaacgctctc ctgagtagga caaatccgcc  4140
gggagcggat ttgaacgttg cgaagcaacg gcccggaggg tggcgggcag gacgcccgcc  4200
ataaactgcc aggcatcaaa ttaagcagaa ggccatcctg acggatggcc tttttgcgtt  4260
tctacaaact ctttcggtcc gttgtttatt tttctaaata cattcaaata tgtatccgct  4320
catgagacaa taaccctgat aaatgcttca ataatattga aaaaggaaga gtatgagtat  4380
tcaacatttc cgtgtcgccc ttattccctt ttttgcggca ttttgccttc ctgtttttgc  4440
tcacccagaa acgctggtga aagtaaaaga tgctgaagat cagttgggtg cacgagtggg  4500
ttacatcgaa ctggatctca acagcggtaa gatccttgag agttttcgcc ccgaagaacg  4560
tttcccaatg atgagcactt ttaaagttct gctatgtggc gcggtattat cccgtgttga  4620
cgccgggcaa gagcaactcg gtcgccgcat acactattct cagaatgact tggttgagta  4680
ctcaccagtc acagaaaagc atcttacgga tggcatgaca gtaagagaat tatgcagtgc  4740
tgccataacc atgagtgata acactgcggc caacttactt ctgacaacga tcggaggacc  4800
gaaggagcta accgcttttt tgcacaacat gggggatcat gtaactcgcc ttgatcgttg  4860
ggaaccggag ctgaatgaag ccataccaaa cgacgagcgt gacaccacga tgcctgtagc  4920
aatggcaaca acgttgcgca aactattaac tggcgaacta cttactctag cttcccggca  4980
acaattaata gactggatgg aggcggataa agttgcagga ccacttctgc gctcggccct  5040
tccggctggc tggtttattg ctgataaatc tggagccggt gagcgtgggt ctcgcggtat  5100
cattgcagca ctggggccag atggtaagcc ctcccgtatc gtagttatct acacgacggg  5160
gagtcaggca actatggatg aacgaaatag acagatcgct gagataggtg cctcactgat  5220
taagcattgg taactgtcag accaagttta ctcatatata ctttagattg atttccttag  5280
gactgagcgt caaccccgta gaaaagatca aaggatcttc ttgagatcct ttttttctgc  5340
gcgtaatctg ctgcttgcaa acaaaaaaac caccgctacc agcggtggtt tgtttgccgg  5400
atcaagagct accaactctt tttccgaagg taactggctt cagcagagcg cagataccaa  5460
atactgtcct tctagtgtag ccgtagttag gccaccactt caagaactct gtagcaccgc  5520
ctacatacct cgctctgcta atcctgttac cagtggctgc tgccagtggc gataagtcgt  5580
gtcttaccgg gttggactca agacgatagt taccggataa ggcgcagcgg tcgggctgaa  5640
cggggggttc gtgcacacag cccagcttgg agcgaacgac ctacaccgaa ctgagatacc  5700
tacagcgtga gctatgagaa agcgccacgc ttcccgaagg gagaaaggcg gacaggtatc  5760
cggtaagcgg cagggtcgga acaggagagc gcacgaggga gcttccaggg ggaaacgcct  5820
ggtatcttta tagtcctgtc gggtttcgcc acctctgact tgagcgtcga tttttgtgat  5880
gctcgtcagg ggggcggagc ctatggaaaa acgccagcaa cgcggccttt ttacggttcc  5940
tggccttttg ctggcctttt gctcacatgt tctttcctgc gttatcccct gattctgtgg  6000
ataaccgtat taccgccttt gagtgagctg ataccgctcg ccgcagccga acgaccgagc  6060
gcagcgagtc agtgagcgag gaagcggaag agcgcctgat gcggtatttt ctccttacgc  6120
atctgtgcgg tatttcacac cgcatataag gtgcactgtg actgggtcat ggctgcgccc  6180
cgacacccgc caacacccgc tgacgcgccc tgacgggctt gtctgctccc ggcatccgct  6240
tacagacaag ctgtgaccgt ctccgggagc tgcatgtgtc agaggttttc accgtcatca  6300
ccgaaacgcg cgaggcagct gcggtaaagc tcatcagcgt ggtcgtgcag cgattcacag  6360
atgtctgcct gttcatccgc gtccagctcg ttgagtttct ccagaagcgt taatgtctgg  6420
cttctgataa agcgggccat gttaagggcg gttttttcct gtttggtcac tgatgcctcc  6480
gtgtaagggg gatttctgtt catgggggta atgataccga tgaaacgaga gaggatgctc  6540
acgatacggg ttactgatga tgaacatgcc cggttactgg aacgttgtga gggtaaacaa  6600
ctggcggtat ggatgcggcg ggaccagaga aaaatcactc agggtcaatg ccagcgcttc  6660
gttaatacag atgtaggtgt tccacagggt agccagcagc atcctgcgat gcagatccgg  6720
aacataatgg tgcagggcgc tgacttccgc gtttccagac tttacgaaac acggaaaccg  6780
aagaccattc atgttgttgc tcaggtcgca gacgttttgc agcagcagtc gcttcacgtt  6840
cgctcgcgta tcggtgattc attctgctaa ccagtaaggc aaccccgcca gcctagccgg  6900
gtcctcaacg acaggagcac gatcatgcgc acccgtggcc aggacccaac gctgcccgaa  6960
att                                                               6963
```

```
SEQ ID NO: 28          moltype = DNA  length = 10103
FEATURE                Location/Qualifiers
misc_feature           1..10103
                       note = Synthetic plasmid.
source                 1..10103
                       mol_type = other DNA
                       organism = synthetic construct
SEQUENCE: 28
ctcgagggtg ttttcacgag caattgacca acaaggacgt ttaaacataa aggaggaata  60
taatgagtcg tcaatctatg tcgaaagccc ataaaaagat cacagagctg tcctgggagc  120
cgacgtttgc cactcccgcc aaacgttttg gtaccgacta cacatttgac aatgctccga  180
aaaaagatcc tctgaagcag attttacgct cgtactttcc catggaggag gaaaaagatt  240
cacgcgtttt cggagcgatg gacggggcca tccgtggtaa tatgtttcgc caggtgcagg  300
agcgttggat ggagtggcag aagttgtttc tgtcaattat cccgtttcct gaaatctccg  360
cggcacgtgc catgccaatg gcgattgacg ccgtgcccaa cccagagatt cataatggtt  420
```

-continued

```
tagctgttca gatgattgat gaagtgcgtc attcgacgat ccaaatgaac ctgaaacgcc  480
tgtacatgaa ttactacatc gatccagcgg gttttgatat gaccgaaaaa gctttcgcaa  540
ataactacgc tggtacaatt ggccgtcaat ttggcgaagg ttttattaca ggggatgcga  600
tcacggcagc caatatctac cttactgtgg ttgcagaaac tgcattcacc aacacgctgt  660
ttgtggcgat gccgagcgaa gctgcggcca atggagacta tctgctgcca actgtgttcc  720
acagtgtcca gagtgatgaa tctcgtcata tttcaaacgg ttactccatc cttctgatgg  780
cgttgtcgga cgaggataac cgtcagctgt tagaacgtga tcttcgctat gcctggtgga  840
acaaccaccg cgtcgttgac gccgcgattg gaaccttcat tgaatatggt accaaagatc  900
gtcgcaaaga ccgtgagtcg tatgcggaaa tgtggcgtcg ctggatttat gacgattatt  960
atcgtgcgta tctgattccg ctggagaaat acgggcttgt gatcccacac gatctgatcg  1020
aggagtcgtg gaaacaaatt tgggagaaag gctatgtcca tgaggtcgcc cagtttttttg  1080
cgacaggctg gcttgcgaat tattggcgca ttgattccat gactgatgaa gatttcgaat  1140
ggttcgaata caagtatcct ggctggtatg ataaatatgg taaatggtgg gaaaactata  1200
atcgcctgag caaaccgaac ggccacaatc cgattgtgtt tgaagatgta gattatgtgt  1260
acccggcacg ctgttggacg tgcatgagcc cctgctggtc agtccgcaca ctcgttacgg  1320
cggaagttga tggccaacat cgcacctatt gccacgaagt atgtcgttgg acggatgtgc  1380
gtgggttccc atccgatgtg ccgggtcgtg aaaccccaaa tatgggtcgc ttagtgggta  1440
aacgtgagtg ggaaacgttg taccacggtt ggaattgggc agatgttgtt tcggatatgg  1500
ggtttgtacg tgatgacggg aagacgatga ccccgaaacc gcatctggat ctggatccaa  1560
aaaaaatgtg gaccctcgat cacatgcgtc gctgtccgcc cctgcagtcg ccgaatgtac  1620
tgtttaacga aatgtccgac gcggagcgtg ctgcctatgt cgcggactac aacaaacagg  1680
gccctgctgg tcgtccggcc ccgcaatcgt aaatatagga ggataataat gggagataaa  1740
catgtagtcc gttttgaacc ggtgggtatc gaaattgaag ttgatgaaga tcagaccatc  1800
ctgcgtgcag cagccgaaca gggtgtgcag ctgatgcacg gctgcaaaga aggtcagtgt  1860
gcggcctgca aaagctttgt tctggaaggt gaggatattg agctggacag ttactctatt  1920
tttacactgc cagattacga gaaagaggag ggatcgacgt tgctgtgtcg tgcgcatgcc  1980
tatgaagact tgaccattga actgttgaac tatgatgaag aaattattcg cagcggtctg  2040
ccgctgcgta aaggtaaggt ccaggtagta gcaaatgatg aagttaccca tgacctgcgt  2100
cgtctggtag taaaactgat tgaaccggaa gagattaaat tttccccgg acagtacatg  2160
gatttcatcg ttccaggaac tgaagagtcg cgtagcttct caatggccaa tacaccaaac  2220
cgtgaaggcg aattcgaatt tgtgatcaag atttatccag atggcctttt tagtgaattt  2280
ctggccgaga aagttcaagt gggtgatcag ctggaagtgg aagcgccgtt tggcactttt  2340
accttacgcg agaaccgtac gtcagatatc gtttttgtgg gcggcggcgc gggtatggcg  2400
ccaatcctgg gtctgctgcg ttctatggca gaacgtggcg tggaacgccg cgcccgcttc  2460
tattacggcg cgcgtgcgac acgcgacctt tgctttgccg aagaaattgc cgcgctgggt  2520
gaacagctgc cgagtggcct tacatatacc ccggcgctga gccatcctga cgacgaaccg  2580
tggagcggcc agaccggcct gatcaccgag gtgttacagg ccaatgaaag tacactggag  2640
ggcgcggatg cctacgtatg tggtccacca ccaatggtcg acgccgcgat tgcgaccctt  2700
accgcccttg gtgtgcgtga ggaaaacatt ttctatgata aatttaccac ccaccgctga  2760
aataaggagg atattaatga cgaccacaga acgtccggaa cgttccgtgc ctaaacctgt  2820
gttcaccgat gcggaggcag gcgcccacga gtttcctgat agcggagcat ccgcgcgccg  2880
ttataattac tataactcaa tcaacgcaag ccgtacgcac tatgaagatg taacggtgga  2940
tgtgcagccg gatccgcgtc attatttgtc gcagggctgg atctacgggt tcgcggatgg  3000
atctgcacgc taccctctga cctggacgaa attgaaagcc gtgggccgtg gctcggcgcg  3060
cgcgcgtgca ttacctcgtt tacgtcgtca gggccttcgc gtctgtccgc cgaccgcttg  3120
gcatgaattt cgcgacccaa acgaggagtg ggaattgacc ttttatcgct ataacgctaa  3180
tgtggtgcgc caggttaacc agaatattga aaatgcccgc tatgcgaaag cgttcgaaca  3240
gtggacaccc aactggattc agttcgtgga acgtaatgtc ggcgcctgga tgcacattga  3300
gcatacgttg ggcctgtatg tcttcgctgc ctgcaatcgt tctgggccta ctaacatgca  3360
caataccgca atggcgtaca ccgcttgcca taaaattcgt tttgcacagg atcttgcact  3420
gtataactta accctcactg aagaaattga aggcttcgat ggaactgcac atttggaggc  3480
gtggaacagc gatccggagt ggcaggccag tggtcgcagt catgaagcgc tgaccgccgt  3540
ggatgacgac tggggcgaaa gtatttttgc cacgaatgtg gtgttcgaac cgttgcttcg  3600
cgagctgttt cgcagtaacc ttgttatgca ggcggctgcc ggtaacggtg atttcgttac  3660
cccgacggtg atgggcgcgg cggaatttga ttttgcgcaa cgtgacttac gttggaccca  3720
agcttgtttt ggtcccttaa cccaagataa ggaatttgcc gattataaca aagatctcat  3780
gcaaggatgg ctgtctcatt gggttccgca ggctatcgaa gcggctcgcg ttttgcagcc  3840
gatctggtcg ctgccagacg ctaaaccacc gcgctttgaa gattcattag accgtgcaaa  3900
aagccgtttt agcggtattg taacggactt agggttatct gtgccgaagg aactgtcaca  3960
ataaatttag gaggaatatt atgacgtctt ttaagacggc agaatctccc tttaaagcag  4020
ataacacggc ttcgggaaag gctggcgtga cccttatgaa caatcaaatt ggtgtggtgg  4080
ttgcagaagt aatggatcag caagaaaatg taaccattac acacttgccg agtatgattc  4140
gtgttgactg tgtgggtcgc atggattttg tgtatgacga tatctcggaa gcgctgggcg  4200
aggagccggg gttttacgac gctgcggaat tcgaagaaaa catgagcacc cattacggga  4260
agatgattca catggatgac cgtactgtaa tgtttgggaa cttagaagaa gccgcagaat  4320
tcattggtga tatgctgccg cctccggtta aataataagt ttaaacggat acgccctcga  4380
atcctgggat agcggccgct cagtgaccgg catagcgtac gcctcgagtt acgcccgttc  4440
tgcttgacct ggtaaagtta caaccaatta accaattctg attagaaaaa ctcatcgagc  4500
atcaaatgaa actgcaattt attcatatca ggattatcaa taccatattt ttgaaaaagc  4560
cgtttctgta atgaaggaga aaactcaccg aggcagttcc ataggatggc aagatcctgg  4620
tatcggtctg cgattccgac tcgtccaaca tcaatacaac ctattaattt cccctcgtca  4680
aaaataaggt tatcaagtga gaaatcacca tgagtgacga ctgaatccgg tgagaatggc  4740
aaaagcttat gcatttcttt ccagacttgt tcaacaggcc agccattacg ctcgtcatca  4800
aaatcactcg catcaaccaa accgttattc attcgtgatt gcgcctgagc gagacgaaat  4860
acgcgatcgc tgttaaaagg acaattacaa acaggaatcg aatgcaaccg gcgcaggaac  4920
actgccagcg catcaacaat attttcacct gaatcaggat attcttctaa tacctggaat  4980
gctgttttcc cggggatcgc agtggtgagt aaccatgcat catcaggagt acggataaaa  5040
tgcttgatgg tcggaagagg cataaattcc gtcagccagt ttagtctgac catctcatct  5100
gtaacatcat tggcaacgct acctttgcca tgtttcagaa acaactctgg cgcatcgggc  5160
```

```
ttcccataca atcgatagat tgtcgcacct gattgcccga cattatcgcg agcccattta  5220
tacccatata aatcagcatc catgttggaa tttaatcgcg gcctcgagca agacgtttcc  5280
cgttgaatat ggctcataac accccttgta ttactgttta tgtaagcaga cagttttatt  5340
gttcatgatg atatattttt atcttgtgca atgtaacatc agagattttg agacacaacg  5400
tggctttgtt gaataaatcg aacttttgct gagttgaagg atcagatcac gcatcttccc  5460
gacaacgcag accgttccgt ggcaaagcaa aagttcaaaa tcaccaactg gtccacctac  5520
aacaaagctc tcatcaaccg tggctccctc actttctggc tggatgatgg ggcgattcag  5580
gcctggtatg agtcagcaac accttcttca cgaggcagac ctcagcgcta gcggagtgta  5640
tactggctta ctatgttggc actgatgagg gtgtcagtga agtgcttcat gtggcaggag  5700
aaaaaaggct gcaccggtgc gtcagcagaa tatgtgatac aggatatatt ccgcttcctc  5760
gctcactgac tcgctacgct cggtcgttcg actgcggcga gcggaaatgg cttacgaacg  5820
gggcggagat ttcctggaag atgccaggaa gatacttaac agggaagtga gagggccgcg  5880
gcaaagccgt ttttccatag gctccgcccc cctgacaagc atcacgaaat ctgacgctca  5940
aatcagtggt ggcgaaaccc gacaggacta taaagatacc aggcgtttcc ccctggcggc  6000
tccctcgtgc gctctcctgt tcctgccttt cggtttaccg gtgtcattcc gctgttatgg  6060
ccgcgtttgt ctcattccac gcctgacact cagttccggg taggcagttc gctccaagct  6120
ggactgtatg cacgaacccc ccgttcagtc cgaccgctgc gccttatccg gtaactatcg  6180
tcttgagtcc aacccggaaa gacatgcaaa agcaccactg gcagcagcca ctggtaattg  6240
atttagagga gttagtcttg aagtcatgcg ccggttaagg ctaaactgaa aggacaagtt  6300
ttggtgactg cgctcctcca agccagttac ctcggttcaa agagttggta gctcagagaa  6360
ccttcgaaaa accgccctgc aaggcggttt tttcgttttc agagcaagag attacgcgca  6420
gaccaaaacg atctcaagaa gatcatctta ttaaggggtc tgacgctcag tggaacgaaa  6480
actcacgtta agggattttg gtcatgagat tatcaaaaag gatcttcacc tagatccttt  6540
taaattaaaa atgaagtttt aaatcaatct aaagtatata tgagtaaact tggtctgaca  6600
ggtgagctga taccgctcgc cgcatgcaca tgcagtcatg tcgtgctaat gtgtaaaaca  6660
tgtacatgca gattgctggg ggtgcagggg gcggagccac cctgtccatg cggggtgtgg  6720
ggcttgcccc gccggtacag acagtgagca ccggggcacc tagtcgcgga tacccccccct  6780
aggtatcgga cacgtaaccc tcccatgtcg atgcaaatct ttaacattga gtacgggtaa  6840
gctggcacgc atagccaagc taggcggcca ccaaacacca ctaaaaatta atagtcccta  6900
gacaagacaa acccccgtgc gagctaccaa ctcatatgca cgggggccac ataacccgaa  6960
ggggtttcaa ttgacaacca tagcactagc taagacaacg ggcacaacac ccgcacaaac  7020
tcgcactgcg caaccccgca caacatcggg tctaggtaac actgaaatag aagtgaacac  7080
ctctaaggaa ccgcaggtca atgagggttc taaggtcact cgcgctaggg cgtggcgtag  7140
gcaaaacgtc atgtacaaga tcaccaatag taaggctctg gcggggtgcc ataggtggcg  7200
cagggacgaa gctgttgcgg tgtcctggtc gtctaacggt gcttcgcagt ttgagggtct  7260
gcaaaactct cactctcgct ggggggtcacc tctggctgaa ttggaagtca tgggcgaacg  7320
ccgcattgag ctggctattg ctactaagaa tcacttggcg gcgggtggcg cgctcatgat  7380
gtttgtgggc actgttcgac acaaccgctc acagtcattt gcgcaggttg aagcgggtat  7440
taagactgcg tactcttcga tggtgaaaac atctcagtgg aagaaagaac gtgcacggta  7500
cggggtggag cacacctata gtgactatga ggtcacagac tcttgggcga acggttggca  7560
cttgcaccgc aacatgctgt tgttcttgga tcgtccactg tctgacgatg aactcaaggc  7620
gtttgaggat tccatgtttt cccgctggtc tgctggtgtg gttaaggccg gtatggacgc  7680
gccactgcgt gagcacgggg tcaaacttga tcaggtgtct acctggggtg gagacgctgc  7740
gaaaatggca acctacctcg ctaagggcat gtctcaggaa ctgactggct ccgctactaa  7800
aaccgcgtct aaggggtcgt acacgccgtt tcagatgttg gatatgttgg ccgatcaaag  7860
cgacgccggc gaggatatgg acgctgtttt ggtggctcgg tggcgtgagt atgaggttgg  7920
ttctaaaaac ctgcgttcgt cctggtcacg tggggctaag cgtgctttgg gcattgatta  7980
catagacgct gatgtacgtc gtgaaatgga agaagaactg tacaagctcg ccggtctgga  8040
agcaccggaa cgggtcgaat caacccgcgt tgctgttgct ttggtgaagc ccgatgattg  8100
gaaactgatt cagtctgatt tcgcggttag gcagtacgtt ctagattgcg tggataaggc  8160
taaggacgtg gccgctgcgc aacgtgtcgc taatgaggtg ctggcaagtc tgggtgtgga  8220
ttccaccccg tgcatgatcg ttatggatga tgtggacttg gacgcggttc tgcctactca  8280
tggggacgct actaagcgtg atctgaatgc ggcggtgttc gcgggtaatg agcagactat  8340
tcttcgcacc cactaaaagc ggcataaacc ccgttcgata ttttgtgcga tgaatttatg  8400
gtcaatgtcg cgggggcaaa ctatgatggg tcttgttgtt gcagccgaac gacctagcgc  8460
agcgagtcag tgagcgagga agcggaagag cgcctgatgc ggtattttct ccttacgcat  8520
ctgtgcggta tttcacaccg catatggtgc actctcagta caatctgctc tgatgccgca  8580
tagttaagcc agtatacact ccgctatcgc tacgtgactg ggtcatggct gcgccccgac  8640
acccgccaac acccgctgac gcgccctgac gggcttgtct gctcccggca tccgcttaca  8700
gacaagctgt gaccgtctcc gggagctgca tgtgtcagag gttttcaccg tcatcaccga  8760
aacgcgcgag gcagcagatc aattcgcgcg cgaaggcgaa gcggcatgca taatgtgcct  8820
gtcaaatgga cgaagcaggg attctgcaaa ccctatgcta ctccgtcaag ccgtcaattg  8880
tctgattcgt taccaattat gacaacttga cggctacatc attcactttt tcttcacaac  8940
cggcacggaa ctcgctcggg ctggccccgg tgcatttttt aaatacccgc gagaaataga  9000
gttgatcgtc aaaaccaaca ttgcgaccga cggtggcgat aggcatccgg gtggtgctca  9060
aaagcagctt cgcctggctg atacgttggt cctcgcgcca gcttaagacg ctaatcccta  9120
actgctggcg gaaaagatgt gacagacgcg acggcgacaa gcaaacatgc tgtgcgacgc  9180
tggcgatatc aaaattgctg tctgccaggt gatcgctgat gtactgacaa gcctcgcgta  9240
cccgattatc catcggtgga tggagcgact cgttaatcgc ttccatgcgc cgcagtaaca  9300
attgctcaag cagatttatc gccagcagct ccgaatagcg cccttcccct tgcccggcgt  9360
taatgatttg cccaaacagg tcgctgaaat gcggctggtg cgcttcatcc gggcgaaaga  9420
accccgtatt ggcaaatatt gacggccagt taagccattc atgccagtag gcgcgcggac  9480
gaaagtaaac ccactggtga taccattcgc gagcctccgg atgacgaccg tagtgatgaa  9540
tctctcctgg cgggaacagc aaaatatcac ccggtcggca aacaaattct cgtccctgat  9600
ttttcaccac cccctgaccg cgaatggtga gattgagaat ataacctttc attcccagcg  9660
gtcggtcgat aaaaaaatcg agataaccgt tggcctcaat cggcgttaaa cccgccacca  9720
gatgggcatt aaacgagtat cccggcagca ggggatcatt ttgcgcttca gccatacttt  9780
tcatactccc gccattcaga gaagaaacca attgtccata ttgcatcaga cattgccgtc  9840
actgcgtctt ttactggctc ttctcgctaa ccaaaccggt aaccccgctt attaaaagca  9900
```

```
ttctgtaaca aagcgggacc aaagccatga caaaaacgcg taacaaaagt gtctataatc  9960
acggcagaaa agtccacatt gattatttgc acggcgtcac actttgctat gccatagcat  10020
ttttatccat aagattagcg gatcctacct gacgcttttt atcgcaactc tctactgttt  10080
ctccataccc gtttttttgg gat                                          10103

SEQ ID NO: 29           moltype = DNA  length = 10025
FEATURE                 Location/Qualifiers
misc_feature            1..10025
                        note = Synthetic plasmid.
source                  1..10025
                        mol_type = other DNA
                        organism = synthetic construct
SEQUENCE: 29
ccagcgacat ggaggcccag aataccctcc ttgacagtct tgacgtgcgc agctcagggg  60
catgatgtga ctgtcgcccg tacatttagc ccatacatcc ccatgtataa tcatttgcat  120
ccatacattt tgatggccgc acggcgcgaa gcaaaaatta cggctcctcg ctgcagacct  180
gcgagcaggg aaacgctccc ctcacagacg cgttgaattg tccccacgcc gcgcccctgt  240
agagaaatat aaaaggttag gatttgccac tgaggttctt ctttcatata cttcctttta  300
aaatcttgct aggatacagt tctcacatca catccgaaca taaacaacca tgggtaagga  360
aaagactcac gtttcgaggc cgcgattaaa ttccaacatg gatgctgatt tatatgggta  420
taaatgggct cgcgataatg tcgggcaatc aggtgcgaca atctatcgat tgtatgggaa  480
gcccgatgcg ccagagttgt ttctgaaaca tggcaaaggt agcgttgcca atgatgttac  540
agatgagatg gtcagactaa actggctgac ggaatttatg cctcttccga ccatcaagca  600
ttttatccgt actcctgatg atgcatggtt actcaccact gcgatccccg gcaaaacagc  660
attccaggta ttagaagaat atcctgattc aggtgaaaat attgttgatg cgctggcagt  720
gttcctgcgc cggttgcatt cgattcctgt ttgtaattgt ccttttaaca gcgatcgcgt  780
atttcgtctc gctcaggcgc aatcacgaat gaataacggt ttggttgatg cgagtgattt  840
tgatgacgag cgtaatggct ggcctgttga acaagtctgg aaagaaatgc ataagctttt  900
gccattctca ccggattcag tcgtcactca tggtgatttc tcacttgata accttatttt  960
tgacgagggg aaattaatag gttgtattga tgttggacga gtcggaatcg cagaccgata  1020
ccaggatctt gccatcctat ggaactgcct cggtgagttt tctccttcat tacagaaacg  1080
gctttttcaa aaatatggta ttgataatcc tgatatgaat aaattgcagt ttcatttgat  1140
gctcgatgag tttttctaat cagtactgac aataaaaaga ttcttgtttt caagaacttg  1200
tcatttgtat agttttttta tattgtagtt gttctatttt aatcaaatgt tagcgtgatt  1260
tatatttttt ttcgcctcga catcatctgc ccagatgcga agttaagtgc gcagaaagta  1320
atatcatgcg tcaatcgtat gtgaatgctg gtcgctatac tgctgtcgat tcgatactaa  1380
cgccaagaag ttgattgaga ctttcaacga gattgctgaa gacaaggaac aattcgagaa  1440
gttttacagt gctttctcca agaacttgaa gttgggtgtc catgaagaca gccaaaacag  1500
atccgcattg gccaagttgc tgagatttaa ctccaccaag tctactgagg agctaacctc  1560
attctctgac tacgtcacca gaatgccaga gcaccagaag aacatctact tcattaccgg  1620
tgagtctgtc aaggctcttg agaaatctcc attcttggat gctttgaagg agaagaactt  1680
tgaggtccta ttgctgaccg atcctattga tgagtacgct atgactcaat tgaaagagat  1740
tgaggacaag aaattggttg acatcactaa agactttgag ctggaagagt ctgaggagga  1800
gaagaaggct agagaggaag aggttaaaga tttcgagcct ttgactaaag ccctgaaaga  1860
gattttgggt gacaaggttg agaaggttgt agtttcctac aagctggttg actctcctgc  1920
tgctattaga acttcccaat tcggctggtc tgctaacatg gaaagaatta tgaaggctca  1980
agctctgaga gacaccaaca ccatgtcctc gtacatggct tcaaagaaga tcttcgagat  2040
ctctccaaag tcgccaatca ttaaggcttt gagaaagaag gttgaggcta ccggtacaga  2100
agagacccca cagaatcagg ggataacgca ggaaagaaca tgtgagcaaa aggccagcaa  2160
aaggccagga accgtaaaaa ggccgcgttg ctggcgtttt tccataggct ccgcccccct  2220
gacgagcatc acaaaaatcg acgctcaagt cagaggtggc gaaacccgac aggactataa  2280
agataccagg cgtttccccc tggaagctcc ctcgtgcgct ctcctgttcc gaccctgccg  2340
cttaccggat acctgtccgc ctttctccct tcgggaagcg tggcgctttc tcaatgctca  2400
cgctgtaggt atctcagttc ggtgtaggtc gttcgctcca agctgggctg tgtgcacgaa  2460
ccccccgttc agcccgaccg ctgcgcctta tccggtaact atcgtcttga gtccaacccg  2520
gtaagacacg acttatcgcc actggcagca gccactggta acaggattag cagagcgagg  2580
tatgtaggcg gtgctacaga gttcttgaag tggtggccta actacggcta cactagaagg  2640
acagtatttg gtatctgcgc tctgctgaag ccagttacct tcggaaaaag agttggtagc  2700
tcttgatccg gcaaacaaac caccgctggt agcggtggtt tttttgtttg caagcagcag  2760
attacgcgca gaaaaaaagg atctcaagaa gatcctttga tcttttctac ggggtctgac  2820
gctcagtgga acgaaaactc acgttaaggg attttggtca tgagattatc aaaaaggatc  2880
ttcacctaga tccttttaaa ttaaaaatga agttttaaat caatctaaag tatatatgag  2940
taaacttggt ctgacagtta ccaatgctta atcagtgagg cacctatctc agcgatctgt  3000
ctatttcgtt catccatagt tgcctgactc cccgtcgtgt agataactac gatacgggag  3060
ggcttaccat ctggccccag tgctgcaatg ataccgcgag acccacgctc accggctcca  3120
gatttatcag caataaacca gccagccgga agggccgagc gcagaagtgg tcctgcaact  3180
ttatccgcct ccatccagtc tattaattgt tgccgggaag ctagagtaag tagttcgcca  3240
gttaatagtt tgcgcaacgt tgttgccatt gctacaggca tcgtggtgtc acgctcgtcg  3300
tttggtatgg cttcattcag ctccggttcc caacgatcaa ggcgagttac atgatccccc  3360
atgttgtgca aaaaagcggt tagctccttc ggtcctccga tcgttgtcag aagtaagttg  3420
gccgcagtgt tatcactcat ggttatggca gcactgcata attctcttac tgtcatgcca  3480
tccgtaagat gcttttctgt gactggtgag tactcaacca agtcattctg agaatagtgt  3540
atgcggcgac cgagttgctc ttgcccggcg tcaatacggg ataataccgc gccacatagc  3600
agaactttaa aagtgctcat cattggaaaa cgttcttcgg ggcgaaaact ctcaaggatc  3660
ttaccgctgt tgagatccag ttcgatgtaa cccactcgtg cacccaactg atcttcagca  3720
tcttttactt tcaccagcgt ttctgggtga gcaaaaacag gaaggcaaaa tgccgcaaaa  3780
aagggaataa gggcgacacg gaaatgttga atactcatac tcttcctttt tcaatattat  3840
tgaagcattt atcagggtta ttgtctcatg agcggataca tatttgaatg tatttagaaa  3900
aataaacaaa taggggttcc gcgcacattt ccccgaaaag tgccacctga cgggtctcac  3960
```

-continued

```
agatgacaga gttgtcaaga acttgaccac tttgttgttc gacacagctt tgttgacttc  4020
cggtttcact ttggatgagc caacttcttt cgctgccaga atcaacggtt tgatctccat  4080
tggtttgaac atcgatgagg aggaagagaa agagccagaa caggctactg aagctccaag  4140
tgaagaagct gttgctgagt ctgccatgga ggaggttgac tagttgaatt taggtatata  4200
tagtgactgt gatatttagc taatgaaatc taattggata tttagaatgc ctcatctcgt  4260
agcctatcaa ttactattag gccatctctt atgggccctt ctttgaaatt gcattcaagg  4320
ggggatggga ctattttgaa tttgaagttt ggactctgtg agctgtttgg ccaattgaag  4380
tcatccactt gtacacaggg attcaccagt agtttagaac aattctctat cgttattctc  4440
ttgtcgtctt tggcaataca agcgtcgatg actgagttgg tgactttatg aagtctaagt  4500
tgatatgagt ttgaaattat gaaacagttt tttacactgg acatgtagat agggcccttg  4560
atgtttagga agaggataca gtttgagatg ttggagatgt gtgtggaggg agcgaccact  4620
tttaaaacca catgatccag acgttgctca gttatcgaag tttcggaaac aacgccagat  4680
ctgtttagct tgggtatttg acaggttggg gagcaaataa gtgatgatgt cccatgaaag  4740
tagaaaatgg ctagtagaag gcaaaaattt gaaattctta gagtcaaata gttagactcc  4800
aagttctaat ccacatttgg tcagtttcat agcatccaga gcttttgcca ctggtgaaca  4860
tatctaccca ttgcgatgca acaagtcact gaaagcctaa aacggagatt cccctatctt  4920
acagcctcgt tcaaaaaaac tgctaccgtt tatctgctat ggccgatgtg aggatgcgct  4980
catgcccaag agtccaactt tatcaaaaac ttgacccgtc atacaggctc tagatcaaga  5040
agcaaactta atctcagcat ctggttacgt aactctggca accagtaaca cgcttaaggt  5100
ttggaacaac actaaactac cttgcggtac taccattgac actacacatc cttaattcca  5160
atcctgtctg gcctccttca ccttttaacc atcttgccca ttccaactcg tgtcagattg  5220
cgtatcaagt gaaaaaaaaa aattttaaaa tctttaaccc aatcaggtaa taactgtcgc  5280
ctcttttatc tgccgcactg catgaggtgt ccccttagtg ggaaagagta ctgagccaac  5340
cctggaggac agcaagggaa aaatacctac aacttgcttc ataatggtcg taaaaacaat  5400
ccttgtcgga tataagtgtt gtagactgtc ccttatcctc tgcgatgttc ttcctctcaa  5460
agtttgcgat ttctctctat cagaattgcc atcaagagac tcaggactaa tttcgcagtc  5520
ccacacgcac tcgtacatga ttggctgaaa tttccctaaa gaatttcttt ttcacgaaaa  5580
ttttttttta cacaagattt tcagcagata taaaatctcg agggagagca ggacctccgc  5640
tgtgactctt cttttttttc ttttattctc actacataca ttttagttat tcgccaacat  5700
ggctatgcac cctcgaaagg actggtatga gttgacaaga gcaacaaact ggacgccatc  5760
ctatgtgaca gaagaacaat tgttcccaga gcgtatgtca ggacatatgg gcataccctt  5820
ggaaaaatgg gagtcatacg atgagcctta taagacttct tacccagagt atgtttccat  5880
ccaaagagaa aaagatgccg gtgcctattc cgtgaaagct gctttagaaa gagctaagat  5940
ctacgaaaat tcagatcctg gatggatctc tactctgaag tcacactatg ggcaattgc   6000
cgtgggcgaa tacgctgctg tcacaggaga gggacgtatg gccagatttt caaaagcacc  6060
cggaaacaga aatatggcta catttggtat gatggatgaa ttaagacatg gtcagctgca  6120
gttattcttt cctcatgaat actgtaaaaa ggacagacaa ttcgattggg cctggagagc  6180
ctaccattca aacgaatggg ccgcaattgc tgctaaacat ttctttgacg atatcattac  6240
tggacgtgat gcaataagtg tcgccatcat gttaactttt tcttttgaaa caggcttcac  6300
taacatgcaa ttcttaggat tggctgcaga cgctgctgaa gctggcgact atacattcgc  6360
taatttgata tcttcaattc agacagatga gtccagacac gctcaacagg gtggtcctgc  6420
tctgcaactt ttgatcgaaa atggtaagag agaagaagca cagaagaaag ttgacatggc  6480
tatatggaga gcttggcgtt tatttgccgt acttactggt ccagtaatgg actattacac  6540
tccattagaa gacagatcac agtcttttaa ggaatttatg tacgagtgga tcataggcca  6600
gtttgaaaga tccctgattg acttgggcct tgacaaacct tggtattggg atttattcct  6660
taaggatatt gatgaactac accactctta ccatatggga gtttggtact ggagaacaac  6720
agcttggtgg aaccccgctg ccggagttac acccgaagaa agggactggt tggaggaaaa  6780
gtatccaggt tggaataaac gttggggaag atgttgggac gtaataactg aaaacgtgtt  6840
gaacgacaga atggatctgg taagtcctga aactctgcca tcagtctgca acatgtctca  6900
aatccctcta gttggtgtgc caggagacga ttggaacata gaagtttttt ctttagagca  6960
caatgggcga ctttatcact tcggatcaga ggttgacaga tgggttttcc aacaagaccc  7020
agtccaatac caaaaccata tgaatatagt tgacaggttt ttggcaggtc aaatccagcc  7080
tatgacctta gagggagctt taaagtacat gggctttcag tctattgagg aaatgggaaa  7140
agacgctcat gattttgcct gggccgataa gtgtaagcca gcaatgaaaa aaagtgcata  7200
agtatctcca gtcgtttaga ttgttagata ttttctttgt gtattcgttt cagtctgatg  7260
tttatgctac aaacgtcatc tggactttaa tccaataagg atattcttca acttaatagt  7320
atcttaataa tatttttttt cttttgattt cttcgtaagg tgttttgttg cactcatgat  7380
ctacgacttt tgttcgtgac tgattttttt tgtagaaatg tcttggtgtc ctcgtccaat  7440
caggtagcca tctctgaaat atctggctcc gttgcaactc cgaacgacct gctggcaacg  7500
taaaattctc cggggtaaaa cttaaatgtg gagtaatgga accagaaacg tctcttccct  7560
tctctctcct tccaccgccc gttaccgtcc ctaggaaatt ttactctgct ggagagcttc  7620
ttctacggcc cccttgcagc aatgctcttc ccagcattac gttgcgggta aaacggaggt  7680
cgtgtacccg acctagcagc ccagggatgg aaaagtcccg gccgtcgctg gcaataatag  7740
cgggcggacg catgtcatga gattattgga aaccaccaga atcgaatata aaaggcgaac  7800
acctttccca attttggttt ctcctgaccc aaagacttta aatttaattt atttgtccct  7860
atttcaatca attgaacaac tatatgtcag cttttcccgt gcacgcagct ttcgagaaag  7920
actttttggt acaactggtt gtagtggatc ttaacgattc aatggatcag gtcgccgaaa  7980
aggttgcata ccattgtgtt aacaggaggg ttgctcctag ggaaggagta atgagagttc  8040
gtaagcacag gtccacagaa ttgtttccaa gagatatgac tatagccgaa tctggtctga  8100
atccaaccga ggttattgac gttgtattcg aggaataaat tcggatagtg taatttaatc  8160
aataacttga aaaaaatatc atttaattta ctatacacac ggacataaac tgaaagggca  8220
aggaagggga aaatgggaaa aataatgagg atatgcaaga tgagagatga gagatgagag  8280
atgtccactt tagtcagttt tggctttact tttatctttt tctatggcat ctttcgtttt  8340
actactagta tacatagaat aaaaacggta atagaactgg gaactaagca gaaacttaca  8400
attcctgaga agccttggcc ttggcagact tctttggcaa caattcggat tgaatgtttg  8460
gcaagacacc accttgggcg atggtgacgt gtcccagcaa cttgttcaat tcctcatcgt  8520
ttctgatggc caattgcaag tgtcttggga taattctgga cttcttgttg tctctggcgg  8580
cgttaccggc caattccaaa atttcagcag ccaagtactc caagacagca gtcaaataga  8640
ctggagcacc agaaccaatt ctttgggcgt agttacctct tctcagaaga cggtggactc  8700
```

```
ttcccacagg gaaggtcaaa cctgccttag aagatcttga ggttgaggcc ttttcagccg  8760
aagatgcttt tcctttacca ccggacattg ttgtagtttt aatatagttt gagtatgaga  8820
tggaactcag aacgaaggaa ttatcaccag tttatatatt ctgaggaaag ggtgtgtcct  8880
aaattggaca gtcacgatgg caataaacgc tcagccaatc agaatgcagg agccataaat  8940
tgttgtatta ttgctgcaag atttatgtgg gttcacattc cactgaatgg ttttcactgt  9000
agaattggtg tcctagttgt tatgtttcga gatgttttca agaaaaacta aaatgcacaa  9060
actgaccaat aatgtgccgt cgcgcttggt acaaacgtca ggattgccac cactttttc  9120
gcactctggt acaaaagttc gcacttccca ctcgtatgta acgaaaaaca gagcagtcta  9180
tccagaacga gacaaattag cgcgtactgt cccattccat aaggtatcat aggaaacgag  9240
agtcctcccc ccatcacgta tatataaaca cactgatatc ccacatccgc ttgtcaccaa  9300
actaatacat ccagttcaag ttacctaaac aaatcaaaat gtctttcgaa aaaatctgct  9360
cattagacga tatttgggtc ggagagatgg agacatttga gacgtccgat ggaactgagg  9420
tcctgattgt taattccgag gaacatggtg tgaaggctta ccaagccatg tgccctcatc  9480
aggagatatt gttgagtgaa ggaagttacg agggaggggt cataacttgc agggctcatt  9540
tgtggacttt taatgatggt actggtcatg gtataaaccc tgatgactgt tgtttggctg  9600
agtaccctgt tgaggtaaaa ggcgatgata tttacgtctc tactaagggt attttgccaa  9660
acaaggctca ctcctagaga catgactgtt cctcagttca agttgggcac ttacgagaag  9720
accggtcttg ctagattcta atcaagagga tgtcagaatg ccatttgcct gagagatgca  9780
ggcttcattt ttgattactt ttttatttgt aacctatata gtataggatt tttttgtca  9840
ttttgtttct tctcgtacga gcttgctcct gatcagccta tctcgcagct gatgaatatc  9900
ttgtggtagg ggtttgggaa aatcattcga gtttgatgtt tttcttggta tttcccactc  9960
ctcttcagag tacagaagat taagtgagag cggccgctcg tccccgccgg gtcacccggc  10020
tcgag                                                             10025

SEQ ID NO: 30          moltype = DNA  length = 10271
FEATURE                Location/Qualifiers
misc_feature           1..10271
                       note = Synthetic plasmid.
source                 1..10271
                       mol_type = other DNA
                       organism = synthetic construct
SEQUENCE: 30
ttcagtaatg tcttgtttct tttgttgcag tggtgagcca ttttgacttc gtgaaagttt  60
ctttagaata gttgtttcca gaggccaaac attccacccg tagtaaagtg caagcgtagg  120
aagaccaaga ctggcataaa tcaggtataa gtgtcgagca ctggcaggtg atcttctgaa  180
agtttctact agcagataag atccagtagt catgcatatg gcaacaatgt accgtgtgga  240
tctaagaacg cgtcctacta accttcgcat tcgttggtcc agtttgttgt tatcgatcaa  300
cgtgacaagg ttgtcgattc cgcgtaagca tgcataccca aggacgcctg ttgcaattcc  360
aagtgagcca gttccaacaa tctttgtaat attagagcac ttcattgtgt tgcgcttgaa  420
agtaaaatgc gaacaaatta agagataatc tcgaaaccgc gacttcaaac gccaatatga  480
tgtgcggcac acaataagcg ttcatatccg ctgggtgact ttctcgcttt aaaaaattat  540
ccgaaaaaat ttatgggtac caccactctt gacgacacgg cttaccggta ccgcaccagt  600
gtcccggggg acgccgaggc catcgaggca ctggatgggt ccttcaccac cgacaccgtc  660
ttccgcgtca ccgccaccgg ggacggcttc accctgcggg aggtgccggt ggacccgccc  720
ctgaccaagg tgttccccga cgacgaatcg gacgacgaat cggacgccgg ggaggacggc  780
gacccggact cccggacgtt cgtcgcgtac ggggacgacg gcgacctggc gggcttcgtg  840
gtcgtctcgt actccggctg gaaccgccgg ctgaccgtcg aggacatcga ggtcgccccg  900
gagcaccggg ggcacggggt cgggcgcgcg ttgatggggc tcgcgacgga gttcgcccgc  960
gagcggggcg ccgggcacct ctggctggag gtcaccaacg tcaacgcacc ggcgatccac  1020
gcgtaccggc ggatggggtt caccctctgc ggcctggaca ccgccctgta cgacggcacc  1080
gcctcggacg gcgagcaggc gctctacatg agcatgccct gcccctaatc agtactgaca  1140
ataaaaagat tcttgttttc aagaacttgt catttgtata gtttttttat attgtagttg  1200
ttctatttta atcaaatgtt agcgtgattt atattttttt tcgcctcgac atcatctgcc  1260
cagatgcgaa gttaagtgcg cagaaagtaa tatcatgcgt caatcgtatg tgaatgctgg  1320
tcgctatact gctgtcgatt cgatactaac gcggccgctc ttaagggtga tgtagccctc  1380
gccgtttttc gaatagctgt agatacattg acggaacaa agagaaactc taagggatac  1440
actctatcat tggtgaaaaa gtttatttca attgttgacg gctttgaagt tcttgacaga  1500
gattaccttg tttcctcgat tgtaactcac atgtcctcat tggatcccaa atgttcggag  1560
tatattgtta ttgctttagc gcttccattg cgatatttgt ctatttcgtc accagagttt  1620
ccaatcaagc tgcagctgtc tgtcaagaat tatctaaagc tagatgagcc ctcaactaga  1680
aatggctatg ttgagttttt aaccaaactt ttggaagcat gtagaaacga agaaaatgat  1740
acaagagctg ttttactaca acaattagta aagaaatgca aatgttctgt gtgatagcct  1800
ttcttttttg aattcagcat gttggtttat ggtgttttat tgaagccatg actgagcctt  1860
tttacttaga tgaccacatg acttatgaga cgtcaattaa ggaggaccag tagaataaga  1920
tcgcaatagt ttctgctgtc atgatgaagc gtatatacag agccaaatct tcatgcatac  1980
aataacatat tgtgtttcct cccaaataat taacaatgac ttacctgtat atccaggaca  2040
ctcctgtact gagaccgacc acagaatcag gggataacgc aggaaagaac atgtgagcaa  2100
aaggccagca aaaggccagg aaccgtaaaa aggccgcgtt gctggcgttt ttccataggc  2160
tccgcccccc tgacgagcat cacaaaaatc gacgctcaag tcagaggtgg cgaaacccga  2220
caggactata aagataccag gcgtttcccc ctggaagctc cctcgtgcgc tctcctgttc  2280
cgaccctgcc gcttaccgga tacctgtccg cctttctccc ttcgggaagc gtggcgcttt  2340
ctcaatgctc acgctgtagg tatctcagtt cggtgtaggt cgttcgctcc aagctgggct  2400
gtgtgcacga acccccgtt cagcccgacc gctgcgcctt atccggtaac tatcgtcttg  2460
agtccaaccc ggtaagacac gacttatcgc cactggcagc agccactggt aacaggatta  2520
gcagagcgag gtatgtaggc ggtgctacag agttcttgaa gtggtggcct aactacggct  2580
acactagaag gacagtattt ggtatctgcg ctctgctgaa gccagttacc ttcggaaaaa  2640
gagttggtag ctcttgatcc ggcaaacaaa ccaccgctgg tagcggtggt ttttttgttt  2700
gcaagcagca gattacgcgc agaaaaaaag gatctcaaga agatcctttg atcttttcta  2760
cggggtctga cgctcagtgg aacgaaaact cacgttaagg gattttggtc atgagattat  2820
```

-continued caaaaaggat cttcacctag atccttttaa attaaaaatg aagttttaaa tcaatctaaa 2880
gtatatatga gtaaacttgg tctgacagtt accaatgctt aatcagtgag gcacctatct 2940
cagcgatctg tctatttcgt tcatccatag ttgcctgact ccccgtcgtg tagataacta 3000
cgatacggga gggcttacca tctggcccca gtgctgcaat gataccgcga gacccacgct 3060
caccggctcc agatttatca gcaataaacc agccagccgg aagggccgag cgcagaagtg 3120
gtcctgcaac tttatccgcc tccatccagt ctattaattg ttgccgggaa gctagagtaa 3180
gtagttcgcc agttaatagt ttgcgcaacg ttgttgccat tgctacaggc atcgtggtgt 3240
cacgctcgtc gtttggtatg gcttcattca gctccggttc ccaacgatca aggcgagtta 3300
catgatcccc catgttgtgc aaaaaagcgg ttagctcctt cggtcctccg atcgttgtca 3360
gaagtaagtt ggccgcagtg ttatcactca tggttatggc agcactgcat aattctctta 3420
ctgtcatgcc atccgtaaga tgcttttctg tgactggtga gtactcaacc aagtcattct 3480
gagaatagtg tatgcggcga ccgagttgct cttgcccggc gtcaatacgg gataataccg 3540
cgccacatag cagaacttta aaagtgctca tcattggaaa acgttcttcg gggcgaaaac 3600
tctcaaggat cttaccgctg ttgagatcca gttcgatgta acccactcgt gcacccaact 3660
gatcttcagc atcttttact ttcaccagcg tttctgggtg agcaaaaaca ggaaggcaaa 3720
atgccgcaaa aaagggaata agggcgacac ggaaatgttg aatactcata ctcttccttt 3780
ttcaatatta ttgaagcatt tatcagggtt attgtctcat gagcggatac atatttgaat 3840
gtatttagaa aaataaacaa ataggggttc cgcgcacatt tccccgaaaa gtgccacctg 3900
acgatgtact gagaccgctc tgtgctctag tattgataat tggtctacta ctagatagat 3960
gcctaacatt aatgatatag tcgtatcagt ctttgctgta aataaagcct ccggaatgag 4020
atctaaagaa tcagcccaga tgtttggaag gagggaaaga tacgcctttc tactaattaa 4080
gccagttttg atctcagttg attgatgtcc tgtctctgcg atagctcaaa actggcaact 4140
gaaacagata gtatattaat tttcagttgc taatgataag ccattgtaac attcctatca 4200
catcggccgt ttgcctcttt tttgggaaaa ctctttccag tgaatgcaca gcttatcgct 4260
ttcaatgctt caaaggcaac ttccctacta agacactaaa tatatataca tcaatgaaca 4320
tatagtggga aaaatggtag tgaagaagta gtcatttgtt tgaatataag ttggctgtac 4380
atgtgcctcc gtagtctgtg gccgagcttc atccacctag caattgaaac tgaagagcta 4440
agctcttcat attctcattc ggttctgtta ttctctttta cttcttcttg tcaaaatatt 4500
atgtattatg tgtagtaccc gaccaacatg gagaattcaa tctaagaaat agatgtcacc 4560
ccaagccgaa caaaaacaac cggtgaagaa aacgtaactg agtgaatgga attgtgattc 4620
aagcaattag agtaattgaa tttcacttct ggtacgagaa ataaagtgaa aaacaaaata 4680
cctccgcata attagtgacg aaaaaaaacca cacgtatact attcactgag tgaaagtgcg 4740
ccagatctgt ttagcttggg tatttgacag gttggggagc aaataagtga tgatgtccca 4800
tgaaagtaga aaatggctag tagaaggcaa aaatttgaaa ttcttagagt caaatagtta 4860
gactccaagt tctaatccac atttggtcag tttcatagca tccagagctt ttgccactgg 4920
tgaacatatc tacccattgc gatgcaacaa gtcactgaaa gcctaaaacg gagattcccc 4980
tatcttacag cctcgttcaa aaaaactgct accgtttatc tgctatggcc gatgtgagga 5040
tgcgctcatg cccaagagtc caactttatc aaaaacttga cccgtcatac aggctctaga 5100
tcaagaagca aacttaatct cagcatctgg ttacgtaact ctggcaacca gtaacacgct 5160
taaggtttgg aacaacacta aactaccttg cggtactacc attgacacta cacatcctta 5220
attccaatcc tgtctggcct ccttcacctt ttaaccatct tgcccattcc aactcgtgtc 5280
agattgcgta tcaagtgaaa aaaaaaaatt ttaaaatctt taacccaatc aggtaataac 5340
tgtcgcctct tttatctgcc gcactgcatg aggtgtcccc ttagtgggaa agagtactga 5400
gccaaccctg gaggacagca agggaaaaat acctacaact tgcttcataa tggtcgtaaa 5460
aacaatcctt gtcggatata agtgttgtag actgtccctt atcctctgcg atgttcttcc 5520
tctcaaagtt tgcgatttct ctctatcaga attgccatca agagactcag gactaatttc 5580
gcagtcccac acgcactcgt acatgattgg ctgaaatttc cctaaagaat ttctttttca 5640
cgaaaatttt tttttacaca agattttcag cagatataaa atctcgaggg agagcaggac 5700
ctccgctgtg actcttcttt tttttctttt attctcacta catacatttt agttattcgc 5760
caacatgtca actctggctg accaggccct acacaataac aacgtcggtc caataattag 5820
agctggcgat ttggtcgaac ctgtgatcga aaccgctgag attgataatc ctggtaagga 5880
gatcacagtt gaagacagaa gagcttacgt cagaatcgct gctgaagggg agttgatatt 5940
gacaagaaag actctggaag aacaattagg gaggccattc aacatgcaag agcttgaaat 6000
taacttagct agttttgccg gtcaaattca ggcagatgaa gatcaaatca ggttctattt 6060
tgataaaact atgtaagtat ctccagtcgt ttagattgtt agatattttc tttgtgtatt 6120
cgtttcagtc tgatgtttat gctacaaacg tcatctggac tttaatccaa taaggatatt 6180
cttcaactta atagtatctt aataatattt tttttctttt gatttcttcg taaggtgttt 6240
tgttgcactc atgatctacg acttttgttc gtgactgatt ttttttgtag aaatgtcttg 6300
gtgtcctcgt ccaatcaggt agccatctct gaaatatctg gctccgttgc aactccgaac 6360
gacctgctgg caacgtaaaa ttctccgggg taaaacttaa atgtggagta atggaaccag 6420
aaacgtctct tcccttctct ctccttccac cgcccgttac cgtccctagg aaattttact 6480
ctgctggaga gcttcttcta cggccccctt gcagcaatgc tcttcccagc attacgttgc 6540
gggtaaaacg gaggtcgtgt acccgaccta gcagcccagg gatggaaaag tcccggccgt 6600
cgctggcaat aatagcgggc ggacgcatgt catgagatta ttggaaacca ccagaatcga 6660
atataaaagg cgaacacctt tcccaatttt ggtttctcct gacccaaaga ctttaaattt 6720
aatttatttg tccctatttc aatcaattga acaactatat gtctttcgaa tctaagaagc 6780
ctatgagaac ttggtcacat cttgctgaga tgcgtaaaaa gccttccgag tacgatatag 6840
tttcaagaaa gttgcattac tctactaata acccagattc cccatgggag ctatctccag 6900
attctcctat gaatttatgg tacaaacaat atagaaacgc ttcccctctg aaacacgaca 6960
actgggatgc tttcacagac ccagatcaac ttgtttatcg tacatataat ctgatgcaag 7020
atggccagga atcatatgtc caaagtcttt tcgaccagtt taacgaaagg gaacatgacc 7080
aaatggtacg tgaaggttgg gaacacacta tggccagatg ttactcccca ttgcgttact 7140
tgtttcactg cttgcagatg tcctctgctt atgtccagca gatggctccc gcctcaacaa 7200
tatctaattg ctgtattttg cagactgctg attctctgag gtggttaacg cacacagctt 7260
acaggacgca cgagttgtct ttgacttacc cagatgctgg tttgggcgag cacgagagag 7320
aactgtggga aaaggaacct ggatggcagg gattgcgaga gcttatggag aagcagttga 7380
ccgcatttga ttggggagag gctttcgttt cccttaattt agttgttaag cctatgattg 7440
tcgaatccat ttttaaacca ctgcagcaac aggcttggga aaacaacgac actttgttgc 7500
cattattaat cgattctcaa ttaaaagacg ctgagcgtca tagtaggtgg tcaaaggctc 7560

```
tggtgaagca tgcccttgaa aatccagata atcatgctgt cattgaagga tggatcgaaa  7620
aatggaggcc attggctgac cgtgctgccg aagcctactt atccatgctg tcctccgaca  7680
tcttgccagc ccaatactta gagagatcaa cctcattgag ggcctcaata ctgactgttt  7740
agattcggat agtgtaattt aatcaataac ttgaaaaaaa tatcatttaa tttactatac  7800
acacggacat aaactgaaag ggcaaggaag gggaaaatgg gaaaaataat gaggatatgc  7860
aagatgagag atgagagatg agagatgtcc actttagtca gttttggctt tacttttatc  7920
tttttctatg gcatctttcg ttttactact agtatacata gaataaaaac ggtaatagaa  7980
ctgggaacta agcagaaact tacaattcct gagaagcctt ggccttggca gacttctttg  8040
gcaacaattc ggattgaatg tttggcaaga caccaccttg ggcgatggtg acgtgtccca  8100
gcaacttgtt caattcctca tcgtttctga tggccaattg caagtgtctt gggataattc  8160
tggacttctt gttgtctctg gcggcgttac cggccaattc caaaatttca gcagccaagt  8220
actccaagac agcagtcaaa tagactggag caccagaacc aattctttgg gcgtagttac  8280
ctcttctcag aagacggtgg actcttccca cagggaaggt caaacctgcc ttagaagatc  8340
ttgaggttga ggcctttttca gccgaagatg cttttccttt accaccggac attgttgtag  8400
ttttaatata gtttgagtat gagatggaac tcagaacgaa ggaattatca ccagtttata  8460
tattctgagg aaagggtgtg tcctaaattg gacagtcacg atggcaataa acgctcagcc  8520
aatcagaatg caggagccat aaattgttgt attattgctg caagatttat gtgggttcac  8580
attccactga atggttttca ctgtagaatt ggtgtcctag ttgttatgtt tcgagatgtt  8640
ttcaagaaaa actaaaatgc acaaactgac caataatgtg ccgtcgcgct tggtacaaac  8700
gtcaggattg ccaccacttt tttcgcactc tggtacaaaa gttcgcactt cccactcgta  8760
tgtaacgaaa aacagagcag tctatccaga acgagacaaa ttagcgcgta ctgtcccatt  8820
ccataaggta tcataggaaa cgagagtcct ccccccatca cgtatatata aacacactga  8880
tatcccacat ccgcttgtca ccaaactaat acatccagtt caagttacct aaacaaatca  8940
aaatgttcaa catccaatct gatgatctgt tgcatcattt cgaggcagat tctaacgata  9000
cattactgtc cgccgccttg cgtgccgaat tggtatttcc ttatgaatgc aactctggag  9060
gatgcggcgc atgtaagata gaattgttgg aaggggaagt ctcaaactta tggccagacg  9120
cacctggtct agccgcccgt gagttgagaa aaaacaggtt tttggcttgc cagtgcaaac  9180
ccttgagtga tctgaaaatt aaagttatta acagagccga agggagagct agtcatccac  9240
ctaaaagatt tagtaccagg gtagtctcta agcgtttttt gtccgatgaa atgtttgagc  9300
ttagactaga ggctgaacag aaggtcgtgt tctctcctgg tcaatacttt atggttgatg  9360
tgcctgaact gggtacccgt gcctactccg ctgctaatcc agttgacggg aatactctga  9420
cacttattgt gaaagccgtt cctaacggta aagtatcttg cgccctggct aatgaaacga  9480
tagaaacatt gcagttggat ggtccttacg gtttgtccgt cctgaaaacc gctgatgaaa  9540
cacaatcagt tttcattgct ggaggctccg gtattgctcc tatggtttcc atggttaata  9600
cacttattgc tcaaggctac gagaaaccaa ttacggtctt ttatggatct agattagaag  9660
cagagttgga ggctgcagag actttattcg gatggaaaga aaatttgaaa ttaatcaatg  9720
tctcttcttc agttgttggt aattctgaga agaaataccc aacgggatac gtccatgaaa  9780
ttatcccaga atacatggaa ggcttgttgg gggccgaatt ttacttgtgc ggacctccac  9840
agatgattaa ctccgttcag aaattgctga tgattgaaaa caaggttcct ttcgaagcaa  9900
ttcattttga tagattcttc tagagacatg actgttcctc agttcaagtt gggcacttac  9960
gagaagaccg gtcttgctag attctaatca agaggatgtc agaatgccat ttgcctgaga  10020
gatgcaggct tcatttttga ttactttttt atttgtaacc tatatagtat aggatttttt  10080
ttgtcatttt gtttcttctc gtacgagctt gctcctgatc agcctatctc gcagctgatg  10140
aatatcttgt ggtaggggtt tgggaaaatc attcgagttt gatgtttttc ttggtatttc  10200
ccactcctct tcagagtaca gaagattaag tgagagcggc cgctcgtccc cgccgggtca  10260
cccggctcga g                                                       10271
```

```
SEQ ID NO: 31           moltype = DNA  length = 10966
FEATURE                 Location/Qualifiers
misc_feature            1..10966
                        note = Synthetic plasmid.
source                  1..10966
                        mol_type = other DNA
                        organism = synthetic construct
SEQUENCE: 31
ctcgagggtg ttttcacgag caattgacca acaaggacgt ttaaacataa aggaggaata  60
taatggcaat tagtgcggcg acgaaagcgg ctactgatgc acttgcggcc aaccgcgcgc  120
caacttcagt gaatgctcaa gaagtccacc gttggctcca atcgtttaac tgggatttta  180
aaaacaaccg taccaaatac gccactaagt ataaaatggc aaacgagaca aaagagcaat  240
tcaaattaat cgcgaaggag tacgcacgta tggaaagcgt gaaagacgag cgtcagttcg  300
gaagccttca agatgcgtta acccgcctgc agagcgctgt gcgtgtgcat ccgaaatgga  360
atgaaactat gaaagtagtg tccaacttcc tcgaagtggg tgagtataac gcaattgccg  420
caactggcat gctttgggac tccgcgcaag cggctgaaca aaagaacggt tatctcgcac  480
aggttttgga tgaaatccgc cacacccatc aatgcgcgta tgttaattat tatttcgcaa  540
agaacggcca ggacccggca gggcacaatg atgcgcgtcg tacacgcacc ttggggccgc  600
tgtggaaagg tatgaaacgt gttttctcag atggcttcat ctccggcgac gcggtcgaat  660
gctcacttaa tctgcaactg gtgggcgaag cctgctttac taatccgctg atcgttgccg  720
ttaccgaatg ggctgccgcg aacggtgatg aaatcacccc gaccgtgttc ctgtcgatcg  780
agacagatga acttcgtcat atggcaaacg ggtatcagac cgttgtttct attgcaaatg  840
atccggccag cgctaaatat atgaatactg acttaaacaa tgcattctgg acacagcaga  900
aatattttac gccggtcctt ggcatgctgt tcgaatacgg ttcaaagttt aaggttgaac  960
cgtgggtgaa aacctggaat cgttgggtct atgaggattg gggcggaatt tggatcggac  1020
gcctgggcaa atatggcgtc gaaagtcctc gctccctgaa ggatgccaaa caggatgcgt  1080
actgggcgca ccacgacctg taccttctgg catatgctct gtggccgacc ggtttcttcc  1140
gcttagcgtt gcctgatcaa gaagagatgg aatggtacga agcgaattac ccaggttggt  1200
acgaccatta cggtaaaatc tatgaagaat ggcgtgcacg cggttgcgaa gatccaagca  1260
gtggtttcat tccgctgcaa tggtttattg aaaacaacca ccccatttat atcgatcgca  1320
cgtcacaggt ccccttttgt ccgagtcttg cgaaacacgc gacgaccttg cgtgtgcacg  1380
aatataacgg tcagctccac acgcatgcgg accaatgggg tgaacgcatg tggctggcgg  1440
```

```
aaccggaacg ctatgagtgt caaaatatgt ttgaacagta tgagggccgt gaattaagcg  1500
aggttatcgc agaactgtgg ggtgtgcgtt cagacggcaa aacacttatc gcgcaaccgc  1560
acgtccgcgg tgataaactc tggaccctgg atgatattaa acgtgttgga tgcgtttttt  1620
caaaccctgc gaaagccctg aaagcgtaaa tataggagga taataatgcc gctgctggac  1680
gaaaaacgtc gtggcttgac cgacccggaa tgggcgagcg ttatcctgaa cgccctgccg  1740
gcagagcctt tggataaaca aaacaagatg ggctactttg ttaccccacg ctggaagcgt  1800
ttgacggaat atgaagctct caccgtttat gctcagccta acgcggattg gattgcgggt  1860
ggtttggatt ggggagactg gactcagaaa tttcacggcg gccgtccgtc gtggggcaac  1920
gaaaccacgg aactgcgcac ggtagattgg tttaaacacc gtgatccact ccgccgctgg  1980
catgccccgt atgtgaaaga taaagcggaa gagtggcgtt acactgatcg ctttctgcaa  2040
ggctatagcg cggacggtca gattcgtacc atggaccctt tctggcgcga tgaattcatt  2100
aacaaatact ggggtgcgtt cctgtttaac gaatacggtc agttcaacgc ccattcagga  2160
ggcgcacgtg aagcgctgtc ggacaccatc cgtgtatcgc tgacgttttg gggttttgat  2220
aaaatcgatc tggcccagat gatccagctg gaacgtggct tcttagctaa aattgtaccg  2280
ggctttgatg aatctacggc ggtgccgaaa gcagaatgga cccagggctc tgtctataaa  2340
agtgctcgtg gcacgatcga ggcattgtgg caagacgtct tcgactggaa cgaaaacgcg  2400
ttttcagtac atgcagtgta cgatagcctg tttggtcaat ttgtgcgtcg cgagttcttt  2460
cagcgcttag cccctaaatt tggcgataat ctcacaccct tttttatcaa ccagagccag  2520
acctattacg gcattgctaa acagggcgtg caggatctct attacacctg tttagcgaat  2580
gatcctgaat tcggtgacta caaccgcaca gtcctccgca attggaccgc taaatggctg  2640
gaagggacgg tgaatgcgct gcgtgatttc atgggtattt ttgcgaagct gccgaccgga  2700
accacacaca aggccgaaat ccaggccagc ttagaacgcg tgatcgacga ttggaccgcg  2760
gatcatgcca gccgtattga tttcaaagtc gatcgtgatg cgattgttcg tcatgtcatg  2820
agcggtctga tttgaaataa ggaggatatt aatggcaaaa aacggtgtcc atgacaacgc  2880
cacacgcgat gcatgggttg taaaaattgg gcagttgaat accctggaca aagccgcggc  2940
tgccttaaaa cagtttcgtc tcgatcatac cactccgttt cgcaaaactt atgaactgga  3000
taatgattat ctgtggatcg aggctaaact ggaggaaaag gttgctgtcc tgaaggcccg  3060
cgctttcaac gatgaagact tccgccataa aaccgctttt ggggaatgcg ctaaaacgct  3120
cttagccgaa gcggtcgcga aaatggctgc tacgggcgat aaatgggaag cagaacgcat  3180
tcatattggc ttccgtcaag ctaataaacc gcccattatg ccggtgaact atttccttga  3240
agccgaacgt gtccttggta cgaagctgat ggaattgcgt aacctcaact actatgatac  3300
accactggaa gaactgcgca aacagcgcgg tgtgaaagtc ttagtagcgc cgcactaaat  3360
ttaggaggaa tattatgtct gtgtccagca atgcgtatta tgcaggtacg acgggtctgt  3420
cgggcaagga gttcgctgaa gcattcttcg cggatgaaaa tcaggttgtg catgaaagcg  3480
ataccgtcgt tttggtgctg aaaaaaagcg acgaaatcaa cacatttatc gaagagatcc  3540
tgctggaaga ttataaaaaa catgtgaacc caaccgtcaa tgttgaagac cgcgccgggt  3600
attggtggat caaagctaac ggtaagattg aagtggactg cgatgaactg tccgagcttc  3660
tgggtcgttc cttcaacgtc tacgacttcc tggtggatgt gagcagcact atcggccgtg  3720
catataccct gggtaataaa ttcacaatta cctctgaatt gatgggttta gaccgtaagt  3780
tggaagatta tcatgcataa ttataggagg tattatatgg ccgcaaccca ctcaattaaa  3840
gtgattactg aagatggcga agccgtgtac tttgattgcc gtcctgatga agatgtcatc  3900
agtgctgcca tccgccagga tatctatctg atgtcctcat gccgcgctgg tggctgcgca  3960
acctgtaaag cgttttgccc ggaaggcgac taccgcttag tgggttgttc ggtgcaagca  4020
ctgccgcctg aagaggaaga agacggccag gttctgctgt gtcgctgtta tccggactcg  4080
gatctggagc tggaagttcc gtatacctac tcacgtattg catttgaacc ggaagctaat  4140
gagttcccgg ccgaggtagt gagcgttggt aaagtcagct cgaatgcagt tcgtctgcat  4200
ttgcgccgcc cgggtatggg caacgaacgc aaagtccgtt ttgatgcagg tcagttcatg  4260
gaactgcaag tacctggttc ggcagtcacg cgcgcgtatt ccccggccaa catctctaac  4320
gacgccggcg acctggagtt tcttattcgt ttattacctg atggccttat gtctaatgct  4380
ctccgtggcg gtgccattca gccgggtcag acgttgcagg tcaaaggtcc gcagggaatc  4440
ttcggcctta aagaaaatgg ctttcgtccg cgctacttta ttgcgggtgg cacgggcctc  4500
gcccctgtac tgagtatggt tcgccatatg cgtgagtggg gtgcgcccca gcagactcgc  4560
ctgtacttcg gcgtcaatac cgaggaagaa gtctttctgc gcgccgaact ggaagccctg  4620
gctgccgcta tgccgaattt aaccgtgaaa gtctgcgtgt ggcgccctac cgatggttgg  4680
gatggtgaac gtggcaacgc aatcgaggta ctccgccgcg acctggaggc gcagccggcg  4740
cagcccgatg tctatctttg tggccgccg ggtatggtcg atgccgcgta tgccgtctgt  4800
gcagagtttg gtatcccagc ggaccaaatc tatctggaga aattcttacc gtcgggaccg  4860
tgtggcgagg cctgtgaccc gggtcaagtg cacggtcatc accagcacgc cacagcctaa  4920
ttataggagg attaaaatga caattgattt cgatcatttg gatccggatg ccctggattt  4980
cttatcggct cgctcgttaa gccaagttcc agcaggtacc cctcgcaccg aactatttca  5040
gcaaggtcgc tacgcagcgt acgcacagga cctgggtttc gcatggcgct gggccattgc  5100
ccgcgacggg cgcgatattc aagaaggccc ggcgctgtcg ctggaatctg cccacctgag  5160
cgcacgccgt gtactggcat tctttgttcg cttagactcg ccgccgacac cggcctaata  5220
agtttaaacg gatacgccct cgaatcctgg gatagcggcc gctcagtgac cggcatagcg  5280
tacgcctcga gttacgcccg ttctgcttga cctggtaaag ttacaaccaa ttaaccaatt  5340
ctgattagaa aaactcatcg agcatcaaat gaaactgcaa tttattcata tcaggattat  5400
caataccata tttttgaaaa agccgtttct gtaatgaagg agaaaactca ccgaggcagt  5460
tccataggat ggcaagatcc tggtatcggt ctgcgattcc gactcgtcca acatcaatac  5520
aacctattaa tttcccctcg tcaaaaataa ggttatcaag tgagaaatca ccatgagtga  5580
cgactgaatc cggtgagaat ggcaaaagct tatgcatttc tttccagact tgttcaacag  5640
gccagccatt acgctcgtca tcaaaatcac tcgcatcaac caaaccgtta ttcattcgtg  5700
attgcgcctg agcgagacga aatacgcgat cgctgttaaa aggacaatta caaacaggaa  5760
tcgaatgcaa ccggcgcagg aacactgcca gcgcatcaac aatattttca cctgaatcag  5820
gatattcttc taatacctgg aatgctgttt tcccggggat cgcagtggtg agtaaccatg  5880
catcatcagg agtacggata aaatgcttga tggtcggaag aggcataaat tccgtcagcc  5940
agtttagtct gaccatctca tctgtaacat cattggcaac gctacctttg ccatgtttca  6000
gaaacaactc tggcgcatcg ggcttcccat acaatcgata gattgtcgca cctgattgcc  6060
cgacattatc gcgagcccat ttatacccat ataaatcagc atccatgttg gaatttaatc  6120
gcggcctcga gcaagacgtt tcccgttgaa tatggctcat aacacccctt gtattactgt  6180
```

-continued

```
ttatgtaagc agacagtttt attgttcatg atgatatatt tttatcttgt gcaatgtaac  6240
atcagagatt ttgagacaca acgtggcttt gttgaataaa tcgaactttt gctgagttga  6300
aggatcagat cacgcatctt cccgacaacg cagaccgttc cgtggcaaag caaaagttca  6360
aaatcaccaa ctggtccacc tacaacaaag ctctcatcaa ccgtggctcc ctcactttct  6420
ggctggatga tggggcgatt caggcctggt atgagtcagc aacaccttct tcacgaggca  6480
gacctcagcg ctagcggagt gtatactggc ttactatgtt ggcactgatg agggtgtcag  6540
tgaagtgctt catgtggcag gagaaaaaag gctgcaccgg tgcgtcagca gaatatgtga  6600
tacaggatat attccgcttc ctcgctcact gactcgctac gctcggtcgt tcgactgcgg  6660
cgagcggaaa tggcttacga acggggcgga gatttcctgg aagatgccag gaagatactt  6720
aacagggaag tgagagggcc gcggcaaagc cgtttttcca taggctccgc ccccctgaca  6780
agcatcacga aatctgacgc tcaaatcagt ggtggcgaaa cccgacagga ctataaagat  6840
accaggcgtt tccccctggc ggctccctcg tgcgctctcc tgttcctgcc tttcggttta  6900
ccggtgtcat tccgctgtta tggccgcgtt tgtctcattc cacgcctgac actcagttcc  6960
gggtaggcag ttcgctccaa gctggactgt atgcacgaac cccccgttca gtccgaccgc  7020
tgcgccttat ccggtaacta tcgtcttgag tccaacccgg aaagacatgc aaaagcacca  7080
ctggcagcag ccactggtaa ttgatttaga ggagttagtc ttgaagtcat gcgccggtta  7140
aggctaaact gaaaggacaa gttttggtga ctgcgctcct ccaagccagt tacctcggtt  7200
caaagagttg gtagctcaga gaaccttcga aaaaccgccc tgcaaggcgg ttttttcgtt  7260
ttcagagcaa gagattacgc gcagaccaaa acgatctcaa gaagatcatc ttattaaggg  7320
gtctgacgct cagtggaacg aaaactcacg ttaagggatt ttggtcatga gattatcaaa  7380
aaggatcttc acctagatcc ttttaaatta aaaatgaagt tttaaatcaa tctaaagtat  7440
atatgagtaa acttggtctg acaggtgagc tgataccgct cgccgcatgc acatgcagtc  7500
atgtcgtgct aatgtgtaaa acatgtacat gcagattgct gggggtgcag ggggcggagc  7560
caccctgtcc atgcggggtg tggggcttgc cccgccggta cagacagtga gcaccggggc  7620
acctagtcgc ggataccccc cctaggtatc ggacacgtaa ccctcccatg tcgatgcaaa  7680
tctttaacat tgagtacggg taagctggca cgcatagcca agctaggcgg ccaccaaaca  7740
ccactaaaaa ttaatagtcc ctagacaaga caaacccccg tgcgagctac caactcatat  7800
gcacgggggc cacataaccc gaaggggttt caattgacaa ccatagcact agctaagaca  7860
acgggcacaa cacccgcaca aactcgcact gcgcaacccc gcacaacatc gggtctaggt  7920
aacactgaaa tagaagtgaa cacctctaag gaaccgcagg tcaatgaggg ttctaaggtc  7980
actcgcgcta gggcgtggcg taggcaaaac gtcatgtaca agatcaccaa tagtaaggct  8040
ctggcggggt gccataggtg gcgcagggac gaagctgttg cggtgtcctg gtcgtctaac  8100
ggtgcttcgc agtttgaggg tctgcaaaac tctcactctc gctgggggtc acctctggct  8160
gaattggaag tcatgggcga acgccgcatt gagctggcta ttgctactaa gaatcacttg  8220
gcggcgggtg gcgcgctcat gatgtttgtg ggcactgttc gacacaaccg ctcacagtca  8280
tttgcgcagg ttgaagcggg tattaagact gcgtactctt cgatggtgaa aacatctcag  8340
tggaagaaag aacgtgcacg gtacggggtg gagcacacct atagtgacta tgaggtcaca  8400
gactcttggg cgaacggttg gcacttgcac cgcaacatgc tgttgttctt ggatcgtcca  8460
ctgtctgacg atgaactcaa ggcgtttgag gattccatgt tttcccgctg gtctgctggt  8520
gtggttaagg ccggtatgga cgcgccactg cgtgagcacg gggtcaaact tgatcaggtg  8580
tctacctggg gtggagacgc tgcgaaaatg gcaacctacc tcgctaaggg catgtctcag  8640
gaactgactg gctccgctac taaaaccgcg tctaaggggt cgtacacgcc gtttcagatg  8700
ttggatatgt tggccgatca aagcgacgcc ggcgaggata tggacgctgt tttggtggct  8760
cggtggcgtg agtatgaggt tggttctaaa aacctgcgtt cgtcctggtc acgtggggct  8820
aagcgtgctt tgggcattga ttacatagac gctgatgtac gtcgtgaaat ggaagaagaa  8880
ctgtacaagc tcgccggtct ggaagcaccg gaacgggtcg aatcaacccg cgttgctgtt  8940
gctttggtga agcccgatga ttggaaactg attcagtctg atttcgcggt taggcagtac  9000
gttctagatt gcgtggataa ggctaaggac gtggccgctg cgcaacgtgt cgctaatgag  9060
gtgctggcaa gtctgggtgt ggattccacc ccgtgcatga tcgttatgga tgatgtggac  9120
ttggacgcgg ttctgcctac tcatggggac gctactaagc gtgatctgaa tgcggcggtg  9180
ttcgcgggta atgagcagac tattcttcgc acccactaaa agcggcataa accccgttcg  9240
atattttgtg cgatgaattt atggtcaatg tcgcgggggc aaactatgat gggtcttgtt  9300
gttgcagccg aacgacctag cgcagcgagt cagtgagcga ggaagcggaa gagcgcctga  9360
tgcggtattt tctccttacg catctgtgcg gtatttcaca ccgcatatgg tgcactctca  9420
gtacaatctg ctctgatgcc gcatagttaa gccagtatac actccgctat cgctacgtga  9480
ctgggtcatg gctgcgcccc gacacccgcc aacacccgct gacgcgccct gacgggcttg  9540
tctgctcccg gcatccgctt acagacaagc tgtgaccgtc tccgggagct gcatgtgtca  9600
gaggttttca ccgtcatcac cgaaacgcgc gaggcagcag atcaattcgc gcgcgaaggc  9660
gaagcggcat gcataatgtg cctgtcaaat ggacgaagca gggattctgc aaaccctatg  9720
ctactccgtc aagccgtcaa ttgtctgatt cgttaccaat tatgacaact tgacggctac  9780
atcattcact ttttcttcac aaccggcacg gaactcgctc gggctggccc cggtgcattt  9840
tttaaatacc cgcgagaaat agagttgatc gtcaaaacca acattgcgac cgacggtggc  9900
gataggcatc cgggtggtgc tcaaaagcag cttcgcctgg ctgatacgtt ggtcctcgcg  9960
ccagcttaag acgctaatcc ctaactgctg gcggaaaaga tgtgacagac gcgacggcga  10020
caagcaaaca tgctgtgcga cgctggcgat atcaaaattg ctgtctgcca ggtgatcgct  10080
gatgtactga caagcctcgc gtacccgatt atccatcggt ggatggagcg actcgttaat  10140
cgcttccatg cgccgcagta acaattgctc aagcagattt atcgccagca gctccgaata  10200
gcgcccttcc ccttgcccgg cgttaatgat ttgcccaaac aggtcgctga aatgcggctg  10260
gtgcgcttca tccgggcgaa agaaccccgt attggcaaat attgacggcc agttaagcca  10320
ttcatgccag taggcgcgcg gacgaaagta aacccactgg tgataccatt cgcgagcctc  10380
cggatgacga ccgtagtgat gaatctctcc tggcgggaac agcaaaatat cacccggtcg  10440
gcaaacaaat tctcgtccct gatttttcac cacccccctga ccgcgaatgg tgagattgag  10500
aatataacct ttcattccca gcggtcggtc gataaaaaaa tcgagataac cgttggcctc  10560
aatcggcgtt aaacccgcca ccagatgggc attaaacgag tatcccggca gcaggggatc  10620
attttgcgct tcagccatac ttttcatact cccgccattc agagaagaaa ccaattgtcc  10680
atattgcatc agacattgcc gtcactgcgt cttttactgg ctcttctcgc taaccaaacc  10740
ggtaaccccg cttattaaaa gcattctgta acaaagcggg accaaagcca tgacaaaaac  10800
gcgtaacaaa agtgtctata atcacggcag aaaagtccac attgattatt tgcacggcgt  10860
cacactttgc tatgccatag catttttatc cataagatta gcggatccta cctgacgctt  10920
```

```
tttatcgcaa ctctctactg tttctccata cccgtttttt tgggat                 10966

SEQ ID NO: 32           moltype = DNA  length = 10954
FEATURE                 Location/Qualifiers
misc_feature            1..10954
                        note = Synthetic plasmid.
source                  1..10954
                        mol_type = other DNA
                        organism = synthetic construct
SEQUENCE: 32
ctcgagggtg ttttcacgag caattgacca acaaggacgt ttaaacataa aggaggaata  60
taatggccat cagcactgcc accaaagccg ccactgacgc tctgggcgtt aatcgtgctc  120
cgacctctgt caatccgcag gaagtccacc gctggttaca gtcgttcaat tgggactttg  180
cgcagaaccg caccaaatac ccgacgaaat accatatggc aaacgatacc aaagagcagt  240
ttaaactgat tgcgaaagag tatgctcgta tggaaagtgt gaaagatgaa cgccagtttg  300
ggactctgct tgatggtctg acccgcctgg aagctggcaa tcgcgtccat ccgcgttggg  360
gcgaaacgat gaaagtagca agtaattttc tcgaagtcgg tgaatacaat gcaatcgctg  420
caaccggtat gctctgggat tcagcaacgg ccgccgaaca aaagaacggt tacctggcgc  480
aagtacttga cgagatccgt cacacacatc agtgtggttt catcaattat tattttgcca  540
agcattatca tgatccggca ggtcataatg atgcgcgccg cacccgtgcg atcggtcctc  600
tgtggaaagg tatgaaacgc gtctttgcgg atggcttcat tagcggcgac gctgttgaat  660
gctcggttaa cttacaattg gtcggtgaag cctgcttcac caatccgctc atcgttgcga  720
tcacggaatg ggcgtcggca aacggcgatg aaatcactcc caccgtgttt ctgtccatcg  780
agactgatga acttcgccat atggccaacg ggtaccagac cgttgtatcc attgcgaacg  840
acccagcggc gcaaaaatat ctgaacacgg acctgaacaa tgccttctgg acgcaacaga  900
aatacttcac cccggtcctg gggatgctct ttgaatacgg gagtaaattc aaagtggagc  960
catgggtgaa aacgtggaat cgctgggtct atgaagattg gggaggtatc tggattggac  1020
gcttggccaa gtatggagtg aacagccccc cgtctctgcg tgatgccaaa aaagatgcgt  1080
attgggcaca tcacgatctg tttctcctgg cgtatgcatt gtggcctacc ggtttcttcc  1140
gcctgtccct gcctgacgaa gaagacatgg aatggtttga ggccaactat cccggttggg  1200
atgaacacta tggtaaaatc cttcgcgaat ggaaagcgct cggctgcgaa gacccgaaat  1260
ctggtttttt acccatccag tggctgatcg aacacggaca caaagtgtat atcgatcgcc  1320
ccagtcaagt tccgttttgc ccaacattgg cgaaatgcag cgggtccctt cgtgttcatg  1380
agttcaatgg tcagaagcat gcgtttgcgg atgattgggg cgagcgtcaa tggctggcgg  1440
agccagaacg ttatgaatgt cagaatattt ttgaacagta tggtggccgc gaactgtctg  1500
atgtggttgt tgaaggccat ggtgtacgcg ctgatggcaa gaccttaatt ggtcaacccc  1560
atgtgcacgg cgaccagctg tggacggtag aagatttgaa acgtgcgaat tgtgtgttcg  1620
ctgatccgct ggcggattta tgaatatagg aggataataa tggcgatcgc gacggccact  1680
accactaaac gcggactgac tgacccggag cgcgcggcta aaattcttgc tgccattccg  1740
gatcacgaat tagacaccca acgtcgtatg aactacttcg ttgaacctcg ctggaaacgc  1800
ctttcggaat atgagattct gacttcctat acccagccca atccggattg gatcgctggt  1860
gggctggact ggggcgattg gacgcagaaa ttccatggag gtcgcccttc ctgggggaac  1920
gagagtactg aactgcgtac cacagactgg ttccgtcacc gcgatccggc tcgccgttgg  1980
catgctccgt atgtgaaaga caaagcggaa gaatggcgtt atacaacgcg ctttctggag  2040
ggctatagtg cggaaggagc cgttcgctca atcgatccaa agtggcgtga cgagatcctg  2100
gcaaaatatt ggggtgcgct gctgtttagt gagtacggtc agtttaacgc ccacagttct  2160
gtggcccgcg atgcgctgag tgacaccatt cgctctaccg cgacctttgc ggcgctcgat  2220
aaggtggatt gcgcccagat gattcagctt gaacgcaact ttcttgcgaa agtggtgcca  2280
ggttttccgg agagcacaga aggcccgaaa aacatttggc tctctgatcc catctataaa  2340
tctgcgcgca cgacggtgga agaattctgg caaggtattc aggattttttc cgagatttta  2400
tgggccgtgc acggggttta tgatccgctg ttcggtcaat ttgcacgccg cgaattcttt  2460
ggtcgtatgg ccgcgcatta tggcgattcg ctcacccgt tctttcttc gcaaacacag   2520
acgtactttc agaccacgaa agcagccatg agcgatctgt ttttttatag cctgggtgat  2580
gatcccgaat ttggcgatca taatcgcact tggttccgcg cctggacgga aaaatggctt  2640
aaaatgactg cggatagcct gcatgatttt ctgggcattt atgccaaagt ggagaaggtc  2700
cccgggctga gtgataaagc aggaattatc gcggcagtct cacgcgtagt taatgactgg  2760
gtggaagact atgctaaaaa aattgatttt aaagtggatg cagatcagct tgtggcaagc  2820
atcacacgcg atgttaaata aaataaggag gatattaatg cccaactata agatccatga  2880
caaccctgta cgctccgaat ggcaggaaaa aatcggtgag ctcaaatcag tcaaagatgc  2940
tacggcattc attcaggatt tccgtaaaaa gtacaccagt cccttccgta cgtcctacgc  3000
attagatgtg gattatctgt tcatcgaagc gaagatcgaa gaacgtctgg cggttcttaa  3060
aacctcaacc tactcggcaa cagatctctt ctcgatggcg acaactgggg aagccgcaca  3120
gaaagtagcc gatacgtgga ttgctaagat ggatgcggag aaagataaat ttgccgcaga  3180
aaaaatcctc attaccttcc gccagctgta caaaccgccg gtgctcccgg taaatgtctt  3240
tttcaaagtt gatactcatt taggtagccg tctgatggaa ttgcgtaacg cggactacta  3300
cgctgatagt ctggaagaat tgcgtaaaaa acgcggtgtg aaagtgctga agctggggaa  3360
tgcggcctaa atttaggagg aatattatga ccgcccgtaa tgcatataac gcgggcatca  3420
tgaaaaaaaa cggcgaagca ttcgcaaagg agttctttgc ggaggagaac caagtggtcc  3480
acgaatccaa caccgtggtt ctggttctga tgaagagcga tgaaattgat gctattgtgg  3540
aagacattat cttaggcgag gaagccaaac gcaatccgac tctggtggtg gaagatcgtg  3600
ctggcttttg gtggatcaag gccgatggga aaattgaggt cgataccgag aaggccgcgg  3660
atctgttggg taaaacctat agcatttatg atttcctggt aaatgtgagt tccacaatcg  3720
gccgcgcgta cactctgggc aacacattta cgattacaag cgagctgatg ggcctggatc  3780
gcaaactcac ggacatctaa ttataggagg tattatatgt acaaagtatc tgttatcaca  3840
gaggatgact tcgaggtgac gtttgagtgc cctccgaatg agaatgtgat ttctgccggg  3900
gtgaaatctg acgtgattct gctcagctct tgccatgaag gtggctgtgc gacgtgtaaa  3960
gcggaatgcc tggagggcga ttatgaactg ggccgttgta gcgttcaggc tttacctccg  4020
gatgaagagg aagcggcagt agtacttctg tgtcagactt acccccgttc ggatctggtt  4080
tttaaagtgc cctacacctt cgaacgcatc tcgttccaga aagttaatac cgattggaaa  4140
```

-continued

```
ggtgaaattg ttgccgtgga gaaaattgca agcaatgttg caaagctgca aattgtacct  4200
aaagatccgg agaacggtca agcggttact attccatttg tgccgggcca atatctggac  4260
atcgaaatcc cggggactca agcgagccgt tgctattcca tggccaccat cgatgatgat  4320
ccacgcctgg atttcttaat tcgtatcctg cccggtggtc gcttttccca gtttttatcg  4380
tcggaagccg aaccgggaat tgtcatgcgc ttacgtggtc cctttggtgg attcaatatc  4440
cgcgagaatg gattgcgtgc acgttatttt gtcgcgggag gcacgggact ggcgccagtg  4500
ctgagtatga tccgttacat gaaacgcgag caacatcctc aggaggcgaa actgttcttc  4560
ggcgtgaccc accagcacga acttttctat ttggatgaac tcgaaaagct ggaagctgaa  4620
atgcccaact taaaagttta tgtgaccgta attaaggccg acgcggcttg gcagggtgga  4680
acgggcaccg tggttgacga actgaccaaa cagttgcagg atgcgaaagc gaaaccggat  4740
atttatctgt gcggcccgcc gccgatgatc gacgccgcgt tcgcagcagc ggcgatttat  4800
ggtgtgccgc cggaacagat gtatgtggaa aaatttcttg ccagtggaca agctgcggca  4860
gccgaataat tataggagga ttaaaatgaa acgcctcatg attgaagaag acccggacgg  4920
accggcgtcg gtgagcagct ttcagggcaa cgcaggtagc gcggccattg caggctttgc  4980
agaggcggct attgcgccgg tagaaatctt caatgatggc cgttattcgg cttttgttca  5040
ggaccttgag tgtgtatggc gttgggaaat tcatcgcgat ggccaatttg tgcaagaagg  5100
ctgtagcctg tcggaacgtt cttcgcgtga agctgtggga tatgtgatgt ctttttatcg  5160
tcgccgcgat gagcgtcagg ccgcagaacc tgcaatctgc gaatgataag tttaaacgga  5220
tacgccctcg aatcctggga tagcggccgc tcagtgaccg gcatagcgta cgcctcgagt  5280
tacgcccgtt ctgcttgacc tggtaaagtt acaaccaatt aaccaattct gattagaaaa  5340
actcatcgag catcaaatga aactgcaatt tattcatatc aggattatca ataccatatt  5400
tttgaaaaag ccgtttctgt aatgaaggag aaaactcacc gaggcagttc cataggatgg  5460
caagatcctg gtatcggtct gcgattccga ctcgtccaac atcaatacaa cctattaatt  5520
tcccctcgtc aaaaataagg ttatcaagtg agaaatcacc atgagtgacg actgaatccg  5580
gtgagaatgg caaaagctta tgcatttctt tccagacttg ttcaacaggc cagccattac  5640
gctcgtcatc aaaatcactc gcatcaacca aaccgttatt cattcgtgat tgcgcctgag  5700
cgagacgaaa tacgcgatcg ctgttaaaag gacaattaca aacaggaatc gaatgcaacc  5760
ggcgcaggaa cactgccagc gcatcaacaa tattttcacc tgaatcagga tattcttcta  5820
atacctggaa tgctgttttc ccggggatcg cagtggtgag taaccatgca tcatcaggag  5880
tacggataaa atgcttgatg gtcggaagag gcataaattc cgtcagccag tttagtctga  5940
ccatctcatc tgtaacatca ttggcaacgc tacctttgcc atgtttcaga aacaactctg  6000
gcgcatcggg cttcccatac aatcgataga ttgtcgcacc tgattgcccg acattatcgc  6060
gagcccattt atacccatat aaatcagcat ccatgttgga atttaatcgc ggcctcgagc  6120
aagacgtttc ccgttgaata tggctcataa cacccccttgt attactgttt atgtaagcag  6180
acagttttat tgttcatgat gatatatttt tatcttgtgc aatgtaacat cagagatttt  6240
gagacacaac gtggctttgt tgaataaatc gaacttttgc tgagttgaag gatcagatca  6300
cgcatcttcc cgacaacgca gaccgttccg tggcaaagca aaagttcaaa atcaccaact  6360
ggtccaccta caacaaagct ctcatcaacc gtggctccct cactttctgg ctggatgatg  6420
gggcgattca ggcctggtat gagtcagcaa caccttcttc acgaggcaga cctcagcgct  6480
agcggagtgt atactggctt actatgttgg cactgatgag ggtgtcagtg aagtgcttca  6540
tgtggcagga gaaaaaaggc tgcaccggtg cgtcagcaga atatgtgata caggatatat  6600
tccgcttcct cgctcactga ctcgctacgc tcggtcgttc gactgcggcg agcggaaatg  6660
gcttacgaac ggggcggaga tttcctggaa gatgccagga agatacttaa cagggaagtg  6720
agagggccgc ggcaaagccg tttttccata ggctccgccc ccctgacaag catcacgaaa  6780
tctgacgctc aaatcagtgg tggcgaaacc cgacaggact ataaagatac caggcgtttc  6840
cccctggcgg ctccctcgtg cgctctcctg ttcctgcctt tcggtttacc ggtgtcattc  6900
cgctgttatg gccgcgtttg tctcattcca cgcctgacac tcagttccgg gtaggcagtt  6960
cgctccaagc tggactgtat gcacgaaccc cccgttcagt ccgaccgctg cgccttatcc  7020
ggtaactatc gtcttgagtc caacccggaa agacatgcaa aagcaccact ggcagcagcc  7080
actggtaatt gatttagagg agttagtctt gaagtcatgc gccggttaag gctaaactga  7140
aaggacaagt tttggtgact gcgctcctcc aagccagtta cctcggttca aagagttggt  7200
agctcagaga accttcgaaa aaccgccctg caaggcggtt ttttcgtttt cagagcaaga  7260
gattacgcgc agaccaaaac gatctcaaga agatcatctt attaaggggt ctgacgctca  7320
gtggaacgaa aactcacgtt aagggatttt ggtcatgaga ttatcaaaaa ggatcttcac  7380
ctagatcctt ttaaattaaa aatgaagttt taaatcaatc taaagtatat atgagtaaac  7440
ttggtctgac aggtgagctg ataccgctcg ccgcatgcac atgcagtcat gtcgtgctaa  7500
tgtgtaaaac atgtacatgc agattgctgg gggtgcaggg ggcggagcca ccctgtccat  7560
gcggggtgtg gggcttgccc cgccggtaca gacagtgagc accggggcac ctagtcgcgg  7620
ataccccccc taggtatcgg acacgtaacc ctcccatgtc gatgcaaatc tttaacattg  7680
agtacgggta agctggcacg catagccaag ctaggcggcc accaaacacc actaaaaatt  7740
aatagtccct agacaagaca aacccccgtg cgagctacca actcatatgc acggggccca  7800
cataacccga aggggtttca attgacaacc atagcactag ctaagacaac gggcacaaca  7860
cccgcacaaa ctcgcactgc gcaacccgc acaacatcgg gtctaggtaa cactgaaata  7920
gaagtgaaca cctctaagga accgcaggtc aatgagggtt ctaaggtcac tcgcgctagg  7980
gcgtggcgta ggcaaaacgt catgtacaag atcaccaata gtaaggctct ggcggggtgc  8040
cataggtggc gcagggacga agctgttgcg gtgtcctggt cgtctaacgg tgcttcgcag  8100
tttgagggtc tgcaaaactc tcactctcgc tgggggtcac ctctggctga attggaagtc  8160
atgggcgaac gccgcattga gctggctatt gctactaaga atcacttggc ggcgggtggc  8220
gcgctcatga tgtttgtggg cactgttcga cacaaccgct cacagtcatt tgcgcaggtt  8280
gaagcgggta ttaagactgc gtactcttcg atggtgaaaa catctcagtg gaagaaagaa  8340
cgtgcacggt acggggtgga gcacacctat agtgactatg aggtcacaga ctcttgggcg  8400
aacggttggc acttgcaccg caacatgctg ttgttcttgg atcgtccact gtctgacgat  8460
gaactcaagg cgtttgagga ttccatgttt tcccgctggt ctgctggtgt ggttaaggcc  8520
ggtatggacg cgccactgcg tgagcacggg gtcaaacttg atcaggtgtc tacctggggt  8580
ggagacgctg cgaaaatggc aacctacctc gctaagggca tgtctcagga actgactggc  8640
tccgctacta aaaccgcgtc taaggggtcg tacacgccgt ttcagatgtt ggatatgttg  8700
gccgatcaaa gcgacgccgg cgaggatatg gacgctgttt tggtggctcg gtggcgtgag  8760
tatgaggttg gttctaaaaa cctgcgttcg tcctggtcac gtggggctaa gcgtgctttg  8820
ggcattgatt acatagacgc tgatgtacgt cgtgaaatgg aagaagaact gtacaagctc  8880
```

```
gccggtctgg aagcaccgga acgggtcgaa tcaacccgcg ttgctgttgc tttggtgaag  8940
cccgatgatt ggaaactgat tcagtctgat ttcgcggtta ggcagtacgt tctagattgc  9000
gtggataagg ctaaggacgt ggccgctgcg caacgtgtcg ctaatgaggt gctggcaagt  9060
ctgggtgtgg attccacccc gtgcatgatc gttatggatg atgtggactt ggacgcggtt  9120
ctgcctactc atggggacgc tactaagcgt gatctgaatg cggcggtgtt cgcgggtaat  9180
gagcagacta ttcttcgcac ccactaaaag cggcataaac cccgttcgat attttgtgcg  9240
atgaatttat ggtcaatgtc gcgggggcaa actatgatgg gtcttgttgt tgcagccgaa  9300
cgacctagcg cagcgagtca gtgagcgagg aagcggaaga gcgcctgatg cggtattttc  9360
tccttacgca tctgtgcggt atttcacacc gcatatggtg cactctcagt acaatctgct  9420
ctgatgccgc atagttaagc cagtatacac tccgctatcg ctacgtgact gggtcatggc  9480
tgcgccccga cacccgccaa cacccgctga cgcgccctga cgggcttgtc tgctcccggc  9540
atccgcttac agacaagctg tgaccgtctc cgggagctgc atgtgtcaga ggttttcacc  9600
gtcatcaccg aaacgcgcga ggcagcagat caattcgcgc gcgaaggcga agcggcatgc  9660
ataatgtgcc tgtcaaatgg acgaagcagg gattctgcaa accctatgct actccgtcaa  9720
gccgtcaatt gtctgattcg ttaccaatta tgacaacttg acggctacat cattcacttt  9780
ttcttcacaa ccggcacgga actcgctcgg gctggccccg gtgcattttt taaatacccg  9840
cgagaaatag agttgatcgt caaaaccaac attgcgaccg acggtggcga taggcatccg  9900
ggtggtgctc aaaagcagct tcgcctggct gatacgttgg tcctcgcgcc agcttaagac  9960
gctaatccct aactgctggc ggaaaagatg tgacagacgc gacggcgaca agcaaacatg  10020
ctgtgcgacg ctggcgatat caaaattgct gtctgccagg tgatcgctga tgtactgaca  10080
agcctcgcgt acccgattat ccatcggtgg atggagcgac tcgttaatcg cttccatgcg  10140
ccgcagtaac aattgctcaa gcagatttat cgccagcagc tccgaatagc gcccttcccc  10200
ttgcccggcg ttaatgattt gcccaaacag gtcgctgaaa tgcggctggt gcgcttcatc  10260
cgggcgaaag aaccccgtat tggcaaatat tgacggccag ttaagccatt catgccagta  10320
ggcgcgcgga cgaaagtaaa cccactggtg ataccattcg cgagcctccg gatgacgacc  10380
gtagtgatga atctctcctg gcgggaacag caaaatatca cccggtcggc aaacaaattc  10440
tcgtccctga tttttcacca ccccctgacc gcgaatggtg agattgagaa tataaccttt  10500
cattcccagc ggtcggtcga taaaaaaatc gagataaccg ttggcctcaa tcggcgttaa  10560
acccgccacc agatgggcat taaacgagta tcccggcagc aggggatcat tttgcgcttc  10620
agccatactt ttcatactcc cgccattcag agaagaaacc aattgtccat attgcatcag  10680
acattgccgt cactgcgtct tttactggct cttctcgcta accaaaccgg taaccccgct  10740
tattaaaagc attctgtaac aaagcgggac caaagccatg acaaaaacgc gtaacaaaag  10800
tgtctataat cacggcagaa aagtccacat tgattatttg cacggcgtca cactttgcta  10860
tgccatagca tttttatcca taagattagc ggatcctacc tgacgctttt tatcgcaact  10920
ctctactgtt tctccatacc cgtttttttg ggat                             10954
```

```
SEQ ID NO: 33           moltype = DNA  length = 10936
FEATURE                 Location/Qualifiers
misc_feature            1..10936
                        note = Synthetic plasmid.
source                  1..10936
                        mol_type = other DNA
                        organism = synthetic construct
SEQUENCE: 33
gaaagaaccc cgtattggca aatattgacg gccagttaag ccattcatgc cagtaggcgc  60
gcggacgaaa gtaaacccac tggtgatacc attcgcgagc ctccggatga cgaccgtagt  120
gatgaatctc tcctggcggg aacagcaaaa tatcacccgg tcggcaaaca aattctcgtc  180
cctgattttt caccaccccc tgaccgcgaa tggtgagatt gagaatataa cctttcattc  240
ccagcggtcg gtcgataaaa aaatcgagat aaccgttggc ctcaatcggc gttaaacccg  300
ccaccagatg ggcattaaac gagtatcccg gcagcagggg atcattttgc gcttcagcca  360
tacttttcat actcccgcca ttcagagaag aaaccaattg tccatattgc atcagacatt  420
gccgtcactg cgtcttttac tggctcttct cgctaaccaa accggtaacc ccgcttatta  480
aaagcattct gtaacaaagc gggaccaaag ccatgacaaa aacgcgtaac aaaagtgtct  540
ataatcacgg cagaaaagtc cacattgatt atttgcacgg cgtcacactt tgctatgcca  600
tagcattttt atccataaga ttagcggatc ctacctgacg ctttttatcg caactctcta  660
ctgtttctcc atacccgttt ttttgggatc tcgagggtgt tttcacgagc aattgaccaa  720
caaggacgtt taaacataaa ggaggaatat aatggccgcg agcaatcttg cagtgaaaca  780
ggcgttgaaa aacaaccctg cgccgtcgtc ggttgacccg caggaagttc ataaatggtt  840
acaggacttc acttgggatt tcaaagaaaa agcaggcaaa tatcccacga agtatgacat  900
ggatgtgaat acccgtgagc aatttaagtt gacggcgaag gaatatgcgc gcatggagtc  960
agccaaagaa gaacgccaat ttggtaccct tcttgacggc ctggatcgcc tcgatgccgg  1020
caacaaggtg catccgcgtt ggggcgaatt tatgaaatta gttgcaaact tcctggaaac  1080
cggtgaatat ggtgcgctcg caggttcggc acttttgtgg gatactgcac aaagcccgga  1140
acaacgcaat ggttacttag cgcaagtgat cgatgaggtg cgccacgtga atcagtgcgc  1200
atcggttagt tactattatt caaaacacta ttacgatccc gctggtttca caaatatgcg  1260
ccagttacgt gctattaacc ctctgtatcc aggtgtgaag cgtgctttcg gtgaaggttt  1320
tctggcgggc gatgccgtcg agtccagcat taatttacag ctggtagcgg aggcgtgctt  1380
taccaacccc ctgatcgtag ctttaaccga atgggcggcg gcaaatgggg atgagatcac  1440
tccaaccgtg ttcttgagca ttgaaaccga tgaattgcgc cacatggcga acggctatca  1500
gacgattgtg tctatcatga ataaccccga taccatgaaa tatctgcaaa ctgatctgga  1560
taacgccttc tggacgcaac acaagttcct gacgccattc gtaggggcgg cgttagaata  1620
tggttcgcgt tttaaagtcg agccgtgggc gaaatcgtgg aaccgctggg tttacgagga  1680
ttgggcaggc atttggttag gccgcctgca acaattcggg ttaaaatccc caaaatgtct  1740
ggccgacgcg aagaaagatg cagtctgggc acatcacgat ctggccctcc tggcgtttgc  1800
gttatggccg ttaacaggta tccgcctcga attgcctgac cgtcaggata tggaatggtt  1860
tgaagcgaat tatccgggct ggtatgaaca ctatggaaaa atttacgaag aatggcgtgc  1920
ccttgggttc gaagatcccc gttccggatt tagtggtgct gtgtggatgc tgcagcgtgg  1980
ccatggcatt tttattgacc atacgtcaag cctgcccttc tgtccgacgt tgggtaaggg  2040
tgctctgaaa ccttcgtttc tggagaagaa cgggaaacgt tttgcattca gtgaaccgca  2100
```

```
cggtgaacgc atgtggttgc aggagccgga gcgctacgaa ttccaaaact tcttcgagca  2160
gtttgaaggc tgggaattga gtgacctcgt aaaagcggct ggtggtgtgc gttcggacgg  2220
caaaactttg atggcgcagc ctcatctgcg ttccactgat atgtggactc tggatgacct  2280
gaagcgtatt aattttaccg tgccggatcc gatgcgcatt ctgaactggc aaccggccca  2340
ttgaatatag gaggataata atgtcctcga actcgtttgt acgtggtatg gtagatcctt  2400
atcgtcagac catcattcag gcagcaattc cggaacagcc gttagaaagc aaacgcgatc  2460
atattccttt tgcgaagcgc ggttggcgcc gtctcactga atatgaggcg gtgatgctcc  2520
acgcacagaa tagcgtagac tccgtgccgg gctcacagga ggtgggtgag tctgtacaga  2580
aatggccggg cggtcgcccg aattactcta ttgagtctac tgctgttatt gcaggtaatt  2640
ggttttactt tcgcgaccca gcgaaacgct ggttcatgcc gtatgttaag cagaaaacgg  2700
aagaaggtca aaccgctgag cgtaccatga aaagctgggc agagtccgga gatgccggaa  2760
tgatgaacgc cgattggcgt aatcaaatcc tgggtaccca ctatggcgcc ttggtgtata  2820
atgaatatgg cctcttctcc gcacattcga cgacagttta tagtgctctg tccgacttgc  2880
tgaagacctg gatctcggaa gcagggttcg ataaaaatga tgccggccaa atgattcaga  2940
tggaacgtat tctgctcggc aaattgtttg ctgatttcga cccgagtctg gccgctgcta  3000
aacaggcctg gatgcaagac ccgatttggc aaccggcgcg tgaattcgtt cagcatatct  3060
ggatgggtgt ctatgattgg gttgaacagc tgtgggccat ccatggcatt tacgatcaca  3120
ttttcgggca attcgtgcgc cgtgaattct tccagcgcct ggcgggcctg cacggtgata  3180
cgcttactcc ctttatccaa tcccaggctc tgacgtacca tcaacaggcc agcgacgcgc  3240
tgcaagcctt ttgtgtaaaa atgttgatcg acgaagagcc ggtatacggg gctcacaatc  3300
gccgctacct gcgcgcatgg accaagcgtt atctccctgg cacccaggcg gcgctgaaag  3360
cgttcctggc tatctacaaa accctgccgc tgcaagtgga aggaattacc tgcaaagcaa  3420
gtgtagaagc agcagtgcgt cgcattgtga acgattgggc ccgccgtttt gccgaaccga  3480
tcgattatcg ctttgatgca gaagcattca ttgccgacgt catgcagggg tactaaaata  3540
aggaggatat taatgagcaa gcagcattgg tatcacacgc caacgcgtga tgagtggctg  3600
gaacgcattg gtaccctgcg caccgcccgt gaaggaattg aaatgttgcg caactttcgt  3660
gagcagcatc tgggtccaga ccgcaagact tatgatctga agaaagaagc aaattggatt  3720
gagtcgcgta ttgaaatgcg tgtgtcccag ctgcacgccg aggaaactct gagtgatgac  3780
gatctcctgc acaaaacgat tgatggccgc tgcgcccgtg aggttgccaa tagttggtgg  3840
gaaaaagcag cacaagttga ttccgcaatc gaactgggcc agctctgcgt ggcctaccgt  3900
aaggcgtgta aaccaccgat gatgcctatt aattactttg cgccagtcga gaaaaaattg  3960
gttagtaaac tgctgaaatt gcgcgcggaa aattacctgg tgacgcctat cgaagaactg  4020
cgtaaagccc gtaatgttac acctatccat gtgcagtgaa tttaggagga atattatgtc  4080
tactaacatc aacggttata attcgggtac caataacaag acgggacaag catttgtcga  4140
cgaatttctg agcgaaaaaa actgcaccct gcctacgtcc gacgcggtag tgcttgccct  4200
gatgaagaca gaagaaatca atgttatcgt cgatgaaatg attcgtccaa tgatggatga  4260
caacccggcc ctggccgtcg acgatcgtgg tgggtactgg tggattaaag tgaacgggaa  4320
aatcgtcatc gactgtgatg aagcaactga gattttgggc aaaaaatata ccgtgtacga  4380
ttttctggtt aatgtgagca ccacaattgg tcgtgctatg accctgggga accaattcgt  4440
actgaccaat gaactgttgg gtctggaaac taaaatcgat tcagtgtact aattatagga  4500
ggtattatat ggattcgcgt tacaccatca cggctaactt tgaagacggc gccctccatc  4560
agttcgaatg cgcggaaaac gaagatatcc tgtcagcggc gcttcgtcag caggttgtgc  4620
tgctgtgctc ttgccgcaaa gcgttctgcg gatcttgtaa agcgctgtgt atggaaggtg  4680
aatacgcctt tggggatcgt gtaaatgtac aggtgctgtc gccgaaagaa gaagaggatg  4740
gtgtcgtggt ggcgtgtgac acttttcccc gtagcgatat ggcactggca ttcccatata  4800
ccagtgaccg cctgggatca tgttcttccg aaaatctcga agctcaggtg gagatcgttg  4860
agcgcctgtc tagcactgtg tacaagctgc tgctgcaggt tcgtgatccg gtgagtcatg  4920
aagctaagcg tatcgagttc caaccgggtc aatacgccga attgcagctg ccggatggtg  4980
agcaaacacg tgcgttttcg tttgcaaata tcgcggacga ttctggcttg ctcgaatttc  5040
tgatccgctt ggttccgggt ggatgtttta gtacctatct gcagcagcgt gcagttccgg  5100
gcgacgtgct gaagctgcgc gcgccgcttg gtgccttcac gttccaaccg gggaccaag   5160
acgaaggcct gcacgcgttt gtgggaggtt cgaccggatt ggccccttg  ctgtctatgc  5220
tgcgtggttt agcccgccaa gattatcgcg gcgaatgtca tctgtttttt ggtatgcagg  5280
accaagccgc gctgtactac gaagacgagc tgcgcgaatt agcggcaagt atgccacgct  5340
taaccttgca tctcgctctc atggatcctc cgccacaatg gcagggctac acggggaatg  5400
ccgtgaccgc gtttgaacaa cactttgccg ctttagcgcg caagccggaa gtctatatct  5460
gcggtccggc tgcaatggtt gaggccactc gcgcatcttg tgaacgtctg aatatcccgg  5520
agcaccgcgt gcaccgtgag gaatttgtcg ccagcggagg ttaattatag gaggattaaa  5580
gtgaacacgc gcagcggcga tacgccggct attccccgtc ttgacggcct gccccaggca  5640
gtgggcgcca cggtgctgat tcatgaagac ggtgaatttc gtgtgtatgc gacggaactt  5700
gaaatgctgc tgcgctggga tctgttccag ggcgatcgcc atctgcacac cggttcagct  5760
ctccgcgttg aaagctgtat cgtttcagcc aagggcaaaa ttggcttttt tcgccgtcct  5820
actgttgcac gtctgatcgc cgcaggcgac gaggcaagcc ccaacgatcc gagctaataa  5880
gtttaaacgg atacgccctc gaatcctggg atagcggccg ctcagtgacc ggcatagcgt  5940
acgcctcgag ttacgcccgt tctgcttgac ctggtaaagt tacaaccaat taaccaattc  6000
tgattagaaa aactcatcga gcatcaaatg aaactgcaat ttattcatat caggattatc  6060
aataccatat ttttgaaaaa gccgtttctg taatgaagga gaaaactcac cgaggcagtt  6120
ccataggatg gcaagatcct ggtatcggtc tgcgattccg actcgtccaa catcaataca  6180
acctattaat ttcccctcgt caaaaataag gttatcaagt gagaaatcac catgagtgac  6240
gactgaatcc ggtgagaatg gcaaaagctt atgcatttct ttccagactt gttcaacagg  6300
ccagccatta cgctcgtcat caaaatcact cgcatcaacc aaaccgttat tcattcgtga  6360
ttgcgcctga gcgagacgaa atacgcgatc gctgttaaaa ggacaattac aaacaggaat  6420
cgaatgcaac cggcgcagga acactgccag cgcatcaaca atattttcac ctgaatcagg  6480
atattcttct aatacctgga atgctgtttt cccggggatc gcagtggtga gtaaccatgc  6540
atcatcagga gtacggataa aatgcttgat ggtcggaaga ggcataaatt ccgtcagcca  6600
gtttagtctg accatctcat ctgtaacatc attggcaacg ctacctttgc catgtttcag  6660
aaacaactct ggcgcatcgg gcttcccata caatcgatag attgtcgcac ctgattgccc  6720
gacattatcg cgagcccatt tatacccata taaatcagca tccatgttgg aatttaatcg  6780
cggcctcgag caagacgttt cccgttgaat atggctcata acaccccttg tattactgtt  6840
```

```
tatgtaagca gacagtttta ttgttcatga tgatatattt ttatcttgtg caatgtaaca  6900
tcagagattt tgagacacaa cgtggctttg ttgaataaat cgaacttttg ctgagttgaa  6960
ggatcagatc acgcatcttc ccgacaacgc agaccgttcc gtggcaaagc aaaagttcaa  7020
aatcaccaac tggtccacct acaacaaagc tctcatcaac cgtggctccc tcactttctg  7080
gctggatgat ggggcgattc aggcctggta tgagtcagca acaccttctt cacgaggcag  7140
acctcagcgc tagcggagtg tatactggct tactatgttg gcactgatga gggtgtcagt  7200
gaagtgcttc atgtggcagg agaaaaaagg ctgcaccggt gcgtcagcag aatatgtgat  7260
acaggatata ttccgcttcc tcgctcactg actcgctacg ctcggtcgtt cgactgcggc  7320
gagcggaaat ggcttacgaa cggggcggag atttcctgga agatgccagg aagatactta  7380
acagggaagt gagagggccg cggcaaagcc gtttttccat aggctccgcc cccctgacaa  7440
gcatcacgaa atctgacgct caaatcagtg gtggcgaaac ccgacaggac tataaagata  7500
ccaggcgttt ccccctggcg gctccctcgt gcgctctcct gttcctgcct ttcggtttac  7560
cggtgtcatt ccgctgttat ggccgcgttt gtctcattcc acgcctgaca ctcagttccg  7620
ggtaggcagt tcgctccaag ctggactgta tgcacgaacc ccccgttcag tccgaccgct  7680
gcgccttatc cggtaactat cgtcttgagt ccaacccgga aagacatgca aaagcaccac  7740
tggcagcagc cactggtaat tgatttagag gagttagtct tgaagtcatg cgccggttaa  7800
ggctaaactg aaaggacaag ttttggtgac tgcgctcctc caagccagtt acctcggttc  7860
aaagagttgg tagctcagag aaccttcgaa aaaccgccct gcaaggcggt tttttcgttt  7920
tcagagcaag agattacgcg cagaccaaaa cgatctcaag aagatcatct tattaagggg  7980
tctgacgctc agtggaacga aaactcacgt taagggattt tggtcatgag attatcaaaa  8040
aggatcttca cctagatcct tttaaattaa aaatgaagtt ttaaatcaat ctaaagtata  8100
tatgagtaaa cttggtctga caggtgagct gataccgctc gccgcatgca catgcagtca  8160
tgtcgtgcta atgtgtaaaa catgtacatg cagattgctg gggtgcaggg gggcggagcc  8220
accctgtcca tgcggggtgt ggggcttgcc ccgccggtac agacagtgag caccggggca  8280
cctagtcgcg gataccccc ctaggtatcg gacacgtaac cctcccatgt cgatgcaaat  8340
ctttaacatt gagtacgggt aagctggcac gcatagccaa gctaggcggc caccaaacac  8400
cactaaaaat taatagtccc tagacaagac aaaccccgt gcgagctacc aactcatatg  8460
cacgggggcc acataacccg aaggggtttc aattgacaac catagcacta gctaagacaa  8520
cgggcacaac acccgcacaa actcgcactg cgcaaccccg cacaacatcg ggtctaggta  8580
acactgaaat agaagtgaac acctctaagg aaccgcaggt caatgagggt tctaaggtca  8640
ctcgcgctag ggcgtggcgt aggcaaaacg tcatgtacaa gatcaccaat agtaaggctc  8700
tggcggggtg ccataggtgg cgcagggacg aagctgttgc ggtgtcctgg tcgtctaacg  8760
gtgcttcgca gtttgagggt ctgcaaaact ctcactctcg ctgggggtca cctctggctg  8820
aattggaagt catgggcgaa cgccgcattg agctggctat tgctactaag aatcacttgg  8880
cggcgggtgg cgcgctcatg atgtttgtgg gcactgttcg acacaaccgc tcacagtcat  8940
ttgcgcaggt tgaagcgggt attaagactg cgtactcttc gatggtgaaa acatctcagt  9000
ggaagaaaga acgtgcacgg tacggggtgg agcacaccta tagtgactat gaggtcacag  9060
actcttgggc gaacggttgg cacttgcacc gcaacatgct gttgttcttg gatcgtccac  9120
tgtctgacga tgaactcaag gcgtttgagg attccatgtt ttcccgctgg tctgctggtg  9180
tggttaaggc cggtatggac gcgccactgc gtgagcacgg ggtcaaactt gatcaggtgt  9240
ctacctgggg tggagacgct gcgaaaatgg caacctacct cgctaagggc atgtctcagg  9300
aactgactgg ctccgctact aaaaccgcgt ctaaggggtc gtacacgccg tttcagatgt  9360
tggatatgtt ggccgatcaa agcgacgccg gcgaggatat ggacgctgtt ttggtggctc  9420
ggtggcgtga gtatgaggtt ggttctaaaa acctgcgttc gtcctggtca cgtggggcta  9480
agcgtgcttt gggcattgat tacatagacg ctgatgtacg tcgtgaaatg gaagaagaac  9540
tgtacaagct cgccggtctg gaagcaccgg aacgggtcga atcaacccgc gttgctgttg  9600
ctttggtgaa gcccgatgat tggaaactga ttcagtctga tttcgcggtt aggcagtacg  9660
ttctagattg cgtggataag gctaaggacg tggccgctgc gcaacgtgtc gctaatgagg  9720
tgctggcaag tctgggtgtg gattccaccc cgtgcatgat cgttatggat gatgtggact  9780
tggacgcggt tctgcctact catggggacg ctactaagcg tgatctgaat gcggcggtgt  9840
tcgcgggtaa tgagcagact attcttcgca cccactaaaa gcggcataaa ccccgttcga  9900
tattttgtgc gatgaattta tggtcaatgt cgcgggggca aactatgatg ggtcttgttg  9960
ttgcagccga acgacctagc gcagcgagtc agtgagcgag gaagcggaag agcgcctgat  10020
gcggtatttt ctccttacgc atctgtgcgg tatttcacac cgcatatggt gcactctcag  10080
tacaatctgc tctgatgccg catagttaag ccagtataca ctccgctatc gctacgtgac  10140
tgggtcatgg ctgcgccccg acacccgcca acacccgctg acgcgccctg acgggcttgt  10200
ctgctcccgg catccgctta cagacaagct gtgaccgtct ccgggagctg catgtgtcag  10260
aggttttcac cgtcatcacc gaaacgcgcg aggcagcaga tcaattcgcg cgcgaaggcg  10320
aagcggcatg cataatgtgc ctgtcaaatg gacgaagcag ggattctgca aaccctatgc  10380
tactccgtca agccgtcaat tgtctgattc gttaccaatt atgacaactt gacggctaca  10440
tcattcactt tttcttcaca accggcacgg aactcgctcg ggctggcccc ggtgcatttt  10500
ttaaataccc gcgagaaata gagttgatcg tcaaaaccaa cattgcgacc gacggtggcg  10560
ataggcatcc gggtggtgct caaaagcagc ttcgcctggc tgatacgttg gtcctcgcgc  10620
cagcttaaga cgctaatccc taactgctgg cggaaaagat gtgacagacg cgacggcgac  10680
aagcaaacat gctgtgcgac gctggcgata tcaaaattgc tgtctgccag gtgatcgctg  10740
atgtactgac aagcctcgcg tacccgatta tccatcggtg gatggagcga ctcgttaatc  10800
gcttccatgc gccgcagtaa caattgctca agcagattta tcgccagcag ctccgaatag  10860
cgcccttccc cttgcccggc gttaatgatt tgcccaaaca ggtcgctgaa atgcggctgg  10920
tgcgcttcat ccgggc                                                  10936
```

```
SEQ ID NO: 34           moltype = DNA  length = 13204
FEATURE                 Location/Qualifiers
misc_feature            1..13204
                        note = Synthetic plasmid.
source                  1..13204
                        mol_type = other DNA
                        organism = synthetic construct
SEQUENCE: 34
ccagcgacat ggaggcccag aataccctcc ttgacagtct tgacgtgcgc agctcagggg  60
```

```
catgatgtga ctgtcgcccg tacatttagc ccatacatcc ccatgtataa tcatttgcat  120
ccatacattt tgatggccgc acggcgcgaa gcaaaaatta cggctcctcg ctgcagacct  180
gcgagcaggg aaacgctccc ctcacagacg cgttgaattg tccccacgcc gcgcccctgt  240
agagaaatat aaaaggttag gatttgccac tgaggttctt ctttcatata cttcctttta  300
aaatcttgct aggatacagt tctcacatca catccgaaca taaacaacca tgggtaagga  360
aaagactcac gtttcgaggc cgcgattaaa ttccaacatg gatgctgatt tatatgggta  420
taaatgggct cgcgataatg tcgggcaatc aggtgcgaca atctatcgat tgtatgggaa  480
gcccgatgcg ccagagttgt ttctgaaaca tggcaaaggt agcgttgcca atgatgttac  540
agatgagatg gtcagactaa actggctgac ggaatttatg cctcttccga ccatcaagca  600
ttttatccgt actcctgatg atgcatggtt actcaccact gcgatccccg gcaaaacagc  660
attccaggta ttagaagaat atcctgattc aggtgaaaat attgttgatg cgctggcagt  720
gttcctgcgc cggttgcatt cgattcctgt ttgtaattgt ccttttaaca gcgatcgcgt  780
atttcgtctc gctcaggcgc aatcacgaat gaataacggt ttggttgatg cgagtgattt  840
tgatgacgag cgtaatggct ggcctgttga acaagtctgg aaagaaatgc ataagctttt  900
gccattctca ccggattcag tcgtcactca tggtgatttc tcacttgata accttatttt  960
tgacgagggg aaattaatag gttgtattga tgttggacga gtcggaatcg cagaccgata  1020
ccaggatctt gccatcctat ggaactgcct cggtgagttt tctccttcat tacagaaacg  1080
gctttttcaa aaatatggta ttgataatcc tgatatgaat aaattgcagt ttcatttgat  1140
gctcgatgag tttttctaat cagtactgac aataaaaaga ttcttgtttt caagaacttg  1200
tcatttgtat agttttttta tattgtagtt gttctatttt aatcaaatgt tagcgtgatt  1260
tatatttttt ttcgcctcga catcatctgc ccagatgcga agttaagtgc gcagaaagta  1320
atatcatgcg tcaatcgtat gtgaatgctg gtcgctatac tgctgtcgat tcgatactaa  1380
cgccaagaag ttgattgaga ctttcaacga gattgctgaa gacaaggaac aattcgagaa  1440
gttttacagt gctttctcca agaacttgaa gttgggtgtc catgaagaca gccaaaacag  1500
atccgcattg gccaagttgc tgagatttaa ctccaccaag tctactgagg agctaacctc  1560
attctctgac tacgtcacca gaatgccaga gcaccagaag aacatctact tcattaccgg  1620
tgagtctgtc aaggctcttg agaaatctcc attcttggat gctttgaagg agaagaactt  1680
tgaggtccta ttgctgaccg atcctattga tgagtacgct atgactcaat tgaaagagat  1740
tgaggacaag aaattggttg acatcactaa agactttgag ctggaagagt ctgaggagga  1800
gaagaaggct agagaggaag aggttaaaga tttcgagcct ttgactaaag ccctgaaaga  1860
gattttgggt gacaaggttg agaaggttgt agtttcctac aagctggttg actctcctgc  1920
tgctattaga acttcccaat tcggctggtc tgctaacatg gaaagaatta tgaaggctca  1980
agctctgaga gacaccaaca ccatgtcctc gtacatggct tcaaagaaga tcttcgagat  2040
ctctccaaag tcgccaatca ttaaggcttt gagaaagaag gttgaggcta ccggtacaga  2100
agagacccca cagaatcagg ggataacgca ggaaagaaca tgtgagcaaa aggccagcaa  2160
aaggccagga accgtaaaaa ggccgcgttg ctggcgtttt tccataggct ccgcccccct  2220
gacgagcatc acaaaaatcg acgctcaagt cagaggtggc gaaacccgac aggactataa  2280
agataccagg cgtttccccc tggaagctcc ctcgtgcgct ctcctgttcc gaccctgccg  2340
cttaccggat acctgtccgc ctttctccct tcgggaagcg tggcgctttc tcaatgctca  2400
cgctgtaggt atctcagttc ggtgtaggtc gttcgctcca agctgggctg tgtgcacgaa  2460
ccccccgttc agcccgaccg ctgcgcctta tccggtaact atcgtcttga gtccaacccg  2520
gtaagacacg acttatcgcc actggcagca gccactggta acaggattag cagagcgagg  2580
tatgtaggcg gtgctacaga gttcttgaag tggtggccta actacggcta cactagaagg  2640
acagtatttg gtatctgcgc tctgctgaag ccagttacct tcggaaaaag agttggtagc  2700
tcttgatccg gcaaacaaac caccgctggt agcggtggtt tttttgtttg caagcagcag  2760
attacgcgca gaaaaaaagg atctcaagaa gatcctttga tcttttctac ggggtctgac  2820
gctcagtgga acgaaaactc acgttaaggg attttggtca tgagattatc aaaaaggatc  2880
ttcacctaga tccttttaaa ttaaaaatga agttttaaat caatctaaag tatatatgag  2940
taaacttggt ctgacagtta ccaatgctta atcagtgagg cacctatctc agcgatctgt  3000
ctatttcgtt catccatagt tgcctgactc cccgtcgtgt agataactac gatacgggag  3060
ggcttaccat ctggccccag tgctgcaatg ataccgcgag acccacgctc accggctcca  3120
gatttatcag caataaacca gccagccgga agggccgagc gcagaagtgg tcctgcaact  3180
ttatccgcct ccatccagtc tattaattgt tgccgggaag ctagagtaag tagttcgcca  3240
gttaatagtt tgcgcaacgt tgttgccatt gctacaggca tcgtggtgtc acgctcgtcg  3300
tttggtatgg cttcattcag ctccggttcc caacgatcaa ggcgagttac atgatccccc  3360
atgttgtgca aaaaagcggt tagctccttc ggtcctccga tcgttgtcag aagtaagttg  3420
gccgcagtgt tatcactcat ggttatggca gcactgcata attctcttac tgtcatgcca  3480
tccgtaagat gcttttctgt gactggtgag tactcaacca agtcattctg agaatagtgt  3540
atgcggcgac cgagttgctc ttgcccggcg tcaatacggg ataataccgc gccacatagc  3600
agaactttaa aagtgctcat cattggaaaa cgttcttcgg ggcgaaaact ctcaaggatc  3660
ttaccgctgt tgagatccag ttcgatgtaa cccactcgtg cacccaactg atcttcagca  3720
tcttttactt tcaccagcgt ttctgggtga gcaaaaacag gaaggcaaaa tgccgcaaaa  3780
aagggaataa gggcgacacg gaaatgttga atactcatac tcttcctttt tcaatattat  3840
tgaagcattt atcagggtta ttgtctcatg agcggataca tatttgaatg tatttagaaa  3900
aataaacaaa taggggttcc gcgcacattt ccccgaaaag tgccacctga cgggtctcac  3960
agatgacaga gttgtcaaga acttgaccac tttgttgttc gacacagctt tgttgacttc  4020
cggtttcact ttggatgagc caacttcttt cgctgccaga atcaacggtt tgatctccat  4080
tggtttgaac atcgatgagg aggaagagaa agagccagaa caggctactg aagctccaag  4140
tgaagaagct gttgctgagt ctgccatgga ggaggttgac tagttgaatt taggtatata  4200
tagtgactgt gatatttagc taatgaaatc taattggata tttagaatgc ctcatctcgt  4260
agcctatcaa ttactattag gccatctctt atgggccctt ctttgaaatt gcattcaagg  4320
ggggatggga ctattttgaa tttgaagttt ggactctgtg agctgtttgg ccaattgaag  4380
tcatccactt gtacacaggg attcaccagt agtttagaac aattctctat cgttattctc  4440
ttgtcgtctt tggcaataca agcgtcgatg actgagttgg tgactttatg aagtctaagt  4500
tgatatgagt ttgaaattat gaaacagttt tttacactgg acatgtagat agggcccttg  4560
atgtttagga agaggataca gtttgagatg ttggagatgt gtgtggaggg agcgaccact  4620
tttaaaacca catgatccag acgttgctca gttatcgaag tttcggaaac aacgccagat  4680
ctgtttagct tgggtatttg acaggttggg gagcaaataa gtgatgatgt cccatgaaag  4740
tagaaaatgg ctagtagaag gcaaaaattt gaaattctta gagtcaaata gttagactcc  4800
```

```
aagttctaat ccacatttgg tcagtttcat agcatccaga gcttttgcca ctggtgaaca  4860
tatctaccca ttgcgatgca acaagtcact gaaagcctaa aacggagatt cccctatctt  4920
acagcctcgt tcaaaaaaac tgctaccgtt tatctgctat ggccgatgtg aggatgcgct  4980
catgcccaag agtccaactt tatcaaaaac ttgacccgtc atacaggctc tagatcaaga  5040
agcaaactta atctcagcat ctggttacgt aactctggca accagtaaca cgcttaaggt  5100
ttggaacaac actaaactac cttgcggtac taccattgac actacacatc cttaattcca  5160
atcctgtctg gcctccttca ccttttaacc atcttgccca ttccaactcg tgtcagattg  5220
cgtatcaagt gaaaaaaaaa aattttaaaa tctttaaccc aatcaggtaa taactgtcgc  5280
ctcttttatc tgccgcactg catgaggtgt ccccttagtg ggaaagagta ctgagccaac  5340
cctggaggac agcaagggaa aaatacctac aacttgcttc ataatggtcg taaaaacaat  5400
ccttgtcgga tataagtgtt gtagactgtc ccttatcctc tgcgatgttc ttcctctcaa  5460
agtttgcgat ttctctctat cagaattgcc atcaagagac tcaggactaa tttcgcagtc  5520
ccacacgcac tcgtacatga ttggctgaaa tttccctaaa gaatttcttt ttcacgaaaa  5580
ttttttttta cacaagattt tcagcagata taaaatctcg agggagagca ggacctccgc  5640
tgtgactctt cttttttttc ttttattctc actacataca ttttagttat tcgccaacat  5700
ggccatctct ttagctacca aagctgctac cgatgcttta aaagtaaacc gtgcccctgt  5760
cggtgttgaa cctcaggaag tgcataaatg gttgcaatcc ttcaactggg acttcaagga  5820
aaaccgtaca aagtacgcaa ctaagtacca tatggcaaat caaacaaagg aacaatttaa  5880
agtaattgca aaagaatatg ccagaatgga agccgctaag gatgaacgac aattcggcac  5940
tttattagac ggcttgacta gattaggtgc tggtaacaag gttcatccca gatggggtga  6000
gactatgaag gttatttcta acttcctgga agtaggtgaa tacaatgcta tcgctgcttc  6060
agctatgctg tgggattccg ctacggccgc agaacagaag aacggttatt tagcacaagt  6120
gctagatgag atccgtcata ctcaccaatg cgcttttata aatcattatt attctaaaca  6180
ctaccatgac ccagctggcc ataacgatgc ccgtcgtaca cgagcaattg gcccactatg  6240
gaagggaatg aaaagagttt ttgctgacgg tttcatttca ggtgatgccg ttgagtgcag  6300
tgttaaccta cagctagtcg gtgaggcttg tttcaccaat cctctaattg ttgccgttac  6360
tgagtgggca tcagccaatg gggacgagat aacaccaact gttttttttgt cagttgagac  6420
agacgaattg agacacatgg ccaatggata tcagacggtt gttagtatag caaatgaccc  6480
agccgctgct aaatacctta acacagactt gaacaatgcc ttttggactc agcaaaaata  6540
ctttacccct gctttgggct atttgtttga gtatggttct aagtttaagg tcgaaccctg  6600
ggttaaaaca tggaataggt gggtgtacga ggattggggt ggtatttgga ttggtagact  6660
gggtaaatac ggcgttgagt ctcctaggtc cttgcgtgat gccaagactg acgcctactg  6720
ggctcatcac gacttagctc ttgctgccta cgctctgtgg ccattaggat ttgccagact  6780
tgcattgcca gacgaggagg accaagaatg gttcgaggct aattatccag ggtgggccga  6840
tcattacgga aagatttaca atgaatggaa aaaattaggc tacgaggatc ctaaatccgg  6900
ttttattcca tacgcatggt tgttgcaaaa tggtcatgat gtctatatcg acagagtgtc  6960
tcaagttccc tttattccct ccttagcaaa aggttcaggc tcccttaggg ttcatgagta  7020
taacggaaag aagcattcct tgacagatga ttggggtgaa aggatgtggt tgtctgagcc  7080
tgaaaggtac gagtgtcact ccattttcga gcaatacgag ggaagagaac tttctgaggt  7140
tattgctgag ggacacgggg ttaggtccga tggtaagact ctgatcgctc agccacatgt  7200
tagaggcgat aatctttgga ctcttgagga catcaagcgt gcaggttgtg tgttcccaga  7260
ccctttggcc aagttctaag tatctccagt cgtttagatt gttagatatt ttctttgtgt  7320
attcgtttca gtctgatgtt tatgctacaa acgtcatctg gactttaatc caataaggat  7380
attcttcaac ttaatagtat cttaataata tttttttttct tttgatttct tcgtaaggtg  7440
ttttgttgca ctcatgatct acgacttttg ttcgtgactg atttttttttg tagaaatgtc  7500
ttggtgtcct cgtccaatca ggtagccatc tctgaaatat ctggctccgt tgcaactccg  7560
aacgacctgc tggcaacgta aaattctccg gggtaaaact taaatgtgga gtaatggaac  7620
cagaaacgtc tcttcccttc tctctccttc caccgcccgt taccgtccct aggaaatttt  7680
actctgctgg agagcttctt ctacggcccc cttgcagcaa tgctcttccc agcattacgt  7740
tgcgggtaaa acggaggtcg tgtacccgac ctagcagccc agggatggaa aagtcccggc  7800
cgtcgctggc aataatagcg ggcggacgca tgtcatgaga ttattggaaa ccaccagaat  7860
cgaatataaa aggcgaacac ctttcccaat tttggtttct cctgacccaa agactttaaa  7920
tttaatttat ttgtccctat ttcaatcaat tgaacaacta tatgtctcag ccacagtctt  7980
ctcaggttac caagagggga ctgacggacc ccgaaagggc agctatcatc gccgcagcta  8040
ttccagatca tgctttggat acccagcgta aataccacta tttcattcag cctagatgga  8100
agaggttaag tgaatatgag cagttgtcct gttacgccca accaaaccca gattggattg  8160
ctggtggttt ggactggggt gactggactc agaagtttca tggtggtaga ccctcttggg  8220
gaaacgaatc tactgaactt aggaccaccg attggtaccg acacagagat ccagcacgta  8280
ggtggcacgc accttacgtc aaagataagt ctgaggaagc tagatataca cagagattct  8340
tggcagcata ctcatctgaa ggttccattc gaaccgtcga cgcatattgg agggacgaaa  8400
ttcttaacaa atattacggt gcattgttat ataacgaata cggtttattc aatgctcact  8460
cttctgtggg cagggactct ctgtctgata caattaggca atccgctata tttgctgctc  8520
ttgataaggt tgataacgca caaatgattc aaatggaaag attatttatt gcaaaattgg  8580
tgccaggttt cgatgcttct acggatgtgc ctaaaaagat ctggacaaca gatccaattt  8640
atgctggcgc tagaggtgca gtcgaagaga tttggcaggg tattcaagat tggaatgaga  8700
tattgtgggc cggtcacgcc gtctacgatg ctaccttcgg gcaattcgct agaagggaat  8760
tttttcaaag acttgctact gtatacggtg atacattgac ccctttcttt acagcccaat  8820
cacaaactta tttccaaatt actagaggtg caattgagga cctgtttgtc tactcccttg  8880
ctaacgaccc cgaatttgga gcccataaca ggacttttct gaatgcatgg actgaacatt  8940
atcttgcaag atctgtgaca gcattgaagg attttgttgg gatctatgct aaggtggaga  9000
aagtggctgg tgccactgac agagctggag tctctgaagc actacagaga gtatttgggg  9060
actggaaagt ggattacgcc gacaagatcg gtttcaagat tgacgtagac cagaaggtcg  9120
acgcagtact ggcaggttac aaaaattaaa ttcggatagt gtaatttaat caataacttg  9180
aaaaaaatat catttaattt actatacaca cggacataaa ctgaaagggc aaggaagggg  9240
aaaatgggaa aaataatgag gatatgcaag atgagagatg agagatgaga gatgtccact  9300
ttagtcagtt ttggctttac ttttatcttt ttctatggca tctttcgttt tactactagt  9360
atacatagaa taaaaacggt aatagaactg ggaactaagc agaaacttac aattcctgag  9420
aagccttggc cttggcagac ttctttggca acaattcgga ttgaatgttt ggcaagacac  9480
caccttgggc gatggtgacg tgtcccagca acttgttcaa ttcctcatcg tttctgatgg  9540
```

```
ccaattgcaa gtgtcttggg ataattctgg acttcttgtt gtctctggcg gcgttaccgg  9600
ccaattccaa aatttcagca gccaagtact ccaagacagc agtcaaatag actggagcac  9660
cagaaccaat tctttgggcg tagttacctc ttctcagaag acggtggact cttcccacag  9720
ggaaggtcaa acctgcctta gaagatcttg aggttgaggc cttttcagcc gaagatgctt  9780
ttcctttacc accggacatt gttgtagttt taatatagtt tgagtatgag atggaactca  9840
gaacgaagga attatcacca gtttatatat tctgaggaaa gggtgtgtcc taaattggac  9900
agtcacgatg gcaataaacg ctcagccaat cagaatgcag gagccataaa ttgttgtatt  9960
attgctgcaa gatttatgtg ggttcacatt ccactgaatg gttttcactg tagaattggt  10020
gtcctagttg ttatgtttcg agatgttttc aagaaaaact aaaatgcaca aactgaccaa  10080
taatgtgccg tcgcgcttgg tacaaacgtc aggattgcca ccactttttt cgcactctgg  10140
tacaaaagtt cgcacttccc actcgtatgt aacgaaaaac agagcagtct atccagaacg  10200
agacaaatta gcgcgtactg tcccattcca taaggtatca taggaaacga gagtcctccc  10260
cccatcacgt atatataaac acactgatat ccccacatcg cttgtcacca aactaataca  10320
tccagttcaa gttacctaaa caaatcaaaa tggcaaagag ggaacctatt cacgaaaatt  10380
ccactcgtac tgagtgggag ggaaagatag ctaaactgaa ctctgttgat caggctacta  10440
agtttatcca agattttcga gttgctaatt cctctccttt taggaagtca tatgatctag  10500
acgtggacta ccaatatatc gagagaaaga ttgaagagag actgtccgta ttaaagaccg  10560
aaaagttatc agttgccgat ttagtcacca aggccacgac tggtgaagac gccgctgctg  10620
ttgaagctac atggattgca aagatgaagg cagccgagtc taaatatgca gccgaacgaa  10680
ttcatgttga attcagacaa ttgtataagc ctcctgttct accagtgaat gttttcctga  10740
gaactgatgc agcattagga actatcttaa tggaacttag aaataccgac tattatgcta  10800
ctcctttaga aggattgaga aaggagcgtg gggttaaagt tctacatctt caggcatagg  10860
cgtgcttctt ttttgtttct ttagttgttt agtttttggc actggttttg gtcgaccttt  10920
tgttttaagt agcctatata tgcagttaaa tgattgatag tttgatttat tccgtgcaac  10980
ttaagggatt gtgattgggc gtggcaatct acctacattc tatttacctg caatcttagg  11040
attgagattg attcagattc tcttgaaggg gaagggttag actatttaaa attcatacat  11100
acagttcatt cttttcccgc gcagctttaa tctttcggca gagaaggcgt tttcatcgta  11160
gcgtgggaac agaataatca gttcatgtgc tatacaggca catggcagca gtcactattt  11220
tgctttttaa ccttaaagtc gttcatcaat cattaactga ccaatcagat tttttgcatt  11280
tgccacttat ctaaaaatac ttttgtatct cgcagatacg ttcagtggtt tccaggacaa  11340
cacccaaaaa aaggtatcaa tgccactagg cagtcggttt tatttttggt cacccacgca  11400
aagaagcacc cacctctttt aggttttaag ttgtgggaac agtaacaccg cctagagctt  11460
caggaaaaac cagtacctgt gaccgcaatt caccatgatg cagaatgtta atttaaacga  11520
gtgccaaatc aagatttcaa cagacaaatc aatcgatcca tagttaccca ttccagcctt  11580
ttcgtcgtcg agcctgcttc attcctgcct caggtgcata actttgcatg aaaagtccag  11640
attagggcag attttgagtt taaaatagga aatataaaca aatataccgc gaaaaaggtt  11700
tgtttatagc ttttcgcctg gtgccgtacg gtataaatac atactctcct cccccccctg  11760
gttctctttt tcttttgtta cttacatttt accgttccgt cactcgcttc actcaacaac  11820
aaaaatgtat cagatcgtga ttgaaactga agatggagaa acttgttcct tcgagtgtgg  11880
gccttctgaa gatgtgatat ccgctggact taggcagtcc gtcatcctgt taagttcctg  11940
ccgagctggg ggatgcgcca cgtgcaaggc cgattgtacg gacggtgatt atgagttgat  12000
cgacgtaaag gtacaggcac tacctcctga tgaggaggaa gatggtaagg tgttactttg  12060
cagaaccttt cctcgatcag atttgcattt aatcgttcca tacacttacg acaggatttc  12120
attcgaggca atccagacta actggctggc cgaaattgtt gaatgcgata gagtatcttc  12180
taatgtagtc agacttgttc tacagccact gaccgctgat ggcgcagctc caatcgcctt  12240
aaacttcgct cctggtcagt ttgtcgatat tgagatcccc ggtactcaca ccagaagatc  12300
ctacagtatg gcatccgttg cagaggatgg gcgtcttgaa ttctttattc gtcttttacc  12360
agatggagct tttttctaagt tcttgcaaac ccaagctaaa gtgggattaa gagtcgccct  12420
acgtggacct gctggttcat ttatgctgca taaatctgaa agaccacgtt tcttcgttgc  12480
tggaggcact ggcttgtctc ctgttttaag tatgataaga cagttgaaaa aagaatccga  12540
tcagcaaccc gctaccttgt tctttggtgt aactaattat gaggagctgt tttatgtcga  12600
agaactgaaa gctctacaaa acgctatgcc ctcccttgat gtgcaagtcg ccgtcgttaa  12660
tgcatctgag gctaatggtg ttgccaaggg aactgtgata gatcttatga gggccgaact  12720
ggagaaactt agaggtaagc cagacattta tttatgtggt cctcctggga tgattgaagc  12780
agcatttgat gctgctgcca cagctggtgt tcccaaagag caagtctacc tggagaaatt  12840
cttggcttca ggctagagac atgactgttc ctcagttcaa gttgggcact tacgagaaga  12900
ccggtcttgc tagattctaa tcaagaggat gtcagaatgc catttgcctg agagatgcag  12960
gcttcatttt tgattacttt tttatttgta acctatatag tataggattt tttttgtcat  13020
tttgtttctt ctcgtacgag cttgctcctg atcagcctat ctcgcagctg atgaatatct  13080
tgtggtaggg gtttgggaaa atcattcgag tttgatgttt ttcttggtat ttcccactcc  13140
tcttcagagt acagaagatt aagtgagagc ggccgctcgt ccccgccggg tcacccggct  13200
cgag                                                              13204
```

```
SEQ ID NO: 35          moltype = DNA  length = 13225
FEATURE                Location/Qualifiers
misc_feature           1..13225
                       note = Synthetic plasmid.
source                 1..13225
                       mol_type = other DNA
                       organism = synthetic construct
SEQUENCE: 35
ctcgagggag agcaggacct ccgctgtgac tcttcttttt tttcttttat tctcactaca  60
tacattttag ttattcgcca acatggctgc ttccaatttg gctgttaagc aagctttaaa  120
gaacaaccca gctccatcat ctgtcgatcc acaagaggtt cacaagtggt tgcaagattt  180
tacctgggac tttaaggaga aggccggtaa gtatcctacc aagtacgaca tggacgtcaa  240
tactcgtgaa cagttcaagt taactgctaa ggaatacgca agaatggagt ccgctaaaga  300
agagagacag ttcggaaccc tgctagatgg attagaccgt ttggatgctg gtaacaaagt  360
gcatccaaga tggggagaat ttatgaaatt agtcgcaaac tttcttgaga ctggggaata  420
tggggcatta gccggtagtg ctttgctttg ggatacagct cagtccccccg aacaacgaaa  480
```

```
cggttacctt gcccaagtga tcgacgaagt tagacacgtg aaccaatgcg catctgtatc  540
atattattac tccaagcatt attatgatcc tgctggattc acgaatatga gacaacttcg  600
agctattaac cctttgtatc caggagttaa acgtgcattc ggcgagggtt ttttggctgg  660
cgacgctgtt gagtcttcca tcaatttgca gttggtggct gaggcttgtt tcacaaatcc  720
attaattgtt gctctaaccg aatgggccgc agctaacggg gacgaaatca cacccaccgt  780
atttctgtct attgagacag acgaattgag acatatggct aatggatatc agaccattgt  840
tagtatcatg aacaaccctg atacaatgaa gtatctgcaa actgacctgg ataatgcttt  900
ttggacgcaa cacaagtttt taactccctt cgtaggtgct gccttggaat atggatctag  960
attcaaagtg gagccatggg caaaaagttg gaataggtgg gtctacgagg attgggctgg  1020
tatctggctt ggccgtcttc agcaattcgg tcttaaatct cctaaatgtt tggccgatgc  1080
aaagaaggac gccgtttggg ctcatcatga tcttgcttta ctggctttcg ctctttggcc  1140
tctgactggt attcgtttag agttaccaga tagacaagat atggaatggt tcgaagctaa  1200
ttaccctgga tggtatgaac actatggtaa gatctacgaa gagtggcgtg ctttaggttt  1260
tgaagatcca cgttccggtt tcagtggtgc cgtctggatg ttgcaaagag ggcatggaat  1320
ttttattgac cacacatcta gtctgccatt ctgccccaca ctgggcaagg gtgccttgaa  1380
accatcattt ttggagaaga atggtaagag atttgctttt tccgaaccac atggtgaaag  1440
aatgtggctg caagaaccag aacgttacga gtttcaaaac tttttcgaac aatttgaagg  1500
ttgggagttg tccgatcttg ttaaagcagc tggtggcgtc agatctgatg gtaagacact  1560
tatggcacag ccacatttga gaagtaccga tatgtggaca ttagacgatt tgaagaggat  1620
aaacttcacg gtaccagatc ctatgaggat tctaaattgg caaccagctc attaagtatc  1680
tccagtcgtt tagattgtta gatattttct ttgtgtattc gtttcagtct gatgtttatg  1740
ctacaaacgt catctggact ttaatccaat aaggatattc ttcaacttaa tagtatctta  1800
ataatatttt ttttcttttg atttcttcgt aaggtgtttt gttgcactca tgatctacga  1860
cttttgttcg tgactgattt tttttgtaga aatgtcttgg tgtcctcgtc caatcaggta  1920
gccatctctg aaatatctgg ctccgttgca actccgaacg acctgctggc aacgtaaaat  1980
tctccggggt aaaacttaaa tgtggagtaa tggaaccaga aacgtctctt cccttctctc  2040
tccttccacc gcccgttacc gtccctagga aattttactc tgctggagag cttcttctac  2100
ggccccccttg cagcaatgct cttcccagca ttacgttgcg ggtaaaacgg aggtcgtgta  2160
cccgacctag cagcccaggg atggaaaagt cccggccgtc gctggcaata atagcgggcg  2220
gacgcatgtc atgagattat tggaaaccac cagaatcgaa tataaaaggc gaacaccttt  2280
cccaattttg gtttctcctg acccaaagac tttaaattta atttatttgt ccctatttca  2340
atcaattgaa caactatatg tcctccaact ccttcgttcg aggaatggta gatccctaca  2400
gacaaactat cattcaggcc gctattccag aacaaccatt ggaatctaag cgtgaccaca  2460
ttccatttgc taagagagga tggcgaagat taaccgagta cgaagcagta atgttacatg  2520
ctcaaaactc cgtcgattca gtgccaggct cacaggaagt tggtgagtca gtccaaaaat  2580
ggcctggcgg tcgtcccaat tactctatag agtctacagc tgttatagca ggaaactggt  2640
tctatttcag ggaccctgca aagagatggt tcatgcccta tgtaaaacag aagactgagg  2700
aaggtcagac cgcagaaaga actatgaagt cctgggctga gagtggagat gcaggtatga  2760
tgaatgctga ctggcgaaat caaattttgg gaacccacta tggtgcactg gtttataacg  2820
aatacggact tttttctgcc cactctacta ctgtttacag tgccttgtcc gatttgctaa  2880
agacatggat ctctgaggct ggtttcgata agaatgatgc aggacaaatg attcagatgg  2940
aaagaatctt gttaggcaag ctgtttgccg actttgatcc atcattggct gctgccaaac  3000
aagcttggat gcaagatcca atctggcaac cagccagaga attcgtccaa catatttgga  3060
tgggtgttta tgactgggtg gagcaacttt gggctataca cggtatttat gatcatatct  3120
tcgggcaatt cgttagacgt gaatttttc aacgtcttgc tggtttacat ggcgacactt  3180
tgactccttt catccagtca caagctctta cttaccatca gcaagctagt gatgcacttc  3240
aagctttctg tgtgaaaatg cttatcgatg aagagcctgt gtacggagcc cataatcgta  3300
gatacctgag agcctggact aagaggtatt tgcctggaac tcaggccgcc ttaaaagctt  3360
ttttggcaat atataagact ttgcctcttc aggttgaggg catcacatgt aaagcttccg  3420
ttgaagccgc agtgagacgt attgttaacg attgggcaag aagattcgcc gaaccaattg  3480
actataggtt cgacgcagag gcatttatcg cagacgttat gcagggttat tgaattcgga  3540
tagtgtaatt taatcaataa cttgaaaaaa atatcattta atttactata cacacggaca  3600
taaactgaaa gggcaaggaa ggggaaaatg ggaaaaataa tgaggatatg caagatgaga  3660
gatgagagat gagagatgtc cactttagtc agttttggct ttactttat cttttctat  3720
ggcatctttc gttttactac tagtatacat agaataaaaa cggtaataga actgggaact  3780
aagcagaaac ttacaattcc tgagaagcct tggccttggc agacttcttt ggcaacaatt  3840
cggattgaat gtttggcaag acaccacctt gggcgatggt gacgtgtccc agcaacttgt  3900
tcaattcctc atcgtttctg atggccaatt gcaagtgtct tgggataatt ctggacttct  3960
tgttgtctct ggcggcgtta ccggccaatt ccaaaatttc agcagccaag tactccaaga  4020
cagcagtcaa atagactgga gcaccagaac caattctttg ggcgtagtta cctcttctca  4080
gaagacggtg gactcttccc acagggaagg tcaaacctgc cttagaagat cttgaggttg  4140
aggccttttc agccgaagat gcttttcctt taccaccgga cattgttgta gttttaatat  4200
agtttgagta tgagatggaa ctcagaacga aggaattatc accagtttat atattctgag  4260
gaaagggtgt gtcctaaatt ggacagtcac gatggcaata aacgctcagc caatcagaat  4320
gcaggagcca taaattgttg tattattgct gcaagattta tgtgggttca cattccactg  4380
aatggttttc actgtagaat tggtgtccta gttgttatgt ttcgagatgt tttcaagaaa  4440
aactaaaatg cacaaactga ccaataatgt gccgtcgcgc ttggtacaaa cgtcaggatt  4500
gccaccactt ttttcgcact ctggtacaaa agttcgcact tcccactcgt atgtaacgaa  4560
aaacagagca gtctatccag aacgagacaa attagcgcgt actgtcccat tccataaggt  4620
atcataggaa acgagagtcc tccccccatc acgtatatat aaacacactg atatcccaca  4680
tccgcttgtc accaaactaa tacatccagt tcaagttacc taaacaaatc aaaatgtcca  4740
agcaacactg gtaccatacg ccaaccagag atgaatggct agagcgtatt ggtaccttgc  4800
gtaccgctcg tgagggtatt gagatgctga ggaactttcg tgagcaacat ttaggtccag  4860
atcgtaaaac ttatgatttg aaaaaggaag ctaattggat tgagagtaga atcgaaatga  4920
gagtcagtca gctgcatgct gaagaaacct tgagtgatga cgatctgtta cacaaaacca  4980
tcgatggacg atgtgctaga gaagtcgcca attcctggtg ggaaaaggct gcccaagtgg  5040
attctgccat tgaacttggc cagttgtgtg tggcctacag aaaggcttgc aagcctccta  5100
tgatgcctat aaactacttt gctccagttg aaaagaagtt agtctccaag ttgttgaagc  5160
taagagccga aaactacctt gtcacgccta ttgaagaact aaggaaagcc agaaatgtga  5220
```

-continued

```
ctccaattca tgtccagtaa gcgtgcttct tttttgtttc tttagttgtt tagtttttgg  5280
cactggtttt ggtcgacctt ttgttttaag tagcctatat atgcagttaa atgattgata  5340
gtttgattta ttccgtgcaa cttaagggat tgtgattggg cgtggcaatc tacctacatt  5400
ctatttacct gcaatcttag gattgagatt gattcagatt ctcttgaagg ggaagggtta  5460
gactatttaa aattcataca tacagttcat tcttttcccg cgcagcttta atctttcggc  5520
agagaaggcg ttttcatcgt agcgtgggaa cagaataatc agttcatgtg ctatacaggc  5580
acatggcagc agtcactatt ttgcttttta accttaaagt cgttcatcaa tcattaactg  5640
accaatcaga tttttttgcat ttgccactta tctaaaaata cttttgtatc tcgcagatac  5700
gttcagtggt ttccaggaca acacccaaaa aaaggtatca atgccactag gcagtcggtt  5760
ttatttttgg tcacccacgc aaagaagcac ccacctcttt taggttttaa gttgtgggaa  5820
cagtaacacc gcctagagct tcaggaaaaa ccagtacctg tgaccgcaat tcaccatgat  5880
gcagaatgtt aatttaaacg agtgccaaat caagatttca acagacaaat caatcgatcc  5940
atagttaccc attccagcct tttcgtcgtc gagcctgctt cattcctgcc tcaggtgcat  6000
aactttgcat gaaaagtcca gattagggca gattttgagt ttaaaatagg aaatataaac  6060
aaatataccg cgaaaaaggt ttgtttatag cttttcgcct ggtgccgtac ggtataaata  6120
catactctcc tcccccccct ggttctcttt ttcttttgtt acttacattt taccgttccg  6180
tcactcgctt cactcaacaa caaaaatgga ctctcgttac accatcactg ctaatttcga  6240
agatggagct ctgcatcagt ttgagtgtgc tgagaacgag gacatccttt ccgctgctct  6300
aagacagcaa gttgttcttc tatgctcttg tcgtaaggca ttttgtggat cctgtaaagc  6360
cttgtgtatg gaaggtgaat acgctttcgg tgatagagtg aacgtccaag ttctaagtcc  6420
caaggaagaa gaggacggtg tcgtggtcgc atgtgacacc ttcccaagat ctgatatggc  6480
cttggcattc ccttatactt ccgatagact gggttcatgt tccagtgaaa atttggaagc  6540
acaggtagag atagttgaac gattgtcttc aactgtatac aaactgctgt tgcaagtccg  6600
tgatcctgtt tctcatgaag ctaaaagaat agagtttcaa ccaggacaat acgcagagtt  6660
gcaattgcca gacggcgaac agactagagc tttttctttt gccaacattg ctgatgacag  6720
tggcttattg gagttcttga taaggttggt ccccggaggt tgtttctcca cttatttgca  6780
acagagggcc gtgcctgggg atgtcttaaa gttaagagct cctttgggcg ctttcacctt  6840
tcagcctggc gatcaagatg aaggtctaca cgcctttgta ggcggttcta ctggacttgc  6900
tcctttattg tctatgttgc gtggtttggc tagacaggac tacaggggtg agtgtcatct  6960
ttttttggt atgcaggatc aagctgcctt gtactacgaa gatgagctta gggagctggc  7020
tgcttctatg cctaggttaa cattgcatct agccctgatg gatcctcctc cacaatggca  7080
aggttacacc ggtaacgctg tgaccgcatt cgagcagcac ttcgctgctc tggcaagaaa  7140
accagaagtc tacatatgcg gtccagcagc tatggtcgaa gccactagag catcttgtga  7200
gaggctaaat ataccagaac atagagtcca tagagaagaa ttcgttgctt caggtggtta  7260
aagacatgac tgttcctcag ttcaagttgg gcacttacga gaagaccggt cttgctagat  7320
tctaatcaag aggatgtcag aatgccattt gcctgagaga tgcaggcttc atttttgatt  7380
actttttat ttgtaaccta tatagtatag gatttttttt gtcattttgt ttcttctcgt  7440
acgagcttgc tcctgatcag cctatctcgc agctgatgaa tatcttgtgg taggggtttg  7500
ggaaaatcat tcgagtttga tgtttttctt ggtatttccc actcctcttc agagtacaga  7560
agattaagtg agagcggccg ctcgtccccg ccgggtcacc cggctcgagc cagcgacatg  7620
gaggcccaga ataccctcct tgacagtctt gacgtgcgca gctcaggggc atgatgtgac  7680
tgtcgcccgt acatttagcc catacatccc catgtataat catttgcatc catacatttt  7740
gatggccgca cggcgcgaag caaaaattac ggctcctcgc tgcagacctg cgagcaggga  7800
aacgctcccc tcacagacgc gttgaattgt ccccacgccg cgcccctgta gagaaatata  7860
aaaggttagg atttgccact gaggttcttc tttcatatac ttccttttaa aatcttgcta  7920
ggatacagtt ctcacatcac atccgaacat aaacaaccat gggtaaggaa aagactcacg  7980
tttcgaggcc gcgattaaat tccaacatgg atgctgattt atatgggtat aaatgggctc  8040
gcgataatgt cgggcaatca ggtgcgacaa tctatcgatt gtatgggaag cccgatgcgc  8100
cagagttgtt tctgaaacat ggcaaaggta gcgttgccaa tgatgttaca gatgagatgg  8160
tcagactaaa ctggctgacg gaatttatgc ctcttccgac catcaagcat tttatccgta  8220
ctcctgatga tgcatggtta ctcaccactg cgatccccgg caaaacagca ttccaggtat  8280
tagaagaata tcctgattca ggtgaaaata ttgttgatgc gctggcagtg ttcctgcgcc  8340
ggttgcattc gattcctgtt tgtaattgtc cttttaacag cgatcgcgta tttcgtctcg  8400
ctcaggcgca atcacgaatg aataacggtt tggttgatgc gagtgatttt gatgacgagc  8460
gtaatggctg gcctgttgaa caagtctgga aagaaatgca taagcttttg ccattctcac  8520
cggattcagt cgtcactcat ggtgatttct cacttgataa ccttattttt gacgagggga  8580
aattaatagg ttgtattgat gttggacgag tcggaatcgc agaccgatac caggatcttg  8640
ccatcctatg gaactgcctc ggtgagtttt ctccttcatt acagaaacgg ctttttcaaa  8700
aatatggtat tgataatcct gatatgaata aattgcagtt tcatttgatg ctcgatgagt  8760
ttttctaatc agtactgaca ataaaaagat tcttgttttc aagaacttgt catttgtata  8820
gttttttat attgtagttg ttctatttta atcaaatgtt agcgtgattt atattttttt  8880
tcgcctcgac atcatctgcc cagatgcgaa gttaagtgcg cagaaagtaa tatcatgcgt  8940
caatcgtatg tgaatgctgg tcgctatact gctgtcgatt cgatactaac gccaagaagt  9000
tgattgagac tttcaacgag attgctgaag acaaggaaca attcgagaag ttttacagtg  9060
ctttctccaa gaacttgaag ttgggtgtcc atgaagacag ccaaaacaga tccgcattgg  9120
ccaagttgct gagatttaac tccaccaagt ctactgagga gctaacctca ttctctgact  9180
acgtcaccag aatgccagag caccagaaga acatctactt cattaccggt gagtctgtca  9240
aggctcttga gaaatctcca ttcttggatg ctttgaagga gaagaacttt gaggtcctat  9300
tgctgaccga tcctattgat gagtacgcta tgactcaatt gaaagagatt gaggacaaga  9360
aattggttga catcactaaa gactttgagc tggaagagtc tgaggaggag aagaaggcta  9420
gagaggaaga ggttaaagat ttcgagcctt tgactaaagc cctgaaagag attttgggtg  9480
acaaggttga gaaggttgta gtttcctaca agctggttga ctctcctgct gctattagaa  9540
cttcccaatt cggctggtct gctaacatgg aaagaattat gaaggctcaa gctctgagag  9600
acaccaacac catgtcctcg tacatggctt caaagaagat cttcgagatc tctccaaagt  9660
cgccaatcat taaggctttg agaaagaagg ttgaggctac cggtacagaa gagaccccac  9720
agaatcaggg gataacgcag gaaagaacat gtgagcaaaa ggccagcaaa aggccaggaa  9780
ccgtaaaaag gccgcgttgc tggcgttttt ccataggctc cgcccccctg acgagcatca  9840
caaaaatcga cgctcaagtc agaggtggcg aaacccgaca ggactataaa gataccaggc  9900
gtttccccct ggaagctccc tcgtgcgctc tcctgttccg accctgccgc ttaccggata  9960
```

```
cctgtccgcc tttctccctt cgggaagcgt ggcgctttct caatgctcac gctgtaggta  10020
tctcagttcg gtgtaggtcg ttcgctccaa gctgggctgt gtgcacgaac cccccgttca  10080
gcccgaccgc tgcgccttat ccggtaacta tcgtcttgag tccaacccgg taagacacga  10140
cttatcgcca ctggcagcag ccactggtaa caggattagc agagcgaggt atgtaggcgg  10200
tgctacagag ttcttgaagt ggtggcctaa ctacggctac actagaagga cagtatttgg  10260
tatctgcgct ctgctgaagc cagttacctt cggaaaaaga gttggtagct cttgatccgg  10320
caaacaaacc accgctggta gcggtggttt ttttgtttgc aagcagcaga ttacgcgcag  10380
aaaaaaagga tctcaagaag atcctttgat cttttctacg gggtctgacg ctcagtggaa  10440
cgaaaactca cgttaaggga ttttggtcat gagattatca aaaaggatct tcacctagat  10500
ccttttaaat taaaaatgaa gttttaaatc aatctaaagt atatatgagt aaacttggtc  10560
tgacagttac caatgcttaa tcagtgaggc acctatctca gcgatctgtc tatttcgttc  10620
atccatagtt gcctgactcc ccgtcgtgta gataactacg atacgggagg gcttaccatc  10680
tggccccagt gctgcaatga taccgcgaga cccacgctca ccggctccag atttatcagc  10740
aataaaccag ccagccggaa gggccgagcg cagaagtggt cctgcaactt tatccgcctc  10800
catccagtct attaattgtt gccgggaagc tagagtaagt agttcgccag ttaatagttt  10860
gcgcaacgtt gttgccattg ctacaggcat cgtggtgtca cgctcgtcgt ttggtatggc  10920
ttcattcagc tccggttccc aacgatcaag gcgagttaca tgatccccca tgttgtgcaa  10980
aaaagcggtt agctccttcg gtcctccgat cgttgtcaga agtaagttgg ccgcagtgtt  11040
atcactcatg gttatggcag cactgcataa ttctcttact gtcatgccat ccgtaagatg  11100
cttttctgtg actggtgagt actcaaccaa gtcattctga gaatagtgta tgcggcgacc  11160
gagttgctct tgcccggcgt caatacggga taataccgcg ccacatagca gaactttaaa  11220
agtgctcatc attggaaaac gttcttcggg gcgaaaactc tcaaggatct taccgctgtt  11280
gagatccagt tcgatgtaac ccactcgtgc acccaactga tcttcagcat cttttacttt  11340
caccagcgtt tctgggtgag caaaaacagg aaggcaaaat gccgcaaaaa agggaataag  11400
ggcgacacgg aaatgttgaa tactcatact cttccttttt caatattatt gaagcattta  11460
tcagggttat tgtctcatga gcggatacat atttgaatgt atttagaaaa ataaacaaat  11520
aggggttccg cgcacatttc cccgaaaagt gccacctgac gggtctcaca gatgacagag  11580
ttgtcaagaa cttgaccact ttgttgttcg acacagcttt gttgacttcc ggtttcactt  11640
tggatgagcc aacttctttc gctgccagaa tcaacggttt gatctccatt ggtttgaaca  11700
tcgatgagga ggaagagaaa gagccagaac aggctactga agctccaagt gaagaagctg  11760
ttgctgagtc tgccatggag gaggttgact agttgaattt aggtatatat agtgactgtg  11820
atatttagct aatgaaatct aattggatat ttagaatgcc tcatctcgta gcctatcaat  11880
tactattagg ccatctctta tgggcccttc tttgaaattg cattcaaggg gggatgggac  11940
tattttgaat ttgaagtttg gactctgtga gctgtttggc caattgaagt catccacttg  12000
tacacaggga ttcaccagta gtttagaaca attctctatc gttattctct tgtcgtcttt  12060
ggcaatacaa gcgtcgatga ctgagttggt gactttatga agtctaagtt gatatgagtt  12120
tgaaattatg aaacagtttt ttacactgga catgtagata gggcccttga tgtttaggaa  12180
gaggatacag tttgagatgt tggagatgtg tgtggaggga gcgaccactt ttaaaaccac  12240
atgatccaga cgttgctcag ttatcgaagt ttcggaaaca acgccagatc tgtttagctt  12300
gggtatttga caggttgggg agcaaataag tgatgatgtc ccatgaaagt agaaaatggc  12360
tagtagaagg caaaaatttg aaattcttag agtcaaatag ttagactcca agttctaatc  12420
cacatttggt cagtttcata gcatccagag cttttgccac tggtgaacat atctacccat  12480
tgcgatgcaa caagtcactg aaagcctaaa acggagattc ccctatctta cagcctcgtt  12540
caaaaaaact gctaccgttt atctgctatg gccgatgtga ggatgcgctc atgcccaaga  12600
gtccaacttt atcaaaaact tgacccgtca tacaggctct agatcaagaa gcaaacttaa  12660
tctcagcatc tggttacgta actctggcaa ccagtaacac gcttaaggtt tggaacaaca  12720
ctaaactacc ttgcggtact accattgaca ctacacatcc ttaattccaa tcctgtctgg  12780
cctccttcac cttttaacca tcttgcccat tccaactcgt gtcagattgc gtatcaagtg  12840
aaaaaaaaaa attttaaaat ctttaaccca atcaggtaat aactgtcgcc tcttttatct  12900
gccgcactgc atgaggtgtc cccttagtgg gaaagagtac tgagccaacc ctggaggaca  12960
gcaagggaaa aatacctaca acttgcttca taatggtcgt aaaaacaatc cttgtcggat  13020
ataagtgttg tagactgtcc cttatcctct gcgatgttct tcctctcaaa gtttgcgatt  13080
tctctctatc agaattgcca tcaagagact caggactaat ttcgcagtcc cacacgcact  13140
cgtacatgat tggctgaaat ttccctaaag aatttctttt tcacgaaaat tttttttac  13200
acaagatttt cagcagatat aaaat                                        13225

SEQ ID NO: 36          moltype = DNA  length = 11683
FEATURE                Location/Qualifiers
misc_feature           1..11683
                       note = Synthetic plasmid.
source                 1..11683
                       mol_type = other DNA
                       organism = synthetic construct
SEQUENCE: 36
ttcagtaatg tcttgtttct tttgttgcag tggtgagcca ttttgacttc gtgaaagttt  60
ctttagaata gttgtttcca gaggccaaac attccacccg tagtaaagtg caagcgtagg  120
aagaccaaga ctggcataaa tcaggtataa gtgtcgagca ctggcaggtg atcttctgaa  180
agtttctact agcagataag atccagtagt catgcatatg gcaacaatgt accgtgtgga  240
tctaagaacg cgtcctacta accttcgcat tcgttggtcc agtttgttgt tatcgatcaa  300
cgtgacaagg ttgtcgattc cgcgtaagca tgcataccca aggacgcctg ttgcaattcc  360
aagtgagcca gttccaacaa tctttgtaat attagagcac ttcattgtgt tgcgcttgaa  420
agtaaaatgc gaacaaatta agagataatc tcgaaaccgc gacttcaaac gccaatatga  480
tgtgcggcac acaataagcg ttcatatccg ctgggtgact ttctcgcttt aaaaaattat  540
ccgaaaaaat ttatgggtac caccactctt gacgacacgg cttaccggta ccgcaccagt  600
gtcccggggg acgccgaggc catcgaggca ctggatgggt ccttcaccac cgacaccgtc  660
ttccgcgtca ccgccaccgg ggacggcttc accctgcggg aggtgccggt ggacccgccc  720
ctgaccaagg tgttccccga cgacgaatcg gacgacgaat cggacgccgg ggaggacggc  780
gacccggact cccggacgtt cgtcgcgtac ggggacgacg gcgacctggc gggcttcgtg  840
gtcgtctcgt actccggctg gaaccgccgg ctgaccgtcg aggacatcga ggtcgccccg  900
```

-continued

```
gagcaccggg ggcacggggt cgggcgcgcg ttgatggggc tcgcgacgga gttcgcccgc  960
gagcggggcg ccgggcacct ctggctggag gtcaccaacg tcaacgcacc ggcgatccac  1020
gcgtaccggc ggatggggtt caccctctgc ggcctggaca ccgccctgta cgacggcacc  1080
gcctcggacg gcgagcaggc gctctacatg agcatgccct gcccctaatc agtactgaca  1140
ataaaaagat tcttgtttc aagaacttgt catttgtata gtttttttat attgtagttg  1200
ttctatttta atcaaatgtt agcgtgattt atattttttt tcgcctcgac atcatctgcc  1260
cagatgcgaa gttaagtgcg cagaaagtaa tatcatgcgt caatcgtatg tgaatgctgg  1320
tcgctatact gctgtcgatt cgatactaac gcggccgctc ttaagggtga tgtagccctc  1380
gccgttttc gaatagctgt agatacattg acgggaacaa agagaaactc taagggatac  1440
actctatcat tggtgaaaaa gtttatttca attgttgacg gctttgaagt tcttgacaga  1500
gattaccttg tttcctcgat tgtaactcac atgtcctcat tggatcccaa atgttcggag  1560
tatattgtta ttgctttagc gcttccattg cgatatttgt ctatttcgtc accagagttt  1620
ccaatcaagc tgcagctgtc tgtcaagaat tatctaaagc tagatgagcc ctcaactaga  1680
aatggctatg ttgagttttt aaccaaactt ttggaagcat gtagaaacga agaaaatgat  1740
acaagagctg ttttactaca acaattagta aagaaatgca aatgttctgt gtgatagcct  1800
ttcttttttg aattcagcat gttggtttat ggtgttttat tgaagccatg actgagcctt  1860
tttacttaga tgaccacatg acttatgaga cgtcaattaa ggaggaccag tagaataaga  1920
tcgcaatagt ttctgctgtc atgatgaagc gtatatacag agccaaatct tcatgcatac  1980
aataacatat tgtgtttcct cccaaataat taacaatgac ttacctgtat atccaggaca  2040
ctcctgtact gagaccgacc acagaatcag gggataacgc aggaaagaac atgtgagcaa  2100
aaggccagca aaaggccagg aaccgtaaaa aggccgcgtt gctggcgttt ttccataggc  2160
tccgcccccc tgacgagcat cacaaaaatc gacgctcaag tcagaggtgg cgaaacccga  2220
caggactata aagataccag gcgtttcccc ctggaagctc cctcgtgcgc tctcctgttc  2280
cgaccctgcc gcttaccgga tacctgtccg cctttctccc ttcgggaagc gtggcgcttt  2340
ctcaatgctc acgctgtagg tatctcagtt cggtgtaggt cgttcgctcc aagctgggct  2400
gtgtgcacga acccccgtt cagcccgacc gctgcgcctt atccggtaac tatcgtcttg  2460
agtccaaccc ggtaagacac gacttatcgc cactggcagc agccactggt aacaggatta  2520
gcagagcgag gtatgtaggc ggtgctacag agttcttgaa gtggtggcct aactacggct  2580
acactagaag gacagtattt ggtatctgcg ctctgctgaa gccagttacc ttcggaaaaa  2640
gagttggtag ctcttgatcc ggcaaacaaa ccaccgctgg tagcggtggt ttttttgttt  2700
gcaagcagca gattacgcgc agaaaaaaag gatctcaaga agatcctttg atcttttcta  2760
cggggtctga cgctcagtgg aacgaaaact cacgttaagg gattttggtc atgagattat  2820
caaaaaggat cttcacctag atccttttaa attaaaaatg aagttttaaa tcaatctaaa  2880
gtatatatga gtaaacttgg tctgacagtt accaatgctt aatcagtgag gcacctatct  2940
cagcgatctg tctatttcgt tcatccatag ttgcctgact ccccgtcgtg tagataacta  3000
cgatacggga gggcttacca tctggcccca gtgctgcaat gataccgcga gacccacgct  3060
caccggctcc agatttatca gcaataaacc agccagccgg aagggccgag cgcagaagtg  3120
gtcctgcaac tttatccgcc tccatccagt ctattaattg ttgccgggaa gctagagtaa  3180
gtagttcgcc agttaatagt ttgcgcaacg ttgttgccat tgctacaggc atcgtggtgt  3240
cacgctcgtc gtttggtatg gcttcattca gctccggttc ccaacgatca aggcgagtta  3300
catgatcccc catgttgtgc aaaaaagcgg ttagctcctt cggtcctccg atcgttgtca  3360
gaagtaagtt ggccgcagtg ttatcactca tggttatggc agcactgcat aattctctta  3420
ctgtcatgcc atccgtaaga tgcttttctg tgactggtga gtactcaacc aagtcattct  3480
gagaatagtg tatgcggcga ccgagttgct cttgcccggc gtcaatacgg gataataccg  3540
cgccacatag cagaacttta aaagtgctca tcattggaaa acgttcttcg gggcgaaaac  3600
tctcaaggat cttaccgctg ttgagatcca gttcgatgta acccactcgt gcacccaact  3660
gatcttcagc atcttttact ttcaccagcg tttctgggtg agcaaaaaca ggaaggcaaa  3720
atgccgcaaa aaagggaata agggcgacac ggaaatgttg aatactcata ctcttccttt  3780
ttcaatatta ttgaagcatt tatcagggtt attgtctcat gagcggatac atatttgaat  3840
gtatttagaa aaataaacaa ataggggttc cgcgcacatt tccccgaaaa gtgccacctg  3900
acgatgtact gagaccgctc tgtgctctag tattgataat tggtctacta ctagatagat  3960
gcctaacatt aatgatatag tcgtatcagt ctttgctgta aataaagcct ccggaatgag  4020
atctaaagaa tcagcccaga tgtttggaag gagggaaaga tacgcctttc tactaattaa  4080
gccagttttg atctcagttg attgatgtcc tgtctctgcg atagctcaaa actggcaact  4140
gaaacagata gtatattaat tttcagttgc taatgataag ccattgtaac attcctatca  4200
catcggccgt ttgcctcttt tttgggaaaa ctctttccag tgaatgcaca gcttatcgct  4260
ttcaatgctt caaaggcaac ttccctacta agacactaaa tatatataca tcaatgaaca  4320
tatagtggga aaaatggtag tgaagaagta gtcatttgtt tgaatataag ttggctgtac  4380
atgtgcctcc gtagtctgtg gccgagcttc atccacctag caattgaaac tgaagagcta  4440
agctcttcat attctcattc ggttctgtta ttctctttta cttcttcttg tcaaaatatt  4500
atgtattatg tgtagtaccc gaccaacatg gagaattcaa tctaagaaat agatgtcacc  4560
ccaagccgaa caaaaacaac cggtgaagaa aacgtaactg agtgaatgga attgtgattc  4620
aagcaattag agtaattgaa tttcacttct ggtacgagaa ataaagtgaa aaacaaaata  4680
cctccgcata attagtgacg aaaaaaacca cacgtatact attcactgag tgaaagtgcg  4740
ccagatctgt ttagcttggg tatttgacag gttggggagc aaataagtga tgatgtccca  4800
tgaaagtaga aaatggctag tagaaggcaa aaatttgaaa ttcttagagt caaatagtta  4860
gactccaagt tctaatccac atttggtcag tttcatagca tccagagctt ttgccactgg  4920
tgaacatatc tacccattgc gatgcaacaa gtcactgaaa gcctaaaacg gagattcccc  4980
tatcttacag cctcgttcaa aaaaactgct accgtttatc tgctatggcc gatgtgagga  5040
tgcgctcatg cccaagagtc caactttatc aaaaacttga cccgtcatac aggctctaga  5100
tcaagaagca aacttaatct cagcatctgg ttacgtaact ctggcaacca gtaacacgct  5160
taaggtttgg aacaacacta aactaccttg cggtactacc attgacacta cacatcctta  5220
attccaatcc tgtctggcct ccttcacctt ttaaccatct tgcccattcc aactcgtgtc  5280
agattgcgta tcaagtgaaa aaaaaaaatt ttaaaatctt taacccaatc aggtaataac  5340
tgtcgcctct tttatctgcc gcactgcatg aggtgtcccc ttagtgggaa agagtactga  5400
gccaaccctg gaggacagca agggaaaaat acctacaact tgcttcataa tggtcgtaaa  5460
aacaatcctt gtcggatata agtgttgtag actgtccctt atcctctgcg atgttcttcc  5520
tctcaaagtt tgcgatttct ctctatcaga attgccatca agagactcag gactaatttc  5580
gcagtcccac acgcactcgt acatgattgg ctgaaatttc cctaaagaat ttcttttttca  5640
```

```
cgaaaatttt tttttacaca agattttcag cagatataaa atctcgaggg agagcaggac  5700
ctccgctgtg actcttcttt tttttctttt attctcacta catacatttt agttattcgc  5760
caacatgtcc tcagcccaca acaactataa tgccggtatt atgcagaaat caggaaaagc  5820
attcgccgat gaattcttcg cagaggagaa ccaagtggta catgaatcaa atgctgtcgt  5880
tttggtcctg atgaagtctg atgaaatcga cgccatcatc gaagacatca tattgaaagg  5940
gggtaaagct aaaaacccat ccatcgttgt tgaggacaag gctggattct ggtggatcaa  6000
agcagatgga gctatcgaaa tcgatgctgc tgaagctgct gatttactgg gcaagccatt  6060
ctctgtttac gatttgctga tcaacgtttc tagtaccgtt ggtcgtgctt acaccttggg  6120
cacgaaattc actatcacta gtgaattaat gggattggat agagccttga cagatattta  6180
agtatctcca gtcgtttaga ttgttagata ttttctttgt gtattcgttt cagtctgatg  6240
tttatgctac aaacgtcatc tggactttaa tccaataagg atattcttca acttaatagt  6300
atcttaataa tattttttt cttttgattt cttcgtaagg tgttttgttg cactcatgat  6360
ctacgacttt tgttcgtgac tgattttttt tgtagaaatg tcttggtgtc ctcgtccaat  6420
caggtagcca tctctgaaat atctggctcc gttgcaactc cgaacgacct gctggcaacg  6480
taaaattctc cggggtaaaa cttaaatgtg gagtaatgga accagaaacg tctcttccct  6540
tctctctcct tccaccgccc gttaccgtcc ctaggaaatt ttactctgct ggagagcttc  6600
ttctacggcc cccttgcagc aatgctcttc ccagcattac gttgcgggta aaacggaggt  6660
cgtgtacccg acctagcagc ccagggatgg aaaagtcccg gccgtcgctg gcaataatag  6720
cgggcggacg catgtcatga gattattgga aaccaccaga atcgaatata aaaggcgaac  6780
acctttccca attttggttt ctcctgaccc aaagacttta aatttaattt atttgtccct  6840
atttcaatca attgaacaac tatatggctc aatgtgccga gcaagccgca gaggaacaaa  6900
gaattttgat ccacgcagat tctagatatg ctgcatatac catggacttg gactatatgt  6960
ggcgttggga gatcctgaga gacggtgagt ttgttcaaga aggatgcagt ctgtctcttg  7020
actcagcaag ggaagctgtt tcacatgttc tgagattttt tcagaggcaa gacgaggctg  7080
ccgcccgtcc aggagacaat tccgcagaga ttaagagatt gcttcaatct ttgggaaccc  7140
caattcctat cgacgataga aacgaaacca caaagaatga gttggctcaa cctgaataga  7200
ttcggatagt gtaatttaat caataacttg aaaaaaatat catttaattt actatacaca  7260
cggacataaa ctgaaagggc aaggaagggg aaaatgggaa aaataatgag gatatgcaag  7320
atgagagatg agagatgaga gatgtccact ttagtcagtt ttggctttac ttttatcttt  7380
ttctatggca tctttcgttt tactactagt atacatagaa taaaaacggt aatagaactg  7440
ggaactaagc agaaacttac aattcctgag aagccttggc cttggcagac ttctttggca  7500
acaattcgga ttgaatgttt ggcaagacac caccttgggc gatggtgacg tgtcccagca  7560
acttgttcaa ttcctcatcg tttctgatgg ccaattgcaa gtgtcttggg ataattctgg  7620
acttcttgtt gtctctggcg gcgttaccgg ccaattccaa aatttcagca gccaagtact  7680
ccaagacagc agtcaaatag actggagcac cagaaccaat tctttgggcg tagttacctc  7740
ttctcagaag acggtggact cttcccacag ggaaggtcaa acctgcctta gaagatcttg  7800
aggttgaggc cttttcagcc gaagatgctt ttcctttacc accggacatt gttgtagttt  7860
taatatagtt tgagtatgag atggaactca gaacgaagga attatcacca gtttatatat  7920
tctgaggaaa gggtgtgtcc taaattggac agtcacgatg gcaataaacg ctcagccaat  7980
cagaatgcag gagccataaa ttgttgtatt attgctgcaa gatttatgtg ggttcacatt  8040
ccactgaatg gttttcactg tagaattggt gtcctagttg ttatgtttcg agatgttttc  8100
aagaaaaact aaaatgcaca aactgaccaa taatgtgccg tcgcgcttgg tacaaacgtc  8160
aggattgcca ccactttttt cgcactctgg tacaaaagtt cgcacttccc actcgtatgt  8220
aacgaaaaac agagcagtct atccagaacg agacaaatta gcgcgtactg tcccattcca  8280
taaggtatca taggaaacga gagtcctccc cccatcacgt atatataaac acactgatat  8340
cccacatccg cttgtcacca aactaataca tccagttcaa gttacctaaa caaatcaaaa  8400
tggcaagaaa tattagattt ggtgatcccg ttagaaaaag acttctggat ggagttgact  8460
ttctagctga cgctgttggt gttaccttgg ggccatgtgg aaggaatgtt gtcatcgaac  8520
atagggcctc cggcttacca cccgtagcca ccaaggacgg tgcaacggtt gctcaggccg  8580
ttgaagccgc cggtcgtact gaaagtgttg gtatcaattt agttagacaa atggccacta  8640
ccgttgcaaa agaggctggt gatgggacga caacctctgt cgttttgaca cgaagggtgg  8700
ctgccgaaac tcgtaaggcc cttgcagctg gaatgaatcc ccgtgacatc acattaggca  8760
tggagagggc cgcaagagca gttgaagcag acttgttgag acgtgcaaga cgttgcaacg  8820
accagaggtc attggctcat gttgccaccc tagccgctgg tggagatgag ggtatcggtg  8880
ctattgttgc acaagctttg gccttagccg gtgagggagg agttgtggat gtagaactag  8940
gtcacggcgt cgccgatgac atcgagtctg ttgagggcat gagatgggag cagggctacc  9000
gttccccata tttcatgaca gactcagcta ggaaggtagc tgagctggaa aatccttata  9060
ttctggtcta tgatagagtt atcaacgaat tctctgagct ggttcctgca cttgagttgg  9120
tcagaagatc tggcggatct cttctagttg tagctgaaaa cataatggag gaagcccttc  9180
caggcttgtt gttgaaccat attagaaaaa atttgtgctc cattgctgtg aaggggccag  9240
gatatggtga ttcaaggtat gaatatttat tggatttagc tgctataacc ggaggtaggg  9300
ctatcatgga agcattcggt gaagacattt ccaatgtaac tatggagcac ttgggtcgtg  9360
ctagaagagt cgttgttagg gaagatgata cgctagtcat tggtggtgag ggagatccta  9420
acgtaatcgc agatagacta gcaagtgcta aacgtcaggc agattggatt gttgaaggag  9480
acgcatctaa gggctcccct tcaggaaaaa gacatgagtt agaaaacttg cagacacgaa  9540
ttaaggccct gagtggacgt atggcaacaa ttagggctgg gggcctgtct gacgtgctga  9600
ttaaggaaag aatgcaaagg atcgaaaatg ctttaaactc tgctagggcc gcacaatctg  9660
atggagtcgt tgctggaggt ggagtgggtt tgtatcgagc aagggctgcc ctggctgaat  9720
taaggggtga gaacctggac cagtctcacg gcgttgccat tgtgcgtgca gcactggatg  9780
aacctatcag aagaatcgca gccaacgctg gggtggatgc tgatgaattc ttgttcgagc  9840
tacgaagaag taatgatgat ttctggggca tggatatgag aagtggtgct tgtggtgatc  9900
ttttcgctgc aggagttatt gatccagttc gagtaaccag acttgcctta agaaatgcag  9960
ttgccactgc agcctctctt atgaccgttg aatgtgccgt cacacatatt cctgtttctg  10020
accctacttt cggatttgat gctagaagag ccgctgaaac gagagaagat cctagagcct  10080
aagcgtgctt cttttttgtt tctttagttg tttagttttt ggcactggtt ttggtcgacc  10140
ttttgtttta agtagcctat atatgcagtt aaatgattga tagtttgatt tattccgtgc  10200
aacttaaggg attgtgattg ggcgtggcaa tctacctaca ttctatttac ctgcaatctt  10260
aggattgaga ttgattcaga ttctcttgaa ggggaagggt tagactattt aaaattcata  10320
catacagttc attcttttcc cgcgcagctt taatctttcg gcagagaagg cgttttcatc  10380
```

```
gtagcgtggg aacagaataa tcagttcatg tgctatacag gcacatggca gcagtcacta  10440
ttttgctttt taaccttaaa gtcgttcatc aatcattaac tgaccaatca gattttttgc  10500
atttgccact tatctaaaaa tacttttgta tctcgcagat acgttcagtg gtttccagga  10560
caacacccaa aaaaaggtat caatgccact aggcagtcgg ttttattttt ggtcacccac  10620
gcaaagaagc acccacctct tttaggtttt aagttgtggg aacagtaaca ccgcctagag  10680
cttcaggaaa aaccagtacc tgtgaccgca attcaccatg atgcagaatg ttaatttaaa  10740
cgagtgccaa atcaagattt caacagacaa atcaatcgat ccatagttac ccattccagc  10800
cttttcgtcg tcgagcctgc ttcattcctg cctcaggtgc ataactttgc atgaaaagtc  10860
cagattaggg cagattttga gtttaaaata ggaaatataa acaaatatac cgcgaaaaag  10920
gtttgtttat agcttttcgc ctggtgccgt acggtataaa tacatactct cctccccccc  10980
ctggttctct ttttcttttg ttacttacat tttaccgttc cgtcactcgc ttcactcaac  11040
aacaaaaatg gctttcagac ccttgcatga tagagtggtc gttaaacgat tggaaggaga  11100
agataaaacc aaaggtggaa tcatcattcc agatactgcc aaggaaaagc ctgctgaggg  11160
taagatcatt gccgttgggc ctggcgcaag agatgagtcc ggaaaattgg tcgcactgga  11220
tgtcaaagaa ggtgatcgag ttttgttcgg taagtggagt gggaccgagg taaagataga  11280
cggagaggac cttttgatta tgaaggagtc tgacatcttg ggcgtgatcg cttgaagaca  11340
tgactgttcc tcagttcaag ttgggcactt acgagaagac cggtcttgct agattctaat  11400
caagaggatg tcagaatgcc atttgcctga gagatgcagg cttcattttt gattactttt  11460
ttatttgtaa cctatatagt ataggatttt ttttgtcatt ttgtttcttc tcgtacgagc  11520
ttgctcctga tcagcctatc tcgcagctga tgaatatctt gtggtagggg tttgggaaaa  11580
tcattcgagt ttgatgtttt tcttggtatt tcccactcct cttcagagta cagaagatta  11640
agtgagagcg gccgctcgtc cccgccgggt cacccggctc gag                    11683

SEQ ID NO: 37          moltype = DNA  length = 11653
FEATURE                Location/Qualifiers
misc_feature           1..11653
                       note = Synthetic plasmid.
source                 1..11653
                       mol_type = other DNA
                       organism = synthetic construct
SEQUENCE: 37
ttcagtaatg tcttgtttct tttgttgcag tggtgagcca ttttgacttc gtgaaagttt  60
ctttagaata gttgtttcca gaggccaaac attccacccg tagtaaagtg caagcgtagg  120
aagaccaaga ctggcataaa tcaggtataa gtgtcgagca ctggcaggtg atcttctgaa  180
agtttctact agcagataag atccagtagt catgcatatg gcaacaatgt accgtgtgga  240
tctaagaacg cgtcctacta accttcgcat tcgttggtcc agtttgttgt tatcgatcaa  300
cgtgacaagg ttgtcgattc cgcgtaagca tgcataccca aggacgcctg ttgcaattcc  360
aagtgagcca gttccaacaa tctttgtaat attagagcac ttcattgtgt tgcgcttgaa  420
agtaaaatgc gaacaaatta agagataatc tcgaaaccgc gacttcaaac gccaatatga  480
tgtgcggcac acaataagcg ttcatatccg ctgggtgact ttctcgcttt aaaaaattat  540
ccgaaaaaat ttatgggtac caccactctt gacgacacgg cttaccggta ccgcaccagt  600
gtcccggggg acgccgaggc catcgaggca ctggatgggt ccttcaccac cgacaccgtc  660
ttccgcgtca ccgccaccgg ggacggcttc accctgcggg aggtgccggt ggacccgccc  720
ctgaccaagg tgttccccga cgacgaatcg gacgacgaat cggacgccgg ggaggacggc  780
gacccggact cccggacgtt cgtcgcgtac ggggacgacg gcgacctggc gggcttcgtg  840
gtcgtctcgt actccggctg gaaccgccgg ctgaccgtcg aggacatcga ggtcgccccg  900
gagcaccggg ggcacggggt cgggcgcgcg ttgatggggc tcgcgacgga gttcgcccgc  960
gagcggggcg ccgggcacct ctggctggag gtcaccaacg tcaacgcacc ggcgatccac  1020
gcgtaccggc ggatggggtt caccctctgc ggcctggaca ccgccctgta cgacggcacc  1080
gcctcggacg gcgagcaggc gctctacatg agcatgccct gcccctaatc agtactgaca  1140
ataaaaagat tcttgttttc aagaacttgt catttgtata gtttttttat attgtagttg  1200
ttctatttta atcaaatgtt agcgtgattt atattttttt tcgcctcgac atcatctgcc  1260
cagatgcgaa gttaagtgcg cagaaagtaa tatcatgcgt caatcgtatg tgaatgctgg  1320
tcgctatact gctgtcgatt cgatactaac gcggccgctc ttaagggtga tgtagccctc  1380
gccgtttttc gaatagctgt agatacattg acgggaacaa agagaaactc taagggatac  1440
actctatcat tggtgaaaaa gtttatttca attgttgacg gctttgaagt tcttgacaga  1500
gattaccttg tttcctcgat tgtaactcac atgtcctcat tggatcccaa atgttcggag  1560
tatattgtta ttgctttagc gcttccattg cgatatttgt ctatttcgtc accagagttt  1620
ccaatcaagc tgcagctgtc tgtcaagaat tatctaaagc tagatgagcc ctcaactaga  1680
aatggctatg ttgagttttt aaccaaactt ttggaagcat gtagaaacga agaaaatgat  1740
acaagagctg ttttactaca acaattagta aagaaatgca aatgttctgt gtgatagcct  1800
ttcttttttg aattcagcat gttggtttat ggtgttttat tgaagccatg actgagcctt  1860
tttacttaga tgaccacatg acttatgaga cgtcaattaa ggaggaccag tagaataaga  1920
tcgcaatagt ttctgctgtc atgatgaagc gtatatacag agccaaatct tcatgcatac  1980
aataacatat tgtgtttcct cccaaataat taacaatgac ttacctgtat atccaggaca  2040
ctcctgtact gagaccgacc acagaatcag gggataacgc aggaaagaac atgtgagcaa  2100
aaggccagca aaaggccagg aaccgtaaaa aggccgcgtt gctggcgttt ttccataggc  2160
tccgcccccc tgacgagcat cacaaaaatc gacgctcaag tcagaggtgg cgaaacccga  2220
caggactata aagataccag gcgtttcccc ctggaagctc cctcgtgcgc tctcctgttc  2280
cgaccctgcc gcttaccgga tacctgtccg cctttctccc ttcgggaagc gtggcgcttt  2340
ctcaatgctc acgctgtagg tatctcagtt cggtgtaggt cgttcgctcc aagctgggct  2400
gtgtgcacga accccccgtt cagcccgacc gctgcgcctt atccggtaac tatcgtcttg  2460
agtccaaccc ggtaagacac gacttatcgc cactggcagc agccactggt aacaggatta  2520
gcagagcgag gtatgtaggc ggtgctacag agttcttgaa gtggtggcct aactacggct  2580
acactagaag gacagtattt ggtatctgcg ctctgctgaa gccagttacc ttcggaaaaa  2640
gagttggtag ctcttgatcc ggcaaacaaa ccaccgctgg tagcggtggt ttttttgttt  2700
gcaagcagca gattacgcgc agaaaaaaag gatctcaaga agatcctttg atcttttcta  2760
cggggtctga cgctcagtgg aacgaaaact cacgttaagg gattttggtc atgagattat  2820
caaaaaggat cttcacctag atccttttaa attaaaaatg aagttttaaa tcaatctaaa  2880
```

```
gtatatatga gtaaacttgg tctgacagtt accaatgctt aatcagtgag gcacctatct  2940
cagcgatctg tctatttcgt tcatccatag ttgcctgact ccccgtcgtg tagataacta  3000
cgatacggga gggcttacca tctggcccca gtgctgcaat gataccgcga gacccacgct  3060
caccggctcc agatttatca gcaataaacc agccagccgg aagggccgag cgcagaagtg  3120
gtcctgcaac tttatccgcc tccatccagt ctattaattg ttgccgggaa gctagagtaa  3180
gtagttcgcc agttaatagt ttgcgcaacg ttgttgccat tgctacaggc atcgtggtgt  3240
cacgctcgtc gtttggtatg gcttcattca gctccggttc ccaacgatca aggcgagtta  3300
catgatcccc catgttgtgc aaaaaagcgg ttagctcctt cggtcctccg atcgttgtca  3360
gaagtaagtt ggccgcagtg ttatcactca tggttatggc agcactgcat aattctctta  3420
ctgtcatgcc atccgtaaga tgcttttctg tgactggtga gtactcaacc aagtcattct  3480
gagaatagtg tatgcggcga ccgagttgct cttgcccggc gtcaatacgg gataataccg  3540
cgccacatag cagaacttta aaagtgctca tcattggaaa acgttcttcg gggcgaaaac  3600
tctcaaggat cttaccgctg ttgagatcca gttcgatgta acccactcgt gcacccaact  3660
gatcttcagc atcttttact ttcaccagcg tttctgggtg agcaaaaaca ggaaggcaaa  3720
atgccgcaaa aaagggaata agggcgacac ggaaatgttg aatactcata ctcttccttt  3780
ttcaatatta ttgaagcatt tatcagggtt attgtctcat gagcggatac atatttgaat  3840
gtatttagaa aaataaacaa ataggggttc cgcgcacatt tccccgaaaa gtgccacctg  3900
acgatgtact gagaccgctc tgtgctctag tattgataat tggtctacta ctagatagat  3960
gcctaacatt aatgatatag tcgtatcagt ctttgctgta aataaagcct ccggaatgag  4020
atctaaagaa tcagcccaga tgtttggaag gagggaaaga tacgcctttc tactaattaa  4080
gccagttttg atctcagttg attgatgtcc tgtctctgcg atagctcaaa actggcaact  4140
gaaacagata gtatattaat tttcagttgc taatgataag ccattgtaac attcctatca  4200
catcggccgt ttgcctcttt tttgggaaaa ctctttccag tgaatgcaca gcttatcgct  4260
ttcaatgctt caaaggcaac ttccctacta agacactaaa tatatataca tcaatgaaca  4320
tatagtggga aaaatggtag tgaagaagta gtcatttgtt tgaatataag ttggctgtac  4380
atgtgcctcc gtagtctgtg gccgagcttc atccacctag caattgaaac tgaagagcta  4440
agctcttcat attctcattc ggttctgtta ttctctttta cttcttcttg tcaaaatatt  4500
atgtattatg tgtagtaccc gaccaacatg gagaattcaa tctaagaaat agatgtcacc  4560
ccaagccgaa caaaaacaac cggtgaagaa aacgtaactg agtgaatgga attgtgattc  4620
aagcaattag agtaattgaa tttcacttct ggtacgagaa ataaagtgaa aaacaaaata  4680
cctccgcata attagtgacg aaaaaaacca cacgtatact attcactgag tgaaagtgcg  4740
ccagatctgt ttagcttggg tatttgacag gttggggagc aaataagtga tgatgtccca  4800
tgaaagtaga aaatggctag tagaaggcaa aaatttgaaa ttcttagagt caaatagtta  4860
gactccaagt tctaatccac atttggtcag tttcatagca tccagagctt ttgccactgg  4920
tgaacatatc tacccattgc gatgcaacaa gtcactgaaa gcctaaaacg gagattcccc  4980
tatcttacag cctcgttcaa aaaaactgct accgtttatc tgctatggcc gatgtgagga  5040
tgcgctcatg cccaagagtc caactttatc aaaaacttga cccgtcatac aggctctaga  5100
tcaagaagca aacttaatct cagcatctgg ttacgtaact ctggcaacca gtaacacgct  5160
taaggtttgg aacaacacta aactaccttg cggtactacc attgacacta cacatcctta  5220
attccaatcc tgtctggcct ccttcacctt ttaaccatct tgcccattcc aactcgtgtc  5280
agattgcgta tcaagtgaaa aaaaaaaatt ttaaaatctt taacccaatc aggtaataac  5340
tgtcgcctct tttatctgcc gcactgcatg aggtgtcccc ttagtgggaa agagtactga  5400
gccaaccctg gaggacagca agggaaaaat acctacaact tgcttcataa tggtcgtaaa  5460
aacaatcctt gtcggatata agtgttgtag actgtccctt atcctctgcg atgttcttcc  5520
tctcaaagtt tgcgatttct ctctatcaga attgccatca agagactcag gactaatttc  5580
gcagtcccac acgcactcgt acatgattgg ctgaaatttc cctaaagaat ttctttttca  5640
cgaaaatttt tttttacaca agattttcag cagatataaa atctcgaggg agagcaggac  5700
ctccgctgtg actcttcttt tttttctttt attctcacta catacatttt agttattcgc  5760
caacatgtca actaacatca atggatacaa tagtggtact aataacaaaa caggtcaagc  5820
cttcgttgac gagttcttat ctgaaaaaaa ctgcacactg cctacaagtg atgcagttgt  5880
acttgctttg atgaagacag aagaaattaa cgtcattgtg gatgaaatga tccgacctat  5940
gatggacgat aacccagctt tggccgtcga tgatagaggt ggttactggt ggattaaggt  6000
taatggaaaa atagttattg attgtgatga agctacagag atattaggta agaagtacac  6060
tgtctatgac tttctagtta atgtgtctac taccattgga agggccatga ctttgggaaa  6120
tcaattcgtc ttgaccaatg agcttttggg actagaaaca aaaatcgact ctgtgtacta  6180
ggtatctcca gtcgtttaga ttgttagata ttttctttgt gtattcgttt cagtctgatg  6240
tttatgctac aaacgtcatc tggactttaa tccaataagg atattcttca acttaatagt  6300
atcttaataa tattttttt  cttttgattt cttcgtaagg tgttttgttg cactcatgat  6360
ctacgacttt tgttcgtgac tgatttttt  tgtagaaatg tcttggtgtc ctcgtccaat  6420
caggtagcca tctctgaaat atctggctcc gttgcaactc cgaacgacct gctggcaacg  6480
taaaattctc cggggtaaaa cttaaatgtg gagtaatgga accagaaacg tctcttccct  6540
tctctctcct tccaccgccc gttaccgtcc ctaggaaatt ttactctgct ggagagcttc  6600
ttctacggcc cccttgcagc aatgctcttc ccagcattac gttgcgggta aaacggaggt  6660
cgtgtacccg acctagcagc ccagggatgg aaaagtcccg gccgtcgctg gcaataatag  6720
cgggcggacg catgtcatga gattattgga aaccaccaga atcgaatata aaaggcgaac  6780
acctttccca attttggttt ctcctgaccc aaagacttta aatttaattt atttgtccct  6840
atttcaatca attgaacaac tatatgaaca ccagatctgg cgatacccc  gctatcccta  6900
gactggacgg acttccacaa gccgttggag ctacagttct gattcatgag gacggggagt  6960
tcagggtgta tgctaccgag cttgagatgt tgctgaggtg ggaccttttt caaggcgatc  7020
gtcacttgca taccggttca gcactgcgtg tggaatcatg tattgtttct gccaaaggta  7080
aaattggttt ctttagaaga cctacagtag ctagattgat cgctgcaggc gatgaagcct  7140
cccctaatga tccatcatag attcggatag tgtaatttaa tcaataactt gaaaaaaata  7200
tcatttaatt tactatacac acggacataa actgaaaggg caaggaaggg gaaaatggga  7260
aaaataatga ggatatgcaa gatgagagat gagagatgag agatgtccac tttagtcagt  7320
tttggcttta cttttatctt tttctatggc atctttcgtt ttactactag tatacataga  7380
ataaaaacgg taatagaact gggaactaag cagaaactta caattcctga gaagccttgg  7440
ccttggcaga cttctttggc aacaattcgg attgaatgtt tggcaagaca ccaccttggg  7500
cgatggtgac gtgtcccagc aacttgttca attcctcatc gtttctgatg gccaattgca  7560
agtgtcttgg gataattctg gacttcttgt tgtctctggc ggcgttaccg gccaattcca  7620
```

```
aaatttcagc agccaagtac tccaagacag cagtcaaata gactggagca ccagaaccaa  7680
ttctttgggc gtagttacct cttctcagaa gacggtggac tcttcccaca gggaaggtca  7740
aacctgcctt agaagatctt gaggttgagg ccttttcagc cgaagatgct tttcctttac  7800
caccggacat tgttgtagtt ttaatatagt ttgagtatga gatggaactc agaacgaagg  7860
aattatcacc agtttatata ttctgaggaa agggtgtgtc ctaaattgga cagtcacgat  7920
ggcaataaac gctcagccaa tcagaatgca ggagccataa attgttgtat tattgctgca  7980
agatttatgt gggttcacat tccactgaat ggttttcact gtagaattgg tgtcctagtt  8040
gttatgtttc gagatgtttt caagaaaaac taaaatgcac aaactgacca ataatgtgcc  8100
gtcgcgcttg gtacaaacgt caggattgcc accacttttt tcgcactctg gtacaaaagt  8160
tcgcacttcc cactcgtatg taacgaaaaa cagagcagtc tatccagaac gagacaaatt  8220
agcgcgtact gtcccattcc ataaggtatc ataggaaacg agagtcctcc ccccatcacg  8280
tatatataaa cacactgata tcccacatcc gcttgtcacc aaactaatac atccagttca  8340
agttacctaa acaaatcaaa atgactaatg gaaagaactg tagggtatct gatggattcg  8400
gagctttggg taagctgtca tctggtatga gaatattagc tgaggtcgtt gctgtaacac  8460
tgggtcctgg aggcaggcat gtgatcctgg agcatagaag tggtttggcc cctagattgt  8520
ctaaggatgg agttgagatc gctaggacta tggaagtagc cggtcgtgag gaggaaatgg  8580
gcgtgcgtct tttgagggac gctgctataa gtattagtgc cagtgtcgga gatggtacta  8640
caactgccat tgtcttgtct gctgccttag ctacacgatg tatggccgct tcttctcatc  8700
cattaaacgt ttctgaaatg agatacggtc tggccatggc tggtgctaca gtgttaagtg  8760
aattagccgc catggccaga ccagctgatc aacacgccct tcaagctgtc gctaggaccg  8820
cagtgaatgg agacgcaccc ttagcagcct tgcttgctga cgcttatgca agagtcggga  8880
gtgagggtgt tattaagatt gaaatgggta atgcaatgca cgatgttcta gatgttaaac  8940
tgggccatcg ttttgagtct ttattgttgg cctccggtct tcccgcttca gcaggcgaga  9000
gacaacttct gaggcctctt accctttgc atgatggtga gctggatgac ctacaagcct  9060
tgattccagc tatggagatc gctagagccg agcaaaggcc tctgttgatt cttgctggtg  9120
atgtatcaga tggtgtcagg acagccattg ttcgtaacgc tcgtgagaac gtcgttgacg  9180
ttactgttgt tcgtgctcca atgtttgggg atactagaca agaatgtctg ggagatcttg  9240
cagctctatg cggtggttca gcttttgtgg agaacggttt tagaacgatt gccgctttgt  9300
ccagggatga tcttggttca gttgatagag ccgtagtcga tgctgggtct gcaatcctac  9360
acggtgcaca cggagatgct agagagagac aagacaggat tgctctgttg agatctgaaa  9420
tggaggggtc tggtagatct actgcatctc catcaggcca gttggatcat tccgataagt  9480
gtcaagaaag attgcaaatt cttcttggag ccactgcatc cctgcaatta ggtggggcca  9540
cggacgtggc tataaaggct agaatgccca ttgccgaaaa cggaagacgt gcattattgg  9600
ctgcagcatc cacaggagtt ttgcctggag gtggagtggc catgctaaga gctgcattag  9660
ccgctaggtc taggctatca actctgcaag atgatgctcg tcttggagct gaggcactac  9720
tttctgcttt acaagctcct tttgcctggg tcgtgagaaa cagtggacat cagcctgaag  9780
agtgtttgga tagagttctt agtgaagctg attgtttcca tggtcttgat gcagctagag  9840
gatgctatgg tgacctgcac gctgcaggcg ttttggattc ctttttgatg gtcagaaaga  9900
tcgtgaccgt tgccacctca atggccggat cattactttc aacgggagcc ttagtgtgcc  9960
gtggaggtga aactgctcta cctgagaact ttcaggggac gcaacaggtt tacagaaagt  10020
tagcagctgg tggagctttt gattcataag cgtgcttctt ttttgtttct ttagttgttt  10080
agtttttggc actggttttg gtcgaccttt tgttttaagt agcctatata tgcagttaaa  10140
tgattgatag tttgatttat tccgtgcaac ttaagggatt gtgattgggc gtggcaatct  10200
acctacattc tatttacctg caatcttagg attgagattg attcagattc tcttgaaggg  10260
gaagggttag actatttaaa attcatacat acagttcatt cttttcccgc gcagctttaa  10320
tctttcggca gagaaggcgt tttcatcgta gcgtgggaac agaataatca gttcatgtgc  10380
tatacaggca catggcagca gtcactattt tgctttttaa ccttaaagtc gttcatcaat  10440
cattaactga ccaatcagat tttttgcatt tgccacttat ctaaaaatac ttttgtatct  10500
cgcagatacg ttcagtggtt tccaggacaa cacccaaaaa aaggtatcaa tgccactagg  10560
cagtcggttt tatttttggt cacccacgca aagaagcacc cacctctttt aggttttaag  10620
ttgtgggaac agtaacaccg cctagagctt caggaaaaac cagtacctgt gaccgcaatt  10680
caccatgatg cagaatgtta atttaaacga gtgccaaatc aagatttcaa cagacaaatc  10740
aatcgatcca tagttaccca ttccagcctt ttcgtcgtcg agcctgcttc attcctgcct  10800
caggtgcata actttgcatg aaaagtccag attagggcag attttgagtt taaaatagga  10860
aatataaaca aatataccgc gaaaaaggtt tgtttatagc ttttcgcctg gtgccgtacg  10920
gtataaatac atactctcct cccccccctg gttctctttt tcttttgtta cttacatttt  10980
accgttccgt cactcgcttc actcaacaac aaaaatgaag ctgcgtccac ttcatgatag  11040
agtcatcgta aagcgattgg aagaagaaaa gaagtctgct ggtggtataa ttataccaga  11100
tgcagccgct gaaaagcctt ccagaggaga agttatcagt gtgggacctg gtaagagagg  11160
ggacgatggt aagttaaatg ctcttgatgt taaagctggt gatatagtat tgtttggtaa  11220
atattctggc agtgaggttc gtgtagatgg tcaagaccta ctggttatga gagaagacga  11280
cattatggct gtttttgcca agtagagaca tgactgttcc tcagttcaag ttgggcactt  11340
acgagaagac cggtcttgct agattctaat caagaggatg tcagaatgcc atttgcctga  11400
gagatgcagg cttcattttt gattactttt ttatttgtaa cctatatagt ataggatttt  11460
ttttgtcatt ttgtttcttc tcgtacgagc ttgctcctga tcagcctatc tcgcagctga  11520
tgaatatctt gtggtagggg tttgggaaaa tcattcgagt ttgatgtttt tcttggtatt  11580
tcccactcct cttcagagta cagaagatta agtgagagcg gccgctcgtc cccgccgggt  11640
caccccggctc gag                                                    11653
```

```
SEQ ID NO: 38          moltype = DNA  length = 4300
FEATURE                Location/Qualifiers
misc_feature           1..4300
                       note = Synthetic plasmid.
source                 1..4300
                       mol_type = other DNA
                       organism = synthetic construct
SEQUENCE: 38
ggaaaccacg taagctccgg cgtttaaaca cccataacag atacggactt tctcaaagga  60
gagttatcag tggcgaatat caaaccgctg gaagataaaa ttgttgtgca ggcaagcgaa  120
```

```
gcggaaacga ccacagccag cggcattgtg attccagaca cggcgaaaga aaaaccgcaa  180
gaaggaaagg ttctggcggt cggcccaggt cgtatcgatg ataacggaaa ccgcgttccg  240
ttagatgtag ctgtcggcga tgtcgtgatc tacagcaaat atggcggaac ggaagtgaaa  300
tacaacgggg aggaatatct gattctgtct gcgcgcgatg tgctggcagt cgtaaattga  360
tccgcgcacg acactgaaca tacgaattta aggaataaag ataatggcca aagaactgaa  420
attcggtgtt gatgcccgtc gcgctttaca ggccggtgtc gatcaactgg cggaagctgt  480
caaatcaacc ctcggcccaa aaggccgtaa tgttgtgtta gaaaaaatca ccggaactcc  540
agaagttacc aatgatggcg taaccattgc tcgtgaaatt catctgcgcg atccgtttga  600
aaacatgggt gcacagatcc tgaaagaagc ggctatcaaa accaacgaca cggtgggcga  660
cgggaccact accgcgacag tggtggccca ggcaatcgtt cgcgaaggca tgaaagccat  720
tcagagcggc ggcaaccctg ttctggtaaa acgtggtatt gatttagcgg tgggccgtat  780
tgttgagcgt cttgccgccg tggcccaccc agtagactct ctggaacacc tgagccgcgt  840
cgctgctatt tctgctaatg acgacgagac gatcggtagc gtcatcgcga aaaccctgca  900
caccgtgggg gatgatggtg ttattagcgt ggatgatggt ccagttctgg gactcaccgt  960
gaactttgtc gaagatttgg aatttgacaa tggatatgtc tcaccgtatt tggtaaccga  1020
cccggggagc atgatggccg ttctggacga cccgtacatc ttattgagcg cggaaaaaat  1080
cacggatgtc cgccaactga tgccggtact ggaaaaactt atgcgtgatc cacgtccact  1140
cgtcattgtg gccgaaaaag tggagggtac ggcgctgcaa atgctggtgc ataaccatgt  1200
aaacggtcac ctgaaagtga ctgcgattca agcgccgggg ttcggggaga aacgcatcca  1260
tttgctggag gatctcgccg cactgacggg tgcgaaagtc cattcaaaag cgagcagttt  1320
tgcgctggaa caaatgacca ctgaacacct tggccgcact acacaagtcc gcgccacgaa  1380
tgaacaatgc gtgtttatcg gtggtcatgg aagcaaagaa gctgttgaac agcgtctgtc  1440
tcagttgcgt gctgagatgg cccgcgccac tatcggtaca gacgaagatt ggttgaacga  1500
tcgtattgca cgcctgagcg gcaaagcggc gatcattagt gttggagcac cgaccaacgc  1560
tgaactgaaa gaaatccgcc atcgcgtcga tgactcactg caagccactc gcgcagctat  1620
ggctgaaggt attgtagcgg gcggcggttc agcgttactg catgccgaga gcgctctgga  1680
tgggttagat gtggatggcg actatcgtat tggcgttgaa attgttcgcg cggctctgag  1740
tgaaccggtg catctgatcg cgtctaatgc aggatacgat ggtgcggacg tagtaaaaca  1800
agtcacggat ttgggtgtgg atgaaggctt tgatgcgctg caaggtcgct ttggtgatat  1860
ggtcgaaatg ggcatcattg acccgctccg cgtcgtgcgt tcagccctgc agaatggggc  1920
tagcgtggct ggcctgattt tgacgacgaa cagccttgtc gcggaagaac aaaccccttg  1980
gaataaagcc ctgatgaccg aatttggccc gttggatgaa ggtattccgc agccttctcc  2040
agatagcagc acgccacaga gcctcggtct gggcccgtcc gtcggctaag tttaaacgcg  2100
gccgcaattt gaacgccagc acatggactc tcgagtctac tagcgcagct taattaacct  2160
aggctgctgc caccgctgag caataactag cataacccct tggggcctct aaacgggtct  2220
tgaggggttt tttgctgaaa cctcaggcat ttgagaagca cacggtcaca ctgcttccgg  2280
tagtcaataa accggtaaac cagcaataga cataagcggc tatttaacga ccctgccctg  2340
aaccgacgac cgggtcatcg tggccggatc ttgcggcccc tcggcttgaa cgaattgtta  2400
gacattattt gccgactacc ttggtgatct cgcctttcac gtagtggaca aattcttcca  2460
actgatctgc gcgcgaggcc aagcgatctt cttcttgtcc aagataagcc tgtctagctt  2520
caagtatgac gggctgatac tgggccggca ggcgctccat tgcccagtcg gcagcgacat  2580
ccttcggcgc gattttgccg gttactgcgc tgtaccaaat gcgggacaac gtaagcacta  2640
catttcgctc atcgccagcc cagtcgggcg gcgagttcca tagcgttaag gtttcattta  2700
gcgcctcaaa tagatcctgt tcaggaaccg gatcaaagag ttcctccgcc gctggaccta  2760
ccaaggcaac gctatgttct cttgcttttg tcagcaagat agccagatca atgtcgatcg  2820
tggctggctc gaagatacct gcaagaatgt cattgcgctg ccattctcca aattgcagtt  2880
cgcgcttagc tggataacgc cacggaatga tgtcgtcgtg cacaacaatg gtgacttcta  2940
cagcgcggag aatctcgctc tctccagggg aagccgaagt ttccaaaagg tcgttgatca  3000
aagctcgccg cgttgtttca tcaagcctta cggtcaccgt aaccagcaaa tcaatatcac  3060
tgtgtggctt caggccgcca tccactgcgg agccgtacaa atgtacggcc agcaacgtcg  3120
gttcgagatg gcgctcgatg acgccaacta cctctgatag ttgagtcgat acttcggcga  3180
tcaccgcttc cctcatactc ttcctttttc aatattattg aagcatttat cagggttatt  3240
gtctcatgag cggatacata tttgaatgta tttagaaaaa taaacaaata gctagctcac  3300
tcggtcgcta cgctccgggc gtgagactgc ggcgggcgct gcggacacat acaaagttac  3360
ccacagattc cgtggataag caggggacta acatgtgagg caaaacagca gggccgcgcc  3420
ggtggcgttt ttccataggc tccgccctcc tgccagagtt cacataaaca gacgcttttc  3480
cggtgcatct gtgggagccg tgaggctcaa ccatgaatct gacagtacgg gcgaaacccg  3540
acaggactta aagatcccca ccgtttccgg cgggtcgctc cctcttgcgc tctcctgttc  3600
cgaccctgcc gtttaccgga tacctgttcc gcctttctcc cttacgggaa gtgtggcgct  3660
ttctcatagc tcacacactg gtatctcggc tcggtgtagg tcgttcgctc caagctgggc  3720
tgtaagcaag aactccccgt tcagcccgac tgctgcgcct tatccggtaa ctgttcactt  3780
gagtccaacc cggaaaagca cggtaaaacg ccactggcag cagccattgg taactgggag  3840
ttcgcagagg atttgtttag ctaaacacgc ggttgctctt gaagtgtgcg ccaaagtccg  3900
gctacactgg aaggacagat ttggttgctg tgctctgcga aagccagtta ccacggttaa  3960
gcagttcccc aactgactta accttcgatc aaaccacctc cccaggtggt tttttcgttt  4020
acagggcaaa agattacgcg cagaaaaaaa ggatctcaag aagatccttt gatcttttct  4080
actgaaccgc tctagatttc agtgcaattt atctcttcaa atgtagcacc tgaagtcagc  4140
cccatacgat ataagttgta attctcatgt tagtcatgcc ccgcgcccac cggaaggagc  4200
tgactgggtt gaaggctctc aagggcatcg gtcgagatcc cggtgcctaa tgagtgagct  4260
aacttttgac agctagctca gtcctaggga ctatgctagc                        4300
```

```
SEQ ID NO: 39           moltype = DNA  length = 4321
FEATURE                 Location/Qualifiers
misc_feature            1..4321
                        note = Synthetic plasmid.
source                  1..4321
                        mol_type = other DNA
                        organism = synthetic construct
SEQUENCE: 39
```

```
ggaaaccacg taagctccgg cgtttaaaca cccataacag atacggactt tctcaaagga  60
gagttatcag tgaaaatccg tccgctgcat gatcgtgtta ttgtcaagcg tctcgaagcg  120
gagcgcaaaa cggcctcagg aatcgttatc ccagattcag caggcgagaa gccggaccaa  180
ggagaagttc tggcggtggg taacggtaaa atccttgacg acggtaaagt ccgtccgatg  240
gccgtcaaag tgggtgataa agttctgttc ggtaagtatg ctggtcaaac cgtcaaagtg  300
gagggcgagg agctcctggt gatgcgtgaa gaagatatta tgggtgtggt ggaggcttaa  360
tccgcgcacg acactgaaca tacgaattta aggaataaag ataatgatta gccttaattg  420
caaaaaaacc actaccggtc tgaccgcaca tttggctctg gtgcgcggca tgaaagcctt  480
agcggagctg gtgggtacga cattaggacc ccaaggtcgc cacgttatgt tagcacaccg  540
tgccgggctg gcgccgcacg taagcaaaga cggtgtggaa gttgcgcgtc atctgtccct  600
gcccgattcg gaagaggaat taggtgttcg cttactgcgt aatgcggctg ttgcagtctc  660
cgagtcattt ggcgatggga cctcaaccgc caccgtcttc accgcggatc tggccgtgcg  720
cgcgcttaaa ttgattggtg ccggtgcgga tacattagaa gttcgccgtg gtctgggctt  780
ggcggcctat gctgcgctgg ttgcactgaa cgatatggcc cgccgtgcgg accgcggaat  840
gctgacggcc gtagctcaaa cggccgctaa cggtgaccgt cgcgtggctg acttgttagt  900
ggaggcgttt gaacgcgtgg gcgcggaagg aacaattgaa gtggaaatgg gtaacagtgt  960
agaggatgtt ttggaagtgg cacaagggag ctattttgat accgtgccct tggttaccgc  1020
actgctgcca ccgaccggcc aagtagaatt tgcgcgtccg ttgattcttt tccattgcga  1080
tgccattgaa accgcagatg aaattcttcc ggccctcgaa ctcgctcgtt ctagccgtcg  1140
cccactgctt attctggcgg actccgtggg tattgatgtt gaaactctgc ttgtccgcaa  1200
tcaaaatgaa ggcaccttag cggtggcagt agtacgtgca ccgatgtatg gtgacacgcg  1260
ccgtgaagct ctcctggatc tgacgtcaaa atttggcgga actgcgttcg gccgcgaggg  1320
ctttgtcgaa ttcgcgctgc gtagcttagg cagcctgagc gaaggagatc tcggtcaggc  1380
ggacgaggcc attttggaag cagatggcgt gactttacgc ggggcgggaa ataacccctc  1440
cgccctggaa gatcgtattg cactggttcg cgcggaactg gatcgcggag atgtgtccgt  1500
tggggattcg ccgtccgcaa aactcgacta cattgagaaa cgcaaagagc gcttaaaact  1560
gcttgccgcc gggagcgcaa aactgcatat tgggggcccg accgatgtcg agatcaagac  1620
gcgtcttccg ctggcagaga atgcgcatcg tgctttgctg gccgctgcca agtctggtgt  1680
tctgcctggg ggcggtgtcg ccatgattcg cgcggcagaa aaagtacagc aggaaatggg  1740
ccgtctggag ggcgatgtgg cgtccggtgc ctcgattttt ctgcagagct tagatactcc  1800
cattcgctgg attgcgcgta acgcgggtct gcgcccggac gaagtcctgg cacgcacatt  1860
ggcaaacgaa tctgattttt acggtctgaa cgcgatgacg ggtcgctacg gcgacctggc  1920
agaagatggt gttctcgatg ctctggacat ggtaaccgac gttattcgtg tggcggtgtc  1980
ggtagtcgga agcatgctcg gagtaggcgc actggtcacg cgcgcgagtc cgaaaccggc  2040
gccggaacgt ttcaagggaa cggagcgcgt acacgataaa ctgatgcgcg aaggtggttt  2100
tgatgagtga gtttaaacgc ggccgcaatt tgaacgccag cacatggact ctcgagtcta  2160
ctagcgcagc ttaattaacc taggctgctg ccaccgctga gcaataacta gcataacccc  2220
ttggggcctc taaacgggtc ttgaggggtt ttttgctgaa acctcaggca tttgagaagc  2280
acacggtcac actgcttccg gtagtcaata aaccggtaaa ccagcaatag acataagcgg  2340
ctatttaacg accctgccct gaaccgacga ccgggtcatc gtggccggat cttgcggccc  2400
ctcggcttga acgaattgtt agacattatt tgccgactac cttggtgatc tcgcctttca  2460
cgtagtggac aaattcttcc aactgatctg cgcgcgaggc caagcgatct tcttcttgtc  2520
caagataagc ctgtctagct tcaagtatga cgggctgata ctgggccggc aggcgctcca  2580
ttgcccagtc ggcagcgaca tccttcggcg cgattttgcc ggttactgcg ctgtaccaaa  2640
tgcgggacaa cgtaagcact acatttcgct catcgccagc ccagtcgggc ggcgagttcc  2700
atagcgttaa ggtttcattt agcgcctcaa atagatcctg ttcaggaacc ggatcaaaga  2760
gttcctccgc cgctggacct accaaggcaa cgctatgttc tcttgctttt gtcagcaaga  2820
tagccagatc aatgtcgatc gtggctggct cgaagatacc tgcaagaatg tcattgcgct  2880
gccattctcc aaattgcagt tcgcgcttag ctggataacg ccacggaatg atgtcgtcgt  2940
gcacaacaat ggtgacttct acagcgcgga gaatctcgct ctctccaggg gaagccgaag  3000
tttccaaaag gtcgttgatc aaagctcgcc gcgttgtttc atcaagcctt acggtcaccg  3060
taaccagcaa atcaatatca ctgtgtggct tcaggccgcc atccactgcg gagccgtaca  3120
aatgtacggc cagcaacgtc ggttcgagat ggcgctcgat gacgccaact acctctgata  3180
gttgagtcga tacttcggcg atcaccgctt ccctcatact cttccttttt caatattatt  3240
gaagcattta tcagggttat tgtctcatga gcggatacat atttgaatgt atttagaaaa  3300
ataaacaaat agctagctca ctcggtcgct acgctccggg cgtgagactg cggcgggcgc  3360
tgcggacaca tacaaagtta cccacagatt ccgtggataa gcaggggact aacatgtgag  3420
gcaaaacagc agggccgcgc cggtggcgtt tttccatagg ctccgccctc ctgccagagt  3480
tcacataaac agacgctttt ccggtgcatc tgtgggagcc gtgaggctca accatgaatc  3540
tgacagtacg ggcgaaaccc gacaggactt aaagatcccc accgtttccg gcgggtcgct  3600
ccctcttgcg ctctcctgtt ccgaccctgc cgtttaccgg atacctgttc cgcctttctc  3660
ccttacggga agtgtggcgc tttctcatag ctcacacact ggtatctcgg ctcggtgtag  3720
gtcgttcgct ccaagctggg ctgtaagcaa gaactccccg ttcagcccga ctgctgcgcc  3780
ttatccggta actgttcact tgagtccaac ccggaaaagc acggtaaaac gccactggca  3840
gcagccattg gtaactggga gttcgcagag gatttgttta gctaaacacg cggttgctct  3900
tgaagtgtgc gccaaagtcc ggctacactg gaaggacaga tttggttgct gtgctctgcg  3960
aaagccagtt accacggtta agcagttccc caactgactt aaccttcgat caaaccacct  4020
ccccaggtgg tttttttcgtt tacagggcaa aagattacgc gcagaaaaaa aggatctcaa  4080
gaagatcctt tgatcttttc tactgaaccg ctctagattt cagtgcaatt tatctcttca  4140
aatgtagcac ctgaagtcag ccccatacga tataagttgt aattctcatg ttagtcatgc  4200
cccgcgccca ccggaaggag ctgactgggt tgaaggctct caagggcatc ggtcgagatc  4260
ccggtgccta atgagtgagc taacttttga cagctagctc agtcctaggg actatgctag  4320
c                                                                  4321
```

SEQ ID NO: 40 moltype = DNA length = 4306
FEATURE Location/Qualifiers
misc_feature 1..4306
note = Synthetic primer.
source 1..4306

```
                         mol_type = other DNA
                         organism = synthetic construct
SEQUENCE: 40
tctactagcg cagcttaatt aacctaggct gctgccaccg ctgagcaata actagcataa  60
ccccttgggg cctctaaacg ggtcttgagg ggtttttttgc tgaaacctca ggcatttgag  120
aagcacacgg tcacactgct tccggtagtc aataaaccgg taaaccagca atagacataa  180
gcggctattt aacgaccctg ccctgaaccg acgaccgggt catcgtggcc ggatcttgcg  240
gcccctcggc ttgaacgaat tgttagacat tatttgccga ctaccttggt gatctcgcct  300
ttcacgtagt ggacaaattc ttccaactga tctgcgcgcg aggccaagcg atcttcttct  360
tgtccaagat aagcctgtct agcttcaagt atgacgggct gatactgggc cggcaggcgc  420
tccattgccc agtcggcagc gacatccttc ggcgcgattt tgccggttac tgcgctgtac  480
caaatgcggg acaacgtaag cactacattt cgctcatcgc cagcccagtc gggcggcgag  540
ttccatagcg ttaaggtttc atttagcgcc tcaaatagat cctgttcagg aaccggatca  600
aagagttcct ccgccgctgg acctaccaag gcaacgctat gttctcttgc ttttgtcagc  660
aagatagcca gatcaatgtc gatcgtggct ggctcgaaga tacctgcaag aatgtcattg  720
cgctgccatt ctccaaattg cagttcgcgc ttagctggat aacgccacgg aatgatgtcg  780
tcgtgcacaa caatggtgac ttctacagcg cggagaatct cgctctctcc aggggaagcc  840
gaagtttcca aaaggtcgtt gatcaaagct cgccgcgttg tttcatcaag ccttacggtc  900
accgtaacca gcaaatcaat atcactgtgt ggcttcaggc cgccatccac tgcggagccg  960
tacaaatgta cggccagcaa cgtcggttcg agatggcgct cgatgacgcc aactacctct  1020
gatagttgag tcgatacttc ggcgatcacc gcttccctca tactcttcct ttttcaatat  1080
tattgaagca tttatcaggg ttattgtctc atgagcggat acatatttga atgtatttag  1140
aaaaataaac aaatagctag ctcactcggt cgctacgctc cgggcgtgag actgcggcgg  1200
gcgctgcgga cacatacaaa gttacccaca gattccgtgg ataagcaggg gactaacatg  1260
tgaggcaaaa cagcagggcc gcgccggtgg cgtttttcca taggctccgc cctcctgcca  1320
gagttcacat aaacagacgc ttttccggtg catctgtggg agccgtgagg ctcaaccatg  1380
aatctgacag tacgggcgaa acccgacagg acttaaagat ccccaccgtt tccggcgggt  1440
cgctccctct tgcgctctcc tgttccgacc ctgccgttta ccggatacct gttccgcctt  1500
tctcccttac gggaagtgtg gcgctttctc atagctcaca cactggtatc tcggctcggt  1560
gtaggtcgtt cgctccaagc tgggctgtaa gcaagaactc cccgttcagc ccgactgctg  1620
cgccttatcc ggtaactgtt cacttgagtc caacccggaa aagcacggta aaacgccact  1680
ggcagcagcc attggtaact gggagttcgc agaggatttg tttagctaaa cacgcggttg  1740
ctcttgaagt gtgcgccaaa gtccggctac actggaagga cagatttggt tgctgtgctc  1800
tgcgaaagcc agttaccacg gttaagcagt tccccaactg acttaacctt cgatcaaacc  1860
acctccccag gtggtttttt cgtttacagg gcaaaagatt acgcgcagaa aaaaaggatc  1920
tcaagaagat cctttgatct tttctactga accgctctag atttcagtgc aatttatctc  1980
ttcaaatgta gcacctgaag tcagccccat acgatataag ttgtaattct catgttagtc  2040
atgccccgcg cccaccggaa ggagctgact gggttgaagg ctctcaaggg catcggtcga  2100
gatcccggtg cctaatgagt gagctaactt ttgacagcta gctcagtcct agggactatg  2160
ctagcaccag cctcgaggga aaccacgtaa gctccggcgt ttaaacaccc ataacagata  2220
cggactttct caaaggagag ttatcagtga aaatccgccc gttacatgac cgtgtcatca  2280
tcaaacgctt ggaagaagag cgtacctcgg cgggcgggat tgtcattcca gatagcgccg  2340
ctgaaaaacc gatgcgtggt gaaatcctgg cagtgggcaa tggaaaagtg cttgataatg  2400
gagaggtacg tgctttacag gtgaaagtgg gtgataaagt gctctttggg aaatacgcgg  2460
gtacggaggt taaagtagat ggggaagatg ttgttgtcat gcgtgaagat gacattctgg  2520
ctgtgttaga atcttaatcc gcgcacgaca ctgaacatac gaatttaagg aataaagata  2580
atggcgaaag aagttgtgta tcgtggtagt gcgcgccagc gtatgatgca gggtattgaa  2640
attctcgctc gcgccgctat tccaacgctg gggggcaaccg gcccgagcgt catgattcaa  2700
catcgcgccg atggtctgcc acccatttct acacgcgatg gcgttaccgt agcgaattct  2760
attgttttaa aagaccgtgt cgcgaacctg ggtgcccgcc tgctgcgcga cgtagccggt  2820
acaatgagcc gtgaagccgg cgacggcacg acgactgcga tcgtattggc ccgccacatc  2880
gcccgtgaga tgtttaaatc gctggccgtg ggtgcagatc cgatcgcgct gaaacgtggt  2940
atcgatcgcg ccgttgctcg tgtgtccgaa gatattgggg cgcgtgcgtg gcgtggcgat  3000
aaagaaagcg tgatcctggg tgtcgctgct gtggcgacga aaggcgaacc gggcgttggc  3060
cgtctgctgc tggaggctct cgatgcagtg ggtgttcacg gtgccgtttc tatcgaactg  3120
ggccaacgtc gtgaagatct gctggacgtc gtcgatggct atcgctggga aaaaggttat  3180
ttatctccct actttgtcac ggaccgtgcc cgcgaactcg cggaactgga ggatgtctac  3240
ctgctcatga ccgaccgcga agtggttgac ttcatcgacc ttgtacctct gctggaggcc  3300
gtgacggaag caggaggctc cctgctgatt gccgcggatc gtgtgcacga aaaggcctta  3360
gcggggctgc ttctgaatca cgtgcgcggt gtcttcaagg ccgtggccgt aaccgctccg  3420
ggttttggcg acaaacgccc gaaccgttta cttgacctgg ccgcgttaac cggcggtcgt  3480
gccgtgctcg aagctcaagg cgaccgtctg gaccgtgtta ccctcgcgga tctgggccgt  3540
gtgcgccgtg ccgtggtgtc ggcagatgat accgcgctgc ttggcatccc gggcaccgaa  3600
gctagccgtg cacgcctcga aggtctgcgt ttagaagcag agcagtaccg tgcgctgaaa  3660
ccagggcagg gttctgccac cgggcgcctg cacgaacttg aagaaattga agcgcgcatt  3720
gtgggtctgt ccggaaagag cgccgtttat cgcgtcggag gtgtgaccga tgtggaaatg  3780
aaagagcgca tggttcgcat cgaaaacgct taccgttcgg tggtaagtgc gctggaggaa  3840
ggcgtgctcc ctggcggtgg tgtcggcttt ctgggtagta tgccggtgct tgcggaattg  3900
gaggcccgcg acgcagatga agctcgcggg attgggattg tacgcagcgc cttaacggag  3960
cctcttcgta ttatcggcga aaatagtggc ttgagcggtg aagccgttgt tgccaaagtc  4020
atggatcatg ccaacccggg atggggttac gaccaggagt ctggctcttt ttgcgacctg  4080
catgcgcgtg ggatctggga tgctgctaaa gtgttacgtc tcgcgttgga gaaggcagcc  4140
tctgttgctg ggacctttct gacaaccgaa gctgttgttc tcgaaattcc ggatacagat  4200
gcgttcgcag ggttcagtgc agaatgggct gccgccacgc gcgaagatcc gcgcgtatga  4260
gtttaaacgc ggccgcaatt tgaacgccag cacatggact ctcgag                4306

SEQ ID NO: 41            moltype = DNA  length = 4357
FEATURE                  Location/Qualifiers
misc_feature             1..4357
```

```
                         note = Synthetic plasmid.
source                   1..4357
                         mol_type = other DNA
                         organism = synthetic construct
SEQUENCE: 41
ggaaaccacg taagctccgg cgtttaaaca cccataacag atacggactt tctcaaagga  60
gagttatcag tggcgtttcg tccgctgcac gatcgtgtgg tggttaaacg tctggaaggc  120
gaggacaaaa ctaaaggtgg gattattatc ccggatacgg ctaaagaaaa accagcggaa  180
ggtaaggtca tcgcagtagg tccaggttcc cgtgatgaaa gcggcaaact ggttgcgctg  240
gatgtgaaag aaggcgatcg tgtgctgttc ggcaagtgga gcggcacaga agtcaaaatc  300
gatggagaag atttgcttat tatgaaggaa tctgatatcc tgggcgtaat cgtataatcc  360
gcgcacgaca ctgaacatac gaatttaagg aataaagata atgactaatc cgcgtaaacg  420
cgaacgccgt cgtccggcat tcgatgtcac acgtgaaaaa ttcgttgccc gtaacattcg  480
ctttggtgat gtggtccgcc gtgatttatt agcgggcgtg gatgcccttg cagacgcggt  540
agcggtgacc ttaggcccgc gcggccgtaa cgttgtaatc gaacatcgcg cggcaggttt  600
gccgccagta gcaaccaaag atggagtgac cgtagcgcag gccgtggaat tggcgggtcg  660
cacccagtcc gtcggtgtga gcttagtacg ccagatggcg acggctgtag ccaaggaggc  720
gggcgatggg accaccacga gcgttgtgct tgctcgtcgc ttggcagccg aaacccgcaa  780
agccctggca gctgggatga atccgcgtga tatcgtactg gggatggaaa aagcggcccg  840
cattgtggat cgtgacctcg cggctcgtgc acgccgttgc gatgacacac gtgcccttgc  900
gcacgtcgct accttggctg ccgggggtga tgagagtatc ggtgccattg tggcggatgc  960
tttaacacgt gcgggcgagg gcggcgtagt agacgtggaa ctgggtgctg cactgtgtga  1020
tgagatggac attgttgagg gcatgcgctg ggaacagggt taccgctcac cgtatttcat  1080
gacggactct gcgcgcaaga tcgcagaact ggaaaatcct tacattctga tctacgatcg  1140
tgttattaat caattttccg aattagttcc ggcgttagaa ttagtccgtc gccaacgcgg  1200
cagcctgtta atcgtcgctg aaaacattgt ggaagaggcc ctccctggcc tgctcctgaa  1260
tcatattcgt aaaaatctgt gttctatcgc cgttaaaggt ccgggttatg gggactcccg  1320
ttacgaattt ctgcacgatc tggcggcctt aaccggaggc cgtgcgatca tggaggcgtg  1380
cggcgaggag ttgtcaaacg ttaccatggc ccatctggga cgcgcaaaac gtgtagtggt  1440
gcgcgaagat gatacggttg tgatcggcgg ggagggggac ggtgcggcca tcactgagcg  1500
tctggccgcg gcgcgtcagc aggcagattg gattaccgac ggcgatccaa gcaaaggaag  1560
cccatccgga aagcgccacg atttagaaaa cctgcagacc cgcattaaag ctctgagcgg  1620
aaaggtagtc acgattaagg ccggcggcct tagtgatatt ctgattaaag aacgcatgca  1680
gcgtattgag aatgctctcg catcggcgcg cgcagcccgc tccgacggag tcgtggccgg  1740
cggcggcgtg ggactgtatc gcgcccgcgc tgcgttgact gaggcaacgg gcgacacctt  1800
ggatcaaacc tacggcattg cgattgtacg cgctgctctc gacgagccca ttcgccgtat  1860
tgctgcgaac gcggggcgcg atgcacatga atttctgttt gaactcaaac gctctaacga  1920
tgatttttgg gggatggata tgcgcagcgg tgaatgcgga gatctttatg ccgcgggcgt  1980
cattgatccg gcgcgtgtta cccgcctggc cctgcgcaac gcggtagcta cggctagcag  2040
cctgatgacc gtcgaatgcg cagtaactca tatcccacct tctgacccca cctatggttt  2100
tgatcctcat ttggcggcgg caacccgtga agacccgcgc tcataagttt aaacgcggcc  2160
gcaatttgaa cgccagcaca tggactctcg agtctactag cgcagcttaa ttaacctagg  2220
ctgctgccac cgctgagcaa taactagcat aaccccttgg ggcctctaaa cgggtcttga  2280
ggggtttttt gctgaaacct caggcatttg agaagcacac ggtcacactg cttccggtag  2340
tcaataaacc ggtaaaccag caatagacat aagcggctat ttaacgaccc tgccctgaac  2400
cgacgaccgg gtcatcgtgg ccggatcttg cggcccctcg gcttgaacga attgttagac  2460
attatttgcc gactaccttg gtgatctcgc ctttcacgta gtggacaaat tcttccaact  2520
gatctgcgcg cgaggccaag cgatcttctt cttgtccaag ataagcctgt ctagcttcaa  2580
gtatgacggg ctgatactgg gccggcaggc gctccattgc ccagtcggca gcgacatcct  2640
tcggcgcgat tttgccggtt actgcgctgt accaaatgcg ggacaacgta agcactacat  2700
ttcgctcatc gccagcccag tcgggcggcg agttccatag cgttaaggtt tcatttagcg  2760
cctcaaatag atcctgttca ggaaccggat caaagagttc ctccgccgct ggacctacca  2820
aggcaacgct atgttctctt gcttttgtca gcaagatagc cagatcaatg tcgatcgtgg  2880
ctggctcgaa gatacctgca agaatgtcat tgcgctgcca ttctccaaat tgcagttcgc  2940
gcttagctgg ataacgccac ggaatgatgt cgtcgtgcac aacaatggtg acttctacag  3000
cgcggagaat ctcgctctct ccaggggaag ccgaagtttc caaaaggtcg ttgatcaaag  3060
ctcgccgcgt tgtttcatca agccttacgg tcaccgtaac cagcaaatca atatcactgt  3120
gtggcttcag gccgccatcc actgcggagc cgtacaaatg tacggccagc aacgtcggtt  3180
cgagatggcg ctcgatgacg ccaactacct ctgatagttg agtcgatact tcggcgatca  3240
ccgcttccct catactcttc ctttttcaat attattgaag catttatcag ggttattgtc  3300
tcatgagcgg atacatattt gaatgtattt agaaaaataa acaaataggt agctcactcg  3360
gtcgctacgc tccgggcgtg agactgcggc gggcgctgcg gacacataca aagttaccca  3420
cagattccgt ggataagcag gggactaaca tgtgaggcaa aacagcaggg ccgcgccggt  3480
ggcgtttttc cataggctcc gccctcctgc cagagttcac ataaacagac gcttttccgg  3540
tgcatctgtg ggagccgtga ggctcaacca tgaatctgac agtacgggcg aaacccgaca  3600
ggacttaaag atccccaccg tttccggcgg gtcgctccct cttgcgctct cctgttccga  3660
ccctgccgtt taccggatac ctgttccgcc tttctccctt acgggaagtg tggcgctttc  3720
tcatagctca cacactggta tctcggctcg gtgtaggtcg ttcgctccaa gctgggctgt  3780
aagcaagaac tccccgttca gcccgactgc tgcgccttat ccggtaactg ttcacttgag  3840
tccaacccgg aaaagcacgg taaaacgcca ctggcagcag ccattggtaa ctgggagttc  3900
gcagaggatt tgtttagcta aacacgcggt tgctcttgaa gtgtgcgcca aagtccggct  3960
acactggaag gacagatttg gttgctgtgc tctgcgaaag ccagttacca cggttaagca  4020
gttccccaac tgacttaacc ttcgatcaaa ccacctcccc aggtggtttt ttcgtttaca  4080
gggcaaaaga ttacgcgcag aaaaaaagga tctcaagaag atcctttgat cttttctact  4140
gaaccgctct agatttcagt gcaatttatc tcttcaaatg tagcacctga agtcagcccc  4200
atacgatata agttgtaatt ctcatgttag tcatgccccg cgcccaccgg aaggagctga  4260
ctgggttgaa ggctctcaag ggcatcggtc gagatcccgg tgcctaatga gtgagctaac  4320
ttttgacagc tagctcagtc ctagggacta tgctagc                           4357
```

```
SEQ ID NO: 42          moltype = DNA  length = 4297
FEATURE                Location/Qualifiers
misc_feature           1..4297
                       note = Synthetic plasmid.
source                 1..4297
                       mol_type = other DNA
                       organism = synthetic construct
SEQUENCE: 42
ggaaaccacg taagctccgg cgtttaaaca cccataacag atacggactt tctcaaagga  60
gagttatcag tgaacattcg tccgctcaat gatcgcgtga ttgtaaaacg tcttgaagag  120
gaacgcacgt caccgggtgg cattgtgatc ccggattcag ccacagagaa accgtcccgt  180
ggtgaaatcc tggcggtcgg cacgggtaaa accctggata atggtcaggt acgtgccttg  240
gccgtcaaag cgggcgacaa agtgctgttt ggtaaatacg cggggacgga agtcaagatt  300
gacggccagg agattcttgt gatgcgtgaa gaagatatta ttgcggtgct tgaggattaa  360
tccgcgcacg acactgaaca tacgaattta aggaataaag ataatgtcaa agcgcctcgt  420
cttcgatggc gaagcccgcg cgggaatttt aaaaggtatt gatattttgg gtcgtgcggt  480
tgagactact tacggttatc aggggccttg cgtaatggta caacaccgca ctcagggtct  540
gcctccgttc tttacacgtg atggcgtaac ggttgcgaac tcggtcgttc tgggtgatcg  600
cctggccgat cttggcgcac gtatgctgcg tgacgttgcg aacgcggtat ctcgcgaagc  660
gggtgatggc acaacaaccg ccgtggtgct ggcgcgcgca atcgcgcgcg gccttttacg  720
ttccttggca gcgggggcgg atccgcatcg tttgcgcgag ggaatggacg ctgccgttaa  780
gctggtggag gatgatctgc gccgccgcgc gctgcctctt caaggggata tggttgctca  840
agttgcagaa gtgtcaatgc gcaaagaagg gcaggttggc cgcttactgc aacaggctta  900
tgcggaagtt ggaccagatg gggctgttac ggtagaaccg ggttggacac gtgcggatac  960
cttggatatc ggcgaaggct tccgttatga actgggattt ctgtccccgg gcttcgaaac  1020
agatccggtt cgtcgtgccg ctgacatcga gggtgcccgc gtgctgctgt atcatggtac  1080
ggttactgac ttcatggacc tgattccgtt gctggaagca gtgaatgagg ctggtcaagc  1140
gctggtaatt gcatgcgatg gaatcgatga gcgtccgtta cagggcttag taatgaacgt  1200
caagcgtggt gtgttccgtg cgctggcagt gaaagcgccg ggccatggtg accgtcgtcg  1260
tgattggctg gatgatctgg cgactgccac gggtgcccgc gtactggtgc cggagcgcgg  1320
agacaatctg gaacgtgcgg caccggaagt gcttggacac gcggccaaag tggtggccga  1380
tgcggacagc gctagtttta ttggctgtgg cggtgaccct gtggcagtag cccgtcgtgt  1440
ggcgggatta ggtaaagagg ccgatgccat tcgcgcgcgc aaaccgggcg aaggttctcc  1500
taccggcaat ctgcatgatc tggaggatct ggaggcgcgc attagtgcgt tagttggtcg  1560
catcgctacc gtccgtgtag gcggcaccac cgagcccgaa attaaagaac gcttgcaacg  1620
cgctgaaaat gcccgtcgtt cagttcgcgc cgcgttggag gaaggagttg tgcctggcgg  1680
tggagtggga ctgcttcaag cccgcgaagc cttaggtcgc cttctcctga cggatctgga  1740
ctggcagcgc ggcgtggcta tcgtaagcga agcactcgaa cagccattcc gtgctctggt  1800
cggaaacgca ggtatcaatc cggtggcggc cctggctcgt atcgaagcgg caggcaacgc  1860
tcgttttggt tacgatgcca gctcaggagc gttcggtgat ctcgtagcag ccggtgtctt  1920
agacccagtg aaagtcctgc gcctggctct ggttcaagct gcggggattg ccgcgacagt  1980
tctgtcttcc ggagcagtcg tgttgaatga gcagtcaggc ttaccgcatc tgcccggctt  2040
ttccgcggaa tgggccgcag caacgcgcga agatccgcgt gcctaagttt aaacgcggcc  2100
gcaatttgaa cgccagcaca tggactctcg agtctactag cgcagcttaa ttaacctagg  2160
ctgctgccac cgctgagcaa taactagcat aaccccttgg ggcctctaaa cgggtcttga  2220
ggggtttttt gctgaaacct caggcatttg agaagcacac ggtcacactg cttccggtag  2280
tcaataaacc ggtaaaccag caatagacat aagcggctat ttaacgaccc tgccctgaac  2340
cgacgaccgg gtcatcgtgg ccggatcttg cggcccctcg gcttgaacga attgttagac  2400
attatttgcc gactaccttg gtgatctcgc ctttcacgta gtggacaaat tcttccaact  2460
gatctgcgcg cgaggccaag cgatcttctt cttgtccaag ataagcctgt ctagcttcaa  2520
gtatgacggg ctgatactgg gccggcaggc gctccattgc ccagtcggca gcgacatcct  2580
tcggcgcgat tttgccggtt actgcgctgt accaaatgcg ggacaacgta agcactacat  2640
ttcgctcatc gccagcccag tcgggcggcg agttccatag cgttaaggtt tcatttagcg  2700
cctcaaatag atcctgttca ggaaccggat caaagagttc ctccgccgct ggacctacca  2760
aggcaacgct atgttctctt gcttttgtca gcaagatagc cagatcaatg tcgatcgtgg  2820
ctggctcgaa gatacctgca agaatgtcat tgcgctgcca ttctccaaat tgcagttcgc  2880
gcttagctgg ataacgccac ggaatgatgt cgtcgtgcac aacaatggtg acttctacag  2940
cgcggagaat ctcgctctct ccaggggaag ccgaagtttc caaaaggtcg ttgatcaaag  3000
ctcgccgcgt tgtttcatca agccttacgg tcaccgtaac cagcaaatca atatcactgt  3060
gtggcttcag gccgccatcc actgcggagc cgtacaaatg tacggccagc aacgtcggtt  3120
cgagatggcg ctcgatgacg ccaactacct ctgatagttg agtcgatact tcggcgatca  3180
ccgcttccct catactcttc ctttttcaat attattgaag catttatcag ggttattgtc  3240
tcatgagcgg atacatattt gaatgtattt agaaaaataa acaaatagct agctcactcg  3300
gtcgctacgc tccgggcgtg agactgcggc gggcgctgcg gacacataca aagttaccca  3360
cagattccgt ggataagcag gggactaaca tgtgaggcaa aacagcaggg ccgcgccggt  3420
ggcgtttttc cataggctcc gccctcctgc cagagttcac ataaacagac gcttttccgg  3480
tgcatctgtg ggagccgtga ggctcaacca tgaatctgac agtacgggcg aaacccgaca  3540
ggacttaaag atccccaccg tttccggcgg gtcgctccct cttgcgctct cctgttccga  3600
ccctgccgtt taccggatac ctgttccgcc tttctccctt acgggaagtg tggcgctttc  3660
tcatagctca cacactggta tctcggctcg gtgtaggtcg ttcgctccaa gctgggctgt  3720
aagcaagaac tccccgttca gcccgactgc tgcgccttat ccggtaactg ttcacttgag  3780
tccaacccgg aaaagcacgg taaaacgcca ctggcagcag ccattggtaa ctgggagttc  3840
gcagaggatt tgtttagcta aacacgcggt tgctcttgaa gtgtgcgcca aagtccggct  3900
acactggaag gacagatttg gttgctgtgc tctgcgaaag ccagttacca cggttaagca  3960
gttccccaac tgacttaacc ttcgatcaaa ccacctcccc aggtggtttt ttcgtttaca  4020
gggcaaaaga ttacgcgcag aaaaaaagga tctcaagaag atcctttgat cttttctact  4080
gaaccgctct agatttcagt gcaatttatc tcttcaaatg tagcacctga agtcagcccc  4140
atacgatata agttgtaatt ctcatgttag tcatgccccg cgcccaccgg aaggagctga  4200
ctgggttgaa ggctctcaag ggcatcggtc gagatcccgg tgcctaatga gtgagctaac  4260
```

```
ttttgacagc tagctcagtc ctagggacta tgctagc                     4297

SEQ ID NO: 43          moltype = DNA  length = 4294
FEATURE                Location/Qualifiers
misc_feature           1..4294
                       note = Synthetic plasmid.
source                 1..4294
                       mol_type = other DNA
                       organism = synthetic construct
SEQUENCE: 43
ggaaaccacg taagctccgg cgtttaaaca cccataacag atacggactt tctcaaagga  60
gagttatcag tggcgttccg cccgctgcat gatcgtgtgg tcgttaagcg cctggagggt  120
gaagataaaa ccaaaggcgg tattatcatt ccggatacag cgaaagaaaa accggccgaa  180
ggcaaaatca tcgctgtagg accgggcgcg cgcgatgaat caggaaaatt ggtggcgctt  240
gatgtcaaag aaggggaccg cgtgctgttc ggaaagtggt cggggacaga ggtaaaaatt  300
gatggcgaag atctgttaat catgaaggaa agtgatattc tgggcgttat cgcgtaatcc  360
gcgcacgaca ctgaacatac gaatttaagg aataaagata atggcgcgta atattcgctt  420
tggtgatccg gtccgtaaac gtctgctgga tggcgtggat tttctggcgg atgccgtggg  480
ggtgactctg ggtccgtgtg gtcgcaacgt cgtgattgaa catcgtgcaa gcggcttgcc  540
gccagtagcg actaaagatg gagcaacggt tgcccaagct gtggaagctg cgggtcgtac  600
cgagtctgta ggcatcaact tggtacgtca gatggcgacc accgtggcga aggaagcggg  660
agatggtaca acgacgtccg tagtgttaac ccgccgtgtc gcagccgaaa cacgtaaggc  720
attagcagcg ggtatgaatc cgcgtgatat taccctggga atggagcgtg ctgcccgtgc  780
agtagaggca gatttgctcc gccgcgcacg tcgctgcaac gaccagcgtt ctcttgcgca  840
cgttgcgact ctggccgctg gtggagacga aggcattggc gcaattgtgg cccaagcgct  900
ggctttagct ggggaaggtg gtgtggtgga tgtggaatta ggtcacggtg tggccgacga  960
catcgaaagc gtcgaaggca tgcgctggga acagggttat cgcagcccgt attttatgac  1020
cgatagcgct cgcaaagtgg ccgaactgga aaacccgtac attttagttt atgaccgtgt  1080
gattaacgag ttttctgaac tggtgccggc ccttgagctg gtccgccgct ccgggggctc  1140
tctgttagta gtggctgaaa acattatgga agaagctctc ccgggtctgc tgctgaatca  1200
tattcgcaaa aacctgtgta gcattgccgt gaagggccct ggttatggcg attctcgcta  1260
tgaatattta ctggaccttg ccgcgattac cggtggccgt gcaatcatgg aagccttcgg  1320
tgaagacatt tcaaatgtca ccatggagca tctgggccgc gcacgtcgcg tcgtagtacg  1380
tgaagatgac acactggtca ttggcggcga gggcgaccca aacgtgatcg ccgaccgtct  1440
ggcatccgcg aaacgtcagg ccgattggat tgtagaagga gacgcatcaa aaggcagccc  1500
gtccggcaaa cgccacgaac ttgaaaatct tcagacgcgc attaaagcac ttagcggtcg  1560
catggccacc atccgcgcgg gtggcctctc cgatgttctt atcaaagagc gcatgcaacg  1620
tattgaaaac gcgctgaata gtgctcgcgc ggcgcagtcc gatggcgttg tcgcgggtgg  1680
tggcgtgggc ctgtaccgcg ctcgcgcagc gctggctgaa ctgcgcggcg aaaatctgga  1740
ccagagccac ggagttgcga ttgtgcgtgc cgcgctggat gagccgattc gtcgcattgc  1800
ggcgaacgcg ggcgttgatg cggatgagtt tctgtttgaa ctgcgccgtt caaatgatga  1860
tttttggggt atggacatgc gtagtggcgc gtgcggagat ctgtttgcag cgggtgtgat  1920
tgatccagtc cgcgttactc gcctggcgtt acgcaacgcg gtggctactg cggcttcgct  1980
tatgacggtg gagtgcgcgg ttacccatat tcccgtgagc gacccgacat tcggctttga  2040
cgcgcgtcgc gcagccgaga ctcgtgaaga tcctcgcgcc taagtttaaa cgcggccgca  2100
atttgaacgc cagcacatgg actctcgagt ctactagcgc agcttaatta acctaggctg  2160
ctgccaccgc tgagcaataa ctagcataac cccttggggc ctctaaacgg gtcttgaggg  2220
gttttttgct gaaacctcag gcatttgaga agcacacggt cacactgctt ccggtagtca  2280
ataaaccggt aaaccagcaa tagacataag cggctattta acgaccctgc cctgaaccga  2340
cgaccgggtc atcgtggccg gatcttgcgg cccctcggct tgaacgaatt gttagacatt  2400
atttgccgac taccttggtg atctcgcctt tcacgtagtg gacaaattct tccaactgat  2460
ctgcgcgcga ggccaagcga tcttcttctt gtccaagata agcctgtcta gcttcaagta  2520
tgacgggctg atactgggcc ggcaggcgct ccattgccca gtcggcagcg acatccttcg  2580
gcgcgatttt gccggttact gcgctgtacc aaatgcggga caacgtaagc actacatttc  2640
gctcatcgcc agcccagtcg ggcggcgagt tccatagcgt taaggtttca tttagcgcct  2700
caaatagatc ctgttcagga accggatcaa agagttcctc cgccgctgga cctaccaagg  2760
caacgctatg ttctcttgct tttgtcagca agatagccag atcaatgtcg atcgtggctg  2820
gctcgaagat acctgcaaga atgtcattgc gctgccattc tccaaattgc agttcgcgct  2880
tagctggata acgccacgga atgatgtcgt cgtgcacaac aatggtgact tctacagcgc  2940
ggagaatctc gctctctcca ggggaagccg aagtttccaa aaggtcgttg atcaaagctc  3000
gccgcgttgt ttcatcaagc cttacggtca ccgtaaccag caaatcaata tcactgtgtg  3060
gcttcaggcc gccatccact gcggagccgt acaaatgtac ggccagcaac gtcggttcga  3120
gatggcgctc gatgacgcca actacctctg atagttgagt cgatacttcg gcgatcaccg  3180
cttccctcat actcttcctt tttcaatatt attgaagcat ttatcagggt tattgtctca  3240
tgagcggata catatttgaa tgtatttaga aaaataaaca aatagctagc tcactcggtc  3300
gctacgctcc gggcgtgaga ctgcggcggg cgctgcggac acatacaaag ttacccacag  3360
attccgtgga taagcagggg actaacatgt gaggcaaaac agcagggccg cgccggtggc  3420
gtttttccat aggctccgcc ctcctgccag agttcacata aacagacgct tttccggtgc  3480
atctgtggga gccgtgaggc tcaaccatga atctgacagt acgggcgaaa cccgacagga  3540
cttaaagatc cccaccgttt ccggcgggtc gctccctctt gcgctctcct gttccgaccc  3600
tgccgtttac cggatacctg ttccgccttt ctcccttacg ggaagtgtgg cgctttctca  3660
tagctcacac actggtatct cggctcggtg taggtcgttc gctccaagct gggctgtaag  3720
caagaactcc ccgttcagcc cgactgctgc gccttatccg gtaactgttc acttgagtcc  3780
aacccggaaa agcacggtaa aacgccactg gcagcagcca ttggtaactg ggagttcgca  3840
gaggatttgt ttagctaaac acgcggttgc tcttgaagtg tgcgccaaag tccggctaca  3900
ctggaaggac agatttggtt gctgtgctct gcgaaagcca gttaccacgg ttaagcagtt  3960
ccccaactga cttaaccttc gatcaaacca cctccccagg tggttttttc gtttacaggg  4020
caaaagatta cgcgcagaaa aaaggatctc caagaagatc ctttgatctt ttctactgaa  4080
ccgctctaga tttcagtgca atttatctct tcaaatgtag cacctgaagt cagccccata  4140
```

```
cgatataagt tgtaattctc atgttagtca tgccccgcgc ccaccggaag gagctgactg  4200
ggttgaaggc tctcaagggc atcggtcgag atcccggtgc ctaatgagtg agctaacttt  4260
tgacagctag ctcagtccta gggactatgc tagc                              4294

SEQ ID NO: 44          moltype = DNA  length = 4315
FEATURE                Location/Qualifiers
misc_feature           1..4315
                       note = Synthetic plasmid.
source                 1..4315
                       mol_type = other DNA
                       organism = synthetic construct
SEQUENCE: 44
accagcctcg agggaaacca cgtaagctcc ggcgtttaaa cacccataac agatacggac  60
tttctcaaag gagagttatc agtgaaactg cgcccgctcc atgaccgtgt aattgtcaaa  120
cgtctggaag aagaaaaaaa atccgccggc ggaattatca tcccggatgc cgcagcagaa  180
aagccaagtc gtggtgaagt aatcagcgtg ggccggggga aacgtggcga cgatggtaaa  240
ctgaatgcac tggatgtgaa agctggtgat attgttttat tcggcaaata ctctggtagt  300
gaagtccgcg tagacggtca agatttgctg gttatgcgcg aagacgacat tatggcggtt  360
tttgccaagt aatccgcgca cgacactgaa catacgaatt taaggaataa agataatgac  420
gaatggcaag aattgccgtg tctcggacgg atttggtgcc ctgggcaaac tgagcagtgg  480
catgcgtatc ctggcggaag tcgttgcagt taccctcggt ccaggcggtc gccatgtgat  540
tctggaacat cgcagcggct tagctcctcg tctgagtaag gatggtgtcg agatcgcccg  600
tactatggaa gtggctggac gtgaagaaga aatgggtgta cgtctgttgc gcgatgcggc  660
aatctcgatt agcgctagcg tgggtgatgg aacaactaca gcgatcgtat tgtcagctgc  720
gctggccacg cgctgtatgg ctgcttccag ccatccgctt aacgtctcgg aaatgcgcta  780
cggattggct atggcggggg cgacagtgct ctctgaatta gctgccatgg cgcgtccggc  840
cgatcaacat gccctgcaag cggtggcgcg cacagctgtt aatggtgatg cgccgctggc  900
cgccctgctt gcggatgcct atgcccgcgt gggtagcgaa ggtgttatta aaatcgagat  960
gggtaatgca atgcatgacg tgttagatgt gaagctcgga caccgcttcg aatccctgct  1020
gctggccagc ggtctgccgg ctagtgcggg cgaacgtcaa ctcctgcgcc ctctgaccct  1080
gcttcacgac ggcgaattgg atgacctcca agcgctgatt cctgcgatgg agattgctcg  1140
tgccgaacaa cgcccgcttc tcattctggc cggcgacgtc agcgatggcg tgcgcaccgc  1200
gattgtgcgt aacgctcgcg aaaatgtggt agatgttact gtagtgcgcg ctccgatgtt  1260
tggggatacc cgtcaggaat gcctgggtga cctggccgcg ctgtgcggag gatcagcctt  1320
cgtggaaaac ggatttcgca ctattgcggc cctgagccgc gatgatctgg gcagcgtgga  1380
tcgtgcggtg gtagatgcgg gaagcgctat tctccacgga gctcatggcg atgcacgcga  1440
acgccaagac cgtatcgcgt tgcttcgtag cgaaatggaa ggtagtggtc gctcgacggc  1500
gtcgccgtct ggccagctgg atcatagcga caagtgtcaa gaacgcctgc agattctgct  1560
tggcgcgacc gcctcgttgc agctgggcgg cgcaacggac gtcgcaatca aagcccgcat  1620
gccgatcgcc gaaaatgggc gccgcgcgtt actggccgca gcgagcaccg gcgtcctgcc  1680
gggtggaggc gtggcgatgc ttcgcgcagc actcgcggca cgttcgcgcc tgtctactct  1740
gcaggacgac gcccgtctcg gtgcagaggc gctcttgtca gcgctgcagg ccccgttcgc  1800
atgggtcgtt cgcaactcgg gacaccaacc tgaggaatgc ctggatcgcg tgttgtctga  1860
agcggattgc tttcacggcc tggacgccgc ccgcgggtgt tacggtgatc tgcatgcggc  1920
gggagtgtta gattcgttct tgatggtccg caaaattgtg acggtggcga cctctatggc  1980
cggtagcctg ctgagcacgg gtgccttagt gtgtcgtggc ggggaaactg ctctcccgga  2040
aaacttccag gggacacaac aggtgtaccg caaattagcg gcaggcggcg ccttcgattc  2100
ttaagtttaa acgcggccgc aatttgaacg ccagcacatg gactctcgag tctactagcg  2160
cagcttaatt aacctaggct gctgccaccg ctgagcaata actagcataa ccccttgggg  2220
cctctaaacg ggtcttgagg ggttttttgc tgaaacctca ggcatttgag aagcacacgg  2280
tcacactgct tccggtagtc aataaaccgg taaaccagca atagacataa gcggctattt  2340
aacgaccctg ccctgaaccg acgaccgggt catcgtggcc ggatcttgcg gcccctcggc  2400
ttgaacgaat tgttagacat tatttgccga ctaccttggt gatctcgcct ttcacgtagt  2460
ggacaaattc ttccaactga tctgcgcgcg aggccaagcg atcttcttct tgtccaagat  2520
aagcctgtct agcttcaagt atgacgggct gatactgggc cggcaggcgc tccattgccc  2580
agtcggcagc gacatccttc ggcgcgattt tgccggttac tgcgctgtac caaatgcggg  2640
acaacgtaag cactacattt cgctcatcgc cagcccagtc gggcggcgag ttccatagcg  2700
ttaaggtttc atttagcgcc tcaaatagat cctgttcagg aaccggatca aagagttcct  2760
ccgccgctgg acctaccaag gcaacgctat gttctcttgc ttttgtcagc aagatagcca  2820
gatcaatgtc gatcgtggct ggctcgaaga tacctgcaag aatgtcattg cgctgccatt  2880
ctccaaattg cagttcgcgc ttagctggat aacgccacgg aatgatgtcg tcgtgcacaa  2940
caatggtgac ttctacagcg cggagaatct cgctctctcc aggggaagcc gaagtttcca  3000
aaaggtcgtt gatcaaagct cgccgcgttg tttcatcaag ccttacggtc accgtaacca  3060
gcaaatcaat atcactgtgt ggcttcaggc cgccatccac tgcggagccg tacaaatgta  3120
cggccagcaa cgtcggttcg agatggcgct cgatgacgcc aactacctct gatagttgag  3180
tcgatacttc ggcgatcacc gcttccctca tactcttcct tttcaatat tattgaagca  3240
tttatcaggg ttattgtctc atgagcggat acatatttga atgtatttag aaaaataaac  3300
aaatagctag ctcactcggt cgctacgctc cgggcgtgag actgcggcgg gcgctgcgga  3360
cacatacaaa gttacccaca gattccgtgg ataagcaggg gactaacatg tgaggcaaaa  3420
cagcagggcc gcgccggtgg cgtttttcca taggctccgc cctcctgcca gagttcacat  3480
aaacagacgc ttttccggtg catctgtggg agccgtgagg ctcaaccatg aatctgacag  3540
tacgggcgaa acccgacagg acttaaagat ccccaccgtt tccggcgggt cgctccctct  3600
tgcgctctcc tgttccgacc ctgccgttta ccggatacct gttccgcctt tctcccttac  3660
gggaagtgtg gcgctttctc atagctcaca cactggtatc tcggctcggt gtaggtcgtt  3720
cgctccaagc tgggctgtaa gcaagaactc cccgttcagc ccgactgctg cgccttatcc  3780
ggtaactgtt cacttgagtc caacccggaa aagcacggta aaacgccact ggcagcagcc  3840
attggtaact gggagttcgc agaggatttg tttagctaaa cacgcggttg ctcttgaagt  3900
gtgcgccaaa gtccggctac actggaagga cagatttggt tgctgtgctc tgcgaaagcc  3960
agttaccacg gttaagcagt tccccaactg acttaacctt cgatcaaacc acctccccag  4020
```

```
gtggtttttt cgtttacagg gcaaaagatt acgcgcagaa aaaaaggatc tcaagaagat  4080
cctttgatct tttctactga accgctctag atttcagtgc aatttatctc ttcaaatgta  4140
gcacctgaag tcagccccat acgatataag ttgtaattct catgttagtc atgccccgcg  4200
cccaccggaa ggagctgact gggttgaagg ctctcaaggg catcggtcga gatcccggtg  4260
cctaatgagt gagctaactt ttgacagcta gctcagtcct agggactatg ctagc       4315

SEQ ID NO: 45          moltype = DNA  length = 10837
FEATURE                Location/Qualifiers
misc_feature           1..10837
                       note = Synthetic plasmid.
source                 1..10837
                       mol_type = other DNA
                       organism = synthetic construct
SEQUENCE: 45
gacgaccggg tcatcgtggc cggatcttgc ggcccctcgg cttgaacgaa ttgttagaca  60
ttatttgccg actaccttgg tgatctcgcc tttcacgtag tggacaaatt cttccaactg  120
atctgcgcgc gaggccaagc gatcttcttc ttgtccaaga taagcctgtc tagcttcaag  180
tatgacgggc tgatactggg ccggcaggcg ctccattgcc cagtcggcag cgacatcctt  240
cggcgcgatt ttgccggtta ctgcgctgta ccaaatgcgg gacaacgtaa gcactacatt  300
tcgctcatcg ccagcccagt cgggcggcga gttccatagc gttaaggttt catttagcgc  360
ctcaaataga tcctgttcag gaaccggatc aaagagttcc tccgccgctg gacctaccaa  420
ggcaacgcta tgttctcttg cttttgtcag caagatagcc agatcaatgt cgatcgtggc  480
tggctcgaag atacctgcaa gaatgtcatt gcgctgccat tctccaaatt gcagttcgcg  540
cttagctgga taacgccacg gaatgatgtc gtcgtgcaca acaatggtga cttctacagc  600
gcggagaatc tcgctctctc caggggaagc cgaagtttcc aaaaggtcgt tgatcaaagc  660
tcgccgcgtt gtttcatcaa gccttacggt caccgtaacc agcaaatcaa tatcactgtg  720
tggcttcagg ccgccatcca ctgcggagcc gtacaaatgt acggccagca acgtcggttc  780
gagatggcgc tcgatgacgc caactacctc tgatagttga gtcgatactt cggcgatcac  840
cgcttccctc atactcttcc tttttcaata ttattgaagc atttatcagg gttattgtct  900
catgagcgga tacatatttg aatgtattta gaaaaataaa caaatagcta gctcactcgg  960
tcgctacgct ccgggcgtga gactgcggcg ggcgctgcgg acacatacaa agttacccac  1020
agattccgtg gataagcagg ggactaacat gtgaggcaaa acagcagggc cgcgccggtg  1080
gcgtttttcc ataggctccg ccctcctgcc agagttcaca taaacagacg cttttccggt  1140
gcatctgtgg gagccgtgag gctcaaccat gaatctgaca gtacgggcga aacccgacag  1200
gacttaaaga tccccaccgt ttccggcggg tcgctccctc ttgcgctctc ctgttccgac  1260
cctgccgttt accggatacc tgttccgcct ttctccctta cgggaagtgt ggcgctttct  1320
catagctcac acactggtat ctcggctcgg tgtaggtcgt tcgctccaag ctgggctgta  1380
agcaagaact ccccgttcag cccgactgct gcgccttatc cggtaactgt tcacttgagt  1440
ccaacccgga aagcacggt aaaacgccac tggcagcagc cattggtaac tgggagttcg  1500
cagaggattt gtttagctaa acacgcggtt gctcttgaag tgtgcgccaa agtccggcta  1560
cactggaagg acagatttgg ttgctgtgct ctgcgaaagc cagttaccac ggttaagcag  1620
ttccccaact gacttaacct tcgatcaaac cacctcccca ggtggttttt tcgtttacag  1680
ggcaaaagat tacgcgcaga aaaaaaggat ctcaagaaga tcctttgatc ttttctactg  1740
aaccgctcta gatttcagtg caatttatct cttcaaatgt agcacctgaa gtcagcccca  1800
tacgatataa gttgtaattc tcatgttagt catgccccgc gcccaccgga aggagctgac  1860
tgggttgaag gctctcaagg gcatcggtcg agatcccggt gcctaatgag tgagctaact  1920
tttgacggct agctcagtcc tagggataat gctagcacca gcctcgaggg aaaccacgta  1980
agctccggcg tttaaacacc cataacagat acggactttc tcaaaggaga gttatcagtg  2040
aaaatccgcc cgttacatga ccgtgtcatc atcaaacgct tggaagaaga gcgtacctcg  2100
gcgggcggga ttgtcattcc agatagcgca gctgaaaaac cgatgcgtgg tgaaatcctg  2160
gcagtgggca atggaaaagt gcttgataat ggagaggtac gtgctttaca ggtgaaagtg  2220
ggtgataaag tgctctttgg gaaatacgcg ggtacggagg ttaaagtaga tggggaagat  2280
gttgttgtca tgcgtgaaga tgacattctg gctgtgttag aatcttaatc cgcgcacgac  2340
actgaacata cgaatttaag gaataaagat aatggcgaaa gaagttgtgt atcgtggtag  2400
tgcgcgccag cgtatgatgc agggtattga aattctcgct cgcgccgcta ttccaacgct  2460
gggggcaacc ggcccgagcg tcatgattca acatcgcgcc gatggtctgc cacccatttc  2520
tacacgcgat ggcgttaccg tagcgaattc tattgtttta aaagaccgtg tcgcgaacct  2580
gggtgcccgc ctgctgcgcg acgtagccgg tacaatgagc cgtgaagccg gcgacggcac  2640
gacgactgcg atcgtattgg cccgccacat cgcccgtgag atgtttaaat cgctggccgt  2700
gggtgcagat ccgatcgcgc tgaaacgtgg tatcgatcgc gccgttgctc gtgtgtccga  2760
agatattggg gcgcgtgcgt ggcgtggcga taaagaaagc gtgatcctgg gtgtcgctgc  2820
tgtggcgacg aaaggcgaac cgggcgttgg ccgtctgctg ctggaggctc tcgatgcagt  2880
gggtgttcac ggtgccgttt ctatcgaact gggccaacgt cgtgaagatc tgctggacgt  2940
cgtcgatggc tatcgctggg aaaaaggtta tttatctccc tactttgtca cggaccgtgc  3000
ccgcgaactc gcggaactgg aggatgtcta cctgctcatg accgaccgcg aagtggttga  3060
cttcatcgac cttgtacctc tgctggaggc cgtgacggaa gcaggaggct ccctgctgat  3120
tgccgcggat cgtgtgcacg aaaaggcctt agcggggctg cttctgaatc acgtgcgcgg  3180
tgtcttcaag gccgtggccg taaccgctcc gggttttggc gacaaacgcc cgaaccgttt  3240
acttgacctg gccgcgttaa ccggcggtcg tgccgtgctc gaagctcaag gcgaccgtct  3300
ggaccgtgtt accctcgcgg atctgggccg tgtgcgccgt gccgtggtgt cggcagatga  3360
taccgcgctg cttggcatcc cgggcaccga agctagccgt gcacgcctcg aaggtctgcg  3420
tttagaagca gagcagtacc gtgcgctgaa accagggcag ggttctgcca ccgggcgcct  3480
gcacgaactt gaagaaattg aagcgcgcat tgtgggtctg tccggaaaga gcgccgttta  3540
tcgcgtcgga ggtgtgaccg atgtggaaat gaaagagcgc atggttcgca tcgaaaacgc  3600
ttaccgttcg gtggtaagtg cgctggagga aggcgtgctc cctggcggtg gtgtcggctt  3660
tctgggtagt atgccggtgc ttgcggaatt ggaggcccgc gacgcagatg aagctcgcgg  3720
gattgggatt gtacgcagcg ccttaacgga gcctcttcgt attatcggcg aaaatagtgg  3780
cttgagcggt gaagccgttg ttgccaaagt catggatcat gccaacccgg gatggggtta  3840
cgaccaggag tctggctctt tttgcgacct gcatgcgcgt gggatctggg atgctgctaa  3900
```

```
agtgttacgt ctcgcgttgg agaaggcagc ctctgttgct gggacctttc tgacaaccga  3960
agctgttgtt ctcgaaattc cggatacaga tgcgttcgca gggttcagtg cagaatgggc  4020
tgccgccacg cgcgaagatc cgcgcgtatg agtttaaacg cggccgcaat ttgaacgcac  4080
ccataacaga tacggacttt ctcaaaggag agttatcaat gaatattcgt ccattgcatg  4140
atcgcgtgat cgtcaagcgt aaagaagttg aaactaaatc tgctggcggc atcgttctga  4200
ccggctctgc agcggctaaa tccacccgcg gcgaagtgct ggctgtcggc aatggccgta  4260
tccttgaaaa tggcgaagtg aagccgctgg atgtgaaagt tggcgacatc gttattttca  4320
acgatggcta cggtgtgaaa tctgagaaga tcgacaatga agaagtgttg atcatgtccg  4380
aaagcgacat tctggcaatt gttgaagcgt aatccgcgca cgacactgaa catacgaatt  4440
taaggaataa agataatggc agctaaagac gtaaaattcg gtaacgacgc tcgtgtgaaa  4500
atgctgcgcg gcgtaaacgt actggcagat gcagtgaaag ttaccctcgg tccaaaaggc  4560
cgtaacgtag ttctggataa atctttcggt gcaccgacca tcaccaaaga tggtgtttcc  4620
gttgctcgtg aaatcgaact ggaagacaag ttcgaaaata tgggtgcgca gatggtgaaa  4680
gaagttgcct ctaaagcaaa cgacgctgca ggcgacggta ccaccactgc aaccgtactg  4740
gctcaggcta tcatcactga aggtctgaaa gctgttgctg cgggcatgaa cccgatggac  4800
ctgaaacgtg gtatcgacaa agcggttacc gctgcagttg aagaactgaa agcgctgtcc  4860
gtaccatgct ctgactctaa agcgattgct caggttggta ccatctccgc taactccgac  4920
gaaaccgtag gtaaactgat cgctgaagcg atggacaaag tcggtaaaga aggcgttatc  4980
accgttgaag acggtaccgg tctgcaggac gaactggacg tggttgaagg tatgcagttc  5040
gaccgtggct acctgtctcc ttacttcatc aacaagccgg aaactggcgc agtagaactg  5100
gaaagcccgt tcatcctgct ggctgacaag aaaatctcca acatccgcga aatgctgccg  5160
gttctggaag ctgttgccaa agcaggcaaa ccgctgctga tcatcgctga agatgtagaa  5220
ggcgaagcgc tggcaactct ggttgttaac accatgcgtg gcatcgtgaa agtcgctgcg  5280
gttaaagcac cgggcttcgg cgatcgtcgt aaagctatgc tgcaggatat cgcaaccctg  5340
actggcggta ccgtgatctc tgaagagatc ggtatggagc tggaaaaagc aaccctggaa  5400
gacctgggtc aggctaaacg tgttgtgatc aacaaagaca ccaccactat catcgatggc  5460
gtgggtgaag aagctgcaat ccagggccgt gttgctcaga tccgtcagca gattgaagaa  5520
gcaacttctg actacgaccg tgaaaaactg caggaacgcg tagcgaaact ggcaggcggc  5580
gttgcagtta tcaaagtggg tgctgctacc gaagttgaaa tgaaagagaa aaaagcacgc  5640
gttgaagatg ccctgcacgc gacccgtgct gcggtagaag aaggcgtggt tgctggtggt  5700
ggtgttgcgc tgatccgcgt agcgtctaaa ctggctgacc tgcgtggtca gaacgaagac  5760
cagaacgtgg gtatcaaagt tgcactgcgt gcaatggaag ctccgctgcg tcagatcgta  5820
ttgaactgcg gcgaagaacc gtctgttgtt gctaacaccg ttaaaggcgg cgacggcaac  5880
tacggttaca acgcagcaac cgaagaatac ggcaacatga tcgacatggg tatcctggat  5940
ccaaccaaag taactcgttc tgctctgcag tacgcagctt ctgtggctgg cctgatgatc  6000
accaccgaat gcatggttac cgacctgccg aaaaacgatg cagctgactt aggcgctgct  6060
ggcggtatgg gcggcatggg tggcatgggc ggcatgatgt aagtttaaac gcggccgcaa  6120
tttgaacgcc agcacatgga ctcccagcac atggactctc gagtctacta gcgcagctta  6180
attaacctag gctgctgcca ccgctgagca ataactagca taaccccttg gggcctctaa  6240
acgggtcttg aggggttttt tgctgaaacc tcaggcattt gagaagcaca cggtcacact  6300
gcttccggta gtcaataaac cggtaaacca gcaatagaca taagcggcta tttaacgacc  6360
ctgccctgaa cccgacacca tcgaatggtg caaaaccttt cgcggtatgg catgatagcg  6420
cccggaagag agtcaattca gggtggtgaa tgtgaaacca gtaacgttat acgatgtcgc  6480
agagtatgcc ggtgtctctt atcagaccgt ttcccgcgtg gtgaaccagg ccagccacgt  6540
ttctgcgaaa acgcgggaaa aagtggaagc ggcgatggcg gagctgaatt acattcccaa  6600
ccgcgtggca caacaactgg cgggcaaaca gtcgttgctg attggcgttg ccacctccag  6660
tctggccctg cacgcgccgt cgcaaattgt cgcggcgatt aaatctcgcg ccgatcaact  6720
gggtgccagc gtggtggtgt cgatggtaga acgaagcggc gtcgaagcct gtaaagcggc  6780
ggtgcacaat cttctcgcgc aacgcgtcag tgggctgatc attaactatc cgctggatga  6840
ccaggatgcc attgctgtgg aagctgcctg cactaatgtt ccggcgttat ttcttgatgt  6900
ctctgaccag acacccatca acagtattat tttctcccat gaagacggta cgcgactggg  6960
cgtggagcat ctggtcgcat tgggtcacca gcaaatcgcg ctgttagcgg gcccattaag  7020
ttctgtctcg gcgcgtctgc gtctggctgg ctggcataaa tatctcactc gcaatcaaat  7080
tcagccgata gcggaacggg aaggcgactg gagtgccatg tccggttttc aacaaaccat  7140
gcaaatgctg aatgagggca tcgttcccac tgcgatgctg gttgccaacg atcagatggc  7200
gctgggcgca atgcgcgcca ttaccgagtc cgggctgcgc gttggtgcgg atatttcggt  7260
agtgggatac gacgataccg aagacagctc atgttatatc ccgccgttaa ccaccatcaa  7320
acaggatttt cgcctgctgg ggcaaaccag cgtggaccgc ttgctgcaac tctctcaggg  7380
ccaggcggtg aagggcaatc agctgttgcc cgtctcactg gtgaaaagaa aaaccaccct  7440
ggcgcccaat acgcaaaccg cctctccccg cgcgttggcc gattcattaa tgcagctggc  7500
acgacaggtt tcccgactgg aaagcgggca gtgagcgcaa cgcaattaat gtaagttagc  7560
tcactcatta ggcacaattc tcatgtttga cagcttatca tcgactgcac ggtgcaccaa  7620
tgcttctggc gtcaggcagc catcggaagc tgtggtatgg ctgtgcaggt cgtaaatcac  7680
tgcataattc gtgtcgctca aggcgcactc ccgttctgga taatgttttt tgcgccgaca  7740
tcataacggt tctggcaaat attctgaaat gagctgttga caattaatca tcggctcgta  7800
taatgtgtgg aattgtgagc ggataacaat ttcacacagg aaacagccag tccgtttagg  7860
tgttttcacg agcaattgac caacaaggac gtcaatagag ttaaggaggg aggggatgaa  7920
agccgccgtg gtcgagcaat tcaaaaaacc actccaggtg aaagaggtcg aaaaaccgaa  7980
aattagttac ggtgaagtgc tggttcgtat taagcttgt ggtgtctgcc acaccgatct  8040
gcatgccgca cacggcgatt ggccggtaaa accgaaactg ccgctcatcc ccggccatga  8100
aggcgtaggc gtcatcgagg aagtcggccc gggtgtgaca caccttaaag ttggcgatcg  8160
tgtgggcatt ccctggctgt attcggcgtg tggccactgt gactattgtc tcagcggcca  8220
ggagactctg tgcgaacgcc agcagaacgc cggctacagc gttgatggtg gctacgccga  8280
gtactgtcgt gctgcggcag attacgtggt gaagattcct gataatcttt cctttgaaga  8340
agcggcgccc attttatgcg cgggcgttac cacttataaa gcgctgaaag tcaccggtgc  8400
caaaccaggc gagtgggtgg ccatttatgg aattgggggc ctcggccatg tggcagttca  8460
gtacgctaaa gcaatgggct taaacgtcgt ggcagtggac ttgggagatg aaaagctgga  8520
actggcaaaa caactgggcg cggacctggt agtgaatccg aaacatgatg atgcagcaca  8580
atggattaaa gaaaaagttg gtggcgtgca tgccacggtg gtgacggcag ttagtaaagc  8640
```

```
cgcttttgaa tcggcgtata agtcaatccg ccgcggagga gcatgcgtcc ttgttggtct  8700
gccaccggag gaaatcccca ttccgatttt tgacacagtt ctgaacggcg tcaaaattat  8760
cggttcaatt gttggcaccc gtaaagacct gcaggaagcc ctccagtttg ctgctgaagg  8820
caaagtgaaa actatcgtgg aagttcagcc gcttgagaac attaacgacg tatttgatcg  8880
tatgctgaaa ggacagatta atggacgtgt ggtcctgaaa gtggattgac atgctaaggt  8940
gctggctgca tgctaagttg atacgcctgc gacaaatttt tctaggagcg ttagtatgga  9000
gaacatggat aaggatttac agagcatcca ggaagtacgc acccttatcg caaaggctaa  9060
gaaagcacag gccgaattta agaacttctc tcaagaggcg gttaacaaag tcattgagaa  9120
gatcgcaaaa gccacggagg tagaggccgt gaagcttgcg aagttagctt atgaggatac  9180
aggatacggt aaatgggagg acaaggtaat taaaaacaaa ttttcctcta tcgtagtata  9240
caactatatt aaagacctta agacggtagg tattttgaaa gaggataaag aaaagaagct  9300
tatcgacatc gcggtaccat tgggggtaat cgcgggcctt attccaagta cgaaccctac  9360
tagcaccgcg attttcaagg tattaattgc attgaaggcg ggcaatgcca ttgtgttcag  9420
ccctcaccca acggcggttc gtagcattac tgagaccgtc aaaatcatgc aaaaagcggc  9480
ggtcgaagca ggtgctcctg atggattaat tcagtgcatg tcgattttaa ctgtcgaagg  9540
aaccgctgaa ttgatgaaga acaaggatac cgcactgatt ttagccaccg gggcgaggg  9600
aatggtacgt gctgcctaca gttcaggcac gcctgcgatc ggtgtggggc ccggcaatgg  9660
cccttgcttt attgagcgca ccgctgacat tcctacggct gtccgcaaag tgattggctc  9720
ggatacattc gataatggtg tgatctgcgc atcggagcaa agtattatcg cagagacggt  9780
taaaaaggcc gagatcattg aagaattcaa acgtcagaaa ggttatttct tgaacgccga  9840
agaatcagag aaagtgggaa agattttatt gcgcgccaac gggacaccta acccagcgat  9900
cgtgggaaag gatgtccaag cattagccaa gttagcaggt atttcgatcc cgagcgacgc  9960
ggttatcctg ttatctgaac agacggacgt atcgcccaag aatccgtatg caaaagagaa  10020
actggccccg gtcttagctt tttacactgt ggaagattgg catgaagcct gtgagaagtc  10080
attggccctt ttgcataacc aaggaagcgg gcatacctta atcattcatt ctcagaacga  10140
ggaaattatc cgcgagtttg cgcttaaaaa gccagtaagt cgtatcttgg ttaacagccc  10200
cggctcactt ggaggaattg gaggcgctac gaatttagtc ccaagcctga ctttagggtg  10260
cggtgcagtc ggtggttcag ccaccagcga taatgttggt ccggagaatt tatttaatat  10320
ccgcaaggtg gcttatggta cgacaaccgt tgaagaaatt cgtgaggcct tcggagtggg  10380
tgcagccagc tcaagtgcgc ccgccgagcc ggaggacaat gaagacgttc aagcaattgt  10440
gaaagcaatc atggccaagc ttaatttgta agtttgtcgg tgaacgctct cctgagtagg  10500
acaaatccgc cgggagcgga tttgaacgtt gcgaagcaac ggcccggagg gtggcgggca  10560
ggacgcccgc cataaactgc caggcatcaa attaagcaga aggccatcct gacggatggc  10620
ctttttgcgt ttctacaaac tctttcggtc cgttgtttat ttttctaaat acattcaaat  10680
atgtatccgc tcatgagaca ataaccctga taaatgcttc aataatattg aaaaaggaag  10740
agtatgagta ttcaacattt ccgtgtcgcc cttattccct tttttgcggc attttgcctt  10800
cctgtttttg ctcacccgac gaccgggtca tcgtggc                           10837
```

```
SEQ ID NO: 46           moltype = DNA  length = 16374
FEATURE                 Location/Qualifiers
misc_feature            1..16374
                        note = Synthetic plasmid.
source                  1..16374
                        mol_type = other DNA
                        organism = synthetic construct
SEQUENCE: 46
ccggaaggag ctgactgggt tgaaggctct caagggcatc ggtcgagatc ccggtgccta  60
atgagtgagc taacttttga cggctagctc agtcctaggg ataatgctag caccagcctc  120
gagggaaacc acgtaagctc cggcgtttaa acacccataa cagatacgga ctttctcaaa  180
ggagagttat cagtgaaaat ccgcccgtta catgaccgtg tcatcatcaa acgcttggaa  240
gaagagcgta cctcggcggg cgggattgtc attccagata gcgcagctga aaaaccgatg  300
cgtggtgaaa tcctggcagt gggcaatgga aaagtgcttg ataatggaga ggtacgtgct  360
ttacaggtga aagtgggtga taaagtgctc tttgggaaat acgcgggtac ggaggttaaa  420
gtagatgggg aagatgttgt tgtcatgcgt gaagatgaca ttctggctgt gttagaatct  480
taatccgcgc acgacactga acatacgaat ttaaggaata aagataatgg cgaaagaagt  540
tgtgtatcgt ggtagtgcgc gccagcgtat gatgcagggt attgaaattc tcgctcgcgc  600
cgctattcca acgctggggg caaccggccc gagcgtcatg attcaacatc gcgccgatgg  660
tctgccaccc atttctacac gcgatggcgt taccgtagcg aattctattg ttttaaaaga  720
ccgtgtcgcg aacctgggtg cccgcctgct gcgcgacgta gccggtacaa tgagccgtga  780
agccggcgac ggcacgacga ctgcgatcgt attggcccgc cacatcgccc gtgagatgtt  840
taaatcgctg gccgtgggtg cagatccgat cgcgctgaaa cgtggtatcg atcgcgccgt  900
tgctcgtgtg tccgaagata ttggggcgcg tgcgtggcgt ggcgataaag aaagcgtgat  960
cctgggtgtc gctgctgtgg cgacgaaagg cgaaccgggc gttggccgtc tgctgctgga  1020
ggctctcgat gcagtgggtg ttcacggtgc cgtttctatc gaactgggcc aacgtcgtga  1080
agatctgctg gacgtcgtcg atggctatcg ctgggaaaaa ggttatttat ctccctactt  1140
tgtcacggac cgtgcccgcg aactcgcgga actggaggat gtctacctgc tcatgaccga  1200
ccgcgaagtg gttgacttca tcgaccttgt acctctgctg gaggccgtga cggaagcagg  1260
aggctccctg ctgattgccg cggatcgtgt gcacgaaaag gccttagcgg ggctgcttct  1320
gaatcacgtg cgcggtgtct tcaaggccgt ggccgtaacc gctccgggtt ttggcgacaa  1380
acgcccgaac cgtttacttg acctggccgc gttaaccggc ggtcgtgccg tgctcgaagc  1440
tcaaggcgac cgtctggacc gtgttaccct cgcggatctg ggccgtgtgc gccgtgccgt  1500
ggtgtcggca gatgataccg cgctgcttgg catcccgggc accgaagcta gccgtgcacg  1560
cctcgaaggt ctgcgtttag aagcagagca gtaccgtgcg ctgaaaccag ggcagggttc  1620
tgccaccggg cgcctgcacg aacttgaaga aattgaagcg cgcattgtgg gtctgtccgg  1680
aaagagcgcc gtttatcgcg tcggaggtgt gaccgatgtg gaaatgaaag agcgcatggt  1740
tcgcatcgaa aacgcttacc gttcggtggt aagtgcgctg gaggaaggcg tgctccctgg  1800
cggtggtgtc ggctttctgg gtagtatgcc ggtgcttgcg gaattggagg cccgcgacgc  1860
agatgaagct cgcgggattg ggattgtacg cagcgcctta acggagcctc ttcgtattat  1920
cggcgaaaat agtggcttga gcggtgaagc cgttgttgcc aaagtcatgg atcatgccaa  1980
```

```
cccgggatgg ggttacgacc aggagtctgg ctctttttgc gacctgcatg cgcgtgggat  2040
ctgggatgct gctaaagtgt tacgtctcgc gttggagaag gcagcctctg ttgctgggac  2100
ctttctgaca accgaagctg ttgttctcga aattccggat acagatgcgt tcgcagggtt  2160
cagtgcagaa tgggctgccg ccacgcgcga agatccgcgc gtatgagttt aaacgcggcc  2220
gcaatttgaa cgcacccata acagatacgg actttctcaa aggagagtta tcaatgaata  2280
ttcgtccatt gcatgatcgc gtgatcgtca agcgtaaaga agttgaaact aaatctgctg  2340
gcggcatcgt tctgaccggc tctgcagcgg ctaaatccac ccgcggcgaa gtgctggctg  2400
tcggcaatgg ccgtatcctt gaaaatggcg aagtgaagcc gctggatgtg aaagttggcg  2460
acatcgttat tttcaacgat ggctacggtg tgaaatctga gaagatcgac aatgaagaag  2520
tgttgatcat gtccgaaagc gacattctgg caattgttga agcgtaatcc gcgcacgaca  2580
ctgaacatac gaatttaagg aataaagata atggcagcta aagacgtaaa attcggtaac  2640
gacgctcgtg tgaaaatgct gcgcggcgta aacgtactgg cagatgcagt gaaagttacc  2700
ctcggtccaa aaggccgtaa cgtagttctg gataaatctt tcggtgcacc gaccatcacc  2760
aaagatggtg tttccgttgc tcgtgaaatc gaactggaag acaagttcga aaatatgggt  2820
gcgcagatgg tgaaagaagt tgcctctaaa gcaaacgacg ctgcaggcga cggtaccacc  2880
actgcaaccg tactggctca ggctatcatc actgaaggtc tgaaagctgt tgctgcgggc  2940
atgaacccga tggacctgaa acgtggtatc gacaaagcgg ttaccgctgc agttgaagaa  3000
ctgaaagcgc tgtccgtacc atgctctgac tctaaagcga ttgctcaggt tggtaccatc  3060
tccgctaact ccgacgaaac cgtaggtaaa ctgatcgctg aagcgatgga caaagtcggt  3120
aaagaaggcg ttatcaccgt tgaagacggt accggtctgc aggacgaact ggacgtggtt  3180
gaaggtatgc agttcgaccg tggctacctg tctccttact tcatcaacaa gccggaaact  3240
ggcgcagtag aactggaaag cccgttcatc ctgctggctg acaagaaaat ctccaacatc  3300
cgcgaaatgc tgccggttct ggaagctgtt gccaaagcag gcaaaccgct gctgatcatc  3360
gctgaagatg tagaaggcga agcgctggca actctggttg ttaacaccat gcgtggcatc  3420
gtgaaagtcg ctgcggttaa agcaccgggc ttcggcgatc gtcgtaaagc tatgctgcag  3480
gatatcgcaa ccctgactgg cggtaccgtg atctctgaag agatcggtat ggagctggaa  3540
aaagcaaccc tggaagacct gggtcaggct aaacgtgttg tgatcaacaa agacaccacc  3600
actatcatcg atggcgtggg tgaagaagct gcaatccagg gccgtgttgc tcagatccgt  3660
cagcagattg aagaagcaac ttctgactac gaccgtgaaa aactgcagga acgcgtagcg  3720
aaactggcag gcggcgttgc agttatcaaa gtgggtgctg ctaccgaagt tgaaatgaaa  3780
gagaaaaaag cacgcgttga agatgccctg cacgcgaccc gtgctgcggt agaagaaggc  3840
gtggttgctg gtggtggtgt tgcgctgatc cgcgtagcgt ctaaactggc tgacctgcgt  3900
ggtcagaacg aagaccagaa cgtgggtatc aaagttgcac tgcgtgcaat ggaagctccg  3960
ctgcgtcaga tcgtattgaa ctgcggcgaa gaaccgtctg ttgttgctaa caccgttaaa  4020
ggcggcgacg gcaactacgg ttacaacgca gcaaccgaag aatacggcaa catgatcgac  4080
atgggtatcc tggatccaac caaagtaact cgttctgctc tgcagtacgc agcttctgtg  4140
gctggcctga tgatcaccac cgaatgcatg gttaccgacc tgccgaaaaa cgatgcagct  4200
gacttaggcg ctgctggcgg tatgggcggc atgggtggca tgggcggcat gatgtaagtt  4260
taaacgcggc cgcaatttga acgccagcac atggactccc agcacatgga ctctcgagtc  4320
tactagcgca gcttaattaa cctaggctgc tgccaccgct gagcaataac tagcataacc  4380
ccttggggcc tctaaacggg tcttgagggg ttttttgctg aaacctcagg catttgagaa  4440
gcacacggtc acactgcttc cggtagtcaa taaaccggta aaccagcaat agacataagc  4500
ggtgcataat gtgcctgtca aatggacgaa gcagggattc tgcaaaccct atgctactcc  4560
gtcaagccgt caattgtctg attcgttacc aattatgaca acttgacggc tacatcattc  4620
actttttctt cacaaccggc acggaactcg ctcgggctgg ccccggtgca tttttttaaat  4680
acccgcgaga aatagagttg atcgtcaaaa ccaacattgc gaccgacggt ggcgataggc  4740
atccgggtgg tgctcaaaag cagcttcgcc tggctgatac gttggtcctc gcgccagctt  4800
aagacgctaa tccctaactg ctggcggaaa agatgtgaca gacgcgacgg cgacaagcaa  4860
acatgctgtg cgacgctggc gatatcaaaa ttgctgtctg ccaggtgatc gctgatgtac  4920
tgacaagcct cgcgtacccg attatccatc ggtggatgga gcgactcgtt aatcgcttcc  4980
atgcgccgca gtaacaattg ctcaagcaga tttatcgcca gcagctccga atagcgccct  5040
tccccttgcc cggcgttaat gatttgccca aacaggtcgc tgaaatgcgg ctggtgcgct  5100
tcatccgggc gaaagaaccc cgtattggca aatattgacg gccagttaag ccattcatgc  5160
cagtaggcgc gcggacgaaa gtaaacccac tggtgatacc attcgcgagc ctccggatga  5220
cgaccgtagt gatgaatctc tcctggcggg aacagcaaaa tatcacccgg tcggcaaaca  5280
aattctcgtc cctgattttt caccaccccc tgaccgcgaa tggtgagatt gagaatataa  5340
cctttcattc ccagcggtcg gtcgataaaa aaatcgagat aaccgttggc ctcaatcggc  5400
gttaaacccg ccaccagatg ggcattaaac gagtatcccg gcagcagggg atcattttgc  5460
gcttcagcca tacttttcat actcccgcca ttcagagaag aaaccaattg tccatattgc  5520
atcagacatt gccgtcactg cgtcttttac tggctcttct cgctaaccaa accggtaacc  5580
ccgcttatta aaagcattct gtaacaaagc gggaccaaag ccatgacaaa aacgcgtaac  5640
aaaagtgtct ataatcacgg cagaaaagtc cacattgatt atttgcacgg cgtcacactt  5700
tgctatgcca tagcattttt atccataaga ttagcggatc ctacctgacg ctttttatcg  5760
caactctcta ctgtttctcc atacccgttt ttttgggcga cctcgtcgga ggttgtatgt  5820
ccggtgttcc gtgacgtcat cgggcattca tcattcatag aatgtgttac ggaggaaaca  5880
agtaatggca cttagcaccg caaccaaggc cgcgacggac gcgctggctg ccaatcgggc  5940
acccaccagc gtgaatgcac aggaagtgca ccgttggctc cagagcttca actgggattt  6000
caagaacaac cggaccaagt acgccaccaa gtacaagatg gcgaacgaga ccaaggaaca  6060
gttcaagctg atcgccaagg aatatgcgcg catggaggca gtcaaggacg aaaggcagtt  6120
cggtagcctg caggatgcgc tgacccgcct caacgccggt gttcgcgttc atccgaagtg  6180
gaacgagacc atgaaagtgg tttcgaactt cctggaagtg ggcgaataca acgccatcgc  6240
cgctaccggg atgctgtggg attccgccca ggcggcggaa cagaagaacg gctatctggc  6300
ccaggtgttg gatgaaatcc gccacaccca ccagtgtgcc tacgtcaact actacttcgc  6360
gaagaacggc caggacccgg ccggtcacaa cgatgctcgc cgcacccgta ccatcggtcc  6420
gctgtggaag ggcatgaagc gcgtgtttc cgacggcttc atttccggcg acgccgtgga  6480
atgctccctc aacctgcagc tggtgggtga ggcctgcttc accaatccgc tgatcgtcgc  6540
agtgaccgaa tgggctgccg ccaacggcga tgaaatcacc ccgacggtgt tcctgtcgat  6600
cgagaccgac gaactgcgcc acatggccaa cggttaccag accgtcgttt ccatcgccaa  6660
cgatccggct tccgccaagt atctcaacac ggacctgaac aacgccttct ggacccagca  6720
```

```
gaagtacttc acgccggtgt tgggcatgct gttcgagtat ggctccaagt tcaaggtcga  6780
gccgtgggtc aagacgtgga accgctgggt gtacgaggac tggggcggca tctggatcgg  6840
ccgtctgggc aagtacgggg tggagtcgcc gcgcagcctc aaggacgcca agcaggacgc  6900
ttactgggct caccacgacc tgtatctgct ggcttatgcg ctgtggccga ccggcttctt  6960
ccgtctggcg ctgccggatc aggaagaaat ggagtggttc gaggccaact accccggctg  7020
gtacgaccac tacggcaaga tctacgagga atggcgcgcc cgcggttgcg aggatccgtc  7080
ctcgggcttc atcccgctga tgtggttcat cgaaaacaac catcccatct acatcgatcg  7140
cgtgtcgcaa gtgccgttct gcccgagctt ggccaagggc gccagcaccc tgcgcgtgca  7200
cgagtacaac ggccagatgc acaccttcag cgaccagtgg ggcgagcgca tgtggctggc  7260
cgagccggag cgctacgagt gccagaacat cttcgaacag tacgaaggac gcgaactgtc  7320
ggaagtgatc gccgaactgc acgggctgcg cagtgatggc aagaccctga tcgcccagcc  7380
gcatgtccgt ggcgacaagc tgtggacgtt ggacgatatc aaacgcctga actgcgtctt  7440
caagaacccg gtgaaggcat tcaattgaaa cgggtgtcgg gctccgtcac agggcggggc  7500
ccgacgcacg atcgttcgat caacctcaaa ccaaaaagga acatcgatat gagcatgtta  7560
ggagaaagac gccgcggtct gaccgatccg gaaatggcgg ccgtcatttt gaaggcgctt  7620
cctgaagctc cgctggacgg caacaacaag atgggttatt tcgtcacccc ccgctggaaa  7680
cgcttgacgg aatatgaagc cctgaccgtt tatgcgcagc ccaacgccga ctggatcgcc  7740
ggcggcctgg actggggcga ctggacccag aaattccacg gcggccgccc ttcctggggc  7800
aacgagacca cggagctgcg caccgtcgac tggttcaagc accgtgaccc gctccgccgt  7860
tggcatgcgc cgtacgtcaa ggacaaggcc gaggaatggc gctacaccga ccgcttcctg  7920
cagggttact ccgccgacgg tcagatccgg gcgatgaacc cgacctggcg ggacgagttc  7980
atcaaccggt attggggcgc cttcctgttc aacgaatacg gattgttcaa cgctcattcg  8040
cagggcgccc gggaggcgct gtcggacgta acccgcgtca gcctggcttt ctggggcttc  8100
gacaagatcg acatcgccca gatgatccaa ctcgaacggg gtttcctcgc caagatcgta  8160
cccggtttcg acgagtccac agcggtgccg aaggccgaat ggacgaacgg ggaggtctac  8220
aagagcgccc gtctggccgt ggaagggctg tggcaggagg tgttcgactg gaacgagagc  8280
gctttctcgg tgcacgccgt ctatgacgcg ctgttcggtc agttcgtccg ccgcgagttc  8340
tttcagcggc tggctccccg cttcggcgac aatctgacgc cattcttcat caaccaggcc  8400
cagacatact tccagatcgc caagcagggc gtacaggatc tgtattacaa ctgtctgggt  8460
gacgatccgg agttcagcga ttacaaccgt accgtgatgc gcaactggac cggcaagtgg  8520
ctggagccca cgatcgccgc tctgcgcgac ttcatggggc tgtttgcgaa gctgccggcg  8580
ggcaccactg acaaggaaga aatcaccgcg tccctgtacc gggtggtcga cgactggatc  8640
gaggactacg ccagcaggat cgacttcaag gcggaccgcg atcagatcgt taaagcggtt  8700
ctggcaggat tgaaataata gaggaactat tacgatgagc gtaaacagca acgcatacga  8760
cgccggcatc atgggcctga aaggcaagga cttcgccgat cagttctttg ccgacgaaaa  8820
ccaagtggtc catgaaagcg acacggtcgt tctggtcctc aagaagtcgg acgagatcaa  8880
tacctttatc gaggagatcc ttctgacgga ctacaagaag aacgtcaatc cgacggtaaa  8940
cgtggaagac cgcgcgggtt actggtggat caaggccaac ggcaagatcg aggtcgattg  9000
cgacgagatt tccgagctgt tggggcggca gttcaacgtc tacgacttcc tcgtcgacgt  9060
ttcctccacc atcggccggg cctataccct gggcaacaag ttcaccatta ccagtgagct  9120
gatgggcctg gaccgcaagc tcgaagacta tcacgcttaa ggagaatgac atggcgaaac  9180
tgggtataca cagcaacgac acccgcgacg cctgggtgaa caagatcgcg cagctcaaca  9240
ccctggaaaa agcggccgag atgctgaagc agttccggat ggaccacacc acgccgttcc  9300
gcaacagcta cgaactggac aacgactacc tctggatcga ggccaagctc gaagagaagg  9360
tcgccgtcct caaggcacgc gccttcaacg aggtggactt ccgtcataag accgctttcg  9420
gcgaggatgc caagtccgtt ctggacggca ccgtcgcgaa gatgaacgcg gccaaggaca  9480
agtgggaggc ggagaagatc catatcggtt tccgccaggc ctacaagccg ccgatcatgc  9540
cggtgaacta tttcctggac ggcgagcgtc agttggggac ccggctgatg gaactgcgca  9600
acctcaacta ctacgacacg ccgctggaag aactgcgcaa acagcgcggt gtgcgggtgg  9660
tgcatctgca gtcgccgcac tgaagggagg aagtctcgcc ctggacgcga cggcatcgcc  9720
gtgaagtcca gggggcaggg atgccgttcc gggccggcag gctggcccgg aatctctggt  9780
tttcaggggg cgtgccggtc cacggctccc ccctccatct ttcgtaagga aatcaccatg  9840
gtcgaatcgg catttcagcc attttcgggc gacgcagacg aatggttcga ggaaccacgg  9900
ccccaggccg gtttcttccc ttccgcggac tggcatctgc tcaaacggga cgagacctac  9960
gcagcctatg ccaaggatct cgatttcatg tggcggtggg tcatcgtccg ggaagaaagg  10020
atcgtccagg agggttgctc gatcagcctg gagtcgtcga tccgcgccgt gacgcacgta  10080
ctgaattatt ttggtatgac cgaacaacgc gccccggcag aggaccggac cggcggagtt  10140
caacattgaa caggtaagtt tatgcagcga gttcacacta tcacggcggt gacggaggat  10200
ggcgaatcgc tccgcttcga atgccgttcg gacgaggacg tcatcaccgc cgccctgcgc  10260
cagaacatct ttctgatgtc gtcctgccgg gagggcggct gtgcgacctg caaggccttg  10320
tgcagcgaag ggactacgga cctcaagggc tgcagcgttc aggcgctgcc gccggaagag  10380
gaggaggaag ggttggtgtt gttgtgccgg acctacccga agaccgacct ggaaatcgaa  10440
ctgccctata cccattgccg catcagtttt ggtgaggtcg gcagtttcga ggcggaggtc  10500
gtcggcctca actgggtttc gagcaacacc gtccagtttc ttttgcagaa gcggcccgac  10560
gagtgcggca accgtggcgt gaaattcgaa cccggtcagt tcatggacct gaccatcccc  10620
ggcaccgatg tctcccgctc ctactcgccg gcgaaccttc ctaatcccga aggccgcctg  10680
gagttcctga tccgcgtgtt accggaggga cggttttcgg actacctgcg caatgacgcg  10740
cgtgtcggac aggtcctctc ggtcaaaggg ccactgggcg tgttcggtct caaggagcgg  10800
ggcatggcgc cgcgctattt cgtggccggc ggcaccgggt tggcgccggt ggtctcgatg  10860
gtgcggcaga tgcaggagtg gaccgcgccg aacgagaccc gcatctattt cggtgtgaac  10920
accgagccgg aattgttcta catcgacgag ctcaaatccc tggaacgatc gatgcgcaat  10980
ctcaccgtga aggcctgtgt ctggcacccg agcggggact gggaaggcga gcagggctcg  11040
cccatcgatg cgttgcggga agacctggag tcctccgacg ccaacccgga catttatttg  11100
tgcggtccgc cgggcatgat cgatgccgcc tgcgagctgg tacgcagccg cggtatcccc  11160
ggcgaacagg tcttcttcga aaaattcctg ccgtccgggg cggcctgaac cggggaagta  11220
ccgtgaccac cgagcagttc ccgccccaat tcctgcgtga aatgatcgag cagctggacg  11280
ccagcatcca ggagctcgca cgcaaggaaa agggacttgc ggcatccctg ggcacgggcc  11340
gggtcgccga gctcaaggaa tactgggacc acgttgttac aaccaattaa ccaattctga  11400
ctatttaacg accctgccct gaaccgacga ccgggtcatc gtggccggat cttgcggccc  11460
```

```
ctcggcttga acgaattgtt agacattatt tgccgactac cttggtgatc tcgcctttca  11520
cgtagtggac aaattcttcc aactgatctg cgcgcgaggc caagcgatct tcttcttgtc  11580
caagataagc ctgtctagct tcaagtatga cgggctgata ctgggccggc aggcgctcca  11640
ttgcccagtc ggcagcgaca tccttcggcg cgattttgcc ggttactgcg ctgtaccaaa  11700
tgcgggacaa cgtaagcact acatttcgct catcgccagc ccagtcgggc ggcgagttcc  11760
atagcgttaa ggtttcattt agcgcctcaa atagatcctg ttcaggaacc ggatcaaaga  11820
gttcctccgc cgctggacct accaaggcaa cgctatgttc tcttgctttt gtcagcaaga  11880
tagccagatc aatgtcgatc gtggctggct cgaagatacc tgcaagaatg tcattgcgct  11940
gccattctcc aaattgcagt tcgcgcttag ctggataacg ccacggaatg atgtcgtcgt  12000
gcacaacaat ggtgacttct acagcgcgga gaatctcgct ctctccaggg gaagccgaag  12060
tttccaaaag gtcgttgatc aaagctcgcc gcgttgtttc atcaagcctt acggtcaccg  12120
taaccagcaa atcaatatca ctgtgtggct tcaggccgcc atccactgcg gagccgtaca  12180
aatgtacggc cagcaacgtc ggttcgagat ggcgctcgat gacgccaact acctctgata  12240
gttgagtcga tacttcggcg atcaccgctt ccctcatact cttccttttt caatattatt  12300
gaagcattta tcagggttat tgtctcatga gcggatacat atttgaatgt atttagaaaa  12360
ataaacaaat agctagctca ctcggtcgct acgctccgct aggtcgttcg gctgcaacaa  12420
caagacccat catagtttgc cccgcgacta ttgaccataa attcatcgca caaaatatcg  12480
aacggggttt atgccgcttt tagtgggtgc gaagaatagt ctgctcatta cccgcgaaca  12540
ccgccgcatt cagatcacgc ttagtagcgt ccccatgagt aggcagaacc gcgtccaagt  12600
ccacatcatc cataacgatc atgcacgggg tggaatccac acccagactt gccagcacct  12660
cattagcgac acgttgcgca gcggccacgt ccttagcctt atccacgcaa tctagaacgt  12720
actgcctaac cgcgaaatca gactgaatca gtttccaatc atcgggcttc accaaagcaa  12780
cagcaacgcg ggttgattcg acccgttccg gtgcttccag accggcgagc ttgtacagtt  12840
cttcttccat ttcacgacgt acatcagcgt ctatgtaatc aatgcccaaa gcacgcttag  12900
ccccacgtga ccaggacgaa cgcaggtttt tagaaccaac ctcatactca cgccaccgag  12960
ccaccaaaac agcgtccata tcctcgccgg cgtcgctttg atcggccaac atatccaaca  13020
tctgaaacgg cgtgtacgac cccttagacg cggttttagt agcggagcca gtcagttcct  13080
gagacatgcc cttagcgagg taggttgcca ttttcgcagc gtctccaccc caggtagaca  13140
cctgatcaag tttgaccccg tgctcacgca gtggcgcgtc cataccggcc ttaaccacac  13200
cagcagacca gcgggaaaac atggaatcct caaacgcctt gagttcatcg tcagacagtg  13260
gacgatccaa gaacaacagc atgttgcggt gcaagtgcca accgttcgcc caagagtctg  13320
tgacctcata gtcactatag gtgtgctcca ccccgtaccg tgcacgttct ttcttccact  13380
gagatgtttt caccatcgaa gagtacgcag tcttaatacc cgcttcaacc tgcgcaaatg  13440
actgtgagcg gttgtgtcga acagtgccca caaacatcat gagcgcgcca cccgccgcca  13500
agtgattctt agtagcaata gccagctcaa tgcggcgttc gcccatgact tccaattcag  13560
ccagaggtga cccccagcga gagtgagagt tttgcagacc ctcaaactgc gaagcaccgt  13620
tagacgacca ggacaccgca acagcttcgt ccctgcgcca cctatggcac cccgccagag  13680
ccttactatt ggtgatcttg tacatgacgt tttgcctacg ccacgcccta gcgcgagtga  13740
ccttagaacc ctcattgacc tgcggttcct tagaggtgtt cacttctatt tcagtgttac  13800
ctagacccga tgttgtgcgg ggttgcgcag tgcgagtttg tgcgggtgtt gtgcccgttg  13860
tcttagctag tgctatggtt gtcaattgaa accccttcgg gttatgtggc ccccgtgcat  13920
atgagttggt agctcgcacg gggtttgtc ttgtctaggg actattaatt tttagtggtg  13980
tttggtggcc gcctagcttg gctatgcgtg ccagcttacc cgtactcaat gttaaagatt  14040
tgcatcgaca tgggagggtt acgtgtccga tacctagggg gggtatccgc gactaggtgc  14100
cccggtgctc actgtctgta ccggcggggc aagccccaca ccccgcatgg acagggtggc  14160
tccgcccccct gcacccccag caatctgcat gtacatgttt tacacattag cacgacatga  14220
ctgcatgtgc atgcggcgag cggtatcagc tcacctgtca gaccaagttt actcatatat  14280
actttagatt gatttaaaac ttcattttta atttaaaagg atctaggtga agatcctttt  14340
tgataatctc atgaccaaaa tcccttaacg tgagttttcg ttccactgag cgtcagaccc  14400
cttaataaga tgatcttctt gagatcgttt tggtctgcgc gtaatctctt gctctgaaaa  14460
cgaaaaaacc gccttgcagg gcggtttttc gaaggttctc tgagctacca actctttgaa  14520
ccgaggtaac tggcttggag gagcgcagtc accaaaactt gtcctttcag tttagcctta  14580
accggcgcat gacttcaaga ctaactcctc taaatcaatt accagtggct gctgccagtg  14640
gtgcttttgc atgtctttcc gggttggact caagacgata gttaccggat aaggcgcagc  14700
ggtcggactg aacggggggt tcgtgcatac agtccagctt ggagcgaact gcctacccgg  14760
aactgagtgt caggcgtgga atgagacaaa cgcggccata acagcggaat gacaccggta  14820
aaccgaaagg caggaacagg agagcgcacg agggagccgc caggggggaaa cgcctggtat  14880
ctttatagtc ctgtcgggtt tcgccaccac tgatttgagc gtcagatttc gtgatgcttg  14940
tcaggggggc ggagcctatg gaaaaacggc tttgccgcgg ccctctcact tccctgttaa  15000
gtatcttcct ggcatcttcc aggaaatctc cgccccgttc gtaagccatt tccgctcgcc  15060
gcagtcgaac gaccgagcgt agcgagtcag tgagcgagga agcggaatat atcctgtatc  15120
acatattctg ctgacgcacc ggtgcagcct tttttctcct gccacatgaa gcacttcact  15180
gacaccctca tcagtgccaa catagtaagc cagtatacac tccgctagcg ctgaggtctg  15240
cctcgtgaag aaggtgttgc tgactcatac caggcctgaa tcgccccatc atccagccag  15300
aaagtgaggg agccacggtt gatgagagct ttgttgtagg tggaccagtt ggtgattttg  15360
aacttttgct ttgccacgga acggtctgcg ttgtcgggaa gatgcgtgat ctgatccttc  15420
aactcagcaa aagttcgatt tattcaacaa agccacgttg tgtctcaaaa tctctgatgt  15480
tacattgcac aagataaaaa tatatcatca tgaacaataa aactgtctgc ttacataaac  15540
agtaatacaa ggggtgttat gagccatatt caacgggaaa cgtcttgctc gaggccgcga  15600
ttaaattcca acatggatgc tgatttatat gggtataaat gggctcgcga taatgtcggg  15660
caatcaggtg cgacaatcta tcgattgtat gggaagcccg atgcgccaga gttgtttctg  15720
aaacatggca aaggtagcgt tgccaatgat gttacagatg agatggtcag actaaactgg  15780
ctgacggaat ttatgcctct tccgaccatc aagcatttta tccgtactcc tgatgatgca  15840
tggttactca ccactgcgat ccccgggaaa acagcattcc aggtattaga agaatatcct  15900
gattcaggtg aaaatattgt tgatgcgctg gcagtgttcc tgcgccggtt gcattcgatt  15960
cctgtttgta attgtccttt taacagcgat cgcgtatttc gtctcgctca ggcgcaatca  16020
cgaatgaata acggtttggt tgatgcgagt gattttgatg acgagcgtaa tggctggcct  16080
gttgaacaag tctggaaaga aatgcataag cttttgccat tctcaccgga ttcagtcgtc  16140
actcatggtg atttctcact tgataacctt atttttgacg aggggaaatt aataggttgt  16200
```

```
attgatgttg gacgagtcgg aatcgcagac cgataccagg atcttgccat cctatggaac  16260
tgcctcggtg agttttctcc ttcattacag aaacggcttt ttcaaaaata tggtattgat  16320
aatcctgata tgaataaatt gcagtttcat ttgatgctcg atgagttttt ctaa        16374

SEQ ID NO: 47          moltype = DNA  length = 7515
FEATURE                Location/Qualifiers
misc_feature           1..7515
                       note = Synthetic plasmid.
source                 1..7515
                       mol_type = other DNA
                       organism = synthetic construct
SEQUENCE: 47
tgtaatgatt ttgtgaacag cctatactgc cgccaggtct ccggaacacc ctgcaatccc  60
gagccaccca gcgttgtaac gtgtcgtttt cgcatctgga agcagtgttt tgcatgacgc  120
gcagttatag aaaggacgct gtctgacccg caagcagacc ggaggaagga aatcccgacg  180
tctccaggta acagaaagtt aacctctgtg cccgtagtcc ccagggaata ataagaacag  240
catgtgggcg ttattcatga taagaaatgt gaaaaaacaa agacctgtta atctggacct  300
acagaccatc cggttcccca tcacggcgat agcgtccatt ctccatcgcg tttccggtgt  360
gatcaccttt gttgcagtgg gcatcctgct gtggcttctg ggtaccagcc tctcttcccc  420
tgaaggtttc gagcaagctt ccgcgattat gggcagcttc ttcgtcaaat ttatcatgtg  480
gggcatcctt accgctctgg cgtatcacgt cgtcgtaggt attcgccaca tgatgatgga  540
ttttggctat ctggaagaaa cattcgaagc gggtaaacgc tccgccaaaa tctcctttgt  600
tattactgtc gtgctttcac ttctcgcagg agtcctcgta tggtaagcaa cgcctccgca  660
ttaggacgca atggcgtaca tgatttcatc ctcgttcgcg ctaccgctat cgtcctgacg  720
ctctacatca tttatatggt cggtttttc gctaccagtg gcgagctgac atatgaagtc  780
tggatcggtt tcttcgcctc tgcgttcacc aaagtgttca ccctgctggc gctgttttct  840
atcttgatcc atgcctggat cggcatgtgg caggtgttga ccgactacgt taaaccgctg  900
gctttgcgcc tgatgctgca actggtgatt gtcgttgcac tggtggttta cgtgatttat  960
ggattcgttg tggtgtgggg tgtgtgatga aattgccagt cagagaattt gatgcagttg  1020
tgattggtgc cggtggcgca ggtatgcgcg cggcgctgca aatttcccag agcggccaga  1080
cctgtgcgct gctctctaaa gtcttcccga cccgttccca taccgtttct gcgcaaggcg  1140
gcattaccgt tgcgctgggt aatacccatg aagataactg ggaatggcat atgtacgaca  1200
ccgtgaaagg gtcggactat atcggtgacc aggacgcgat tgaatatatg tgtaaaaccg  1260
ggccggaagc gattctggaa ctcgaacaca tgggcctgcc gttctcgcgt ctcgatgatg  1320
gtcgtatcta tcaacgtccg tttggcggtc agtcgaaaaa cttcggcggc gagcaggcgg  1380
cacgcactgc ggcagcagct gaccgtaccg gtcacgcact gttgcacacg ctttatcagc  1440
agaacctgaa aaaccacacc accattttct ccgagtggta tgcgctggat ctggtgaaaa  1500
accaggatgg cgcggtggtg ggttgtaccg cactgtgcat cgaaaccggt gaagtggttt  1560
atttcaaagc ccgcgctacc gtgctggcga ctggcggagc agggcgtatt tatcagtcca  1620
ccaccaacgc ccacattaac accggcgacg gtgtcggcat ggctatccgt gccggcgtac  1680
cggtgcagga tatggaaatg tggcagttcc acccgaccgg cattgccggt gcgggcgtac  1740
tggtcaccga aggttgccgt ggtgaaggcg gttatctgct gaacaaacat ggcgaacgtt  1800
ttatggagcg ttatgcgccg aacgccaaag acctggcggg ccgtgacgtg gttgcgcgtt  1860
ccatcatgat cgaaatccgt gaaggtcgcg gctgtgatgg tccgtggggg ccacacgcga  1920
aactgaaact cgatcacctg ggtaaagaag ttctcgaatc ccgtctgccg ggtatcctgg  1980
agctttcccg taccttcgct cacgtcgatc cggtgaaaga gccgattccg gttatcccaa  2040
cctgtcacta catgatgggc ggtattccga ccaaagttac cggtcaggca ctgactgtga  2100
atgagaaagg cgaagatgtg gttgttccgg gactgtttgc cgttggtgaa atcgcttgtg  2160
tatcggtaca cggcgctaac cgtctgggcg gcaactcgct gctggacctg gtggtctttg  2220
gtcgcgcggc aggtctgcat ctgcaagagt ctatcgccga gcagggcgca ctgcgcgatg  2280
ccagcgagtc tgatgttgaa gcgtctctgg atcgcctgaa ccgctggaac aataatcgta  2340
acggtgaaga tccggtggcg atccgtaaag cgctgcaaga atgtatgcag cataacttct  2400
cggtcttccg tgaaggtgat gcgatggcga aagggcttga gcagttgaaa gtgatccgcg  2460
agcgtctgaa aaatgcccgt ctggatgaca cttccagcga gttcaacacc cagcgcgttg  2520
agtgcctgga actggataac ctgatggaaa cggcgtatgc aacggctgtt tctgccaact  2580
tccgtaccga aagccgtggc gcgcatagcc gcttcgactt cccggatcgt gatgatgaaa  2640
actggctgtg ccactccctg tatctgccag agtcggaatc catgacgcgc cgaagcgtca  2700
acatggaacc gaaactgcgc ccggcattcc cgccgaagat tcgtacttac taatgcggag  2760
acaggaaaat gagactcgag ttttcaattt atcgctataa cccggatgtt gatgatgctc  2820
cgcgtatgca ggattacacc ctggaagcgg atgaaggtcg cgacatgatg ctgctggatg  2880
cgcttatcca gctaaaagag aaagatccca gcctgtcgtt ccgccgctcc tgccgtgaag  2940
gtgtgtgcgg ttccgacggt ctgaacatga acggcaagaa tggtctggcc tgtattaccc  3000
cgatttcggc actcaaccag ccgggcaaga agattgtgat tcgcccgctg ccaggtttac  3060
cggtgatccg cgatttggtg gtagacatgg gacaattcta tgcgcaatat gagaaaatta  3120
agccttacct gttgaataat ggacaaaatc cgccagctcg cgagcattta cagatgccag  3180
agcagcgcga aaaactcgac gggctgtatg aatgtattct ctgcgcatgt tgttcaacct  3240
cttgtccgtc tttctggtgg aatcccgata agtttatcgg cccggcaggc ttgttagcgg  3300
catatcgttt cctgattgat agccgtgata ccgagactga cagccgcctc gacggtttga  3360
gtgatgcatt cagcgtattc cgctgtcaca gcatcatgaa ctgcgtcagt gtatgtccga  3420
aggggctgaa cccgacgcgc gccatcggcc atatcaagtc gatgttgttg caacgtaatg  3480
cgtaaacctg tttcctgtgt gaaattgtta tccgctcaca attccacaca ttatacgagc  3540
cggatgatta attgtcaagt gtaggctgga gctgcttcga agttcctata ctttctagag  3600
aataggaact tcggaatagg aacttcattt aaatggcgcg ccttacgccc cgccctgcca  3660
ctcatcgcag tactgttgta ttcattaagc atctgccgac atggaagcca tcacaaacgg  3720
catgatgaac ctgaatcgcc agcggcatca gcaccttgtc gccttgcgta taatatttgc  3780
ccatggtgaa aacgggggcg aagaagttgt ccatattggc cacgtttaaa tcaaaactgg  3840
tgaaactcac ccagggattg gctgagacga aaaacatatt ctcaataaac cctttaggga  3900
aataggccag gttttcaccg taacacgcca catcttgcga atatatgtgt agaaactgcc  3960
ggaaatcgtc gtggtattca ctccagagcg atgaaaacgt ttcagtttgc tcatggaaaa  4020
```

```
cggtgtaaca agggtgaaca ctatcccata tcaccagctc accgtctttc attgccatac  4080
gtaattccgg atgagcattc atcaggcggg caagaatgtg aataaaggcc ggataaaact  4140
tgtgcttatt tttctttacg gtctttaaaa aggccgtaat atccagctga acggtctggt  4200
tataggtaca ttgagcaact gactgaaatg cctcaaaatg ttctttacga tgccattggg  4260
atatatcaac ggtggtatat ccagtgattt ttttctccat tttagcttcc ttagctcctg  4320
aaaatctcga caactcaaaa aatacgcccg gtagtgatct tatttcatta tggtgaaagt  4380
tggaacctct tacgtgccga tcaacgtctc attttcgcca aaagttggcc cagggcttcc  4440
cggtatcaac agggacacca ggatttattt attctgcgaa gtgatcttcc gtcacaggta  4500
ggcgcgccga agttcctata ctttctagag aataggaact tcggaatagg aactaaggag  4560
gatattcata tggaccatgg ctaattccca tgtcggttcc ttcgcgagcc actacgtaga  4620
caagagctcg caagtgaacc ccggcacgca catcactgtg cgtggtagta tccacggcga  4680
agtaagcata aaaaagatgc ttaagggatc acgatgcaga acagcgcttt gaaagcctgg  4740
ttggactctt cttacctctc tggcgcaaac cagagctgga tagaacagct ctatgaagac  4800
ttcttaaccg atcctgactc ggttgacgct aactggcgtt cgacgttcca gcagttacct  4860
ggtacgggag tcaaaccgga tcaattccac tctcaaacgc gtgaatattt ccgccgcctg  4920
gcgaaagacg cttcacgtta ctcttcaacg atctccgacc ctgacaccaa tgtgaagcag  4980
gttaaagtcc tgcagctcat taacgcatac cgcttccgtg gtcaccagca tgcgaatctc  5040
gatccgctgg gactgtggca gcaagataaa gtggccgatc tggatccgtc tttccacgat  5100
ctgaccgaag cagacttcca ggagaccttc aacgtcggtt catttgccag cggcaaagaa  5160
accatgaaac tcggcgagct gctggaagcc ctcaagcaaa cctactgcgg cccgattggt  5220
gccgagtata tgcacattac cagcaccgaa gaaaaacgct ggatccaaca gcgtatcgag  5280
tctggtcgcg cgactttcaa tagcgaagag aaaaaacgct tcttaagcga actgaccgcc  5340
gctgaaggtc ttgaacgtta cctcggcgca aaattccctg gcgcaaaacg cttctcgctg  5400
gaaggcggtg acgcgttaat cccgatgctt aaagagatga tccgccacgc tggcaacagc  5460
ggcacccgcg aagtggttct cgggatggcg caccgtggtc gtctgaacgt gctggtgaac  5520
gtgctgggta aaaaaccgca agacttgttc gacgagttcg ccggtaaaca taaagaacac  5580
ctcggcacgg gtgacgtgaa ataccacatg ggcttctcgt ctgacttcca gaccgatggc  5640
ggcctggtgc acctggcgct ggcgtttaac ccgtctcacc ttgagattgt aagcccggta  5700
gttatcggtt ctgttcgtgc ccgtctggac agacttgatg agccgagcag caacaaagtg  5760
ctgccaatca ccatccacgg tgacgccgca gtgaccgggc agggcgtggt tcaggaaacc  5820
ctgaacatgt cgaaagcgcg tggttatgaa gttggcggta cggtacgtat cgttatcaac  5880
aaccaggttg gtttcaccac ctctaatccg ctggatgccc gttctacgcc gtactgtact  5940
gatatcggta agatggttca ggccccgatt ttccacgtta acgcggacga tccggaagcc  6000
gttgcctttg tgacccgtct ggcgctcgat ttccgtaaca cctttaaacg tgatgtcttc  6060
atcgacctgg tgtgctaccg ccgtcacggc cacaacgaag ccgacgagcc gagcgcaacc  6120
cagccgctga tgtatcagaa aatcaaaaaa catccgacac cgcgcaaaat ctacgctgac  6180
aagctggagc aggaaaaagt ggcgacgctg gaagatgcca ccgagatggt taacctgtac  6240
cgcgatgcgc tggatgctgg cgattgcgta gtggcagagt ggcgtccgat gaacatgcac  6300
tctttcacct ggtcgccgta cctcaaccac gaatgggacg aagagtaccc gaacaaagtt  6360
gagatgaagc gcctgcagga gctggcgaaa cgcatcagca cggtgccgga agcagttgaa  6420
atgcagtctc gcgttgccaa gatttatggc gatcgccagg cgatggctgc cggtgagaaa  6480
ctgttcgact ggggcggtgc ggaaaacctc gcttacgcca cgctggttga tgaaggcatt  6540
ccggttcgcc tgtcgggtga agactccggt cgcggtacct tcttccaccg ccacgcggtg  6600
atccacaacc agtctaacgg ttccacttac acgccgctgc aacatatcca taacgggcag  6660
ggcgcgttcc gtgtctggga ctccgtactg tctgaagaag cagtgctggc gtttgaatat  6720
ggttatgcca ccgcagaacc acgcactctg accatctggg aagcgcagtt cggtgacttc  6780
gccaacggtg cgcaggtggt tatcgaccag ttcatctcct ctggcgaaca gaaatggggc  6840
cggatgtgtg gtctggtgat gttgctgccg cacggttacg aagggcaggg gccggagcac  6900
tcctccgcgc gtctggaacg ttatctgcaa ctttgtgctg agcaaaacat gcaggtttgc  6960
gtaccgtcta ccccggcaca ggtttaccac atgctgcgtc gtcaggcgct gcgcgggatg  7020
cgtcgtccgc tggtcgtgat gtcgccgaaa tccctgctgc gtcatccgct ggcggtttcc  7080
agcctcgaag aactggcgaa cggcaccttc ctgccagcca tcggtgaaat cgacgagctt  7140
gatccgaagg gcgtgaagcg cgtagtgatg tgttctggta aggtttatta cgacctgctg  7200
gaacagcgtc gtaagaacaa tcaacacgat gtcgccattg tgcgtatcga gcaactctac  7260
ccgttcccgc ataaagcgat gcaggaagtg ttgcagcagt ttgctcacgt caaggatttt  7320
gtctggtgcc aggaagagcc gctcaaccag ggcgcatggt actgcagcca gcatcatttc  7380
cgtgaagtga ttccgtttgg ggcttctctg cgttatgcag gccgcccggc ctccgcctct  7440
ccggcggtag ggtatatgtc cgttcaccag aaacagcaac aagatctggt taatgacgcg  7500
ctgaacgtcg aataa                                                    7515
```

```
SEQ ID NO: 48          moltype = DNA  length = 2676
FEATURE                Location/Qualifiers
source                 1..2676
                       mol_type = genomic DNA
                       organism = Escherichia coli
SEQUENCE: 48
atggctgtta ctaatgtcgc tgaacttaac gcactcgtag agcgtgtaaa aaaagcccag  60
cgtgaatatg ccagtttcac tcaagagcaa gtagacaaaa tcttccgcgc cgccgctctg  120
gctgctgcag atgctcgaat cccactcgcg aaaatggccg ttgccgaatc cggcatgggt  180
atcgtcgaag ataaagtgat caaaaaccac tttgcttctg aatatatcta caacgcctat  240
aaagatgaaa aaacctgtgg tgttctgtct gaagacgaca cttttggtac catcactatc  300
gctgaaccaa tcggtattat ttgcggtatc gttccgacca ctaacccgac ttcaactgct  360
atcttcaaat cgctgatcag tctgaagacc cgtaacgcca ttatcttctc cccgcacccg  420
cgtgcaaaag atgccaccaa caaagcggct gatatcgttc tgcaggctgc tatcgctgcc  480
ggtgctccga aagatctgat cggctggatc gatcaacctt ctgttgaact gtctaacgca  540
ctgatgcacc acccagacat caacctgatc ctcgcgactg gtggtccggg catggttaaa  600
gccgcataca gctccggtaa accagctatc ggtgtaggcg cgggcaacac tccagttgtt  660
atcgatgaaa ctgctgatat caaacgtgca gttgcatctg tactgatgtc caaaaccttc  720
gacaacggcg taatctgtgc ttctgaacag tctgttgttg ttgttgactc tgtttatgac  780
```

```
gctgtacgtg aacgttttac aacccacggc ggctatctgt tgcagggtaa agagctgaaa  840
gctgttcagg atgttatcct gaaaaacggt gcgctgaacg cggctatcgt tggtcagcca  900
gcctataaaa ttgctgaact ggcaggcttc tctgtaccag aaaacaccaa gattctgatc  960
ggtgaagtga ccgttgttga tgaaagcgaa ccgttcgcac atgaaaaact gtccccgact  1020
ctggcaatgt accgcgctaa agatttcgaa gacgcggtag aaaaagcaga gaaactggtt  1080
gctatgggcg gtatcggtca tacctcttgc ctgtacactg accaggataa ccaaccggct  1140
cgcgtttctt acttcggtca gaaaatgaaa acggcgcgta tcctgattaa caccccagcg  1200
tctcagggtg gtatcggtga cctgtataac ttcaaactcg caccttccct gactctgggt  1260
tgtggttctt ggggtggtaa ctccatctct gaaaacgttg gtccgaaaca cctgatcaac  1320
aagaaaaccg ttgctaagcg agctgaaaac atgttgtggc acaaacttcc gaaatctatc  1380
tacttccgcc gtggctccct gccaatcgcg ctggatgaag tgattactga tggccacaaa  1440
cgtgcgctca tcgtgactga ccgcttcctg ttcaacaatg gttatgctga tcagatcact  1500
tccgtactga aagcagcagg cgttgaaact gaagtcttct tcgaagtaga agcggacccg  1560
accctgagca tcgttcgtaa aggtgcagaa ctggcaaact ccttcaaacc agacgtgatt  1620
atcgcgctgg gtggtggttc cccgatggac gccgcgaaga tcatgtgggt tatgtacgaa  1680
catccggaaa ctcacttcga aaagctggcg ctgcgcttta tggatatccg taaacgtatc  1740
tacaagttcc cgaaaatggg cgtgaaagcg aaaatgatcg ctgtcaccac cacttctggt  1800
acaggttctg aagtcactcc gtttgcggtt gtaactgacg acgctactgg tcagaaatat  1860
ccgctggcag actatgcgct gactccggat atggcgattg tcgacgccaa cctggttatg  1920
gacatgccga agtccctgtg tgctttcggt ggtctggacg cagtaactca cgccatggaa  1980
gcttatgttt ctgtactggc atctgagttc tctgatggtc aggctctgca ggcactgaaa  2040
ctgctgaaag aatatctgcc agcgtcctac cacgaagggt ctaaaaatcc ggtagcgcgt  2100
gaacgtgttc acagtgcagc gactatcgcg ggtatcgcgt ttgcgaacgc cttcctgggt  2160
gtatgtcact caatggcgca caaactgggt tcccagttcc atattccgca cggtctggca  2220
aacgccctgc tgatttgtaa cgttattcgc tacaatgcga acgacaaccc gaccaagcag  2280
actgcattca gccagtatga ccgtccgcag gctcgccgtc gttatgctga aattgccgac  2340
cacttgggtc tgagcgcacc gggcgaccgt actgctgcta agatcgagaa actgctggca  2400
tggctggaaa cgctgaaagc tgaactgggt attccgaaat ctatccgtga agctggcgtt  2460
caggaagcag acttcctggc gaacgtggat aaactgtctg aagatgcatt cgatgaccag  2520
tgcaccggcg ctaacccgcg ttacccgctg atctccgagc tgaaacagat tctgctggat  2580
acctactacg gtcgtgatta tgtagaaggt gaaactgcag cgaagaaaga agctgctccg  2640
gctaaagctg agaaaaaagc gaaaaaatcc gcttaa                          2676

SEQ ID NO: 49           moltype = AA  length = 891
FEATURE                 Location/Qualifiers
source                  1..891
                        mol_type = protein
                        organism = Escherichia coli
SEQUENCE: 49
MAVTNVAELN ALVERVKKAQ REYASFTQEQ VDKIFRAAAL AAADARIPLA KMAVAESGMG  60
IVEDKVIKNH FASEYIYNAY KDEKTCGVLS EDDTFGTITI AEPIGIICGI VPTTNPTSTA  120
IFKSLISLKT RNAIIFSPHP RAKDATNKAA DIVLQAAIAA GAPKDLIGWI DQPSVELSNA  180
LMHHPDINLI LATGGPGMVK AAYSSGKPAI GVGAGNTPVV IDETADIKRA VASVLMSKTF  240
DNGVICASEQ SVVVVDSVYD AVRERFTTHG GYLLQGKELK AVQDVILKNG ALNAAIVGQP  300
AYKIAELAGF SVPENTKILI GEVTVVDESE PFAHEKLSPT LAMYRAKDFE DAVEKAEKLV  360
AMGGIGHTSC LYTDQDNQPA RVSYFGQKMK TARILINTPA SQGGIGDLYN FKLAPSLTLG  420
CGSWGGNSIS ENVGPKHLIN KKTVAKRAEN MLWHKLPKSI YFRRGSLPIA LDEVITDGHK  480
RALIVTDRFL FNNGYADQIT SVLKAAGVET EVFFEVEADP TLSIVRKGAE LANSFKPDVI  540
IALGGGSPMD AAKIMWVMYE HPETHFEKLA LRFMDIRKRI YKFPKMGVKA KMIAVTTTSG  600
TGSEVTPFAV VTDDATGQKY PLADYALTPD MAIVDANLVM DMPKSLCAFG GLDAVTHAME  660
AYVSVLASEF SDGQALQALK LLKEYLPASY HEGSKNPVAR ERVHSAATIA GIAFANAFLG  720
VCHSMAHKLG SQFHIPHGLA NALLICNVIR YNANDNPTKQ TAFSQYDRPQ ARRRYAEIAD  780
HLGLSAPGDR TAAKIEKLLA WLETLKAELG IPKSIREAGV QEADFLANVD KLSEDAFDDQ  840
CTGANPRYPL ISELKQILLD TYYGRDYVEG ETAAKKEAAP AKAEKKAKKS A          891

SEQ ID NO: 50           moltype = DNA  length = 1032
FEATURE                 Location/Qualifiers
misc_feature            1..1032
                        note = Synthetic plasmid.
source                  1..1032
                        mol_type = other DNA
                        organism = synthetic construct
SEQUENCE: 50
atgaaagccg ccgtggtcga gcaattcaaa aaaccactcc aggtgaaaga ggtcgaaaaa  60
ccgaaaatta gttacggtga agtgctggtt cgtattaaag cttgtggtgt ctgccacacc  120
gatctgcatg ccgcacacgg cgattggccg gtaaaaccga aactgccgct catccccggc  180
catgaaggcg taggcgtcat cgaggaagtc ggcccgggtg tgacacacct taaagttggc  240
gatcgtgtgg gcattccctg gctgtattcg gcgtgtggcc actgtgacta ttgtctcagc  300
ggccaggaga ctctgtgcga acgccagcag aacgccggct acagcgttga tggtggctac  360
gccgagtact gtcgtgctgc ggcagattac gtggtgaaga ttcctgataa tctttccttt  420
gaagaagcgg cgcccatttt atgcgcgggc gttaccactt ataaagcgct gaaagtcacc  480
ggtgccaaac caggcgagtg ggtggccatt tatggaattg gggcctcgg ccatgtggca  540
gttcagtacg ctaaagcaat gggcttaaac gtcgtggcag tggacttggg agatgaaaag  600
ctggaactgg caaaacaact gggcgcggac ctggtagtga atccgaaaca tgatgatgca  660
gcacaatgga ttaaagaaaa agttggtggc gtgcatgcca cggtggtgac ggcagttagt  720
aaagccgctt ttgaatcggc gtataagtca atccgccgcg gaggagcatg cgtccttgtt  780
ggtctgccac cggaggaaat ccccattccg atttttgaca cagttctgaa cggcgtcaaa  840
attatcggtt caattgttgg cacccgtaaa gacctgcagg aagccctcca gtttgctgct  900
gaaggcaaag tgaaaactat cgtggaagtt cagccgcttg agaacattaa cgacgtattt  960
```

```
gatcgtatgc tgaaaggaca gattaatgga cgtgtggtcc tgaaagtgga tcatcatcac  1020
catcaccact ga                                                      1032

SEQ ID NO: 51          moltype = AA  length = 343
FEATURE                Location/Qualifiers
source                 1..343
                       mol_type = protein
                       organism = Escherichia coli
SEQUENCE: 51
MKAAVVEQFK KPLQVKEVEK PKISYGEVLV RIKACGVCHT DLHAAHGDWP VKPKLPLIPG  60
HEGVGVIEEV GPGVTHLKVG DRVGIPWLYS ACGHCDYCLS GQETLCERQQ NAGYSVDGGY  120
AEYCRAAADY VVKIPDNLSF EEAAPILCAG VTTYKALKVT GAKPGEWVAI YGIGGLGHVA  180
VQYAKAMGLN VVAVDLGDEK LELAKQLGAD LVVNPKHDDA AQWIKEKVGG VHATVVTAVS  240
KAAFESAYKS IRRGGACVLV GLPPEEIPIP IFDTVLNGVK IIGSIVGTRK DLQEALQFAA  300
EGKVKTIVEV QPLENINDVF DRMLKGQING RVVLKVDHHH HHH                    343

SEQ ID NO: 52          moltype = DNA  length = 951
FEATURE                Location/Qualifiers
source                 1..951
                       mol_type = genomic DNA
                       organism = Escherichia coli
SEQUENCE: 52
atgagtaagc gtaaagtcgc cattatcggt tctggcaaca ttggcaccga tctgatgatt  60
aaaattttgc gtcacggtca gcatctggag atggcggtga tggttggcat tgatcctcag  120
tccgacggtc tggcgcgcgc cagacgtatg ggcgtcgcca ccacccatga aggggtgatc  180
ggactgatga acatgcctga atttgctgat atcgacattg tatttgatgc gaccagcgcc  240
ggtgctcatg tgaaaaacga tgccgcttta cgcgaagcga aaccggatat tcgcttaatt  300
gacctgacgc ctgctgccat cggcccttac tgcgtgccgg tggttaacct cgaggcgaac  360
gtcgatcaac tgaacgtcaa catggtcacc tgcggcggcc aggccaccat tccaatggtg  420
gcggcagttt cacgcgtggc gcgtgttcat tacgccgaaa ttatcgcttc tatcgccagt  480
aaatctgccg gacctggcac gcgtgccaat atcgatgaat ttacggaaac cacttcccga  540
gccattgaag tggtgggcgg cgcggcaaaa gggaaggcga ttattgtgct taacccagca  600
gagccaccgt tgatgatgcg tgacacggtg tatgtattga gcgacgaagc ttcacaagat  660
gatatcgaag cctcaatcaa tgaaatggct gaggcggtgc aggcttacgt accgggttat  720
cgcctgaaac agcgcgtgca gtttgaagtt atcccgcagg ataaaccggt caatttaccg  780
ggcgtggggc aattctccgg actgaaaaca gcggtctggc tggaagtcga aggcgcagcg  840
cattatctgc ctgcctatgc gggcaacctc gacattatga cttccagtgc gctggcgaca  900
gcggaaaaaa tggcccagtc actggcgcgc aaggcaggag aagcggcatg a           951

SEQ ID NO: 53          moltype = AA  length = 316
FEATURE                Location/Qualifiers
source                 1..316
                       mol_type = protein
                       organism = Escherichia coli
SEQUENCE: 53
MSKRKVAIIG SGNIGTDLMI KILRHGQHLE MAVMVGIDPQ SDGLARARRM GVATTHEGVI  60
GLMNMPEFAD IDIVFDATSA GAHVKNDAAL REAKPDIRLI DLTPAAIGPY CVPVVNLEAN  120
VDQLNVNMVT CGGQATIPMV AAVSRVARVH YAEIIASIAS KSAGPGTRAN IDEFTETTSR  180
AIEVVGGAAK GKAIIVLNPA EPPLMMRDTV YVLSDEASQD DIEASINEMA EAVQAYVPGY  240
RLKQRVQFEV IPQDKPVNLP GVGQFSGLKT AVWLEVEGAA HYLPAYAGNL DIMTSSALAT  300
AEKMAQSLAR KAGEAA                                                  316

SEQ ID NO: 54          moltype = DNA  length = 1476
FEATURE                Location/Qualifiers
misc_feature           1..1476
                       note = Synthetic plasmid.
source                 1..1476
                       mol_type = other DNA
                       organism = synthetic construct
SEQUENCE: 54
atggagataa tggataagga cttacagtca atacaggaag taagaactct tatagcaaaa  60
gcaaagaaag ctcaagcaga atttaaaaat ttttctcaag aagctgtaaa caaggtaata  120
gaaaaaatag ctaaggctac agaagttgaa gctgtaaaac ttgcaaaatt ggcatatgaa  180
gatacaggat atggaaaatg ggaagataaa gtaataaaga ataagttttc aagtatagta  240
gtttataact atattaaaga tttgaaaacg gttggaattt taaaagaaga caaggaaaag  300
aaattaatag atatagctgt tccacttgga gttatagcag gacttatacc ttcaactaac  360
ccaacttcaa cagcaatatt caaggtatta atagcattaa aggcaggaaa tgcaatagta  420
ttctcaccac atccaacagc agtaagaagt attacagaaa ctgtaaagat aatgcagaaa  480
gctgcagtag aagcaggagc accagatgga ttaatccaat gtatgtcaat attgacagta  540
gaaggtactg ctgaattgat gaagaataag gatacagcac ttatccttgc aacaggtgga  600
gaaggaatgg taagagcagc ttacagttca ggaacaccag ctataggagt tggacctgga  660
aacggcccat gctttattga aagaacagca gatattccta cagcagtaag aaaagtaata  720
ggcagtgata cttttgataa tggagtaata tgtgcttcag aacaatcaat aatagcagag  780
acagtaaaga aagcagagat aattgaagaa ttcaagagac aaaaaggata tttcttaaat  840
gcagaagaat cagaaaaagt aggcaagatt ttattaagag ctaatggaac accaaaccca  900
gcaatagtag gaaaagatgt tcaagcatta gcaaaattag caggaataag cataccaagc  960
gatgcggtaa tattactttc agagcagaca gatgtgagtc caaagaaccc ttatgcaaag  1020
gaaaaattag ctccagtact tgcattctat acagtagaag actggcatga agcatgtgaa  1080
aaatccttag cacttcttca taaccaagga agtggacata cattaataat tcactcacag  1140
```

```
aatgaagaaa tcataagaga attcgcattg aagaaaccag tatcaagaat acttgtaaat  1200
tcacctggat cacttggagg aataggtgga gctacaaatc ttgtaccatc acttacatta  1260
ggctgtggag cagtaggtgg aagtgcaact tcagataacg taggaccaga aaacttattc  1320
aacataagaa aagtagctta tggaactacg acagtagaag aaataagaga agcttttggt  1380
gtaggagcag cttcatcaag tgcaccagca gaaccagaag ataatgaaga tgtacaggct  1440
atagtaaaag ctataatggc taaattaaat ctttaa                            1476

SEQ ID NO: 55          moltype = AA  length = 491
FEATURE                Location/Qualifiers
source                 1..491
                       mol_type = protein
                       organism = Clostridium kluyveri
SEQUENCE: 55
MEIMDKDLQS IQEVRTLIAK AKKAQAEFKN FSQEAVNKVI EKIAKATEVE AVKLAKLAYE  60
DTGYGKWEDK VIKNKFSSIV VYNYIKDLKT VGILKEDKEK KLIDIAVPLG VIAGLIPSTN  120
PTSTAIFKVL IALKAGNAIV FSPHPTAVRS ITETVKIMQK AAVEAGAPDG LIQCMSILTV  180
EGTAELMKNK DTALILATGG EGMVRAAYSS GTPAIGVGPG NGPCFIERTA DIPTAVRKVI  240
GSDTFDNGVI CASEQSIIAE TVKKAEIIEE FKRQKGYFLN AEESEKVGKI LLRANGTPNP  300
AIVGKDVQAL AKLAGISIPS DAVILLSEQT DVSPKNPYAK EKLAPVLAFY TVEDWHEACE  360
KSLALLHNQG SGHTLIIHSQ NEEIIREFAL KKPVSRILVN SPGSLGGIGG ATNLVPSLTL  420
GCGAVGGSAT SDNVGPENLF NIRKVAYGTT TVEEIREAFG VGAASSSAPA EPEDNEDVQA  480
IVKAIMAKLN L                                                       491

SEQ ID NO: 56          moltype = DNA  length = 12188
FEATURE                Location/Qualifiers
misc_feature           1..12188
                       note = Synthetic plasmid.
source                 1..12188
                       mol_type = other DNA
                       organism = synthetic construct
SEQUENCE: 56
cgaggacgtc atcaccgccg ccctgcgcca gaacatcttt ctgatgtcgt cctgccggga  60
gggcggctgt gcgacctgca aggccttgtg cagcgaaggg gactacgacc tcaagggctg  120
cagcgttcag gcgctgccgc cggaagagga ggaggaaggg ttggtgttgt tgtgccggac  180
ctacccgaag accgacctgg aaatcgaact gccctatacc cattgccgca tcagttttgg  240
tgaggtcggc agtttcgagg cggaggtcgt cggcctcaac tgggttcga gcaacaccgt  300
ccagtttctt ttgcagaagc ggcccgacga gtgcggcaac cgtggcgtga aattcgaacc  360
cggtcagttc atggacctga ccatccccgg caccgatgtc tcccgctcct actcgccggc  420
gaaccttcct aatcccgaag gccgcctgga gttcctgatc cgcgtgttac cggagggacg  480
gttttcggac tacctgcgca atgacgcgct tgtcggacag gtcctctcgg tcaaagggcc  540
actgggcgtg ttcggtctca aggagcgggg catggcgccg cgctatttcg tggccggcgg  600
caccgggttg gcgccggtgg tctcgatggt gcggcagatg caggagtgga ccgcgccgaa  660
cgagacccgc atctatttcg gtgtgaacac cgagccggaa ttgttctaca tcgacgagct  720
caaatccctg gaacgatcga tgcgcaatct caccgtgaag gcctgtgtct ggcacccgag  780
cggggactgg gaaggcgagc agggctcgcc catcgatgcg ttgcgggaag acctggagtc  840
ctccgacgcc aacccggaca tttatttgtg cggtccgccg ggcatgatcg atgccgcctg  900
cgagctggta cgcagccgcg gtatccccgg cgaacaggtc ttcttcgaaa aattcctgcc  960
gtccggggcg gcctgaaccg gggaagtacc gtgaccaccg agcagttccc gccccaattc  1020
ctgcgtgaaa tgatcgagca gctggacgcc agcatccagg agctcgcacg caaggaaaag  1080
ggacttgcgg catccctggg cacgggcgg gtcgccgagc tcaaggaata ctgggaccac  1140
gttgttacaa ccaattaacc aattctgatt atacacgggg ttctgcagga ataaccgaga  1200
tgccgcgaaa cgagtcagtc aacttcgggc gccattcggt acgtgcacga aggacttcgc  1260
tgccaccctc caattgaagg aggtgatcgc ataccaaccc agcttcggag ctcccaccgc  1320
tcacagtggt taagctacgt aacacgctgt cacgggtaca ctcacgacga tactcaagcg  1380
tgaaacttga aatgtggtga gactcgaaga tcgagtcggg cacggtttcg aatacccaag  1440
ccacgtattt taaattattc acatgctggt tgacatccaa atcgttccag cgcggcgtta  1500
aacctccttg gatatagtct gcggttgaat cattaagttt ttgcaacttc ttgatttcgt  1560
catctttcac tgcaacatta tcgataaatg ccggtccgat ttcaccacgg acttcatccg  1620
ggatcgtact caaacgacgt gtacgtgtgt tcattaagac ggaaagagag gtacaacgcg  1680
tcaaaatctc gcctgtttta caatcgcgga ccaggaaatc acgacgcatc ccgttgttgc  1740
cggaagcccc gatccaacac tcgacttcga cggtgtcccc ccatgttgga taacgttcca  1800
ccgctacgtg tgtgcggcga acaacccaca ttaaatcacg tttagacatc tcaagagttg  1860
taccgaaccc gtcacctaaa ataccaacac ttttggcgtg attcaaagtg gcctcttgca  1920
tgtggttcat aactgccaaa atggatgtcg agcggtccgg ccccacctca taggaacgga  1980
tagcaaaagt acgacgaaat acaagaccgt gaagcccaaa gtggtcatct aataattggg  2040
gcagctttgg cttaggtttc cactcaagca tttaatatat acctcttttt accaatgctt  2100
aatcagtgag gcacctatct cagcgatctg tctatttcgt tcatccatag ttgcctgact  2160
ccccgtcgtg tagataacta cgatacggga gggcttacca tctggcccca gtgctgcaat  2220
gataccgcga gacccacgct caccggctcc agatttatca gcaataaacc agccagccgg  2280
aagggccgag cgcagaagtg gtcctgcaac tttatccgcc tccatccagt ctattaattg  2340
ttgccgggaa gctagagtaa gtagttcgcc agttaatagt ttgcgcaacg ttgttgccat  2400
tgctacaggc atcgtggtgt cacgctcgtc gtttggtatg gcttcattca gctccggttc  2460
ccaacgatca aggcgagtta catgatcccc catgttgtgc aaaaaagcgg ttagctcctt  2520
cggtcctccg atcgttgtca gaagtaagtt ggccgcagtg ttatcactca tggttatggc  2580
agcactgcat aattctctta ctgtcatgcc atccgtaaga tgcttttctg tgactggtga  2640
gtactcaacc aagtcattct gagaatagtg tatgcggcga ccgagttgct cttgcccggc  2700
gtcaatacgg gataataccg cgccacatag cagaacttta aaagtgctca tcattggaaa  2760
acgttcttcg gggcgaaaac tctcaaggat cttaccgctg ttgagatcca gttcgatgta  2820
acccactcgt gcacccaact gatcttcagc atcttttact ttcaccagcg tttctgggtg  2880
```

```
agcaaaaaca ggaaggcaaa atgccgcaaa aaagggaata agggcgacac ggaaatgttg  2940
aatactcata acaccccttg tattactgtt tatgtaagca gacagtttta ttgttcatga  3000
tgatatattt ttatcttgtg caatgtaaca tcagagattt tgagacacaa cgtggctttg  3060
ttgaataaat cgaacttttg ctgagttgaa ggatcagatc acgcatcttc ccgacaacgc  3120
agaccgttcc gtggcaaagc aaaagttcaa aatcaccaac tggtccacct acaacaaagc  3180
tctcatcaac cgtggctccc tcactttctg gctggatgat ggggcgattc aggcctggta  3240
tgagtcagca acaccttctt cacgaggcag acctcagcgc tagcggagtg tatactggct  3300
tactatgttg gcactgatga gggtgtcagt gaagtgcttc atgtggcagg agaaaaaagg  3360
ctgcaccggt gcgtcagcag aatatgtgat acaggatata ttccgcttcc tcgctcactg  3420
actcgctacg ctcggtcgtt cgactgcggc gagcggaaat ggcttacgaa cggggcggag  3480
atttcctgga agatgccagg aagatactta acagggaagt gagagggccg cggcaaagcc  3540
gtttttccat aggctccgcc cccctgacaa gcatcacgaa atctgacgct caaatcagtg  3600
gtggcgaaac ccgacaggac tataaagata ccaggcgttt ccccctggcg gctccctcgt  3660
gcgctctcct gttcctgcct ttcggtttac cggtgtcatt ccgctgttat ggccgcgttt  3720
gtctcattcc acgcctgaca ctcagttccg ggtaggcagt tcgctccaag ctggactgta  3780
tgcacgaacc ccccgttcag tccgaccgct gcgccttatc cggtaactat cgtcttgagt  3840
ccaacccgga aagacatgca aaagcaccac tggcagcagc cactggtaat tgatttagag  3900
gagttagtct tgaagtcatg cgccggttaa ggctaaactg aaaggacaag ttttggtgac  3960
tgcgctcctc caagccagtt acctcggttc aaagagttgg tagctcagag aaccttcgaa  4020
aaaccgccct gcaaggcggt tttttcgttt tcagagcaag agattacgcg cagaccaaaa  4080
cgatctcaag aagatcatct tattaagggg tctgacgctc agtggaacga aaactcacgt  4140
taagggattt tggtcatgag attatcaaaa aggatcttca cctagatcct tttaaattaa  4200
aaatgaagtt ttaaatcaat ctaaagtata tatgagtaaa cttggtctga caggtgagct  4260
gataccgctc gccgcatgca catgcagtca tgtcgtgcta atgtgtaaaa catgtacatg  4320
cagattgctg gggtgcaggg gggcggagcc accctgtcca tgcggggtgt ggggcttgcc  4380
ccgccggtac agacagtgag caccggggca cctagtcgcg gatacccccc ctaggtatcg  4440
gacacgtaac cctcccatgt cgatgcaaat ctttaacatt gagtacgggt aagctggcac  4500
gcatagccaa gctaggcggc caccaaacac cactaaaaat taatagtccc tagacaagac  4560
aaaccccgt gcgagctacc aactcatatg cacgggggcc acataacccg aaggggtttc  4620
aattgacaac catagcacta gctaagacaa cgggcacaac acccgcacaa actcgcactg  4680
cgcaaccccg cacaacatcg ggtctaggta acactgaaat agaagtgaac acctctaagg  4740
aaccgcaggt caatgagggt tctaaggtca ctcgcgctag ggcgtggcgt aggcaaaacg  4800
tcatgtacaa gatcaccaat agtaaggctc tggcggggtg ccataggtgg cgcagggacg  4860
aagctgttgc ggtgtcctgg tcgtctaacg gtgcttcgca gtttgagggt ctgcaaaact  4920
ctcactctcg ctgggggtca cctctggctg aattggaagt catgggcgaa cgccgcattg  4980
agctggctat tgctactaag aatcacttgg cggcgggtgg cgcgctcatg atgtttgtgg  5040
gcactgttcg acacaaccgc tcacagtcat ttgcgcaggt tgaagcgggt attaagactg  5100
cgtactcttc gatggtgaaa acatctcagt ggaagaaaga acgtgcacgg tacggggtgg  5160
agcacaccta tagtgactat gaggtcacag actcttgggc gaacggttgg cacttgcacc  5220
gcaacatgct gttgttcttg gatcgtccac tgtctgacga tgaactcaag gcgtttgagg  5280
attccatgtt ttcccgctgg tctgctggtg tggttaaggc cggtatggac gcgccactgc  5340
gtgagcacgg ggtcaaactt gatcaggtgt ctacctgggg tggagacgct gcgaaaatgg  5400
caacctacct cgctaagggc atgtctcagg aactgactgg ctccgctact aaaaccgcgt  5460
ctaaggggtc gtacacgccg tttcagatgt tggatatgtt ggccgatcaa agcgacgccg  5520
gcgaggatat ggacgctgtt ttggtggctc ggtggcgtga gtatgaggtt ggttctaaaa  5580
acctgcgttc gtcctggtca cgtggggcta agcgtgcttt gggcattgat tacatagacg  5640
ctgatgtacg tcgtgaaatg gaagaagaac tgtacaagct cgccggtctg gaagcaccgg  5700
aacgggtcga atcaacccgc gttgctgttg ctttggtgaa gcccgatgat tggaaactga  5760
ttcagtctga tttcgcggtt aggcagtacg ttctagattg cgtggataag gctaaggacg  5820
tggccgctgc gcaacgtgtc gctaatgagg tgctggcaag tctgggtgtg gattccaccc  5880
cgtgcatgat cgttatggat gatgtggact tggacgcggt tctgcctact catggggacg  5940
ctactaagcg tgatctgaat gcggcggtgt tcgcgggtaa tgagcagact attcttcgca  6000
cccactaaaa gcggcataaa ccccgttcga tattttgtgc gatgaattta tggtcaatgt  6060
cgcgggggca aactatgatg ggtcttgttg ttgcagccga acgacctagc gcagcgagtc  6120
agtgagcgag gaagcggaag agcgcctgat gcggtatttt ctccttacgc atctgtgcgg  6180
tatttcacac cgcatatggt gcactctcag tacaatctgc tctgatgccg catagttaag  6240
ccagtataca ctccgctatc gctacgtgac tgggtcatgg ctgcgccccg acacccgcca  6300
acacccgctg acgcgccctg acgggcttgt ctgctcccgg catccgctta cagacaagct  6360
gtgaccgtct ccgggagctg catgtgtcag aggttttcac cgtcatcacc gaaacgcgcg  6420
aggcagcaga tcaattcgcg cgcgaaggcg aagcggcatg cataatgtgc ctgtcaaatg  6480
gacgaagcag ggattctgca aaccctatgc tactccgtca agccgtcaat tgtctgattc  6540
gttaccaatt atgacaactt gacggctaca tcattcactt tttcttcaca accggcacgg  6600
aactcgctcg ggctggcccc ggtgcatttt ttaaataccc gcgagaaata gagttgatcg  6660
tcaaaaccaa cattgcgacc gacggtggcg ataggcatcc gggtggtgct caaaagcagc  6720
ttcgcctggc tgatacgttg gtcctcgcgc cagcttaaga cgctaatccc taactgctgg  6780
cggaaaagat gtgacagacg cgacggcgac aagcaaacat gctgtgcgac gctggcgata  6840
tcaaaattgc tgtctgccag gtgatcgctg atgtactgac aagcctcgcg tacccgatta  6900
tccatcggtg gatggagcga ctcgttaatc gcttccatgc gccgcagtaa caattgctca  6960
agcagattta tcgccagcag ctccgaatag cgcccttccc cttgcccggc gttaatgatt  7020
tgcccaaaca ggtcgctgaa atgcggctgg tgcgcttcat ccgggcgaaa gaaccccgta  7080
ttggcaaata ttgacggcca gttaagccat tcatgccagt aggcgcgcgg acgaaagtaa  7140
acccactggt gataccattc gcgagcctcc ggatgacgac cgtagtgatg aatctctcct  7200
ggcgggaaca gcaaaatatc acccggtcgg caaacaaatt ctcgtccctg atttttcacc  7260
accccctgac cgcgaatggt gagattgaga atataacctt tcattcccag cggtcggtcg  7320
ataaaaaaat cgagataacc gttggcctca atcggcgtta aacccgccac cagatgggca  7380
ttaaacgagt atcccggcag caggggatca ttttgcgctt cagccatact tttcatactc  7440
ccgccattca gagaagaaac caattgtcca tattgcatca gacattgccg tcactgcgtc  7500
ttttactggc tcttctcgct aaccaaaccg gtaaccccgc ttattaaaag cattctgtaa  7560
caaagcggga ccaaagccat gacaaaaacg cgtaacaaaa gtgtctataa tcacggcaga  7620
```

```
aaagtccaca ttgattattt gcacggcgtc acactttgct atgccatagc atttttatcc  7680
ataagattag cggatcctac ctgacgcttt ttatcgcaac tctctactgt ttctccatac  7740
ccgttttttt gggcgacctc gtcggaggtt gtatgtccgg tgttccgtga cgtcatcggg  7800
cattcatcat tcatagaatg tgttacggag gaaacaagta atggcactta gcaccgcaac  7860
caaggccgcg acggacgcgc tggctgccaa tcgggcaccc accagcgtga atgcacagga  7920
agtgcaccgt tggctccaga gcttcaactg ggatttcaag aacaaccgga ccaagtacgc  7980
caccaagtac aagatggcga acgagaccaa ggaacagttc aagctgatcg ccaaggaata  8040
tgcgcgcatg gaggcagtca aggacgaaag gcagttcggt agcctgcagg atgcgctgac  8100
ccgcctcaac gccggtgttc gcgttcatcc gaagtggaac gagaccatga aagtggtttc  8160
gaacttcctg gaagtgggcg aatacaacgc catcgccgct accgggatgc tgtgggattc  8220
cgcccaggcg gcggaacaga agaacggcta tctggcccag gtgttggatg aaatccgcca  8280
cacccaccag tgtgcctacg tcaactacta cttcgcgaag aacggccagg acccggccgg  8340
tcacaacgat gctcgccgca cccgtaccat cggtccgctg tggaagggca tgaagcgcgt  8400
gttttccgac ggcttcattt ccggcgacgc cgtggaatgc tccctcaacc tgcagctggt  8460
gggtgaggcc tgcttcacca atccgctgat cgtcgcagtg accgaatggg ctgccgccaa  8520
cggcgatgaa atcaccccga cggtgttcct gtcgatcaac accgacgaac tgcgccacat  8580
ggccaacggt taccagaccg tcgtttccat cgccaacgat ccggcttccg ccaagtatct  8640
caacacggac ctgaacaacg ccttctggac ccagcagaag tacttcacgc cggtgttggg  8700
catgctgttc gagtatggct ccaagttcaa ggtcgagccg tgggtcaaga cgtggaaccg  8760
ctgggtgtac gaggactggg gcggcatctg gatcggccgt ctgggcaagt acggggtgga  8820
gtcgccgcgc agcctcaagg acgccaagca ggacgcttac tgggctcacc acgacctgta  8880
tctgctggct tatgcgctgt ggccgaccgg cttcttccgt ctggcgctgc cggatcagga  8940
agaaatggag tggttcgagg ccaactaccc cggctggtac gaccactacg gcaagatcta  9000
cgaggaatgg cgcgcccgcg gttgcgagga tccgtcctcg ggcttcatcc cgctgatgtg  9060
gttcatcgaa aacaaccatc ccatctacat cgatcgcgtg tcgcaagtgc cgttctgccc  9120
gagcttggcc aagggcgcca gcaccctgcg cgtgcacgag tacaacggcc agatgcacac  9180
cttcagcgac cagtggggcg agcgcatgtg gctggccgag ccggagcgct acgagtgcca  9240
gaacatcttc gaacagtacg aaggacgcga actgtcggaa gtgatcgccg aactgcacgg  9300
gctgcgcagt gatggcaaga ccctgatcgc ccagccgcat gtccgtggcg acaagctgtg  9360
gacgttggac gatatcaaac gcctgaactg cgtcttcaag aacccggtga aggcattcaa  9420
ttgaaacggg tgtcgggctc cgtcacaggg cggggcccga cgcacgatcg ttcgatcaac  9480
ctcaaaccaa aaaggaacat cgatatgagc atgttaggag aaagacgccg cggtctgacc  9540
gatccggaaa tggcggccgt cattttgaag gcgcttcctg aagctccgct ggacggcaac  9600
aacaagatgg gttatttcgt cacccccgc tggaaacgct tgacggaata tgaagccctg  9660
accgtttatg cgcagcccaa cgccgactgg atcgccggcg gcctggactg gggcgactgg  9720
acccagaaat tccacggcgg ccgcccttcc tggggcaacg agaccacgga gctgcgcacc  9780
gtcgactggt tcaagcaccg tgacccgctc cgccgttggc atgcgccgta cgtcaaggac  9840
aaggccgagg aatggcgcta caccgaccgc ttcctgcagg gttactccgc cgacggtcag  9900
atccgggcga tgaacccgac ctggcgggac gagttcatca accggtattg gggcgccttc  9960
ctgttcaacg aatacggatt gttcaacgct cattcgcagg gcgcccggga ggcgctgtcg  10020
gacgtaaccc gcgtcagcct ggctttctgg ggcttcgaca agatcgacat cgcccagatg  10080
atccaactcg aacggggttt cctcgccaag atcgtacccg gtttcgacga gtccacagcg  10140
gtgccgaagg ccgaatggac gaacggggag gtctacaaga gcgcccgtct ggccgtggaa  10200
gggctgtggc aggaggtgtt cgactggaac gagagcgctt tctcggtgca cgccgtctat  10260
gacgcgctgt tcggtcagtt cgtccgccgc gagttctttc agcggctggc tccccgcttc  10320
ggcgacaatc tgacgccatt cttcatcaac caggcccaga catacttcca gatcgccaag  10380
cagggcgtac aggatctgta ttacaactgt ctgggtgacg atccggagtt cagcgattac  10440
aaccgtaccg tgatgcgcaa ctggaccggc aagtggctgg agcccacgat cgccgctctg  10500
cgcgacttca tggggctgtt tgcgaagctg ccggcgggca ccactgacaa ggaagaaatc  10560
accgcgtccc tgtaccgggt ggtcgacgac tggatcgagg actacgccag caggatcgac  10620
ttcaaggcgg accgcgatca gatcgttaaa gcggttctgg caggattgaa ataatagagg  10680
aactattacg atgagcgtaa acagcaacgc atacgacgcc ggcatcatgg gcctgaaagg  10740
caaggacttc gccgatcagt tctttgccga cgaaaaccaa gtggtccatg aaagcgacac  10800
ggtcgttctg gtcctcaaga agtcggacga gatcaatacc tttatcgagg agatccttct  10860
gacggactac aagaagaacg tcaatccgac ggtaaacgtg gaagaccgcg cgggttactg  10920
gtggatcaag gccaacggca agatcgaggt cgattgcgac gagatttccg agctgttggg  10980
gcggcagttc aacgtctacg acttcctcgt cgacgtttcc tccaccatcg gccgggccta  11040
taccctgggc aacaagttca ccattaccag tgagctgatg ggcctggacc gcaagctcga  11100
agactatcac gcttaaggag aatgacatgg cgaaactggg tatacacagc aacgacaccc  11160
gcgacgcctg ggtgaacaag atcgcgcagc tcaacaccct ggaaaaagcg gccgagatgc  11220
tgaagcagtt ccggatggac cacaccacgc cgttccgcaa cagctacgaa ctggacaacg  11280
actacctctg gatcgaggcc aagctcgaag agaaggtcgc cgtcctcaag gcacgcgcct  11340
tcaacgaggt ggacttccgt cataagaccg ctttcggcga ggatgccaag tccgttctgg  11400
acggcaccgt cgcgaagatg aacgcggcca aggacaagtg ggaggcggag aagatccata  11460
tcggtttccg ccaggcctac aagccgccga tcatgccggt gaactatttc ctggacggcg  11520
agcgtcagtt ggggacccgg ctgatggaac tgcgcaacct caactactac gacacgccgc  11580
tggaagaact gcgcaaacag cgcggtgtgc gggtggtgca tctgcagtcg ccgcactgaa  11640
gggaggaagt ctcgccctgg acgcgacggc atcgccgtga agtccagggg gcagggatgc  11700
cgttccgggc cggcaggctg gcccggaatc tctggttttc agggggcgtg ccggtccacg  11760
gctccccccct ccatctttcg taaggaaatc accatggtcg aatcggcatt tcagccattt  11820
tcgggcgacg cagacgaatg gttcgaggaa ccacggcccc aggccggttt cttcccttcc  11880
gcggactggc atctgctcaa acgggacgag acctacgcag cctatgccaa ggatctcgat  11940
ttcatgtggc ggtgggtcat cgtccgggaa gaaaggatcg tccaggaggg ttgctcgatc  12000
agcctggagt cgtcgatccg cgccgtgacg cacgtactga attattttgg tatgaccgaa  12060
caacgcgccc cggcagagga ccggaccggc ggagttcaac attgaacagg taagtttatg  12120
cagcgagttc acactatcac ggcggtgacg gaggatggcg aatcgctccg cttcgaatgc  12180
cgttcgga                                                            12188
```

SEQ ID NO: 57 moltype = DNA length = 13886

```
FEATURE                 Location/Qualifiers
misc_feature            1..13886
                        note = Synthetic plasmid.
source                  1..13886
                        mol_type = other DNA
                        organism = synthetic construct
SEQUENCE: 57
gtgccacctg acgggtctca cagatgacag agttgtcaag aacttgacca ctttgttgtt  60
cgacacagct ttgttgactt ccggtttcac tttggatgag ccaacttctt tcgctgccag  120
aatcaacggt ttgatctcca ttggtttgaa catcgatgag gaggaagaga aagagccaga  180
acaggctact gaagctccaa gtgaagaagc tgttgctgag tctgccatgg aggaggttga  240
ctagttgaat ttaggtatat atagtgactg tgatatttag ctaatgaaat ctaattggat  300
atttagaatg cctcatctcg tagcctatca attactatta ggccatctct tatgggccct  360
tctttgaaat tgcattcaag gggggatggg actattttga atttgaagtt tggactctgt  420
gagctgtttg gccaattgaa gtcatccact tgtacacagg gattcaccag tagtttagaa  480
caattctcta tcgttattct cttgtcgtct ttggcaatac aagcgtcgat gactgagttg  540
gtgactttat gaagtctaag ttgatatgag tttgaaatta tgaaacagtt ttttacactg  600
gacatgtaga tagggccctt gatgtttagg aagaggatac agtttgagat gttggagatg  660
tgtgtggagg gagcgaccac ttttaaaacc acatgatcca gacgttgctc agttatcgaa  720
gtttcggaaa caacgccaga tctgtttagc ttgggtattt gacaggttgg ggagcaaata  780
agtgatgatg tcccatgaaa gtagaaaatg gctagtagaa ggcaaaaatt tgaaattctt  840
agagtcaaat agttagactc caagttctaa tccacatttg gtcagtttca tagcatccag  900
agcttttgcc actggtgaac atatctaccc attgcgatgc aacaagtcac tgaaagccta  960
aaacggagat tcccctatct tacagcctcg ttcaaaaaaa ctgctaccgt ttatctgcta  1020
tggccgatgt gaggatgcgc tcatgcccaa gagtccaact ttatcaaaaa cttgaccccgt  1080
catacaggct ctagatcaag aagcaaactt aatctcagca tctggttacg taactctggc  1140
aaccagtaac acgcttaagg tttggaacaa cactaaacta ccttgcggta ctaccattga  1200
cactacacat ccttaattcc aatcctgtct ggcctccttc acctttttaac catcttgccc  1260
attccaactc gtgtcagatt gcgtatcaag tgaaaaaaaa aaattttaaa atctttaacc  1320
caatcaggta ataactgtcg cctcttttat ctgccgcact gcatgaggtg tccccttagt  1380
gggaaagagt actgagccaa ccctggagga cagcaaggga aaaataccta caacttgctt  1440
cataatggtc gtaaaaacaa tccttgtcgg atataagtgt tgtagactgt cccttatcct  1500
ctgcgatgtt cttcctctca aagtttgcga tttctctcta tcagaattgc catcaagaga  1560
ctcaggacta atttcgcagt cccacacgca ctcgtacatg attggctgaa atttccctaa  1620
agaatttctt tttcacgaaa atttttttt acacaagatt ttcagcagat ataaaatgga  1680
gagcaggacc tccgctgtga ctcttctttt ttttctttta ttctcactac atacatttta  1740
gttattcgcc aacatgggtg aactcaagga aatcttgaaa cagaggtatc atgagttgct  1800
tgactggaat gtcaaagccc ctcatgtccc tctcagtcaa cgactgaagc attttacatg  1860
gtcttggttt gcatgtacta tggcaactgg tggtgttggt ttgattattg gttctttccc  1920
ctttcgattt tatggtctta atacaattgg caaaattgtt tatattcttc aaatcttttt  1980
gtttctctc tttggatcat gcatgctttt tcgctttatt aaatatcctt caactatcaa  2040
ggattcctgg aaccatcatt tggaaaagct tttcattgct acttgtcttc tttcaatatc  2100
cacgttcatc gacatgcttg ccatatacgc ctatcctgat accggcgagt ggatggtgtg  2160
ggtcattcga atcctttatt acatttacgt tgcagtatcc tttatatact gcgtaatggc  2220
ttttttaca attttcaaca accatgtata taccattgaa accgcatctc ctgcttggat  2280
tcttcctatt ttccctccta tgatttgtgg tgtcattgct ggcgccgtca attctacaca  2340
acccgctcat caattaaaaa atatggttat ctttggtatc ctctttcaag gacttggttt  2400
ttgggtttat cttttactgt ttgccgtcaa tgtcttacgg ttttttactg taggcctggc  2460
aaaaccccaa gatcgacctg gtatgtttat gtttgtcggt ccaccagctt tctcaggttt  2520
ggccttaatt aatattgcgc gtggtgctat gggcagtcgc ccttatattt ttgttggcgc  2580
caactcatcc gagtatcttg gttttgtttc tacctttatg gctatttta tttggggtct  2640
tgctgcttgg tgttactgtc tcgccatggt tagcttttta gcgggctttt tcactcgagc  2700
ccctctcaag tttgcttgtg gatggtttgc attcattttc cccaacgtgg gttttgttaa  2760
ttgtaccatt gagataggta aaatgataga ttccaaagct ttccaaatgt ttggacatat  2820
cattggggtc attctttgta ttcagtggat cctcctaatg tatttaatgg tccgtgcgtt  2880
tctcgtcaat gatctttgct atcctggcaa agacgaagat gcccatcctc caccaaaacc  2940
aaatacaggt gtccttaacc ctaccttccc acctgaaaaa gcacctgcat ctttggaaaa  3000
agtcgataca catgtcacat ctactggtgg tgaatcggat cctcctagta gtgaacatga  3060
aagcgtttaa acaggcccct tttcctttgt cgatatcatg taattagtta tgtcacgctt  3120
acattcacgc cctcctccca catccgctct aaccgaaaag gaaggagtta gacaacctga  3180
agtctaggtc cctatttatt tttttaata gttatgttag tattaagaac gttatttata  3240
tttcaaattt ttcttttttt tctgtacaaa cgcgtgtacg catgtaacat tatactgaaa  3300
accttgcttg agaaggtttt gggacgctcg aaggctttaa tttgcaagct ttttttgtag  3360
aaatgtcttg gtgtcctcgt ccaatcaggt agccatctct gaaatatctg gctccgttgc  3420
aactccgaac gacctgctgg caacgtaaaa ttctccgggg taaaacttaa atgtggagta  3480
atggaaccag aaacgtctct tcccttctct ctccttccac cgcccgttac cgtccctagg  3540
aaattttact ctgctggaga gcttcttcta cggcccccttgcagcaatgc tcttcccagc  3600
attacgttgc gggtaaaacg gaggtcgtgt acccgaccta gcagcccagg gatggaaaag  3660
tcccggccgt cgctggcaat aatagcgggc ggacgcatgt catgagatta ttggaaacca  3720
ccagaatcga atataaaagg cgaacacctt tcccaatttt ggtttctcct gacccaaaga  3780
ctttaaattt aatttatttg tccctatttc aatcaattga acaactatca aaacacaatg  3840
gtcaaagtcg caattcttgg cgcttctggt ggcgtgggac aaccgctatc attactgcta  3900
aaattaagcc cttacgtttc cgagctggcg ttgtacgata tccgagctgc ggaaggcatt  3960
ggtaaggatt tatctcacat caacaccaac tcaagttgtg tcggttatga taaggatagt  4020
attgagaaca ccttgtcaaa tgctcaggtg gtgctaatac cggctggtgt tcccagaaag  4080
cccggtttaa ctagagatga tttgttcaag atgaacgccg gtattgtcaa aagcctggta  4140
accgctgttg gaaagttcgc accaaatgcg aggattttag tcatttcaaa ccctgtaaac  4200
agtttggtcc ctattgctgt ggaaactttg aagaaaatgg gtaagttcaa acctggaaac  4260
gttatgggtg tgacgaacct tgacctggta cgtgcagaaa cctttttggt agattatttg  4320
```

```
atgctaaaaa accccaaaat tggacaagaa caagacaaaa ctacaatgca cagaaaggtc  4380
actgttattg ggggtcattc aggggaaacc attatcccaa taatcaccga caaatcgctg  4440
gtatttcaac ttgataagca gtacgagcac ttcattcata gggtccagtt cggaggtgat  4500
gaaattgtca aagctaaaca gggcgccggt tccgccacgt tgtccatggc gttcgcgggg  4560
gccaagtttg ctgaagaagt tttgaggagc ttccataatg agaaaccaga aacggagtca  4620
ctttccgcat tcgtttattt accaggctta aaaaacggta agaaagcgca gcaattagtt  4680
ggcgacaact ctattgagta tttttccttg ccaattgttt tgagaaatgg tagcgtagta  4740
tccatcgata ccagtgttct ggaaaaactg tctccgagag aggaacaact cgttaatact  4800
gcggtcaaag agctacgcaa gaatattgaa aaaggcaaga gtttcatcct agactcttaa  4860
gtatctccag tcgtttagat tgttagatat tttctttgtg tattcgtttc agtctgatgt  4920
ttatgctaca aacgtcatct ggactttaat ccaataagga tattcttcaa cttaatagta  4980
tcttaataat atttttttc ttttgatttc ttcgtaaggt gttttgttgc actcatgatc  5040
tacgactttt gttcgtgact gattgccaga tctagggagg gcatcattga ggtttccaca  5100
aaaggaagaa acatggatcc agagacatca acagagagga aagcgggtag tgaagccgaa  5160
gccacaacac agcccgattt ggaagggagt tcacaatcaa ggtgagtcca gccatttttt  5220
ttcttttttt tttttttatt caggtgaacc cacctaacta tttttaactg ggatccagtg  5280
agctcgctgg gtgaaagcca accatctttt gtttcgggga accgtgctcg ccccgtaaag  5340
ttaatttttt tttcccgcgc agctttaatc tttcggcaga gaaggcgttt tcatcgtagc  5400
gtgggaacag aataatcagt tcatgtgcta tacaggcaca tggcagcagt cactattttg  5460
ctttttaacc ttaaagtcgt tcatcaatca ttaactgacc aatcagattt tttgcatttg  5520
ccacttatct aaaaatactt ttgtatctcg cagatacgtt cagtggtttc caggacaaca  5580
cccaaaaaaa ggtatcaatg ccactaggca gtcggtttta tttttggtca cccacgcaaa  5640
gaagcaccca cctcttttag gttttaagtt gtgggaacag taacaccgcc tagagcttca  5700
ggaaaaacca gtacctgtga ccgcaattca ccatgatgca gaatgttaat ttaaacgagt  5760
gccaaatcaa gatttcaaca gacaaatcaa tcgatccata gttacccatt ccagcctttt  5820
cgtcgtcgag cctgcttcat tcctgcctca ggtgcataac tttgcatgaa aagtccagat  5880
tagggcagat tttgagttta aaataggaaa tataaacaaa tataccgcga aaaaggtttg  5940
tttatagctt ttcgcctggt gccgtacggt ataaatacat actctcctcc ccccctggt  6000
tctctttttc ttttgttact tacattttac cgttccgtca ctcgcttcac tcaacaacaa  6060
aaatgagcag tagcaagaaa ttggccggtc ttagggacaa tttcagtttg ctcggcgaaa  6120
agaataagat cttggtcgcc aatagaggtg aaattccgat tagaattttt agatctgctc  6180
atgagctgtc tatgagaacc atcgccatat actcccatga ggaccgtctt tcaatgcaca  6240
ggttgaaggc ggacgaagcg tatgttatcg gggaggaggg ccagtataca cctgtgggtg  6300
cttacttggc aatggacgag atcatcgaaa ttgcaaagaa gcataaggtg gatttcatcc  6360
atccaggtta tggtttcttg tctgaaaatt cggaatttgc cgacaaagta gtgaaggccg  6420
gtatcacttg gatcggccct ccagctgaag ttattgactc tgtgggtgac aaagtctctg  6480
ccagacactt ggcagcaaga gctaacgttc ctaccgttcc cggtactcca ggacctatcg  6540
aaactgtgca agaggcactt gacttcgtta atgaatacgg ctacccggtg atcattaagg  6600
ccgcctttgg tggtggtggt agaggtatga gagtcgttag agaaggtgac gacgtggcag  6660
atgcctttca acgtgctacc tccgaagcca gtactgcctt cggtaatggt acctgctttg  6720
tggaaagatt cttggacaag ccaaagcata ttgaagttca attgttggct gataaccacg  6780
gaaacgtggt tcatcttttc gaaagagact gttctgtgca aagaagacac caaaaagttg  6840
tcgaagtcgc tccagcaaag actttgcccc gtgaagttcg tgacgctatt ttgacagatg  6900
ctgttaaatt agctaaggta tgtggttaca gaaacgcagg taccgccgaa ttcttggttg  6960
acaaccaaaa cagacactat ttcattgaaa ttaatccaag aattcaagtg gagcatacca  7020
tcactgaaga aatcaccggt attgacattg tttctgccca aatccagatt gccgcaggtg  7080
ccactttgac tcaactaggt ctattacagg ataaaatcac cacccgtggg ttttccatcc  7140
aatgtcgtat taccactgaa gatccctcta agaatttcca accggatacc ggtcgcctgg  7200
aggtctatcg ttctgccggt ggtaatggtg tgagattgga cggtggtaac gcttatgcag  7260
gtgctactat ctcgcctcac tacgactcaa tgctggtcaa atgttcatgc tctggttcta  7320
cttatgaaat cgtccgtagg aagatgattc gtgccctgat cgaattcaga atcagaggtg  7380
ttaagaccaa cattcccttc ctattgactc ttttgaccaa tccagttttt attgagggta  7440
catactggac gacttttatt gacgacaccc cacaactgtt ccaaatggta tcgtcacaaa  7500
acagagcgca aaaactgtta cactatttgg cagacttggc agttaacggt tcttctatta  7560
agggtcaaat tggcttgcca aaactaaaat caaatccaag tgtcccccat ttgcacgatg  7620
ctcagggcaa tgtcatcaac gttacaaagt ctgcaccacc atccggatgg agacaagtgc  7680
tactggaaaa gggaccatct gaatttgcca agcaagtcag acagttcaat ggtactctac  7740
tgatggacac cacctggaga gacgctcatc aatctctact tgcaacaaga gtcagaaccc  7800
acgatttggc tacaatcgct ccaacaaccg cacatgccct tgcaggtgct ttcgctttag  7860
aatgttgggg tggtgctaca ttcgacgttg caatgagatt cttgcatgag gatccatggg  7920
aacgtctgag aaaattaaga tctctggtgc ctaatattcc attccaaatg ttattacgtg  7980
gtgccaacgg tgtggcttac tcttcattac ctgacaatgc tattgaccat tttgtcaagc  8040
aagccaagga taatggtgtt gatatattta gagtttttga tgccttgaat gatttagaac  8100
aattaaaagt tggtgtgaat gctgtcaaga aggccggtgg tgttgtcgaa gctactgttt  8160
gttactctgg tgacatgctt cagccaggta agaaatacaa cttagactac tacctagaag  8220
ttgttgaaaa aatagttcaa atgggtacac atatcttggg tattaaggat atggcaggta  8280
ctatgaaacc ggccgctgcc aaattattaa ttggctccct aagaaccaga tatccggatt  8340
taccaattca tgttcacagt catgactccg caggtactgc tgttgcgtct atgactgcat  8400
gtgccctagc aggtgctgat gttgtcgatg tagctatcaa ttcaatgtcg ggcttaactt  8460
cccaaccatc aattaatgca ctgttggctt cattagaagg taacattgat actgggatta  8520
acgttgagca tgttcgtgaa ttagatgcat actgggccga aatgagactg ttgtattctt  8580
gtttcgaggc cgacttgaag ggaccagatc cagaagttta ccaacatgaa atcccaggtg  8640
gtcaattgac taacttgtta ttccaagctc aacaactggg tcttggtgaa caatgggctg  8700
aaactaaaag agcttacaga gaagccaatt acctactggg agatattgtt aaagttaccc  8760
caacttctaa ggttgtcggt gatttagctc aattcatggt ttctaacaaa ctgacttccg  8820
acgatattag acgtttagct aattctttgg actttcctga ctctgttatg gacttttttg  8880
aaggtttaat tggtcaacca tacggtgggt tcccagaacc attaagatct gatgtattga  8940
gaaacaagag aagaaagttg acgtgccgtc caggtttaga attagaacca tttgatctcg  9000
aaaaaattag agaagacttg cagaacagat tcggtgatat tgatgaatgc gatgttgctt  9060
```

```
cttacaatat gtatccaagg gtctatgaag atttccaaaa gatcagagaa acatacggtg  9120
atttatcagt tctaccaacc aaaaatttcc tagcaccagc agaacctgat gaagaaatcg  9180
aagtcaccat cgaacaaggt aagactttga ttatcaaatt gcaagctgtt ggtgacttaa  9240
ataagaaaac tgggcaaaga gaagtgtatt ttgaattgaa cggtgaatta agaaagatca  9300
gagttgcaga caagtcacaa aacatacaat ctgttgctaa accaaaggct gatgtccacg  9360
atactcacca aatcggtgca ccaatggctg gtgttatcat agaagttaaa gtacataaag  9420
ggtctttggt gaaaaagggc gaatcgattg ctgttttgag tgccatgaaa atggaaatgg  9480
ttgtctcttc accagcagat ggtcaagtta aagacgtttt cattaaggat ggtgaaagtg  9540
ttgacgcatc agatttgttg gttgtcctag aagaagaaac cctacccccca tcccaaaaaa  9600
agtaaagaca tgactgttcc tcagttcaag ttgggcactt acgagaagac cggtcttgct  9660
agattctaat caagaggatg tcagaatgcc atttgcctga gagatgcagg cttcattttt  9720
gattactttt ttatttgtaa cctatatagt ataggatttt ttttgtcatt ttgtttcttc  9780
tcgtacgagc ttgctcctga tcagcctatc tcgcagctga tgaatatctt gtggtagggg  9840
tttgggaaaa tcattcgagt ttgatgtttt tcttggtatt tcccactcct cttcagagta  9900
cagaagatta agtgagagcg gccgctcgtc cccgccgggt cacccggcca gcgacatgga  9960
ggcccagaat accctccttg acagtcttga cgtgcgcagc tcaggggcat gatgtgactg  10020
tcgcccgtac atttagccca tacatcccca tgtataatca tttgcatcca tacattttga  10080
tggccgcacg gcgcgaagca aaaattacgg ctcctcgctg cagacctgcg agcagggaaa  10140
cgctcccctc acagacgcgt tgaattgtcc ccacgccgcg cccctgtaga gaaatataaa  10200
aggttaggat ttgccactga ggttcttctt tcatatactt ccttttaaaa tcttgctagg  10260
atacagttct cacatcacat ccgaacataa acaaccatgg gtaaggaaaa gactcacgtt  10320
tcgaggccgc gattaaattc caacatggat gctgatttat atgggtataa atgggctcgc  10380
gataatgtcg ggcaatcagg tgcgacaatc tatcgattgt atgggaagcc cgatgcgcca  10440
gagttgtttc tgaaacatgg caaaggtagc gttgccaatg atgttacaga tgagatggtc  10500
agactaaact ggctgacgga atttatgcct cttccgacca tcaagcattt tatccgtact  10560
cctgatgatg catggttact caccactgcg atccccggca aaacagcatt ccaggtatta  10620
gaagaatatc ctgattcagg tgaaaatatt gttgatgcgc tggcagtgtt cctgcgccgg  10680
ttgcattcga ttcctgtttg taattgtcct tttaacagcg atcgcgtatt tcgtctcgct  10740
caggcgcaat cacgaatgaa taacggtttg gttgatgcga gtgattttga tgacgagcgt  10800
aatggctggc ctgttgaaca agtctggaaa gaaatgcata agcttttgcc attctcaccg  10860
gattcagtcg tcactcatgg tgatttctca cttgataacc ttatttttga cgaggggaaa  10920
ttaataggtt gtattgatgt tggacgagtc ggaatcgcag accgatacca ggatcttgcc  10980
atcctatgga actgcctcgg tgagttttct ccttcattac agaaacggct ttttcaaaaa  11040
tatggtattg ataatcctga tatgaataaa ttgcagtttc atttgatgct cgatgagttt  11100
ttctaatcag tactgacaat aaaaagattc ttgttttcaa gaacttgtca tttgtatagt  11160
ttttttatat tgtagttgtt ctattttaat caaatgttag cgtgatttat attttttttc  11220
gcctcgacat catctgccca gatgcgaagt taagtgcgca gaaagtaata tcatgcgtca  11280
atcgtatgtg aatgctggtc gctatactgc tgtcgattcg atactaacgc caagaagttg  11340
attgagactt tcaacgagat tgctgaagac aaggaacaat tcgagaagtt ttacagtgct  11400
ttctccaaga acttgaagtt gggtgtccat gaagacagcc aaaacagatc cgcattggcc  11460
aagttgctga gatttaactc caccaagtct actgaggagc taacctcatt ctctgactac  11520
gtcaccagaa tgccagagca ccagaagaac atctacttca ttaccggtga gtctgtcaag  11580
gctcttgaga aatctccatt cttggatgct ttgaaggaga agaactttga ggtcctattg  11640
ctgaccgatc ctattgatga gtacgctatg actcaattga aagagattga ggacaagaaa  11700
ttggttgaca tcactaaaga ctttgagctg gaagagtctg aggaggagaa gaaggctaga  11760
gaggaagagg ttaaagattt cgagcctttg actaaagccc tgaaagagat tttgggtgac  11820
aaggttgaga aggttgtagt ttcctacaag ctggttgact ctcctgctgc tattagaact  11880
tcccaattcg gctggtctgc taacatggaa agaattatga aggctcaagc tctgagagac  11940
accaacacca tgtcctcgta catggcttca aagaagatct tcgagatctc tccaaagtcg  12000
ccaatcatta aggctttgag aaagaaggtt gaggctaccg gtacagaaga gaccccacag  12060
aatcagggga taacgcagga aagaacatgt gagcaaaagg ccagcaaaag gccaggaacc  12120
gtaaaaaggc cgcgttgctg gcgtttttcc ataggctccg cccccctgac gagcatcaca  12180
aaaatcgacg ctcaagtcag aggtggcgaa acccgacagg actataaaga taccaggcgt  12240
ttccccctgg aagctccctc gtgcgctctc ctgttccgac cctgccgctt accggatacc  12300
tgtccgcctt tctcccttcg ggaagcgtgg cgctttctca atgctcacgc tgtaggtatc  12360
tcagttcggt gtaggtcgtt cgctccaagc tgggctgtgt gcacgaaccc cccgttcagc  12420
ccgaccgctg cgccttatcc ggtaactatc gtcttgagtc caacccggta agacacgact  12480
tatcgccact ggcagcagcc actggtaaca ggattagcag agcgaggtat gtaggcggtg  12540
ctacagagtt cttgaagtgg tggcctaact acggctacac tagaaggaca gtatttggta  12600
tctgcgctct gctgaagcca gttaccttcg gaaaaagagt tggtagctct tgatccggca  12660
aacaaaccac cgctggtagc ggtggttttt ttgtttgcaa gcagcagatt acgcgcagaa  12720
aaaaaggatc tcaagaagat cctttgatct tttctacggg gtctgacgct cagtggaacg  12780
aaaactcacg ttaagggatt ttggtcatga gattatcaaa aaggatcttc acctagatcc  12840
ttttaaatta aaaatgaagt tttaaatcaa tctaaagtat atatgagtaa acttggtctg  12900
acagttacca atgcttaatc agtgaggcac ctatctcagc gatctgtcta tttcgttcat  12960
ccatagttgc ctgactcccc gtcgtgtaga taactacgat acgggagggc ttaccatctg  13020
gccccagtgc tgcaatgata ccgcgagacc cacgctcacc ggctccagat ttatcagcaa  13080
taaaccagcc agccggaagg gccgagcgca gaagtggtcc tgcaacttta tccgcctcca  13140
tccagtctat taattgttgc cgggaagcta gagtaagtag ttcgccagtt aatagtttgc  13200
gcaacgttgt tgccattgct acaggcatcg tggtgtcacg ctcgtcgttt ggtatggctt  13260
cattcagctc cggttcccaa cgatcaaggc gagttacatg atcccccatg ttgtgcaaaa  13320
aagcggttag ctccttcggt cctccgatcg ttgtcagaag taagttggcc gcagtgttat  13380
cactcatggt tatggcagca ctgcataatt ctcttactgt catgccatcc gtaagatgct  13440
tttctgtgac tggtgagtac tcaaccaagt cattctgaga atagtgtatg cggcgaccga  13500
gttgctcttg cccggcgtca atacgggata ataccgcgcc acatagcaga actttaaaag  13560
tgctcatcat tggaaaacgt tcttcggggc gaaaactctc aaggatctta ccgctgttga  13620
gatccagttc gatgtaaccc actcgtgcac ccaactgatc ttcagcatct tttactttca  13680
ccagcgtttc tgggtgagca aaaacaggaa ggcaaaatgc cgcaaaaaag ggaataaggg  13740
cgacacggaa atgttgaata ctcatactct tcctttttca atattattga agcatttatc  13800
```

-continued

```
agggttattg tctcatgagc ggatacatat ttgaatgtat ttagaaaaat aaacaaatag  13860
gggttccgcg cacatttccc cgaaaa                                        13886

SEQ ID NO: 58           moltype = DNA  length = 1047
FEATURE                 Location/Qualifiers
misc_feature            1..1047
                        note = Methylococcus capsulatus (Bath)
source                  1..1047
                        mol_type = genomic DNA
                        organism = Methylococcus capsulatus
SEQUENCE: 58
atgcagcgag ttcacactat cacggcggtg acggaggatg gcgaatcgct ccgcttcgaa  60
tgccgttcgg acgaggacgt catcaccgcc gccctgcgcc agaacatctt tctgatgtcg  120
tcctgccggg agggcggctg tgcgacctgc aaggccttgt gcagcgaagg ggactacgac  180
ctcaagggct gcagcgttca ggcgctgccg ccggaagagg aggaggaagg gttggtgttg  240
ttgtgccgga cctacccgaa gaccgacctg gaaatcgaac tgccctatac ccattgccgc  300
atcagttttg gtgaggtcgg cagtttcgag gcggaggtcg tcggcctcaa ctgggtttcg  360
agcaacaccg tccagtttct tttgcagaag cggcccgacg agtgcggcaa ccgtggcgtg  420
aaattcgaac ccggtcagtt catggacctg accatccccg gcaccgatgt ctcccgctcc  480
tactcgccgg cgaaccttcc taatcccgaa ggccgcctgg agttcctgat ccgcgtgtta  540
ccggagggac ggttttcgga ctacctgcgc aatgacgcgc gtgtcggaca ggtcctctcg  600
gtcaaagggc cactgggcgt gttcggtctc aaggagcggg gcatggcgcc gcgctatttc  660
gtggccggcg gcaccgggtt ggcgccggtg gtctcgatgg tgcggcagat gcaggagtgg  720
accgcgccga acgagacccg catctatttc ggtgtgaaca ccgagccgga attgttctac  780
atcgacgagc tcaaatccct ggaacgatcg atgcgcaatc tcaccgtgaa ggcctgtgtc  840
tggcacccga gcggggactg ggaaggcgag cagggctcgc ccatcgatgc gttgcgggaa  900
gacctggagt cctccgacgc caacccggac atttatttgt gcggtccgcc gggcatgatc  960
gatgccgcct gcgagctggt acgcagccgc ggtatccccg gcgaacaggt cttcttcgaa  1020
aaattcctgc cgtccggggc ggcctga                                       1047

SEQ ID NO: 59           moltype = AA  length = 348
FEATURE                 Location/Qualifiers
REGION                  1..348
                        note = misc_feature - Methylococcus capsulatus (Bath)
source                  1..348
                        mol_type = protein
                        organism = Methylococcus capsulatus
SEQUENCE: 59
MQRVHTITAV TEDGESLRFE CRSDEDVITA ALRQNIFLMS SCREGGCATC KALCSEGDYD  60
LKGCSVQALP PEEEEGLVL LCRTYPKTDL EIELPYTHCR ISFGEVGSFE AEVVGLNWVS  120
SNTVQFLLQK RPDECGNRGV KFEPGQFMDL TIPGTDVSRS YSPANLPNPE GRLEFLIRVL  180
PEGRFSDYLR NDARVGQVLS VKGPLGVFGL KERGMAPRYF VAGGTGLAPV VSMVRQMQEW  240
TAPNETRIYF GVNTEPELFY IDELKSLERS MRNLTVKACV WHPSGDWEGE QGSPIDALRE  300
DLESSDANPD IYLCGPPGMI DAACELVRSR GIPGEQVFFE KFLPSGAA               348

SEQ ID NO: 60           moltype = DNA  length = 312
FEATURE                 Location/Qualifiers
misc_feature            1..312
                        note = Methylococcus capsulatus (Bath)
source                  1..312
                        mol_type = genomic DNA
                        organism = Methylococcus capsulatus
SEQUENCE: 60
atggtcgaat cggcatttca gccattttcg ggcgacgcag acgaatggtt cgaggaacca  60
cggccccagg ccggtttctt cccttccgcg gactggcatc tgctcaaacg ggacgagacc  120
tacgcagcct atgccaagga tctcgatttc atgtggcggt gggtcatcgt ccgggaagaa  180
aggatcgtcc aggagggttg ctcgatcagc ctggagtcgt cgatccgcgc cgtgacgcac  240
gtactgaatt attttggtat gaccgaacaa cgcgccccgg cagaggaccg gaccggcgga  300
gttcaacatt ga                                                       312

SEQ ID NO: 61           moltype = AA  length = 103
FEATURE                 Location/Qualifiers
REGION                  1..103
                        note = misc_feature - Methylococcus capsulatus (Bath)
source                  1..103
                        mol_type = protein
                        organism = Methylococcus capsulatus
SEQUENCE: 61
MVESAFQPFS GDADEWFEEP RPQAGFFPSA DWHLLKRDET YAAYAKDLDF MWRWVIVREE  60
RIVQEGCSIS LESSIRAVTH VLNYFGMTEQ RAPAEDRTGG VQH                     103

SEQ ID NO: 62           moltype = DNA  length = 1680
FEATURE                 Location/Qualifiers
misc_feature            1..1680
                        note = Methylococcus capsulatus (Bath)
source                  1..1680
                        mol_type = genomic DNA
                        organism = Methylococcus capsulatus
SEQUENCE: 62
```

```
atggcaaagg aagtggttta caggggggagt gcgcggcagc gcatgatgca aggcatcgag  60
atactcgcgc gggcggcgat accgacgctg ggagccaccg gccccagcgt catgatccag  120
caccgcgccg atggcctgcc ccccatttcg acgcgggacg gcgtcacggt ggctaactcc  180
atcgtactca aggaccgtgt cgcgaatctc ggtgcccggc tgctgcggga cgtcgccggc  240
accatgtccc gcgaagcagg ggatggcacc accaccgcca tcgtgctggc ccgccatatc  300
gcccgggaga tgttcaagag cctcgccgtc ggtgccgatc ccatcgctct caagcgtggt  360
atcgaccgtg ccgtcgcccg cgtgagcgag gacatcgggg ctcgggcctg gcgcggcgac  420
aaggaatcgg tcatcctggg ggtggccgcg gtggcgacca agggcgagcc gggcgtgggc  480
cggctgctgc tggaggcgct ggacgcggtc ggcgtccatg gcgccgtgtc gatcgaactg  540
gggcagcggc gcgaggacct gctcgacgtg gtcgacgggt atcgttggga aaaaggttat  600
ctgtcgccct attttgtgac cgatcgggct cgcgagctgg ccgaactcga agacgtctac  660
ctcttgatga ccgatcggga ggtggtcgat ttcatcgatt tggtacccct gctggaggcg  720
gtgaccgagg ctggtggcag cctcctgatc gccgccgacc gtgtccacga gaaggcactg  780
gccggccttt tgctcaatca cgttcgcggc gtcttcaagg ccgtcgcggt caccgcgccc  840
gggttcggcg acaagcggcc gaaccgcctt ttggatctgg cggcgttgac cggtgggcgg  900
gcggtcctgg aagcccaggg cgaccgattg gaccgggtca cgctggccga cctggggcgg  960
gtgcggcggg cggtcgtcag cgctgacgac accgcgctgc tcggcatacc gggcaccgaa  1020
gcctcccggg cccgcttgga gggtttgcgc ctggaagcgg agcagtaccg ggcgctcaag  1080
cccggtcagg gatcggcgac ggggcgcttg cacgagctcg aggaaatcga ggcccggatc  1140
gtcggtctga gcggcaagtc cgcggtctac cgcgtgggcg gcgtgaccga cgtggagatg  1200
aaggagcgga tggtacggat cgaaaatgcc taccgctcgg tggtgtctgc actggaggag  1260
ggggtgttgc ccggcggcgg tgtcgggttt ctgggcagca tgcccgtttt ggccgagctg  1320
gaagcgcgcg atgccgacga agcacgcggc atcggcatcg tccgttccgc gctgacggag  1380
cccctccgga tcatcggaga aaattcggga ctgtcagggg aggccgtcgt cgccaaggtc  1440
atggatcacg ccaatcccgg ttggggttac gatcaggaaa gcggaagttt ctgcgacctc  1500
cacgccaggg gcatttggga tgccgccaag gtgctcaggc tggccctgga aaaagccgcg  1560
tcggtggccg gcacgtttct caccaccgaa gccgtggtac tggagattcc ggacactgac  1620
gctttcgccg gtttcagtgc ggagtgggcc gccgcgaccc gggaggatcc gcgggtctga  1680
```

```
SEQ ID NO: 63          moltype = AA  length = 559
FEATURE                Location/Qualifiers
REGION                 1..559
                       note = misc_feature - Methylococcus capsulatus (Bath)
source                 1..559
                       mol_type = protein
                       organism = Methylococcus capsulatus
SEQUENCE: 63
MAKEVVYRGS ARQRMMQGIE ILARAAIPTL GATGPSVMIQ HRADGLPPIS TRDGVTVANS  60
IVLKDRVANL GARLLRDVAG TMSREAGDGT TTAIVLARHI AREMFKSLAV GADPIALKRG  120
IDRAVARVSE DIGARAWRGD KESVILGVAA VATKGEPGVG RLLLEALDAV GVHGAVSIEL  180
GQRREDLLDV VDGYRWEKGY LSPYFVTDRA RELAELEDVY LLMTDREVVD FIDLVPLLEA  240
VTEAGGSLLI AADRVHEKAL AGLLLNHVRG VFKAVAVTAP GFGDKRPNRL LDLAALTGGR  300
AVLEAQGDRL DRVTLADLGR VRRAVVSADD TALLGIPGTE ASRARLEGLR LEAEQYRALK  360
PGQGSATGRL HELEEIEARI VGLSGKSAVY RVGGVTDVEM KERMVRIENA YRSVVSALEE  420
GVLPGGGVGF LGSMPVLAEL EARDADEARG IGIVRSALTE PLRIIGENSG LSGEAVVAKV  480
MDHANPGWGY DQESGSFCDL HARGIWDAAK VLRLALEKAA SVAGTFLTTE AVVLEIPDTD  540
AFAGFSAEWA AATREDPRV                                               559

SEQ ID NO: 64          moltype = DNA  length = 294
FEATURE                Location/Qualifiers
source                 1..294
                       mol_type = genomic DNA
                       organism = Escherichia coli
SEQUENCE: 64
atgaatattc gtccattgca tgatcgcgtg atcgtcaagc gtaaagaagt tgaaactaaa  60
tctgctggcg gcatcgttct gaccggctct gcagcggcta aatccacccg cggcgaagtg  120
ctggctgtcg gcaatggccg tatccttgaa aatggcgaag tgaagccgct ggatgtgaaa  180
gttggcgaca tcgttatttt caacgatggc tacggtgtga aatctgagaa gatcgacaat  240
gaagaagtgt tgatcatgtc cgaaagcgac attctggcaa ttgttgaagc gtaa        294

SEQ ID NO: 65          moltype = AA  length = 97
FEATURE                Location/Qualifiers
source                 1..97
                       mol_type = protein
                       organism = Escherichia coli
SEQUENCE: 65
MNIRPLHDRV IVKRKEVETK SAGGIVLTGS AAAKSTRGEV LAVGNGRILE NGEVKPLDVK  60
VGDIVIFNDG YGVKSEKIDN EEVLIMSESD ILAIVEA                           97

SEQ ID NO: 66          moltype = DNA  length = 1647
FEATURE                Location/Qualifiers
source                 1..1647
                       mol_type = genomic DNA
                       organism = Escherichia coli
SEQUENCE: 66
atggcagcta aagacgtaaa attcggtaac gacgctcgtg tgaaaatgct gcgcggcgta  60
aacgtactgg cagatgcagt gaaagttacc ctcggtccaa aaggccgtaa cgtagttctg  120
gataaatctt tcggtgcacc gaccatcacc aaagatggtg tttccgttgc tcgtgaaatc  180
gaactggaag acaagttcga aaatatgggt gcgcagatgg tgaaagaagt tgcctctaaa  240
```

```
gcaaacgacg ctgcaggcga cggtaccacc actgcaaccg tactggctca ggctatcatc  300
actgaaggtc tgaaagctgt tgctgcgggc atgaacccga tggacctgaa acgtggtatc  360
gacaaagcgg ttaccgctgc agttgaagaa ctgaaagcgc tgtccgtacc atgctctgac  420
tctaaagcga ttgctcaggt tggtaccatc tccgctaact ccgacgaaac cgtaggtaaa  480
ctgatcgctg aagcgatgga caaagtcggt aaagaaggcg ttatcaccgt tgaagacggt  540
accggtctgc aggacgaact ggacgtggtt gaaggtatgc agttcgaccg tggctacctg  600
tctccttact tcatcaacaa gccggaaact ggcgcagtag aactggaaag cccgttcatc  660
ctgctggctg acaagaaaat ctccaacatc cgcgaaatgc tgccggttct ggaagctgtt  720
gccaaagcag gcaaaccgct gctgatcatc gctgaagatg tagaaggcga agcgctggca  780
actctggttg ttaacaccat gcgtggcatc gtgaaagtcg ctgcggttaa agcaccgggc  840
ttcggcgatc gtcgtaaagc tatgctgcag gatatcgcaa ccctgactgg cggtaccgtg  900
atctctgaag agatcggtat ggagctggaa aaagcaaccc tggaagacct gggtcaggct  960
aaacgtgttg tgatcaacaa agacaccacc actatcatcg atggcgtggg tgaagaagct  1020
gcaatccagg gccgtgttgc tcagatccgt cagcagattg aagaagcaac ttctgactac  1080
gaccgtgaaa aactgcagga acgcgtagcg aaactggcag gcggcgttgc agttatcaaa  1140
gtgggtgctg ctaccgaagt tgaaatgaaa gagaaaaaag cacgcgttga agatgccctg  1200
cacgcgaccc gtgctgcggt agaagaaggc gtggttgctg gtggtggtgt tgcgctgatc  1260
cgcgtagcgt ctaaactggc tgacctgcgt ggtcagaacg aagaccagaa cgtgggtatc  1320
aaagttgcac tgcgtgcaat ggaagctccg ctgcgtcaga tcgtattgaa ctgcggcgaa  1380
gaaccgtctg ttgttgctaa caccgttaaa ggcggcgacg gcaactacgg ttacaacgca  1440
gcaaccgaag aatacggcaa catgatcgac atgggtatcc tggatccaac caaagtaact  1500
cgttctgctc tgcagtacgc agcttctgtg gctggcctga tgatcaccac cgaatgcatg  1560
gttaccgacc tgccgaaaaa cgatgcagct gacttaggcg ctgctggcgg tatgggcggc  1620
atgggtggca tgggcggcat gatgtaa                                     1647

SEQ ID NO: 67          moltype = AA  length = 548
FEATURE                Location/Qualifiers
source                 1..548
                       mol_type = protein
                       organism = Escherichia coli
SEQUENCE: 67
MAAKDVKFGN DARVKMLRGV NVLADAVKVT LGPKGRNVVL DKSFGAPTIT KDGVSVAREI  60
ELEDKFENMG AQMVKEVASK ANDAAGDGTT TATVLAQAII TEGLKAVAAG MNPMDLKRGI  120
DKAVTAAVEE LKALSVPCSD SKAIAQVGTI SANSDETVGK LIAEAMDKVG KEGVITVEDG  180
TGLQDELDVV EGMQFDRGYL SPYFINKPET GAVELESPFI LLADKKISNI REMLPVLEAV  240
AKAGKPLLII AEDVEGEALA TLVVNTMRGI VKVAAVKAPG FGDRRKAMLQ DIATLTGGTV  300
ISEEIGMELE KATLEDLGQA KRVVINKDTT TIIDGVGEEA AIQGRVAQIR QQIEEATSDY  360
DREKLQERVA KLAGGVAVIK VGAATEVEMK EKKARVEDAL HATRAAVEEG VVAGGGVALI  420
RVASKLADLR GQNEDQNVGI KVALRAMEAP LRQIVLNCGE EPSVVANTVK GGDGNYGYNA  480
ATEEYGNMID MGILDPTKVT RSALQYAASV AGLMITTECM VTDLPKNDAA DLGAAGGMGG  540
MGGMGGMM                                                          548

SEQ ID NO: 68          moltype = DNA  length = 291
FEATURE                Location/Qualifiers
misc_feature           1..291
                       note = Methylococcus capsulatus (Bath)
source                 1..291
                       mol_type = genomic DNA
                       organism = Methylococcus capsulatus
SEQUENCE: 68
gtgaaaatcc gcccgttaca tgaccgtgtc atcatcaaac gcttggaaga agagcgtacc  60
tcggcgggcg ggattgtcat tccagatagc gcagctgaaa aaccgatgcg tggtgaaatc  120
ctggcagtgg gcaatggaaa agtgcttgat aatggagagg tacgtgcttt acaggtgaaa  180
gtgggtgata aagtgctctt tgggaaatac gcgggtacgg aggttaaagt agatggggaa  240
gatgttgttg tcatgcgtga agatgacatt ctggctgtgt tagaatctta a          291

SEQ ID NO: 69          moltype = AA  length = 96
FEATURE                Location/Qualifiers
REGION                 1..96
                       note = misc_feature - Methylococcus capsulatus (Bath)
source                 1..96
                       mol_type = protein
                       organism = Methylococcus capsulatus
SEQUENCE: 69
MKIRPLHDRV IIKRLEEERT SAGGIVIPDS AAEKPMRGEI LAVGNGKVLD NGEVRALQVK  60
VGDKVLFGKY AGTEVKVDGE DVVVMREDDI LAVLES                            96

SEQ ID NO: 70          moltype = DNA  length = 60
FEATURE                Location/Qualifiers
misc_feature           1..60
                       note = Synthetic primer.
source                 1..60
                       mol_type = other DNA
                       organism = synthetic construct
SEQUENCE: 70
tgagtttaaa cgcggccgca atttgaacgc acccataaca gatacggact ttctcaaagg  60

SEQ ID NO: 71          moltype = DNA  length = 30
FEATURE                Location/Qualifiers
```

```
misc_feature          1..30
                      note = Synthetic primer.
source                1..30
                      mol_type = other DNA
                      organism = synthetic construct
SEQUENCE: 71
cgtgaaaggc gagatcacca aggtagtcgg                                   30

SEQ ID NO: 72         moltype = DNA  length = 2244
FEATURE               Location/Qualifiers
misc_feature          1..2244
                      note = Synthetic plasmid.
source                1..2244
                      mol_type = other DNA
                      organism = synthetic construct
SEQUENCE: 72
cctcctgcca gagttcacat aaacagacgc ttttccggtg catctgtggg agccgtgagg  60
ctcaaccatg aatctgacag tacgggcgaa acccgacagg acttaaagat ccccaccgtt  120
tccggcgggt cgctccctct tgcgctctcc tgttccgacc ctgccgttta ccggatacct  180
gttccgcctt tctcccttac gggaagtgtg gcgctttctc atagctcaca cactggtatc  240
tcggctcggt gtaggtcgtt cgctccaagc tgggctgtaa gcaagaactc cccgttcagc  300
ccgactgctg cgccttatcc ggtaactgtt cacttgagtc caacccggaa aagcacggta  360
aaacgccact ggcagcagcc attggtaact gggagttcgc agaggatttg tttagctaaa  420
cacgcggttg ctcttgaagt gtgcgccaaa gtccggctac actggaagga cagatttggt  480
tgctgtgctc tgcgaaagcc agttaccacg gttaagcagt tccccaactg acttaacctt  540
cgatcaaacc acctccccag gtggtttttt cgtttacagg gcaaaagatt acgcgcagaa  600
aaaaaggatc tcaagaagat cctttgatct tttctactga accgctctag atttcagtgc  660
aatttatctc ttcaaatgta gcacctgaag tcagccccat acgatataag ttgtaattct  720
catgttagtc atgccccgcg cccaccggaa ggagctgact gggttgaagg ctctcaaggg  780
catcggtcga gatcccggtg cctaatgagt gagctaactt ttgacagcta gctcagtcct  840
agggactatg ctagcaccag cctcgaggga aaccacgtaa gctccggcgt ttaaacgcgg  900
ccgcaatttg aacgccagca catggactct cgagtctact agcgcagctt aattaaccta  960
ggctgctgcc accgctgagc aataactagc ataacccctt ggggcctcta aacgggtctt  1020
gaggggtttt ttgctgaaac ctcaggcatt tgagaagcac acggtcacac tgcttccggt  1080
agtcaataaa ccggtaaacc agcaatagac ataagcggct atttaacgac cctgccctga  1140
accgacgacc gggtcatcgt ggccggatct tgcggcccct cggcttgaac gaattgttag  1200
acattatttg ccgactacct tggtgatctc gcctttcacg tagtggacaa attcttccaa  1260
ctgatctgcg cgcgaggcca agcgatcttc ttcttgtcca agataagcct gtctagcttc  1320
aagtatgacg ggctgatact gggccggcag gcgctccatt gcccagtcgg cagcgacatc  1380
cttcggcgcg attttgccgg ttactgcgct gtaccaaatg cgggacaacg taagcactac  1440
atttcgctca tcgccagccc agtcgggcgg cgagttccat agcgttaagg tttcatttag  1500
cgcctcaaat agatcctgtt caggaaccgg atcaaagagt tcctccgccg ctggacctac  1560
caaggcaacg ctatgttctc ttgcttttgt cagcaagata gccagatcaa tgtcgatcgt  1620
ggctggctcg aagatacctg caagaatgtc attgcgctgc cattctccaa attgcagttc  1680
gcgcttagct ggataacgcc acggaatgat gtcgtcgtgc acaacaatgg tgacttctac  1740
agcgcggaga atctcgctct ctccagggga agccgaagtt tccaaaaggt cgttgatcaa  1800
agctcgccgc gttgtttcat caagccttac ggtcaccgta accagcaaat caatatcact  1860
gtgtggcttc aggccgccat ccactgcgga gccgtacaaa tgtacggcca gcaacgtcgg  1920
ttcgagatgg cgctcgatga cgccaactac ctctgatagt tgagtcgata cttcggcgat  1980
caccgcttcc ctcatactct tcctttttca atattattga agcatttatc agggttattg  2040
tctcatgagc ggatacatat ttgaatgtat ttagaaaaat aaacaaatag ctagctcact  2100
cggtcgctac gctccgggcg tgagactgcg gcgggcgctg cggacacata caaagttacc  2160
cacagattcc gtggataagc aggggactaa catgtgaggc aaaacagcag ggccgcgccg  2220
gtggcgtttt tccataggct ccgc                                         2244

SEQ ID NO: 73         moltype = DNA  length = 7100
FEATURE               Location/Qualifiers
misc_feature          1..7100
                      note = Synthetic plasmid.
source                1..7100
                      mol_type = other DNA
                      organism = synthetic construct
SEQUENCE: 73
tcctgcgatg cagatccgga acataatggt gcagggcgct gacttccgcg tttccagact  60
ttacgaaaca cggaaaccga agaccattca tgttgttgct caggtcgcag acgttttgca  120
gcagcagtcg cttcacgttc gctcgcgtat cggtgattca ttctgctaac cagtaaggca  180
accccgccag cctagccggg tcctcaacga caggagcacg atcatgcgca cccgtggcca  240
ggacccaacg ctgcccgaaa ttccgacacc atcgaatggt gcaaaacctt tcgcggtatg  300
gcatgatagc gcccggaaga gagtcaattc agggtggtga atgtgaaacc agtaacgtta  360
tacgatgtcg cagagtatgc cggtgtctct tatcagaccg tttcccgcgt ggtgaaccag  420
gccagccacg tttctgcgaa aacgcgggaa aaagtggaag cggcgatggc ggagctgaat  480
tacattccca accgcgtggc acaacaactg gcgggcaaac agtcgttgct gattggcgtt  540
gccacctcca gtctggccct gcacgcgccg tcgcaaattg tcgcggcgat taaatctcgc  600
gccgatcaac tgggtgccag cgtggtggtg tcgatggtag aacgaagcgg cgtcgaagcc  660
tgtaaagcgg cggtgcacaa tcttctcgcg caacgcgtca gtgggctgat cattaactat  720
ccgctggatg accaggatgc cattgctgtg gaagctgcct gcactaatgt tccggcgtta  780
tttcttgatg tctctgacca gacacccatc aacagtatta ttttctccca tgaagacggt  840
acgcgactgg gcgtggagca tctggtcgca ttgggtcacc agcaaatcgc gctgttagcg  900
ggcccattaa gttctgtctc ggcgcgtctg cgtctggctg gctggcataa atatctcact  960
```

```
cgcaatcaaa ttcagccgat agcggaacgg gaaggcgact ggagtgccat gtccggtttt  1020
caacaaacca tgcaaatgct gaatgagggc atcgttccca ctgcgatgct ggttgccaac  1080
gatcagatgg cgctgggcgc aatgcgcgcc attaccgagt ccgggctgcg cgttggtgcg  1140
gatatttcgg tagtgggata cgacgatacc gaagacagct catgttatat cccgccgtta  1200
accaccatca aacaggattt tcgcctgctg gggcaaacca gcgtggaccg cttgctgcaa  1260
ctctctcagg gccaggcggt gaagggcaat cagctgttgc ccgtctcact ggtgaaaaga  1320
aaaaccaccc tggcgcccaa tacgcaaacc gcctctcccc gcgcgttggc cgattcatta  1380
atgcagctgg cacgacaggt ttcccgactg gaaagcgggc agtgagcgca acgcaattaa  1440
tgtaagttag ctcactcatt aggcacaatt ctcatgtttg acagcttatc atcgactgca  1500
cggtgcacca atgcttctgg cgtcaggcag ccatcggaag ctgtggtatg gctgtgcagg  1560
tcgtaaatca ctgcataatt cgtgtcgctc aaggcgcact cccgttctgg ataatgtttt  1620
ttgcgccgac atcataacgg ttctggcaaa tattctgaaa tgagctgttg acaattaatc  1680
atcggctcgt ataatgtgtg gaattgtgag cggataacaa tttcacacag gaaacagcca  1740
gtccgtttag gtgttttcac gagcaattga ccaacaagga ggatattatg gctgttacta  1800
atgtcgctga acttaacgca ctcgtagagc gtgtaaaaaa agcccagcgt gaatatgcca  1860
gtttcactca agagcaagta gacaaaatct tccgcgccgc cgctctggct gctgcagatg  1920
ctcgaatccc actcgcgaaa atggccgttg ccgaatccgg catgggtatc gtcgaagata  1980
aagtgatcaa aaaccacttt gcttctgaat atatctacaa cgcctataaa gatgaaaaaa  2040
cctgtggtgt tctgtctgaa gacgacactt ttggtaccat cactatcgct gaaccaatcg  2100
gtattatttg cggtatcgtt ccgaccacta acccgacttc aactgctatc ttcaaatcgc  2160
tgatcagtct gaagacccgt aacgccatta tcttctcccc gcacccgcgt gcaaaagatg  2220
ccaccaacaa agcggctgat atcgttctgc aggctgctat cgctgccggt gctccgaaag  2280
atctgatcgg ctggatcgat caaccttctg ttgaactgtc taacgcactg atgcaccacc  2340
cagacatcaa cctgatcctc gcgactggtg gtccgggcat ggttaaagcc gcatacagct  2400
ccggtaaacc agctatcggt gtaggcgcgg gcaacactcc agttgttatc gatgaaactg  2460
ctgatatcaa acgtgcagtt gcatctgtac tgatgtccaa aaccttcgac aacggcgtaa  2520
tctgtgcttc tgaacagtct gttgttgttg ttgactctgt ttatgacgct gtacgtgaac  2580
gttttacaac ccacggcggc tatctgttgc agggtaaaga gctgaaagct gttcaggatg  2640
ttatcctgaa aaacggtgcg ctgaacgcgg ctatcgttgg tcagccagcc tataaaattg  2700
ctgaactggc aggcttctct gtaccagaaa acaccaagat tctgatcggt gaagtgaccg  2760
ttgttgatga aagcgaaccg ttcgcacatg aaaaactgtc cccgactctg gcaatgtacc  2820
gcgctaaaga tttcgaagac gcggtagaaa aagcagagaa actggttgct atgggcggta  2880
tcggtcatac ctcttgcctg tacactgacc aggataacca accggctcgc gtttcttact  2940
tcggtcagaa aatgaaaacg gcgcgtatcc tgattaacac cccagcgtct cagggtggta  3000
tcggtgacct gtataacttc aaactcgcac cttccctgac tctgggttgt ggttcttggg  3060
gtggtaactc catctctgaa aacgttggtc cgaaacacct gatcaacaag aaaaccgttg  3120
ctaagcgagc tgaaaacatg ttgtggcaca aacttccgaa atctatctac ttccgccgtg  3180
gctccctgcc aatcgcgctg gatgaagtga ttactgatgg ccacaaacgt gcgctcatcg  3240
tgactgaccg cttcctgttc aacaatggtt atgctgatca gatcacttcc gtactgaaag  3300
cagcaggcgt tgaaactgaa gtcttcttcg aagtagaagc ggacccgacc ctgagcatcg  3360
ttcgtaaagg tgcagaactg gcaaactcct tcaaaccaga cgtgattatc gcgctgggtg  3420
gtggttcccc gatggacgcc gcgaagatca tgtgggttat gtacgaacat ccggaaactc  3480
acttcgaaaa gctggcgctg cgctttatgg atatccgtaa acgtatctac aagttcccga  3540
aaatgggcgt gaaagcgaaa atgatcgctg tcaccaccac ttctggtaca ggttctgaag  3600
tcactccgtt tgcggttgta actgacgacg ctactggtca gaaatatccg ctggcagact  3660
atgcgctgac tccggatatg gcgattgtcg acgccaacct ggttatggac atgccgaagt  3720
ccctgtgtgc tttcggtggt ctggacgcag taactcacgc catggaagct tatgtttctg  3780
tactggcatc tgagttctct gatggtcagg ctctgcaggc actgaaactg ctgaaagaat  3840
atctgccagc gtcctaccac gaagggtcta aaaatccggt agcgcgtgaa cgtgttcaca  3900
gtgcagcgac tatcgcgggt atcgcgtttg cgaacgcctt cctgggtgta tgtcactcaa  3960
tggcgcacaa actgggttcc cagttccata ttccgcacgg tctggcaaac gccctgctga  4020
tttgtaacgt tattcgctac aatgcgaacg acaacccgac caagcagact gcattcagcc  4080
agtatgaccg tccgcaggct cgccgtcgtt atgctgaaat tgccgaccac ttgggtctga  4140
gcgcaccggg cgaccgtact gctgctaaga tcgagaaact gctggcatgg ctggaaacgc  4200
tgaaagctga actgggtatt ccgaaatcta tccgtgaagc tggcgttcag gaagcagact  4260
tcctggcgaa cgtggataaa ctgtctgaag atgcattcga tgaccagtgc accggcgcta  4320
acccgcgtta cccgctgatc tccgagctga aacagattct gctggatacc tactacggtc  4380
gtgattatgt agaaggtgaa actgcagcga agaaagaagc tgctccggct aaagctgaga  4440
aaaaagcgaa aaaatccgct taactcagtc gaaagactgg gcctttcgtt ttatctgttg  4500
tttgtcggtg aacgctctcc tgagtaggac aaatccgccg ggagcggatt tgaacgttgc  4560
gaagcaacgg cccggagggt ggcgggcagg acgcccgcca taaactgcca ggcatcaaat  4620
taagcagaag gccatcctga cggatggcct ttttgcgttt ctacaaactc tttcggtccg  4680
ttgtttattt ttctaaatac attcaaatat gtatccgctc atgagacaat aaccctgata  4740
aatgcttcaa taatattgaa aaaggaagag tatgagtatt caacatttcc gtgtcgccct  4800
tattcccttt tttgcggcat tttgccttcc tgtttttgct cacccagaaa cgctggtgaa  4860
agtaaaagat gctgaagatc agttgggtgc acgagtgggt tacatcgaac tggatctcaa  4920
cagcggtaag atccttgaga gttttcgccc cgaagaacgt ttcccaatga tgagcacttt  4980
taaagttctg ctatgtggcg cggtattatc ccgtgttgac gccgggcaag agcaactcgg  5040
tcgccgcata cactattctc agaatgactt ggttgagtac tcaccagtca cagaaaagca  5100
tcttacggat ggcatgacag taagagaatt atgcagtgct gccataacca tgagtgataa  5160
cactgcggcc aacttacttc tgacaacgat cggaggaccg aaggagctaa ccgctttttt  5220
gcacaacatg ggggatcatg taactcgcct tgatcgttgg gaaccggagc tgaatgaagc  5280
cataccaaac gacgagcgtg acaccacgat gcctgtagca atggcaacaa cgttgcgcaa  5340
actattaact ggcgaactac ttactctagc ttcccggcaa caattaatag actggatgga  5400
ggcggataaa gttgcaggac cacttctgcg ctcggccctt ccggctggct ggtttattgc  5460
tgataaatct ggagccggtg agcgtgggtc tcgcggtatc attgcagcac tggggccaga  5520
tggtaagccc tcccgtatcg tagttatcta cacgacgggg agtcaggcaa ctatggatga  5580
acgaaataga cagatcgctg agataggtgc ctcactgatt aagcattggt aactgtcaga  5640
ccaagtttac tcatatatac tttagattga tttccttagg actgagcgtc aaccccgtag  5700
```

```
aaaagatcaa aggatcttct tgagatcctt tttttctgcg cgtaatctgc tgcttgcaaa  5760
caaaaaaacc accgctacca gcggtggttt gtttgccgga tcaagagcta ccaactcttt  5820
ttccgaaggt aactggcttc agcagagcgc agataccaaa tactgtcctt ctagtgtagc  5880
cgtagttagg ccaccacttc aagaactctg tagcaccgcc tacatacctc gctctgctaa  5940
tcctgttacc agtggctgct gccagtggcg ataagtcgtg tcttaccggg ttggactcaa  6000
gacgatagtt accggataag gcgcagcggt cgggctgaac ggggggttcg tgcacacagc  6060
ccagcttgga gcgaacgacc tacaccgaac tgagatacct acagcgtgag ctatgagaaa  6120
gcgccacgct tcccgaaggg agaaaggcgg acaggtatcc ggtaagcggc agggtcggaa  6180
caggagagcg cacgagggag cttccagggg gaaacgcctg gtatctttat agtcctgtcg  6240
ggtttcgcca cctctgactt gagcgtcgat ttttgtgatg ctcgtcaggg gggcggagcc  6300
tatggaaaaa cgccagcaac gcggcctttt tacggttcct ggccttttgc tggccttttg  6360
ctcacatgtt ctttcctgcg ttatcccctg attctgtgga taaccgtatt accgcctttg  6420
agtgagctga taccgctcgc cgcagccgaa cgaccgagcg cagcgagtca gtgagcgagg  6480
aagcggaaga gcgcctgatg cggtattttc tccttacgca tctgtgcggt atttcacacc  6540
gcatataagg tgcactgtga ctgggtcatg gctgcgcccc gacacccgcc aacacccgct  6600
gacgcgccct gacgggcttg tctgctcccg gcatccgctt acagacaagc tgtgaccgtc  6660
tccgggagct gcatgtgtca gaggttttca ccgtcatcac cgaaacgcgc gaggcagctg  6720
cggtaaagct catcagcgtg gtcgtgcagc gattcacaga tgtctgcctg ttcatccgcg  6780
tccagctcgt tgagtttctc cagaagcgtt aatgtctggc ttctgataaa gcgggccatg  6840
ttaagggcgg tttttcctg tttggtcact gatgcctccg tgtaaggggg atttctgttc  6900
atgggggtaa tgataccgat gaaacgagag aggatgctca cgatacgggt tactgatgat  6960
gaacatgccc ggttactgga acgttgtgag ggtaaacaac tggcggtatg gatgcggcgg  7020
gaccagagaa aaatcactca gggtcaatgc cagcgcttcg ttaatacaga tgtaggtgtt  7080
ccacagggta gccagcagca                                              7100
```

```
SEQ ID NO: 74          moltype = DNA  length = 57
FEATURE                Location/Qualifiers
misc_feature           1..57
                       note = Synthetic primer.
source                 1..57
                       mol_type = other DNA
                       organism = synthetic construct
SEQUENCE: 74
catttgacag gcacattatg caccgcttat gtctattgct ggtttaccgg tttattg     57

SEQ ID NO: 75          moltype = DNA  length = 60
FEATURE                Location/Qualifiers
misc_feature           1..60
                       note = Synthetic primer.
source                 1..60
                       mol_type = other DNA
                       organism = synthetic construct
SEQUENCE: 75
gggaccacgt tgttacaacc aattaaccaa ttctgactat ttaacgaccc tgccctgaac  60

SEQ ID NO: 76          moltype = DNA  length = 32
FEATURE                Location/Qualifiers
misc_feature           1..32
                       note = Synthetic primer.
source                 1..32
                       mol_type = other DNA
                       organism = synthetic construct
SEQUENCE: 76
tgcataatgt gcctgtcaaa tggacgaagc ag                                32

SEQ ID NO: 77          moltype = DNA  length = 34
FEATURE                Location/Qualifiers
misc_feature           1..34
                       note = Synthetic primer.
source                 1..34
                       mol_type = other DNA
                       organism = synthetic construct
SEQUENCE: 77
gttgtaacaa cgtggtccca gtattccttg agct                              34

SEQ ID NO: 78          moltype = DNA  length = 46
FEATURE                Location/Qualifiers
misc_feature           1..46
                       note = Synthetic primer.
source                 1..46
                       mol_type = other DNA
                       organism = synthetic construct
SEQUENCE: 78
tgctcgatga gtttttctaa ccggaaggag ctgactgggt tgaagg                 46

SEQ ID NO: 79          moltype = DNA  length = 26
FEATURE                Location/Qualifiers
misc_feature           1..26
                       note = Synthetic primer.
```

```
source                  1..26
                        mol_type = other DNA
                        organism = synthetic construct
SEQUENCE: 79
ggagcgtagc gaccgagtga gctagc                                        26

SEQ ID NO: 80           moltype = DNA  length = 47
FEATURE                 Location/Qualifiers
misc_feature            1..47
                        note = Synthetic primer.
source                  1..47
                        mol_type = other DNA
                        organism = synthetic construct
SEQUENCE: 80
gctagctcac tcggtcgcta cgctccgcta ggtcgttcgg ctgcaac                 47

SEQ ID NO: 81           moltype = DNA  length = 54
FEATURE                 Location/Qualifiers
misc_feature            1..54
                        note = Synthetic primer.
source                  1..54
                        mol_type = other DNA
                        organism = synthetic construct
SEQUENCE: 81
acccagtcag ctccttccgg ttagaaaaac tcatcgagca tcaaatgaaa ctgc          54

SEQ ID NO: 82           moltype = DNA  length = 4716
FEATURE                 Location/Qualifiers
misc_feature            1..4716
                        note = Synthetic plasmid.
source                  1..4716
                        mol_type = other DNA
                        organism = synthetic construct
SEQUENCE: 82
ccacagaatc aggggataac gcaggaaaga acatgtgagc aaaaggccag caaaaggcca  60
ggaaccgtaa aaaggccgcg ttgctggcgt ttttccatag gctccgcccc cctgacgagc  120
atcacaaaaa tcgacgctca agtcagaggt ggcgaaaccc gacaggacta taaagatacc  180
aggcgtttcc ccctggaagc tccctcgtgc gctctcctgt tccgaccctg ccgcttaccg  240
gatacctgtc cgcctttctc ccttcgggaa gcgtggcgct ttctcaatgc tcacgctgta  300
ggtatctcag ttcggtgtag gtcgttcgct ccaagctggg ctgtgtgcac gaaccccccg  360
ttcagcccga ccgctgcgcc ttatccggta actatcgtct tgagtccaac ccggtaagac  420
acgacttatc gccactggca gcagccactg gtaacaggat tagcagagcg aggtatgtag  480
gcggtgctac agagttcttg aagtggtggc ctaactacgg ctacactaga aggacagtat  540
ttggtatctg cgctctgctg aagccagtta ccttcggaaa aagagttggt agctcttgat  600
ccggcaaaca aaccaccgct ggtagcggtg gtttttttgt ttgcaagcag cagattacgc  660
gcagaaaaaa aggatctcaa gaagatcctt tgatcttttc tacggggtct gacgctcagt  720
ggaacgaaaa ctcacgttaa gggattttgg tcatgagatt atcaaaaagg atcttcacct  780
agatcctttt aaattaaaaa tgaagtttta aatcaatcta aagtatatat gagtaaactt  840
ggtctgacag ttaccaatgc ttaatcagtg aggcacctat ctcagcgatc tgtctatttc  900
gttcatccat agttgcctga ctccccgtcg tgtagataac tacgatacgg gagggcttac  960
catctggccc cagtgctgca atgataccgc gagacccacg ctcaccggct ccagatttat  1020
cagcaataaa ccagccagcc ggaagggccg agcgcagaag tggtcctgca actttatccg  1080
cctccatcca gtctattaat tgttgccggg aagctagagt aagtagttcg ccagttaata  1140
gtttgcgcaa cgttgttgcc attgctacag gcatcgtggt gtcacgctcg tcgtttggta  1200
tggcttcatt cagctccggt tcccaacgat caaggcgagt tacatgatcc cccatgttgt  1260
gcaaaaaagc ggttagctcc ttcggtcctc cgatcgttgt cagaagtaag ttggccgcag  1320
tgttatcact catggttatg gcagcactgc ataattctct tactgtcatg ccatccgtaa  1380
gatgcttttc tgtgactggt gagtactcaa ccaagtcatt ctgagaatag tgtatgcggc  1440
gaccgagttg ctcttgcccg gcgtcaatac gggataatac cgcgccacat agcagaactt  1500
taaaagtgct catcattgga aaacgttctt cggggcgaaa actctcaagg atcttaccgc  1560
tgttgagatc cagttcgatg taacccactc gtgcacccaa ctgatcttca gcatctttta  1620
ctttcaccag cgtttctggg tgagcaaaaa caggaaggca aaatgccgca aaaaagggaa  1680
taagggcgac acggaaatgt tgaatactca tactcttcct ttttcaatat tattgaagca  1740
tttatcaggg ttattgtctc atgagcggat acatatttga atgtatttag aaaaataaac  1800
aaataggggt tccgcgcaca tttccccgaa aagtgccacc tgacgggtct cacagatgac  1860
agagttgtca agaacttgac cactttgttg ttcgacacag ctttgttgac ttccggtttc  1920
actttggatg agccaacttc tttcgctgcc agaatcaacg gtttgatctc cattggtttg  1980
aacatcgatg aggaggaaga gaaagagcca gaacaggcta ctgaagctcc aagtgaagaa  2040
gctgttgctg agtctgccat ggaggaggtt gactagttga atttaggtat atatagtgac  2100
tgtgatattt agctaatgaa atctaattgg atatttagaa tgcctcatct cgtagcctat  2160
caattactat taggccatct cttatgggcc cttctttgaa attgcattca aggggggatg  2220
ggactatttt gaatttgaag tttggactct gtgagctgtt tggccaattg aagtcatcca  2280
cttgtacaca gggattcacc agtagtttag aacaattctc tatcgttatt ctcttgtcgt  2340
ctttggcaat acaagcgtcg atgactgagt tggtgacttt atgaagtcta agttgatatg  2400
agtttgaaat tatgaaacag ttttttacac tggacatgta gatagggccc ttgatgttta  2460
ggaagaggat acagtttgag atgttggaga tgtgtgtgga gggagcgacc acttttaaaa  2520
ccacatgatc cagacgttgc tcagttatcg aagtttcgga aacaacgcca gatctgttta  2580
gcttgcctcg tccccgccgg gtcacccggc cagcgacatg gaggcccaga ataccctcct  2640
tgacagtctt gacgtgcgca gctcaggggc atgatgtgac tgtcgcccgt acatttagcc  2700
```

```
catacatccc catgtataat catttgcatc catacatttt gatggccgca cggcgcgaag  2760
caaaaattac ggctcctcgc tgcagacctg cgagcaggga aacgctcccc tcacagacgc  2820
gttgaattgt ccccacgccg cgcccctgta gagaaatata aaaggttagg atttgccact  2880
gaggttcttc tttcatatac ttccttttaa aatcttgcta ggatacagtt ctcacatcac  2940
atccgaacat aaacaaccat gggtaaggaa aagactcacg tttcgaggcc gcgattaaat  3000
tccaacatgg atgctgattt atatgggtat aaatgggctc gcgataatgt cgggcaatca  3060
ggtgcgacaa tctatcgatt gtatgggaag cccgatgcgc cagagttgtt tctgaaacat  3120
ggcaaaggta gcgttgccaa tgatgttaca gatgagatgg tcagactaaa ctggctgacg  3180
gaatttatgc ctcttccgac catcaagcat tttatccgta ctcctgatga tgcatggtta  3240
ctcaccactg cgatccccgg caaaacagca ttccaggtat tagaagaata tcctgattca  3300
ggtgaaaata ttgttgatgc gctggcagtg ttcctgcgcc ggttgcattc gattcctgtt  3360
tgtaattgtc cttttaacag cgatcgcgta tttcgtctcg ctcaggcgca atcacgaatg  3420
aataacggtt tggttgatgc gagtgatttt gatgacgagc gtaatggctg gcctgttgaa  3480
caagtctgga aagaaatgca taagcttttg ccattctcac cggattcagt cgtcactcat  3540
ggtgatttct cacttgataa ccttattttt gacgagggga aattaatagg ttgtattgat  3600
gttggacgag tcggaatcgc agaccgatac caggatcttg ccatcctatg gaactgcctc  3660
ggtgagtttt ctccttcatt acagaaacgg ctttttcaaa aatatggtat tgataatcct  3720
gatatgaata aattgcagtt tcatttgatg ctcgatgagt ttttctaatc agtactgaca  3780
ataaaaagat tcttgttttc aagaacttgt catttgtata gtttttttat attgtagttg  3840
ttctatttta atcaaatgtt agcgtgattt atattttttt tcgcctcgac atcatctgcc  3900
cagatgcgaa gttaagtgcg cagaaagtaa tatcatgcgt caatcgtatg tgaatgctgg  3960
tcgctatact gctgtcgatt cgatactaac gccaagaagt tgattgagac tttcaacgag  4020
attgctgaag acaaggaaca attcgagaag ttttacagtg ctttctccaa gaacttgaag  4080
ttgggtgtcc atgaagacag ccaaaacaga tccgcattgg ccaagttgct gagatttaac  4140
tccaccaagt ctactgagga gctaacctca ttctctgact acgtcaccag aatgccagag  4200
caccagaaga acatctactt cattaccggt gagtctgtca aggctcttga gaaatctcca  4260
ttcttggatg ctttgaagga gaagaacttt gaggtcctat tgctgaccga tcctattgat  4320
gagtacgcta tgactcaatt gaaagagatt gaggacaaga aattggttga catcactaaa  4380
gactttgagc tggaagagtc tgaggaggag aagaaggcta gagaggaaga ggttaaagat  4440
ttcgagcctt tgactaaagc cctgaaagag attttgggtg acaaggttga gaaggttgta  4500
gtttcctaca agctggttga ctctcctgct gctattagaa cttcccaatt cggctggtct  4560
gctaacatgg aaagaattat gaaggctcaa gctctgagag acaccaacac catgtcctcg  4620
tacatggctt caaagaagat cttcgagatc tctccaaagt cgccaatcat taaggctttg  4680
agaaagaagg ttgaggctac cggtacagaa gagacc                            4716
```

```
SEQ ID NO: 83          moltype = DNA  length = 9557
FEATURE                Location/Qualifiers
misc_feature           1..9557
                       note = Synthetic plasmid.
source                 1..9557
                       mol_type = other DNA
                       organism = synthetic construct
SEQUENCE: 83
acagaatcag ggataacgc aggaaagaac atgtgagcaa aaggccagca aaaggccagg  60
aaccgtaaaa aggccgcgtt gctggcgttt ttccataggc tccgcccccc tgacgagcat  120
cacaaaaatc gacgctcaag tcagaggtgg cgaaacccga caggactata aagataccag  180
gcgtttcccc ctggaagctc cctcgtgcgc tctcctgttc cgaccctgcc gcttaccgga  240
tacctgtccg cctttctccc ttcgggaagc gtggcgcttt ctcaatgctc acgctgtagg  300
tatctcagtt cggtgtaggt cgttcgctcc aagctgggct gtgtgcacga accccccgtt  360
cagcccgacc gctgcgcctt atccggtaac tatcgtcttg agtccaaccc ggtaagacac  420
gacttatcgc cactggcagc agccactggt aacaggatta gcagagcgag gtatgtaggc  480
ggtgctacag agttcttgaa gtggtggcct aactacggct acactagaag gacagtattt  540
ggtatctgcg ctctgctgaa gccagttacc ttcggaaaaa gagttggtag ctcttgatcc  600
ggcaaacaaa ccaccgctgg tagcggtggt ttttttgttt gcaagcagca gattacgcgc  660
agaaaaaaag gatctcaaga agatcctttg atcttttcta cggggtctga cgctcagtgg  720
aacgaaaact cacgttaagg gattttggtc atgagattat caaaaaggat cttcacctag  780
atccttttaa attaaaaatg aagttttaaa tcaatctaaa gtatatatga gtaaacttgg  840
tctgacagtt accaatgctt aatcagtgag gcacctatct cagcgatctg tctatttcgt  900
tcatccatag ttgcctgact ccccgtcgtg tagataacta cgatacggga gggcttacca  960
tctggcccca gtgctgcaat gataccgcga gacccacgct caccggctcc agatttatca  1020
gcaataaacc agccagccgg aagggccgag cgcagaagtg gtcctgcaac tttatccgcc  1080
tccatccagt ctattaattg ttgccgggaa gctagagtaa gtagttcgcc agttaatagt  1140
ttgcgcaacg ttgttgccat tgctacaggc atcgtggtgt cacgctcgtc gtttggtatg  1200
gcttcattca gctccggttc ccaacgatca aggcgagtta catgatcccc catgttgtgc  1260
aaaaaagcgg ttagctcctt cggtcctccg atcgttgtca gaagtaagtt ggccgcagtg  1320
ttatcactca tggttatggc agcactgcat aattctctta ctgtcatgcc atccgtaaga  1380
tgcttttctg tgactggtga gtactcaacc aagtcattct gagaatagtg tatgcggcga  1440
ccgagttgct cttgcccggc gtcaatacgg gataataccg cgccacatag cagaacttta  1500
aaagtgctca tcattggaaa acgttcttcg gggcgaaaac tctcaaggat cttaccgctg  1560
ttgagatcca gttcgatgta acccactcgt gcacccaact gatcttcagc atcttttact  1620
ttcaccagcg tttctgggtg agcaaaaaca ggaaggcaaa atgccgcaaa aaagggaata  1680
agggcgacac ggaaatgttg aatactcata ctcttccttt ttcaatatta ttgaagcatt  1740
tatcagggtt attgtctcat gagcggatac atatttgaat gtatttagaa aaataaacaa  1800
ataggggttc cgcgcacatt tccccgaaaa gtgccacctg acgggtctca cagatgacag  1860
agttgtcaag aacttgacca ctttgttgtt cgacacagct ttgttgactt ccggtttcac  1920
tttggatgag ccaacttctt tcgctgccag aatcaacggt ttgatctcca ttggtttgaa  1980
catcgatgag gaggaagaga aagagccaga acaggctact gaagctccaa gtgaagaagc  2040
tgttgctgag tctgccatgg aggaggttga ctagttgaat ttaggtatat atagtgactg  2100
tgatatttag ctaatgaaat ctaattggat atttagaatg cctcatctcg tagcctatca  2160
```

```
attactatta ggccatctct tatgggccct tctttgaaat tgcattcaag gggggatggg  2220
actattttga atttgaagtt tggactctgt gagctgtttg gccaattgaa gtcatccact  2280
tgtacacagg gattcaccag tagtttagaa caattctcta tcgttattct cttgtcgtct  2340
ttggcaatac aagcgtcgat gactgagttg gtgactttat gaagtctaag ttgatatgag  2400
tttgaaatta tgaaacagtt ttttacactg gacatgtaga tagggccctt gatgtttagg  2460
aagaggatac agtttgagat gttggagatg tgtgtggagg gagcgaccac ttttaaaacc  2520
acatgatcca gacgttgctc agttatcgaa gtttcggaaa caacgccaga tctgtttagc  2580
ttgctcgagc agatctaggg agggcatcat tgaggtttcc acaaaaggaa gaaacatgga  2640
tccagagaca tcaacagaga ggaaagcggg tagtgaagcc gaagccacaa cacagcccga  2700
tttggaaggg agttcacaat caaggtgagt ccagccattt tttttctttt ttttttttt  2760
attcaggtga acccacctaa ctatttttaa ctgggatcca gtgagctcgc tgggtgaaag  2820
ccaaccatct tttgtttcgg ggaaccgtgc tcgccccgta aagttaattt tttttcccg  2880
cgcagcttta atctttcggc agagaaggcg ttttcatcgt agcgtgggaa cagaataatc  2940
agttcatgtg ctatacaggc acatggcagc agtcactatt ttgcttttta accttaaagt  3000
cgttcatcaa tcattaactg accaatcaga tttttttgcat ttgccactta tctaaaaata  3060
cttttgtatc tcgcagatac gttcagtggt ttccaggaca acacccaaaa aaaggtatca  3120
atgccactag gcagtcggtt ttatttttgg tcacccacgc aaagaagcac ccacctcttt  3180
taggttttaa gttgtgggaa cagtaacacc gcctagagct tcaggaaaaa ccagtacctg  3240
tgaccgcaat tcaccatgat gcagaatgtt aatttaaacg agtgccaaat caagatttca  3300
acagacaaat caatcgatcc atagttaccc attccagcct tttcgtcgtc gagcctgctt  3360
cattcctgcc tcaggtgcat aactttgcat gaaaagtcca gattagggca gattttgagt  3420
ttaaaatagg aaatataaac aaatataccg cgaaaaaggt ttgtttatag cttttcgcct  3480
ggtgccgtac ggtataaata catactctcc tcccccccct ggttctcttt ttcttttgtt  3540
acttacattt taccgttccg tcactcgctt cactcaacaa caaaaaatgag cagtagcaag  3600
aaattggccg gtcttaggga caatttcagt ttgctcggcg aaaagaataa gatcttggtc  3660
gccaatagag gtgaaattcc gattagaatt tttagatctg ctcatgagct gtctatgaga  3720
accatcgcca tatactccca tgaggaccgt ctttcaatgc acaggttgaa ggcggacgaa  3780
gcgtatgtta tcggggagga gggccagtat acacctgtgg gtgcttactt ggcaatggac  3840
gagatcatcg aaattgcaaa gaagcataag gtggatttca tccatccagg ttatgggttc  3900
ttgtctgaaa attcggaatt tgccgacaaa gtagtgaagg ccggtatcac ttggatcggc  3960
cctccagctg aagttattga ctctgtgggt gacaaagtct ctgccagaca cttggcagca  4020
agagctaacg ttcctaccgt tcccggtact ccaggaccta tcgaaactgt gcaagaggca  4080
cttgacttcg ttaatgaata cggctacccg gtgatcatta aggccgcctt tggtggtggt  4140
ggtagaggta tgagagtcgt tagagaaggt gacgacgtgg cagatgcctt tcaacgtgct  4200
acctccgaag cccgtactgc cttcggtaat ggtacctgct ttgtggaaag attcttggac  4260
aagccaaagc atattgaagt tcaattgttg gctgataacc acggaaacgt ggttcatctt  4320
ttcgaaagag actgttctgt gcaaagaaga caccaaaaag ttgtcgaagt cgctccagca  4380
aagactttgc cccgtgaagt tcgtgacgct attttgacag atgctgttaa attagctaag  4440
gtatgtggtt acagaaacgc aggtaccgcc gaattcttgg ttgacaacca aaacagacac  4500
tatttcattg aaattaatcc aagaattcaa gtggagcata ccatcactga agaaatcacc  4560
ggtattgaca ttgtttctgc ccaaatccag attgccgcag gtgccacttt gactcaacta  4620
ggtctattac aggataaaat caccacccgt gggttttcca tccaatgtcg tattaccact  4680
gaagatccct ctaagaattt ccaaccggat accggtcgcc tggaggtcta tcgttctgcc  4740
ggtggtaatg gtgtgagatt ggacggtggt aacgcttatg caggtgctac tatctcgcct  4800
cactacgact caatgctggt caaatgttca tgctctggtt ctacttatga aatcgtccgt  4860
aggaagatga ttcgtgccct gatcgaattc agaatcagag gtgttaagac caacattccc  4920
ttcctattga ctcttttgac caatccagtt tttattgagg gtacatactg gacgactttt  4980
attgacgaca ccccacaact gttccaaatg gtatcgtcac aaaacagagc gcaaaaactg  5040
ttacactatt tggcagactt ggcagttaac ggttcttcta ttaagggtca aattggcttg  5100
ccaaaactaa aatcaaatcc aagtgtcccc catttgcacg atgctcaggg caatgtcatc  5160
aacgttacaa agtctgcacc accatccgga tggagacaag tgctactgga aaagggacca  5220
tctgaatttg ccaagcaagt cagacagttc aatggtactc tactgatgga caccacctgg  5280
agagacgctc atcaatctct acttgcaaca agagtcagaa ccacgatttt ggctacaatc  5340
gctccaacaa ccgcacatgc ccttgcaggt gctttcgctt tagaatgttg gggtggtgct  5400
acattcgacg ttgcaatgag attcttgcat gaggatccat gggaacgtct gagaaaatta  5460
agatctctgg tgcctaatat tccattccaa atgttattac gtggtgccaa cggtgtggct  5520
tactcttcat tacctgacaa tgctattgac cattttgtca agcaagccaa ggataatggt  5580
gttgatatat ttagagtttt tgatgccttg aatgatttag aacaattaaa agttggtgtg  5640
aatgctgtca agaaggccgg tggtgttgtc gaagctactg tttgttactc tggtgacatg  5700
cttcagccag gtaagaaata caacttagac tactacctag aagttgttga aaaaatagtt  5760
caaatgggta cacatatctt gggtattaag gatatggcag gtactatgaa accggccgct  5820
gccaaattat taattggctc cctaagaacc agatatccgg atttaccaat tcatgttcac  5880
agtcatgact ccgcaggtac tgctgttgcg tctatgactg catgtgccct agcaggtgct  5940
gatgttgtcg atgtagctat caattcaatg tcgggcttaa cttcccaacc atcaattaat  6000
gcactgttgg cttcattaga aggtaacatt gatactggga ttaacgttga gcatgttcgt  6060
gaattagatg catactgggc cgaaatgaga ctgttgtatt cttgtttcga ggccgacttg  6120
aagggaccag atccagaagt ttaccaacat gaaatcccag gtggtcaatt gactaacttg  6180
ttattccaag ctcaacaact gggtcttggt gaacaatggg ctgaaactaa aagagcttac  6240
agagaagcca attacctact gggagatatt gttaaagtta ccccaacttc taaggttgtc  6300
ggtgatttag ctcaattcat ggtttctaac aaactgactt ccgacgatat tagacgttta  6360
gctaattctt tggactttcc tgactctgtt atggactttt ttgaaggttt aattggtcaa  6420
ccatacggtg ggttcccaga accattaaga tctgatgtat tgagaaacaa gagaagaaag  6480
ttgacgtgcc gtccaggttt agaattagaa ccatttgatc tcgaaaaaat tagagaagac  6540
ttgcagaaca gattcggtga tattgatgaa tgcgatgttg cttcttacaa tatgtatcca  6600
agggtctatg aagatttcca aaagatcaga gaaacatacg gtgatttatc agttctacca  6660
accaaaaatt tcctagcacc agcagaacct gatgaagaaa tcgaagtcac catcgaacaa  6720
ggtaagactt tgattatcaa attgcaagct gttggtgact taaataagaa aactgggcaa  6780
agagaagtgt attttgaatt gaacggtgaa ttaagaaaga tcagagttgc agacaagtca  6840
caaaacatac aatctgttgc taaaccaaag gctgatgtcc acgatactca ccaaatcggt  6900
```

```
gcaccaatgg ctggtgttat catagaagtt aaagtacata aagggtcttt ggtgaaaaag  6960
ggcgaatcga ttgctgtttt gagtgccatg aaaatggaaa tggttgtctc ttcaccagca  7020
gatggtcaag ttaaagacgt tttcattaag gatggtgaaa gtgttgacgc atcagatttg  7080
ttggttgtcc tagaagaaga aaccctaccc ccatcccaaa aaaagtaaag acatgactgt  7140
tcctcagttc aagttgggca cttacgagaa gaccggtctt gctagattct aatcaagagg  7200
atgtcagaat gccatttgcc tgagagatgc aggcttcatt tttgattact tttttatttg  7260
taacctatat agtataggat tttttttgtc attttgtttc ttctcgtacg agcttgctcc  7320
tgatcagcct atctcgcagc tgatgaatat cttgtggtag gggtttggga aaatcattcg  7380
agtttgatgt ttttcttggt atttcccact cctcttcaga gtacagaaga ttaagtgaga  7440
gcggccgccc agcgacatgg aggcccagaa taccctcctt gacagtcttg acgtgcgcag  7500
ctcaggggca tgatgtgact gtcgcccgta catttagccc atacatcccc atgtataatc  7560
atttgcatcc atacattttg atggccgcac ggcgcgaagc aaaaattacg gctcctcgct  7620
gcagacctgc gagcagggaa acgctcccct cacagacgcg ttgaattgtc cccacgccgc  7680
gcccctgtag agaaatataa aaggttagga tttgccactg aggttcttct ttcatatact  7740
tcctttttaaa atcttgctag gatacagttc tcacatcaca tccgaacata aacaaccatg  7800
ggtaaggaaa agactcacgt ttcgaggccg cgattaaatt ccaacatgga tgctgattta  7860
tatgggtata aatgggctcg cgataatgtc gggcaatcag gtgcgacaat ctatcgattg  7920
tatgggaagc ccgatgcgcc agagttgttt ctgaaacatg gcaaaggtag cgttgccaat  7980
gatgttacag atgagatggt cagactaaac tggctgacgg aatttatgcc tcttccgacc  8040
atcaagcatt ttatccgtac tcctgatgat gcatggttac tcaccactgc gatccccggc  8100
aaaacagcat tccaggtatt agaagaatat cctgattcag gtgaaaatat tgttgatgcg  8160
ctggcagtgt tcctgcgccg gttgcattcg attcctgttt gtaattgtcc ttttaacagc  8220
gatcgcgtat ttcgtctcgc tcaggcgcaa tcacgaatga ataacggttt ggttgatgcg  8280
agtgattttg atgacgagcg taatggctgg cctgttgaac aagtctggaa agaaatgcat  8340
aagcttttgc cattctcacc ggattcagtc gtcactcatg gtgatttctc acttgataac  8400
cttatttttg acgaggggaa attaataggt tgtattgatg ttggacgagt cggaatcgca  8460
gaccgatacc aggatcttgc catcctatgg aactgcctcg gtgagttttc tccttcatta  8520
cagaaacggc tttttcaaaa atatggtatt gataatcctg atatgaataa attgcagttt  8580
catttgatgc tcgatgagtt tttctaatca gtactgacaa taaaaagatt cttgttttca  8640
agaacttgtc atttgtatag tttttttata ttgtagttgt tctattttaa tcaaatgtta  8700
gcgtgattta tatttttttt cgcctcgaca tcatctgccc agatgcgaag ttaagtgcgc  8760
agaaagtaat atcatgcgtc aatcgtatgt gaatgctggt cgctatactg ctgtcgattc  8820
gatactaacg ccaagaagtt gattgagact ttcaacgaga ttgctgaaga caaggaacaa  8880
ttcgagaagt tttacagtgc tttctccaag aacttgaagt tgggtgtcca tgaagacagc  8940
caaaacagat ccgcattggc caagttgctg agatttaact ccaccaagtc tactgaggag  9000
ctaacctcat tctctgacta cgtcaccaga atgccagagc accagaagaa catctacttc  9060
attaccggtg agtctgtcaa ggctcttgag aaatctccat tcttggatgc tttgaaggag  9120
aagaactttg aggtcctatt gctgaccgat cctattgatg agtacgctat gactcaattg  9180
aaagagattg aggacaagaa attggttgac atcactaaag actttgagct ggaagagtct  9240
gaggaggaga agaaggctag agaggaagag gttaaagatt tcgagccttt gactaaagcc  9300
ctgaaagaga ttttgggtga caaggttgag aaggttgtag tttcctacaa gctggttgac  9360
tctcctgctg ctattagaac ttcccaattc ggctggtctg ctaacatgga aagaattatg  9420
aaggctcaag ctctgagaga caccaacacc atgtcctcgt acatggcttc aaagaagatc  9480
ttcgagatct ctccaaagtc gccaatcatt aaggctttga gaaagaaggt tgaggctacc  9540
ggtacagaag agacccc                                              9557
```

```
SEQ ID NO: 84           moltype = DNA  length = 6428
FEATURE                 Location/Qualifiers
misc_feature            1..6428
                        note = Synthetic plasmid.
source                  1..6428
                        mol_type = other DNA
                        organism = synthetic construct
SEQUENCE: 84
tcgtccccgc cgggtcaccc ggccagcgac atggaggccc agaataccct ccttgacagt  60
cttgacgtgc gcagctcagg ggcatgatgt gactgtcgcc cgtacattta gcccatacat  120
ccccatgtat aatcatttgc atccatacat tttgatggcc gcacggcgcg aagcaaaaat  180
tacggctcct cgctgcagac ctgcgagcag ggaaacgctc ccctcacaga cgcgttgaat  240
tgtccccacg ccgcgcccct gtagagaaat ataaaaggtt aggatttgcc actgaggttc  300
ttctttcata tacttccttt taaaatcttg ctaggataca gttctcacat cacatccgaa  360
cataaacaac catgggtaag gaaaagactc acgtttcgag gccgcgatta aattccaaca  420
tggatgctga tttatatggg tataaatggg ctcgcgataa tgtcgggcaa tcaggtgcga  480
caatctatcg attgtatggg aagcccgatg cgccagagtt gtttctgaaa catggcaaag  540
gtagcgttgc caatgatgtt acagatgaga tggtcagact aaactggctg acggaattta  600
tgcctcttcc gaccatcaag cattttatcc gtactcctga tgatgcatgg ttactcacca  660
ctgcgatccc cggcaaaaca gcattccagg tattagaaga atatcctgat tcaggtgaaa  720
atattgttga tgcgctggca gtgttcctgc gccggttgca ttcgattcct gtttgtaatt  780
gtccttttaa cagcgatcgc gtatttcgtc tcgctcaggc gcaatcacga atgaataacg  840
gtttggttga tgcgagtgat tttgatgacg agcgtaatgg ctggcctgtt gaacaagtct  900
ggaaagaaat gcataagctt ttgccattct caccggattc agtcgtcact catggtgatt  960
tctcacttga taaccttatt tttgacgagg ggaaattaat aggttgtatt gatgttggac  1020
gagtcggaat cgcagaccga taccaggatc ttgccatcct atggaactgc ctcggtgagt  1080
tttctccttc attacagaaa cggctttttc aaaaatatgg tattgataat cctgatatga  1140
ataaattgca gtttcatttg atgctcgatg agtttttcta atcagtactg acaataaaaa  1200
gattcttgtt ttcaagaact tgtcatttgt atagtttttt tatattgtag ttgttctatt  1260
ttaatcaaat gttagcgtga tttatatttt ttttcgcctc gacatcatct gcccagatgc  1320
gaagttaagt gcgcagaaag taatatcatg cgtcaatcgt atgtgaatgc tggtcgctat  1380
actgctgtcg attcgatact aacgccaaga agttgattga gactttcaac gagattgctg  1440
aagacaagga acaattcgag aagttttaca gtgctttctc caagaacttg aagttgggtg  1500
```

```
tccatgaaga cagccaaaac agatccgcat tggccaagtt gctgagattt aactccacca  1560
agtctactga ggagctaacc tcattctctg actacgtcac cagaatgcca gagcaccaga  1620
agaacatcta cttcattacc ggtgagtctg tcaaggctct tgagaaatct ccattcttgg  1680
atgctttgaa ggagaagaac tttgaggtcc tattgctgac cgatcctatt gatgagtacg  1740
ctatgactca attgaaagag attgaggaca agaaattggt tgacatcact aaagactttg  1800
agctggaaga gtctgaggag gagaagaagg ctagagagga agaggttaaa gatttcgagc  1860
ctttgactaa agccctgaaa gagattttgg gtgacaaggt tgagaaggtt gtagtttcct  1920
acaagctggt tgactctcct gctgctatta gaacttccca attcggctgg tctgctaaca  1980
tggaaagaat tatgaaggct caagctctga gagacaccaa caccatgtcc tcgtacatgg  2040
cttcaaagaa gatcttcgag atctctccaa agtcgccaat cattaaggct ttgagaaaga  2100
aggttgaggc taccggtaca gaagagaccc cacagaatca ggggataacg caggaaagaa  2160
catgtgagca aaaggccagc aaaaggccag gaaccgtaaa aaggccgcgt tgctggcgtt  2220
tttccatagg ctccgccccc ctgacgagca tcacaaaaat cgacgctcaa gtcagaggtg  2280
gcgaaacccg acaggactat aaagatacca ggcgtttccc cctggaagct ccctcgtgcg  2340
ctctcctgtt ccgaccctgc cgcttaccgg atacctgtcc gcctttctcc cttcgggaag  2400
cgtggcgctt tctcaatgct cacgctgtag gtatctcagt tcggtgtagg tcgttcgctc  2460
caagctgggc tgtgtgcacg aaccccccgt tcagcccgac cgctgcgcct tatccggtaa  2520
ctatcgtctt gagtccaacc cggtaagaca cgacttatcg ccactggcag cagccactgg  2580
taacaggatt agcagagcga ggtatgtagg cggtgctaca gagttcttga agtggtggcc  2640
taactacggc tacactagaa ggacagtatt tggtatctgc gctctgctga agccagttac  2700
cttcggaaaa agagttggta gctcttgatc cggcaaacaa accaccgctg gtagcggtgg  2760
tttttttgtt tgcaagcagc agattacgcg cagaaaaaaa ggatctcaag aagatccttt  2820
gatcttttct acggggtctg acgctcagtg gaacgaaaac tcacgttaag ggattttggt  2880
catgagatta tcaaaaagga tcttcaccta gatcctttta aattaaaaat gaagttttaa  2940
atcaatctaa agtatatatg agtaaacttg gtctgacagt taccaatgct taatcagtga  3000
ggcacctatc tcagcgatct gtctatttcg ttcatccata gttgcctgac tccccgtcgt  3060
gtagataact acgatacggg agggcttacc atctggcccc agtgctgcaa tgataccgcg  3120
agacccacgc tcaccggctc cagatttatc agcaataaac cagccagccg gaagggccga  3180
gcgcagaagt ggtcctgcaa ctttatccgc ctccatccag tctattaatt gttgccggga  3240
agctagagta agtagttcgc cagttaatag tttgcgcaac gttgttgcca ttgctacagg  3300
catcgtggtg tcacgctcgt cgtttggtat ggcttcattc agctccggtt cccaacgatc  3360
aaggcgagtt acatgatccc ccatgttgtg caaaaaagcg gttagctcct tcggtcctcc  3420
gatcgttgtc agaagtaagt tggccgcagt gttatcactc atggttatgg cagcactgca  3480
taattctctt actgtcatgc catccgtaag atgcttttct gtgactggtg agtactcaac  3540
caagtcattc tgagaatagt gtatgcggcg accgagttgc tcttgcccgg cgtcaatacg  3600
ggataatacc gcgccacata gcagaacttt aaaagtgctc atcattggaa aacgttcttc  3660
ggggcgaaaa ctctcaagga tcttaccgct gttgagatcc agttcgatgt aacccactcg  3720
tgcacccaac tgatcttcag catcttttac tttcaccagc gtttctgggt gagcaaaaac  3780
aggaaggcaa aatgccgcaa aaaagggaat aagggcgaca cggaaatgtt gaatactcat  3840
actcttcctt tttcaatatt attgaagcat ttatcagggt tattgtctca tgagcggata  3900
catatttgaa tgtatttaga aaaataaaca aataggggtt ccgcgcacat ttccccgaaa  3960
agtgccacct gacgggtctc acagatgaca gagttgtcaa gaacttgacc actttgttgt  4020
tcgacacagc tttgttgact tccggtttca ctttggatga gccaacttct ttcgctgcca  4080
gaatcaacgg tttgatctcc attggtttga acatcgatga ggaggaagag aaagagccag  4140
aacaggctac tgaagctcca agtgaagaag ctgttgctga gtctgccatg gaggaggttg  4200
actagttgaa tttaggtata tatagtgact gtgatattta gctaatgaaa tctaattgga  4260
tatttagaat gcctcatctc gtagcctatc aattactatt aggccatctc ttatgggccc  4320
ttctttgaaa ttgcattcaa ggggggatgg gactattttg aatttgaagt ttggactctg  4380
tgagctgttt ggccaattga agtcatccac ttgtacacag ggattcacca gtagtttaga  4440
acaattctct atcgttattc tcttgtcgtc tttggcaata caagcgtcga tgactgagtt  4500
ggtgacttta tgaagtctaa gttgatatga gtttgaaatt atgaaacagt tttttacact  4560
ggacatgtag atagggccct tgatgtttag gaagaggata cagtttgaga tgttggagat  4620
gtgtgtggag ggagcgacca cttttaaaac cacatgatcc agacgttgct cagttatcga  4680
agtttcggaa acaacgccag atctgtttag cttgtttttt gtagaaatgt cttggtgtcc  4740
tcgtccaatc aggtagccat ctctgaaata tctggctccg ttgcaactcc gaacgacctg  4800
ctggcaacgt aaaattctcc ggggtaaaac ttaaatgtgg agtaatggaa ccagaaacgt  4860
ctcttccctt ctctctcctt ccaccgcccg ttaccgtccc taggaaattt tactctgctg  4920
gagagcttct tctacggccc ccttgcagca atgctcttcc cagcattacg ttgcgggtaa  4980
aacggaggtc gtgtacccga cctagcagcc cagggatgga aaagtcccgg ccgtcgctgg  5040
caataatagc gggcggacgc atgtcatgag attattggaa accaccagaa tcgaatataa  5100
aaggcgaaca cctttcccaa ttttggtttc tcctgaccca aagactttaa atttaattta  5160
tttgtcccta tttcaatcaa ttgaacaact atcaaaacac aatggtcaaa gtcgcaattc  5220
ttggcgcttc tggtggcgtg ggacaaccgc tatcattact gctaaaatta agcccttacg  5280
tttccgagct ggcgttgtac gatatccgag ctgcggaagg cattggtaag gatttatctc  5340
acatcaacac caactcaagt tgtgtcggtt atgataagga tagtattgag aacaccttgt  5400
caaatgctca ggtggtgcta ataccggctg gtgttcccag aaagcccggt ttaactagag  5460
atgatttgtt caagatgaac gccggtattg tcaaaagcct ggtaaccgct gttggaaagt  5520
tcgcaccaaa tgcgaggatt ttagtcattt caaaccctgt aaacagtttg gtccctattg  5580
ctgtggaaac tttgaagaaa atgggtaagt tcaaacctgg aaacgttatg ggtgtgacga  5640
accttgacct ggtacgtgca gaaacctttt tggtagatta tttgatgcta aaaaacccca  5700
aaattggaca agaacaagac aaaactacaa tgcacagaaa ggtcactgtt attgggggtc  5760
attcagggga aaccattatc ccaataatca ccgacaaatc gctggtattt caacttgata  5820
agcagtacga gcacttcatt catagggtcc agttcggagg tgatgaaatt gtcaaagcta  5880
aacagggcgc cggttccgcc acgttgtcca tggcgttcgc gggggccaag tttgctgaag  5940
aagttttgag gagcttccat aatgagaaac cagaaacgga gtcactttcc gcattcgttt  6000
atttaccagg cttaaaaaac ggtaagaaag cgcagcaatt agttggcgac aactctattg  6060
agtatttttc cttgccaatt gttttgagaa atggtagcgt agtatccatc gataccagtg  6120
ttctggaaaa actgtctccg agagaggaac aactcgttaa tactgcggtc aaagagctac  6180
gcaagaatat tgaaaaaggc aagagtttca tcctagactc ttaagtatct ccagtcgttt  6240
```

```
agattgttag atattttctt tgtgtattcg tttcagtctg atgtttatgc tacaaacgtc  6300
atctggactt taatccaata aggatattct tcaacttaat agtatcttaa taatattttt  6360
tttcttttga tttcttcgta aggtgttttg ttgcactcat gatctacgac ttttgttcgt  6420
gactgatt                                                           6428

SEQ ID NO: 85           moltype = DNA  length = 7311
FEATURE                 Location/Qualifiers
misc_feature            1..7311
                        note = Synthetic plasmid.
source                  1..7311
                        mol_type = other DNA
                        organism = synthetic construct
SEQUENCE: 85
tcgtccccgc cgggtcaccc ggccagcgac atggaggccc agaataccct ccttgacagt  60
cttgacgtgc gcagctcagg ggcatgatgt gactgtcgcc cgtacattta gcccatacat  120
ccccatgtat aatcatttgc atccatacat tttgatggcc gcacggcgcg aagcaaaaat  180
tacggctcct cgctgcagac ctgcgagcag ggaaacgctc ccctcacaga cgcgttgaat  240
tgtccccacg ccgcgcccct gtagagaaat ataaaaggtt aggatttgcc actgaggttc  300
ttctttcata tacttccttt taaaatcttg ctaggataca gttctcacat cacatccgaa  360
cataaacaac catgggtaag gaaaagactc acgtttcgag gccgcgatta aattccaaca  420
tggatgctga tttatatggg tataaatggg ctcgcgataa tgtcgggcaa tcaggtgcga  480
caatctatcg attgtatggg aagcccgatg cgccagagtt gtttctgaaa catggcaaag  540
gtagcgttgc caatgatgtt acagatgaga tggtcagact aaactggctg acggaattta  600
tgcctcttcc gaccatcaag cattttatcc gtactcctga tgatgcatgg ttactcacca  660
ctgcgatccc cggcaaaaca gcattccagg tattagaaga atatcctgat tcaggtgaaa  720
atattgttga tgcgctggca gtgttcctgc gccggttgca ttcgattcct gtttgtaatt  780
gtccttttaa cagcgatcgc gtatttcgtc tcgctcaggc gcaatcacga atgaataacg  840
gtttggttga tgcgagtgat tttgatgacg agcgtaatgg ctggcctgtt gaacaagtct  900
ggaaagaaat gcataagctt ttgccattct caccggattc agtcgtcact catggtgatt  960
tctcacttga taaccttatt tttgacgagg ggaaattaat aggttgtatt gatgttggac  1020
gagtcggaat cgcagaccga taccaggatc ttgccatcct atggaactgc ctcggtgagt  1080
tttctccttc attacagaaa cggctttttc aaaaatatgg tattgataat cctgatatga  1140
ataaattgca gtttcatttg atgctcgatg agtttttcta atcagtactg acaataaaaa  1200
gattcttgtt ttcaagaact tgtcatttgt atagtttttt tatattgtag ttgttctatt  1260
ttaatcaaat gttagcgtga tttatatttt ttttcgcctc gacatcatct gcccagatgc  1320
gaagttaagt gcgcagaaag taatatcatg cgtcaatcgt atgtgaatgc tggtcgctat  1380
actgctgtcg attcgatact aacgccaaga agttgattga gactttcaac gagattgctg  1440
aagacaagga acaattcgag aagttttaca gtgctttctc caagaacttg aagttgggtg  1500
tccatgaaga cagccaaaac agatccgcat tggccaagtt gctgagattt aactccacca  1560
agtctactga ggagctaacc tcattctctg actacgtcac cagaatgcca gagcaccaga  1620
agaacatcta cttcattacc ggtgagtctg tcaaggctct tgagaaatct ccattcttgg  1680
atgctttgaa ggagaagaac tttgaggtcc tattgctgac cgatcctatt gatgagtacg  1740
ctatgactca attgaaagag attgaggaca agaaattggt tgacatcact aaagactttg  1800
agctggaaga gtctgaggag gagaagaagg ctagagagga agaggttaaa gatttcgagc  1860
ctttgactaa agccctgaaa gagattttgg gtgacaaggt tgagaaggtt gtagtttcct  1920
acaagctggt tgactctcct gctgctatta gaacttccca attcggctgg tctgctaaca  1980
tggaaagaat tatgaaggct caagctctga gagacaccaa caccatgtcc tcgtacatgg  2040
cttcaaagaa gatcttcgag atctctccaa agtcgccaat cattaaggct ttgagaaaga  2100
aggttgaggc taccggtaca gaagagaccc cacagaatca ggggataacg caggaaagaa  2160
catgtgagca aaaggccagc aaaaggccag gaaccgtaaa aaggccgcgt tgctggcgtt  2220
tttccatagg ctccgccccc ctgacgagca tcacaaaaat cgacgctcaa gtcagaggtg  2280
gcgaaacccg acaggactat aaagatacca ggcgtttccc cctggaagct ccctcgtgcg  2340
ctctcctgtt ccgaccctgc cgcttaccgg atacctgtcc gcctttctcc cttcgggaag  2400
cgtggcgctt tctcaatgct cacgctgtag gtatctcagt tcggtgtagg tcgttcgctc  2460
caagctgggc tgtgtgcacg aaccccccgt tcagcccgac cgctgcgcct tatccggtaa  2520
ctatcgtctt gagtccaacc cggtaagaca cgacttatcg ccactggcag cagccactgg  2580
taacaggatt agcagagcga ggtatgtagg cggtgctaca gagttcttga agtggtggcc  2640
taactacggc tacactagaa ggacagtatt tggtatctgc gctctgctga agccagttac  2700
cttcggaaaa agagttggta gctcttgatc cggcaaacaa accaccgctg gtagcggtgg  2760
tttttttgtt tgcaagcagc agattacgcg cagaaaaaaa ggatctcaag aagatccttt  2820
gatcttttct acggggtctg acgctcagtg gaacgaaaac tcacgttaag ggattttggt  2880
catgagatta tcaaaaagga tcttcaccta gatcctttta aattaaaaat gaagttttaa  2940
atcaatctaa agtatatatg agtaaacttg gtctgacagt taccaatgct taatcagtga  3000
ggcacctatc tcagcgatct gtctatttcg ttcatccata gttgcctgac tccccgtcgt  3060
gtagataact acgatacggg agggcttacc atctggcccc agtgctgcaa tgataccgcg  3120
agacccacgc tcaccggctc cagatttatc agcaataaac cagccagccg gaagggccga  3180
gcgcagaagt ggtcctgcaa ctttatccgc ctccatccag tctattaatt gttgccggga  3240
agctagagta agtagttcgc cagttaatag tttgcgcaac gttgttgcca ttgctacagg  3300
catcgtggtg tcacgctcgt cgtttggtat ggcttcattc agctccggtt cccaacgatc  3360
aaggcgagtt acatgatccc ccatgttgtg caaaaaagcg gttagctcct tcggtcctcc  3420
gatcgttgtc agaagtaagt tggccgcagt gttatcactc atggttatgg cagcactgca  3480
taattctctt actgtcatgc catccgtaag atgcttttct gtgactggtg agtactcaac  3540
caagtcattc tgagaatagt gtatgcggcg accgagttgc tcttgcccgg cgtcaatacg  3600
ggataatacc gcgccacata gcagaacttt aaaagtgctc atcattggaa aacgttcttc  3660
ggggcgaaaa ctctcaagga tcttaccgct gttgagatcc agttcgatgt aacccactcg  3720
tgcacccaac tgatcttcag catcttttac tttcaccagc gtttctgggt gagcaaaaac  3780
aggaaggcaa aatgccgcaa aaaagggaat aagggcgaca cggaaatgtt gaatactcat  3840
actcttcctt tttcaatatt attgaagcat ttatcagggt tattgtctca tgagcggata  3900
catatttgaa tgtatttaga aaaataaaca aataggggtt ccgcgcacat ttccccgaaa  3960
```

```
agtgccacct gacgggtctc acagatgaca gagttgtcaa gaacttgacc actttgttgt  4020
tcgacacagc tttgttgact tccggtttca ctttggatga gccaacttct ttcgctgcca  4080
gaatcaacgg tttgatctcc attggtttga acatcgatga ggaggaagag aaagagccag  4140
aacaggctac tgaagctcca agtgaagaag ctgttgctga gtctgccatg gaggaggttg  4200
actagttgaa tttaggtata tatagtgact gtgatattta gctaatgaaa tctaattgga  4260
tatttagaat gcctcatctc gtagcctatc aattactatt aggccatctc ttatgggccc  4320
ttctttgaaa ttgcattcaa ggggggatgg gactattttg aatttgaagt ttggactctg  4380
tgagctgttt ggccaattga agtcatccac ttgtacacag ggattcacca gtagtttaga  4440
acaattctct atcgttattc tcttgtcgtc tttggcaata caagcgtcga tgactgagtt  4500
ggtgacttta tgaagtctaa gttgatatga gtttgaaatt atgaaacagt tttttacact  4560
ggacatgtag atagggccct tgatgtttag gaagaggata cagtttgaga tgttggagat  4620
gtgtgtggag ggagcgacca cttttaaaac cacatgatcc agacgttgct cagttatcga  4680
agtttcggaa acaacgccag atctgtttag cttgggtatt tgacaggttg gggagcaaat  4740
aagtgatgat gtcccatgaa agtagaaaat ggctagtaga aggcaaaaat ttgaaattct  4800
tagagtcaaa tagttagact ccaagttcta atccacattt ggtcagtttc atagcatcca  4860
gagcttttgc cactggtgaa catatctacc cattgcgatg caacaagtca ctgaaagcct  4920
aaaacggaga ttcccctatc ttacagcctc gttcaaaaaa actgctaccg tttatctgct  4980
atggccgatg tgaggatgcg ctcatgccca agagtccaac tttatcaaaa acttgacccg  5040
tcatacaggc tctagatcaa gaagcaaact taatctcagc atctggttac gtaactctgg  5100
caaccagtaa cacgcttaag gtttggaaca acactaaact accttgcggt actaccattg  5160
acactacaca tccttaattc caatcctgtc tggcctcctt cacctttaa ccatcttgcc  5220
cattccaact cgtgtcagat tgcgtatcaa gtgaaaaaaa aaaattttaa aatctttaac  5280
ccaatcaggt aataactgtc gcctctttta tctgccgcac tgcatgaggt gtccccttag  5340
tgggaaagag tactgagcca accctggagg acagcaaggg aaaaatacct acaacttgct  5400
tcataatggt cgtaaaaaca atccttgtcg gatataagtg ttgtagactg tcccttatcc  5460
tctgcgatgt tcttcctctc aaagtttgcg atttctctct atcagaattg ccatcaagag  5520
actcaggact aatttcgcag tcccacacgc actcgtacat gattggctga aatttcccta  5580
aagaatttct ttttcacgaa aattttttt tacacaagat tttcagcaga tataaaatgg  5640
agagcaggac ctccgctgtg actcttcttt tttttctttt attctcacta catacatttt  5700
agttattcgc caacatgggt gaactcaagg aaatcttgaa acagaggtat catgagttgc  5760
ttgactggaa tgtcaaagcc cctcatgtcc ctctcagtca acgactgaag cattttacat  5820
ggtcttggtt tgcatgtact atggcaactg gtggtgttgg tttgattatt ggttctttcc  5880
cctttcgatt ttatggtctt aatacaattg gcaaaattgt ttatattctt caaatctttt  5940
tgttttctct ctttggatca tgcatgcttt ttcgctttat taaatatcct tcaactatca  6000
aggattcctg gaaccatcat ttggaaaagc ttttcattgc tacttgtctt ctttcaatat  6060
ccacgttcat cgacatgctt gccatatacg cctatcctga taccggcgag tggatggtgt  6120
gggtcattcg aatcctttat tacatttacg ttgcagtatc ctttatatac tgcgtaatgg  6180
cttttttac aattttcaac aaccatgtat ataccattga aaccgcatct cctgcttgga  6240
ttcttcctat tttccctcct atgatttgtg gtgtcattgc tggcgccgtc aattctacac  6300
aacccgctca tcaattaaaa aatatggtta tctttggtat cctctttcaa ggacttggtt  6360
tttgggttta tcttttactg tttgccgtca atgtcttacg gtttttact gtaggcctgg  6420
caaaacccca agatcgacct ggtatgttta tgtttgtcgg tccaccagct ttctcaggtt  6480
tggccttaat taatattgcg cgtggtgcta tgggcagtcg cccttatatt tttgttggcg  6540
ccaactcatc cgagtatctt ggttttgttt ctacctttat ggctattttt atttggggtc  6600
ttgctgcttg gtgttactgt ctcgccatgg ttagcttttt agcgggcttt ttcactcgag  6660
cccctctcaa gtttgcttgt ggatggtttg cattcatttt ccccaacgtg ggttttgtta  6720
attgtaccat tgagataggt aaaatgatag attccaaagc tttccaaatg tttggacata  6780
tcattggggt cattctttgt attcagtgga tcctcctaat gtatttaatg gtccgtgcgt  6840
ttctcgtcaa tgatctttgc tatcctggca aagacgaaga tgcccatcct ccaccaaaac  6900
caaatacagg tgtccttaac cctaccttcc cacctgaaaa agcacctgca tctttggaaa  6960
aagtcgatac acatgtcaca tctactggtg gtgaatcgga tcctcctagt agtgaacatg  7020
aaagcgttta aacaggcccc ttttcctttg tcgatatcat gtaattagtt atgtcacgct  7080
tacattcacg ccctcctccc acatccgctc taaccgaaaa ggaaggagtt agacaacctg  7140
aagtctaggt ccctatttat tttttaat agttatgtta gtattaagaa cgttatttat  7200
atttcaaatt tttcttttt ttctgtacaa acgcgtgtac gcatgtaaca ttatactgaa  7260
aaccttgctt gagaaggttt tggacgctc gaaggcttta atttgcaagc t          7311
```

```
SEQ ID NO: 86          moltype = DNA  length = 9033
FEATURE                Location/Qualifiers
misc_feature           1..9033
                       note = Synthetic plasmid.
source                 1..9033
                       mol_type = other DNA
                       organism = synthetic construct
SEQUENCE: 86
tcgtccccgc cgggtcaccc ggccagcgac atggaggccc agaataccct ccttgacagt  60
cttgacgtgc gcagctcagg ggcatgatgt gactgtcgcc cgtacattta gcccatacat  120
ccccatgtat aatcatttgc atccatacat tttgatggcc gcacggcgcg aagcaaaaat  180
tacggctcct cgctgcagac ctgcgagcag ggaaacgctc ccctcacaga cgcgttgaat  240
tgtccccacg ccgcgcccct gtagagaaat ataaaaggtt aggatttgcc actgaggttc  300
ttctttcata tacttccttt taaaatcttg ctaggataca gttctcacat cacatccgaa  360
cataaacaac catgggtaag gaaaagactc acgtttcgag gccgcgatta aattccaaca  420
tggatgctga tttatatggg tataaatggg ctcgcgataa tgtcgggcaa tcaggtgcga  480
caatctatcg attgtatggg aagcccgatg cgccagagtt gtttctgaaa catggcaaag  540
gtagcgttgc caatgatgtt acagatgaga tggtcagact aaactggctg acggaattta  600
tgcctcttcc gaccatcaag cattttatcc gtactcctga tgatgcatgg ttactcacca  660
ctgcgatccc cggcaaaaca gcattccagg tattagaaga atatcctgat tcaggtgaaa  720
atattgttga tgcgctggca gtgttcctgc gccggttgca ttcgattcct gtttgtaatt  780
gtccttttaa cagcgatcgc gtatttcgtc tcgctcaggc gcaatcacga atgaataacg  840
```

-continued gtttggttga tgcgagtgat tttgatgacg agcgtaatgg ctggcctgtt gaacaagtct 900
ggaaagaaat gcataagctt ttgccattct caccggattc agtcgtcact catggtgatt 960
tctcacttga taaccttatt tttgacgagg ggaaattaat aggttgtatt gatgttggac 1020
gagtcggaat cgcagaccga taccaggatc ttgccatcct atggaactgc ctcggtgagt 1080
tttctccttc attacagaaa cggctttttc aaaaatatgg tattgataat cctgatatga 1140
ataaattgca gtttcatttg atgctcgatg agtttttcta atcagtactg acaataaaaa 1200
gattcttgtt ttcaagaact tgtcatttgt atagtttttt tatattgtag ttgttctatt 1260
ttaatcaaat gttagcgtga tttatatttt ttttcgcctc gacatcatct gcccagatgc 1320
gaagttaagt gcgcagaaag taatatcatg cgtcaatcgt atgtgaatgc tggtcgctat 1380
actgctgtcg attcgatact aacgccaaga agttgattga gactttcaac gagattgctg 1440
aagacaagga acaattcgag aagttttaca gtgctttctc caagaacttg aagttgggtg 1500
tccatgaaga cagccaaaac agatccgcat tggccaagtt gctgagattt aactccacca 1560
agtctactga ggagctaacc tcattctctg actacgtcac cagaatgcca gagcaccaga 1620
agaacatcta cttcattacc ggtgagtctg tcaaggctct tgagaaatct ccattcttgg 1680
atgctttgaa ggagaagaac tttgaggtcc tattgctgac cgatcctatt gatgagtacg 1740
ctatgactca attgaaagag attgaggaca agaaattggt tgacatcact aaagactttg 1800
agctggaaga gtctgaggag gagaagaagg ctagagagga agaggttaaa gatttcgagc 1860
ctttgactaa agccctgaaa gagattttgg gtgacaaggt tgagaaggtt gtagtttcct 1920
acaagctggt tgactctcct gctgctatta gaacttccca attcggctgg tctgctaaca 1980
tggaaagaat tatgaaggct caagctctga gagacaccaa caccatgtcc tcgtacatgg 2040
cttcaaagaa gatcttcgag atctctccaa agtcgccaat cattaaggct ttgagaaaga 2100
aggttgaggc taccggtaca gaagagaccc cacagaatca ggggataacg caggaaagaa 2160
catgtgagca aaaggccagc aaaaggccag gaaccgtaaa aaggccgcgt tgctggcgtt 2220
tttccatagg ctccgccccc ctgacgagca tcacaaaaat cgacgctcaa gtcagaggtg 2280
gcgaaacccg acaggactat aaagatacca ggcgtttccc cctggaagct ccctcgtgcg 2340
ctctcctgtt ccgaccctgc cgcttaccgg atacctgtcc gcctttctcc cttcgggaag 2400
cgtggcgctt tctcaatgct cacgctgtag gtatctcagt tcggtgtagg tcgttcgctc 2460
caagctgggc tgtgtgcacg aaccccccgt tcagcccgac cgctgcgcct tatccggtaa 2520
ctatcgtctt gagtccaacc cggtaagaca cgacttatcg ccactggcag cagccactgg 2580
taacaggatt agcagagcga ggtatgtagg cggtgctaca gagttcttga agtggtggcc 2640
taactacggc tacactagaa ggacagtatt tggtatctgc gctctgctga agccagttac 2700
cttcggaaaa agagttggta gctcttgatc cggcaaacaa accaccgctg gtagcggtgg 2760
tttttttgtt tgcaagcagc agattacgcg cagaaaaaaa ggatctcaag aagatccttt 2820
gatcttttct acggggtctg acgctcagtg gaacgaaaac tcacgttaag ggattttggt 2880
catgagatta tcaaaaagga tcttcaccta gatcctttta aattaaaaat gaagttttaa 2940
atcaatctaa agtatatatg agtaaacttg gtctgacagt taccaatgct taatcagtga 3000
ggcacctatc tcagcgatct gtctatttcg ttcatccata gttgcctgac tccccgtcgt 3060
gtagataact acgatacggg agggcttacc atctggcccc agtgctgcaa tgataccgcg 3120
agacccacgc tcaccggctc cagatttatc agcaataaac cagccagccg gaagggccga 3180
gcgcagaagt ggtcctgcaa ctttatccgc ctccatccag tctattaatt gttgccggga 3240
agctagagta agtagttcgc cagttaatag tttgcgcaac gttgttgcca ttgctacagg 3300
catcgtggtg tcacgctcgt cgtttggtat ggcttcattc agctccggtt cccaacgatc 3360
aaggcgagtt acatgatccc ccatgttgtg caaaaaagcg gttagctcct tcggtcctcc 3420
gatcgttgtc agaagtaagt tggccgcagt gttatcactc atggttatgg cagcactgca 3480
taattctctt actgtcatgc catccgtaag atgcttttct gtgactggtg agtactcaac 3540
caagtcattc tgagaatagt gtatgcggcg accgagttgc tcttgcccgg cgtcaatacg 3600
ggataatacc gcgccacata gcagaacttt aaaagtgctc atcattggaa aacgttcttc 3660
ggggcgaaaa ctctcaagga tcttaccgct gttgagatcc agttcgatgt aacccactcg 3720
tgcacccaac tgatcttcag catcttttac tttcaccagc gtttctgggt gagcaaaaac 3780
aggaaggcaa aatgccgcaa aaaagggaat aagggcgaca cggaaatgtt gaatactcat 3840
actcttcctt tttcaatatt attgaagcat ttatcagggt tattgtctca tgagcggata 3900
catatttgaa tgtatttaga aaaataaaca aataggggtt ccgcgcacat ttccccgaaa 3960
agtgccacct gacgggtctc acagatgaca gagttgtcaa gaacttgacc actttgttgt 4020
tcgacacagc tttgttgact tccggtttca ctttggatga gccaacttct ttcgctgcca 4080
gaatcaacgg tttgatctcc attggtttga acatcgatga ggaggaagag aaagagccag 4140
aacaggctac tgaagctcca agtgaagaag ctgttgctga gtctgccatg gaggaggttg 4200
actagttgaa tttaggtata tatagtgact gtgatattta gctaatgaaa tctaattgga 4260
tatttagaat gcctcatctc gtagcctatc aattactatt aggccatctc ttatgggccc 4320
ttctttgaaa ttgcattcaa gggggggatg gactattttg aatttgaagt ttggactctg 4380
tgagctgttt ggccaattga agtcatccac ttgtacacag ggattcacca gtagtttaga 4440
acaattctct atcgttattc tcttgtcgtc tttggcaata caagcgtcga tgactgagtt 4500
ggtgacttta tgaagtctaa gttgatatga gtttgaaatt atgaaacagt tttttacact 4560
ggacatgtag atagggccct tgatgtttag gaagaggata cagtttgaga tgttggagat 4620
gtgtgtggag ggagcgacca cttttaaaac cacatgatcc agacgttgct cagttatcga 4680
agtttcggaa acaacgccag atctgtttag cttgggtatt tgacaggttg gggagcaaat 4740
aagtgatgat gtcccatgaa agtagaaaat ggctagtaga aggcaaaaat ttgaaattct 4800
tagagtcaaa tagttagact ccaagttcta atccacattt ggtcagtttc atagcatcca 4860
gagcttttgc cactggtgaa catatctacc cattgcgatg caacaagtca ctgaaagcct 4920
aaaacggaga ttccccctatc ttacagcctc gttcaaaaaa actgctaccg tttatctgct 4980
atggccgatg tgaggatgcg ctcatgccca agagtccaac tttatcaaaa acttgacccg 5040
tcatacaggc tctagatcaa gaagcaaact taatctcagc atctggttac gtaactctgg 5100
caaccagtaa cacgcttaag gtttggaaca acactaaact accttgcggt actaccattg 5160
acactacaca tccttaattc caatcctgtc tggcctcctt caccttttaa ccatcttgcc 5220
cattccaact cgtgtcagat tgcgtatcaa gtgaaaaaaa aaaattttaa aatctttaac 5280
ccaatcaggt aataactgtc gcctctttta tctgccgcac tgcatgaggt gtccccttag 5340
tgggaaagag tactgagcca accctggagg acagcaaggg aaaaatacct acaacttgct 5400
tcataatggt cgtaaaaaca atccttgtcg gatataagtg ttgtagactg tcccttatcc 5460
tctgcgatgt tcttcctctc aaagtttgcg atttctctct atcagaattg ccatcaagag 5520
actcaggact aatttcgcag tcccacacgc actcgtacat gattggctga aatttcccta 5580

```
aagaatttct ttttcacgaa aatttttttt tacacaagat tttcagcaga tataaaatgg  5640
agagcaggac ctccgctgtg actcttcttt tttttctttt attctcacta catacatttt  5700
agttattcgc caacatgggt gaactcaagg aaatcttgaa acagaggtat catgagttgc  5760
ttgactggaa tgtcaaagcc cctcatgtcc ctctcagtca acgactgaag cattttacat  5820
ggtcttggtt tgcatgtact atggcaactg gtggtgttgg tttgattatt ggttctttcc  5880
cctttcgatt ttatggtctt aatacaattg gcaaaattgt ttatattctt caaatctttt  5940
tgttttctct ctttggatca tgcatgcttt ttcgctttat taaatatcct tcaactatca  6000
aggattcctg gaaccatcat ttggaaaagc ttttcattgc tacttgtctt ctttcaatat  6060
ccacgttcat cgacatgctt gccatatacg cctatcctga taccggcgag tggatggtgt  6120
gggtcattcg aatcctttat tacatttacg ttgcagtatc ctttatatac tgcgtaatgg  6180
cttttttttac aattttcaac aaccatgtat ataccattga aaccgcatct cctgcttgga  6240
ttcttcctat tttccctcct atgatttgtg gtgtcattgc tggcgccgtc aattctacac  6300
aacccgctca tcaattaaaa aatatggtta tctttggtat cctctttcaa ggacttggtt  6360
tttgggttta tcttttactg tttgccgtca atgtcttacg gttttttact gtaggcctgg  6420
caaaaacccca agatcgacct ggtatgttta tgtttgtcgg tccaccagct ttctcaggtt  6480
tggccttaat taatattgcg cgtggtgcta tgggcagtcg cccttatatt tttgttggcg  6540
ccaactcatc cgagtatctt ggttttgttt ctacctttat ggctattttt atttggggtc  6600
ttgctgcttg gtgttactgt ctcgccatgg ttagcttttt agcgggcttt ttcactcgag  6660
cccctctcaa gtttgcttgt ggatggtttg cattcatttt ccccaacgtg ggttttgtta  6720
attgtaccat tgagataggt aaaatgatag attccaaagc tttccaaatg tttggacata  6780
tcattggggt cattctttgt attcagtgga tcctcctaat gtatttaatg gtccgtgcgt  6840
ttctcgtcaa tgatctttgc tatccggcaa aagacgaaga tgcccatcct ccaccaaaac  6900
caaatacagg tgtccttaac cctaccttcc cacctgaaaa agcacctgca tctttggaaa  6960
aagtcgatac acatgtcaca tctactggtg gtgaatcgga tcctcctagt agtgaacatg  7020
aaagcgttta aacaggcccc ttttcctttg tcgatatcat gtaattagtt atgtcacgct  7080
tacattcacg ccctcctccc acatccgctc taaccgaaaa ggaaggagtt agacaacctg  7140
aagtctaggt ccctatttat ttttttttaat agttatgtta gtattaagaa cgttatttat  7200
atttcaaatt tttctttttt ttctgtacaa acgcgtgtac gcatgtaaca ttatactgaa  7260
aaccttgctt gagaaggttt tgggacgctc gaaggcttta atttgcaagc tttttttgta  7320
gaaatgtctt ggtgtcctcg tccaatcagg tagccatctc tgaaatatct ggctccgttg  7380
caactccgaa cgacctgctg gcaacgtaaa attctccggg gtaaaactta aatgtggagt  7440
aatggaacca gaaacgtctc ttcccttctc tctccttcca ccgcccgtta ccgtccctag  7500
gaaattttac tctgctggag agcttcttct acggccccct tgcagcaatg ctcttcccag  7560
cattacgttg cgggtaaaac ggaggtcgtg tacccgacct agcagcccag ggatggaaaa  7620
gtcccggccg tcgctggcaa taatagcggg cggacgcatg tcatgagatt attggaaacc  7680
accagaatcg aatataaaag gcgaacacct ttcccaattt tggtttctcc tgacccaaag  7740
actttaaatt taatttattt gtccctattt caatcaattg aacaactatc aaaacacaat  7800
ggtcaaagtc gcaattcttg gcgcttctgg tggcgtggga caaccgctat cattactgct  7860
aaaattaagc ccttacgttt ccgagctggc gttgtacgat atccgagctg cggaaggcat  7920
tggtaaggat ttatctcaca tcaacaccaa ctcaagttgt gtcggttatg ataaggatag  7980
tattgagaac accttgtcaa atgctcaggt ggtgctaata ccggctggtg ttcccagaaa  8040
gcccggttta actagagatg atttgttcaa gatgaacgcc ggtattgtca aaagcctggt  8100
aaccgctgtt ggaaagttcg caccaaatgc gaggatttta gtcatttcaa accctgtaaa  8160
cagtttggtc cctattgctg tggaaacttt gaagaaaatg ggtaagttca aacctggaaa  8220
cgttatgggt gtgacgaacc ttgacctggt acgtgcagaa accttttttgg tagattattt  8280
gatgctaaaa aaccccaaaa ttggacaaga acaagacaaa actacaatgc acagaaaggt  8340
cactgttatt gggggtcatt caggggaaac cattatccca ataatcaccg acaaatcgct  8400
ggtatttcaa cttgataagc agtacgagca cttcattcat agggtccagt tcggaggtga  8460
tgaaattgtc aaagctaaac agggcgccgg ttccgccacg ttgtccatgg cgttcgcggg  8520
ggccaagttt gctgaagaag ttttgaggag cttccataat gagaaaccag aaacggagtc  8580
actttccgca ttcgtttatt taccaggctt aaaaaaacggt aagaaagcgc agcaattagt  8640
tggcgacaac tctattgagt atttttcctt gccaattgtt ttgagaaatg gtagcgtagt  8700
atccatcgat accagtgttc tggaaaaact gtctccgaga gaggaacaac tcgttaatac  8760
tgcggtcaaa gagctacgca agaatattga aaaaggcaag agtttcatcc tagactctta  8820
agtatctcca gtcgtttaga ttgttagata ttttctttgt gtattcgttt cagtctgatg  8880
tttatgctac aaacgtcatc tggactttaa tccaataagg atattcttca acttaatagt  8940
atcttaataa tattttttttt cttttgattt cttcgtaagg tgttttgttg cactcatgat  9000
ctacgacttt tgttcgtgac tgattgcggc cgc                                9033
```

```
SEQ ID NO: 87          moltype = DNA  length = 1587
FEATURE                Location/Qualifiers
misc_feature           1..1587
                       note = Synthetic plasmid
source                 1..1587
                       mol_type = other DNA
                       organism = synthetic construct
SEQUENCE: 87
atggcaatta gtgcggcgac gaaagcggct actgatgcac ttgcggccaa ccgcgcgcca  60
acttcagtga atgctcaaga agtccaccgt tggctccaat cgtttaactg ggattttaaa  120
aacaaccgta ccaaatacgc cactaagtat aaaatggcaa acgagacaaa agagcaattc  180
aaattaatcg cgaaggagta cgcacgtatg gaaagcgtga aagacgagcg tcagttcgga  240
agccttcaag atgcgttaac ccgcctgcag agcgctgtgc gtgtgcatcc gaaatggaat  300
gaaactatga aagtagtgtc caacttcctc gaagtgggtg agtataacgc aattgccgca  360
actggcatgc tttgggactc cgcgcaagcg gctgaacaaa agaacggtta tctcgcacag  420
gttttggatg aaatccgcca cacccatcaa tgcgcgtatg ttaattatta tttcgcaaag  480
aacggccagg acccggcagg gcacaatgat gcgcgtcgta cacgcacctt ggggccgctg  540
tggaaaggta tgaaacgtgt ttctcagat ggcttcatct ccggcgacgc ggtcgaatgc  600
tcacttaatc tgcaactggt gggcgaagcc tgctttacta atccgctgat cgttgccgtt  660
accgaatggg ctgccgcgaa cggtgatgaa atcaccccga ccgtgttcct gtcgatcgag  720
```

```
acagatgaac ttcgtcatat ggcaaacggg tatcagaccg ttgtttctat tgcaaatgat  780
ccggccagcg ctaaatatat gaatactgac ttaaacaatg cattctggac acagcagaaa  840
tattttacgc cggtccttgg catgctgttc gaatacggtt caaagtttaa ggttgaaccg  900
tgggtgaaaa cctggaatcg ttgggtctat gaggattggg gcggaatttg gatcggacgc  960
ctgggcaaat atggcgtcga aagtcctcgc tccctgaagg atgccaaaca ggatgcgtac  1020
tgggcgcacc acgacctgta ccttctggca tatgctctgt ggccgaccgg tttcttccgc  1080
ttagcgttgc ctgatcaaga agagatggaa tggtacgaag cgaattaccc aggttggtac  1140
gaccattacg gtaaaatcta tgaagaatgg cgtgcacgcg gttgcgaaga tccaagcagt  1200
ggtttcattc cgctgcaatg gtttattgaa aacaaccacc ccatttatat cgatcgcacg  1260
tcacaggtcc ccttttgtcc gagtcttgcg aaacacgcga cgaccttgcg tgtgcacgaa  1320
tataacggtc agctccacac gcatgcggac caatggggtg aacgcatgtg gctggcggaa  1380
ccggaacgct atgagtgtca aaatatgttt gaacagtatg agggccgtga attaagcgag  1440
gttatcgcag aactgtgggg tgtgcgttca gacggcaaaa cacttatcgc gcaaccgcac  1500
gtccgcggtg ataaactctg gaccctggat gatattaaac gtgttggatg cgttttttca  1560
aaccctgcga aagccctgaa agcgtaa                                      1587

SEQ ID NO: 88          moltype = AA  length = 528
FEATURE                Location/Qualifiers
REGION                 1..528
                       note = misc_feature - Methylocaldum sp.175
source                 1..528
                       mol_type = protein
                       organism = Methylocaldum sp.
SEQUENCE: 88
MAISAATKAA TDALAANRAP TSVNAQEVHR WLQSFNWDFK NNRTKYATKY KMANETKEQF  60
KLIAKEYARM ESVKDERQFG SLQDALTRLQ SAVRVHPKWN ETMKVVSNFL EVGEYNAIAA  120
TGMLWDSAQA AEQKNGYLAQ VLDEIRHTHQ CAYVNYYFAK NGQDPAGHND ARRTRTLGPL  180
WKGMKRVFSD GFISGDAVEC SLNLQLVGEA CFTNPLIVAV TEWAAANGDE ITPTVFLSIE  240
TDELRHMANG YQTVVSIAND PASAKYMNTD LNNAFWTQQK YFTPVLGMLF EYGSKFKVEP  300
WVKTWNRWVY EDWGGIWIGR LGKYGVESPR SLKDAKQDAY WAHHDLYLLA YALWPTGFFR  360
LALPDQEEME WYEANYPGWY DHYGKIYEEW RARGCEDPSS GFIPLQWFIE NNHPIYIDRT  420
SQVPFCPSLA KHATTLRVHE YNGQLHTHAD QWGERMWLAE PERYECQNMF EQYEGRELSE  480
VIAELWGVRS DGKTLIAQPH VRGDKLWTLD DIKRVGCVFS NPAKALKA                528

SEQ ID NO: 89          moltype = DNA  length = 1170
FEATURE                Location/Qualifiers
misc_feature           1..1170
                       note = Synthetic plasmid
source                 1..1170
                       mol_type = other DNA
                       organism = synthetic construct
SEQUENCE: 89
atgccgctgc tggacgaaaa acgtcgtggc ttgaccgacc cggaatgggc gagcgttatc  60
ctgaacgccc tgccggcaga gcctttggat aaacaaaaca agatgggcta ctttgttacc  120
ccacgctgga agcgtttgac ggaatatgaa gctctcaccg tttatgctca gcctaacgcg  180
gattggattg cgggtggttt ggattgggga gactggactc agaaatttca cggcggccgt  240
ccgtcgtggg gcaacgaaac cacggaactg cgcacggtag attggtttaa acaccgtgat  300
ccactccgcc gctggcatgc cccgtatgtg aaagataaag cggaagagtg gcgttacact  360
gatcgctttc tgcaaggcta tagcgcggac ggtcagattc gtaccatgga ccctttctgg  420
cgcgatgaat tcattaacaa atactggggt gcgttcctgt ttaacgaata cggtcagttc  480
aacgcccatt caggaggcgc acgtgaagcg ctgtcggaca ccatccgtgt atcgctgacg  540
ttttggggtt ttgataaaat cgatctggcc cagatgatcc agctggaacg tggcttctta  600
gctaaaattg taccgggctt tgatgaatct acggcggtgc cgaaagcaga atggacccag  660
ggctctgtct ataaaagtgc tcgtggcacg atcgaggcat tgtggcaaga cgtcttcgac  720
tggaacgaaa acgcgttttc agtacatgca gtgtacgata gcctgtttgg tcaatttgtg  780
cgtcgcgagt tctttcagcg cttagcccct aaatttggcg ataatctcac acccttttt  840
atcaaccaga gccagaccta ttacggcatt gctaaacagg gcgtgcagga tctctattac  900
acctgtttag cgaatgatcc tgaattcggt gactacaacc gcacagtcct ccgcaattgg  960
accgctaaat ggctggaagg gacggtgaat gcgctgcgtg atttcatggg tatttttgcg  1020
aagctgccga ccggaaccac acacaaggcc gaaatccagg ccagcttaga acgcgtgatc  1080
gacgattgga ccgcggatca tgccagccgt attgatttca aagtcgatcg tgatgcgatt  1140
gttcgtcatg tcatgagcgg tctgatttga                                  1170

SEQ ID NO: 90          moltype = AA  length = 389
FEATURE                Location/Qualifiers
REGION                 1..389
                       note = misc_feature - Methylocaldum sp.175
source                 1..389
                       mol_type = protein
                       organism = Methylocaldum sp.
SEQUENCE: 90
MPLLDEKRRG LTDPEWASVI LNALPAEPLD KQNKMGYFVT PRWKRLTEYE ALTVYAQPNA  60
DWIAGGLDWG DWTQKFHGGR PSWGNETTEL RTVDWFKHRD PLRRWHAPYV KDKAEEWRYT  120
DRFLQGYSAD GQIRTMDPFW RDEFINKYWG AFLFNEYGQF NAHSGGAREA LSDTIRVSLT  180
FWGFDKIDLA QMIQLERGFL AKIVPGFDES TAVPKAEWTQ GSVYKSARGT IEALWQDVFD  240
WNENAFSVHA VYDSLFGQFV RREFFQRLAP KFGDNLTPFF INQSQTYYGI AKQGVQDLYY  300
TCLANDPEFG DYNRTVLRNW TAKWLEGTVN ALRDFMGIFA KLPTGTTHKA EIQASLERVI  360
DDWTADHASR IDFKVDRDAI VRHVMSGLI                                     389
```

```
SEQ ID NO: 91           moltype = DNA  length = 507
FEATURE                 Location/Qualifiers
misc_feature            1..507
                        note = Synthetic plasmid
source                  1..507
                        mol_type = other DNA
                        organism = synthetic construct
SEQUENCE: 91
atggcaaaaa acggtgtcca tgacaacgcc acacgcgatg catgggttgt aaaaattggg  60
cagttgaata ccctggacaa agccgcggct gccttaaaac agtttcgtct cgatcatacc  120
actccgtttc gcaaaactta tgaactggat aatgattatc tgtggatcga ggctaaactg  180
gaggaaaagg ttgctgtcct gaaggcccgc gctttcaacg atgaagactt ccgccataaa  240
accgcttttg gggaatgcgc taaaacgctc ttagccgaag cggtcgcgaa aatggctgct  300
acgggcgata aatgggaagc agaacgcatt catattggct tccgtcaagc taataaaccg  360
cccattatgc cggtgaacta tttccttgaa gccgaacgtg tccttggtac gaagctgatg  420
gaattgcgta acctcaacta ctatgataca ccactggaag aactgcgcaa acagcgcggt  480
gtgaaagtct tagtagcgcc gcactaa                                     507

SEQ ID NO: 92           moltype = AA  length = 168
FEATURE                 Location/Qualifiers
REGION                  1..168
                        note = misc_feature - Methylocaldum sp.175
source                  1..168
                        mol_type = protein
                        organism = Methylocaldum sp.
SEQUENCE: 92
MAKNGVHDNA TRDAWVVKIG QLNTLDKAAA ALKQFRLDHT TPFRKTYELD NDYLWIEAKL  60
EEKVAVLKAR AFNDEDFRHK TAFGECAKTL LAEAVAKMAA TGDKWEAERI HIGFRQANKP  120
PIMPVNYFLE AERVLGTKLM ELRNLNYYDT PLEELRKQRG VKVLVAPH              168

SEQ ID NO: 93           moltype = DNA  length = 426
FEATURE                 Location/Qualifiers
misc_feature            1..426
                        note = Synthetic plasmid
source                  1..426
                        mol_type = other DNA
                        organism = synthetic construct
SEQUENCE: 93
atgtctgtgt ccagcaatgc gtattatgca ggtacgacgg gtctgtcggg caaggagttc  60
gctgaagcat tcttcgcgga tgaaaatcag gttgtgcatg aaagcgatac cgtcgttttg  120
gtgctgaaaa aaagcgacga aatcaacaca tttatcgaag agatcctgct ggaagattat  180
aaaaaacatg tgaacccaac cgtcaatgtt gaagaccgcg ccgggtattg gtggatcaaa  240
gctaacggta agattgaagt ggactgcgat gaactgtccg agcttctggg tcgttccttc  300
aacgtctacg acttcctggt ggatgtgagc agcactatcg gccgtgcata taccctgggt  360
aataaattca caattacctc tgaattgatg ggtttagacc gtaagttgga agattatcat  420
gcataa                                                            426

SEQ ID NO: 94           moltype = AA  length = 141
FEATURE                 Location/Qualifiers
REGION                  1..141
                        note = misc_feature - Methylocaldum sp.175
source                  1..141
                        mol_type = protein
                        organism = Methylocaldum sp.
SEQUENCE: 94
MSVSSNAYYA GTTGLSGKEF AEAFFADENQ VVHESDTVVL VLKKSDEINT FIEEILLEDY  60
KKHVNPTVNV EDRAGYWWIK ANGKIEVDCD ELSELLGRSF NVYDFLVDVS STIGRAYTLG  120
NKFTITSELM GLDRKLEDYH A                                           141

SEQ ID NO: 95           moltype = DNA  length = 1104
FEATURE                 Location/Qualifiers
misc_feature            1..1104
                        note = Synthetic plasmid
source                  1..1104
                        mol_type = other DNA
                        organism = synthetic construct
SEQUENCE: 95
atggccgcaa cccactcaat taaagtgatt actgaagatg gcgaagccgt gtactttgat  60
tgccgtcctg atgaagatgt catcagtgct gccatccgcc aggatatcta tctgatgtcc  120
tcatgccgcg ctggtggctg cgcaacctgt aaagcgtttt gcccggaagg cgactaccgc  180
ttagtgggtt gttcggtgca agcactgccg cctgaagagg aagaagacgg ccaggttctg  240
ctgtgtcgct gttatccgga ctcggatctg gagctggaag ttccgtatac ctactcacgt  300
attgcatttg aaccggaagc taatgagttc ccggccgagg tagtgagcgt tggtaaagtc  360
agctcgaatg cagttcgtct gcatttgcgc cgcccgggta tgggcaacga acgcaaagtc  420
cgttttgatg caggtcagtt catggaactg caagtacctg gttcggcagt cacgcgcgcg  480
tattccccgg ccaacatctc taacgacgcc ggcgacctgg agtttcttat tcgtttatta  540
cctgatggcc ttatgtctaa tgctctccgt ggcggtgcca ttcagccggg tcagacgttg  600
caggtcaaag gtccgcaggg aatcttcggc cttaaagaaa atggctttcg tccgcgctac  660
tttattgcgg gtggcacggg cctcgcccct gtactgagta tggttcgcca tatgcgtgag  720
```

```
tggggtgcgc cccagcagac tcgcctgtac ttcggcgtca ataccgagga agaagtcttt  780
ctgcgcgccg aactggaagc cctggctgcc gctatgccga atttaaccgt gaaagtctgc  840
gtgtggcgcc ctaccgatgg ttgggatggt gaacgtggca acgcaatcga ggtactccgc  900
cgcgacctgg aggcgcagcc ggcgcagccc gatgtctatc tttgtgggcc gccgggtatg  960
gtcgatgccg cgtatgccgt ctgtgcagag tttggtatcc cagcggacca aatctatctg  1020
gagaaattct taccgtcggg accgtgtggc gaggcctgtg acccgggtca agtgcacggt  1080
catcaccagc acgccacagc ctaa                                          1104

SEQ ID NO: 96          moltype = AA  length = 367
FEATURE                Location/Qualifiers
REGION                 1..367
                       note = misc_feature - Methylocaldum sp.175
source                 1..367
                       mol_type = protein
                       organism = Methylocaldum sp.
SEQUENCE: 96
MAATHSIKVI TEDGEAVYFD CRPDEDVISA AIRQDIYLMS SCRAGGCATC KAFCPEGDYR  60
LVGCSVQALP PEEEEDGQVL LCRCYPDSDL ELEVPYTYSR IAFEPEANEF PAEVVSVGKV  120
SSNAVRLHLR RPGMGNERKV RFDAGQFMEL QVPGSAVTRA YSPANISNDA GDLEFLIRLL  180
PDGLMSNALR GGAIQPGQTL QVKGPQGIFG LKENGFRPRY FIAGGTGLAP VLSMVRHMRE  240
WGAPQQTRLY FGVNTEEEVF LRAELEALAA AMPNLTVKVC VWRPTDGWDG ERGNAIEVLR  300
RDLEAQPAQP DVYLCGPPGM VDAAYAVCAE FGIPADQIYL EKFLPSGPCG EACDPGQVHG  360
HHQHATA                                                             367

SEQ ID NO: 97          moltype = DNA  length = 282
FEATURE                Location/Qualifiers
misc_feature           1..282
                       note = Synthetic plasmid
source                 1..282
                       mol_type = other DNA
                       organism = synthetic construct
SEQUENCE: 97
atgacaattg atttcgatca tttggatccg gatgccctgg atttcttatc ggctcgctcg  60
ttaagccaag ttccagcagg taccccctcgc accgaactat ttcagcaagg tcgctacgca  120
gcgtacgcac aggacctggg tttcgcatgg cgctgggcca ttgcccgcga cgggcgcgat  180
attcaagaag gcccggcgct gtcgctggaa tctgcccacc tgagcgcacg ccgtgtactg  240
gcattctttg ttcgcttaga ctcgccgccg acaccggcct aa                     282

SEQ ID NO: 98          moltype = AA  length = 93
FEATURE                Location/Qualifiers
REGION                 1..93
                       note = misc_feature - Methylocaldum sp.175
source                 1..93
                       mol_type = protein
                       organism = Methylocaldum sp.
SEQUENCE: 98
MTIDFDHLDP DALDFLSARS LSQVPAGTPR TELFQQGRYA AYAQDLGFAW RWAIARDGRD  60
IQEGPALSLE SAHLSARRVL AFFVRLDSPP TPA                                93

SEQ ID NO: 99          moltype = DNA  length = 1593
FEATURE                Location/Qualifiers
misc_feature           1..1593
                       note = Synthetic plasmid
source                 1..1593
                       mol_type = other DNA
                       organism = synthetic construct
SEQUENCE: 99
atggccgcga gcaatcttgc agtgaaacag gcgttgaaaa acaaccctgc gccgtcgtcg  60
gttgaccccgc aggaagttca taaatggtta caggacttca cttgggattt caaagaaaaa  120
gcaggcaaat atcccacgaa gtatgacatg gatgtgaata cccgtgagca atttaagttg  180
acggcgaagg aatatgcgcg catggagtca gccaaagaag aacgccaatt tggtaccctt  240
cttgacggcc tggatcgcct cgatgccggc aacaaggtgc atccgcgttg gggcgaattt  300
atgaaattag ttgcaaactt cctggaaacc ggtgaatatg gtgcgctcgc aggttcggca  360
cttttgtggg atactgcaca aagcccggaa caacgcaatg gttacttagc gcaagtgatc  420
gatgaggtgc gccacgtgaa tcagtgcgca tcggttagtt actattattc aaaacactat  480
tacgatcccg ctggtttcac aaatatgcgc cagttacgtg ctattaaccc tctgtatcca  540
ggtgtgaagc gtgctttcgg tgaaggtttt ctggcgggcg atgccgtcga gtccagcatt  600
aatttacagc tggtagcgga ggcgtgcttt accaaccccc tgatcgtagc tttaaccgaa  660
tgggcggcgg caaatgggga tgagatcact ccaaccgtgt tcttgagcat tgaaaccgat  720
gaattgcgcc acatggcgaa cggctatcag acgattgtgt ctatcatgaa taaccccgat  780
accatgaaat atctgcaaac tgatctggat aacgccttct ggacgcaaca caagttcctg  840
acgccattcg taggggcggc gttagaatat ggttcgcgtt ttaaagtcga gccgtgggcg  900
aaatcgtgga accgctgggt ttacgaggat tgggcaggca tttggttagg ccgcctgcaa  960
caattcgggt taaaatcccc aaaatgtctg gccgacgcga agaaagatgc agtctgggca  1020
catcacgatc tggccctcct ggcgtttgcg ttatggccgt taacaggtat ccgcctcgaa  1080
ttgcctgacc gtcaggatat ggaatggttt gaagcgaatt atccgggctg gtatgaacac  1140
tatggaaaaa tttacgaaga atggcgtgcc cttgggttcg aagatccccg ttccggattt  1200
agtggtgctg tgtggatgct gcagcgtggc catggcattt ttattgacca tacgtcaagc  1260
ctgcccttct gtccgacgtt gggtaagggt gctctgaaac cttcgtttct ggagaagaac  1320
```

```
gggaaacgtt ttgcattcag tgaaccgcac ggtgaacgca tgtggttgca ggagccggag  1380
cgctacgaat tccaaaactt cttcgagcag tttgaaggct gggaattgag tgacctcgta  1440
aaagcggctg gtggtgtgcg ttcggacggc aaaactttga tggcgcagcc tcatctgcgt  1500
tccactgata tgtggactct ggatgacctg aagcgtatta attttaccgt gccggatccg  1560
atgcgcattc tgaactggca accggcccat tga                               1593

SEQ ID NO: 100          moltype = AA  length = 530
FEATURE                 Location/Qualifiers
source                  1..530
                        mol_type = protein
                        organism = Solimonas aquatica
SEQUENCE: 100
MAASNLAVKQ ALKNNPAPSS VDPQEVHKWL QDFTWDFKEK AGKYPTKYDM DVNTREQFKL  60
TAKEYARMES AKEERQFGTL LDGLDRLDAG NKVHPRWGEF MKLVANFLET GEYGALAGSA  120
LLWDTAQSPE QRNGYLAQVI DEVRHVNQCA SVSYYYSKHY YDPAGFTNMR QLRAINPLYP  180
GVKRAFGEGF LAGDAVESSI NLQLVAEACF TNPLIVALTE WAAANGDEIT PTVFLSIETD  240
ELRHMANGYQ TIVSIMNNPD TMKYLQTDLD NAFWTQHKFL TPFVGAALEY GSRFKVEPWA  300
KSWNRWVYED WAGIWLGRLQ QFGLKSPKCL ADAKKDAVWA HHDLALLAFA LWPLTGIRLE  360
LPDRQDMEWF EANYPGWYEH YGKIYEEWRA LGFEDPRSGF SGAVWMLQRG HGIFIDHTSS  420
LPFCPTLGKG ALKPSFLEKN GKRFAFSEPH GERMWLQEPE RYEFQNFFEQ FEGWELSDLV  480
KAAGGVRSDG KTLMAQPHLR STDMWTLDDL KRINFTVPDP MRILNWQPAH             530

SEQ ID NO: 101          moltype = DNA  length = 1176
FEATURE                 Location/Qualifiers
misc_feature            1..1176
                        note = Synthetic plasmid
source                  1..1176
                        mol_type = other DNA
                        organism = synthetic construct
SEQUENCE: 101
atgtcctcga actcgtttgt acgtggtatg gtagatcctt atcgtcagac catcattcag  60
gcagcaattc cggaacagcc gttagaaagc aaacgcgatc atattccttt tgcgaagcgc  120
ggttggcgcc gtctcactga atatgaggcg gtgatgctcc acgcacagaa tagcgtagac  180
tccgtgccgg gctcacagga ggtgggtgag tctgtacaga aatggccggg cggtcgcccg  240
aattactcta ttgagtctac tgctgttatt gcaggtaatt ggttttactt tcgcgaccca  300
gcgaaacgct ggttcatgcc gtatgttaag cagaaaacgg aagaaggtca aaccgctgag  360
cgtaccatga aaagctgggc agagtccgga gatgccggaa tgatgaacgc cgattggcgt  420
aatcaaatcc tgggtaccca ctatggcgcc ttggtgtata atgaatatgg cctcttctcc  480
gcacattcga cgacagttta tagtgctctg tccgacttgc tgaagacctg gatctcggaa  540
gcagggttcg ataaaaatga tgccggccaa atgattcaga tggaacgtat tctgctcggc  600
aaattgtttg ctgatttcga cccgagtctg gccgctgcta aacaggcctg gatgcaagac  660
ccgatttggc aaccggcgcg tgaattcgtt cagcatatct ggatgggtgt ctatgattgg  720
gttgaacagc tgtgggccat ccatggcatt tacgatcaca ttttcgggca attcgtgcgc  780
cgtgaattct tccagcgcct ggcgggcctg cacggtgata cgcttactcc ctttatccaa  840
tcccaggctc tgacgtacca tcaacaggcc agcgacgcgc tgcaagcctt ttgtgtaaaa  900
atgttgatcg acgaagagcc ggtatacggg gctcacaatc gccgctacct gcgcgcatgg  960
accaagcgtt atctccctgg cacccaggcg gcgctgaaag cgttcctggc tatctacaaa  1020
accctgccgc tgcaagtgga aggaattacc tgcaaagcaa gtgtagaagc agcagtgcgt  1080
cgcattgtga acgattgggc ccgccgtttt gccgaaccga tcgattatcg ctttgatgca  1140
gaagcattca ttgccgacgt catgcagggg tactaa                            1176

SEQ ID NO: 102          moltype = AA  length = 391
FEATURE                 Location/Qualifiers
source                  1..391
                        mol_type = protein
                        organism = Solimonas aquatica
SEQUENCE: 102
MSSNSFVRGM VDPYRQTIIQ AAIPEQPLES KRDHIPFAKR GWRRLTEYEA VMLHAQNSVD  60
SVPGSQEVGE SVQKWPGGRP NYSIESTAVI AGNWFYFRDP AKRWFMPYVK QKTEEGQTAE  120
RTMKSWAESG DAGMMNADWR NQILGTHYGA LVYNEYGLFS AHSTTVYSAL SDLLKTWISE  180
AGFDKNDAGQ MIQMERILLG KLFADFDPSL AAAKQAWMQD PIWQPAREFV QHIWMGVYDW  240
VEQLWAIHGI YDHIFGQFVR REFFQRLAGL HGDTLTPFIQ SQALTYHQQA SDALQAFCVK  300
MLIDEEPVYG AHNRRYLRAW TKRYLPGTQA ALKAFLAIYK TLPLQVEGIT CKASVEAAVR  360
RIVNDWARRF AEPIDYRFDA EAFIADVMQG Y                                391

SEQ ID NO: 103          moltype = DNA  length = 507
FEATURE                 Location/Qualifiers
misc_feature            1..507
                        note = Synthetic plasmid
source                  1..507
                        mol_type = other DNA
                        organism = synthetic construct
SEQUENCE: 103
atgagcaagc agcattggta tcacacgcca acgcgtgatg agtggctgga acgcattggt  60
accctgcgca ccgcccgtga aggaattgaa atgttgcgca actttcgtga gcagcatctg  120
ggtccagacc gcaagactta tgatctgaag aaagaagcaa attggattga gtcgcgtatt  180
gaaatgcgtg tgtcccagct gcacgccgag gaaactctga gtgatgacga tctcctgcac  240
aaaacgattg atggccgctg cgcccgtgag gttgccaata gttggtggga aaaagcagca  300
caagttgatt ccgcaatcga actgggccag ctctgcgtgg cctaccgtaa ggcgtgtaaa  360
```

```
ccaccgatga tgcctattaa ttactttgcg ccagtcgaga aaaaattggt tagtaaactg  420
ctgaaattgc gcgcggaaaa ttacctggtg acgcctatcg aagaactgcg taaagcccgt  480
aatgttacac ctatccatgt gcagtga                                      507

SEQ ID NO: 104          moltype = AA  length = 168
FEATURE                 Location/Qualifiers
source                  1..168
                        mol_type = protein
                        organism = Solimonas aquatica
SEQUENCE: 104
MSKQHWYHTP TRDEWLERIG TLRTAREGIE MLRNFREQHL GPDRKTYDLK KEANWIESRI  60
EMRVSQLHAE ETLSDDDLLH KTIDGRCARE VANSWWEKAA QVDSAIELGQ LCVAYRKACK  120
PPMMPINYFA PVEKKLVSKL LKLRAENYLV TPIEELRKAR NVTPIHVQ               168

SEQ ID NO: 105          moltype = DNA  length = 417
FEATURE                 Location/Qualifiers
misc_feature            1..417
                        note = Synthetic plasmid
source                  1..417
                        mol_type = other DNA
                        organism = synthetic construct
SEQUENCE: 105
atgtctacta acatcaacgg ttataattcg ggtaccaata acaagacggg acaagcattt  60
gtcgacgaat ttctgagcga aaaaaactgc accctgccta cgtccgacgc ggtagtgctt  120
gccctgatga agacagaaga aatcaatgtt atcgtcgatg aaatgattcg tccaatgatg  180
gatgacaacc cggccctggc cgtcgacgat cgtggtgggt actggtggat taaagtgaac  240
gggaaaatcg tcatcgactg tgatgaagca actgagattt tgggcaaaaa atataccgtg  300
tacgattttc tggttaatgt gagcaccaca attggtcgtg ctatgaccct ggggaaccaa  360
ttcgtactga ccaatgaact gttgggtctg gaaactaaaa tcgattcagt gtactaa     417

SEQ ID NO: 106          moltype = AA  length = 138
FEATURE                 Location/Qualifiers
source                  1..138
                        mol_type = protein
                        organism = Solimonas aquatica
SEQUENCE: 106
MSTNINGYNS GTNNKTGQAF VDEFLSEKNC TLPTSDAVVL ALMKTEEINV IVDEMIRPMM  60
DDNPALAVDD RGGYWWIKVN GKIVIDCDEA TEILGKKYTV YDFLVNVSTT IGRAMTLGNQ  120
FVLTNELLGL ETKIDSVY                                                138

SEQ ID NO: 107          moltype = DNA  length = 1056
FEATURE                 Location/Qualifiers
misc_feature            1..1056
                        note = Synthetic plasmid
source                  1..1056
                        mol_type = other DNA
                        organism = synthetic construct
SEQUENCE: 107
atggattcgc gttacaccat cacggctaac tttgaagacg gcgccctcca tcagttcgaa  60
tgcgcggaaa acgaagatat cctgtcagcg gcgcttcgtc agcaggttgt gctgctgtgc  120
tcttgccgca aagcgttctg cggatcttgt aaagcgctgt gtatggaagg tgaatacgcc  180
tttggggatc gtgtaaatgt acaggtgctg tcgccgaaag aagaagagga tggtgtcgtg  240
gtggcgtgtg acacttttcc ccgtagcgat atggcactgg cattccccata taccagtgac  300
cgcctgggat catgttcttc cgaaaatctc gaagctcagg tggagatcgt tgagcgcctg  360
tctagcactg tgtacaagct gctgctgcag gttcgtgatc cggtgagtca tgaagctaag  420
cgtatcgagt tccaaccggg tcaatacgcc gaattgcagc tgccggatgg tgagcaaaca  480
cgtgcgtttt cgtttgcaaa tatcgcggac gattctggct tgctcgaatt tctgatccgc  540
ttggttccgg gtggatgttt tagtacctat ctgcagcagc gtgcagttcc gggcgacgtg  600
ctgaagctgc gcgcgccgct tggtgccttc acgttccaac cgggggacca agacgaaggc  660
ctgcacgcgt ttgtgggagg ttcgaccgga ttggcccctt tgctgtctat gctgcgtggt  720
ttagcccgcc aagattatcg cggcgaatgt catctgtttt ttggtatgca ggaccaagcc  780
gcgctgtact acgaagacga gctgcgcgaa ttagcggcaa gtatgccacg cttaaccttg  840
catctcgctc tcatggatcc tccgccacaa tggcagggct acacggggaa tgccgtgacc  900
gcgtttgaac aacactttgc cgctttagcg cgcaagccgg aagtctatat ctgcggtccg  960
gctgcaatgg ttgaggccac tcgcgcatct tgtgaacgtc tgaatatccc ggagcaccgc  1020
gtgcaccgtg aggaatttgt cgccagcgga ggttaa                            1056

SEQ ID NO: 108          moltype = AA  length = 351
FEATURE                 Location/Qualifiers
source                  1..351
                        mol_type = protein
                        organism = Solimonas aquatica
SEQUENCE: 108
MDSRYTITAN FEDGALHQFE CAENEDILSA ALRQQVVLLC SCRKAFCGSC KALCMEGEYA  60
FGDRVNVQVL SPKEEEDGVV VACDTFPRSD MALAFPYTSD RLGSCSSENL EAQVEIVERL  120
SSTVYKLLLQ VRDPVSHEAK RIEFQPGQYA ELQLPDGEQT RAFSFANIAD DSGLLEFLIR  180
LVPGGCFSTY LQQRAVPGDV LKLRAPLGAF TFQPGDQDEG LHAFVGGSTG LAPLLSMLRG  240
LARQDYRGEC HLFFGMQDQA ALYYEDELRE LAASMPRLTL HLALMDPPPQ WQGYTGNAVT  300
AFEQHFAALA RKPEVYICGP AAMVEATRAS CERLNIPEHR VHREEFVASG G            351
```

```
SEQ ID NO: 109          moltype = DNA  length = 300
FEATURE                 Location/Qualifiers
misc_feature            1..300
                        note = Synthetic plasmid
source                  1..300
                        mol_type = other DNA
                        organism = synthetic construct
SEQUENCE: 109
gtgaacacgc gcagcggcga tacgccggct attccccgtc ttgacggcct gccccaggca  60
gtgggcgcca cggtgctgat tcatgaagac ggtgaatttc gtgtgtatgc gacggaactt  120
gaaatgctgc tgcgctggga tctgttccag ggcgatcgcc atctgcacac cggttcagct  180
ctccgcgttg aaagctgtat cgtttcagcc aagggcaaaa ttggcttttt tcgccgtcct  240
actgttgcac gtctgatcgc cgcaggcgac gaggcaagcc ccaacgatcc gagctaataa  300

SEQ ID NO: 110          moltype = AA  length = 98
FEATURE                 Location/Qualifiers
source                  1..98
                        mol_type = protein
                        organism = Solimonas aquatica
SEQUENCE: 110
MNTRSGDTPA IPRLDGLPQA VGATVLIHED GEFRVYATEL EMLLRWDLFQ GDRHLHTGSA  60
LRVESCIVSA KGKIGFFRRP TVARLIAAGD EASPNDPS                         98

SEQ ID NO: 111          moltype = DNA  length = 1650
FEATURE                 Location/Qualifiers
misc_feature            1..1650
                        note = Synthetic plasmid
source                  1..1650
                        mol_type = other DNA
                        organism = synthetic construct
SEQUENCE: 111
atgagtcgtc aatctatgtc gaaagcccat aaaaagatca cagagctgtc ctgggagccg  60
acgtttgcca ctcccgccaa acgttttggt accgactaca catttgacaa tgctccgaaa  120
aaagatcctc tgaagcagat tttacgctcg tactttccca tggaggagga aaaagattca  180
cgcgttttcg gagcgatgga cggggccatc cgtggtaata tgtttcgcca ggtgcaggag  240
cgttggatgg agtggcagaa gttgtttctg tcaattatcc cgtttcctga aatctccgcg  300
gcacgtgcca tgccaatggc gattgacgcc gtgcccaacc cagagattca taatggttta  360
gctgttcaga tgattgatga agtgcgtcat tcgacgatcc aaatgaacct gaaacgcctg  420
tacatgaatt actacatcga tccagcgggt tttgatatga ccgaaaaagc tttcgcaaat  480
aactacgctg gtacaattgg ccgtcaattt ggcgaaggtt ttattacagg ggatgcgatc  540
acggcagcca atatctacct tactgtggtt gcagaaactg cattcaccaa cacgctgttt  600
gtggcgatgc cgagcgaagc tgcggccaat ggagactatc tgctgccaac tgtgttccac  660
agtgtccaga gtgatgaatc tcgtcatatt tcaaacggtt actccatcct tctgatggcg  720
ttgtcggacg aggataaccg tcagctgtta gaacgtgatc ttcgctatgc ctggtggaac  780
aaccaccgcg tcgttgacgc cgcgattgga accttcattg aatatggtac caaagatcgt  840
cgcaaagacc gtgagtcgta tgcggaaatg tggcgtcgct ggatttatga cgattattat  900
cgtgcgtatc tgattccgct ggagaaatac gggcttgtga tcccacacga tctgatcgag  960
gagtcgtgga aacaaatttg ggagaaaggc tatgtccatg aggtcgccca gtttttgcg  1020
acaggctggc ttgcgaatta ttggcgcatt gattccatga ctgatgaaga tttcgaatgg  1080
ttcgaataca agtatcctgg ctggtatgat aaatatggta aatggtggga aaactataat  1140
cgcctgagca aaccgaacgg ccacaatccg attgtgtttg aagatgtaga ttatgtgtac  1200
ccggcacgct gttggacgtg catgagcccc tgctggtcag tccgcacact cgttacggcg  1260
gaagttgatg gccaacatcg cacctattgc cacgaagtat gtcgttggac ggatgtgcgt  1320
gggttcccat ccgatgtgcc gggtcgtgaa accccaaata tgggtcgctt agtgggtaaa  1380
cgtgagtggg aaacgttgta ccacggttgg aattgggcag atgttgtttc ggatatgggg  1440
tttgtacgtg atgacgggaa gacgatgacc ccgaaaccgc atctggatct ggatccaaaa  1500
aaaatgtgga ccctcgatca catgcgtcgc tgtccgcccc tgcagtcgcc gaatgtactg  1560
tttaacgaaa tgtccgacgc ggagcgtgct gcctatgtcg cggactacaa caaacagggc  1620
cctgctggtc gtccggcccc gcaatcgtaa                                  1650

SEQ ID NO: 112          moltype = AA  length = 549
FEATURE                 Location/Qualifiers
REGION                  1..549
                        note = misc_feature - Pseudonocardia TY7
source                  1..549
                        mol_type = protein
                        organism = Pseudonocardia sp.
SEQUENCE: 112
MSRQSMSKAH KKITELSWEP TFATPAKRFG TDYTFDNAPK KDPLKQILRS YFPMEEEKDS  60
RVFGAMDGAI RGNMFRQVQE RWMEWQKLFL SIIPFPEISA ARAMPMAIDA VPNPEIHNGL  120
AVQMIDEVRH STIQMNLKRL YMNYYIDPAG FDMTEKAFAN NYAGTIGRQF GEGFITGDAI  180
TAANIYLTVV AETAFTNTLF VAMPSEAAAN GDYLLPTVFH SVQSDESRHI SNGYSILLMA  240
LSDEDNRQLL ERDLRYAWWN NHRVVDAAIG TFIEYGTKDR RKDRESYAEM WRRWIYDDYY  300
RAYLIPLEKY GLVIPHDLIE ESWKQIWEKG YVHEVAQFFA TGWLANYWRI DSMTDEDFEW  360
FEYKYPGWYD KYGKWWENYN RLSKPNGHNP IVFEDVDYVY PARCWTCMSP CWSVRTLVTA  420
EVDGQHRTYC HEVCRWTDVR GFPSDVPGRE TPNMGRLVGK REWETLYHGW NWADVVSDMG  480
FVRDDGKTMT PKPHLDLDPK KMWTLDHMRR CPPLQSPNVL FNEMSDAERA AYVADYNKQG  540
PAGRPAPQS                                                         549
```

```
SEQ ID NO: 113          moltype = DNA  length = 1032
FEATURE                 Location/Qualifiers
misc_feature            1..1032
                        note = Synthetic plasmid
source                  1..1032
                        mol_type = other DNA
                        organism = synthetic construct
SEQUENCE: 113
atgggagata aacatgtagt ccgttttgaa ccggtgggta tcgaaattga agttgatgaa  60
gatcagacca tcctgcgtgc agcagccgaa cagggtgtgc agctgatgca cggctgcaaa  120
gaaggtcagt gtgcggcctg caaaagcttt gttctggaag gtgaggatat tgagctggac  180
agttactcta tttttacact gccagattac gagaaagagg agggatcgac gttgctgtgt  240
cgtgcgcatg cctatgaaga cttgaccatt gaactgttga actatgatga agaaattatt  300
cgcagcggtc tgccgctgcg taaaggtaag gtccaggtag tagcaaatga tgaagttacc  360
catgacctgc gtcgtctggt agtaaaactg attgaaccgg aagagattaa atttttcccc  420
ggacagtaca tggatttcat cgttccagga actgaagagt cgcgtagctt ctcaatggcc  480
aatacaccaa accgtgaagg cgaattcgaa tttgtgatca agatttatcc agatggcctt  540
tttagtgaat ttctggccga gaaagttcaa gtgggtgatc agctggaagt ggaagcgccg  600
tttggcactt ttaccttacg cgagaaccgt acgtcagata tcgtttttgt gggcggcggc  660
gcgggtatgg cgccaatcct gggtctgctg cgttctatgg cagaacgtgg cgtggaacgc  720
cgcgcccgct tctattacgg cgcgcgtgcg acacgcgacc tttgctttgc cgaagaaatt  780
gccgcgctgg gtgaacagct gccgagtggc cttacatata ccccggcgct gagccatcct  840
gacgacgaac cgtggagcgg ccagaccggc ctgatcaccg aggtgttaca ggccaatgaa  900
agtacactgg agggcgcgga tgcctacgta tgtggtccac caccaatggt cgacgccgcg  960
attgcgaccc ttaccgccct tggtgtgcgt gaggaaaaca ttttctatga taaatttacc  1020
acccaccgct ga                                                      1032

SEQ ID NO: 114          moltype = AA  length = 343
FEATURE                 Location/Qualifiers
REGION                  1..343
                        note = misc_feature - Pseudonocardia TY7
source                  1..343
                        mol_type = protein
                        organism = Pseudonocardia sp.
SEQUENCE: 114
MGDKHVVRFE PVGIEIEVDE DQTILRAAAE QGVQLMHGCK EGQCAACKSF VLEGEDIELD  60
SYSIFTLPDY EKEEGSTLLC RAHAYEDLTI ELLNYDEEII RSGLPLRKGK VQVVANDEVT  120
HDLRRLVVKL IEPEEIKFFP GQYMDFIVPG TEESRSFSMA NTPNREGEFE FVIKIYPDGL  180
FSEFLAEKVQ VGDQLEVEAP FGTFTLRENR TSDIVFVGGG AGMAPILGLL RSMAERGVER  240
RARFYYGARA TRDLCFAEEI AALGEQLPSG LTYTPALSHP DDEPWSGQTG LITEVLQANE  300
STLEGADAYV CGPPPMVDAA IATLTALGVR EENIFYDKFT THR                   343

SEQ ID NO: 115          moltype = DNA  length = 1188
FEATURE                 Location/Qualifiers
misc_feature            1..1188
                        note = Synthetic plasmid
source                  1..1188
                        mol_type = other DNA
                        organism = synthetic construct
SEQUENCE: 115
atgacgacca cagaacgtcc ggaacgttcc gtgcctaaac ctgtgttcac cgatgcggag  60
gcaggcgccc acgagtttcc tgatagcgga gcatccgcgc gccgttataa ttactataac  120
tcaatcaacg caagccgtac gcactatgaa gatgtaacgg tggatgtgca gccggatccg  180
cgtcattatt tgtcgcaggg ctggatctac gggttcgcgg atggatctgc acgctaccct  240
ctgacctgga cgaaattgaa agccgtgggc cgtggctcgg cgcgcgcgcg tgcattacct  300
cgtttacgtc gtcagggcct tcgcgtctgt ccgccgaccg cttggcatga atttcgcgac  360
ccaaacgagg agtgggaatt gaccttttat cgctataacg ctaatgtggt gcgccaggtt  420
aaccagaata ttgaaaatgc ccgctatgcg aaagcgttcg aacagtggac acccaactgg  480
attcagttcg tggaacgtaa tgtcggcgcc tggatgcaca ttgagcatac gttgggcctg  540
tatgtcttcg ctgcctgcaa tcgttctggg cctactaaca tgcacaatac cgcaatggcg  600
tacaccgctt gccataaaat tcgttttgca caggatcttg cactgtataa cttaaccctc  660
actgaagaaa ttgaaggctt cgatggaact gcacatttgg aggcgtggaa cagcgatccg  720
gagtggcagg ccagtggtcg cagtcatgaa gcgctgaccg ccgtggatga cgactggggc  780
gaaagtattt ttgccacgaa tgtggtgttc gaaccgttgc ttcgcgagct gtttcgcagt  840
aaccttgtta tgcaggcggc tgccggtaac ggtgatttcg ttaccccgac ggtgatgggc  900
gcggcggaat ttgattttgc gcaacgtgac ttacgttgga cccaagcttg ttttggtccc  960
ttaacccaag ataaggaatt tgccgattat aacaaagatc tcatgcaagg atggctgtct  1020
cattgggttc cgcaggctat cgaagcggct cgcgttttgc agccgatctg gtcgctgcca  1080
gacgctaaac caccgcgctt tgaagattca ttagaccgtg caaaaagccg ttttagcggt  1140
attgtaacgg acttagggtt atctgtgccg aaggaactgt cacaataa               1188

SEQ ID NO: 116          moltype = AA  length = 395
FEATURE                 Location/Qualifiers
REGION                  1..395
                        note = misc_feature - Pseudonocardia TY7
source                  1..395
                        mol_type = protein
                        organism = Pseudonocardia sp.
```

```
SEQUENCE: 116
MTTTERPERS VPKPVFTDAE AGAHEFPDSG ASARRYNYYN SINASRTHYE DVTVDVQPDP  60
RHYLSQGWIY GFADGSARYP LTWTKLKAVG RGSARARALP RLRRQGLRVC PPTAWHEFRD  120
PNEEWELTFY RYNANVVRQV NQNIENARYA KAFEQWTPNW IQFVERNVGA WMHIEHTLGL  180
YVFAACNRSG PTNMHNTAMA YTACHKIRFA QDLALYNLTL TEEIEGFDGT AHLEAWNSDP  240
EWQASGRSHE ALTAVDDDWG ESIFATNVVF EPLLRELFRS NLVMQAAAGN GDFVTPTVMG  300
AAEFDFAQRD LRWTQACFGP LTQDKEFADY NKDLMQGWLS HWVPQAIEAA RVLQPIWSLP  360
DAKPPRFEDS LDRAKSRFSG IVTDLGLSVP KELSQ                            395

SEQ ID NO: 117         moltype = DNA  length = 375
FEATURE                Location/Qualifiers
misc_feature           1..375
                       note = Synthetic plasmid
source                 1..375
                       mol_type = other DNA
                       organism = synthetic construct
SEQUENCE: 117
atgacgtctt ttaagacggc agaatctccc tttaaagcag ataacacggc ttcgggaaag  60
gctggcgtga cccttatgaa caatcaaatt ggtgtggtgg ttgcagaagt aatggatcag  120
caagaaaatg taaccattac acacttgccg agtatgattc gtgttgactg tgtgggtcgc  180
atggattttg tgtatgacga tatctcggaa gcgctgggcg aggagccggg gttttacgac  240
gctgcggaat tcgaagaaaa catgagcacc cattacggga agatgattca catggatgac  300
cgtactgtaa tgtttgggaa cttagaagaa gccgcagaat tcattggtga tatgctgccg  360
cctccggtta aataa                                                  375

SEQ ID NO: 118         moltype = AA  length = 124
FEATURE                Location/Qualifiers
REGION                 1..124
                       note = misc_feature - Pseudonocardia TY7
source                 1..124
                       mol_type = protein
                       organism = Pseudonocardia sp.
SEQUENCE: 118
MTSFKTAESP FKADNTASGK AGVTLMNNQI GVVVAEVMDQ QENVTITHLP SMIRVDCVGR  60
MDFVYDDISE ALGEEPGFYD AAEFEENMST HYGKMIHMDD RTVMFGNLEE AAEFIGDMLP  120
PPVK                                                              124

SEQ ID NO: 119         moltype = DNA  length = 288
FEATURE                Location/Qualifiers
misc_feature           1..288
                       note = Synthetic plasmid
source                 1..288
                       mol_type = other DNA
                       organism = synthetic construct
SEQUENCE: 119
atggctttca gacccttgca tgatagagtg gtcgttaaac gattggaagg agaagataaa  60
accaaaggtg gaatcatcat tccagatact gccaaggaaa agcctgctga gggtaagatc  120
attgccgttg ggcctggcgc aagagatgag tccggaaaat tggtcgcact ggatgtcaaa  180
gaaggtgatc gagttttgtt cggtaagtgg agtgggaccg aggtaaagat agacggagag  240
gacctttga ttatgaagga gtctgacatc ttgggcgtga tcgcttga               288

SEQ ID NO: 120         moltype = AA  length = 95
FEATURE                Location/Qualifiers
REGION                 1..95
                       note = misc_feature - Methylocystis sp. LW5
source                 1..95
                       mol_type = protein
                       organism = Methylocystis sp.
SEQUENCE: 120
MAFRPLHDRV VVKRLEGEDK TKGGIIIPDT AKEKPAEGKI IAVGPGARDE SGKLVALDVK  60
EGDRVLFGKW SGTEVKIDGE DLLIMKESDI LGVIA                            95

SEQ ID NO: 121         moltype = DNA  length = 1683
FEATURE                Location/Qualifiers
misc_feature           1..1683
                       note = Synthetic plasmid
source                 1..1683
                       mol_type = other DNA
                       organism = synthetic construct
SEQUENCE: 121
atggcaagaa atattagatt tggtgatccc gttagaaaaa gacttctgga tggagttgac  60
tttctagctg acgctgttgg tgttaccttg ggccatgtg gaaggaatgt tgtcatcgaa  120
catagggcct ccggcttacc acccgtagcc accaaggacg gtgcaacggt tgctcaggcc  180
gttgaagccg ccggtcgtac tgaaagtgtt ggtatcaatt tagttagaca aatggccact  240
accgttgcaa aagaggctgg tgatgggacg acaacctctg tcgttttgac acgaagggtg  300
gctgccgaaa ctcgtaaggc ccttgcagct ggaatgaatc cccgtgacat cacattaggc  360
atggagaggg ccgcaagagc agttgaagca gacttgttga gacgtgcaag acgttgcaac  420
gaccagaggt cattggctca tgttgccacc ctagccgctg gtggagatga gggtatcggt  480
gctattgttg cacaagcttt ggccttagcc ggtgagggag gagttgtgga tgtagaacta  540
```

```
ggtcacggcg tcgccgatga catcgagtct gttgagggca tgagatggga gcagggctac  600
cgttccccat atttcatgac agactcagct aggaaggtag ctgagctgga aaatccttat  660
attctggtct atgatagagt tatcaacgaa ttctctgagc tggttcctgc acttgagttg  720
gtcagaagat ctggcggatc tcttctagtt gtagctgaaa acataatgga ggaagcccctt  780
ccaggcttgt tgttgaacca tattagaaaa aatttgtgct ccattgctgt gaaggggcca  840
ggatatggtg attcaaggta tgaatattta ttggatttag ctgctataac cggaggtagg  900
gctatcatgg aagcattcgg tgaagacatt tccaatgtaa ctatggagca cttgggtcgt  960
gctagaagag tcgttgttag ggaagatgat acgctagtca ttggtggtga gggagatcct  1020
aacgtaatcg cagatagact agcaagtgct aaacgtcagg cagattggat tgttgaagga  1080
gacgcatcta agggctcccc ttcaggaaaa agacatgagt tagaaaactt gcagacacga  1140
attaaggccc tgagtggacg tatggcaaca attagggctg ggggcctgtc tgacgtgctg  1200
attaaggaaa gaatgcaaag gatcgaaaat gctttaaact ctgctagggc cgcacaatct  1260
gatggagtcg ttgctggagg tggagtgggt ttgtatcgag caagggctgc cctggctgaa  1320
ttaaggggtg agaacctgga ccagtctcac ggcgttgcca ttgtgcgtgc agcactggat  1380
gaacctatca gaagaatcgc agccaacgct ggggtggatg ctgatgaatt cttgttcgag  1440
ctacgaagaa gtaatgatga tttctggggc atggatatga gaagtggtgc ttgtggtgat  1500
cttttcgctg caggagttat tgatccagtt cgagtaacca gacttgcctt aagaaatgca  1560
gttgccactg cagcctctct tatgaccgtt gaatgtgccg tcacacatat tcctgtttct  1620
gaccctactt tcggatttga tgctagaaga gccgctgaaa cgagagaaga tcctagagcc  1680
taa                                                                1683

SEQ ID NO: 122         moltype = AA  length = 560
FEATURE                Location/Qualifiers
REGION                 1..560
                       note = misc_feature - Methylocystis sp. LW5
source                 1..560
                       mol_type = protein
                       organism = Methylocystis sp.
SEQUENCE: 122
MARNIRFGDP VRKRLLDGVD FLADAVGVTL GPCGRNVVIE HRASGLPPVA TKDGATVAQA  60
VEAAGRTESV GINLVRQMAT TVAKEAGDGT TTSVVLTRRV AAETRKALAA GMNPRDITLG  120
MERAARAVEA DLLRRARRCN DQRSLAHVAT LAAGGDEGIG AIVAQALALA GEGGVVDVEL  180
GHGVADDIES VEGMRWEQGY RSPYFMTDSA RKVAELENPY ILVYDRVINE FSELVPALEL  240
VRRSGGSLLV VAENIMEEAL PGLLLNHIRK NLCSIAVKGP GYGDSRYEYL LDLAAITGGR  300
AIMEAFGEDI SNVTMEHLGR ARRVVVREDD TLVIGGEGDP NVIADRLASA KRQADWIVEG  360
DASKGSPSGK RHELENLQTR IKALSGRMAT IRAGGLSDVL IKERMQRIEN ALNSARAAQS  420
DGVVAGGGVG LYRARAALAE LRGENLDQSH GVAIVRAALD EPIRRIAANA GVDADEFLFE  480
LRRSNDDFWG MDMRSGACGD LFAAGVIDPV RVTRLALRNA VATAASLMTV ECAVTHIPVS  540
DPTFGFDARR AAETREDPRA                                              560

SEQ ID NO: 123         moltype = DNA  length = 291
FEATURE                Location/Qualifiers
misc_feature           1..291
                       note = Synthetic plasmid
source                 1..291
                       mol_type = other DNA
                       organism = synthetic construct
SEQUENCE: 123
gtgaaaatcc gtccgctgca tgatcgtgtt attgtcaagc gtctcgaagc ggagcgcaaa  60
acggcctcag gaatcgttat cccagattca gcaggcgaga agccggacca aggagaagtt  120
ctggcggtgg gtaacggtaa aatccttgac gacggtaaag tccgtccgat ggccgtcaaa  180
gtgggtgata aagttctgtt cggtaagtat gctggtcaaa ccgtcaaagt ggagggcgag  240
gagctcctgg tgatgcgtga agaagatatt atgggtgtgg tggaggctta a           291

SEQ ID NO: 124         moltype = AA  length = 96
FEATURE                Location/Qualifiers
source                 1..96
                       mol_type = protein
                       organism = Thauera butanivorans
SEQUENCE: 124
MKIRPLHDRV IVKRLEAERK TASGIVIPDS AGEKPDQGEV LAVGNGKILD DGKVRPMAVK  60
VGDKVLFGKY AGQTVKVEGE ELLVMREEDI MGVVEA                            96

SEQ ID NO: 125         moltype = DNA  length = 1707
FEATURE                Location/Qualifiers
misc_feature           1..1707
                       note = Synthetic plasmid
source                 1..1707
                       mol_type = other DNA
                       organism = synthetic construct
SEQUENCE: 125
atgattagcc ttaattgcaa aaaaaccact accggtctga ccgcacattt ggctctggtg  60
cgcggcatga aagccttagc ggagctggtg ggtacgacat taggacccca aggtcgccac  120
gttatgttag cacaccgtgc cgggctggcg ccgcacgtaa gcaaagacgg tgtggaagtt  180
gcgcgtcatc tgtccctgcc cgattcggaa gaggaattag gtgttcgctt actgcgtaat  240
gcggctgttg cagtctccga gtcatttggc gatgggacct caaccgccac cgtcttcacc  300
gcggatctgg ccgtgcgcgc gcttaaattg attggtgccg gtgcggatac attagaagtt  360
cgccgtggtc tgggcttggc ggcctatgct gcgctggttg cactgaacga tatggcccgc  420
cgtgcggacc gcggaatgct gacggccgta gctcaaacgg ccgctaacgg tgaccgtcgc  480
```

```
gtggctgact tgttagtgga ggcgtttgaa cgcgtgggcg cggaaggaac aattgaagtg  540
gaaatgggta acagtgtaga ggatgttttg gaagtggcac aagggagcta ttttgatacc  600
gtgcccttgg ttaccgcact gctgccaccg accggccaag tagaatttgc gcgtccgttg  660
attcttttcc attgcgatgc cattgaaacc gcagatgaaa ttcttccggc cctcgaactc  720
gctcgttcta gccgtcgccc actgcttatt ctggcggact ccgtgggtat tgatgttgaa  780
actctgcttg tccgcaatca aaatgaaggc accttagcgg tggcagtagt acgtgcaccg  840
atgtatggtg acacgcgccg tgaagctctc ctggatctga cgtcaaaatt tggcggaact  900
gcgttcggcc gcgagggctt tgtcgaattc gcgctgcgta gcttaggcag cctgagcgaa  960
ggagatctcg gtcaggcgga cgaggccatt ttggaagcag atggcgtgac tttacgcggg  1020
gcgggaaata acccctccgc cctggaagat cgtattgcac tggttcgcgc ggaactggat  1080
cgcggagatg tgtccgttgg ggattcgccg tccgcaaaac tcgactacat tgagaaacgc  1140
aaagagcgct taaaactgct tgccgccggg agcgcaaaac tgcatattgg gggcccgacc  1200
gatgtcgaga tcaagacgcg tcttccgctg gcagagaatg cgcatcgtgc tttgctggcc  1260
gctgccaagt ctggtgttct gcctgggggc ggtgtcgcca tgattcgcgc ggcagaaaaa  1320
gtacagcagg aaatgggccg tctggagggc gatgtggcgt ccggtgcctc gatttttctg  1380
cagagcttag atactcccat tcgctggatt gcgcgtaacg cgggtctgcg cccggacgaa  1440
gtcctggcac gcacattggc aaacgaatct gatttttacg gtctgaacgc gatgacgggt  1500
cgctacggcg acctggcaga agatggtgtt ctcgatgctc tggacatggt aaccgacgtt  1560
attcgtgtgg cggtgtcggt agtcggaagc atgctcggag taggcgcact ggtcacgcgc  1620
gcgagtccga aaccggcgcc ggaacgtttc aagggaacgg agcgcgtaca cgataaactg  1680
atgcgcgaag gtggttttga tgagtga                                     1707

SEQ ID NO: 126          moltype = AA  length = 568
FEATURE                 Location/Qualifiers
source                  1..568
                        mol_type = protein
                        organism = Thauera butanivorans
SEQUENCE: 126
MISLNCKKTT TGLTAHLALV RGMKALAELV GTTLGPQGRH VMLAHRAGLA PHVSKDGVEV  60
ARHLSLPDSE EELGVRLLRN AAVAVSESFG DGTSTATVFT ADLAVRALKL IGAGADTLEV  120
RRGLGLAAYA ALVALNDMAR RADRGMLTAV AQTAANGDRR VADLLVEAFE RVGAEGTIEV  180
EMGNSVEDVL EVAQGSYFDT VPLVTALLPP TGQVEFARPL ILFHCDAIET ADEILPALEL  240
ARSSRRPLLI LADSVGIDVE TLLVRNQNEG TLAVAVVRAP MYGDTRREAL LDLTSKFGGT  300
AFGREGFVEF ALRSLGSLSE GDLGQADEAI LEADGVTLRG AGNNPSALED RIALVRAELD  360
RGDVSVGDSP SAKLDYIEKR KERLKLLAAG SAKLHIGGPT DVEIKTRLPL AENAHRALLA  420
AAKSGVLPGG GVAMIRAAEK VQQEMGRLEG DVASGASIFL QSLDTPIRWI ARNAGLRPDE  480
VLARTLANES DFYGLNAMTG RYGDLAEDGV LDALDMVTDV IRVAVSVVGS MLGVGALVTR  540
ASPKPAPERF KGTERVHDKL MREGGFDE                                    568

SEQ ID NO: 127          moltype = DNA  length = 288
FEATURE                 Location/Qualifiers
misc_feature            1..288
                        note = Synthetic plasmid
source                  1..288
                        mol_type = other DNA
                        organism = synthetic construct
SEQUENCE: 127
gtggcgtttc gtccgctgca cgatcgtgtg gtggttaaac gtctggaagg cgaggacaaa  60
actaaaggtg ggattattat cccggatacg gctaaagaaa aaccagcgga aggtaaggtc  120
atcgcagtag gtccaggttc ccgtgatgaa agcggcaaac tggttgcgct ggatgtgaaa  180
gaaggcgatc gtgtgctgtt cggcaagtgg agcggcacag aagtcaaaat cgatggagaa  240
gatttgctta ttatgaagga atctgatatc ctgggcgtaa tcgtataa              288

SEQ ID NO: 128          moltype = AA  length = 95
FEATURE                 Location/Qualifiers
REGION                  1..95
                        note = misc_feature - Methylosinus trichosporium OB3b
source                  1..95
                        mol_type = protein
                        organism = Methylosinus trichosporium
SEQUENCE: 128
MAFRPLHDRV VVKRLEGEDK TKGGIIIPDT AKEKPAEGKV IAVGPGSRDE SGKLVALDVK  60
EGDRVLFGKW SGTEVKIDGE DLLIMKESDI LGVIV                            95

SEQ ID NO: 129          moltype = DNA  length = 1746
FEATURE                 Location/Qualifiers
misc_feature            1..1746
                        note = Synthetic plasmid
source                  1..1746
                        mol_type = other DNA
                        organism = synthetic construct
SEQUENCE: 129
atgactaatc cgcgtaaacg cgaacgccgt cgtccggcat tcgatgtcac acgtgaaaaa  60
ttcgttgccc gtaacattcg ctttggtgat gtggtccgcc gtgatttatt agcgggcgtg  120
gatgcccttg cagacgcggt agcggtgacc ttaggcccgc gcggccgtaa cgttgtaatc  180
gaacatcgcg cggcaggttt gccgccagta gcaaccaaag atggagtgac cgtagcgcag  240
gccgtggaat tggcgggtcg cacccagtcc gtcggtgtga gcttagtacg ccagatggcg  300
acggctgtag ccaaggaggc gggcgatggg accaccacga gcgttgtgct tgctcgtcgc  360
ttggcagccg aaacccgcaa agccctggca gctgggatga atccgcgtga tatcgtactg  420
```

```
gggatggaaa aagcggcccg cattgtggat cgtgacctcg cggctcgtgc acgccgttgc  480
gatgacacac gtgcccttgc gcacgtcgct accttggctg ccgggggtga tgagagtatc  540
ggtgccattg tggcggatgc tttaacacgt gcgggcgagg gcggcgtagt agacgtggaa  600
ctgggtgctg cactgtgtga tgagatggac attgttgagg gcatgcgctg ggaacagggt  660
taccgctcac cgtatttcat gacggactct gcgcgcaaga tcgcagaact ggaaaatcct  720
tacattctga tctacgatcg tgttattaat caattttccg aattagttcc ggcgttagaa  780
ttagtccgtc gccaacgcgg cagcctgtta atcgtcgctg aaaacattgt ggaagaggcc  840
ctccctggcc tgctcctgaa tcatattcgt aaaaatctgt gttctatcgc cgttaaaggt  900
ccgggttatg ggactcccg ttacgaattt ctgcacgatc tggcggcctt aaccggaggc  960
cgtgcgatca tggaggcgtg cggcgaggag ttgtcaaacg ttaccatggc ccatctggga  1020
cgcgcaaaac gtgtagtggt gcgcgaagat gatacggttg tgatcggcgg ggagggggac  1080
ggtgcggcca tcactgagcg tctggccgcg gcgcgtcagc aggcagattg gattaccgac  1140
ggcgatccaa gcaaaggaag cccatccgga aagcgccacg atttagaaaa cctgcagacc  1200
cgcattaaag ctctgagcgg aaaggtagtc acgattaagg ccggcggcct tagtgatatt  1260
ctgattaaag aacgcatgca gcgtattgag aatgctctcg catcggcgcg cgcagcccgc  1320
tccgacggag tcgtggccgg cggcggcgtg ggactgtatc gcgcccgcgc tgcgttgact  1380
gaggcaacgg gcgacacctt ggatcaaacc tacggcattg cgattgtacg cgctgctctc  1440
gacgagccca ttcgccgtat tgctgcgaac gcggggcgcg atgcacatga atttctgttt  1500
gaactcaaac gctctaacga tgatttttgg gggatggata tgcgcagcgg tgaatgcgga  1560
gatctttatg ccgcgggcgt cattgatccg gcgcgtgtta cccgcctggc cctgcgcaac  1620
gcggtagcta cggctagcag cctgatgacc gtcgaatgcg cagtaactca tatcccacct  1680
tctgacccca cctatggttt tgatcctcat ttggcggcgg caacccgtga agacccgcgc  1740
tcataa                                                             1746

SEQ ID NO: 130         moltype = AA  length = 581
FEATURE                Location/Qualifiers
REGION                 1..581
                       note = misc_feature - Methylosinus trichosporium OB3b
source                 1..581
                       mol_type = protein
                       organism = Methylosinus trichosporium
SEQUENCE: 130
MTNPRKRERR RPAFDVTREK FVARNIRFGD VVRRDLLAGV DALADAVAVT LGPRGRNVVI  60
EHRAAGLPPV ATKDGVTVAQ AVELAGRTQS VGVSLVRQMA TAVAKEAGDG TTTSVVLARR  120
LAAETRKALA AGMNPRDIVL GMEKAARIVD RDLAARARRC DDTRALAHVA TLAAGGDESI  180
GAIVADALTR AGEGGVVDVE LGAALCDEMD IVEGMRWEQG YRSPYFMTDS ARKIAELENP  240
YILIYDRVIN QFSELVPALE LVRRQRGSLL IVAENIVEEA LPGLLLNHIR KNLCSIAVKG  300
PGYGDSRYEF LHDLAALTGG RAIMEACGEE LSNVTMAHLG RAKRVVVRED DTVVIGGEGD  360
GAAITERLAA ARQQADWITD GDPSKGSPSG KRHDLENLQT RIKALSGKVV TIKAGGLSDI  420
LIKERMQRIE NALASARAAR SDGVVAGGGV GLYRARAALT EATGDTLDQT YGIAIVRAAL  480
DEPIRRIAAN AGRDAHEFLF ELKRSNDDFW GMDMRSGECG DLYAAGVIDP ARVTRLALRN  540
AVATASSLMT VECAVTHIPP SDPTYGFDPH LAAATREDPR S                      581

SEQ ID NO: 131         moltype = DNA  length = 291
FEATURE                Location/Qualifiers
misc_feature           1..291
                       note = Synthetic plasmid
source                 1..291
                       mol_type = other DNA
                       organism = synthetic construct
SEQUENCE: 131
atgaacattc gtccgctcaa tgatcgcgtg attgtaaaac gtcttgaaga ggaacgcacg  60
tcaccgggtg gcattgtgat cccggattca gccacagaga aaccgtcccg tggtgaaatc  120
ctggcggtcg gcacgggtaa aaccctggat aatggtcagg tacgtgcctt ggccgtcaaa  180
gcgggcgaca aagtgctgtt tggtaaatac gcggggacgg aagtcaagat tgacggccag  240
gagattcttg tgatgcgtga agaagatatt attgcggtgc ttgaggatta a           291

SEQ ID NO: 132         moltype = AA  length = 96
FEATURE                Location/Qualifiers
REGION                 1..96
                       note = misc_feature - Methylocaldum sp.175
source                 1..96
                       mol_type = protein
                       organism = Methylocaldum sp.
SEQUENCE: 132
MNIRPLNDRV IVKRLEEERT SPGGIVIPDS ATEKPSRGEI LAVGTGKTLD NGQVRALAVK  60
AGDKVLFGKY AGTEVKIDGQ EILVMREEDI IAVLED                            96

SEQ ID NO: 133         moltype = DNA  length = 1683
FEATURE                Location/Qualifiers
misc_feature           1..1683
                       note = Synthetic plasmid
source                 1..1683
                       mol_type = other DNA
                       organism = synthetic construct
SEQUENCE: 133
atgtcaaagc gcctcgtctt cgatggcgaa gcccgcgcgg gaattttaaa aggtattgat  60
atttgggtc gtgcggttga gactacttac ggttatcagg ggccttgcgt aatggtacaa  120
caccgcactc agggtctgcc tccgttcttt acacgtgatg gcgtaacggt tgcgaactcg  180
```

```
gtcgttctgg gtgatcgcct ggccgatctt ggcgcacgta tgctgcgtga cgttgcgaac  240
gcggtatctc gcgaagcggg tgatggcaca acaaccgccg tggtgctggc gcgcgcaatc  300
gcgcgcggcc ttttacgttc cttggcagcg ggggcggatc cgcatcgttt gcgcgaggga  360
atggacgctg ccgttaagct ggtggaggat gatctgcgcc gccgcgcgct gcctcttcaa  420
ggggatatgg ttgctcaagt tgcagaagtg tcaatgcgca aagaagggca ggttggccgc  480
ttactgcaac aggcttatgc ggaagttgga ccagatgggg ctgttacggt agaaccgggt  540
tggacacgtg cggatacctt ggatatcggc gaaggcttcc gttatgaact gggatttctg  600
tccccgggct tcgaaacaga tccggttcgt cgtgccgctg acatcgaggg tgcccgcgtg  660
ctgctgtatc atggtacggt tactgacttc atggacctga ttccgttgct ggaagcagtg  720
aatgaggctg gtcaagcgct ggtaattgca tgcgatggaa tcgatgagcg tccgttacag  780
ggcttagtaa tgaacgtcaa gcgtggtgtg ttccgtgcgc tggcagtgaa agcgccgggc  840
catggtgacc gtcgtcgtga ttggctggat gatctggcga ctgccacggg tgcccgcgta  900
ctggtgccgg agcgcggaga caatctggaa cgtgcggcac cggaagtgct tggacacgcg  960
gccaaagtgg tggccgatgc ggacagcgct agttttattg gctgtggcgg tgaccctgtg  1020
gcagtagccc gtcgtgtggc gggattaggt aaagaggccg atgccattcg cgcgcgcaaa  1080
ccgggcgaag gttctcctac cggcaatctg catgatctgg aggatctgga ggcgcgcatt  1140
agtgcgttag ttggtcgcat cgctaccgtc cgtgtaggcg gcaccaccga gcccgaaatt  1200
aaagaacgct tgcaacgcgc tgaaaatgcc cgtcgttcag ttcgcgccgc gttggaggaa  1260
ggagttgtgc ctggcggtgg agtgggactg cttcaagccc gcgaagcctt aggtcgcctt  1320
ctcctgacgg atctggactg gcagcgcggc gtggctatcg taagcgaagc actcgaacag  1380
ccattccgtg ctctggtcgg aaacgcaggt atcaatccgg tggcggccct ggctcgtatc  1440
gaagcggcag gcaacgctcg ttttggttac gatgccagct caggagcgtt cggtgatctc  1500
gtagcagccg gtgtcttaga cccagtgaaa gtcctgcgcc tggctctggt tcaagctgcg  1560
gggattgccg cgacagttct gtcttccgga gcagtcgtgt tgaatgagca gtcaggctta  1620
ccgcatctgc ccggcttttc cgcggaatgg gccgcagcaa cgcgcgaaga tccgcgtgcc  1680
taa                                                                 1683
```

```
SEQ ID NO: 134         moltype = AA  length = 560
FEATURE                Location/Qualifiers
REGION                 1..560
                       note = misc_feature - Methylocaldum sp.175
source                 1..560
                       mol_type = protein
                       organism = Methylocaldum sp.
SEQUENCE: 134
MSKRLVFDGE ARAGILKGID ILGRAVETTY GYQGPCVMVQ HRTQGLPPFF TRDGVTVANS  60
VVLGDRLADL GARMLRDVAN AVSREAGDGT TTAVVLARAI ARGLLRSLAA GADPHRLREG  120
MDAAVKLVED DLRRRALPLQ GDMVAQVAEV SMRKEGQVGR LLQQAYAEVG PDGAVTVEPG  180
WTRADTLDIG EGFRYELGFL SPGFETDPVR RAADIEGARV LLYHGTVTDF MDLIPLLEAV  240
NEAGQALVIA CDGIDERPLQ GLVMNVKRGV FRALAVKAPG HGDRRRDWLD DLATATGARV  300
LVPERGDNLE RAAPEVLGHA AKVVADADSA SFIGCGGDPV AVARRVAGLG KEADAIRARK  360
PGEGSPTGNL HDLEDLEARI SALVGRIATV RVGGTTEPEI KERLQRAENA RRSVRAALEE  420
GVVPGGGVGL LQAREALGRL LLTDLDWQRG VAIVSEALEQ PFRALVGNAG INPVAALARI  480
EAAGNARFGY DASSGAFGDL VAAGVLDPVK VLRLALVQAA GIAATVLSSG AVVLNEQSGL  540
PHLPGFSAEW AAATREDPRA                                               560
```

```
SEQ ID NO: 135         moltype = DNA  length = 288
FEATURE                Location/Qualifiers
misc_feature           1..288
                       note = Synthetic plasmid
source                 1..288
                       mol_type = other DNA
                       organism = synthetic construct
SEQUENCE: 135
atggcgttcc gcccgctgca tgatcgtgtg gtcgttaagc gcctggaggg tgaagataaa  60
accaaaggcg gtattatcat tccggataca gcgaaagaaa aaccggccga aggcaaaatc  120
atcgctgtag gaccgggcgc gcgcgatgaa tcaggaaaat tggtggcgct tgatgtcaaa  180
gaaggggacc gcgtgctgtt cggaaagtgg tcggggacag aggtaaaaat tgatggcgaa  240
gatctgttaa tcatgaagga aagtgatatt ctgggcgtta tcgcgtaa                288
```

```
SEQ ID NO: 136         moltype = AA  length = 95
FEATURE                Location/Qualifiers
REGION                 1..95
                       note = misc_feature - Methylocystis sp. LW5
source                 1..95
                       mol_type = protein
                       organism = Methylocystis sp.
SEQUENCE: 136
MAFRPLHDRV VVKRLEGEDK TKGGIIIPDT AKEKPAEGKI IAVGPGARDE SGKLVALDVK  60
EGDRVLFGKW SGTEVKIDGE DLLIMKESDI LGVIA                              95
```

```
SEQ ID NO: 137         moltype = DNA  length = 1683
FEATURE                Location/Qualifiers
misc_feature           1..1683
                       note = Synthetic plasmid
source                 1..1683
                       mol_type = other DNA
                       organism = synthetic construct
SEQUENCE: 137
```

```
atggcgcgta atattcgctt tggtgatccg gtccgtaaac gtctgctgga tggcgtggat  60
tttctggcgg atgccgtggg ggtgactctg ggtccgtgtg gtcgcaacgt cgtgattgaa  120
catcgtgcaa gcggcttgcc gccagtagcg actaaagatg gagcaacggt tgcccaagct  180
gtggaagctg cgggtcgtac cgagtctgta ggcatcaact tggtacgtca gatggcgacc  240
accgtggcga aggaagcggg agatggtaca acgacgtccg tagtgttaac ccgccgtgtc  300
gcagccgaaa cacgtaaggc attagcagcg ggtatgaatc cgcgtgatat taccctggga  360
atggagcgtg ctgcccgtgc agtagaggca gatttgctcc gccgcgcacg tcgctgcaac  420
gaccagcgtt ctcttgcgca cgttgcgact ctggccgctg gtggagacga aggcattggc  480
gcaattgtgg cccaagcgct ggctttagct ggggaaggtg gtgtggtgga tgtggaatta  540
ggtcacggtg tggccgacga catcgaaagc gtcgaaggca tgcgctggga acagggctac  600
cgcagcccgt attttatgac cgatagcgct cgcaaagtgg ccgaactgga aaacccgtac  660
attttagttt atgaccgtgt gattaacgag ttttctgaac tggtgccggc ccttgagctg  720
gtccgccgct ccgggggctc tctgttagta gtggctgaaa acattatgga agaagctctc  780
ccgggtctgc tgctgaatca tattcgcaaa aacctgtgta gcattgccgt gaagggccct  840
ggttatggcg attctcgcta tgaatattta ctggaccttg ccgcgattac cggtggccgt  900
gcaatcatgg aagccttcgg tgaagacatt tcaaatgtca ccatggagca tctgggccgc  960
gcacgtcgcg tcgtagtacg tgaagatgac acactggtca ttggcggcga gggcgaccca  1020
aacgtgatcg ccgaccgtct ggcatccgcg aaacgtcagg ccgattggat tgtagaagga  1080
gacgcatcaa aaggcagccc gtccggcaaa cgccacgaac ttgaaaatct tcagacgcgc  1140
attaaagcac ttagcggtcg catggccacc atccgcgcgg gtggcctctc cgatgttctt  1200
atcaaagagc gcatgcaacg tattgaaaac gcgctgaata gtgctcgcgc ggcgcagtcc  1260
gatggcgttg tcgcgggtgg tggcgtgggc ctgtaccgcg ctcgcgcagc gctggctgaa  1320
ctgcgcggcg aaaatctgga ccagagccac ggagttgcga ttgtgcgtgc cgcgctggat  1380
gagccgattc gtcgcattgc ggcgaacgcg ggcgttgatg cggatgagtt tctgtttgaa  1440
ctgcgccgtt caaatgatga tttttggggt atggacatgc gtagtggcgc gtgcggagat  1500
ctgtttgcag cgggtgtgat tgatccagtc cgcgttactc gcctggcgtt acgcaacgcg  1560
gtggctactg cggcttcgct tatgacggtg gagtgcgcgg ttacccatat tcccgtgagc  1620
gacccgacat tcggctttga cgcgcgtcgc gcagccgaga ctcgtgaaga tcctcgcgcc  1680
taa                                                                1683
```

```
SEQ ID NO: 138          moltype = AA  length = 560
FEATURE                 Location/Qualifiers
REGION                  1..560
                        note = misc_feature - Methylocystis sp. LW5
source                  1..560
                        mol_type = protein
                        organism = Methylocystis sp.
SEQUENCE: 138
MARNIRFGDP VRKRLLDGVD FLADAVGVTL GPCGRNVVIE HRASGLPPVA TKDGATVAQA  60
VEAAGRTESV GINLVRQMAT TVAKEAGDGT TTSVVLTRRV AAETRKALAA GMNPRDITLG  120
MERAARAVEA DLLRRARRCN DQRSLAHVAT LAAGGDEGIG AIVAQALALA GEGGVVDVEL  180
GHGVADDIES VEGMRWEQGY RSPYFMTDSA RKVAELENPY ILVYDRVINE FSELVPALEL  240
VRRSGGSLLV VAENIMEEAL PGLLLNHIRK NLCSIAVKGP GYGDSRYEYL LDLAAITGGR  300
AIMEAFGEDI SNVTMEHLGR ARRVVVREDD TLVIGGEGDP NVIADRLASA KRQADWIVEG  360
DASKGSPSGK RHELENLQTR IKALSGRMAT IRAGGLSDVL IKERMQRIEN ALNSARAAQS  420
DGVVAGGGVG LYRARAALAE LRGENLDQSH GVAIVRAALD EPIRRIAANA GVDADEFLFE  480
LRRSNDDFWG MDMRSGACGD LFAAGVIDPV RVTRLALRNA VATAASLMTV ECAVTHIPVS  540
DPTFGFDARR AAETREDPRA                                              560
```

```
SEQ ID NO: 139          moltype = DNA  length = 291
FEATURE                 Location/Qualifiers
misc_feature            1..291
                        note = Synthetic plasmid
source                  1..291
                        mol_type = other DNA
                        organism = synthetic construct
SEQUENCE: 139
atgaaactgc gcccgctcca tgaccgtgta attgtcaaac gtctggaaga agaaaaaaaa  60
tccgccggcg gaattatcat cccggatgcc gcagcagaaa agccaagtcg tggtgaagta  120
atcagcgtgg ggccggggaa acgtggcgac gatggtaaac tgaatgcact ggatgtgaaa  180
gctggtgata ttgttttatt cggcaaatac tctggtagtg aagtccgcgt agacggtcaa  240
gatttgctgg ttatgcgcga agacgacatt atggcggttt ttgccaagta a           291
```

```
SEQ ID NO: 140          moltype = AA  length = 96
FEATURE                 Location/Qualifiers
source                  1..96
                        mol_type = protein
                        organism = Solimonas aquatica
SEQUENCE: 140
MKLRPLHDRV IVKRLEEEKK SAGGIIIPDA AAEKPSRGEV ISVGPGKRGD DGKLNALDVK  60
AGDIVLFGKY SGSEVRVDGQ DLLVMREDDI MAVFAK                            96
```

```
SEQ ID NO: 141          moltype = DNA  length = 1689
FEATURE                 Location/Qualifiers
misc_feature            1..1689
                        note = Synthetic plasmid
source                  1..1689
                        mol_type = other DNA
                        organism = synthetic construct
```

```
SEQUENCE: 141
atgacgaatg gcaagaattg ccgtgtctcg gacggatttg gtgccctggg caaactgagc  60
agtggcatgc gtatcctggc ggaagtcgtt gcagttaccc tcggtccagg cggtcgccat  120
gtgattctgg aacatcgcag cggcttagct cctcgtctga gtaaggatgg tgtcgagatc  180
gcccgtacta tggaagtggc tggacgtgaa gaagaaatgg gtgtacgtct gttgcgcgat  240
gcggcaatct cgattagcgc tagcgtgggt gatggaacaa ctacagcgat cgtattgtca  300
gctgcgctgg ccacgcgctg tatggctgct tccagccatc cgcttaacgt ctcggaaatg  360
cgctacggat tggctatggc gggggcgaca gtgctctctg aattagctgc catggcgcgt  420
ccggccgatc aacatgccct gcaagcggtg gcgcgcacag ctgttaatgg tgatgcgccg  480
ctggccgccc tgcttgcgga tgcctatgcc cgcgtgggta gcgaaggtgt tattaaaatc  540
gagatgggta atgcaatgca tgacgtgtta gatgtgaagc tcggacaccg cttcgaatcc  600
ctgctgctgg ccagcggtct gccggctagt gcgggcgaac gtcaactcct gcgccctctg  660
accctgcttc acgacggcga attggatgac ctccaagcgc tgattcctgc gatggagatt  720
gctcgtgccg aacaacgccc gcttctcatt ctggccggcg acgtcagcga tggcgtgcgc  780
accgcgattg tgcgtaacgc tcgcgaaaat gtggtagatg ttactgtagt gcgcgctccg  840
atgtttgggg atacccgtca ggaatgcctg ggtgacctgg ccgcgctgtg cggaggatca  900
gccttcgtgg aaaacggatt tcgcactatt gcggccctga gccgcgatga tctgggcagc  960
gtggatcgtg cggtggtaga tgcgggaagc gctattctcc acggagctca tggcgatgca  1020
cgcgaacgcc aagaccgtat cgcgttgctt cgtagcgaaa tggaaggtag tggtcgctcg  1080
acggcgtcgc cgtctggcca gctggatcat agcgacaagt gtcaagaacg cctgcagatt  1140
ctgcttggcg cgaccgcctc gttgcagctg ggcggcgcaa cggacgtcgc aatcaaagcc  1200
cgcatgccga tcgccgaaaa tgggcgccgc gcgttactgg ccgcagcgag caccggcgtc  1260
ctgccgggtg gaggcgtggc gatgcttcgc gcagcactcg cggcacgttc gcgcctgtct  1320
actctgcagg acgacgcccg tctcggtgca gaggcgctct tgtcagcgct gcaggccccg  1380
ttcgcatggg tcgttcgcaa ctcgggacac caacctgagg aatgcctgga tcgcgtgttg  1440
tctgaagcgg attgctttca cggcctggac gccgcccgcg ggtgttacgg tgatctgcat  1500
gcggcgggag tgttagattc gttcttgatg gtccgcaaaa ttgtgacggt ggcgacctct  1560
atggccggta gcctgctgag cacgggtgcc ttagtgtgtc gtggcgggga aactgctctc  1620
ccggaaaact tccaggggac acaacaggtg taccgcaaat tagcggcagg cggcgccttc  1680
gattcttaa                                                          1689

SEQ ID NO: 142          moltype = AA  length = 562
FEATURE                 Location/Qualifiers
source                  1..562
                        mol_type = protein
                        organism = Solimonas aquatica
SEQUENCE: 142
MTNGKNCRVS DGFGALGKLS SGMRILAEVV AVTLGPGGRH VILEHRSGLA PRLSKDGVEI  60
ARTMEVAGRE EEMGVRLLRD AAISISASVG DGTTTAIVLS AALATRCMAA SSHPLNVSEM  120
RYGLAMAGAT VLSELAAMAR PADQHALQAV ARTAVNGDAP LAALLADAYA RVGSEGVIKI  180
EMGNAMHDVL DVKLGHRFES LLLASGLPAS AGERQLLRPL TLLHDGELDD LQALIPAMEI  240
ARAEQRPLLI LAGDVSDGVR TAIVRNAREN VVDVTVVRAP MFGDTRQECL GDLAALCGGS  300
AFVENGFRTI AALSRDDLGS VDRAVVDAGS AILHGAHGDA RERQDRIALL RSEMEGSGRS  360
TASPSGQLDH SDKCQERLQI LLGATASLQL GGATDVAIKA RMPIAENGRR ALLAAASTGV  420
LPGGGVAMLR AALAARSRLS TLQDDARLGA EALLSALQAP FAWVVRNSGH QPEECLDRVL  480
SEADCFHGLD AARGCYGDLH AAGVLDSFLM VRKIVTVATS MAGSLLSTGA LVCRGGETAL  540
PENFQGTQQV YRKLAAGGAF DS                                           562

SEQ ID NO: 143          moltype = DNA  length = 1581
FEATURE                 Location/Qualifiers
misc_feature            1..1581
                        note = Synthetic plasmid
source                  1..1581
                        mol_type = other DNA
                        organism = synthetic construct
SEQUENCE: 143
atggccatct ctttagctac caaagctgct accgatgctt taaaagtaaa ccgtgcccct  60
gtcggtgttg aacctcagga agtgcataaa tggttgcaat ccttcaactg ggacttcaag  120
gaaaaccgta caaagtacgc aactaagtac catatggcaa atcaaacaaa ggaacaattt  180
aaagtaattg caaaagaata tgccagaatg gaagccgcta aggatgaacg acaattcggc  240
actttattag acggcttgac tagattaggt gctggtaaca aggttcatcc cagatggggt  300
gagactatga aggttatttc taacttcctg gaagtaggtg aatacaatgc tatcgctgct  360
tcagctatgc tgtgggattc cgctacggcc gcagaacaga agaacggtta tttagcacaa  420
gtgctagatg agatccgtca tactcaccaa tgcgctttta taaatcatta ttattctaaa  480
cactaccatg acccagctgg ccataacgat gcccgtcgta cacgagcaat tggcccacta  540
tggaagggaa tgaaaagagt tttgctgac ggtttcattt caggtgatgc cgttgagtgc  600
agtgttaacc tacagctagt cggtgaggct tgtttcacca atcctctaat tgttgccgtt  660
actgagtggg catcagccaa tggggacgag ataacaccaa ctgttttttt gtcagttgag  720
acagacgaat tgagacacat ggccaatgga tatcagacgg ttgttagtat agcaaatgac  780
ccagccgctg ctaaatacct taacacagac ttgaacaatg ccttttggac tcagcaaaaa  840
tactttaccc ctgctttggg ctatttgttt gagtatggtt ctaagtttaa ggtcgaaccc  900
tgggttaaaa catggaatag gtgggtgtac gaggattggg gtggtatttg gattggtaga  960
ctgggtaaat acggcgttga gtctcctagg tccttgcgtg atgccaagac tgacgcctac  1020
tgggctcatc acgacttagc tcttgctgcc tacgctctgt ggccattagg atttgccaga  1080
cttgcattgc cagacgagga ggaccaagaa tggttcgagg ctaattatcc agggtgggcc  1140
gatcattacg gaaagattta caatgaatgg aaaaaattag gctacgagga tcctaaatcc  1200
ggttttattc catacgcatg gttgttgcaa aatggtcatg atgtctatat cgacagagtg  1260
tctcaagttc cctttattcc ctccttagca aaggttcag gctcccttag ggttcatgag  1320
tataacggaa agaagcattc cttgacagat gattggggtg aaaggatgtg gttgtctgag  1380
```

```
cctgaaaggt acgagtgtca ctccattttc gagcaatacg agggaagaga actttctgag  1440
gttattgctg agggacacgg ggttaggtcc gatggtaaga ctctgatcgc tcagccacat  1500
gttagaggcg ataatctttg gactcttgag gacatcaagc gtgcaggttg tgtgttccca  1560
gaccctttgg ccaagttcta a                                            1581

SEQ ID NO: 144          moltype = AA  length = 526
FEATURE                 Location/Qualifiers
REGION                  1..526
                        note = misc_feature - Methylocystis sp. LW5
source                  1..526
                        mol_type = protein
                        organism = Methylocystis sp.
SEQUENCE: 144
MAISLATKAA TDALKVNRAP VGVEPQEVHK WLQSFNWDFK ENRTKYATKY HMANQTKEQF  60
KVIAKEYARM EAAKDERQFG TLLDGLTRLG AGNKVHPRWG ETMKVISNFL EVGEYNAIAA  120
SAMLWDSATA AEQKNGYLAQ VLDEIRHTHQ CAFINHYYSK HYHDPAGHND ARRTRAIGPL  180
WKGMKRVFAD GFISGDAVEC SVNLQLVGEA CFTNPLIVAV TEWASANGDE ITPTVFLSVE  240
TDELRHMANG YQTVVSIAND PAAAKYLNTD LNNAFWTQQK YFTPALGYLF EYGSKFKVEP  300
WVKTWNRWVY EDWGGIWIGR LGKYGVESPR SLRDAKTDAY WAHHDLALAA YALWPLGFAR  360
LALPDEEDQE WFEANYPGWA DHYGKIYNEW KKLGYEDPKS GFIPYAWLLQ NGHDVYIDRV  420
SQVPFIPSLA KGSGSLRVHE YNGKKHSLTD DWGERMWLSE PERYECHSIF EQYEGRELSE  480
VIAEGHGVRS DGKTLIAQPH VRGDNLWTLE DIKRAGCVFP DPLAKF                 526

SEQ ID NO: 145          moltype = DNA  length = 1188
FEATURE                 Location/Qualifiers
misc_feature            1..1188
                        note = Synthetic plasmid
source                  1..1188
                        mol_type = other DNA
                        organism = synthetic construct
SEQUENCE: 145
atgtctcagc cacagtcttc tcaggttacc aagaggggac tgacggaccc cgaaagggca  60
gctatcatcg ccgcagctat tccagatcat gctttggata cccagcgtaa ataccactat  120
ttcattcagc ctagatggaa gaggttaagt gaatatgagc agttgtcctg ttacgcccaa  180
ccaaacccag attggattgc tggtggtttg gactggggtg actggactca gaagtttcat  240
ggtggtagac cctcttgggg aaacgaatct actgaactta ggaccaccga ttggtaccga  300
cacagagatc cagcacgtag gtggcacgca ccttacgtca aagataagtc tgaggaagct  360
agatatacac agagattctt ggcagcatac tcatctgaag gttccattcg aaccgtcgac  420
gcatattgga gggacgaaat tcttaacaaa tattacggtg cattgttata taacgaatac  480
ggtttattca atgctcactc ttctgtgggc agggactctc tgtctgatac aattaggcaa  540
tccgctatat ttgctgctct tgataaggtt gataacgcac aaatgattca aatggaaaga  600
ttatttattg caaaattggt gccaggtttc gatgcttcta cggatgtgcc taaaaagatc  660
tggacaacag atccaattta tgctggcgct agaggtgcag tcgaagagat ttggcagggt  720
attcaagatt ggaatgagat attgtgggcc ggtcacgccg tctacgatgc taccttcggg  780
caattcgcta gaagggaatt ttttcaaaga cttgctactg tatacggtga tacattgacc  840
cctttcttta cagcccaatc acaaacttat ttccaaatta ctagaggtgc aattgaggac  900
ctgtttgtct actcccttgc taacgacccc gaatttggag cccataacag gacttttctg  960
aatgcatgga ctgaacatta tcttgcaaga tctgtgacag cattgaagga ttttgttggg  1020
atctatgcta aggtggagaa agtggctggt gccactgaca gagctggagt ctctgaagca  1080
ctacagagag tatttgggga ctggaaagtg gattacgccg acaagatcgg tttcaagatt  1140
gacgtagacc agaaggtcga cgcagtactg gcaggttaca aaaattaa               1188

SEQ ID NO: 146          moltype = AA  length = 395
FEATURE                 Location/Qualifiers
REGION                  1..395
                        note = misc_feature - Methylocystis sp. LW5
source                  1..395
                        mol_type = protein
                        organism = Methylocystis sp.
SEQUENCE: 146
MSQPQSSQVT KRGLTDPERA AIIAAAIPDH ALDTQRKYHY FIQPRWKRLS EYEQLSCYAQ  60
PNPDWIAGGL DWGDWTQKFH GGRPSWGNES TELRTTDWYR HRDPARRWHA PYVKDKSEEA  120
RYTQRFLAAY SSEGSIRTVD AYWRDEILNK YYGALLYNEY GLFNAHSSVG RDSLSDTIRQ  180
SAIFAALDKV DNAQMIQMER LFIAKLVPGF DASTDVPKKI WTTDPIYAGA RGAVEEIWQG  240
IQDWNEILWA GHAVYDATFG QFARREFFQR LATVYGDTLT PFFTAQSQTY FQITRGAIED  300
LFVYSLANDP EFGAHNRTFL NAWTEHYLAR SVTALKDFVG IYAKVEKVAG ATDRAGVSEA  360
LQRVFGDWKV DYADKIGFKI DVDQKVDAVL AGYKN                             395

SEQ ID NO: 147          moltype = DNA  length = 510
FEATURE                 Location/Qualifiers
misc_feature            1..510
                        note = Synthetic plasmid
source                  1..510
                        mol_type = other DNA
                        organism = synthetic construct
SEQUENCE: 147
atggcaaaga gggaacctat tcacgaaaat tccactcgta ctgagtggga gggaaagata  60
gctaaactga actctgttga tcaggctact aagtttatcc aagattttcg agttgctaat  120
tcctctcctt ttaggaagtc atatgatcta gacgtggact accaatatat cgagagaaag  180
```

```
attgaagaga gactgtccgt attaaagacc gaaaagttat cagttgccga tttagtcacc  240
aaggccacga ctggtgaaga cgccgctgct gttgaagcta catggattgc aaagatgaag  300
gcagccgagt ctaaatatgc agccgaacga attcatgttg aattcagaca attgtataag  360
cctcctgttc taccagtgaa tgttttcctg agaactgatg cagcattagg aactatctta  420
atggaactta gaaataccga ctattatgct actcctttag aaggattgag aaaggagcgt  480
ggggttaaag ttctacatct tcaggcatag                                  510

SEQ ID NO: 148         moltype = AA  length = 169
FEATURE                Location/Qualifiers
REGION                 1..169
                       note = misc_feature - Methylocystis sp. LW5
source                 1..169
                       mol_type = protein
                       organism = Methylocystis sp.
SEQUENCE: 148
MAKREPIHEN STRTEWEGKI AKLNSVDQAT KFIQDFRVAN SSPFRKSYDL DVDYQYIERK  60
IEERLSVLKT EKLSVADLVT KATTGEDAAA VEATWIAKMK AAESKYAAER IHVEFRQLYK  120
PPVLPVNVFL RTDAALGTIL MELRNTDYYA TPLEGLRKER GVKVLHLQA             169

SEQ ID NO: 149         moltype = DNA  length = 417
FEATURE                Location/Qualifiers
misc_feature           1..417
                       note = Synthetic plasmid
source                 1..417
                       mol_type = other DNA
                       organism = synthetic construct
SEQUENCE: 149
atgtcctcag cccacaacaa ctataatgcc ggtattatgc agaaatcagg aaaagcattc  60
gccgatgaat tcttcgcaga ggagaaccaa gtggtacatg aatcaaatgc tgtcgttttg  120
gtcctgatga agtctgatga aatcgacgcc atcatcgaag acatcatatt gaaagggggt  180
aaagctaaaa acccatccat cgttgttgag gacaaggctg gattctggtg gatcaaagca  240
gatggagcta tcgaaatcga tgctgctgaa gctgctgatt tactgggcaa gccattctct  300
gtttacgatt tgctgatcaa cgtttctagt accgttggtc gtgcttacac cttgggcacg  360
aaattcacta tcactagtga attaatggga ttggatagag ccttgacaga tatttaa     417

SEQ ID NO: 150         moltype = AA  length = 138
FEATURE                Location/Qualifiers
REGION                 1..138
                       note = misc_feature - Methylocystis sp. LW5
source                 1..138
                       mol_type = protein
                       organism = Methylocystis sp.
SEQUENCE: 150
MSSAHNNYNA GIMQKSGKAF ADEFFAEENQ VVHESNAVVL VLMKSDEIDA IIEDIILKGG  60
KAKNPSIVVE DKAGFWWIKA DGAIEIDAAE AADLLGKPFS VYDLLINVSS TVGRAYTLGT  120
KFTITSELMG LDRALTDI                                               138

SEQ ID NO: 151         moltype = DNA  length = 1032
FEATURE                Location/Qualifiers
misc_feature           1..1032
                       note = Synthetic plasmid
source                 1..1032
                       mol_type = other DNA
                       organism = synthetic construct
SEQUENCE: 151
atgtatcaga tcgtgattga aactgaagat ggagaaactt gttccttcga gtgtgggcct  60
tctgaagatg tgatatccgc tggacttagg cagtccgtca tcctgttaag ttcctgccga  120
gctgggggat gcgccacgtg caaggccgat tgtacggacg gtgattatga gttgatcgac  180
gtaaaggtac aggcactacc tcctgatgag gaggaagatg gtaaggtgtt actttgcaga  240
acctttcctc gatcagattt gcatttaatc gttccataca cttacgacag gatttcattc  300
gaggcaatcc agactaactg gctggccgaa attgttgaat gcgatagagt atcttctaat  360
gtagtcagac ttgttctaca gccactgacc gctgatggcg cagctccaat cgccttaaac  420
ttcgctcctg gtcagtttgt cgatattgag atccccggta ctcacaccag aagatcctac  480
agtatggcat ccgttgcaga ggatgggcgt cttgaattct ttattcgtct tttaccagat  540
ggagcttttt ctaagttctt gcaaacccaa gctaaagtgg gattaagagt cgccctacgt  600
ggacctgctg gttcatttat gctgcataaa tctgaaagac cacgtttctt cgttgctgga  660
ggcactggct tgtctcctgt tttaagtatg ataagacagt tgaaaaaaga atccgatcag  720
caacccgcta ccttgttctt tggtgtaact aattatgagg agctgtttta tgtcgaagaa  780
ctgaaagctc tacaaaacgc tatgccctcc cttgatgtgc aagtcgccgt cgttaatgca  840
tctgaggcta atggtgttgc caagggaact gtgatagatc ttatgagggc cgaactggag  900
aaacttagag gtaagccaga catttattta tgtggtcctc ctgggatgat tgaagcagca  960
tttgatgctg ctgccacagc tggtgttccc aaagagcaag tctacctgga gaaattcttg  1020
gcttcaggct ag                                                     1032

SEQ ID NO: 152         moltype = AA  length = 343
FEATURE                Location/Qualifiers
REGION                 1..343
                       note = misc_feature - Methylocystis sp. LW5
source                 1..343
```

```
                        mol_type = protein
                        organism = Methylocystis sp.
SEQUENCE: 152
MYQIVIETED GETCSFECGP SEDVISAGLR QSVILLSSCR AGGCATCKAD CTDGDYELID  60
VKVQALPPDE EEDGKVLLCR TFPRSDLHLI VPYTYDRISF EAIQTNWLAE IVECDRVSSN  120
VVRLVLQPLT ADGAAPIALN FAPGQFVDIE IPGTHTRRSY SMASVAEDGR LEFFIRLLPD  180
GAFSKFLQTQ AKVGLRVALR GPAGSFMLHK SERPRFFVAG GTGLSPVLSM IRQLKKESDQ  240
QPATLFFGVT NYEELFYVEE LKALQNAMPS LDVQVAVVNA SEANGVAKGT VIDLMRAELE  300
KLRGKPDIYL CGPPGMIEAA FDAAATAGVP KEQVYLEKFL ASG                   343

SEQ ID NO: 153          moltype = DNA  length = 336
FEATURE                 Location/Qualifiers
misc_feature            1..336
                        note = Synthetic plasmid
source                  1..336
                        mol_type = other DNA
                        organism = synthetic construct
SEQUENCE: 153
atggctcaat gtgccgagca agccgcagag gaacaaagaa ttttgatcca cgcagattct  60
agatatgctg catataccat ggacttggac tatatgtggc gttgggagat cctgagagac  120
ggtgagtttg ttcaagaagg atgcagtctg tctcttgact cagcaaggga agctgtttca  180
catgttctga gattttttca gaggcaagac gaggctgccg cccgtccagg agacaattcc  240
gcagagatta agagattgct tcaatctttg ggaaccccaa ttcctatcga cgatagaaac  300
gaaaccacaa agaatgagtt ggctcaacct gaatag                            336

SEQ ID NO: 154          moltype = AA  length = 111
FEATURE                 Location/Qualifiers
REGION                  1..111
                        note = misc_feature - Methylocystis sp. LW5
source                  1..111
                        mol_type = protein
                        organism = Methylocystis sp.
SEQUENCE: 154
MAQCAEQAAE EQRILIHADS RYAAYTMDLD YMWRWEILRD GEFVQEGCSL SLDSAREAVS  60
HVLRFFQRQD EAAARPGDNS AEIKRLLQSL GTPIPIDDRN ETTKNELAQP E           111
```

HETEROLOGOUS EXPRESSION OF SHORT-CHAIN MONOOXYGENASES IN MICROORGANISMS

PRIORITY CLAIM

This application is a continuation of U.S. patent application Ser. No. 17/149,394, filed Jan. 14, 2021, which claims priority to and the benefit as a continuation application of U.S. patent application Ser. No. 15/777,158, filed May 17, 2018, which is a National Stage entry of PCT/US2016/062623, filed on Nov. 17, 2016, which claims priority to U.S. Provisional Application No. 62/320,725, filed Apr. 11, 2016, U.S. Provisional Application No. 62/270,039, filed Dec. 21, 2015, and U.S. Provisional Application No. 62/257,061 filed Nov. 18, 2015, each of which is incorporated by reference herein in their entirety, including any drawings, as if they are part of the original application as filed.

This invention was made with Government support under SBIR Grant No. 1520425 awarded by the National Science Foundation. The Government has certain rights in this invention.

SEQUENCE LISTINGS

The application contains a Sequence Listing which has been submitted electronically in .XML format and is hereby incorporated by reference in its entirety. Said .XML copy, created on Sep. 29, 2023, is named "1107367.00050.xml" and is 619,837 bytes in size. The sequence listing contained in this .XML file is part of the specification and is hereby incorporated by reference herein in its entirety.

INTRODUCTION

Biological enzymes are catalysts capable of facilitating chemical reactions, often at ambient temperature and/or pressure. Some chemical reactions are catalyzed by either inorganic catalysts or certain enzymes, while others can be catalyzed by just one of these. For industrial uses, enzymes are advantageous catalysts if the alternative process requires expensive or energy-intensive conditions, such as high temperature or pressure, or if the complete process is to be integrated with other enzyme-catalyzed steps. Enzymes can also be engineered to control the range of raw materials or substrates required and/or the range of products formed.

Recent technological advances in synthetic biology have demonstrated the power and versatility of enzymatic pathways in living cells to convert organic molecules into industrial products. The petrochemical processes that currently manufacture these industrial products may be replaced by these biotechnological processes that can often provide the same products at a lower cost and with a lower environmental impact. The discovery of new pathways and enzymes that can operate and be engineered in genetically tractable microorganisms will further advance synthetic biology.

Sugar (including simple sugars, starches, carbohydrates, and sugar alcohols) is often a raw material for biological fermentations. But sugar has a relatively high cost as a raw material which severely limits the economic viability of the fermentation process. Although synthetic biology could expand to produce thousands of products that are currently petroleum-sourced, companies often must limit themselves to the production of select niche chemicals due to the high cost of sugar.

Short alkanes, such as methane and ethane, are significantly less expensive raw materials compared to sugar. Given the enormous supply of natural gas and the emergence of renewable methane-production technologies, short alkanes are expected to remain inexpensive for decades to come. Accordingly, industrial products made by engineered microorganisms from short alkanes, such as methane or ethane, should he less expensive to manufacture than those made by sugar and should remain so for decades.

Any biological system capable of converting short alkanes into industrial products must include an enzyme that can activate the alkane. Naturally occurring bacteria that can activate methane use dioxygen to convert methane to methanol. As an example, an enzyme capable of performing this reaction belongs to the class known as soluble diiron monooxygenases.

But, soluble diiron monooxygenases have been difficult to functionally express in industrially-relevant host cells. Successful functional expression of soluble diiron monooxygenases in an industrially relevant host would be a critical first step in a system capable of converting inexpensive methane or ethane into methanol or ethanol, respectively. Methanol or ethanol can be separated as an industrial product itself or used as a metabolic intermediate and further converted into other industrial products via enzyme-mediated pathways in a cell.

The invention provided herein is drawn to the ability to functionally express a useful enzyme in an industrial host.

BRIEF DESCRIPTION OF THE INVENTION

In a first aspect, a monooxygenase synthetic polynucleotide for a soluble diiron monooxygenase enzyme which can be expressed in a microorganism of interest or its complement is disclosed, comprising at least one monooxygenase coding region encoding a soluble diiron monooxygenase enzyme, the at least one monooxygenase coding region linked to at least one promoter which will function in the microorganism of interest. In an embodiment, the monooxygenase synthetic polynucleotide further comprises at least one protein folding chaperone coding region encoding at least one protein folding chaperone, the at least one protein chaperone coding region linked to at least one promoter which will function in the microorganism of interest.

An embodiment provides for a monooxygenase synthetic polynucleotide comprising a synthetic polynucleotide which is at least 60%, preferably about 65%, preferably about 70%, preferably about 75%, preferably about 80%, preferably about 85%, preferably about 90% or preferably about 95% identical to any one or more of the nucleotide sequences set forth in SEQ ID NO: 7 or SEQ ID NO: 9 or SEQ ID NO: 11 or SEQ ID NO: 13 or SEQ ID NO: 58 or SEQ ID NO: 60 or SEQ ID NO: 87 or SEQ ID NO: 89 or SEQ ID NO: 91 or SEQ ID NO: 93 or SEQ ID NO: 95 or SEQ ID NO: 97 or SEQ ID NO: 99 or SEQ ID NO: 101 or SEQ ID NO: 103 or SEQ ID NO: 105 or SEQ ID NO: 107 or SEQ ID NO: 109 or SEQ ID NO: 111 or SEQ ID NO: 113 or SEQ ID NO: 115 or SEQ ID NO: 117 or SEQ ID NO: 143 or SEQ ID NO: 145 or SEQ ID NO: 147 or SEQ ID NO: 149 or SEQ ID NO: 151 or SEQ ID NO: 153. An embodiment provides for a monooxygenase synthetic polynucleotide comprising a synthetic polynucleotide which is at least 60%, preferably about 65%, preferably about 70%, preferably about 75%, preferably about 80%, preferably about 85%, preferably about 90% or preferably about 95% identical to the nucleotide sequences set forth in SEQ ID NO: 7 and SEQ ID NO: 9 and SEQ ID NO: 11 and SEQ ID NO: 13 and SEQ ID NO: 58 and SEQ ID NO: 60. A further embodiment provides for a monooxygenase synthetic polynucleotide comprising a synthetic polynucleotide which is at least 60%, preferably about 65%, preferably about 70%, preferably about 75%, preferably about 80%, preferably about 85%, preferably about 90% or preferably about 95% identical to the complement of any one or more of the nucleotide sequences set forth in SEQ ID NO: 7 or SEQ ID NO: 9 or SEQ ID NO: 11 or SEQ ID NO: 13 or SEQ ID NO: 58 or SEQ ID NO: 60 or SEQ ID NO: 87 or SEQ ID NO: 89 or SEQ ID NO: 91 or SEQ ID NO: 93 or SEQ ID NO: 95 or SEQ ID NO: 97 or SEQ ID NO: 99 or SEQ ID NO: 101 or SEQ ID NO: 103 or SEQ ID NO: 105 or SEQ ID NO: 107 or SEQ ID NO: 109 or SEQ ID NO: 111 or SEQ ID NO: 113 or SEQ ID NO: 115 or SEQ ID NO: 117 or SEQ ID NO: 143 or SEQ ID NO: 145 or SEQ ID NO: 147 or SEQ ID NO: 149 or SEQ ID NO: 151 or SEQ ID NO: 153. A further embodiment provides for a monooxygenase synthetic polynucleotide comprising a synthetic polynucleotide which is at least 60%, preferably about 65%, preferably about 70%, preferably about 75%, preferably about 80%, preferably about 85%, preferably about 90% or preferably about 95% identical to the complement of the nucleotide sequences set forth in SEQ ID NO: 7 and SEQ ID NO: 9 and SEQ ID NO: 11 and SEQ ID NO: 13 and SEQ ID NO: 58 and SEQ ID NO: 60.

The disclosure is intended to encompass monooxygenase enzymes as disclosed herein, as well as subunits in any combination and amount.

A further embodiment provides for a monooxygenase synthetic polynucleotide comprising a synthetic polynucleotide which encodes a polypeptide which is at least 60%, preferably about 65%, preferably about 70%, preferably about 75%, preferably about 80%, preferably about 85%, preferably about 90% or preferably about 95% identical to any one or more of the amino acid sequences set forth in SEQ ID NO: 8 or SEQ ID NO: 10 or SEQ ID NO: 12 or SEQ ID NO: 14 or SEQ ID NO: 59 or SEQ ID NO: 61 or SEQ ID NO: 88 or SEQ ID NO: 90 or SEQ ID NO: 92 or SEQ ID NO: 94 or SEQ ID NO: 96 or SEQ ID NO: 98 or SEQ ID NO: 100 or SEQ ID NO: 102 or SEQ ID NO: 104 or SEQ ID NO: 106 or SEQ ID NO: 108 or SEQ ID NO: 110 or SEQ ID NO: 112 or SEQ ID NO: 114 or SEQ ID NO: 116 or SEQ ID NO: 118 or SEQ ID NO: 144 or SEQ ID NO: 146 or SEQ ID NO: 148 or SEQ ID NO: 150 or SEQ ID NO: 152 or SEQ ID NO: 154. A further embodiment provides for a monooxygenase synthetic polynucleotide comprising a synthetic polynucleotide which encodes a polypeptide which is at least 60%, preferably about 65%, preferably about 70%, preferably about 75%, preferably about 80%, preferably about 85%, preferably about 90% or preferably about 95% identical to the amino acid sequences set forth in SEQ ID NO: 8 and SEQ ID NO: 10 and SEQ ID NO: 12 and SEQ ID NO: 14 and SEQ ID NO: 59 and SEQ ID NO: 61. A further embodiment provides for a complement to a monooxygenase synthetic polynucleotide comprising a synthetic polynucleotide which encodes a polypeptide which is at least 60%, preferably about 65%, preferably about 70%, preferably about 75%, preferably about 80%, preferably about 85%, preferably about 90% or preferably about 95% to any one or more of the amino acid sequences set forth in SEQ ID NO: 8 or SEQ ID NO: 10 or SEQ ID NO: 12 or SEQ ID NO: 14 or SEQ ID NO: 59 or SEQ ID NO: 61 or SEQ ID NO: 88 or SEQ ID NO: 90 or SEQ ID NO: 92 or SEQ ID NO: 94 or SEQ ID NO: 96 or SEQ ID NO: 98 or SEQ ID NO: 100 or SEQ ID NO: 102 or SEQ ID NO: 104 or SEQ ID NO: 106 or SEQ ID NO: 108 or SEQ ID NO: 110 or SEQ ID NO: 112 or SEQ ID NO: 114 or SEQ ID NO: 116 or SEQ ID NO: 118 or SEQ ID NO: 144 or SEQ ID NO: 146 or SEQ ID NO: 148 or SEQ ID NO: 150 or SEQ ID NO: 152 or SEQ ID NO: 154. A further embodiment provides for a complement to a monooxygenase synthetic polynucleotide comprising a complement to a polynucleotide which encodes a polypeptide which is at least 60%, preferably about 65%, preferably about 70% preferably about 75%, preferably about 80%, preferably about 85%, preferably about 90% or preferably about 95% to the amino acid sequences set forth in SEQ ID NO: 8 and SEQ ID NO: 10 and SEQ ID NO: 12 and SEQ ID NO: 14 and SEQ ID NO: 59 and SEQ ID NO: 61.

In a second aspect, a monooxygenase synthetic polynucleotide for a soluble diiron monooxygenase enzyme which can be expressed in a microorganism of interest, or its complement, is disclosed, comprising at least one monooxygenase coding region encoding a soluble diiron monooxygenase enzyme, the at least one monooxygenase coding region linked to at least one promoter which will function in the microorganism of interest, wherein the monooxygenase synthetic polynucleotide comprises at least one mutation in SEQ ID NO: 21 or SEQ ID NO: 22 or SEQ ID NO: 28 or SEQ ID NO: 29 or SEQ ID NO: 30 or SEQ ID NO: 31 or SEQ ID NO: 32 or SEQ ID NO: 33 or SEQ ID NO: 34 or SEQ ID NO: 35 or SEQ ID NO: 36 or SEQ ID NO: 37 or SEQ ID NO: 46, wherein the at least one mutation increases specificity for a monooxygenase substrate and/or increases production of a chemical as compared, respectively, to SEQ ID NO: 21 or SEQ ID NO: 22 or SEQ ID NO: 28 or SEQ ID NO: 29 or SEQ ID NO: 30 or SEQ ID NO: 31 or SEQ ID NO: 32 or SEQ ID NO: 33 or SEQ ID NO: 34 or SEQ ID NO: 35 or SEQ ID NO: 36 or SEQ ID NO: 37 or SEQ ID NO: 46. In an embodiment, the monooxygenase synthetic polynucleotide comprises at least one mutation in any of the sequences disclosed herein, wherein the at least one mutation increases specificity for a monooxygenase substrate and/or increases production of a chemical as opposed to its respective wild type sequence. In an embodiment, the at least one mutation comprises one or more mutations being one or more of a Y or S substitution for K at position 61, an N for E substitution at position 240 and/or an A or T substitution for S at position 421 in SEQ ID NO: 10; an M for L at position 67 in SEQ ID NO: 12; and T for P at position 167 in SEQ ID NO: 14.

In an embodiment, the monooxygenase synthetic polynucleotide further comprises at least one accessory protein or protein folding chaperone coding region encoding at least one protein folding chaperone, the at least one protein folding chaperone coding region linked to at least one promoter which will function in the microorganism of interest.

In a third aspect, a dehydrogenase synthetic polynucleotide for at least one alcohol dehydrogenase and/or an acetaldehyde dehydrogenase which can be expressed in a microorganism of interest or its complement is disclosed, comprising at least one alcohol dehydrogenase and/or an acetaldehyde dehydrogenase coding region encoding an alcohol dehydrogenase and/or an acetaldehyde dehydrogenase, the at least one alcohol dehydrogenase and/or an acetaldehyde dehydrogenase coding region linked to at least one promoter which will function in the microorganism of interest. In an embodiment, the alcohol dehydrogenase and/or an acetaldehyde dehydrogenase is at least one, two or all of mdh from *Bacillus stearothermophilus* (SEQ ID NO: 51), mhpF from *Escherichia coli* (SEQ ID NO: 53) or acdH from *Clostridium kluyveri* (SEQ ID NO: 55). In an embodiment, the dehydrogenase synthetic polynucleotide comprises a mutation of a T for an A at position 267 and a K for an E at position 568 of the adhE gene of *Escherichia coli* as set forth in SEQ NO: 49.

Another embodiment provides for a dehydrogenase synthetic polynucleotide which comprises a synthetic polynucleotide which is at least 60%, preferably about 65%, preferably about 70%, preferably about 75%, preferably about 80%, preferably about 85%, preferably about 90% or preferably about 95% identical to the nucleotide sequence set forth in SEQ ID NO: 48 or SEQ ID NO: 50 or SEQ ID NO: 52 or SEQ ID NO: 54. A further embodiment provides for a dehydrogenase synthetic polynucleotide which comprises a synthetic polynucleotide which is at least 60%, preferably about 65%, preferably about 70%, preferably about 75%, preferably about 80%, preferably about 85%, preferably about 90% or preferably about 95% complementary to the nucleotide sequence set forth in SEQ ID NO: 48 or SEQ ID NO: 50 or SEQ ID NO: 52 or SEQ ID NO: 54.

A further embodiment provides for a dehydrogenase synthetic polynucleotide which comprises a synthetic polynucleotide which encodes a polypeptide which is at least 60%, preferably about 65%, preferably about 70%, preferably about 75%, preferably about 80%, preferably about 85%, preferably about 90% or preferably about 95% identical to the amino acid sequence set forth SEQ ID NO: 49 or SEQ ID NO: 51 or SEQ ID NO: 53 or SEQ ID NO: 55. A further embodiment provides for a complement to a dehydrogenase synthetic polynucleotide which comprises a synthetic polynucleotide complementary to a polynucleotide which encodes a polypeptide which is at least 60%, preferably about 65%, preferably about 70%, preferably about 75%, preferably about 80%, preferably about 85%, preferably about 90% or preferably about 95% to the amino acid sequence set forth in SEQ ID NO: 49 or SEQ ID NO: 51 or SEQ ID NO: 53 or SEQ ID NO: 55.

In an embodiment, the monooxygenase synthetic polynucleotide and/or dehydrogenase synthetic polynucleotide is a synthetic polynucleotide comprising any one of the sequences set forth herein. In an embodiment, the synthetic polynucleotide additionally comprises at least one promoter operably linked to any one or more of the synthetic polynucleotides disclosed herein. In an embodiment, the promoter is at least one of pBAD, pTrc, ptac, pLac, pT5 and/or J23116. In an embodiment, the promoter is at least one of pADH1, pTEF1, pTEF2, pGAP and/or pGCW14. Any promoter disclosed herein or known to one skilled in the art should also be considered part of the disclosure of this application. In an embodiment, random mutations are introduced in the promoter regions using degenerate primers. In an embodiment, one or more terminators are incorporated into the expression construct.

In an embodiment, the synthetic polynucleotide comprises one or more of plasmids pBZ13 (SEQ ID NO: 15), pBZ15 (SEQ ID NO: 16), pBZ21 (SEQ ID NO: 17), pBZ23 (SEQ ID NO: 18), pBZ4 (SEQ ID NO: 19), pDG5 (SEQ ID NO: 21), pDG6 (SEQ ID NO: 22), pLC100 (SEQ ID NO: 23), pLC12 (SEQ ID NO: 24), pLC37 (SEQ ID NO: 25), pLC39 (SEQ ID NO: 26), pLC99 (SEQ ID NO: 27), pNH100 (SEQ ID NO: 28), pNH104 (SEQ ID NO: 29), pN132 (SEQ ID NO: 30), pNH157 (SEQ ID NO: 31), pNH158 (SEQ ID NO: 32), pNH160 (SEQ ID NO: 33), pNH166 (SEQ ID NO: 34), pNH167 (SEQ ID NO: 35), pNH172 (SEQ ID NO: 36), pNH173 (SEQ ID NO: 37), pNH177 (SEQ ID NO: 38), pNH178 (SEQ ID NO: 39), pNH180 (SEQ ID NO: 40), pNH181 (SEQ ID NO: 41), pNH185 (SEQ ID NO: 42), pNH187 (SEQ ID NO: 43), pNH188 (SEQ ID NO: 44), pNH225 (SEQ ID NO: 45) and/or pNH238 (SEQ ID NO: 46) or any other synthetic polynucleotide or synthetic polypeptide disclosed herein.

The disclosure is intended to include any complement sequences to the sequences set forth herein. The disclosure is also intended to encompass any polypeptides or synthetic polypeptides encoded by the synthetic polynucleotides of the current invention. Where synthetic sequences of the invention are disclosed, the invention is meant to encompass any sequence that has an identity to the sequences, as set forth herein.

The disclosure also provides synthetic microorganisms engineered to functionally express a monooxygenase enzyme and/or dehydrogenase enzyme that converts a wide range of organic substrates into an even broader range of products. The disclosure provides synthetic microorganisms engineered to consume molecules containing carbon, such as alkane or other molecules, such molecules as methane or methanol, ethane or ethanol. The invention also provides microorganisms engineered to convert methane and/or methanol or ethane and/or ethanol into industrial products.

In a fourth aspect, disclosed herein is a synthetic microorganism comprising at least one exogenous synthetic polynucleotide, wherein the synthetic polynucleotide comprises at least one of the synthetic polynucleotides set forth herein. In an embodiment, the synthetic polypeptide is heterologous. The microorganism is intended to encompass prokaryotic cells or eukaryotic cells, such as yeast and fungi, and also intended to include archaea. In one embodiment, the microorganism is at least one of *Escherichia coli, Bacillus subtilis, Bacillus methanolicus, Pseudomonas putida, Saccharomyces cerevisiae, Pichia pastoris, Pichia methanolica, Salmonella enterica, Corynebacterium glutamicum, Klebsiella oxytoca, Anaerobiospirillum succiniciproducens, Actinobacillus succinogenes, Mannheimia succiniciproducens, Rhizobium etli, Gluconobacter oxydans, Zymomonas mobilis, Lactococcus lactis, Lactobacillus plantarum, Streptomyces coelicolor, Clostridium acetobutylicum, Pseudomonas fluorescens, Schizosaccharomyces pombe, Kluyveromyces lactis, Kluyveromyces marxianus, Aspergillus terreus, Aspergillus niger*, and *Candida utilis*. In an embodiment, the microorganism is at least one of *Escherichia coli, Saccharomyces cerevisiae, Pichia pastoris, Bacillus methanolicus, Bacillus subtilis* or *Corynebacterium glutamicum*. In an embodiment, the microorganism is *Escherichia coli*. In an embodiment, the microorganism is *Pichia pastoris*. In an embodiment, the microorganism is *Saccharomyces cerevisiae*. In an embodiment, the microorganism is *Corynebacterium glutamicum*. In an embodiment, the microorganism is *Bacillus methanolicus*.

In an embodiment, the synthetic microorganism has improved growth on or is capable of growth on a monooxygenase substrate, alcohol dehydrogenase substrate and/or an acetaldehyde dehydrogenase substrate as a sole or major carbon source. In an embodiment, the substrate is at least one of methane, ethane, propane, butane, pentane, hexane, heptane, octane, 2-methylpropane, 2,3-dimethylpentane, propene (propylene), but-1-ene, cis-but-2-ene, trans-but-2-ene, cyclohexane, methylene cyclohexane, -pinene, adamantane, cis-1,4-dimethylcyclohexane, cis-1,3-dimethylcyclohexane, trichloroethene, vinyl chloride, 1,1-dichloroethene, trifluoroethylene, chlorotrifluoroethylene, tribromoethylene, benzene, toluene, ethylbenzene, styrene, pyridine, naphthalene, biphenyl, 2-hydroxybiphenyl, 2-methylbiphenyl, 2-chlorobiphenyl, 2-bromobiphenyl, 2-iodobiphenyl, chloromethane, dichloromethane, bromomethane, nitromethane, methanethiol, methanol, ethanol, diethyl ether, carbon monoxide, cyclohexene, dimethyl ether, difluoromethane, fluorobenzene, fluoromethane, isopentane, methylamine, methylcyanide, nitrobenzene, phenylalanine or xylene. In an embodiment, the monooxygenase substrate is methane, ethane, propane, butane or naphthalene. In an embodiment, the substrate is methanol or ethanol. Other substrates can be found, for example, without limitation, in Vazquez-Duhalt and Quintero-Ramirez, *Petroleum Biotechnology,* 2004; Green and Dalton, Substrate Specificity of Soluble Methane Monooxygenase, J. Biol. Chem., Vol. 264 No. 30, pp. 17698-17703, 1989; BRENDA online database http://www.brenda-enzymes.org/enzyme.php?ecno=1.14.13.25, which is incorporated by reference herein including any drawings. In an embodiment, the substrate is ethane. In an embodiment, the substrate is ethane and the at least one mutation increases specificity for ethane.

In an embodiment, the synthetic microorganism produces a chemical. In an embodiment, the chemical is at least one of dicarboxylic acid, malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, isoprene, farnesene, farnesane, squalene, squalane, carotenoids, any or all of the amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkalies, alkenes, olefins, animal feed additives, mixtures of amino acids, and proteins. Other examples of chemicals include, but are not limited to, ethanol, propanol, isopropanol, butanol, fatty alcohols, fatty acid esters, ethyl esters, wax esters; hydrocarbons and alkanes such as propane, octane, diesel, Jet Propellant 8 (JP8); terephthalate, 1,3-propanediol, 1,4-butanediol, acrylate, adipic acid, c-caprolactone, isoprene, caprolactam, and polymers of these, plus other polymers, such as polyols, polyhydroxyalkanoates (PHA), poly-beta-hydroxybutyrate (PHB), rubber; commodity chemicals such as lactate, docosahexaenoic acid (DHA), 3-hydroxypropionate, y-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, nutraceuticals, polymers, paraffin replacements, personal care products and pharmaceuticals. Other examples of chemicals include, without limitation, all compounds that can be produced with the methods set forth herein. Such compounds are intended to include all molecules that can be constructed with the methods set forth herein including, for example without limitation, all organic and inorganic molecules that can be made with the methods set forth herein. The term chemical is intended to include natural and non-natural compounds. Examples of natural molecules include, but are not limited to, amino acids, nucleic acids, nucleotides and polynucleotides and all related biological molecules. Non-natural compounds include, but are not limited to, amino acids and nucleotides that are modified in a way differently than they are normally modified in biological systems (such as, for example, without limitation, non-natural amino acids). In an embodiment, the chemical is methanol, ethanol, propanol, butanol, or naphthol. In another embodiment, the chemical is succinate, malate, fatty acids, lysine, and/or glutamate. In an embodiment, the chemical is 3-hydroxypropionate or a polymer of 3-hydroxypropionate.

In an embodiment, the microorganism comprises *Escherichia coli* and the synthetic microorganism is *Escherichia coli* and the monooxygenase synthetic polynucleotide encodes for a soluble diiron monooxygenase enzyme or one, some or any of its subunits. In an embodiment, the soluble diiron monooxygenase enzyme comprises a methane monooxygenase or an ethane monooxygenase. In an embodiment, the synthetic microorganism comprises *Escherichia coli* that has been transformed with the synthetic polynucleotide and the synthetic microorganism has improved growth on ethane or consumes ethane as a sole carbon source or as a major carbon source as compared to a microorganism that has not been transformed with the monooxygenase synthetic polynucleotide. In an embodiment, the synthetic microorganism comprises *Escherichia coli* that has been transformed with the monooxygenase synthetic polynucleotide, the monooxygenase substrate is ethane and the chemical is ethanol. In an embodiment, the synthetic microorganism comprises *Escherichia coli* that has been transformed with the monooxygenase synthetic polynucleotide, the araBAD gene has been deleted, the substrate comprises ethane and the chemical comprises ethanol. In an embodiment, the synthetic microorganism comprises *Escherichia coli* that has been transformed with the monooxygenase synthetic polynucleotide, the monooxygenase substrate comprises methane and the chemical comprises methanol. In an embodiment, the synthetic microorganism comprises *Escherichia coli* that has been transformed with the monooxygenase synthetic polynucleotide, the araBAD gene has been deleted, the substrate comprises methane and the chemical comprises methanol In an embodiment, the synthetic microorganism comprises *Escherichia coli* that has been transformed with the monooxygenase synthetic polynucleotide, the monooxygenase substrate comprises naphthalene and the chemical comprises 1-naphthol. In an embodiment, the synthetic microorganism comprises *Escherichia coli* that has been transformed with the monooxygenase synthetic polynucleotide, the monooxygenase substrate comprises ethane and the chemical comprises a fatty acid. In an embodiment, the synthetic microorganism comprises *Escherichia* coli that has been transformed with the monooxygenase synthetic polynucleotide, the monooxygenase substrate comprises ethane and the chemical comprises succinate.

In an embodiment, the microorganism comprises *Escherichia coli* and the synthetic microorganism is *Escherichia coli* and the monooxygenase synthetic polynucleotide encodes for a soluble diiron monooxygenase enzyme which encodes a polypeptide which is at least 60%, preferably about 65%, preferably about 70%, preferably about 75%, preferably about 80%, preferably about 85%, preferably about 90% or preferably about 95% identical to the amino acid sequences set forth in SEQ ID NO: 8 and SEQ ID NO:

10 and SEQ ID NO: 12 and SEQ ID NO: 14 and SEQ ID NO: 59 and SEQ ID NO: 61. In an embodiment, the microorganism comprises *Escherichia coli* and the synthetic microorganism is *Escherichia coli* and the monooxygenase synthetic polynucleotide encodes for a soluble diiron monooxygenase enzyme which encodes a polypeptide that has the amino acid sequences set forth in SEQ ID NO: 8 and SEQ ID NO: 10 and SEQ ID NO: 12 and SEQ ID NO: 14 and SEQ ID NO: 59 and SEQ ID NO: 61 and the at least one protein folding chaperone has the amino acid sequences set forth in SEQ ID NO: 63 and SEQ ID NO: 65 and SEQ ID NO: 67 and SEQ ID NO: 69.

In an embodiment of anything disclosed herein, the at least one protein folding chaperone comprises at least one heterologous groES and/or groEL. In an embodiment, the at least one protein folding chaperone comprises at least one protein which is at least 60%, preferably about 65%, preferably about 70%, preferably about 75%, preferably about 80%, preferably about 85%, preferably about 90% or preferably about 95% identical to the amino acid sequence set forth in SEQ ID NO: 63 or SEQ ID NO: 65 or SEQ ID NO: 67 or SEQ ID NO: 69 or SEQ ID NO: 120 or SEQ ID NO: 122 or SEQ ID NO: 124 or SEQ ID NO: 126 or SEQ ID NO: 128 or SEQ ID NO: 130 or SEQ ID NO: 132 or SEQ ID NO: 134 or SEQ ID NO: 136 or SEQ ID NO: 138 or SEQ ID NO: 140 or SEQ ID NO: 142. In an embodiment, the at least one protein folding chaperone comprises at least one protein which is at least 60%, preferably about 65%, preferably about 70%, preferably about 75%, preferably about 80%, preferably about 85%, preferably about 90% or preferably about 95% identical to the amino acid sequence of any sequence disclosed herein. In an embodiment for any disclosure provided herein, the at least one protein folding chaperone comprises at least two protein folding chaperones. In an embodiment for any disclosure provided herein, the at least one protein folding chaperone comprises a protein that is a GroES and/or GroEL from at least one of *Escherichia coli, Methylocaldum* sp175, *Methylococcus capsulatus* or *Solimonas aquatica* DSM 25927. In an embodiment for any disclosure provided herein, the at least one protein folding chaperone comprises *Escherichia coli* groES, and/or GroEL and *Methylococcus capsulatus* GroES and/or GroEL-2. In an embodiment for any disclosure herein, protein folding chaperones are each selectively, completely or in particular combinations co-expressed to improve monooxygenase activity. In an embodiment, protein folding chaperones are each selectively, completely or in particular combinations overexpressed to improve monooxygenase activity. In an embodiment of anything disclosed herein, the soluble diiron monooxygenase enzyme is a methane monooxygenase or an ethane monooxygenase. In an embodiment for any disclosure provided herein, the monooxygenase is a monooxygenase from at least one of *Solimonas aquatica* DSM 25927*, Methyloferula stellata*, Methylocaldurn sp 175, *Methylococcus capsulatus, Methylocella silvestris* and/or *Methylosinus trichosporium*. In an embodiment, the monooxygenase is any one or more monooxygenase(s) from Table 16. In an embodiment for any disclosure herein, monooxygenase(s) are each selectively, completely or in particular combinations chosen and combined to improve overall monooxygenase activity. In an embodiment for any disclosure provided herein, the monooxygenase and/or protein folding chaperones are any proteins homologous enough to be suitable for the present disclosure and that may be utilized in any amount and combination which would be suitable to carry out the claimed invention.

In an embodiment, the microorganism comprises *Escherichia coli*, the synthetic microorganism comprises *Escherichia coli* and the dehydrogenase synthetic polynucleotide encodes for an alcohol dehydrogenase and/or an acetaldehyde dehydrogenase. In an embodiment, the alcohol dehydrogenase and/or an acetaldehyde dehydrogenase comprises at least one, two or all of Mdh from *Bacillus stearothermophilus* (SEQ ID NO: 51), MhpF from *Escherichia coli* (SEQ ID NO: 53) or AcdH from *Clostridium kluyveri* (SEQ TD NO: 55). In an embodiment, the protein comprises a mutation of a T for an A at position 267 and a K for an E at position 568 of the protein encoded by the *Escherichia coli* adhE gene of the amino acid sequence set forth in SEQ NO: 49. In an embodiment, the synthetic microorganism comprises an *Escherichia coli* that has been transformed with the dehydrogenase synthetic polynucleotide and the synthetic microorganism has improved growth on ethanol or consumes ethanol as a sole carbon source or as a major carbon source as compared to a microorganism that has not been transformed with the dehydrogenase synthetic polynucleotide. In an embodiment, the synthetic microorganism comprises *Escherichia coli* that has been transformed with the dehydrogenase synthetic polynucleotide, the substrate is ethanol and the chemical is a fatty acid. In an embodiment, the synthetic microorganism comprises *Escherichia coli* that has been transformed with the dehydrogenase synthetic polynucleotide, the araBAD gene has been deleted, the synthetic microorganism has been transformed with the fatB1 gene from *Umbellularia californica*, the substrate comprises ethanol and the chemical comprises a fatty acid. In an embodiment, the synthetic microorganism comprises *Escherichia coli* that has been transformed with the dehydrogenase synthetic polynucleotide, the substrate is ethanol and the chemical is succinate. In a preferred embodiment, the synthetic microorganism comprises *Escherichia coli* that has been transformed with the dehydrogenase synthetic polynucleotide and the araBAD, ic1R, and/or sdhAB genes have been deleted and/or their expression has been reduced, the substrate comprises ethanol and the chemical comprises succinate. In an embodiment for any disclosure herein, dehydrogenase(s) are each selectively, completely or in particular combinations chosen and combined to improve overall dehydrogenase activity.

In an embodiment for any disclosure provided herein, the microorganism comprises *Corynebacterium glutamicum*. In an embodiment, the microorganism comprises *Corynebacterium glutamicum*, the synthetic microorganism comprises *Corynebacterium glutamicum* and the monooxygenase synthetic polynucleotide encodes for a soluble diiron monooxygenase enzyme. In an embodiment, the soluble diiron monooxygenase enzyme comprises a methane monooxygenase or an ethane monooxygenase. In an embodiment, the synthetic microorganism comprises *Corynebacterium glutamicum* that has been transformed with the synthetic polynucleotide and the synthetic microorganism has improved growth on methane or ethane or consumes methane or ethane as a sole carbon source or as a major carbon source as compared to a microorganism that has not been transformed with the monooxygenase synthetic polynucleotide. In an embodiment, the synthetic microorganism comprises *Corynebacterium glutamicum* that has been transformed with the monooxygenase synthetic polynucleotide, the monooxygenase substrate comprises ethane and the chemical comprises ethanol. In an embodiment, the synthetic microorganism comprises *Corynebacterium glutamicum* that has been transformed with the monooxygenase synthetic polynucleotide, the monooxygenase substrate comprises methane and the chemical comprises methanol. In an embodiment, the synthetic microorganism comprises *Corynebacterium glutamicum* that has been transformed with the monooxygenase synthetic polynucleotide, the monooxygenase substrate comprises naphthalene and the chemical comprises 1-naphthol. In an embodiment, the synthetic microorganism comprises *Corynebacterium glutamicum* that has been transformed with the monooxygenase synthetic polynucleotide, the monooxygenase substrate comprises ethane and the chemical comprises an amino acid, such as glutamate, lysine, or methionine.

In an embodiment, the microorganism comprises *Corynebacterium glutamicum* and the synthetic microorganism is *Corynebacterium glutamicum* and the monooxygenase synthetic polynucleotide encodes for a soluble diiron monooxygenase enzyme which encodes a polypeptide which is at least 60%, preferably about 65%, preferably about 70%, preferably about 75%, preferably about 80%, preferably about 85%, preferably about 90% or preferably about 95% identical to the amino acid sequences set forth in SEQ ID NO: 8 and SEQ ID NO: 10 and SEQ ID NO: 12 and SEQ ID NO: 14 and SEQ ID NO: 59 and SEQ ID NO: 61. In an embodiment, the microorganism comprises *Corynebacterium glutamicum* and the synthetic microorganism is *Corynebacterium glutamicum* and the monooxygenase synthetic polynucleotide encodes for a soluble diiron monooxygenase enzyme which encodes a polypeptide that has the amino acid sequences set forth in SEQ ID NO: 8 and SEQ ID NO: 10 and SEQ ID NO: 12 and SEQ ID NO: 14 and SEQ ID NO: 59 and SEQ ID NO: 61 and the at least one protein folding chaperone has the amino acid sequences set forth in SEQ ID NO: 63 and SEQ ID NO: 65 and SEQ ID NO: 67 and SEQ ID NO: 69.

In an embodiment, synthetic polynucleotides encode enzymes selected from the group consisting of methanol dehydrogenase (EC 1.1.1.244 or 1.1.99.37 or 1.1.2.7), alcohol dehydrogenase (EC 1.1.1.1 or 1.1.1.2 or 1.1.2.8 or 1.1.3.13), aldehyde dehydrogenase (EC 1.2.1.3), acetaldehyde dehydrogenase (EC 1.2.1.10), acetyl-CoA synthetase (EC 6.2.1.1), isocitrate lyase (EC 4.1.3.1), malate synthase (EC 2.3.3.9), isocitrate dehydrogenase kinase/phosphatase (EC 2.7.11.5, EC 3.1.3). In an embodiment, the dehydrogenase enzyme or enzymes can be any one or more of methanol dehydrogenase (EC 1.1.1.244 or 1.1.99.37 or 1.1.2.7), alcohol dehydrogenase (EC 1.1.1.1 or 1.1.1.2 or 1.1.2.8 or 1.1.3.13), aldehyde dehydrogenase (EC 1.2.1.3), and/or acetaldehyde dehydrogenase (EC 1.2.1.10).

In an embodiment, the microorganism comprises *Pichia pastoris*. In an embodiment, the synthetic microorganism comprises *Pichia pastoris* and the monooxygenase synthetic polynucleotide encodes for a soluble diiron monooxygenase enzyme. In an embodiment, the soluble diiron monooxygenase enzyme comprises a methane monooxygenase, an ethane monooxygenase or a toluene-4-monooxygenase. In an embodiment, the synthetic microorganism comprises *Pichia pastoris* that has been transformed with the monooxygenase synthetic polynucleotide and the synthetic microorganism has improved growth on methane, ethane or naphthalene or consumes methane, ethane or naphthalene as a sole carbon source or as a major carbon source as compared to a microorganism that has not been transformed with the monooxygenase synthetic polynucleotide. In an embodiment, the synthetic microorganism comprises *Pichia pastoris* that has been transformed with the monooxygenase synthetic polynucleotide incorporating a monooxygenase from *Methylocystis* sp. LW5 and/or *Solimonas aquatica*, synthetic polynucleotide encoding groES and groEL chaperonin subunits, the monooxygenase substrate comprises methane and the chemical comprises methanol In an embodiment, there are two plasmids involved in the *Pichia pastoris* transformation. In an embodiment, the synthetic microorganism comprises *Pichia pastoris* that has been transformed with the monooxygenase synthetic polynucleotide, the monooxygenase substrate comprises ethane and the chemical comprises ethanol. In an embodiment, the synthetic microorganism comprises *Pichia pastoris* that has been transformed with the monooxygenase synthetic polynucleotide, the monooxygenase substrate comprises ethane and the chemical comprises malate. In an embodiment, the synthetic microorganism comprises *Pichia pastoris* that has been transformed with an additional synthetic polynucleotide encoding the PYC2, MDH3(0 SKL) and MAE1 genes, the monooxygenase substrate comprises ethane and the chemical comprises malate. In an embodiment, the synthetic microorganism comprises *Pichia pastoris* that has been transformed with the monooxygenase synthetic polynucleotide, the araBAD gene has been deleted, the substrate comprises methane and the chemical comprises methanol. In an embodiment, the synthetic microorganism comprises *Pichia pastoris* that has been transformed with the monooxygenase synthetic polynucleotide, the monooxygenase substrate is naphthalene and the chemical is 1-naphthol. In an embodiment, the monooxygenase is toluene-4-monooxygenase from *Pseudomonas mendocina* KR1, the monooxygenase substrate comprises naphthalene and the chemical is 1-naphthol. In an embodiment for any disclosure herein, monooxygenase(s) and/or protein folding chaperones are each selectively, completely or in particular combinations chosen and combined to improve overall monooxygenase activity. In an embodiment for any disclosure provided herein, the monooxygenase and/or protein folding chaperones are any proteins homologous enough to be suitable for the present disclosure and may be utilized in any amount and combination which would be suitable to carry out the claimed invention.

In an embodiment, the microorganism comprises *Pichia pastoris* and the synthetic microorganism is *Pichia pastoris* and the monooxygenase synthetic polynucleotide encodes for a soluble diiron monooxygenase enzyme which encodes a polypeptide which is at least 60%, preferably about 65%, preferably about 70%, preferably about 75%, preferably about 80%, preferably about 85%, preferably about 90% or preferably about 95% identical to the amino acid sequences set forth in SEQ ID NO: 144 and SEQ ID NO: 146 and SEQ ID NO: 148 and SEQ ID NO: 150 and SEQ ID NO: 152 and SEQ ID NO: 154. In an embodiment, the microorganism comprises *Pichia pastoris* and the synthetic microorganism is *Pichia pastoris* and the monooxygenase synthetic polynucleotide encodes for a soluble diiron monooxygenase enzyme which encodes a polypeptide that has the amino acid sequences set forth in SEQ ID NO: 144 and SEQ ID NO: 146 and SEQ ID NO: 148 and SEQ ID NO: 150 and SEQ ID NO: 152 and SEQ ID NO: 154 and the at least one protein folding chaperone has the amino acid sequences set forth in SEQ ID NO: 120 and SEQ ID NO: 122.

In a preferred embodiment, a microorganism is disclosed that comprises any one of the synthetic polynucleotides set forth herein. In an embodiment, the synthetic polynucleotide is a monooxygenase synthetic polynucleotide and/or dehydrogenase synthetic polynucleotide that comprises one or more of plasmids pBZ13 (SEQ ID NO: 15), pBZ15 (SEQ ID NO: 16), pBZ21 (SEQ ID NO: 17), pBZ23 (SEQ ID NO: 18), pBZ4 (SEQ ID NO: 19), pDG5 (SEQ ID NO: 21), pDG6 (SEQ ID NO: 22), pLC100 (SEQ ID NO: 23), pLC12

(SEQ ID NO: 24), pLC37 (SEQ ID NO: 25), pLC39 (SEQ ID NO: 26), pLC99 (SEQ ID NO: 27), pNH100 (SEQ ID NO: 28), pNH104 (SEQ ID NO: 29), pNH132 (SEQ ID NO: 30), pNH157 (SEQ ID NO: 31), pNH158 (SEQ ID NO: 32), pNH160 (SEQ ID NO: 33), pNH166 (SEQ ID NO: 34), pNH167 (SEQ ID NO: 35), pNH172 (SEQ ID NO: 36), pNH173 (SEQ ID NO: 37), pNH177 (SEQ ID NO: 38), pNH178 (SEQ ID NO: 39), pNH180 (SEQ ID NO: 40), pNH181 (SEQ ID NO: 41), pNH185 (SEQ ID NO: 42), pNH187 (SEQ ID NO: 43), pNH188 (SEQ ID NO: 44), pNH225 (SEQ ID NO: 45) and/or pNH238 (SEQ ID NO: 46) or any other synthetic polynucleotide or synthetic polypeptide disclosed herein. In a preferred embodiment, the microorganism is *Escherichia coli* that has been transformed with plasmids pBZ15 (SEQ ID NO: 16) and pNH225 (SEQ ID NO: 45).

In an embodiment for any disclosure provided herein, the microorganism is *Bacillus methanolicus*. In an embodiment for any disclosure provided herein, the microorganism is *Saccharomyces cerevisiae*.

Any of the embodiments provided herein may be carried out in a monoculture or carried out in a co-culture. In an embodiment, a methane assimilation pathway is incorporated into a heterologous host. In an embodiment, a methanol assimilation pathway is incorporated into a heterologous host.

A fourth aspect of the invention is drawn to a method for producing a chemical, comprising culturing any of the synthetic microorganisms provided herein under suitable culture conditions and for a sufficient period of time to produce the chemical. In an embodiment, the suitable culture conditions comprise a culture media containing at least one of methane, methanol, ethane, ethanol, propane, butane, or naphthalene as a sole carbon source or as a major carbon source. In an embodiment, the synthetic microorganism is cultured under conditions such that the synthetic microorganism produces a chemical that is converted into a second chemical by a second microorganism or a second synthetic microorganism.

BRIEF DESCRIPTION OF THE DRAWINGS

FIG. 15 shows a representative plasmid map illustrating the coding regions for plasmid pNH172 (SEQ ID NO: 36). This plasmid enables the expression of two subunits of the

*Methylocystis* methane monooxygenase mmoB and mmoD, plus the *Methylocystis* chaperone groES and groEL from different promoters for expression in *Pichia pastoris*. This plasmid can be restriction digested with BsaI enzyme in order to generate a linear fragment for integration into the chromosome. The plasmid pNH173 (SEQ ID NO: 37) is nearly identical, with the exception being the substitution of the coding sequences for the MMO subunits and chaperones deriving from *Solimonas aquatica*.

Figure 16:
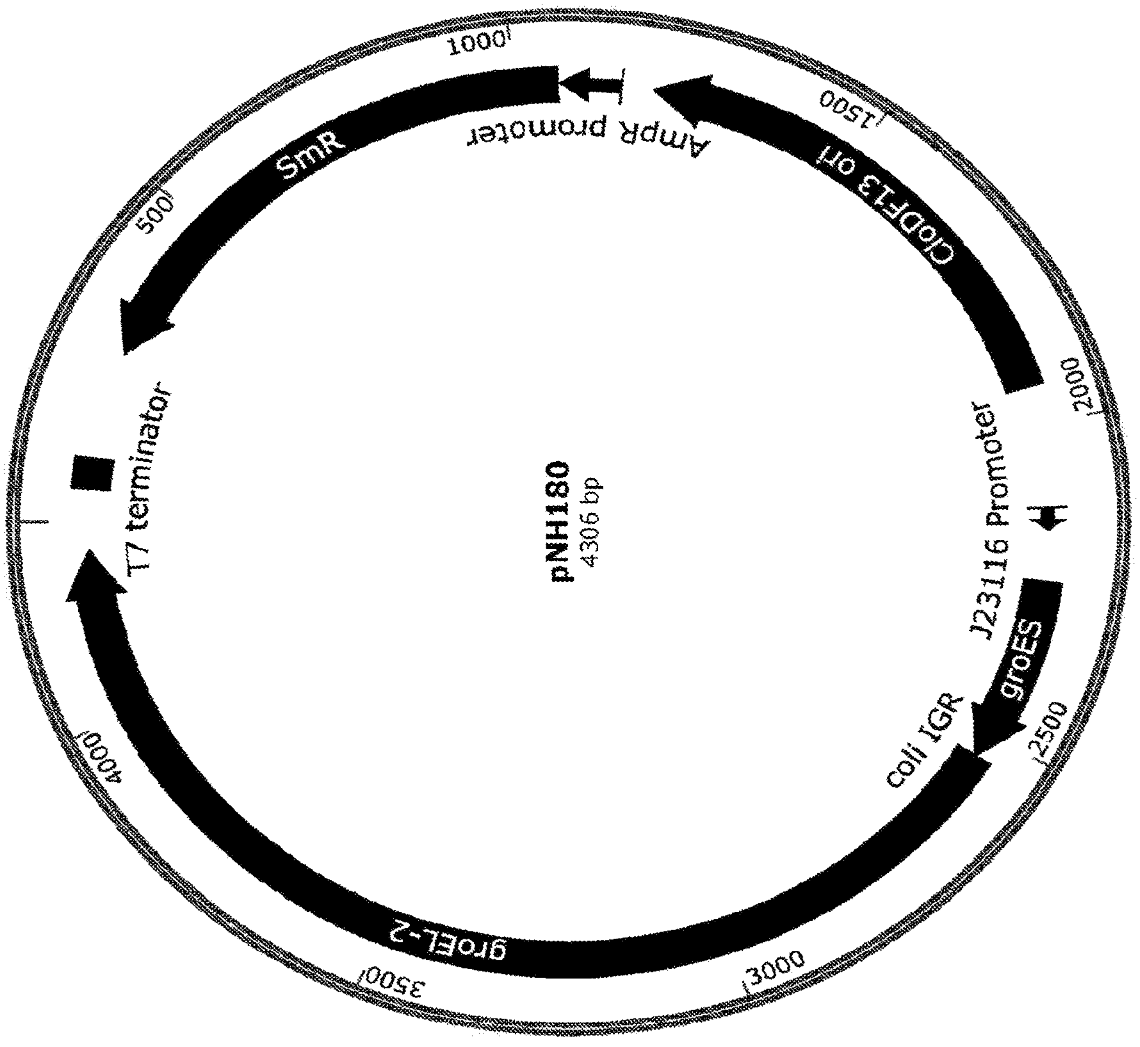

FIG. 16 shows a representative plasmid map illustrating the coding regions for plasmid pNH180 (SEQ ID NO: 40). This plasmid enables the expression of the *M. capsulatus* (Bath) chaperones groES and groEL-2 for expression in *E. coli*. The plasmids pNH177 (SEQ ID NO: 38), pNH178 (SEQ ID NO: 39), pNH181 (SEQ ID NO: 41), pNH185 (SEQ ID NO: 42), pNH187 (SEQ ID NO: 43), and pNH188 (SEQ ID NO: 44) are all nearly identical to plasmid pNH180, with the exception of the substitution of the coding sequences for the groES and groEL genes deriving from *Pseudonocardia autotrophica, Thauera butanivora, Methylosinus trichosporium, Methylocaldum* sp. 175, *Methylocystis* sp. LW5, and *Solimonas aquatica*, respectively.

Figure 17:
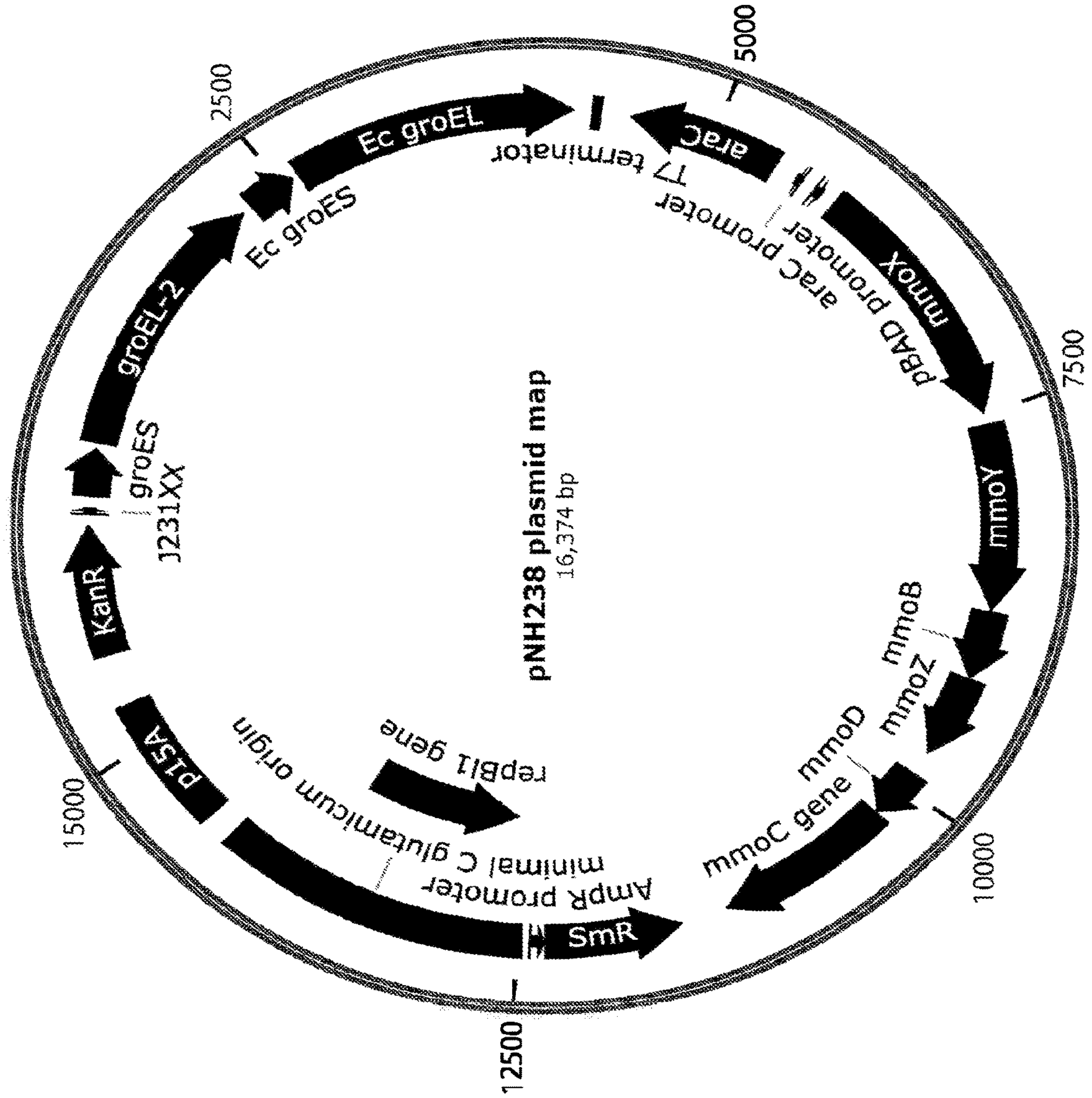

FIG. 17 shows a representative plasmid map illustrating the coding regions for plasmid pNH238 (SEQ ID NO: 46). This plasmid enables the expression of the *M. capsulatus* (Bath) sMMO subunits and groES/groEL-2 genes, plus the *E. coli* groES/groEL chaperone genes for expression in *E. coli, C. glutamicum*, and other Gram-positive bacteria. The plasmid pBZ21 (SEQ ID NO: 17) is nearly identical, with the exception of the fragment containing the *C. glutamicum* origin of replication and the KanR cassette.

FIG. 18 shows the multiple sequence alignment between three monooxygenase subunits: the prmla subunit of the propane monooxygenase (in pNH100 (SEQ ID NO: 28), from *Pseudonocardia* TY-7), the mmoX subunit of the ethane monooxygenase (in pNH160 (SEQ ID NO: 33), from *Solimonas aquatica*), and the mmoX subunits of the methane monooxygenase (in pDG5 (SEQ ID NO: 21), from *Methylococcus capsulatus* (Bath)). Stars beneath the sequences indicate positions at which the three sequences have a strictly conserved amino acid residue.

DETAILED DESCRIPTION OF THE INVENTION

The disclosure provides synthetic polypeptides and proteins. The disclosure also provides microorganisms engineered to functionally express a monooxygenase enzyme that converts a wide range of organic substrates into an even broader range of products. The disclosure also provides microorganisms engineered to consume molecules containing carbon, such as alkane or molecules such as methane or methanol, ethane or ethanol. The invention also provides microorganisms engineered to convert methane and/or methanol or ethane and/or ethanol into industrial products.

Compositions and methods comprising using said microorganisms to produce chemicals are further provided. The methods provide for superior low-cost production as compared to existing sugar-consuming fermentation.

Unless defined otherwise, all technical and scientific terms used herein have the meaning commonly understood by one of ordinary skill in the art to which this invention belongs. Practitioners are particularly directed to (M R Green and J Sambrook, eds, Molecular Cloning: A Laboratory Manual, 4th ed., Cold Spring Harbor Laboratory Press, 2012), (F M Ausubel, Current Protocols in Molecular Biology (Supplement 99), John Wiley & Sons, New York, 2012), and (Bornscheuer, U. and R. J. Kazlauskas, *Curr Protoc Protein Sci,* 2011). Standard methods also appear in (Bindereif, Schott, & Westhof, Handbook of RNA Biochemistry, Wiley-VCH, Weinheim, Germany, 2005) which describes detailed methods for RNA manipulation and analysis, and (S L Beaucage et al., *Curr Protoc Nucleic Acid Chem,* 2009) and (A Y Keel et al., Methods Enzymol 469:3-25, 2009) which describe methods of chemical synthesis and purification of RNA, and are incorporated herein by reference. Examples of appropriate molecular techniques for generating nucleic acids, and instructions sufficient to direct persons of skill through many cloning exercises are found in (M R Green et al., Guide to Molecular Cloning Techniques, Methods in Enzymology, Volume 152 Academic Press, Inc., San Diego, C A, 1987); and (PCR Protocols: A Guide to Methods and Applications, Academic Press, San Diego, C A, 1990), which are incorporated by reference herein.

As used herein, the terms "accessory protein" and "helper protein" are intended to mean proteins that enable the function of a separate enzyme, collection of enzymes, enzyme complex made of more than one protein, or non-enzymatic protein. One example of the function of an accessory or helper protein is a protein that is known to aid in folding of other proteins (so called "protein folding chaperones" or "chaperonins"). Another example is a protein that modifies another protein, including post-translational modifications such as acetylation, methylation, acylation, farnesylation, etc., as well as the reverse reactions de-acetylation, de-methylation, etc., as well as removing a fraction of a protein. Other examples are proteins that aid an enzyme or enzyme complex in correctly assembling a prosthetic group, or loading a metal center, or enabling the enzyme or complex to become localized to the proper physical location in the cell, or enabling the transfer of electrons or other chemical groups to the enzyme. In some cases, accessory proteins enable the function of an enzyme, even though the exact mechanism of action is not yet known.

As used herein, the term "biomass" is intended to mean the collection of biological matter, made up of cells, that results from the culturing process of a microorganism under suitable conditions for the growth of that organism in culture. In some cases, the biomass includes simply the cells and their contents and in some cases, the biomass includes additionally any macromolecules, such as proteins, that are secreted into the culture, outside the boundary of the cell membrane.

As used herein, the term "carbon source" is intended to mean a raw material input to an industrial process that contains carbon atoms that can be used by the microorganisms in a culture. For example, industrial cultures of microorganisms may use glucose as a source of carbon atoms. As provided herein, in addition to typical carbon sources such as sugars and amino acids, the carbon source can additionally be methane, methanol, ethane, ethanol, or any of the compounds in Column A of Table 1. In some cases, a culture is grown in a medium containing a single usable compound that contains carbon atoms. As carbon is an element that is essential for life, the culture must have, in this example, metabolic pathways for converting the single compound containing carbon atoms into many other biological molecules necessary for the organism's survival.

As used herein, "sole carbon source" is intended to mean suitable conditions comprising a culture media containing either methane, methanol, ethane, ethanol, or any of the compounds in Column A of Table 1 as a carbon source such that, as a fraction of the total usable carbon atoms in the media, those compounds cited above, respectively, represent about 100% of the total usable carbon atoms in the media.

As used herein, "major carbon source" is intended to mean that where the suitable conditions comprise a culture media containing methane, methanol, ethane, or ethanol, or any of the compounds in Column A of Table 1 as a carbon source as a fraction of the total carbon atoms in the media, those compounds cited above represent, respectively, at least about 10% or more of the total usable carbon atoms in the media, about 20% or more of the total usable carbon atoms in the media, about 30% or more of the total usable carbon atoms in the media, about 40% or more of the total usable carbon atoms in the media, about 50% or more of the total usable carbon atoms in the media, about 60% or more of the total usable carbon atoms in the media, about 70% or more of the total usable carbon atoms in the media, about 80% or more of the total usable carbon atoms in the media or about 90% or more of the total usable carbon atoms in the media.

As used herein, the term "chemical" is broadly meant to include any substance used in or resulting from a reaction involving changes to atoms or molecules, especially one derived according to any of the processes set forth herein. As such, a chemical is intended to mean a substance obtained by a chemical process or a substance having a chemical effect. Examples of chemicals contemplated by the invention, without limitation, are dicarboxylic acid, malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, isoprene, farnesene, farnesane, squalene, squalane, carotenoids, any or all of the amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and proteins. Other examples of chemicals include, but are not limited to, ethanol, propanol, isopropanol, butanol, fatty alcohols, fatty acid esters, ethyl esters, wax esters; hydrocarbons and alkanes such as propane, octane, diesel, Jet Propellant 8 (JP8); terephthalate, 1,3-propanediol, 1,4-butanediol, acrylate, adipic acid, F-caprolactone, isoprene, caprolactam, polyols, Polyhydroxyalkanoates (PHA), poly-beta-hydroxybutyrate (PHB), rubber, and polymers made from terephthalate, 1,3-propanediol, 1,4-butanediol, acrylate, adipic acid, c-caprolactone, isoprene, caprolactam; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, nutraceuticals, polymers, paraffin replacements, personal care products and pharmaceuticals. Other examples of chemicals include, without limitation, all compounds that can be produced with the methods set forth herein. Such compounds are intended to include all molecules that can be constructed with the methods set forth herein including, for example without limitation, all organic and inorganic molecules that can be made with the methods set forth herein. The term chemical is intended to include natural and non-natural compounds. Examples of natural molecules include, but are not limited to, amino acids, nucleic acids, nucleotides and polynucleotides and all related biological molecules. Non-natural compounds include, but are not limited to, amino acids and nucleotides that are modified in a way differently than they are normally modified in biological systems, and compounds not normally found in nature.

As used herein, the term "coding region" or "coding sequences" are intended to mean DNA or RNA that encodes a region of, for example, but not limited to, polypeptides (i.e. proteins) using the genetic code. A coding region is often bounded at the 5' end by a start codon and nearer the 3' end with a stop codon. The start and stop codons do necessarily have to be at the beginning and end, respectively, of the coding region.

As used herein, the term "culturing" is intended to mean the growth or maintenance of microorganisms under laboratory or industrial conditions. The culturing of microorganisms is a standard practice in the field of microbiology. Microorganisms can be cultured using liquid or solid media as a source of nutrients for the microorganisms. In addition, some microorganisms can be cultured in defined media, in which the liquid or solid media are generated by preparation using purified chemical components. The composition of the culture media can be adjusted to suit the microorganism or the industrial purpose for the culture.

As used herein, the term "endogenous polynucleotides" is intended to mean polynucleotides derived from naturally occurring polynucleotides in a given organism. The term "endogenous" refers to a referenced molecule or activity that is present in the host. Similarly, the term when used in reference to expression of an encoding nucleic acid or polynucleotide it refers to expression of the encoding nucleic acid or polynucleotide contained within the microbial organism.

As used herein, the term "exogenous polynucleotides" is intended to mean polynucleotides that are not derived from naturally occurring polynucleotides in a given organism. Exogenous polynucleotides may be derived from polynucleotides present in a different organism. The exogenous polynucleotides can be introduced into the organism by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. The term "heterologous" refers to a molecule or activity derived from a source other than the referenced species whereas "homologous" refers to a molecule or activity derived from the host microbial organism.

Accordingly, exogenous expression of an encoding nucleic acid of the invention can utilize either or both a heterologous or homologous encoding nucleic acid. As set forth in the invention a nucleic acid need not include all of its relevant or even complete coding regions on a single polymer and the invention provided herein contemplates having complete or partial coding regions on different polymers.

As used herein, the term "enzyme" is intended to refer to molecules that accelerate or catalyze chemical reactions. Almost all metabolic processes in the cell need enzymes in order to occur at rates fast enough to sustain life. Some of the enzymes useful in the invention are, without limitation, methanol dehydrogenase (EC 1.1.1.244 or 1.L99.37 or L1.2.7), alcohol dehydrogenase (EC 1.1.1.1 or 1.1.1.2 or 1.1.2.8 or 1.1.3.13), aldehyde dehydrogenase (EC 1.2.1.3), acetaldehyde dehydrogenase (EC 1.2.1.10), acetyl-CoA synthetase (EC 6.2.1.1), isocitrate lyase (EC 4.1.3.1), malate synthase (EC 2.3.3.9), isocitrate dehydrogenase kinase/phosphatase (EC 3.1.3.-), soluble methane monooxygenase (EC 1.14.13.25) and particulate methane monooxygenase (EC 1.14.18.3).

As used herein, the term "enzyme specificity" or "specificity of an enzyme" is intended to mean the degree to which an enzyme is able to catalyze a chemical reaction on more than one substrate molecule. An enzyme that can catalyze a reaction on exactly one molecular substrate, but is unable to catalyze a reaction on any other substrate, is said to have very high specificity for its substrate. An enzyme that can catalyze chemical reactions on many substrates is said to have low specificity. In some cases, the specificity of an enzyme is described relative to one or more defined substrates. With respect to the invention described herein, the specificity of a monooxygenase for methane (as the substrate) can be compared to that of another monooxygenase for methane by comparing the relative activities of the monooxygenases for methane against their relative activities against other substrates, such as ethane. In some cases, mutations to a monooxygenase can shift the enzyme specificity from preferring methane (i.e. having a higher activity for methane over ethane) to preferring ethane (i.e. having a higher activity for ethane over methane).

As used herein, the terms "ethanol-consuming organism", "ethylotroph", "ethylotrophic microorganism", "ethylotrophic organism", and "ethylotrophic" are intended to mean any organism that is able to convert ethanol (i.e. "ethyl alcohol", CH30H) into a chemical or into biomass or into molecules that the organism can use in its metabolic pathways which generate energy or reducing equivalents so that the organism can grow using ethanol as a sole carbon source or major carbon source and/or energy source. For example, some naturally-occurring microorganisms are known to consume ethanol by converting it first into acetaldehyde, and then subsequently converting the acetaldehyde into acetate. Acetate is often converted into acetyl-CoA, a central node of metabolism common to all organisms. Some microorganisms convert acetaldehyde directly into acetyl-CoA in a single step. Other pathways that enable organisms to assimilate ethanol into metabolism are also possible and this example is not meant to limit the invention to the above-mentioned assimilation pathway.

As used herein, the terms "ethanotroph", "ethane-consuming organism", "ethanotrophic organism", "ethanotrophic microorganism", and "ethanotrophic" are intended to mean a microorganism that can consume ethane as its major carbon source and/or as its sole energy and/or sole carbon source. In contrast, a "non-ethanotrophic microorganism" is one that is incapable of survival on ethane as a sole carbon source or major carbon source.

As used herein, the term "methanotroph" is intended to mean an organism that is capable of growth using methane as the sole or major carbon source.

As used herein, the term "synthetic ethylotroph" is intended to mean a non-ethanol-consuming microorganism that has been modified to be able to consume ethanol as its sole energy and/or sole carbon source and/or major carbon source. Some ethylotrophs are naturally occurring, while others, described here in this invention, are synthetic. Synthetic ethylotrophs are organisms that are capable of surviving on ethanol as a sole carbon source or major carbon source due to the addition of a pathway that allows the assimilation of ethanol. Modification may be a genetic modification such as one or more mutations to the microorganisms' nucleic acids, the introduction of an episomal plasmid, and/or the introduction of exogenous polynucleotides.

As used herein, the term "synthetic ethanotroph" is intended to mean a non-ethane consuming microorganism that has been modified to be able to consume ethane as its sole energy and/or sole carbon source and/or major carbon source. Some ethanotrophs are naturally occurring, while others, described herein, are synthetic. Synthetic ethanotrophs are organisms that are capable of surviving on ethane as a sole carbon source or major carbon source due to the addition of a pathway that allows the assimilation of ethane. Modification may be a genetic modification such as one or more mutations to the microorganisms' nucleic acids, the introduction of an episomal plasmid, and/or the introduction of exogenous polynucleotides.

As used herein, the terms "ethanol assimilation pathway" and "ethanol utilization pathway" are intended to mean at least one enzyme, or a group or set of enzymes, that enable an organism to convert ethanol into metabolites that the organism can use as a source of mass (carbon, oxygen and hydrogen atoms) and energy.

As used herein, the term "improved growth" is intended to mean a situation in which a microbial strain has been modified in some way, usually through genetic modification, so that, under the prescribed conditions and relative to the original strain, the modified strain grows at a faster rate or achieves a higher density of cells. A direct comparison of two strains can be made by growing the strains under identical conditions and measuring the optical density (e.g. absorbance at 600 nm, "OD600") or doubling rate at various times in the cell growth. One strain will demonstrate improved growth, relative to the other strain, if it is quantitatively growing faster (i.e. doubling more often) or to a measurably higher cell density. A quantitative measure at each time point, such as the ratio of the OD600 values of the two strains or the ratio of the doubling rates, can be used to identify and track strains with improved growth.

As used herein, the terms "microbe", "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "mutation" is intended to mean a change from one nucleotide to another in a DNA sequence or in a polynucleotide or a change from one amino acid to another in a protein sequence or in a polypeptide.

As used herein, the term "naturally occurring" is intended to mean normally found in nature.

As used herein, the term "non-naturally occurring" when used in reference to a microbial organism or microorganism of the invention is intended to mean that the microbial organism has at least one genetic alteration or addition not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions, and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes capable of oxidizing hydrocarbons, such as alkanes and aromatic compounds or enzymes within a methanol-consuming or methane-consuming pathway or enzymes within an ethanol consuming or ethane-consuming pathway.

As used herein, the term "single-cell protein" is intended to mean a source of mixed protein extracted from pure or mixed cultures of microorganisms. Single-cell protein is used as a substitute for protein-rich foods in human and animal feeds.

As used herein, the term "soluble diiron monooxygenase" is intended to mean the class of enzymes and enzyme complexes characterized by a catalytic core of two iron atoms and the ability to utilize molecular oxygen ($O_2$) to catalyze hydroxylation or epoxidation of hydrocarbon bonds. These enzymes typically require NADH or NADPH as an electron donor. The soluble diiron monooxygenases (SDIMOs) are usually composed of three or four components: a hydroxylase (itself composed of multiple subunits), an oxidoreductase subunit, a coupling protein, and sometimes a ferredoxin protein. The class contains at least enzymes belonging to the subclasses: soluble methane monooxygenases, phenol hydroxylases, toluene monooxygenases, and alkene monooxygenases (Leahy et al., *Evolution of the Soluble Diiron Monoxygenases*, FEMS Microbiology Reviews, Vol. 27., p. 449-479, 2003). Despite their different names, each SDIMO may be active against a range of substrates. For example, the soluble methane monooxygenase (sMMO) has been shown to oxidize dozens of different hydrocarbon substrates.

As used herein, the term "methane monooxygenase enzyme" is intended to mean the class of enzymes and enzyme complexes capable of oxidizing a carbon-hydrogen bond of the methane molecule to result in a molecule of methanol. Naturally occurring methane-consuming microorganisms have evolved at least two classes of methane monooxygenase enzymes: soluble and particulate. Any enzyme or enzyme complex of these categories, any mutated enzyme or complex, or any researcher-designed enzyme or enzyme complex that converts methane into methanol would be considered a methane monooxygenase enzyme. Many of these enzymes are known to also oxidize a wide range of substrates, such as methane to methanol or ethane into ethanol, and thus, are relevant for the purpose of this invention.

As used herein, the term "ethane monooxygenase enzyme" is intended to mean the class of enzymes and enzyme complexes capable of oxidizing a carbon-hydrogen bond of the ethane molecule to result in a molecule of ethanol. Any enzyme or enzyme complex of these categories, any mutated enzyme or complex, or any researcher-designed enzyme or enzyme complex that converts ethane into ethanol would be considered an ethane monooxygenase enzyme. Many of these enzymes are known to also oxidize a wide range of substrates, such as methane to methanol or ethane into ethanol or propane to propanol, and thus, are relevant for the purpose of this invention.

As used herein, the term "hybrid monooxygenase" or "hybrid SDIMO" is intended to mean an enzyme complex comprised of subunits from at least two different sources. Whereas a typical enzyme complex may be sourced from a single microorganism, it may be possible to swap in a particular subunit from a different microorganism and maintain catalytic activity. The source microorganisms may be closely related organisms, or not. If the subunits are somewhat homologous to each other, they may be interchangeable to some degree. This may lead to useful discoveries or enzyme properties. For example, the mmoX from one sMMO enzyme complex might be replaced from the mmoX from another, homologous sMMO enzyme.

As used herein, the term "dehydrogenase" is intended to mean an enzyme belonging to the group of oxidoreductases that oxidizes a substrate by a reduction reaction that removes one or more hydrogen atoms from a substrate to an electron acceptor. Acetaldehyde dehydrogenases are dehydrogenase enzymes which catalyze the conversion of acetaldehyde into acetic acid. Alcohol dehydrogenases are a group of dehydrogenase enzymes that occur in many organisms and facilitate the interconversion between alcohols and aldehydes or ketones with the reduction of nicotinamide adenine dinucleotide. As is relevant herein, alcohol dehydrogenase oxidizes methanol to formaldehyde and/or ethanol to acetaldehyde. Some enzymes, such as adhE from *E. coli*, can catalyze both the alcohol dehydrogenase and acetaldehyde dehydrogenase reactions.

As used herein, the term "pathway" is intended to mean a set of enzymes that catalyze the conversion of substrate chemical(s) into product chemical(s) using one or more enzymatic steps. Glycolysis is an example of a pathway in many living cells. In the context of this invention, a pathway may be a synthetic pathway (comprised of exogenous enzymes) or a partially synthetic pathway (comprised of both exogenous and endogenous enzymes).

As used herein, the term "percent identity", as it refers to a multi-subunit protein complex, is intended to mean the maximum value for the percent identity between any pair-wise combination of amino acid sequences, calculated between all the subunits in one complex measured against all the subunits in the second complex. The percent identity between two subunits can be calculated using publicly available computational tools, such as BLASTp from NCBI.

The terms "polynucleotide", "oligonucleotide", "nucleotide sequence", and "nucleic acid sequence" are intended to mean one or more polymers of nucleic acids and include, but are not limited to, coding regions, which are transcribed or translated into a polypeptide or chaperone, appropriate regulatory or control sequences, controlling sequences, e.g., translational start and stop codons, promoter sequences, ribosome binding sites, polyadenylation signals, transcription factor binding sites, termination sequences, regulatory domains and enhancers, among others. A polynucleotide, as used herein, need not include all of its relevant or even complete coding regions on a single polymer and the invention provided herein contemplates having complete or partial coding region on different polymers.

As used herein, the term "complementary nucleotide" refers to a nucleotide in which, when conditions permit the annealing or hybridization of nucleic acid strands to a polynucleotide of interest, anneals or hybridizes to the polynucleotide of interest.

As used herein, the term "homolog" or "homologous" are used to describe a nucleotide or protein sequence or part of a nucleotide or protein sequence that has a high similarity or identity to a respective nucleotide protein sequence disclosed herein. Homology is often manifested by significant similarity in nucleotide or amino acid sequence and almost always manifested in three-dimensional structure. Different organisms may have proteins that are homologous and certain positions in the respective proteins may have an equivalent position in homologous proteins. Homology and equivalence and conserved residues among different organisms may be identified by using computer programs such as BLAST, ClustalW or ClustalX, among others. If a specific residue in an amino acid sequence is disclosed herein, the invention is also meant to encompass residues in homologous proteins in different species where the proteins are determined to be equivalent at that position in those different species.

As used herein, the term "promoter" is intended to mean a fragment of DNA that initiates the process of transcription of when it is functionally linked or operatively linked to one or more gene(s), coding region(s), or open reading frame(s). In some cases, a promoter is functionally linked to exactly one gene, while in other cases a promoter may be functionally linked to more than one gene.

As used herein, "functionally linked" or "operatively linked" shall refer to a relationship between at least two fragments of nucleic acid when they are placed into a functional disposition with respect to each other. For example, a promoter or enhancer is operatively linked to a coding sequence if it affects the transcription of the sequence or a ribosome binding site is operatively linked to a coding sequence if it is positioned so as to facilitate translation. Generally, "functionally linked" or "operatively linked" means that DNA sequences being linked are contiguous or in a dispositional relationship that makes one or the other functional. Sequences do not, however, have to be contiguous to be operatively linked or functionally linked.

As used herein, the terms "protein folding chaperone" and "folding chaperone" and "chaperone" are intended to mean one or more proteins that improve the folding of polypeptide (amino acid) chains into 3-dimensional structures. Protein folding chaperones help their substrates, namely other proteins, to become properly folded and often more highly soluble. Since most proteins must be folded in a particular shape to be functional, the expression of protein folding chaperones can assist in the proper assembly of certain enzymes in a cell and thereby can result in an increase in the enzymatic activity of the substrate proteins.

As used herein, the term "subunit" shall mean a protein molecule which assembles or coassembles with other protein molecules to form a protein complex, or enzyme. In the case of the current disclosure, for example, without limitation, a monooxygenase enzyme may be composed of one or more of the following subunits: mmoB, mmoC, mmoD, mmoX, mmoY and/or mmoZ. The disclosure is intended to include some or all of the subunits from any microorganism or combination of microorganisms, as determined by one skilled in the art.

As used herein, the term "suitable conditions" is intended to mean any set of culturing parameters that provide the microorganism with an environment that enables the culture to consume the available nutrients. In so doing, the microbiological culture may grow and/or produce chemicals or byproducts. Culturing parameters may include, but not be limited to, such features as the temperature of the culture media, the dissolved oxygen concentration, the dissolved carbon dioxide concentration, the rate of stirring of the liquid media, the pressure in the vessel, etc.

As used herein, the term "sufficient period of time" is intended to mean at least a minimum amount of time required to allow microorganisms in the culture to produce a chemical of interest. Beyond the minimum, a "sufficient period of time" encompasses any amount of time that enables the culture to produce the chemical to a desired level. An industrial-scale culture may require as little as 5 minutes to begin production of detectable amounts of a chemical and some cultures can be productive for several months.

As used herein, the term "synthetic" is intended to mean a molecule or microorganism, for example, without limitation, that has been manipulated into a form not normally found in nature. For example, a synthetic microorganism shall include, without limitation, a microorganism that has been manipulated to overexpress a polypeptide or transformed to include and/or express a synthetic polynucleotide of interest. A synthetic polynucleotide shall mean a polynucleotide that has been manipulated, for example by moving segments, introducing or rearranging segments or introducing a mutation. A synthetic polypeptide shall mean an amino acid sequence that has been manipulated.

As used herein, the term "transporter" is intended to mean a component of the cell that regulates the passage of a chemical, small molecule, or protein across a biological membrane.

As used herein, "variant" shall mean an amino acid sequence or a nucleotide sequence that has been modified wherein the resulting modified polypeptide and/or nucleotide sequence still has substantially the same function, performs its function in substantially the same way and/or achieves the same result. Variants of the polypeptides disclosed herein shall mean, for example without limitation, one or more differences or variations between the polypeptides disclosed herein and the polypeptide of interest.

Enzymes are useful catalysts for performing chemical reactions.

Chemistry is fundamentally about efficiently rearranging atoms from one molecule into another. Biological enzymes that can perform chemical reactions are useful tools for a range of applications, such as the fermentative production of chemicals, pharmaceutical manufacturing, and environmental bioremediation of toxic molecules. Some enzymes are capable of catalyzing reactions that are difficult (or expensive, or energy-intensive, or hazardous, or use environmentally unfavorable catalysts, etc.) for traditional bulk chemistry. A low-cost, low-energy, low-impact method of catalysis is a significant advance.

Carbon-hydrogen bonds are highly stable.

The bond between a carbon atom and a hydrogen atom in an organic compound is one of the most stable and difficult to break bonds. The bond is non-polar and has a bond dissociation energy around 100 kcal/mol, depending on the other atoms and bonds in its immediate surroundings.

Chemical methods for oxidizing carbon-hydrogen bonds are energy intensive and wasteful.

In order to combine organic compounds with each other, chemists have long sought an efficient technique for activating the carbon-hydrogen bond for a range of substrates, from simple alkanes such as methane, ethane and propane, up through aromatic compounds, like naphthalene. Some of these types of reactions can be done using halide chemistry, but those methods are wasteful, energy-intensive, and non-specific. Other chemical reactions on hydrocarbons, such as Fischer-Tropsch, are also very energy-intensive and must operate at high temperatures.

Nature has evolved monooxygenase enzyme complexes to oxidize organic compounds.

Hydrocarbons are rich in energy and microorganisms have evolved pathways to consume them as sources of carbon atoms and energy. Bacteria that can consume methane as a sole carbon source are called methanotrophs. A great deal of scientific research has focused on these bacteria and the pathways they use to assimilate methane. The enzyme complexes that activate methane belong to one of two classes: the particulate (membrane-bound) methane monooxygenase (pMMO) or the soluble methane monooxygenase (sMMO). Both enzymes oxidize methane to methanol. In the course of studying these complicated enzymes, researchers discovered that pMMO was capable of oxidizing some other short hydrocarbons (such as ethane, propane, butane, ethylene, propylene, etc.) while sMMO was capable of oxidizing a wide range of hydrocarbons. (Vazquez-Duhalt and Quintero-Ramirez, Petroleum Biotechnology, 2004).

Some microorganisms have been discovered that cannot consume methane, but instead can assimilate other hydrocarbons, such as ethane, propane, butane, and so on. Though there are some variations, enzymes active against short alkanes frequently appear evolutionarily related to the sMMO. Some researchers have thus classified them by their structure as soluble diiron monooxygenases (SDIMOs). Their structure is characterized by a hydroxylase unit (often composed of 2 or 3 polypeptide subunits), a reductase, and sometimes a ferredoxin and a helper protein.

Functional heterologous expression of monooxygenase enzymes in industrial hosts is an important tool for biotechnology.

The SDIMOs are an important enzyme class for biotechnology because they catalyze a difficult chemical reaction: the oxidation of a carbon-hydrogen bond or of a carbon-carbon double bond. Most industrially useful biotechnology processes are conducted in genetically tractable model organisms, such as *Escherichia coli, Corynebacterium glutarnicurn, Bacillus subtilis, Saccharornyces cerevisiae, Pichia pastoris*, and others. None of these organisms has enzymes for oxidizing short alkanes or many other hydrocarbons. The functional heterologous expression of an SDIMO in these organisms would enable a range of applications. In particular, the wide substrate acceptance range of SDIMOs will provide new connections for metabolic engineering of these valuable organisms. For example, the sMMO from methanotrophic bacteria has, so far, been shown to accept at least 50 unique substrates, which are summarized in Table 1. Given the wide range of substrates that have been found to be hydroxylated by this enzyme, it is likely that the list is incomplete. As additional substrates are tested, this list will likely grow and as such, Table 1 is not meant to be limiting, but instead exemplary of the many substrates of this class of enzymes.

TABLE 1

List of substrates and products that have been positively identified as being catalyzed by sMMO (Vazquez-Duhalt and Quintero-Ramirez, Petroleum Biotechnology, 2004; Green and Dalton, Substrate Specificity of Soluble Methane Monooxygenase, J. Biol. Chem., Vol. 264 No. 30, pp. 17698-17703, 1989; BRENDA online database http://www.brenda-enzymes.org/enzyme.php?ecno=1.14.13.25):

| COLUMN A Substrate | COLUMN B Product(s) |
|---|---|
| methane | methanol |
| ethane | ethanol |
| propane | propan-1-ol, propan-2-ol |
| butane | butan-1-ol; butan-2-ol |
| pentane | pentan-1-ol; pentan-2-ol |
| hexane | hexan-1-ol; hexan-2-ol |
| heptane | heptan-1-ol; heptan-2-ol |
| octane | octan-1-ol; octan-2-ol |
| 2-methylpropane | 2-methylpropan-1-ol; 2-methylpropan-2-ol |
| 2,3-dimethylpentane | 3,4-dimethylpentan-2-ol |
| ethane | epoxyethane |
| propene (propylene) | 1,2-epoxypropane; propylene oxide |
| but-1-ene | 1,2-epoxybutane |
| cis-but-2-ene | cis-2,3-epoxybutane; cis-2-buten-1-ol, 2-butanone |
| trans-hut-2-ene | trans-2,3-epoxybutane; trans-2-buten-1-ol |
| cyclohexane | cyclohexanol |
| methylene cyclohexane | 1-cyclohexane-l-methanol; methylenecyclohexane oxide; 4-hydroxymethylene cyclohexane |
| -pinene | 6,6-dimethylbicyclo[3.1.1]hept-2-ene-2-methanol; -pinene oxide |
| adamantane | 1-adamantol; 2-adamantol |
| cis-1,4-dimethylcyclohexane | 1-cis-4-dimethylcyclohexanol; 1-trans-4-dimethylcyclohexanol; cis-2,5-dimethylcyclohexanol |
| cis-1,3-dimethylcyclohexane | 3,5-dimethylcyclohexanol; 1-cis-3-dimethylcyclohexanol; 1-trans-3-dimethylcyclohexanol |
| trichloroethene | formate; CO; glyoxyl ate; dichloroacetate; chloral |
| vinyl chloride | |
| 1,1-dichloroethene | glycolate; dichloroacetaldehyde |
| trifluoroethylene | glyoxylate; difluoroacetate; fluoral |
| chlorotrifluoroethylene | oxalate |

TABLE 1-continued

List of substrates and products that have been positively identified as being catalyzed by sMMO (Vazquez-Duhalt and Quintero-Ramirez, Petroleum Biotechnology, 2004; Green and Dalton, Substrate Specificity of Soluble Methane Monooxygenase, J. Biol. Chem., Vol. 264 No. 30, pp. 17698-17703, 1989; BRENDA online database http://www.brenda-enzymes.org/enzyme.php?ecno=1.14.13.25):

| COLUMN A Substrate | COLUMN B Product(s) |
|---|---|
| tribromoethylene | formate; bromal |
| benzene | phenol, cyclohexanol, hydroquinone |
| toluene | benzyl alcohol; 4-cresol |
| ethylbenzene | 1-phenylethanol; 3-ethylphenol; 4-ethylphenol; 4-hydroxyethylbenzene |
| styrene | styrene oxide; styrene epoxide |
| pyridine | pyridine N-oxide |
| naphthalene | 1-naphthol; 2-naphthol |
| biphenyl | 2-hydroxybiphenyl; 3-hydroxybiphenyl; 4-hydroxybiphenyl |
| 2-hydroxybiphenyl | dihydroxybiphenyls |
| 2-methylbiphenyl | ring and sidechain hydroxylated products |
| 2-chlorobiphenyl | hydroxychlorobiphenyls |
| 2-bromobiphenyl | hydroxybromobiphenyls; 2-hydroxybiphenyl |
| 2-iodobiphenyl | hydroxyiodobiphenyls; 2-hydroxybiphenyl |
| chloromethane | formaldehyde |
| dichloromethane | carbon monoxide |
| bromomethane | |
| nitromethane | |
| methanethiol | |
| methanol | |
| diethyl ether | ethanol; acetaldehyde |
| carbon monoxide | carbon dioxide |
| cyclohexene | epoxycyclohexane; 2-cyclohexen-l-ol |
| dimethyl ether | methanol; formaldehyde |
| difluoromethane | difluoromethanol |
| fluorobenzene | fluorophenol |
| fluoromethane | fluoromethanol |
| isopentane | 2-methylbutan-1-ol; 3-methylbutan-1-ol; 2-methylbutan-2-ol; 3-methylbutan-2-ol |
| methyl amine | hydroxymethylamine |
| methylcyanide | hydroxymethylcyanide |
| nitrobenzene | nitrophenol |
| phenylalanine | tyrosine |
| xylene | xylenol |

Monooxygenases will allow industrial biotechnology to use less expensive raw materials for the manufacture of many commercially available chemicals.

One particularly valuable application of SDIMO expression in industrial biotechnology is the utilization of low cost raw materials for the production of commodity and specialty chemicals. Recent advances in technologies for the extraction of natural gas have flooded the market with low-cost short gaseous alkanes. These gases (methane, ethane, etc.) could be used as a feedstock for a wide range of fermentation-derived chemicals. The functional expression of SDIMOs in industrial hosts, such as *E. coli* and yeast, provides a key catalytic step that will enable a complete pathway from the inexpensive feedstock (i.e. methane, ethane, etc.) into central metabolism, from which a myriad of industrial chemicals can be produced at lower cost. Another application may be the repurposing of low value fractions of petroleum. SDIMOs may be able to perform the difficult first step of adding a useful chemical handle onto the hydrocarbon that can be used by subsequent enzymes or can be passed to a chemical reactor or may be a product in itself.

Soluble methane monooxygenases and other SDIMOs are highly promiscuous enzymes that can catalyze many chemical reactions.

One of the most well-studied SDIMOs is the sMMO from *Methylococcus capsulatus* (Bath). Studies of sMMO in vitro have identified many key aspects of its structure, biochemical mechanism, and substrate specificity. Remarkably, this enzyme is able to hydroxylate a large number of substrates. As summarized in *Petroleum Biotechnology* by Vazquez-Duhalt and Quintero-Romero in 2004, sMMO is able to hydroxylate dozens of substrates into an even larger number of products, when assayed in vitro. Other SDIMOs have evolved different substrate specificities. For example, the butane monooxygenase of Thauera butanivorans is most active on butane, and maintains some activity against shorter alkanes. Another example is toluene-4-monooxygenase from *Pseudomonas mendocina* KR1. This enzyme is evolutionarily-related to sMMO, but has significantly higher activity against aromatic hydrocarbon substrates.

Heterologous expression of monooxygenase enzymes has been limited.

Several attempts over the last 25 years to express the complete sMMO in *E. coli*, primarily with the intention of easing the purification procedure of the enzyme, have been unsuccessful. Though proteins B and C have been purified from *E. coli* and shown to be functional (West et al., *Functional Expression in Escherichia coli of Proteins B and C from Soluble Methane Monooxygenase of Methylococcus capsulatus* (*Bath*), J. General Microbiology, Vol. 138, p. 1301-1307, 1992), the remaining subunits have been notoriously difficult to express (Lloyd et al., *Heterologous expression of soluble methane monooxygenase genes in methanotrophs containing on particulate methane monooxygenase*, Arch. Microbiol., Vol. 171, p. 364-370, 1999; Smith et al., *Improved system for protein engineering of the*

*hydroxylase component of soluble methane monooxygenase*, Appl. Env. Micro., Vol. 68 No. 11, p. 5265-73, 2002; Nichol et al., *Controlling the activities of the diiron centre in bacterial monooxygenases: lessonsfrom mutagenesis and biodiversity*, Eur. J. Inorg. Chem., p. 3419-31, 2015). In fact, researchers wishing to isolate the sMMO enzyme for in vitro or mechanistic studies have devised complicated methods to express mutants in the native host, in order to specifically circumvent the problematic expression of the functional enzyme in a heterologous host (Ali and Murrell, *Development and validation of promoter probe vectors for the study of methane monooxygenase gene expression in Methylococcus capsulatus Bath*, Microbiology, vol. 155, p. 761-'71, 2009; Smith et al., *Improved system for protein engineering of the hydroxylase component of soluble methane monooxygenase*, Appl. Env. Micro., Vol. 68 No. 11, p. 5265-73, 2002; Nichol et al., Controlling the activities of the diiron centre in bacterial monooxygenases: lessons from mutagenesis and biodiversity, Eur. J. Inorg. Chem., p. 3419-31, 2015).

The invention described below is the first reported functional heterologous expression of the soluble methane monooxygenase in an industrially-relevant microorganism.

The examples below describe the first successful demonstration of the sMMO expressed in microorganisms that are commonly used in industrial biotechnology. The invention is drawn to the expression of an SDIMO enzyme in a heterologous host microorganism. In one embodiment, the host microorganism is at least one of *Escherichia coli, Bacillus subtilis, Bacillus methanolicus, Pseudomonas putida, Saccharomyces cerevisiae, Pichia pastoris, Pichia methanolica, Salmonella enterica, Corynebacterium glutamicum, Klebsiella oxytoca, Anaerobiospirillum succiniciproducens, Actinobacillus succinogenes, Mannheimia succiniciproducens, Rhizobium etli, Gluconobacter oxydans, Zymomonas mobilis, Lactococcus lactis, Lactobacillus plantarum, Streptornyces coelicolor, Clostridium acetobutylicum, Pseudomonas fluorescens, Schizosaccharomyces pombe, Kluyveromyces lactis, Kluyveromyces marxianus, Aspergillus terreus, Aspergillus niger*, and *Candida utilis*. In an embodiment, the microorganism is *Escherichia coli*. In an embodiment, the microorganism is *Pichia pastoris*. In an embodiment, the microorganism is *Saccharomyces cerevisiae*. In an embodiment, the microorganism is *Corynebacterium glutamicum*. In an embodiment, the microorganism is *Bacillus methanolicus*. In another embodiment, the SDIMO enzyme is more than about 80% homologous (at the amino acid sequence level) to the SDIMOs found in the microorganisms *Pseudomonas mendocina* KR1, *Methylosinus trichosporium* OB3b, *Methylomonas methanica, Methylococcus capsulatus* (Bath), *Methylocella silvestris, Methylocaldurn* sp. 175, *Methyloferula stellata, Methylocystis* LW5, *Solimonas aquatica* (DSM 25927), *Methylovulum miyakonense, Mycobacterium chubuense* NBB4, *Mycobacterium smegmatis* mc2-155, *Thauera butanivorans, Pseudonocardia* TY-7, *Pseudonocardia autotrophica, Amycolatopsis methanolica, Rhodococcus ruber* IGEM 231, and *Conexibacter woesei*. In an embodiment, the SDIMO is a soluble methane monooxygenase. In an embodiment, the SDIMO is an ethane, propane, or butane monooxygenase. In an embodiment, the SDIMO is a soluble methane monooxygenase expressed in a microorganism that is at least one of *Escherichia soli, Saccharomyces cerevisiae, Pichia pastoris, Bacillus methanolicus*, and *Corynebacterium glutamicum*. In an embodiment, the SDIMO is neither the mimABCD from *Mycobacterium smegmatis* mc2-155 nor the toluene-4-monooxygenase from *Pseudomonas mendocina* KR1 expressed in the microorganism *Escherichia coli*. In an embodiment, the SDIMO is the sMMO from *Methylococcus capsulatus* (Bath) expressed in the microorganism *Escherichia coli*. In an embodiment, the SDIMO is expressed in the microorganism along with the expression of at least one protein that improves the folding or solubility of the SDIMO subunits or the SDIMO complex. In an embodiment, the SDIMO is a hybrid enzyme wherein each polypeptide subunit may not be derived from a single SDIMO enzyme complex from a single microorganism.

This is a major advance for biotechnology as it opens the door to additional metabolic engineering for the production of chemicals from inexpensive feedstocks in an environmentally-friendly manner.

Ethane is an Ideal Raw Material for Chemical Production

An ethane-consuming industrial microorganism may produce fuels and commodity chemicals that are impossible to profitably generate using sugar. Ethane is an ideal feedstock for fuel and chemical production due to its low cost, high energy density, abundance in the US, and year-round availability. On a per carbon basis, ethane is significantly cheaper than sugar. Ethane is a useful feedstock in the chemicals industry already, and thus, there is an established infrastructure and industrial experience with ethane as a feedstock.

Advantages of Ethane Over Methane as a Feedstock

Methane is an excellent feedstock, as well, for industrial fermentations, for many of the same reasons above. Recently, their cost has been approximately the same. However, there are significant advantages to ethane over methane, in many cases. First, ethane is assimilated into central metabolism at acetyl-CoA directly, whereas methane is assimilated through the pentose-phosphate pathway ultimately generating one glycolysis intermediate (e.g. DHAP) for each 3 methane molecules. Thus, some products that are made from DHAP, for example, may be more efficient to make from methane; however, many products are made through the acetyl-CoA node, and these would be perfect candidates for an ethane-fed fermentation. This also avoids the loss of a CO2 molecule between pyruvate and acetyl-CoA, conserving carbon atoms and improving the carbon emissions profile of the fermentation. Second, it's more efficient for carbon to be assimilated in 2-carbon units, rather than 1-carbon units, since building carbon-carbon bonds is difficult and energy-intensive. Third, more of the standard microorganisms of industrial biotechnology already (without further modification) can consume ethanol aerobically, while only a subset of organisms, such as *Pichia pastoris* and the lesser-used *Bacillus methanolicus*, can consume methanol.

Advantages of Developing Synthetic Ethanotrophic Microorganisms

Several microorganisms have received the majority of study by microbiologists and metabolic engineers over the past few decades. These model organisms, *Escherichia coli, Saccharomyces cerevisiae, Clostridium acetobutylicum, Corynebacterium glutamicum, Pichia pastoris, Bacillus subtilis, Psuedomonas putida*, and *Chlorella* protothecoides, are the host cells that provide the most flexible, well-understood, genetically tractable starting points for further engineering. A range of tools and techniques has been developed to iteratively construct and evaluate modified derivatives of these strains. The invention of any new core functionality, such as the ability to consume ethane, in any of these strains is a significant achievement. A modular genetic component, or set of components, to consume ethane may be combined with existing engineered strains to produce a range of industrial products. Several of these strains are naturally capable of consuming ethanol as a sole or major carbon and energy source, as we have observed ourselves. Such microorganisms are already in industrial use as engineered biocatalysts, turning carbohydrates into a range of biological and chemical products. The ability to engineer these strains further to broaden their feedstock options to include ethane will be a valuable product in itself. Since ethane is one of the least-expensive carbon-based feedstocks, chemical producers, for instance, would prefer to feed ethane to their fermentations.

Pathways for Ethane Assimilation

Ethane can be utilized by some naturally occurring microorganisms as the sole carbon and energy source. So far, all known ethanotrophic microorganisms first oxidize the ethane to ethanol. The enzyme that performs this chemistry belongs to one of a few classes of monooxygenase enzymes (described herein). Thus, for most organisms (that can assimilate ethanol), the task of engineering ethane assimilation primarily (though not exclusively) focuses on achieving functional heterologous expression of at least one of the monooxygenase enzymes.

Enzymes that Transform Ethane

Under aerobic conditions, ethanotrophs fix ethane into central metabolism by first oxidizing ethane to ethanol, and then by converting ethanol into acetyl-CoA, via acetaldehyde. The biochemistry of the first step (ethane to ethanol) is carried out by one of a set of monooxygenase enzymes. Some utilize a soluble enzyme complex, while others utilize a membrane-bound "particulate" monooxygenase (N V Coleman et al., *Hydrocarbon monooxygenase in Mycobacterium: recombinant expression of a member of the ammonia monooxygenase superfamily,* 6 The ISME Journal 171-182, 2012). For natural methanotrophs, scientists have shown (J Green & H Dalton, *Substrate specificity of soluble methane monooxygenase. Mechanistic implications.,* 264 Journal of Biological Chemistry 17698-17703, 1989) that their methane monooxygenase (MMO) enzymes will also oxidize ethane (in addition to methane) Meanwhile, some non-methanotrophic microorganisms are capable of growth on ethane, propane, and butane, but not methane (M C Redmond et al., *Identification of novel methane-, ethane-, and propane-oxidizing bacteria at marine hydrocarbon seeps by stable isotope probing,* 76 Applied and Environmental Microbiology 6412-6422, 2010). These two enzyme types are generally quite closely related by evolution, despite their differences in substrate specificity. Some such propane-oxidizing or butane-oxidizing bacteria have been discovered, such as *Mycobacterium smegmatis* mc2-155, *Gordonia* TY-7 and *Thauera butanivorans*. Yet another class of monooxygenases is the P450 enzymes. Some of these have been engineered using directed evolution to oxidize ethane, though the natural substrate specificity was quite different (F Xu et al., *The Heme Monooxygenase Cytochrome P*450, 4029¬4032, 2005); (P Meinhold et al., *Direct Conversion of Ethane to Ethanol by Engineered Cytochrome,* 0017 1765-1768, 2005)

Prior Work Expressing Monooxygenases in *E. coli* and *S. cerevisiae*

There are no reports of successful ethane oxidation in vivo in the model organisms *E. coli* and *S. cerevisiae*. Though some of the MMO components have been expressed in *E. coli*, these components did not assemble into a functional MMO enzyme complex (C A West et al., *Functional expression in Escherichia coli of proteins B and C from soluble methane monooxygenase of Methylococcus capsulatus* (*Bath*), 138 Journal of general microbiology 1301-1307, 1992). The heterologous expression of alkane monooxygenases with longer chain specificity has mostly failed, with a few exceptions in which the source organism is closely related to the expression host. A toluene 4-monooxygenase (T4MO) was reported to have been functionally expressed in *E. coli*. (K Canada et al., *Directed Evolution of Toluene ortho-Monooxygenase for Enhanced 1-Naphthol Synthesis and Chlorinated Ethene Degradation Directed Evolution of Toluene ortho-Monooxygenase for Enhanced 1-Naphthol Synthesis and Chlorinated Ethene Degradation,* 184 344-349, 2002). Toluene is a rather different substrate than ethane, but the genomic structure of the T4MO operon suggests evolutionary conservation between T4MO and sMMO, so it is worthy of note. A second interesting report of a monooxygenase expressed in a new host came from an experiment in which a pMMO enzyme was apparently expressed in *Rhodococcus erythropolis* in 2006 and functional at a very slow rate (Z Gou et al., *Functional expression of the particulate methane monooxygenase gene in recombinant Rhodococcus erythropolis,* 263 FEMS Microbiology Letters 136-141, 2006). *R. erythropolis* is a remarkable strain with a very wide range of endogenous monooxygenases (C de Carvalho, *The remarkable Rhodococcus erythropolis,* 715-726, 2005). No additional reports have confirmed this original publication. A phenol hydroxylase enzyme and its chaperonin was refactored and successfully expressed in *E. coli* (T Furuya et al., *Reconstitution of active mycobacterial binuclear iron monooxygenase complex in Escherichia coli,* 79 Applied and Environmental Microbiology 6033-6039, 2013). Despite all this work, no group has reported a standard industrial microorganism having been engineered to consume methane or ethane or to convert methane, ethane or ethanol into a commercial product.

Many Industrial Chemical Classes are Possible Commercial Products

Over the last few decades, several companies have successfully commercialized or developed microorganisms capable of producing industrial chemicals from sugar feedstocks. These projects would benefit from reduced feedstock costs, such as being able to use ethane instead of sugar. Products currently developed include, but are not limited to, malic acid, fumaric acid, succinic acid, malic acid salt, fumaric acid salt, succinic acid salt, L-malic acid, D-malic acid, maleic acid, lactic acid, adipic acid, 1,3-propanediol, 2,3-butanediol, 1,4-butanediol, butadiene, fatty acid derivatives, fatty alcohols, fatty acids, fatty acid esters, fatty acid methyl esters, fatty acid ethyl esters, branched fatty acids, branched fatty acid derivatives, omega-3 fatty acids, isoprenoids, farnesene, farnesane, squalene, squalane, carotenoids, amino acids, alanine, arginine, asparagine, aspartic acid, cysteine, glutamic acid, monosodium glutamate, glutamine, glycine, histidine, isoleucine, leucine, lysine, methionine, phenylalanine, threonine, tryptophan, valine, ornithine, proline, selenocysteine, serine, tyrosine, ethanol, propanol, 1-butanol, 2-butanol, isobutanol (2-methylpropan-1-ol), alcohols, alkanes, alkenes, olefins, animal feed additives, mixtures of amino acids, and others.

In an embodiment, the monooxygenase is not a toluene 4-monooxygenase when the microorganism is *Escherichia coli*. In an embodiment, the methane monooxygenase is not from *Methylococcus capsulatus* when the microorganism is *Escherichia coli*. In an embodiment, the monooxygenase is not a methane monooxygenase from *Methylococcus capsulatus* when the MMOC, MMOB, MMOX, MMOY, and MMOZ subunits are expressed in *Escherichia coli*. In an embodiment, the monooxygenase is not a methane monooxygenase from *Methylococcus capsulatus* when the MMOC, MMOB, MMOX, MMOY, and MMOZ subunits are expressed in *Escherichia coli* when the chaperones GroEL and GroES from *Escherichia coli* are overexpressed. In an embodiment, the monooxygenase is not a methane monooxygenase from *Methylococcus capsulatus* when the MMOC, MMOB, MMOX, MMOY, and MMOZ subunits are expressed in *Escherichia coli* when the chaperones GroEL and GroES from *Escherichia coli* are overexpressed from a plasmid. In an embodiment, the monooxygenase is not a methane monooxygenase from *Methylococcus capsulatus* when the MMOC, MMOB, MMOX, MMOY, and MMOZ subunits are expressed in *Escherichia coli* when the chaperones GroEL and GroES from *Escherichia coli* are overexpressed from a plasmid for use in an anaerobic atmosphere. In an embodiment, the monooxygenase is not a methane monooxygenase from *Methylococcus capsulatus* when the MMOC, MMOB, MMOX, MMOY, and MMOZ subunits are expressed in *Escherichia coli* when the chaperones GroEL and GroES from *Escherichia coli* are overexpressed from a plasmid for use in a cow's rumen. In an embodiment, the monooxygenase is not the monooxygenase genes from *Methylococcus capsulatus* when transferred into the pSBA1A3 vector.

In an embodiment, the monooxygenase is not the methane monooxygenase from either *Methylococcus capsulatus* or *Methylosinus trichosporium* OB3b when expressed in *Methylocystis Parvus* OBBP or *Methylomicrobium* album BG8. In an embodiment, the monooxygenase is not the soluble methane monooxygenase from *Methylosinus trichosporium* OB3b when expressed in *Methylocystis Parvus* OBBP. In an embodiment, the monooxygenase is not the monooxygenase from either *Methylococcus capsulatus* or *Methylosinus trichosporium* OB3b when expressed in *Methylomicrobium* album BG8 in low copper to biomass ratios.

In an embodiment, the synthetic microorganism is not an *Escherichia coli* with a mutation at position 267 of the adhE gene as set forth in SEQ ID NO: 49. In an embodiment, the synthetic microorganism is not *Escherichia coli* with a mutation of a T for an A at position 267 and a K for an E at position 568 of the adhE gene as set forth in SEQ ID NO: 49.

In an embodiment, the monooxygenase is not an actinomycetes monooxygenase when expressed in *Escherichia coli*, especially when expressed with the GroEL-like protein MimG. In an embodiment, the monooxygenase is not the methane monooxygenase from either *Mycobacterium smegmatis* or *Mycobacterium* goodii when expressed in *Escherichia coli* with the GroEL-like protein MimG. In an embodiment, the monooxygenase is not the methane monooxygenase from either *Mycobacterium smegmatis* or *Mycobacterium* goodii when expressed in *Escherichia coli* with the GroEL-like protein MimG; wherein the mimB and/or mimD gene has or have been optimized for expression in *Escherichia coli.*

EXAMPLES

Example 1. Active Soluble Diiron Monooxygenase Converts Ethane to Ethanol

This example describes a strain and method for culturing a strain to produce ethanol from an ethane feedstock.

Yeast strains have been used to produce ethanol in fermentations of sugar for thousands of years. As such, there are numerous strains of yeast that have been identified to tolerate high levels of ethanol. Ethanol is a commercially useful product for a range of applications including cleaning products and transportation fuels.

The techniques for constructing a yeast strain that is expressing a heterologous enzyme, enzyme complex, or multiple enzymes or enzyme complexes have been described elsewhere herein. Briefly, each gene is expressed from a unique promoter. The gene can be expressed from a plasmid or from a chromosomal locus. In some cases, additional proteins may assist in the folding or assembly of the enzyme or enzyme complex.

The ethane monooxygenase may be selected from Table 16. Any additional genetic elements may be identified as described herein and expressed in a similar manner A yeast strain expressing a functional ethane monooxygenase is capable of converting ethane into ethanol. While under certain conditions, the yeast strain may consume the ethanol as a carbon or energy source; under other conditions, the yeast strain may overproduce the ethanol and secrete it into the culture medium.

This strain may be cultured in a minimal media containing glucose (or other sugars or starches), glycerol, ethanol or ethane as the carbon and energy source. After the strain has reached a sufficient cell density in the culture, the culture can be switched into a minimal media containing no carbon source and these cells can be used to perform a bioconversion of ethane into ethanol by providing ethane in the headspace. Alternatively, the strain can be cultured in a bioreactor in which the ethane (and other gases, such as oxygen) can be continuously bubbled or sparged.

Once the ethanol is produced in sufficient quantity, it can be separated in batch or continuously by methods such as distillation or evaporation.

Though this example describes an example of producing ethanol from ethane in a yeast strain, such as *Saccharomyces cerevisiae* or *Pichia pastoris*, there is not much difference, in principle, from using another strain, such as a bacterial strain like *Escherichia coli* or *Bacillus subtilis*, to produce ethanol. In any case, an important factor is the ethanol tolerance of the strain. Various strains, such as *E. coli*, have been engineered or adapted to higher levels of ethanol tolerance (H Chong et al., *Improving Ethanol Tolerance of Escherichia coli by Rewiring Its Global Regulator cAMP Receptor Protein* (*CRP*), 8 PLoS ONE 1-9, 2013); (L H Luo et al., *Improved ethanol tolerance in Escherichia coli by changing the cellular fatty acids composition through genetic manipulation.*, 31 Biotechnology letters 1867-1871, 2009), and these general procedures may be applied to other microbiological strains as well.

This part of the example describes work actually performed that describes a strain and method for culturing a strain to produce ethanol from an ethane feedstock.

The techniques for constructing an *E. coli* strain that expresses a heterologous enzyme, enzyme complex, or multiple enzymes or enzyme complexes have been described above and elsewhere. In this example, an enzyme capable of oxidizing ethane to ethanol was expressed from an inducible promoter on a plasmid in an *E. coli* strain and shown to convert ethane to ethanol.

The strain NH283 was constructed by the deletion of a region of DNA from the *E. coli* genome that contains the genes araBAD using the method of Datsenko and Wanner (K. Datsenko and B. Wanner, *One-step inactivation of chromosomal genes in Escherichia coli K*-12 *using PCR Products*, Proceedings of the National Academy of Sciences, Vol 97, Issue 12, p. 6640-5, 2000). Homology sequences were amplified from *E. coli* genomic DNA using primers LC95/LC96 (SEQ ID NO:3, SEQ ID NO:4) and LC97/LC98 (SEQ ID NO: 5, SEQ ID NO: 6). The antibiotic resistance gene cat was amplified from pKD3 using LC93/LC94 (SEQ ID NO: 1, SEQ ID NO: 2). These fragments were combined in a single tube and assembled using overlap extension PCR ("SOEing") with the outside primers LC96/LC98. Transformants were isolated on agar plates containing 17 ug/mL chloramphenicol and confirmed by colony PCR. NH283 was chosen as one of these clones to use in subsequent experiments.

Two plasmids were made, each of which contains the genes for the sMMO from *M. capsulatus* (Bath). The genomic region that contains the operon that expresses mmoX, mmoY, mmoB, mmoZ, mmoD, mmoC, hypothetical protein, mmoG, was amplified by PCR from *M. capsulatus* (Bath) genomic DNA. This region was Gibson-cloned (D. Gibson et al., *Enzymatic assembly of DNA molecules up to several hundred kilobases*, NATURE METHODS Vol 6, Issue 5, p. 343-345, 2009) behind either the arabinose-inducible pBAD promoter or the IPTG-inducible pTRC promoter in a plasmid with a p15A origin and also a gene for kanamycin resistance. The plasmids were sequence-confirmed by Sanger sequencing to contain the expected DNA sequence (listed in SEQ ID NO:19 and SEQ ID NO:26 below). The plasmids were separately transformed into strain NH283 (Table 2).

volume of 60 mL of either ethane or air was measured into syringes and injected through the stopper and into each of the two bottles. The bottles were shaken at 37° C. for 7 days, at which point the supernatant was sampled in order to measure ethanol concentration.

Figure 2:
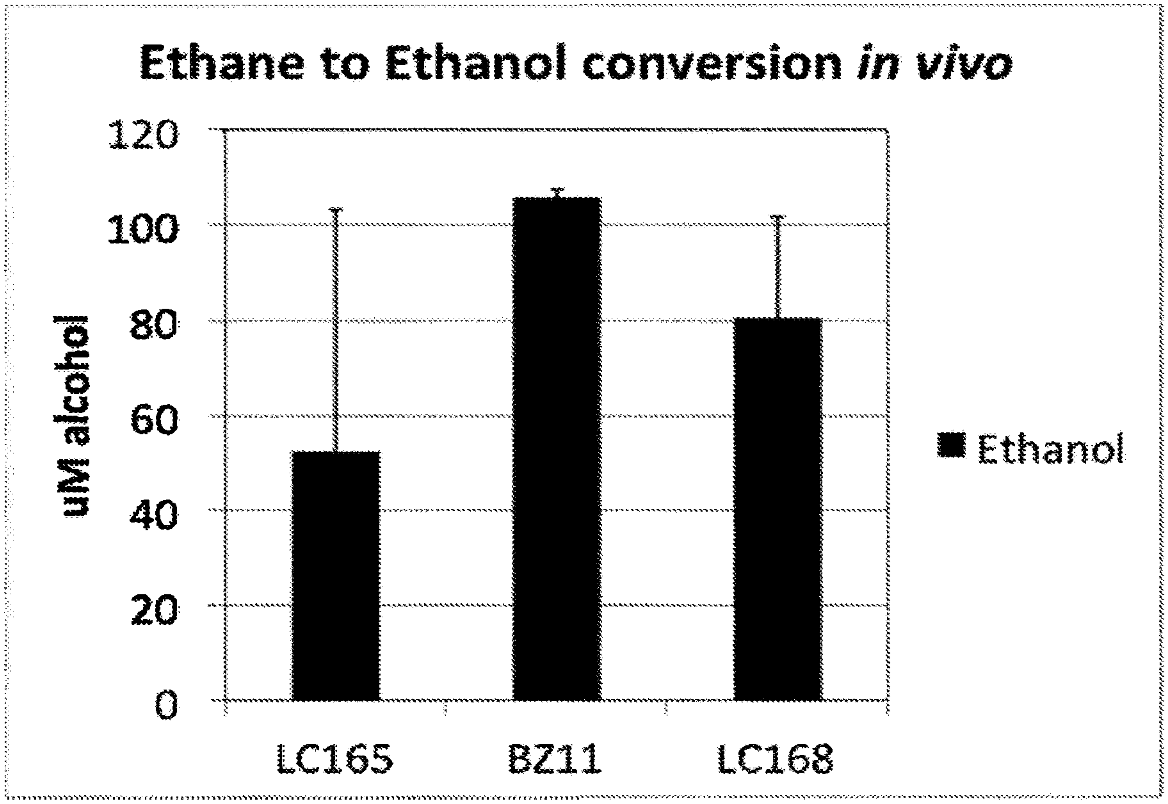
FIG. 2 shows the comparison of the amount of ethanol generated in three strains: LC165 (control), BZ11 (inducible sMMO converting ethane to ethanol), and LC168 (inducible sMMO converting ethane to ethanol).

Ethanol was measured using a colorimetric assay (Cell Biolabs catalog number STA-620). Briefly, it measures ethanol using an enzymatic reaction that produces hydrogen peroxide, which reacts with a colorimetric probe. 90 μL of a reaction mixture was combined with 10 μL of sample, and incubated at 37° C. for 30 minutes. The composition of the assay mixture is described in Table 3. The absorbance at 570 nm was compared to a standard curve, and ethanol in each sample was quantified. FIG. 2 compares the conversion of ethane to ethanol in three strains of *E. coli*. The control strain (left) had no ethane-oxidizing enzyme, and this strain does not convert ethane to ethanol. The two other strains had ethane-oxidizing enzymes and they converted ethane to ethanol.

TABLE 2

Strains and plasmids

| Strain ID | Base strain genotype | Plasmid |
|---|---|---|
| NH283 | fhuA2 [1on] ompT gal sulA11 R(mcr-73::miniTn10--TetS)2 [dcm] R[zgb-210::Tn10--TetS) endAl Δ(mcrC-mrr) 114::IS10 Δ(araBAD)::cat | None |
| LC165 | fhuA2 [1on] ompT gal sulA11 R(mcr-73::miniTn10--TetS)2 [dcm] R(zgb-210::Tn10--TetS) endA1 Δ(mcrC-mrr) 114::IS10 Δ(araBAD)::cat | pLC12 (pl5A origin, $Kan^R$, empty plasmid control) |
| BZ11 | fhuA2 [1on] ompT gal sulA11 R(mcr-73::miniTn10--TetS)2 [dcm] R(zgb-210::Tn10--TetS) endA1 Δ(mcrC-mrr) 114::IS10 Δ(araBAD)::cat | pBZ4 (p15A origin, $Kan^R$, pTRC_mmoX, mmoY, mmoB, mmoZ, mmoD, mmoC, ypothetical protein, mmoG); SEQ ID NO: 19 |
| LC168 | fhuA2 [1on] ompT gal sulA11 R(mcr-73::miniTn10--TetS)2 [dcm] R(zgb-210::Tn10--TetS) endA1 Δ(mcrC-mrr) 114::IS10 Δ(araBAD)::cat | pLC39 (p15A origin, $Kan^R$, pBAD_mmoX, mmoY, mmoB, mmoZ, mmoD, mmoC, hypothetical protein, mmoG); SEQ ID NO: 26 |
| LC160 | fhuA2 [1on] ompT gal sulA11 R(mcr-73::miniTn10--TetS)2 [dcm] R(zgb-210::Tn10---TetS) endA1 Δ(mcrC-mrr) 114::IS10 Δ(araBAD)::cat | pLC37 (cloDF13 origin, $Kan^R$, $Spec^R$, pBAD_mmoX, mmoY, mmoB, mmoZ, mmoD, mmoC, hypothetical protein, mmoG; $P_{constitutive}$_*E. coli* groESL); SEQ ID NO: 25 |

The following describes the method for culturing the strains and measuring the bioconversion of ethane to ethanol. All strains were inoculated in 1 mL LB Miller supplemented with kanamycin (50 μg/mL) and grown at 37° C. for 18 hours with shaking at 280 rpm. The cultures grew to stationary phase and 0.1 mL of these cultures was then used to inoculate two flasks containing sterile 10 mL LB+kanamycin (50 μg/mL)+either 1 mM IPTG or 1 mM arabinose. The cultures were grown with shaking at 37° C. until OD600~1.2 (approximately 4.0-4.5 hours). The cells were spun for 5 minutes at 4000 rpm, and re-suspended in 10 mL phosphate buffer solution (PBS). This 10 mL was split equally into two glass serum bottles, 5 mL in each. The bottles were then sealed with butyl rubber stoppers. A

TABLE 3

Composition of the reaction mixture for the ethanol assay

| | |
|---|---|
| Deionized water (mL) | 2.175 |
| 10x assay buffer (mL) | 0.25 |
| 100x Enzyme mixture (μL) | 25 |
| 50x colorimetric probe (μL) | 50 |
| Total reaction volume (mL) | 2.5 |

After raw absorbance data was collected, the data were processed as follows: Background absorbance (media only) was subtracted from all samples, including the calibration samples. Each strain had been tested either with air injected or with ethane injected. The absorbance from the air-injected sample was subtracted from the absorbance from the ethane-injected sample. This absorbance value was compared with the calibration curve to determine the amount of the ethanol. The data shown in FIG. 2 demonstrate the production of ethanol under conditions where the strain is expressing the monooxygenase enzyme.

Example 2. Active Soluble Diiron Monooxygenase in *E. coli* Converts Methane into Methanol This example describes a strain and method for culturing a strain to produce methanol from a methane feedstock.

In this example, the same soluble diiron monooxygenase enzyme capable of oxidizing ethane to ethanol in Example 1 above was shown to convert methane to methanol The strains and plasmids, as well as their methods of construction, are identical to those in Example 1. The method of analysis is also nearly identical, with the following modifications.

Figure 3:
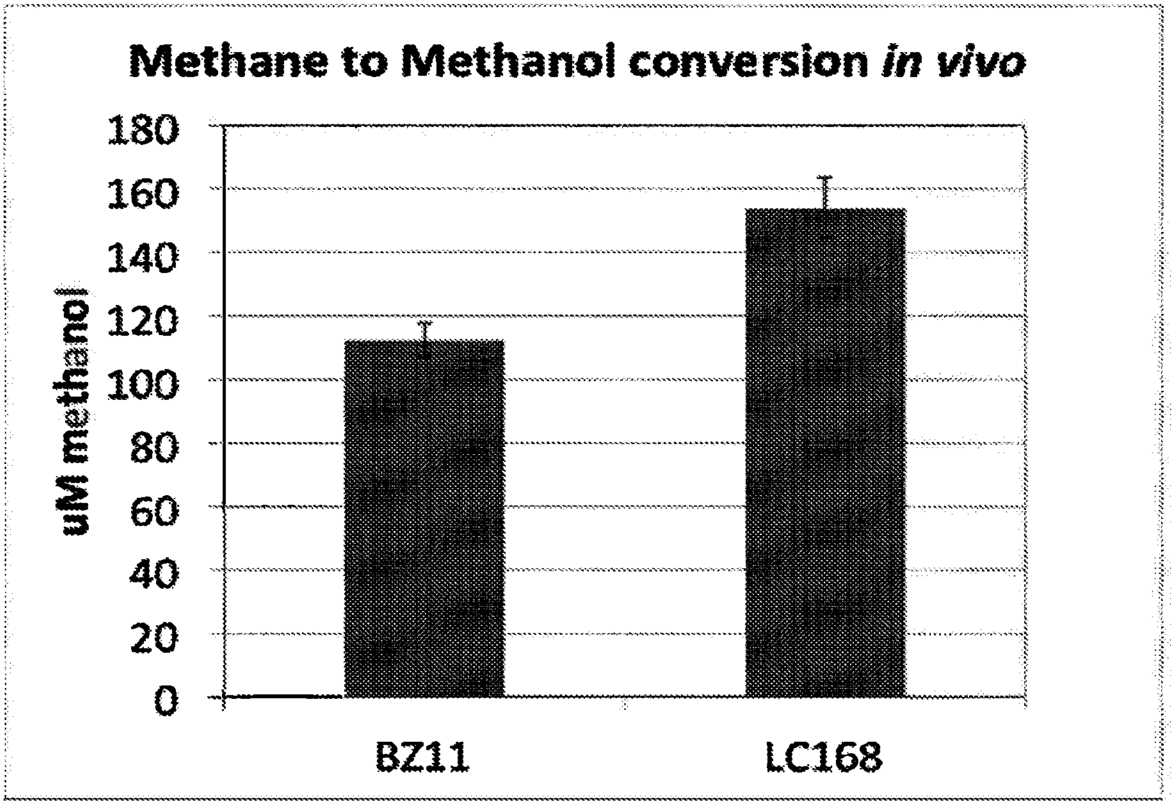
FIG. 3 shows the production of methanol from a methane feedstock. *E. coli* strains BZ11 and LC168 each express a functional monooxygenase.

The headspace above the culture in the stoppered, glass serum bottles were injected with methane, instead of ethane. Subsequently, the colorimetric analysis measures the methanol concentration in the sample taken from the serum bottle, using the same method of determining first a standard curve, adjusting the samples to their corresponding air-injected sample control and then comparing this absorbance (the difference of methane-injected minus air-injected absorbances) to that standard curve. The background value for the control strain is subtracted and those values are plotted for strains BZ11 and LC168 in FIG. 3.

Example 3. Strain Improvements to Increase Conversion of Methane and Ethane into Methanol and Ethanol by an Engineered *E. coli*

This example describes an improved strain and method for culturing a strain to produce methanol from a methane feedstock or ethanol from an ethane feedstock.

Improved strains may be constructed using a variety of techniques known to those skilled in the art. Some of those techniques include: changing plasmid copy number, changing promoter strength, varying inducer concentration, varying cultivation temperature, integrating genes into the chromosome, combining multiple genes on one plasmid, separating genes onto multiple plasmids.

LC160 is similar to strain LC168, except for the origin of replication (cloDF13 instead of p15A) and also has a second operon, which constitutively expresses the *E. coli* genes groES and groEL. The DNA sequence for the groES/groEL operon was amplified from *E. coli* genomic DNA (Table 2). Sequence for the plasmid in LC160 is provided as SEQ ID NO:25.

Figure 4:
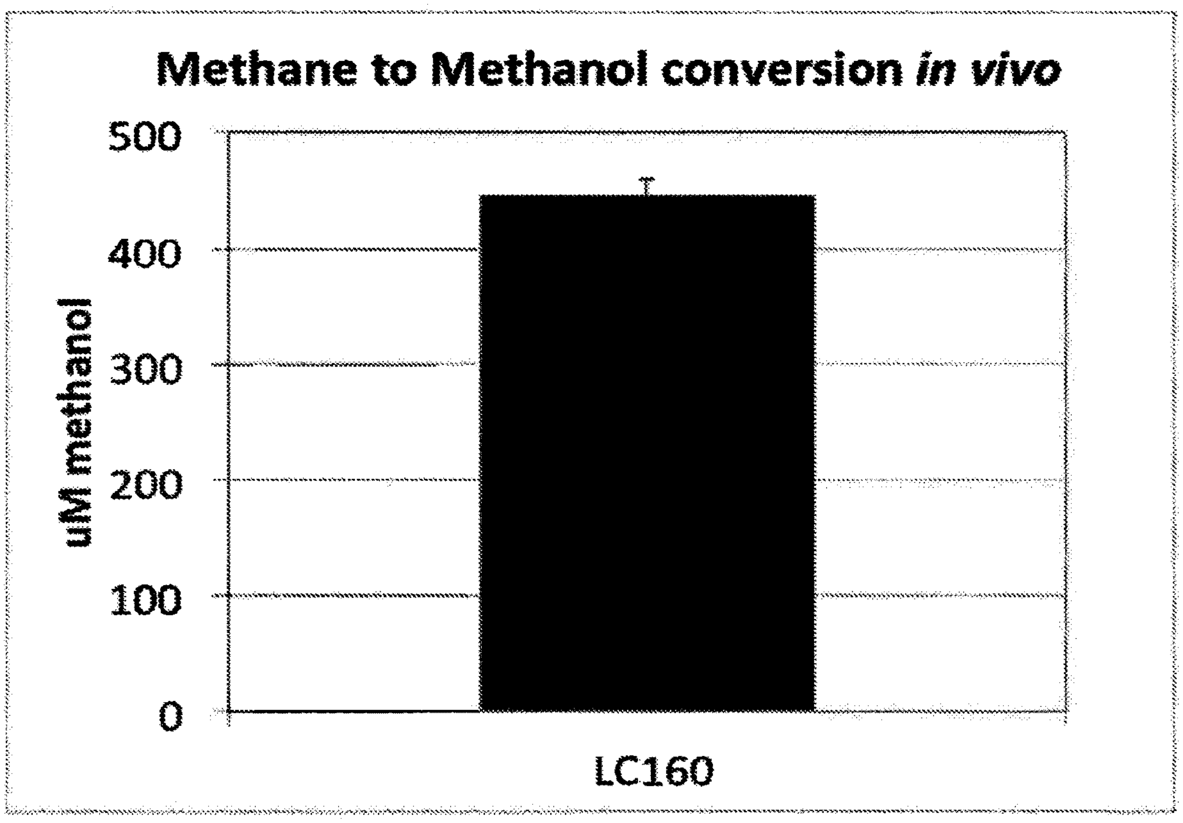
FIG. 4 shows the amount of methanol generated in LC160 (inducible sMMO converting methane to methanol). *E. coli* strain LC160 expresses both a functional monooxygenase and overexpression of *E. coli* groES and groEL genes.

Cells were cultured and methanol was measured as described in herein. FIG. 4 illustrates the conversion of methane to methanol in *E. coli*. The control strain LC165 has no methane-oxidizing enzyme, and this strain does not convert methane to methanol. The strain LC160 (FIG. 4) expressed sMMO from *M. capsulatus* and groESL from *E. coli*. More than 400 μM of methanol was measured resulting from the bioconversion of methane to methanol in LC160.

Figure 5:
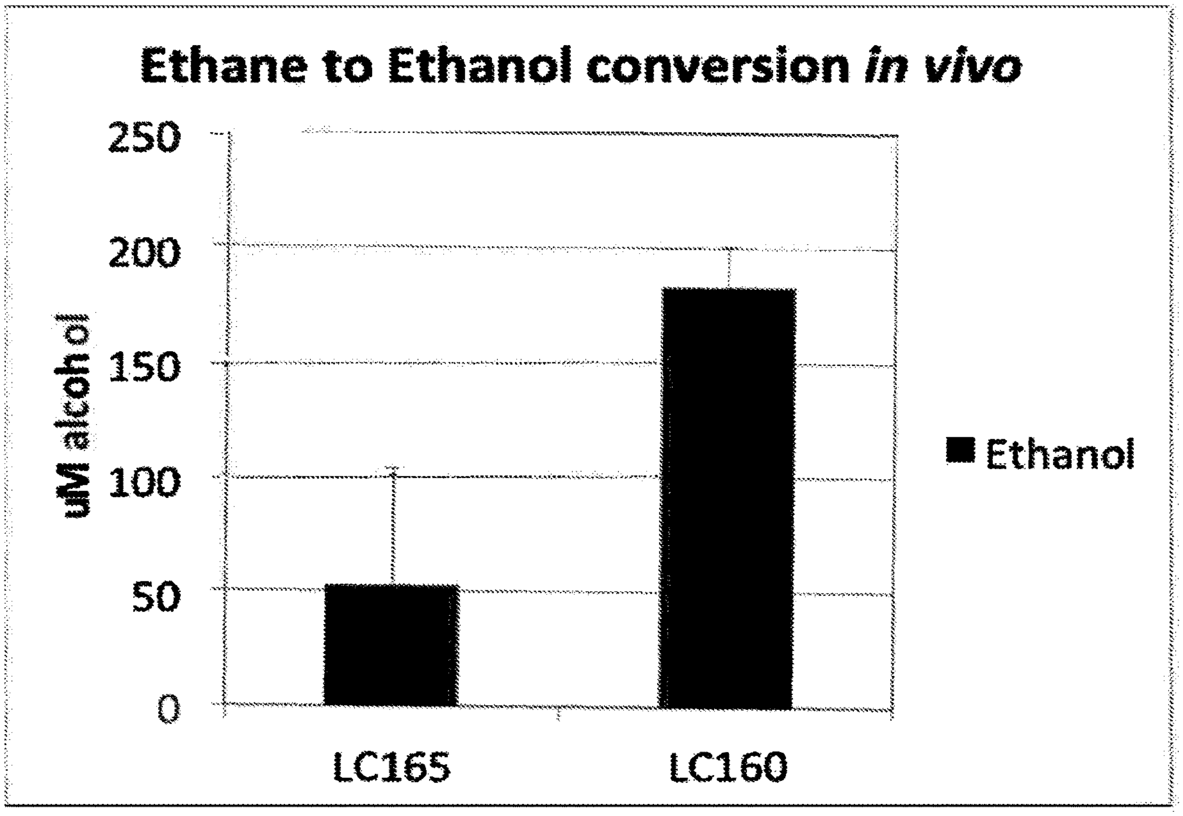
FIG. 5 shows the improved production of ethanol from an ethane feedstock. *E. coli* strain LC160 expresses both a functional monooxygenase and overexpression of *E. coli* groES and groEL genes.

Cells were cultured and ethanol was measured as described herein. FIG. 5 compares the conversion of ethane to ethanol in two strains of *E. coli*. The control strain LC165 (FIG. 5, left) has no ethane-oxidizing enzyme, and this strain does not convert ethane to ethanol. The strain LC160 (FIG. 5, right) expressed sMMO from *M. capsulatus* and groESL from *E. coli*.

Example 4. Bioconversion of Naphthalene to 1-Naphthol in *E. coli*

Figure 10:
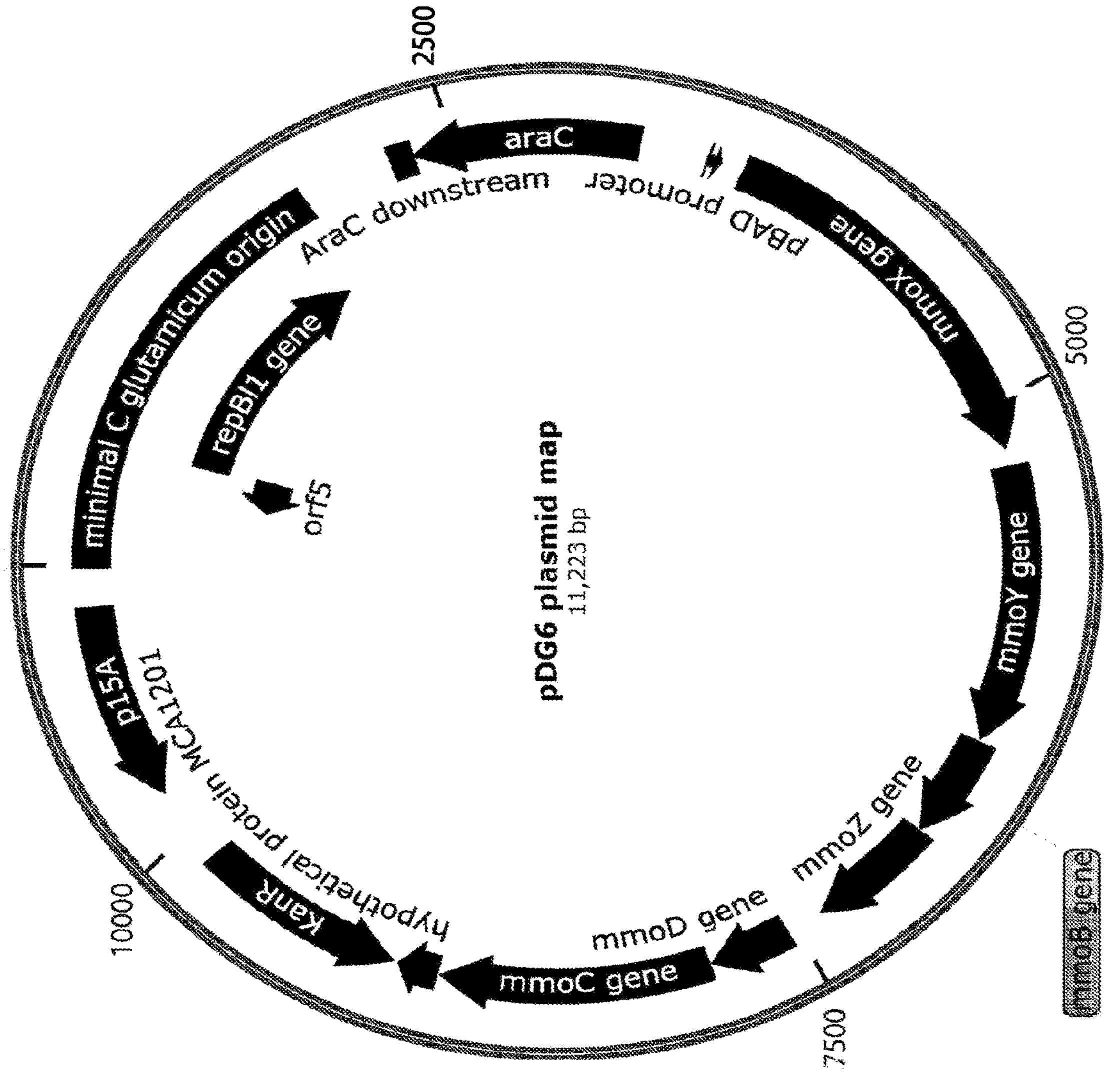
FIG. 10 shows a representative plasmid map illustrating the coding regions for plasmid pDG6 (SEQ ID NO: 22). This plasmid enables the expression of the *M. capsulatus* (Bath) sMMO genes mmoXYBZCD, linked to the pBAD promoter. The plasmid map for pDG5 (SEQ ID NO: 21) would be nearly identical with the sole addition of *M. capsulatus* (Bath) mmoG gene at the 3' end of the MMO operon.
Figure 11:
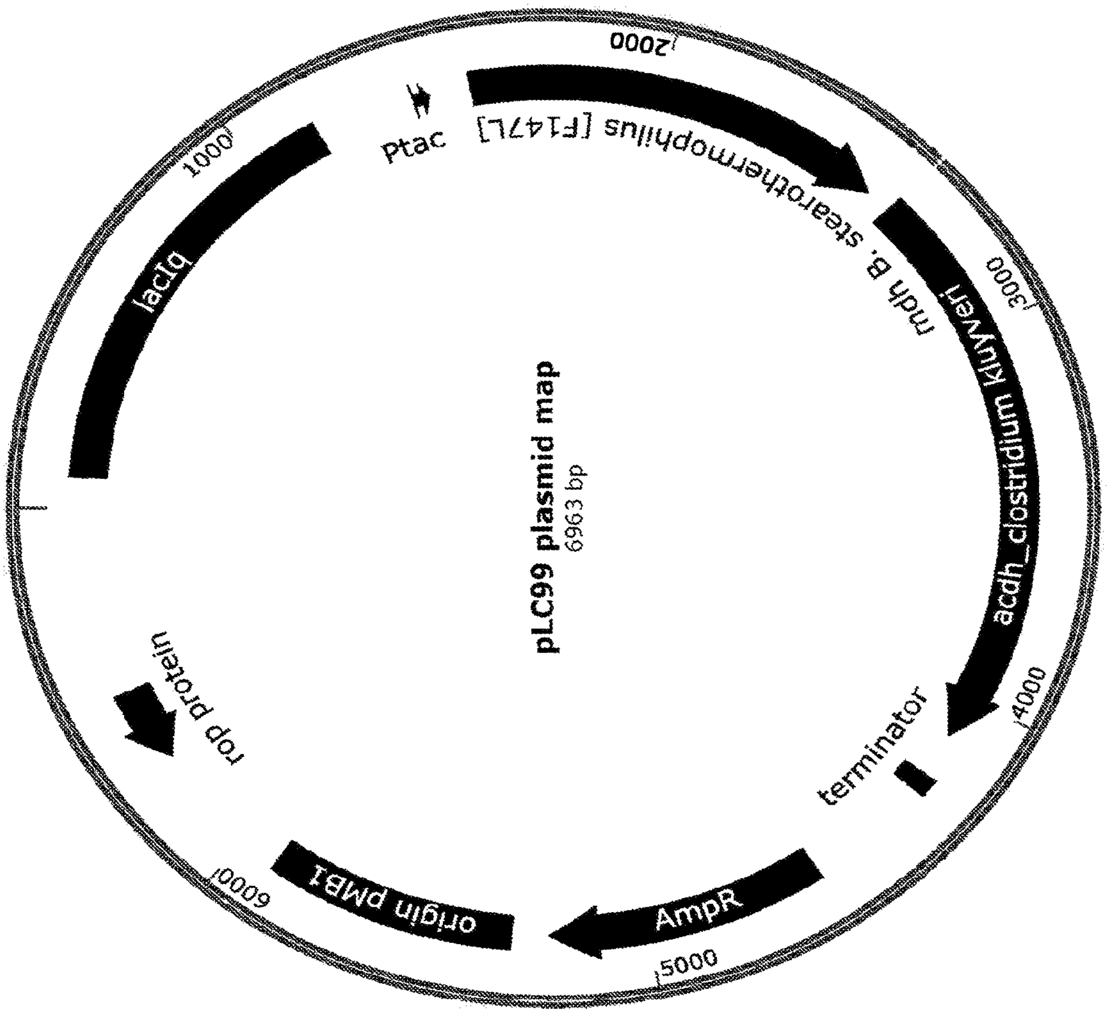
FIG. 11 shows a representative plasmid map illustrating the coding regions for plasmid pLC99 (SEQ ID NO: 27). This plasmid enables the expression of an ethanol-assimilation pathway in *E. coli*. The plasmid map for pLC100 (SEQ ID NO: 23) would be nearly identical, since the only changes are the nucleotides around the ribosome binding sites to the 5' side of the two ethanol-assimilation genes.
Figure 12:
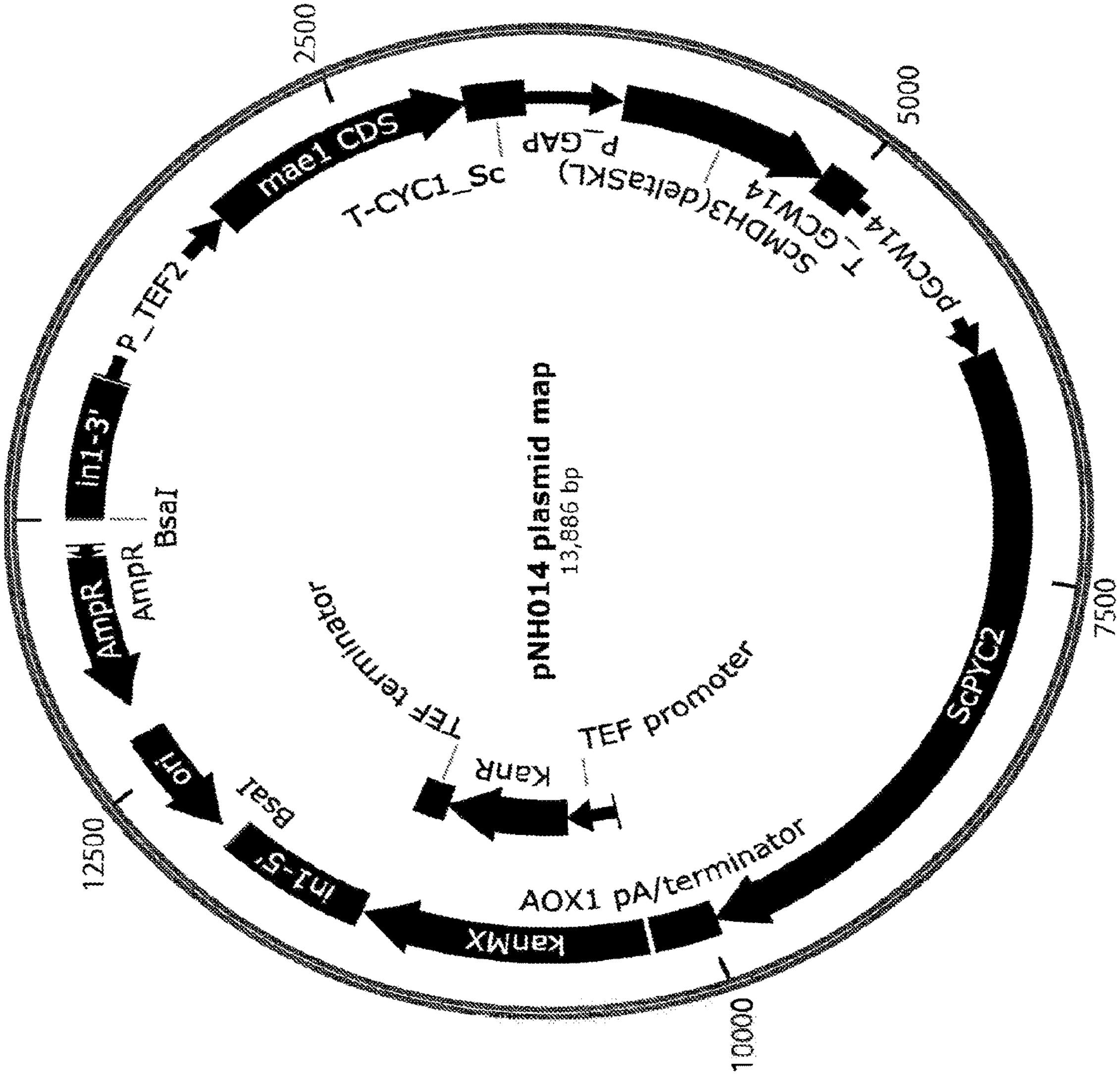
FIG. 12 shows a representative plasmid map illustrating the coding regions for plasmid pNH014 (SEQ ID NO: 57). This plasmid enables the expression of a 3-gene malate-production pathway in *Pichia pastoris*.
Figure 13:
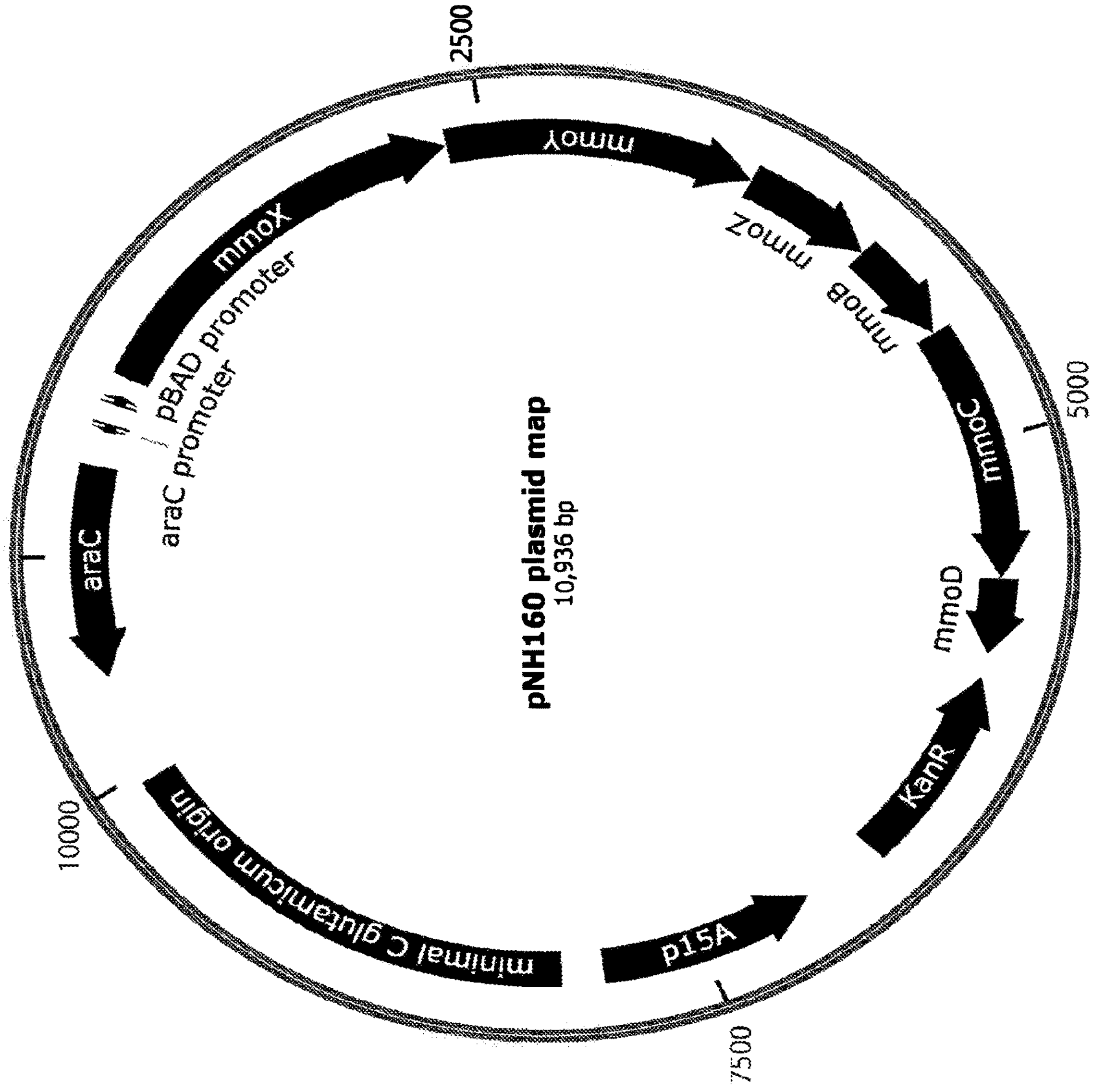
FIG. 13 shows a representative plasmid map illustrating the coding regions for plasmid pNH160 (SEQ ID NO: 33). This plasmid enables the expression of soluble diiron monooxygenase from *Solimonas aquatica* in *E. coli*. The plasmids pNH157 (SEQ ID NO: 31), pNH158 (SEQ ID NO: 32), and pNH100 (SEQ ID NO: 28) are nearly identical, with the exception of the substitution of the coding sequences of the *S. aquatica* monooxygenase being replaced with those of *Methylocaldum* sp. 175, *Methyloferula stellata*, and *Pseudonocardia* TY7, respectively.
Figure 14:
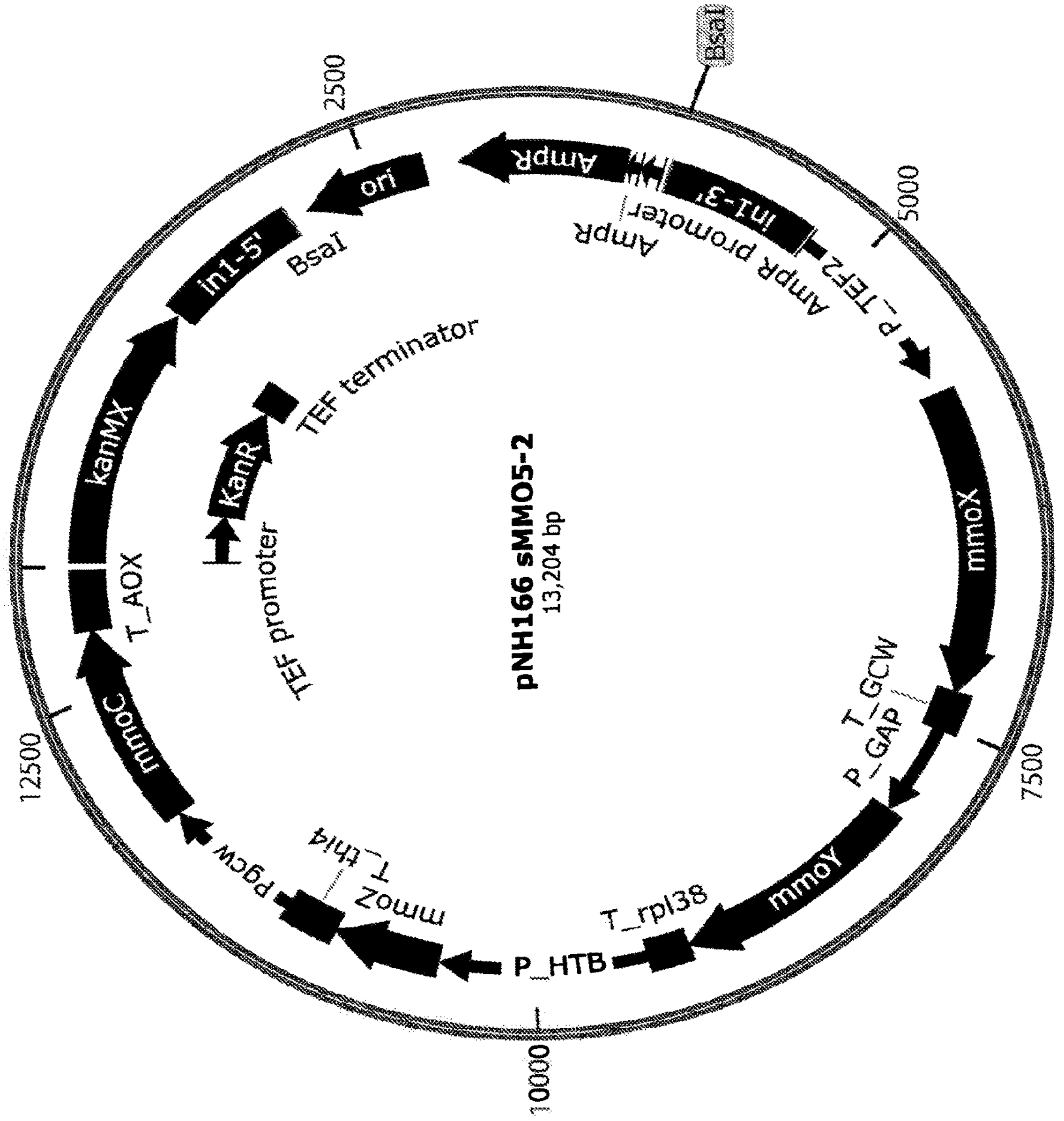
FIG. 14 shows a representative plasmid map illustrating the coding regions for plasmid pNH166 (SEQ ID NO: 34). This plasmid enables the expression of four subunits of the *Methylocystis* methane monooxygenase mmoX, mmoY, mmoZ, and mmoC from different promoters for expression in *Pichia pastoris*. This plasmid can be restriction digested with BsaI enzyme in order to generate a linear fragment for integration into the chromosome. The plasmid pNH167 (SEQ ID NO: 35) is nearly identical, with the exception being the substitution of the coding sequences for the MMO subunits deriving from *Solimonas aquatica*.
Figure 15:
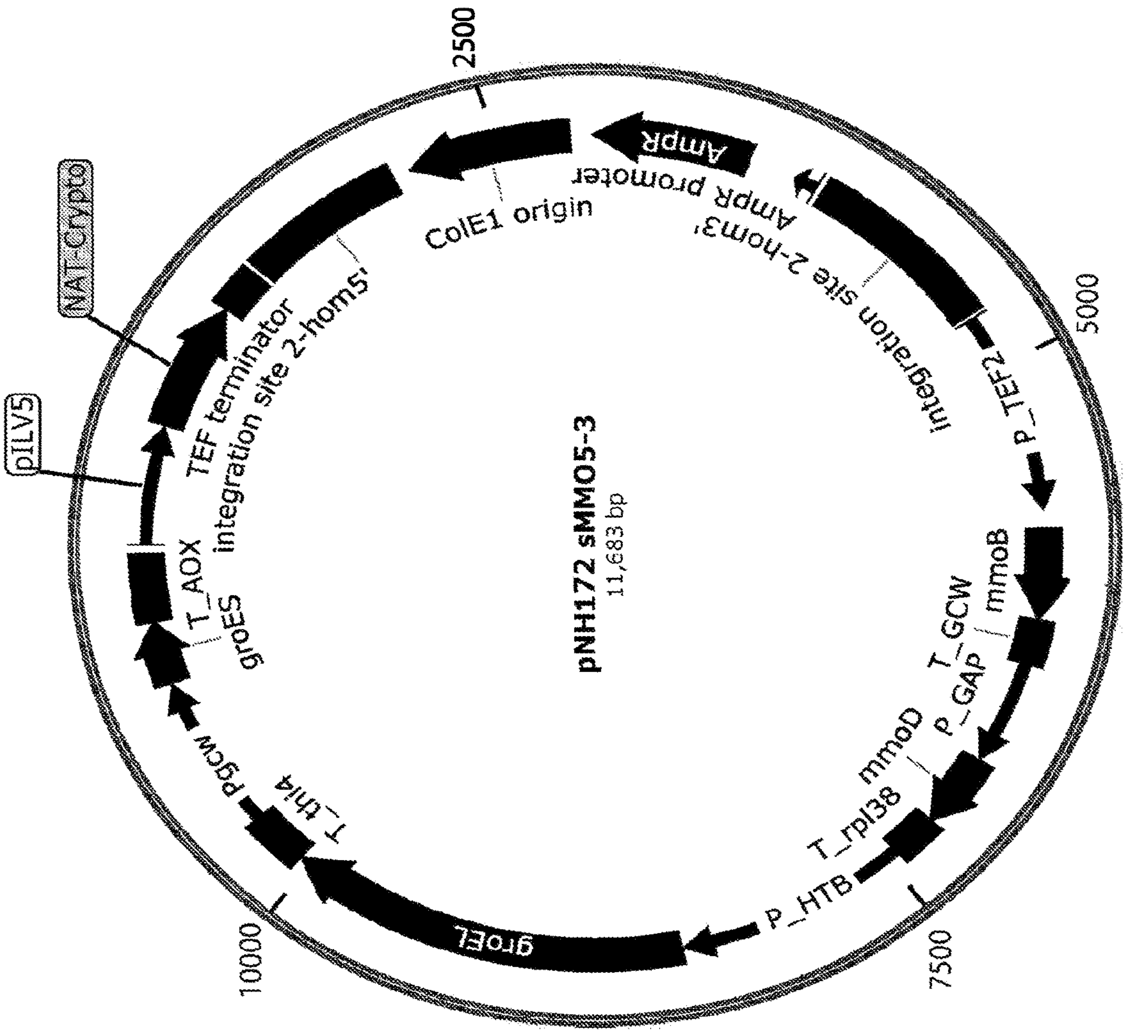

The following describes the high-throughput method for culturing the strains and measuring the bioconversion of naphthalene to 1-naphthol by sMMO in multi-well microplates. The plasmid pDG5 (SEQ ID NO: 21) was constructed by amplification of the relevant section of genomic DNA from *Methylococcus capsulatus* (Bath) containing the MMO operon of genes mmoXYBZCDG and cloning this DNA fragment into a pACYC vector containing a p15a origin of replication, a kanamycin-resistance gene, and a pBAD promoter. This plasmid pDG5 is nearly identical to the plasmid pDG6 (SEQ ID NO: 22, FIG. 10), except for the presence of mmoG (groEL-2) at the 3' end of the operon. Strain LC151 was constructed by transforming strain NH283 with plasmid pDG5 and selecting for transformants on LB agar plates supplemented with kanamycin at 50 μg/mL. All strains were inoculated in 2 mL 96-well plates with each well containing 0.4 mL LB media supplemented with antibiotics as appropriate (kanamycin at 50 μg/mL and spectinomycin at 100 μg/mL) and grown at 37° C. overnight with shaking. For the induction of sMMO, aliquots of 40 μL/well of overnight seed cultures were inoculated in fresh 96-well plates with each well containing 400 μL LB culture media supplemented with antibiotics and 1.0 mM L-arabinose. The cultures were grown with shaking at 37° C. for 4 to 5 hours. The cells were spun for 10 minutes at 3700×g, and the spent LB media was removed by a 96-pin aspirator connected to a vacuum pump. The cells were resuspended in 1.0 mL of phosphate buffered saline (PBS) and spun again for 10 minutes at 3700×g, the PBS wash buffer was again removed by aspiration. The washed cell pellets were re-suspended in 0.25 mL of PBS assay buffer containing 0.4% glycerol (v/v), 1 mM L-arabinose, and 80 μM $FeSO_4$.

The naphthalene assay plate was prepared by adding 10 μL/well of 0.5 M naphthalene dissolved in pure ethyl alcohol. Small naphthalene crystals formed at the bottom of each well after all alcohol evaporated, approximately 2 hours. Aliquots of 200 μL/well of the re-suspended cells in assay buffer were transferred into the naphthalene plate and mixed with naphthalene crystals. The naphthalene assay plate was then sealed and incubated at 37° C. overnight with shaking. The supernatant containing 1-naphthol was separated from cell pellets by spinning the assay plate for 10 minutes at 3700×g, and supernatant of 150 μL/well was transferred into a 96-well clear flat-bottom microtiter plate.

1-naphthol was measured using a colorimetric assay. The 1-naphthol in the 150 μL, supernatant was reacted with 50 μL of freshly prepared 0.2% (w/w) solution by dissolving Fast Blue B (tetrazotized o-dianisidine) in deionized water. The colored diazo complex was measured on a plate reader at 540 nM. The concentration of the diazo complex is proportional to the concentration of the 1-naphthol product.

Figure 6:
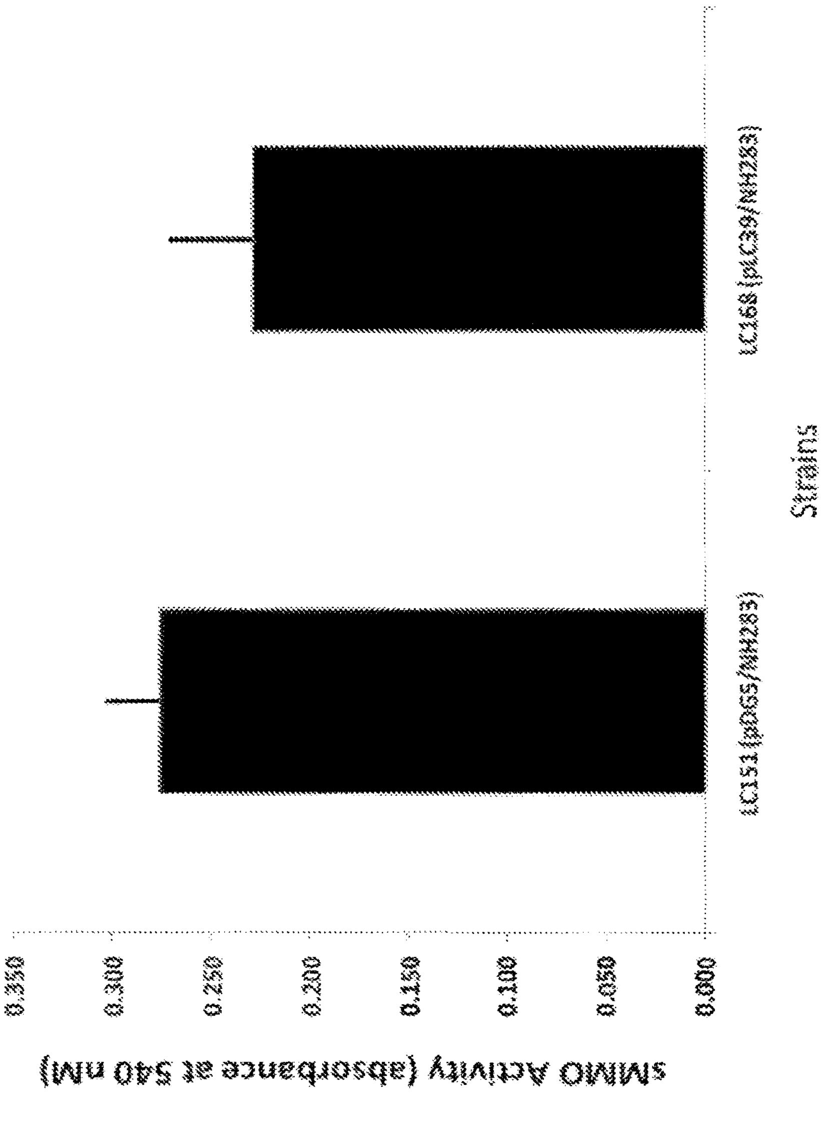
FIG. 6 shows the production of 1-naphthol from a naphthalene feedstock. *E. coli* strains LC151 and LC168 each express a functional monooxygenase. The 1-naphthol concentration is measured by the addition of a naphthol-sensitive dye and subsequent measurement of the optical absorbance at 540 nm. The absorbance value of a control strain (lacking any monooxygenase) is subtracted as a baseline value.

The sMMO activity was expressed as relative absorbance (A540) after subtracting buffer blank and the absorbance in the empty vector control strain LC165. As shown in FIG. 6, both strains (LC151 and LC168) expressing the *M. capsulatus* sMMO operon showed significantly higher activities than LC165 expressing the empty vector control.

This is the first example for successful expression of active *M. capsulatus* sMMOs in engineered *E. coli* strains that can be detected by the naphthalene colorimetric assay. The high throughput method described here can be used for strain improvement by optimizing and balancing sMMOs and their homologs in *E. coli* and other heterologous hosts.

Example 5. Chaperone Expression Improves MMO Activity: Naphthalene to Naphthol

In one example we showed that the *M. capsulatus* MMOG, a groEL-2 chaperone homolog, is critical for MMO activity in *E. coli* strains expressing a native *M. capsulatus* MMO operon on single plasmids (pDG5 (SEQ ID NO: 21), pLC39 (SEQ ID NO: 26)). In another example we further demonstrated that a re-factored *M. capsulatus* groES-EL2 operon on a compatible plasmid (pNH180 (SEQ ID NO: 40)) greatly improved the MMO activity in *E. coli* strains harboring a mmoG-minus plasmid (pDG6 (SEQ ID NO: 22)).

This example describes a method that improved MMO activity by more than an order of magnitude. This novel approach involves overexpression of both the *E. coli* groES-groEL and the *M. capsulatus* groES-EL2 in pNH180. The *E. coli* groES-groEL fragment was PCR amplified from *E. coli* BW25113 genomic DNA, gel-purified, and cloned into a vector in front of a terminator sequence. After sequence verification, the groES-groEL-terminator fragment was amplified by PCR using primers BZ111 (SEQ ID NO:70) and LC166 (SEQ ID NO:71), gel purified, and cloned behind the *M. capsulatus* groES-EL2 in pNH180 by mega-priming method (Ulrich et al., *Exponential Megapriming PCR (EMP) Cloning—Seamless DNA Insertion into Any Target Plasmid without Sequence Constraints*, PLoS One, 7(12), e53360, 2012). After DpnI digestion to remove the pNH180 plasmid DNA, the reaction mixture was transformed into NH283 carrying the MMO plasmid pDG6. The transformants were grown on an LB agar plate supplemented with kanamycin at 50 μg/mL for selection of pDG6 and spectinomycin at 100 μg/mL for selection of desired recombinant plasmid (pBZ13 (SEQ ID NO: 15)). A number of colonies were screened by naphthalene assay, leading to a new MMO strain (BZ25) carrying both pDG6 and pBZ13 plasmids. As shown in Table 4, MMO activity in BZ25 is a significant improvement over that of DG80. The pBZ13 plasmid was then separated from pDG6, purified, and sequence verified. One base strain (BZ26) was made by transforming the pBZ13 plasmid into NH283. The pDG6 plasmid was then introduced into BZ26 to confirm that the resulted strain is equivalent to the original BZ25.

TABLE 4

Improvement of MMO activity by co-expression of *M capsulatus* and *E. coli* chaperone proteins

| Strain | Plasmids | *M. capsulatus* groES/groEL-2 | *E. coli* groES/groEL | MMO activity (A540 nm) |
|---|---|---|---|---|
| DG80 | pDG6, pNH180 | + | | 0.07 |
| BZ25 | pDG6, pBZ13 | + | + | 1.15 |

Example 6. Chaperone Expression Improves MMO Activity: Methane to Methanol

This example describes the evaluation of the improved MMO strain (BZ25) for direct methane oxidation by a bio-conversion method detailed in Example 3. Both strains were grown in LB broth supplemented with kanamycin at 50 μg/mL and spectinomycin at 100 μg/mL. Method for MMO induction and bio-conversion of methane to methanol was performed as described elsewhere herein. The methanol titer was measured 20 hours after injection of methane gas. The MMO activity for D080 and BZ25 are shown in Table 5.

TABLE 5

Methane oxidation by DG80 and BZ25

| Strain | MMO plasmid | Chaperone Plasmid | Methanol (mM)/0D600 |
|---|---|---|---|
| DG80 | pDG6 | pNH180 | 4.16 |
| BZ25 | pDG6 | pBZ13 | 6.33 |

Example 7. Homologs of Methane Monooxygenase in *E. coli*

Homologs of sMMO from *Methylococcus capsulatus* (Bath) can be determined using publicly available databases and search algorithms, such as BLASTp from NCBI. A wide range of sequences can be discovered in this manner and these sequences can be tested in the process described herein. The DNA sequences encoding these homologs can be extracted from genomic DNA isolates, PCR amplified from lysates of the relevant strains, or can be designed, codon optimized for expression in the desired host organism and synthesized using commercially available DNA synthesis services.

In one example, the DNA sequence encoding sMMO homologs from methanotrophs such as *Methylocella silvestris* and *Methylosinus trichosporium* was synthesized by a commercial vendor. The sequence was cloned into the same vector as that described herein, using standard techniques such as restriction digestion and isothermal assembly (D. Gibson et al., *Enzymatic assembly of DNA molecules up to several hundred kilobases*, NATURE METHODS Vol 6, Issue 5, p. 343-345, 2009). The assembled DNA was transformed into strain NH283 and verified by colony PCR and Sanger sequencing.

These strains can be tested using the same process as described herein.

Organisms were identified that contain homologs of the *M. capsulatus* sMMO. Sequences of the mmoXYBZDC genes from these organisms were codon optimized and synthesized in an operon using synthetic linkers containing strong ribosome binding sites between the genes. The groESL genes from these same organisms were similarly codon optimized and synthesized in an operon. Synthetic DNA was provided by a commercial vendor (Gen9, Inc.). Each operon was cloned into a different plasmid. The mmoXYBZDC operons were cloned into the plasmid pDG6 (SEQ ID NO: 22) backbone, which contains a pACYC origin, kanamycin resistance gene, araC repressor gene, and a pBAD promoter driving the expression of the operon. The groESL operons were transformed into the plasmid pDG11 backbone, which contains a cloDF13 origin, spectinomycin resistance gene, and synthetic J23116 promoter driving the expression of the operon.

For each organism, both plasmids were serially transformed into strain NH283 and selected on appropriate antibiotics. Source organisms for the sMMO and groESL enzymes are listed in Table 6, along with strain and plasmid names.

Plasmids pNH157 (SEQ ID NO: 31), pNH160 (SEQ ID NO: 33), and pDG6 (SEQ ID NO: 22) each contain 6 genes (mmoX, mmoY, mmoZ, mmoB, mmoC, mmoD) encoding an sMMO enzyme complex from a different organism.

Plasmids pNH185 (SEQ ID NO: 42), pNH188 (SEQ ID NO: 44), and pNH180 (SEQ ID NO: 40) each contain 2 genes (groES, groEL) encoding a groESL enzyme complex from a different organism.

The following describes the method for culturing the strains and measuring the bioconversion of methane to methanol or ethane to ethanol. All strains were inoculated in 1 mL LB Miller supplemented with kanamycin (50 μg/mL) and spectinomycin (100 μg/mL) and grown at 37° C. for 18 hours with shaking. The cultures grew to stationary phase and 0.2 mL of these cultures was then used to inoculate flasks containing sterile 20 mL LB Miller, kanamycin (50 μg/mL), spectinomycin (100 μg/mL), 1 mM arabinose, and 80 μM $FeSO_4$. The cultures were grown with shaking at 37° C. for 5 hours. The cells were spun for 10 minutes at 4000 rpm, and washed in an equal volume of phosphate buffer solution pH 7.5 (PBS). The cells were spun again and re-suspended in an equal volume of PBS containing 1 mM arabinose, 80 μM $FeSO_4$, and 0.4% glycerol. Three aliquots of 5 mL each were transferred into identical glass serum bottles. The bottles were then sealed with butyl rubber stoppers. A volume of 60 mL of either methane, ethane, or air was measured into a syringe and injected through the stopper and into each of the bottles. The bottles were shaken at 37° C. for 43 hours, at which point the cell suspension was centrifuged and the supernatant was sampled in order to measure methanol and ethanol concentrations.

Alcohols were measured using a colorimetric assay described elsewhere herein (Cell Biolabs STA-620).

Table 6 shows the alcohol measurements. These data demonstrate that strains DG68, DG72, and DG80 containing diverse sMMO/groESL genes all have activity to oxidize methane to methanol, and also activity to oxidize ethane to ethanol. Percent homologies between enzymes is tabulated in Table 8.

TABLE 6

Methane and ethane oxidation activity of strains containing various homologs of sMMO and their cognate groESL enzymes.

| Strain | Plasmids | sMMO source | Methanol (mM) | Ethanol (mM) |
|---|---|---|---|---|
| DG68 | pNH157, pNH185 | *Methylocaldum* sp.175 | 1.36 | 0.39 |
| DG72 | pNH160, pNH188 | *Solimonas aquatica* DSM 25927 | 0.027 | 0.12 |
| DG80 | pDG6, pNH180 | *Methylococcus capsulatus* (Bath) | 3.56 | 1.52 |

Example 8. MMO Enzyme Homologs are Active when Co-Expressed with a Heterologous Chaperone Organisms were identified that contain homologs of the sMMO. The mmoXYBZDC and groESL genes were identified, codon-optimized, synthesized, cloned into vectors, and transformed into strain NH283 as described elsewhere herein.

Source organisms for the sMMO and groESL enzymes are listed in Table 7, along with strain and plasmid names. Percent homologies between homologs is tabulated in Table 8. Plasmids pNH157 (SEQ ID NO: 31), pNH158 (SEQ ID NO: 32), pNH160 (SEQ ID NO: 33), and pDG6 (SEQ ID NO: 22) each contain 6 genes (mmoX, mmoY, mmoZ, mmoB, mmoC, mmoD) encoding an sMMO enzyme complex from a different organism. Plasmids pNH185 (SEQ ID NO: 42), pNH188 (SEQ ID NO: 44), and pNH180 (SEQ ID NO: 40) each contain 2 genes (groES, groEL) encoding a groESL enzyme complex from a different organism.

The method for culturing the strains and measuring the bioconversion of methane to methanol or ethane to ethanol was performed as described herein. Measurement of alcohol concentrations, including use of air controls and technique for data processing, was performed as above.

Table 7 shows the alcohol measurements. These data demonstrate that strains DG68, DG69, DG71, DG72, DG73, and DG80 containing various combinations of sMMO and groESL genes all have activity to oxidize methane to methanol, and also activity to oxidize ethane to ethanol.

TABLE 7

Methane and ethane oxidation activity of strains containing diverse sMMO enzymes co-expressed with the chaperone groES/groEL from *M. capsulatus* (Bath).

| Strain | Plasmids | sMMO source | Methanol (mM) | Ethanol (mM) |
|---|---|---|---|---|
| DG69 | pNH157, pNH180 | *Methylocaldum* sp.175 | 1.99 | 0.50 |
| DG71 | pNH158, pNH180 | *Methyloferula stellata* | 0.40 | 0.10 |
| DG73 | pNH160, pNH180 | *Solimonas aquatica* DSM 25927 | 0.025 | 0.96 |

TABLE 8

Percent identity between sMMO enzymes from different organisms. Values calculated using Clustal Omega for sMMO enzymes using mmoX sequences, using the definition of percent identity for multi-gene enzymes, as well as groEL and groES.

| sMMO *Organism* | *Solimonas aquatica* DSM 25927 | *Methyloferula stellata* | *Methylocaldum* sp.175 | *Methylococcus capsulatus* (Bath) |
|---|---|---|---|---|
| *Solimonas aquatica* DSM 25927 | 100.0% | 64.1% | 62.4% | 63.4% |
| *Methyloferula stellata* | | 100.0% | 82.5% | 83.3% |
| *Methylocaldum* sp.175 | | | 100.0% | 95.3% |

TABLE 8-continued

| Percent identity between sMMO enzymes from different organisms. Values calculated using Clustal Omega for sMMO enzymes using mmoX sequences, using the definition of percent identity for multi-gene enzymes, as well as groEL and groES. | | | |
|---|---|---|---|
| *Methylococcus capsulatus* (Bath) | | | 100.0% |

| GroEL Organism | *Methylocaldum* sp 175 | *Methylococcus capsulatus* (Bath) | *Solimonas aquatica* DSM 25927 |
|---|---|---|---|
| *Methylocaldum* sp. 175 | 100.0% | 50.3% | 43.6% |
| *M. capsulatus* (Bath) | | 100.0% | 49.2% |
| *Solimonas aquatic* DSM 25927 | | | 100.0% |

| GroES Organism | *Solimonas aquatica* DSM 25927 | *Methylococcus capsulatus* (Bath) | *Methylocaldum* sp 175 |
|---|---|---|---|
| *Solimonas aquatica* DSM 25927 | 100.0% | 66.8% | 65.4% |
| *M. capsulatus* (Bath) | | 100.0% | 72.2% |
| *Methylocaldum* sp. 175 | | | 100.0% |

The amino acid sequences for these enzymes were compared to each other using the online software Clustal Omega and the results are shown below in Table 8. The functional enzymes demonstrated in Table 7 show a low stringency of sequence identity between the mmoXYZCBD homologs, or between the groESL components.

The scope of the invention is meant to encompass variants of the synthetic nucleotides and/or amino acid sequences disclosed herein. As disclosed in scientific literature, in databases, in the present disclosure or as known to one skilled in the art at the filing date of the application, certain positions of a polypeptide sequence are typically conserved residues, which can be determined according to polar, electro-physical, hydrophobic and spatial properties of the polypeptide. One skilled in the art would be able to modify the amino acid sequences of the current disclosure, maintain conserved residues and/or apply conservative substitutions in those conserved residues and determine whether those variants still maintain functionality. FIG. 18 shows a multiple sequence alignment of the alpha subunit of the monooxygenase hydroxylase enzyme from three different microorganisms and is illustrative of the degree to which the monooxygenase amino acid sequences can be varied and maintain the observed function. Any mutation to one sequence that confers improved enzyme properties (e.g. activity and/or specificity) can be substituted into another homologous sequence using such a sequence alignment, using publicly available software such as BLASTp, for example, to identify the equivalent position in the homolog. It is clear to one skilled in the art how one would identify and construct the equivalent mutation in the homologous sequence.

The characteristics of soluble diiron monooxygenase enzymes have been studied in academia for years to understand the structure, function and mechanism. A paper by Coufal et al. in 2000 (Coufal et al., *Sequencing and analysis of the Methylococcus capsulatus* (*Bath*) *soluble methane monooxygenase genes*, Eur. J. Biochem., vol. 267., p. 2174-2185, 2000, which is incorporated by reference in its entirety herein, including any drawings) described conserved residues of the MMO subunits.

In the MMOX subunit of the MMOH enzyme, the iron ligand residue sequence pattern E . . . EX2H has been noted as a hallmark of proteins containing carboxylate-bridged non-heme diiron centers and is the only sequence conserved across the sMMO, R2, and stearoyl-ACP desaturase families As such, there are often conserved residues in the following positions of SEQ ID NO:10: E114, E144, H147, E209, E243, and H246. Also, the lower half of the active site has a set of residues involved in hydrogen bonding between the C and F helices (D143, R146, 5238, D242, and R245) and are absolutely conserved among proteins. These residues might be part of a framework to hold the iron center in place or possibly to deliver protons to the active site. Two residues are conserved for steric reasons; both A117 and G250 are located in positions where the packing is very tight. Finally, there is a triad of surface-accessible residues, comprising A224, G228, and D229, located at the turn between helices E and F.

Conserved residues in other parts of the a-subunit are shown in FIG. 6. of Coufal. W371 is solvent exposed on one edge of the indole ring. Two Tyr residues are buried in the protein interior. In addition, a proline residue, P377, is absolutely conserved and may be important structurally. A model for the hydroxylase-reductase binding interaction places the reductase-binding site in this region, suggesting that this entire cluster of residues may serve as a docking site for another protein or as part of an electron-transfer path. In addition, T213, N214 may aid in proton transfer. Another set of conserved residues comprises P424, G443, P461 and Y464 and is located in the second domain of the hydroxylase a subunit. These amino acids are positioned slightly beneath the surface of the protein near the γ-subunit interface.

Finally, a set of residues found on the surface of the protein in the 'canyon' area above the active site is often conserved. These residues are Y67, K74, L321, G325, and P329, which are indicated in yellow in FIG. 6 of Coufal. It has been hypothesized that the canyon may be a docking site for protein B or possibly the reductase. Thus, these conserved residues may be important in mediating the interactions between two proteins. In particular, K74 and Y67 are very close to the surface and are located in the canyon. Combined with the E/F helix 'handle' described above, these residues might be key interaction points between the coupling protein B and the hydroxylase MMOH.

Figure 7:
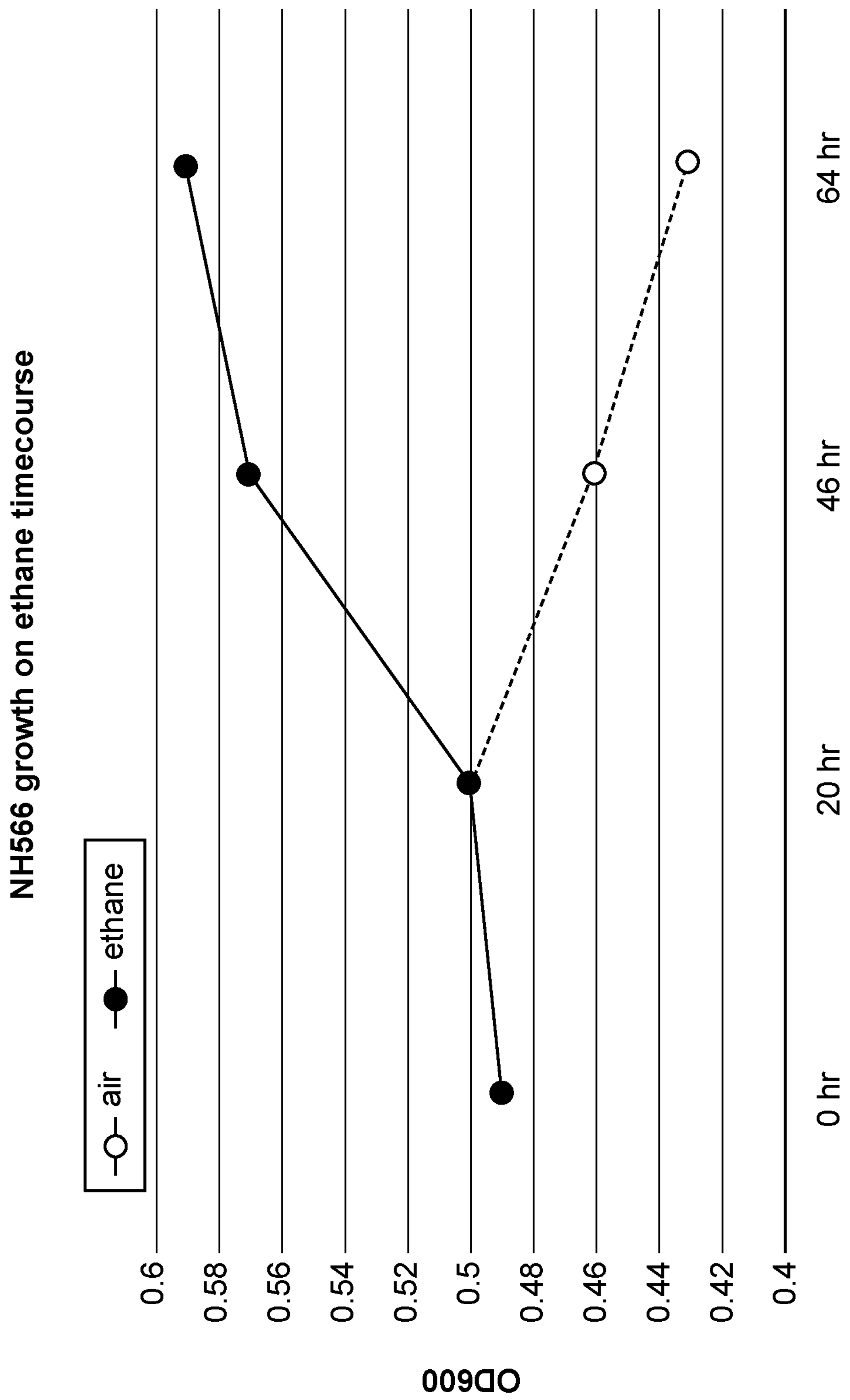
FIG. 7 shows the growth of NH566 on an ethane feedstock. Strain NH566 was sealed in two serum bottles, where one was injected with air and the other with ethane. This plot shows the culture density as a function of time after the injections which illustrates the increase in culture density for the bottle injected with ethane and a decrease in culture density for the bottle injected with air.

Additionally, in the β-subunit mmoY (SEQ ID NO:12), the interface between the a and 13 subunits comprising D100, P101, and D185 is conserved as seen in FIG. 7 Coufal. These residues may be involved in intersubunit interactions, although there are no conserved hydrogen-bonding or salt-bridge partners in the a subunit. A second group of residues, W218, R228 and A331, can be found under the surface of the 13 subunit, and a third set of amino acids containing mainly polar residues (D240, E243, Q313, and W320) is very near the protein surface. Further, 24 highly conserved residues have been identified in the alignment of the β-subunit analogs as seen FIG. 4A of Coufal. Most notably, two charged amino acids, K44 and E48, are conserved in the hydroxylase canyon, where they could participate in protein-protein interactions. The eight conserved aromatic residues may be part of an electron-transfer pathway from a putative reductase binding site on the β subunit to the diiron active site. It should be noted that no residue near the 3-3 interface is highly conserved across this group of enzymes. Protein B (SEQ ID NO:8) also has certain conserved residues. Sequence alignment of the coupling proteins (see Coufal, FIG. 4B) revealed five absolutely conserved residues (V38, E53, 179, G97, and G114), eight highly conserved residues (152, V70, 185, E94, R98, V107, D108, and S111) and eight moderately conserved residues (V41, 155, V68, G83, V87, 192, L96, and F100). The surface of protein B is largely hydrophobic, making it well suited for binding the hydrophobic canyon on the hydroxylase. The MMOH-protein B docking model derived from NMR binding studies is consistent with the suggestion that hydrophobic interactions dominate hydroxylase-protein B binding and with cross-linking studies of the *M. triehosporium* OB3b sMMO system, in which protein B was shown to bind the a-subunit of the hydroxylase. The finding that many of these conserved residues, including L96, G97, F100, V107, D108, and G114, are affected by hydroxylase binding suggests that the hydroxylase-coupling protein-binding mode is similar for all of the enzyme systems examined. Therefore, using sequence homology alignments to identify protein-protein binding sites appears to be valid for this group of proteins. Complementary residues on the hydroxylase, presumably located in the canyon region, are likely to be conserved as well. Protein C (SEQ ID NO:59) also has conserved residues. The sMMO reductase is a member of the FNR family of oxidoreductases that contain well-characterized 12Fe-251 and FAD cofactor sites and NADH-binding pockets. Conserved residues in the reductase components have been discussed previously.

If a residue is not conserved, it may be deleted, modified and/or replaced with another amino acid whose incorporation does not substantially affect functioning of the disclosed protein. Thus, the original peptides disclosed herein can be modified by the substitution of one or more residues at different, possibly selective, sites within the peptide. Such substitutions may be a conservative substitution, such as replacement of a hydrophobic residue with another hydrophobic residue, or may be less than conservative substitutions in the case where a particular residue is not a conserved residue. Some substitutions are tolerated better than others based upon the location of the residue. However, non-conservative or even radical substitutions may even be tolerated based upon the location of the residue, as can be demonstrated by one skilled in the art.

Substitutions are also meant to encompass those other than the common L-amino acids, such as D-amino acids or other amino acids with non-standard R groups. Each of these substitutions is intended to be within the disclosure of the application.

Example 9. Several Heterologous Chaperones Improve Methane into Methanol Conversion by sMMO This example describes the ability of the sMMO from *M. capsulatus* (Bath) to have improved activity against methane as a substrate with the coexpression of a panel of groES/groEL chaperones.

The strain NH283, described elsewhere herein, was transformed with two plasmids simultaneously: pDG6 (SEQ ID NO:22, containing the coding regions corresponding to the *M. capsulatus* (Bath) mmoX, mmoY, mmoZ, mmoC, mmoB, and mmoD genes) and one plasmid selected from the set of plasmids containing pNH178 (SEQ ID NO:39), pNH180 (SEQ ID NO:40), pNH181 (SEQ ID NO:41), pNH185 (SEQ ID NO:42), pNH187 (SEQ ID NO:43), and pCDF1b (SEQ ID NO:20) (containing codon-optimized groES/groEL genes from the microorganisms *T. butanivorans, M. capsulatus, M. trichosporium, Methylocaldum* sp. 175, *Methylocystis* sp. LW5, respectively, and a control vector pCDF1b). These transformants were selected on LB agar plates supplemented with kanamycin (50 μg/mL) and spectinomycin (100 μg/mL).

One colony of each of these transformations was selected for growth in 2 mL liquid LB media supplemented with antibiotics, as above, and incubated at 37° C., shaking at 280 rpm. After 16 hours, 1 mL of the culture was added to 10 mL of LB supplemented with kanamycin (50 μg/mL) and spectinomycin (100 μg/mL) and arabinose (1 mM) and $FeSO_4$ (80 μM) to induce the expression of the monooxygenase. Each 10 mL culture was incubated at 37° C., shaking at 280 rpm. After 4 hours, each culture was centrifuged and resuspended in 10 mL PBS to wash the cells. These were each centrifuged again and resuspended in 10 mL PBS supplemented with arabinose (1 mM), $FeSO_4$ (80 μM), and glycerol (0.4% final concentration). This 10 mL volume was split equally between two serum bottles and sealed with butyl rubber stoppers. A volume of 60 mL of air was injected through the stopper of one serum bottle, while 60 mL of methane was injected through the stopper of the other serum bottle. All serum bottles were placed at 37° C., shaking at 280 rpm. After 44 hours, the bottles were opened and sampled for the presence of methanol, using the technique described herein. By comparison with a standard curve, the strains produced the following concentration of methanol as shown in the table below.

TABLE 9

| *M. capsulatus* sMMO is functional in *E. coli* when co-expressed with many groES/groEL chaperone homologs | | | | |
|---|---|---|---|---|
| sMMO organism | sMMO plasmid | groESL organism | groESL plasmid | Methanol (mM) |
| *M capsulatus* | pDG6 | *T butanivorans* | pNH178 | 0.10 |
| *M capsulatus* | pDG6 | *M capsulatus* | pNH180 | 2.67 |
| *M capsulatus* | pDG6 | *M trichosporium* | pNH181 | 1.49 |
| *M capsulatus* | pDG6 | *Methylocaldum* sp.175 | pNH185 | 2.65 |
| *M capsulatus* | pDG6 | *Methylocystis* sp. LW5 | pNH187 | 1.09 |
| M capsulatus | pDG6 | none | pCDFlb | 0.00 |

Example 10. Several Heterologous Chaperones Improve Ethane into Ethanol Conversion by sMMO This example describes the ability of the sMMO from *Solimonas aquatica* to have improved activity against ethane as a substrate with the coexpression of a panel of groES/groEL chaperones.

The strain NH283, described elsewhere herein, was transformed with two plasmids simultaneously: pNH160 (SEQ ID NO: 33, containing the coding regions corresponding to the *S. aquatica* mmoX, mmoY, mmoZ, mmoB, mmoC, and mmoD genes) and one plasmid selected from the set of plasmids containing pNH188 (SEQ ID NO:44), pNH180 (SEQ ID NO:40), pNH185 (SEQ ID NO:42), pNH187 (SEQ ID NO:43), and pCDFlb (SEQ ID NO:20) (containing codon-optimized groES/groEL genes from the microorganisms *S. aquatica, M. capsulatus, Methylocaldum* sp. 175, *Methylocystis* sp. LW5, respectively, and a control vector pCDF1b). These transformants were selected on LB agar plates supplemented with kanamycin (50 μg/mL) and spectinomycin (100 μg/mL).

One colony of each of these transformations was selected for growth in 2 mL liquid LB media supplemented with antibiotics, as above, and incubated at 37° C., shaking at 280 rpm. After 16 hours, 1 mL of the culture was added to 10 mL of LB supplemented with kanamycin (50 μg/mL) and spectinomycin (100 μg/mL) and arabinose (1 mM) and $FeSO_4$ (80 μM) to induce the expression of the monooxygenase. Each 10 mL culture was incubated at 37° C., shaking at 280 rpm. After 4 hours, each culture was centrifuged and resuspended in 10 mL PBS to wash the cells. These were each centrifuged again and resuspended in 10 mL PBS supplemented with arabinose (1 mM), $FeSO_4$ (80 μM), and glycerol (0.4% final concentration). This 10 mL volume was split equally between two serum bottles and sealed with butyl rubber stoppers. A volume of 60 mL of air was injected through the stopper of one serum bottle, while 60 mL of ethane was injected through the stopper of the other serum bottle. All serum bottles were placed at 37° C., shaking at 280 rpm. After 24 hours, the bottles were opened and samples for the presence of ethanol, using the technique described herein. By comparison with a standard curve, the strains produced the following concentration of ethanol as shown in the table below.

TABLE 10

| *S. aquatica* ethane monooxygenase is functional in *E. coli* with many groES/groEL pairs | | | | |
|---|---|---|---|---|
| sMMO organism | sMMO plasmid | groESL organism | groESL plasmid | Ethanol (mM) |
| *S. aquatica* | pNH160 | *S. aquatica* | pNH188 | 0.52 |
| *S. aquatica* | pNH160 | *M capsulatus* | pNH180 | 0.17 |
| *S. aquatica* | pNH160 | *Methylocaldum* sp. 175 | pNH185 | 0.33 |
| *S. aquatica* | pNH160 | *Methylocystis* sp. LW5 | pNH187 | 0.08 |
| *S. aquatica* | pNH160 | none | pCDFlb | 0 |

These results demonstrate the wide range of groES/groEL sequences capable of improving functionality of the sMMO, even when the sMMO and groES/groEL microorganisms are distantly-related.

Example 11. Distantly-Related Diiron Monooxygenases are Capable of Converting Ethane into Ethanol This example describes functional diiron monooxygenases expressed in *E. coli*, converting ethane into ethanol. *Pseudonocardia* sp. TY-7 prml A and *Solimonas aquatica* mmoX are 31% identical at the amino acid level.

The strain NH283, described elsewhere herein, was transformed with two plasmids simultaneously: pNH100 (SEQ ID NO:28, containing the coding regions corresponding to the *Pseudonocardia* sp. TY-7 propane monooxygenase genes) and pNH177 (SEQ ID NO:38, containing codon-optimized groES/groEL genes from the microorganism *Pseudonocardia autotrophica*). The strain containing the *S. aquatica* monooxygenase and *S. aquatica* groES/groEL was constructed as described elsewhere herein. These transformants were selected on LB agar plates supplemented with kanamycin (50 ug/mL) and spectinomycin (100 ug/mL).

The method for culturing these strains and for measuring the ethanol concentration has been described in the prior example. The results of this measurement are shown in Table 11.

TABLE 11

| Comparison of ethane to ethanol conversion with distantly-related ethane monooxygenase enzymes | | | | |
|---|---|---|---|---|
| SMMO organism | plasmid | groESL organism | plasmid | Ethanol (mM) |
| *Pseudonocardia* sp. TY-7 | pNH100 | *P. autotrophica* | pNH177 | 0.08 |
| *S. aquatica* | pNH160 | *S. aquatica* | pNH188 | 0.52 |

Example 12. Mutations in Soluble Methane Monooxygenase that Improve Function in *E. coli*

This example describes finding mutations that improve the function of sMMO in *E. coli*. The process for improving sMMO involves three steps: generating genetic diversity, screening the diversified library of clones to identify beneficial or neutral mutations, and recombining these mutations in a new library. This process is iterative and can begin with any functional enzyme sequence for which a screen exists.

Genetic diversity can be generated by well-known techniques, such as error-prone PCR and site saturation mutagenesis. Screening these mutated clones for improved function, using for example the screens described in the examples above, separates clones that have improved or neutral function. (Other screens may also be useful in order to identify, perhaps indirectly, improved enzymes.) These clones can be sequenced in order to identify the mutation(s) connected to the improved function. Recombining mutations can be done using one of several possible methods, such as T-PCR, SOEing PCR, gene shuffling, and commercially available kits like Quikchange Multisite Mutagenesis. These recombined libraries can be tested for improved variants using a range of screens or selections tied to features of the enzyme which one is attempting to alter, such as activity or substrate specificity.

Example 13. MMO Mutations Improving Activity and Specificity in *E. coli*

This example describes the directed evolution of MMO and the identification of sites and mutations that are important for MMO activity and substrate specificity for ethane and methane. Enzyme specificity, solubility, folding, and activity can all be improved by altering the structure of the protein using site-directed or random mutagenesis. Various MMO libraries were constructed by random error-prone PCR and site-directed mutagenesis. Libraries were first screened in 96-well plates using surrogate substrates to identify primary hits. The highest hits from each plate were validated for conversion of ethane to ethanol in 125 mL glass bottles. Approximately one third of the hits from the primary screening showed improved oxidation of ethane to ethanol during validation. One mmoX mutation conferring ethane specificity was identified; there was an amino acid substitution of N for E at amino acid position 240 in mmoX (SEQ ID NO:10) in this plasmid, which was subsequently named pBZ15 (SEQ ID NO:16). The mutant strain (BZ27) and wild type strain (BZ25) were assayed for ethane and methane oxidation as described elsewhere herein.

TABLE 12

Methane and ethane oxidation by BZ25 and BZ27. Mutation mmoX (E240N) improves activity against ethane compared to wild-type.

| Strain | mmoX mutation | Methanol (mM)/OD600 | Ethanol (mM)/OD600 |
|---|---|---|---|
| BZ25 | Wild type | 5.45 | 0.94 |
| BZ27 | E240N | 2.67 | 1.61 |

This example also demonstrates directed evolution by generating and screening enzyme diversity in iterative rounds, similar to how natural selection operates in evolution. Beneficial mutations at amino acid position 61 and 421 in mmoX were further mutagenized and combined. The identified mmoX variants showing improvement in ethane oxidation activity over E240N (BZ27) are shown in Table 13. The combination of pBZ13 (SEQ ID NO:15) and the E240N mutation in mmoX resulted in nearly an order of magnitude improvement over DG80 expressing wild type mmoX in the presence of pNH180 (SEQ ID NO:40).

TABLE 13

Mutations in mmoX improve conversion of ethane to ethanol

| Strain | mmoX mutations | Ethanol (mM)/OD600 |
|---|---|---|
| DG80 | Wild type | 0.04 |
| BZ27 | E240N | 0.32 |
| BZ45 | K61Y, E240N, S421A | 0.47 |
| BZ46 | K61S, E240N, S421T | 0.45 |

The MMO plasmid in BZ46 carrying three mutations in mmoX (K61S, E240N, S421T) was subjected to another round of mutagenesis and selection, resulting in further improvement in MMO activity (Table 14). Mutations in mmoY (L67M) and mmoC (P167T) arc proven beneficial, pointing to the importance of both positions. The MMO plasmid in BZ67, subsequently named pBZ23 (SEQ ID NO:18), is being used as a template for more iterative rounds of mutagenesis and selection.

TABLE 14

Mutations in multiple subunits of MMO improve conversion of ethane to ethanol

| | MMO mutations | | | Ethanol (mM)/ |
|---|---|---|---|---|
| Strains | mmoX | mmoY | mmoC | OD600 |
| BZ46 | K61S, E240N, S241T | Wild type | Wild type | 0.60 |
| BZ56 | K61S, E240N, S241T | L67M | Wild type | 0.96 |
| BZ67 | K61S, E240N, S241T | L67M | P167T | 1.16 |

Example 14. Hybrid Monooxygenases in *E. coli*

The sequences of closely related soluble diiron monoxygenases (SDIMOs) can be a source of genetic diversity that can be recombined to identify improved enzymes. In the case of a multi-subunit enzyme, such as the SDIMOs, one method to improve the enzyme complex is to combine subunits from one SDIMO with those from another. In the simplest example, a single subunit from one SDIMO would replace the homologous subunit from the second. A more complicated scheme would exchange more than one subunit. An even-more complicated scheme would clone, into a single library, all the subunits from multiple homologous SDIMOs in a manner that allows for all possible combinations allowing for exactly one of each subunit. Methods for cloning such a library have been described in the literature, such as Golden Gate Assembly (Engler and Marillonnet, Combinatorial DNA assembly using Golden Gate cloning, *Methods Molecular Biology*, vol 1073, p. 141-156, 2013) and Gibson assembly (D. Gibson et al., *Enzymatic assembly of DNA molecules up to several hundred kilobases*, NATURE METHODS Vol 6, Issue 5, p. 343-345, 2009). These constructs can then be screened using, for example, the assays described herein.

Example 15. Connecting Product of Monooxygenase to Other Metabolic Pathways: In a Single Cell This example describes the expression of a monooxygenase enzyme in a cell that additionally comprises metabolic pathways to consume the product of the monooxygenase reaction and/or to produce the substrate of the monooxygenase reaction, thus connecting the monooxygenase enzyme into a metabolic pathway in the cell.

The cells and methods for constructing those cells containing a monooxygenase enzyme have been described herein. These monooxygenase enzymes and the nucleic acids from which they are expressed are modular components that can be added to cells with metabolic pathways to, for example, consume the product of the monooxygenase reaction. These metabolic pathways may be endogenous to the naturally occurring strain or they may be heterologously expressed from engineered nucleic acids that have been added to the cell.

In one example, the sMMO enzyme is expressed in *P. pastoris*. This strain is cultured in minimal media with methane as the only carbon source. The monooxygenase can oxidize the methane to methanol. *P. pastoris* endogenously contains a pathway to consume methanol. The net result is a strain capable of converting methane into methanol via heterologously expressed sMMO, and subsequently methanol into other metabolites, using enzymatic pathways endogenous to *P. pastoris*.

In a similar example, the sMMO enzyme is expressed in an engineered *E. coli* strain. *E. coli* does not naturally consume methanol, but if this engineered *E. coli* strain is expressing a pathway to consume methanol, then a similar metabolic pathway will function. This strain is cultured in minimal media containing methane, and a similar pathway is operational in this *E. coli* strain.

Given the many substrates and products of sMMO (in Table 1), it is not difficult to imagine many other metabolic pathways that could be connected to/by the sMMO enzyme. Identifying all possible metabolic pathways that could be constructed using sMMO as a possible chemical reaction (i.e. a "link between nodes" of metabolites) is a task suitable for a computer.

Example 16. Connecting Product of Monooxygenase to Other Metabolic Pathways: More than One Cell This example describes the expression of a monooxygenase enzyme in a biological system of multiple cell types that additionally comprises metabolic pathways to consume the product of the monooxygenase reaction and/or to produce the substrate of the monooxygenase reaction, thus connecting the monooxygenase enzyme into a metabolic pathway in the biological system.

The cells and methods for constructing those cells containing a monooxygenase enzyme have been described herein. In a conceptually similar manner to the example setting forth the connection of a metabolic pathway in a single cell, the metabolites involved in a metabolic pathway can be converted by enzymes in a single cell or in multiple cell types in a culture (i.e. a "co-culture") or in a co-culture wherein some of the enzymatic steps occur outside of any cells, in the fermentation broth.

The method of co-culturing multiple strains in a single fermentation is straightforward. The strains can be grown up separately and combined in a single fermentation vessel. In one instance, an *E. coli* strain expressing the sMMO is co-cultured with a methylotrophic strain, such as *P. pastoris*. This fermentation can be performed in minimal media lacking a carbon source. When the strains are sealed in a fermentation vessel, methane can be added to the vessel. The sMMO in *E. coli* will convert the methane into methanol, which can diffuse out of the *E. coli* cell and enter the *P. pastoris* cell where it can be consumed and converted into intracellular metabolites and/or used as a carbon source for growth. If the *P. pastoris* strain is engineered to produce a chemical, the *E. coli* strain is simply biologically converting the methane into methanol for use as a substrate in a metabolic pathway inside the co-cultured yeast strain.

This example is not meant to be limiting to methane-fed fermentations, as the concept is extensible to the biological conversion of many substrates (e.g. those shown in Table 1) into many products that can be used by natural or engineered microorganisms of a similar or different species. There is no reason, in principle, that the entire metabolic pathway from feedstock to product must reside in a single cell as long as the metabolite(s) being exchanged can diffuse from one cell to another. If metabolite(s) are unable to naturally diffuse in or out of a cell, the expression of a transporter or porin protein may enable active or passive transport of the metabolite in or out of a cell. Many examples of metabolite-specific or general transporters or porins are known.

Example 17. Improved Aerobic Growth on Ethanol as a Major or Sole Carbon Source in *E. coli*

Strains of *E. coli* capable of aerobic growth on ethanol have been previously reported (D Clark & J E Cronan, *Escherichia coli* mutants with dehydrogenase and nitrate *Escherichia coli* Mutants with Altered Control of Alcohol Dehydrogenase and Nitrate Reductase, 141 177-183, 1980); (J Membrillo-Hernandez et al., Evolution of the adhE gene product of *Escherichia coli* from a functional reductase to a dehydrogenase: Genetic and biochemical studies of the mutant proteins, 275 Journal of Biological Chemistry 33869-33875, 2000).

Figure 1:
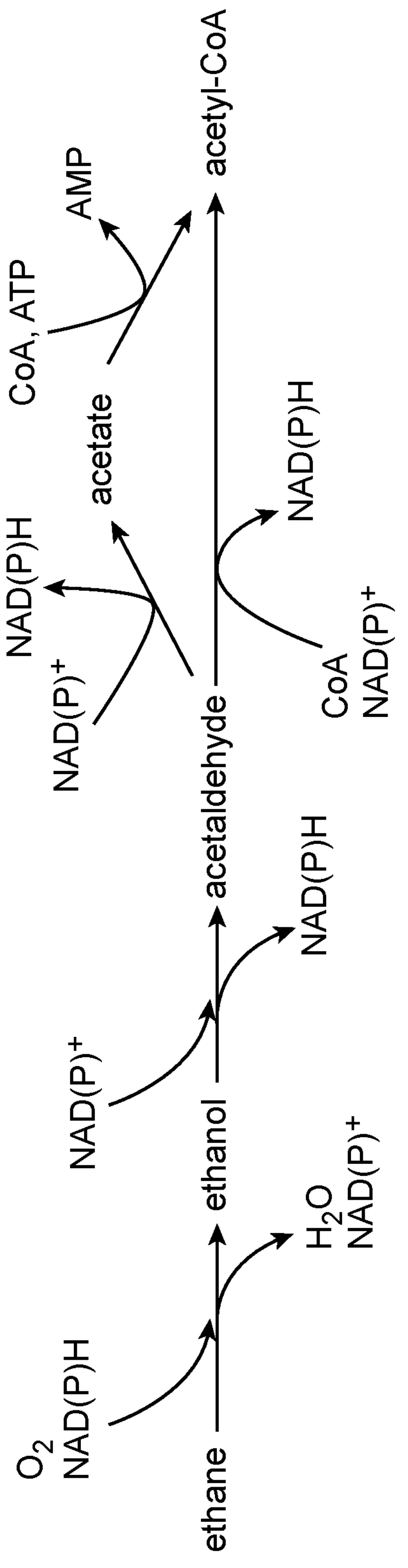
FIG. 1 shows two representative pathways from ethane to acetyl-CoA. Many enzymes or enzyme classes are known which catalyze each of these reaction steps. Depending on the exact enzymes present in a particular strain, the pathway may proceed via acetate or just directly from acetaldehyde to acetyl-CoA. Acetyl-CoA is a major node of central metabolism from which other key metabolites are built.

The growth rate of *E. coli* on minimal ethanol media depends on the rate of assimilation of ethanol (FIG. 1). Thus, strains may be engineered or evolved to increase the rate of growth on minimal ethanol media. Many strategies may be employed to improve the growth rate on ethanol, such as (but not limited to) chemical mutagenesis, overexpression of targeted genes in the pathway (e.g. alcohol-aldehyde dehydrogenase, glyoxylate shunt enzymes), overexpression libraries/transduction from strains with faster growth on ethanol or acetate.

In order to improve the growth rate of *E. coli* on ethanol as a major or sole carbon source, an expression library of the adhE(A267T, E568K) (SEQ ID NO:49) mutant was constructed.

The plasmid-based expression library of the adhE(A267T, E568K) mutant was constructed by first generating pNH045 (SEQ ID NO:73), using standard molecular biology methods. The adhE gene was amplified by colony PCR from genomic DNA prepared from *E. coli* NEB Turbo. Primers were designed to introduce the two desired mutations and the parts were assembled using the Gibson assembly technique (D G Gibson et al., Enzymatic assembly of DNA molecules up to several hundred kilobases., 6 Nature methods 343-345, 2009) into the plasmid pMAL-c5x from New England Biolabs. This plasmid contains an IPTG-inducible Ptac promoter. Successful transformants were screened by colony PCR and sequenced using Sanger sequencing. One clone, with the correct sequence through the promoter, open reading frame, and terminator, was named pNH045.

In order to vary the promoter strength, a PCR was performed using pNH045 as the template. Degenerate primers were used with degenerate bases and non-standard bases (see for example, haps://www.idtdna.com/pages/docs/quick-looks/quick-look---degenerate-sequences-and-non-standard-bases.pdf?sfvrsn=1). The two primers that were used to introduce variation at the key promoter nucleotides in the sequence are shown below:

Ptac library fwd=gctgttSaMaattaatcatcggctcgKaHRatgtgtggaattgtgagcggataac

Ptac library rev=catYDtMcgagccgatgattaattKtSaacagctcatttcagaatatttgccagaacc

This PCR was performed such that the reaction generated a DNA fragment that could be self-ligated using the Gibson protocol. This reaction was purified and transformed into the desired strain of *E. coli*, NEB Turbo. Several of these clones were sequence verified to contain a variable sequence in the promoter region. The colonies were scraped from the agar plate and combined in a single DNA library by miniprep extraction, and named pNH069L.

The identification of an optimal expression level of adhE (A267T, E568K) for growth on ethanol as a major or sole carbon and energy source is a straightforward growth competition. The plasmid library pNH069L was transformed into an *E. coli* strain of interest (e.g. BL21) by electroporation. These cells were scraped from the agar plate the following day and grown in a minimal media with ethanol as the sole carbon source at the desired temperature (e.g. 37° C.) under inducing conditions (e.g. with IPTG at a saturating final concentration of 1 mM). Minimal ethanol media may contain the standard M9 salts recipe plus thiamine and ethanol at 1% final concentration, though other minimal media recipes also have been described (J Tamarit, *Identification of the Major Oxidatively Damaged Proteins in Escherichia coli Cells Exposed to Oxidative Stress,* 273 Journal of Biological Chemistry 3027-3032, 1998). Passaging these cells through this media allowed the fastest growing strains to dominate the population of the culture. This culture was then streaked on rich media (LB+carbenicillin antibiotic at 100 ug/mL) to isolate single clones. Each of these was then grown in minimal ethanol media to compare the growth rate against the growth on minimal glucose media and against a control strain (e.g. DC272) (J Membrillo-Hernandez et al., *Evolution of the adhE gene product of Escherichia coli from a functional reductase to a dehydrogenase: Genetic and biochemical studies of the mutant proteins,* 275 Journal of Biological Chemistry 33869-33875, 2000)

Example 18. Improved Growth on Ethanol in *E. coli*

This example describes a series of gene over-expressions which allow *E. coli* to grow robustly across many concentrations of ethanol. These genes are either from heterologous organisms or from *E. coli.*

Previous work has shown that introducing two point mutations in *E. coli* adhE—A267T and E568K (SEQ ID NO:49)—is sufficient to allow *E. coli* to grow on ethanol. AdhE is a bifunctional enzyme that can act as both an alcohol dehydrogenase (ADH) and an acetaldehyde dehydrogenase (ACDH). Based on our own work and also published characterization of this enzyme, we determined that the ADH activity of adhE (A267T, E568K) could be limiting for applications where the concentration of ethanol is low, because it has a high KM for ethanol.

We searched for new enzyme pathways that have high activity at low ethanol concentrations. We identified a panel of ADH and ACDH enzymes from organisms that naturally grow on ethanol, and synthesized codon-optimized versions of the relevant genes. We also included genes from *E. coli* that have been shown to perform the desired chemistries. Operons of all possible two-gene combinations were constructed using Gibson assembly into a pBR322-origin plasmid under control of a Ptac promoter, and the expression levels of these genes were simultaneously varied using degenerate bases in the ribosome binding sites. Some strains combined adhE (A267T, E568K) expressed from the genome with single ADH genes overexpressed from the plasmid. The resulting colonies were screened for growth across a wide range of ethanol concentrations. The optical density was measured 20 hours after cells were inoculated into minimal ethanol media. Table 15 shows the results. The wild-type *E. coli* does not grow on ethanol at any concentration, and different combinations of ADH's and ACDH's confer different magnitudes of growth benefit.

The following describes the method for culturing the strains and measuring the growth of the strains on ethanol. The strains were cultured in LB broth supplemented with carbenicillin (100 ug/mL) for an overnight growth at 37° C., and then washed by spinning the culture down and washing two times in phosphate buffered saline media (PBS). Minimal media BEMO was formulated as follows. First a 1000× metals solution was mixed containing the following compounds in the concentrations provided: 0.1 M $FeCl_3*6H_2O$, 1 M $CaCl_2$, 1 M $MnCl_2*4H_2O$, 1 M $ZnSO_4*7H_2O$, 0.2 M $CoCl_2*6H_2O$, 0.2 M $NiCl_2*H_2O$, 0.1 M $NaMoO_4*2\ H_2O$, 0.1 M $Na_2SeO_3*5\ H_2O$, 0.1 M $H_3BO_3$. The minimal media called BEMO contains (in $ddH_2O$): 25 mM $(NH_4)_2SO_4$, 50 mM $KH_2PO_4$, 50 mM $Na_2HPO_4$, 1 mM $MgSO_4$, 0.15% LB, 1 mM IPTG, and 0.1% of the 1000× metals solution, plus a desired concentration of ethanol. The cells were then resuspended in minimal BEMO media with different concentrations of ethanol to a starting OD600 of 0.1. These cultures were aliquoted to 96-well plates, sealed, and shaken overnight at 37° C. for 20 hours. 100 μL media was sampled and an absorbance at

TABLE 15

Improved ethanol assimilation pathways allows faster growth across a wide range of ethanol concentrations. Data are averages of measurements made from two independent cultures.

| | Base strain | | | OD600 at each [Ethanol] | | | |
|---|---|---|---|---|---|---|---|
| | change | ADH | ACDH | 0% | 0.03% | 0.06% | 0.13% |
| WT *E. coli* | none | | | 0.11 | 0.11 | 0.10 | 0.10 |
| LC55 | genomic adhE (A267T, E568K) | | | 0.12 | 0.12 | 0.12 | 0.59 |

TABLE 15-continued

Improved ethanol assimilation pathways allows faster growth across a wide range of ethanol concentrations. Data are averages of measurements made from two independent cultures.

| | Base strain change | ADH | ACDH | OD600 at each [Ethanol] 0% | 0.03% | 0.06% | 0.13% |
|---|---|---|---|---|---|---|---|
| LC253 | genomic adhE (A267T, E568K) | adh (*B. stearothermophilus*) | | 0.11 | 0.13 | 013 | 0.83 |
| LC294 | none | adh (*B. stearothermophilus*) | mhpF (*E. coli*) | 0.12 | 0.14 | 0.23 | 0.30 |
| LC292 | none | adh (*B. stearothermophilus*) | acdH (*Clostridium kluyveri*) | 0.10 | 0.23 | 0.51 | 0.85 |

Plasmid pLC99 (SEQ ID NO:27) was isolated by mini-prep from LC292. Another clone with similar growth phenotype was isolated and its plasmid was named pLC100 (SEQ ID NO:23). Both plasmids were subsequently used in follow-up experiments to confer improved ethanol assimilation properties on *E. coli* strains.

Example 19. Synthetic Ethanotroph in *E. coli*

This example provides a description of a strain of *E. coli* capable of growth on ethane as a major or sole carbon source.

Since *E. coli* strains have been described here and elsewhere (D Clark & J E Cronan, *Escherichia coli* mutants with dehydrogenase and nitrate *Escherichia coli* Mutants with Altered Control of Alcohol Dehydrogenase and Nitrate Reductase, 141 177-183, 1980) and (J Membrillo-Hermindez et al., Evolution of the adhE gene product of *Escherichia coli* from a functional reductase to a dehydrogenase: Genetic and biochemical studies of the mutant proteins, 275 Journal of Biological Chemistry 33869-33875, 2000) that are able to grow on ethanol as a major or sole carbon and energy source, these strains can be the basis for a strain capable of growth on ethane, provided a functional enzyme or enzyme complex can be expressed that can convert ethane into ethanol.

Enzymes exist that are capable of converting a hydrocarbon or an alkane into an alcohol. These enzymes classes include the soluble methane monooxygenases (sMMOs), particulate methane monooxygenases, hybrid methane monooxygenases, alkane/alkene monooxygenases, toluene monooxygenases, some ammonium monooxygenases, and some P450 monooxygenases. To date, however, there are no reports of any group describing the successful, functional expression of a monooxygenase enzyme in *E. coli* capable of oxidizing ethane into ethanol.

These enzymes can be expressed, along with any accessory proteins, protein folding chaperones, and/or electron donation mediators/reductases, using standard molecular biology techniques. The genes can be expressed from DNA extracted from the native organism and cloned into expression vectors suitable for *E. coli*. These vectors can be transformed into *E. coli*, using standard techniques, such as electroporation. Alternatively, DNA can be designed and constructed to allow integration of the genes into the *E. coli* chromosome, such that expression of the genes would produce the desired protein components. Another option is to synthesize the genes, using vendors such as IDT or DNA2.0, and express the genes from either a plasmid or a chromosomal locus. Synthesized DNA allows the researcher to choose the desired codon at each position along the gene and can be used to optimize the nucleic acid sequence for expression. Synthesized DNA also allows the choice of nucleic acid sequences between genes in a polycistronic operon. These genes or operons can be expressed from any promoter that is functional in *E. coli*, including the most well-studied promoters, such as Ptac, Plac, Ptrc, Pbad (which are inducible) and PT5 (which is constitutive).

These monooxygenase enzyme complexes can be expressed in *E. coli*. Examples of monooxygenases that may oxidize ethane to ethanol are given in Table 1. This set of monooxygenases is not meant to be limiting but just as an example of a set that could be able to oxidize ethane to ethanol. It is clear that by a simple BLAST search (S Altschul et al., *Basic Local Alignment Search Tool,* 215 J Mol Biol. 403-410, 1990), one could identify alternative monooxygenases that are closely related to the set listed in Table 16.

TABLE 16

Examples of monooxygenase enzymes that may oxidize ethane

| Organism | Gene names | Accession number |
|---|---|---|
| *Pseudomonas mendocina* KR1 | tmoABCDEF | AY552601.1 |
| *Methylocella silvestris* BL2 | Msi11651-1647 | NC 011666.1 |
| *Mycobacterium* NBB4 | smoXYC1B1Z, groL (Myech 5901 - Mycch_5897, Mycch_5390) | CP003054.1 |
| *Thauera butanivorans* | bmoXYBZDC | AAM19732.1, AAM19731.1, AAM19730.1, AAM19729.1, AAM19728.1, AAM19727.1, ABU68845.2 |

TABLE 16-continued

| Examples of monooxygenase enzymes that may oxidize ethane | | |
|---|---|---|
| Organism | Gene names | Accession number |
| *Mycobacterium smegmatis* mc2-155 | mimABCD | CP000480.1 |
| *Gordonia* TY-5 | prmABCDG | AB 112920.1 |
| *Pseudonocardia autotrophica* | WP 037052656.1 to WP 037052662.1 | NZ JNYD01000036.1 |
| *Amycolatopsis methanolic* a 239 | AMETH 2368-2375 | CP009110.1 |
| *Mycobacterium* HXN-1500 | CYP153A6 (ahpGHI) | AJ783967.1 |
| *Bacillus megaterium* | P450-BM3 | WP 034650526.1 |
| *Pseudomonas putida* | P450cam | WP 032492633.1 |
| *Methyl ocella silvestris* BL2 | mmoXYBZDC (Msi11262 - Msi1 1 267) | NC 011666.1 |
| *Methylococcus capsulatus* (Bath) | mmoXYBZDC_G | AF525283.1, M90050.3 |
| *Methylosinus trichosporium* OB3b | mmoXYBZDC, groEL | X55394.3, EF685207.1 |
| *Methylococcus capsulatus* (Bath) | pmoCAB | L40804.2 |
| *Methylosinus trichosporium* OB3b | pmoCAB | U31650.2 |
| *Pseudomonas putida* (OCT plasmid) | a1kBFGHJKLNST | NG 035191.1 |
| *Rhodococcus corallinus* B-276 | amoABCD | D37875.1 |

The fusion monooxygenase spmoB (R Balasubramanian et al., Oxidation of methane by a biological dicopper centre., 465 Nature 115-119, 2010) contains two fused domains of the pIVMO complex from *Methylococcus capsulatus* (Bath). It was demonstrated that spmoB was not soluble when expressed in *E. coli*, but that it could be extracted and resolubilized in vitro in a method that demonstrated some functionality at oxidizing methane. This spmoB enzyme may be expressed in *E. coli* strains that are simultaneously expressing protein-folding chaperones, such as groES/groEL from *E. coli* or from the native organism *M. capsulatus*. spmoB can also be expressed from a construct that targets the enzyme to the periplasmic space, between the inner and outer plasma membranes of *E. coli*. Since the spmoB enzyme is a fusion of domains that were both taken from the periplasmic part of the pmoB protein, spmoB may function properly in the periplasm. Periplasmic-targeting sequences have been described previously.

The particulate methane monooxygenase (pMMO) may also oxidize ethane to ethanol in *E. coli*. This protein complex is composed of three subunits and resides in the inner membrane of the native organism. To successfully express the pMMO in *E. coli*, correct N-terminal leader sequences must be properly fused to each of the three subunits.

The assay for successful expression of a monooxygenase converting ethane to ethanol may be the growth of the *E. coli* strain on ethane as a major or sole carbon source. The *E. coli* host strain may be chosen to be one that can grow on ethanol as a major or sole carbon source, so that any functional ethane monooxygenase that converts ethane to ethanol will be able to provide a carbon-based substrate for the bacterium to grow and reproduce. The minimal salts media provides the necessary nutrients, other than the carbon source, to sustain the bacterium. Minimal salts media for *E. coli* can be based on the M9 recipe, widely used in microbiology, along with the necessary minerals, such as iron or copper, that may be required for the functionality of the monooxygenase. The media and the strain containing the monooxygenase, or a library of monooxygenases, can be inoculated into a sterile bottle and sealed using, for example, a butyl rubber stopper. Then, using a syringe and needle, ethane gas can be injected into the headspace above the culture. This sealed bottle can be incubated for a prolonged period to allow the ethane to dissolve into the media and for the cells to consume the ethane and grow. Growth can be measured either by an increase in optical density of the culture, relative to a control into which no ethane has been injected, or by counting the colony forming units for both the experiment and control.

In some cases, the rate of ethanol production via oxidation of ethane will be too slow for the strain to grow. Strains may then be grown in a media containing a limiting concentration of ethanol for a moderate growth rate—still limited by the amount of carbon available. Any cell that contains a functional monooxygenase that is making even small amounts of ethanol will have a growth advantage, since carbon is the limiting element for growth in this experimental design. These cultures may be grown continuously, as in bioreactors, turbidostats, or chemostats, or they may be serially passaged from one bottle to the next, so as to allow growth over a longer period of time. The exponential rate of the growth of microbial cells is a key advantage of this strategy.

The following describes the actual work performed to demonstrate a synthetic ethanotroph in *E. coli*, Specifically, this part of the example describes the construction and testing of a strain containing a functional sMMO and an ethanol-assimilation pathway, capable of growth on ethane as a major or sole carbon source.

Strain Construction of NH566

The strain NH566 was constructed in the following series of steps. The plasmid pBZ15 (SEQ ID NO: 16) was constructed as described elsewhere herein. The plasmid pNH225 (SEQ ID NO: 45) was cloned by adding a DNA fragment from pLC99 (SEQ ID NO: 27) encoding lacI-Ptrc-adh (*B. stearothermophilus*)-acdH (*C. kluyveri*) ethanol-assimilation pathway into pBZ13, which contains expression cassettes for the groES/groEL from *E. coli* and for the groES/groEL from *M. capsulatus*. Strain NH283 was constructed, as described above. NH566 was selected from transformants of NH283 transformed with both plasmids pBZ15 (SEQ ID NO: 16) and pNH225 (SEQ ID NO: 45).

Culturing NH566 with Ethane Vs Air

NH566 was streaked onto LB agar plates supplemented with spectinomycin (100 μg/mL) and kanamycin (50 μg/mL) and incubated at room temperature for 3 days. A single colony was picked into 1 mL liquid LB broth supplemented with spectinomycin (100 μg/mL) and kanamycin (50 μg/mL) and grown at 37° C., shaking at 280 rpm. After 4 hours, the 1 mL was added to 9 mL of the same media and grown at 37° C., 280 rpm for another 2 hours. This 10 mL culture was centrifuged and washed in 10 mL PBS once. From this, 1 mL of the PBS was centrifuged again and resuspended in 10 mL of BEM4 media supplemented with ethanol to a final concentration of 0.5% (v/v). This culture was placed at 37° C., shaking at 280 rpm for 23 hours. From this culture, 5 mL was centrifuged and the supernatant was discarded. The pellet was resuspended in 10 mL PBS to wash. The resuspension was centrifuged again, the supernatant was discarded and the pellet was resuspended in 10 mL BEM4 base media lacking any ethanol. (The minimal media called BEM4 contains (in ddH2O): 50 mM $KH_2PO_4$, 50 mM $Na_2HPO_4$*7 $H_2O$, 1 mM $MgSO_4$, 0.15% LB, 6.25 mM glutamine, 80 1 aM $FeSO_4$, 0.1 mM $CaCl_2$, 1 mM IPTG, 0.1% of the 1000× metals solution, and 1 mM arabinose (where required for induction of promoter pBAD), plus a desired concentration of ethanol.) From this culture, 4.5 mL was pipetted into each of two serum bottles and sealed with butyl rubber stoppers. The initial cell density was measured by OD600 and found to be approximately 0.5 as desired. Into one serum bottle, a syringe was used to inject 60 mL of air, while into the other serum bottle, a syringe was used to inject 60 mL of ethane. The serum bottles were incubated at 37° C., shaking at 280 rpm. After 20 hr, 46 hr, and 64 hr of incubation, both serum bottles were sampled through the rubber stoppers using a small syringe. The cell density of both samples was measured by OD600 and by plating on LB agar plates overnight for colony counting. FIG. 7 shows a timecourse of the OD600 measurements for the two serum bottles which demonstrates that the ethane-fed culture grows to a higher OD600 than its starting density, while the air-fed culture drops in density, due to a loss in cell viability. The increase in cell density due to the presence of the ethane in the serum bottle confirms that the cells are able to metabolize the ethane. Cell viability increases due to ethane were confirmed by counting the colony forming units on the agar plates from the 46 hr and 64 hr timepoints. At 46 hrs, there were 1.44× more colonies from the ethane-fed culture over the air-fed culture. By 64 hrs, this ratio had increased to 1.75×.

Example 20. Bioconversion of Ethanol to Free Fatty Acids in *E. coli*

This example describes potential pathways to increase production of fatty acids in *E. coli* from ethanol as a feedstock. This example also describes work performed that increased the production of fatty acids in *E. coli* from ethanol.

Previous work has demonstrated the ability to overproduce fatty acids and derivatives from *E. coli*, using glucose or other sugar mixtures as the feedstock (H Cho & J. E. Cronan, *Defective Export Of A Periplasmic Enzyme Disrupts Regulation Of Fatty Acid Synthesis*, Journal of Biological Chemistry 270 4216-4219). Sugars are metabolized into acetyl-CoA as a central node of metabolism, and acetyl-CoA is used by the cell to produce fatty acids using the fatty acid biosynthesis pathway.

Previous work has also shown that *E. coli* mutants can be isolated with the ability to consume ethanol as a major or sole carbon and energy source, under aerobic conditions (D Clark & J E Cronan, *Escherichia coli mutants with dehydrogenase and nitrate Escherichia coli Mutants with Altered Control of Alcohol Dehydrogenase and Nitrate Reductase,* 141 177-183, 1980). In some cases, this ability was traced back to the overexpression of the native *E. coli* gene adhE, while, in other cases, mutations were discovered in the adhE gene that seemed to further enhance the growth rate of *E. coli* on ethanol (J Membrillo-Hernandez et al., *Evolution of the adhE gene product of Escherichia coli from afunctional reductase to a dehydrogenase: Genetic and biochemical studies of the mutant proteins,* 275 Journal of Biological Chemistry 33869-33875, 2000) The adhE gene encodes aldehyde-alcohol dehydrogenase, which has both alcohol dehydrogenase and coenzyme A-dependent acetaldehyde dehydrogenase activity.

In order to generate a strain of *E. coli* that can convert ethanol into fatty acids under aerobic culturing conditions, the adhE gene (or a mutant thereof, such as adhE(A267T, E568K)) may be overexpressed from a plasmid or chromosomal locus. Standard methods for expression libraries in *E. coli* have been described that involve the cloning of the gene with a degenerate oligonucleotide to randomize the base pairs at critical locations, inside, for instance, the ribosomal binding site or the promoter. Such a library may be used to create a diverse set of *E. coli* strains that vary in their expression levels of adhE. Since the object is to identify the strain that can grow fastest on ethanol as a major or sole carbon source, this library of *E. coli* can be tested under such conditions, in a single culture. The fastest growing strains will outcompete other strains, will become the most common genotype in the mixed population, and can be isolated by standard microbiology methods, and retested as clonal populations against each other. Using this technique, optimal levels of adhE(A267T, E568K) expression have been identified in *E. coli* strains such as NEB Turbo, BL21(DE3), and EPI300.

The production of fatty acids from glucose or other sugar mixtures in *E. coli* has been shown elsewhere (H Cho & J E Cronan, *Defective Export Of A Periplasmic Enzyme Disrupts Regulation Of Fatty Acid Synthesis*, Journal of Biological Chemistry 270 4216-4219). A thioesterase, such as *E. coli* 'tesA or *U. calfonica*' fatB1 (L Yuan et al., *Modification of the substrate specificity of an acyl-acyl carrier protein thioesterase by protein engineering.,* 92 Proceedings of the National Academy of Sciences of the United States of America 10639-10643, 1995), is expressed in *E. coli* from a plasmid or chromosomal locus. This thioesterase hydrolyzes the acyl-ACP bond and releases a fatty acid. An expression library, similar to that described in the previous paragraph, can be used to adjust the expression of the thioesterase to an optimal level under the desired culture conditions.

In order to generate a strain of *E. coli* capable of producing fatty acids from ethanol, an ethanol-consuming strain can be used as a host for a plasmid expressing the thioesterase library. Screening a moderate number of clones, e.g. less than 100, would be sufficient to find a clone with an optimal level of thioesterase expression, under the given culture conditions.

The analytical method for identifying fatty acids from the culture broth has been described previously (S Del Cardayre, US patent no. 20100257778, 2010). In brief, the culture is mixed with an equal volume of an organic solvent, such as butyl acetate, and agitated to enable the fatty acids to separate into the organic layer. The sample is centrifuged to separate the organic layer from the aqueous layer. A small volume of the organic layer can be run on a gas chromatograph to identify the fatty acid peaks.

This part of the example describes work actually performed that increased the production of fatty acids in *E. coli* from ethanol. Strain DC272 was received from the *E. coli* Genetic Stock Center at Yale University. The araB AD operon was deleted using the method of Datsenko and Wanner to create strain LC55 (DC272 araBAD::cat). Synthetic DNA encoding fatB1 from *Umbellularia californica* was codon optimized, purchased from a commercial vendor (Integrated DNA Technologies), and cloned into a plasmid in an operon behind the bla gene (conferring resistance to ampicillin) in a standard cloning vector containing a p 15a origin of replication. After the DNA sequence had been verified, the plasmid (named pBZ22, SEQ ID NO: 56) was transformed into LC55, generating strain NH671. As a control, LC55 was transformed with a different plasmid containing the same antibiotic resistance (bla).

The fluorescent Nile Red assay was used to measure the free fatty acid production of NH671 as follows. Both strains (NH671 and control) were inoculated in LB broth supplemented with carbenicillin (100 μg/mL) overnight at 37° C., 280 rpm. After 16 hours, 10 μL of the overnight culture was transferred into 2 mL of BEMO media (composition described elsewhere herein plus 0.5% final concentration of ethanol) and capped tightly. After two days, the cultures were sampled and the cell densities were normalized. From each culture, a 100 μL sample was taken and mixed with 0.5 μL of Nile Red stock solution (250 mg/mL in DMSO) as described by Hoovers (Hoovers et al., *Bacterial production of free fatty acids from fresh water magroalgal cellulose*, Appl. Microbiol. Biotechnology, Vol. 91(2), 2011). The fluorescence was measured using an excitation wavelength of 485 nm and an emission wavelength of 590 nm.

A blank media control was used to measure the background fluorescence and measured 296 counts. Strain NH671 measured 5950 counts, while the control strain (containing no fatB1 gene) measured 2151. This corresponds to a 2.77-fold higher fluorescence due to the free fatty acids in the sample.

Example 21. Bioconversion of Ethanol to Succinate in *E. coli*

In order to construct strains capable of converting ethanol into succinate, *E. coli* strains were modified by the deletion of ic1R and by the reduction or removal of expression of sdhAB, which encodes the succinate dehydrogenase enzyme. This example describes the construction of two strains with the ability to convert ethanol into succinate, along with the method for performing the conversion with the strains.

Strain Construction of NH533 and NH610

A strain capable of producing succinate was generated by deletion of three genetic loci in the *E. coli* strain NEB Express (New England Biolabs), a BL21-derivative. The three loci (araBAD, iclR, and sdhAB) were deleted sequentially using the method of Datsenko and Wanner (2000). Briefly, a deletion cassette was amplified from plasmids pKD3 or pKD13 using primers with homology to the target locus. The strain was made electrocompetent and transformed with the deletion cassette. Strains with the deletion were verified by colony PCR and the markers were removed using pCP20, as described elsewhere, leaving an FRT scar. The resulting strain (NEB Express AaraBAD::1-.RT Aic1R::FRT AsdhAB::FRT) was named LC344. This strain was then transformed with a plasmid that confers improved assimilation of ethanol, pLC100 (SEQ ID NO: 23), and was named NH533.

Strain NH610 was constructed by sequential deletion of araBAD and ic1R from NEB Express, as above. To reduce the expression of the sdhAB genes, without completely deleting them, a DNA fragment with homology to the 3' end of the sdhAB operon plus a Ptrc promoter and a chloramphenicol resistance marker was constructed to direct the Ptrc promoter in the opposite direction to the transcription of the sdhAB genes (SEQ ID NO: 47). This DNA cassette was integrated into the strain, using pKD46 as the lambda red system, as described above and elsewhere. Transformants were selected on LB agar plates supplemented with chloramphenicol (17 μg/mL). The resulting strains were then transformed with pLC100 (SEQ ID NO: 23) to improve the ability to assimilate ethanol into central metabolism. NH610 was selected from this transformation as a single clone.

Bioconversion of Ethanol into Succinate with NH533

NH533 was inoculated into 1 mL of LB broth supplemented with carbenicillin (100 μg/mL) directly from a glycerol stock and placed in a shaking incubator at 37° C., 280 rpm overnight. The following morning, the strain was diluted 1:100 into 2 mL of LB broth supplemented with carbenicillin, and grown at 37° C., 280 rpm for 4 hours. After 4 hours, the strain was washed once in 2 mL of PBS and resuspended in 1 mL of PBS+glycerol (0.8% final concentration)+$FeSO_4$ (80 μM)+1PTG (1 mM)+ethanol (0.5% v/v). The tube was capped tightly and placed at 37° C., 280 rpm for 48 hours.

When the bioconversion was complete at 48 hours, the culture was centrifuged at 16 krpm for 2 min and the supernatant was sampled into a separate tube. This sample was used for HPLC analysis of succinate using a Shimadzu 10 AVP equipped with a Phenomenex Synergy Hydro RP 51Lim column, 20 mM $KH_2PO_4$ (pH 3) mobile phase, in an isocratic gradient. Succinic acid was detected using a UV detector at 200 nm. The HPLC was calibrated with succinic acid in water at different known concentrations. Using these readings as a standard curve, it was determined that NH533 converted ethanol into 0.5 mg/mL of succinate.

Conversion of Ethanol into Succinate with NH610

Strain NH610 was inoculated into 2 mL of LB broth supplemented with carbenicillin (100 μg/mL) directly from a glycerol stock and placed in a shaking incubator at 37° C., 280 rpm overnight. The following morning, the strain was diluted 1:100 into 2 mL of LB broth supplemented with carbenicillin, and grown at 37° C., 280 rpm for 4 hours. After 4 hours, the strain was washed once in 2 mL of PBS and inoculated with 25 μL into 1 mL of BEMO media (described elsewhere herein) containing 0.5% final concentration of ethanol. The tube was capped tightly and placed at 37° C., 280 rpm for 48 hours. After 48 hours, the culture was centrifuged at 16 krpm for 2 min and the supernatant was sampled into a separate tube. This sample was used for HPLC analysis of succinate using the method described above. Using a standard curve, it was determined that NH610 converted ethanol into 0.41 mg/mL of succinate.

Example 22. Bioconversion of Ethane to Succinate in *E. coli* Using a Monoculture This example describes the conversion of ethane into succinate in a culture of an engineered strain of *E. coli*. To conclusively demonstrate that the succinate that is produced is derived from the ethane, the experiment was conducted with 13C-labeled ethane and it was observed that a significant fraction of the measured succinate was 13C-labeled.

Strain Construction of NH606

The strain NH606 was constructed by the following steps. First, using the method of Datsenko and Wanner (2000), the genes ic1R, sdhAB, and araBAD were sequentially deleted from the *E. coli* strain NEB Express using FRT-flanked cassettes providing resistance to kanamycin. The antibiotic resistance cassette was removed using pCP20, as described elsewhere, leaving only FRT scars in the three loci. This strain, NH558, was then made electrocompetent and transformed with the plasmids pBZ15 (SEQ ID NO: 16) and pBZ13 (SEQ ID NO: 15), as described herein, and transformants were selected on LB agar plates supplemented with kanamycin (50 μg/mL) and spectinomycin (100 μg/mL). A single colony of NH558 was grown in LB supplemented with the antibiotics, made electrocompetent, and transformed with pLC99 (SEQ TD NO: 27), a plasmid which confers improved ethanol assimilation, as described herein. These transformants were selected on LB agar plates supplemented with kanamycin (25 μg/mL), spectinomycin (50 μg/mL), and carbenicillin (50 μg/mL). One of these colonies was selected for further study and given the name NH606.

Bioconversion of 13C-Ethane into Succinate

The strain NH606 was inoculated into 1 mL of LB supplemented with carbenicillin (50 μg/mL), kanamycin (25 μg/mL), and spectinomycin (50 μg/mL) for 16 hours. A volume of 0.2 mL of the culture was transferred into 1.8 mL of LB media supplemented with the above antibiotics plus 1 mM L-arabinose, 1 mM IPTG, 50 μM ferric citrate, and 200 μM L-cysteine. After 4 hours, the cultures were centrifuged at 4000 rpm for 5 minutes. The supernatant was discarded and the pellet was resuspended in an equal volume of PBS. The samples were centrifuged again and resuspended in BEM6 media to an OD600 of 2.0. (The minimal media called BEM6 contains (in $ddH_2O$): 50 mM $KH_2PO_4$, 50 mM $Na_2HPO_4$*7 $H_2O$, 1 mM $MgSO_4$, 0.15% LB, 1.5625 mM glutamine, 80 μM $FeSO_4$, 0.1 mM $CaCl_2$), 1 mM IPTG, 0.1% of the 1000× metals solution, and 1 mM L-arabinose (where required for induction of promoter pBAD), plus a desired concentration of ethanol.) From this culture, 500 μL was pipetted into each of two sterile glass vials, each containing a single glass bead to prevent cell clumping. These vials were sealed with rubber stoppers. Using a syringe, 1 mL of 13C-labeled ethane was injected into the headspace above the liquid in one of the vials, while 1 mL of air was injected into the other vial. All vials were placed at 37° C., 280 rpm. After incubating at 37° C. for 46 hours, the samples were centrifuged at 16.1 krpm for 2 min. Each sample was analyzed for 13C-labeled succinic acid by LC/MS/MS and compared to an analytical standard. 60 μL, of methanol was mixed with 20 μL of samples and centrifuged. Twenty μL of supernatant was diluted 5× with 12.5% methanol 0.1% formic acid. Calibration standards were prepared by serial dilution of succinate stock solution in 12.5% methanol 0.1% formic acid. Sixty μL of the above sample was mixed with 60 μL of the internal standard solution (2-HG-d3 in 12.5% methanol 0.1% formic acid) prior to the injection to the LC/MS/MS. The HPLC was a Shimadzu LC-20AD with an Agilent Zorbax SB-C18 column (3×100 mm, 3 5 pm). The mobile phases were 0.005% formic acid, 0.5 mM ammonium acetate in water and a mixture of methanol:water (95:5) with 0.5 mM ammonium acetate. The flow rate was 0 5 mL/min and the column was held at room temperature. The mass spectrometry was performed using a AB Sciex API4000 system using turbo ionspray and negative ionization. Succinic acid was detected by measuring the peak heights at m/z values of 117.0 (for 12C-succinic acid), 118.0 (for singly-labeled 13C succinic acid) and 119.0 (for doubly-labeled 13C2-succinic acid).

Figure 8A:
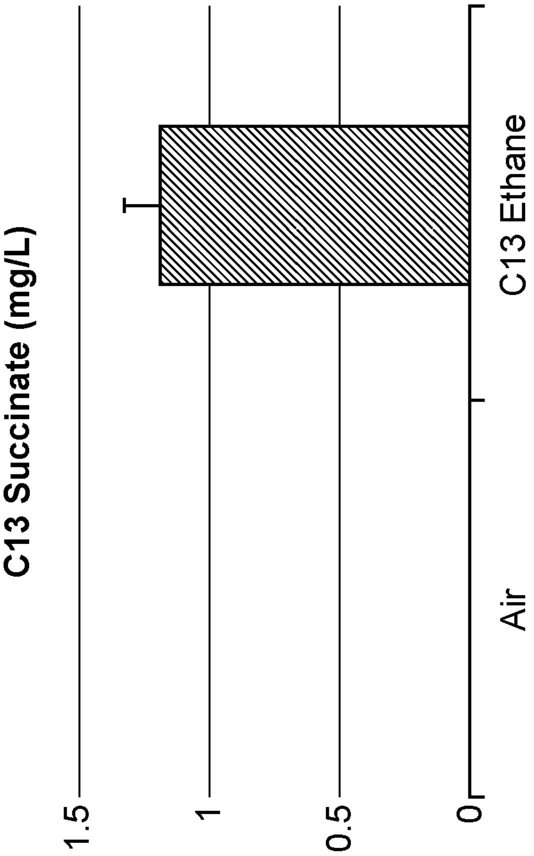
FIG. 8 shows the 13C-labeled succinate produced from a 13C-labeled ethane feedstock. Strain NH606 was sealed into two serum bottles, where one was injected with air and the other with 13C-labeled ethane. The plot in (a) shows the difference in detected 13C-succinate between the two bottles. The peak in (b) is the result of detection of the 13C-succinate peak from the LC/MS/MS method described elsewhere in the specification.
Figure 8B:
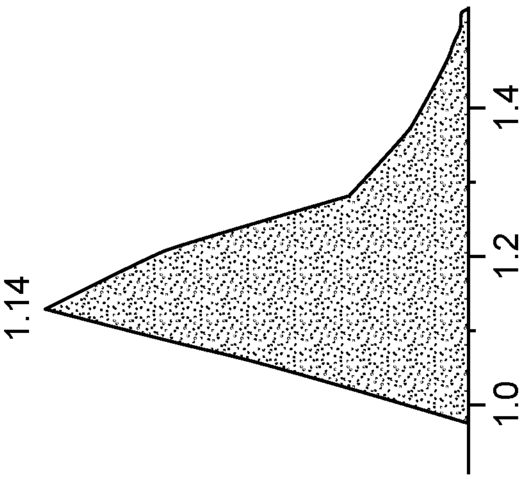
Figure 9:
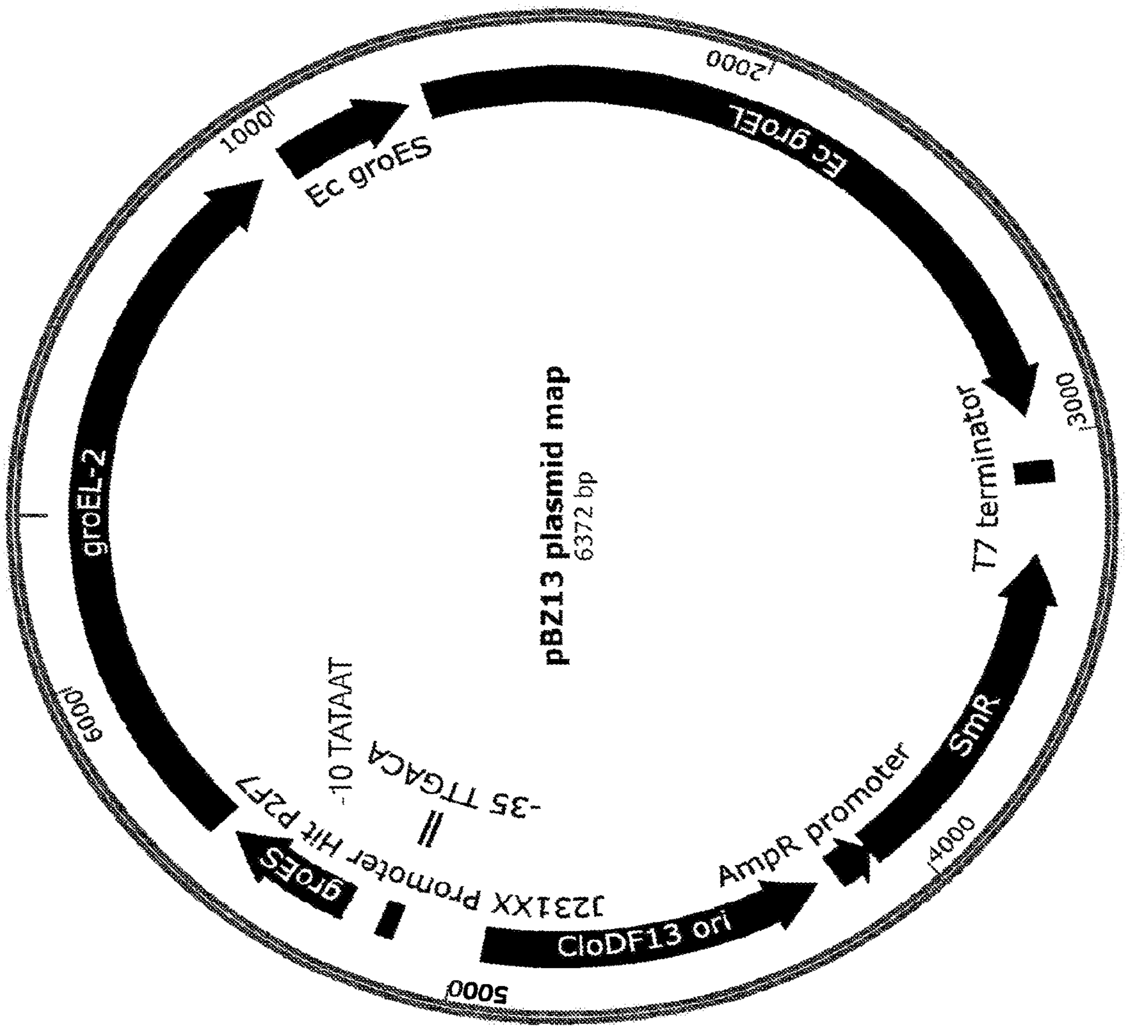
FIG. 9 shows a representative plasmid map illustrating the coding regions for plasmid pBZ13 (SEQ ID NO: 15). This plasmid enables the expression of two sets of chaperone proteins, groES/groEL from *E. coli* and *M. capsulatus* (Bath).

The results of this analysis are shown in FIG. 8. The vial that received an injection of air produced no detectable 13C-succinic acid, while the vial that received an injection of 13C-ethane produced 1.14 mg/L of 13C-succinic acid. This result conclusively shows the functionality of the entire pathway from ethane to succinic acid. This is the first report of a functional soluble diiron monooxygenase in *E. coli* used in a pathway to generate an industrial product from a hydrocarbon feedstock.

Example 23. Ethane to Succinate in *E. coli*—Co-Culture

This example describes the conversion of ethane into succinate in a culture containing two engineered microorganisms. One microorganism was a strain of *E. coli* engineered to convert ethane to ethanol. The other microorganism was a strain of *E. coli* engineered to convert ethanol into succinate.

Strain Construction of BZ55 and NH585

The strain BZ55 was constructed in the following steps. First, the strain NH283 was constructed as described elsewhere herein. Next the plasmid pBZ13 (SEQ ID NO: 15) was transformed into NH283 by electroporation. The plasmid pBZ23 (SEQ ID NO: 18) contains the sMMO from *M. capsulatus* (Bath) plus mutations to the following genes: mmoX (K61S, E240N, S421T), mmoY (L67M). The strain NH283 with plasmid pBZ13 was subsequently transformed with this second plasmid, pBZ23, by electroporation, and selected on LB supplemented with kanamycin (50 μg/mL) and spectinomycin (100 μg/mL).

Bioconversion of 13C-Ethane into Succinate

BZ55 was inoculated into 2 mL of LB supplemented with spectinomycin (100 μg/mL) and kanamycin (50 μg/mL) and NH585 was inoculated into 2 mL of LB supplemented with carbenicillin (100 μg/mL). Both cultures were incubated at 37° C., 280 rpm overnight. After 16 hours, 1 mL of BZ55 culture was transferred into 9 mL of LB+spectinomycin+kanamycin+Fe(III)-citrate (50 μM)+L-cysteine (200 μM)+L-arabinose (1 mM) and 200 μL of NH585 culture was transferred into 10 mL of LB+IPTG (1 mM). Both 10 mL cultures were incubated at 37° C., 280 rpm for 4 hours. After 4 hours, both cultures were centrifuged for 5 mM at 3 krpm. The pellets were resuspended in 30 mL of PBS to wash and centrifuged again. Then the NH585 pellet was resuspended in 5 mL of PBS+glycerol (0.4%)+IPTG+arabinose+Fe(III)-citrate+L-cysteine. This resuspension was used to resuspend the BZ55 pellet, resulting in a 5 mL mixture of the two strains. From this mixture, 1 mL was pipetted into each of two vials and sealed with a rubber stopper. A syringe was used to inject 1.5 mL of air into the headspace above one of the cultures, while another syringe was used to inject 1.5 mL of 13C-labeled ethane (Cambridge Isotope Laboratories) into the headspace above the other. Both vials were incubated at 37° C., 280 rpm. After 48 hours, samples were centrifuged for 3 mM at 16.1 krpm and the supernatant was removed and filtered. These filtrates were analyzed by LC/MS/MS, as described in the Example 22 above. The concentrations (in mg/L) of succinate in the air-injected sample and ethane-injected sample are compared in Table 17.

TABLE 17

Comparison of succinate production in co-culture due to 13C ethane feeding

| Condition | 12C-succinate | 13C-succinate |
|---|---|---|
| Air | 52.1 | 1.05 |
| 13C-Ethane | 56.6 | 1.85 |

The increased amount of 13C-succinate is evidence that the 13C-ethane was converted through the metabolic pathways of the cells into 13C-succinate. It is worth noting that the higher background levels of succinate derive from the glycerol (which is absent in Example 22), and that the significant percentage-wise increase in 13C-succinate in the 13C-ethane-fed condition can be seen relative to the small change in 12C-succinate production. This large percentage increase in 13C-succinate cannot be caused by background fluctuations, but instead must be derived from the 13C-ethane feeding.

Example 24. Ethane to Chemicals in *E. coli*: Ethane to Fatty Acids

This example describes a strain of *E. coli* capable of converting ethane into a chemical product.

The strains of *E. coli* described herein may be combined to generate a single strain of *E. coli* capable of converting ethane into a fatty acid. In principle, a similar strategy may be employed to build strains capable of converting ethane into other chemical products, starting from a strain that is already able to make a chemical product and adding the enzymes responsible for converting ethane to ethanol and, ultimately, into acetyl-CoA.

Methods for combining the two strains are well-known to one skilled in the art. In the simplest case, the genes responsible for key functions, such as ethane assimilation, are localized to a plasmid, which can be transformed into the *E. coli* strain which already comprises a pathway to the fatty acid product. Alternatively, the product pathway genes may be localized to a plasmid which may be transformed into an ethane-consuming strain of *E. coli*.

Another possible embodiment may be comprised of two *E. coli* strains which each have the genetic elements integrated into the chromosome. In this case, the individual genetic elements can be amplified by PCR and transformed into the other strain. Another option is to utilize transduction to move genetic elements between strains. Still another option is to utilize mobilizable genetic elements via conjugation. Still another option is to synthesize part or all of a synthetic chromosome that contains the appropriate genetic elements from both strains and introduce the DNA into a donor strain.

The method for culturing a strain that can consume ethane and produce a fatty acid is straightforward as set forth herein. Briefly, the *E. coli* strain can be grown up in rich media or minimal ethanol media and then transferred to a minimal media without a carbon source. That culture may be transferred to a stoppered bottle and injected with ethane into the headspace. Alternatively, the culture can be grown in a bioreactor with continuous feeding of ethane via sparging. The fatty acids can be harvested by either organic solvent extraction or centrifugation or settling or a combination of these methods.

Example 25. Identifying Genetic Elements that Improve Monooxygenase Function This example describes the construction of a genetically engineered host cell wherein the expression of exogenous genes coding for proteins or RNAs of unknown function in the engineered host cell results in an engineered cell improved for growth on ethane. This example further describes a natural hydrocarbon-consuming organism that has been modified to consume ethane at a different rate, in order to identify genes or enzymes necessary for ethane consumption.

Complementation libraries may be searched for protein partners or chaperones that are missing from the host strain, and whose expression increases the growth rate on ethane. Here, libraries will be constructed by cloning plasmids containing random genomic DNA fragments from natural microorganisms with monooxygenase or hydrocarbon-oxidation activity. DNA will be isolated from one or more of such strains, digested or sheared into fragments, and cloned into a plasmid suitable to the host strain. In some cases, for expression in a yeast host strain, a yeast artificial chromosome may be appropriate. In some cases, for expression in a bacterial host strain, a cosmid, or a bacterial artificial chromosome may be appropriate. In some cases, the digested genomic DNA is linked to a selective marker, and integrated directly into a host cell chromosome. Improvements in growth rate or product formation may be measured, as described herein. Genome-scale analysis may reduce the size of such libraries, and genomic intersection techniques may identify genes common to monooxygenase-expressing organisms and absent in the engineered host (M G Kalyuzhnaya et al., Functional metagenomics of methylotrophs, 495 Methods in Enzymology 81-98, 2011).

Loss-of-function strain libraries may be used to identify genes essential for oxidation of ethane to ethanol. Here, a strain collection with random genetic changes ("a library") may be generated in a natural microorganism that can consume hydrocarbons, and the reduction (or loss) of its ability to grow on ethane is used to identify key genes. These genes may then be expressed in the engineered host cell and tested for improvements in host cell growth using ethane as the carbon source.

One example of this type of library is a transposon library. A large library may be generated in a natural hydrocarbon-consuming organism. This library would be plated onto ethanol-containing agar plates and then replica-plated onto agar plates without ethanol, but grown in the presence of gaseous ethane. Mutants with diminished ethane-oxidation activity will be able to grow on ethanol, but will have decreased growth rate on ethane. Mutations can be identified using arbitrarily primed PCR methods or by DNA sequencing using primers common to the transposon DNA. This method identifies genetic elements that are tested in our synthetic ethanotrophs for growth improvement in an ethane-fed fermentation. This example of transposon mutagenesis is exemplary and not meant to be limiting. The method of screening a mutated hydrocarbon-consuming organism applies equally well to other methods of mutagenesis, such as, but not limited to, chemical mutagenesis, ultraviolet-light-induced mutagenesis, targeted mutagenesis, and others. In these cases, it may be most helpful to identify relevant mutations by whole genome sequencing.

Another method for improving monooxygenase function is protein engineering. There are many techniques for performing protein engineering. In one method, mutations are discovered by error-prone PCR and screened for improved function. These mutations are identified by DNA sequencing and a recombination library may be built in which mutations (either beneficial or neutral) may be combined randomly. The method of building the recombination library may be chosen from a range of previously described methods, such as tPCR (A Erijman et al., *Transfer-PCR* (*TPCR*): *A highway for DNA cloning and protein engineering,* 175 Journal of Structural Biology 171-177, 2011). The recombination library may be screened for improved function. The most improved enzymes can be sequenced, and can also be used as templates for further engineering.

All of the above methods can be equally well applied to methanotrophs. Complementation and overexpression libraries can be constructed from the genomic DNA of natural methanotrophs for expression in heterologous hosts. Loss-of-function mutagenic libraries and transposon libraries can be built in methanotrophic bacteria to search for critical genetic elements. Protein engineering monooxygenases for improved activity against a range of substrates (e.g. methane, ethane, propane, butane, naphthalene, etc.) can be carried out as described above, provided that a suitable measurement technique (such as a colorimetric assay or the alcohol assay described elsewhere herein) can be employed in moderate throughput.

Example 26. Screening eDNA Libraries for Ethane Monooxygenase Function or Improved Monooxygenase Function This example describes the construction and screening of libraries of environmental DNA samples in order to find functional ethane monooxygenase enzymes or to find components that improve the function of a monooxygenase.

As described in the example above, one may construct a library of genomic DNA and screen that library for desirable functions. In a similar manner, one may construct and screen libraries of environmental DNA. Methods for the construction of such libraries are described in the academic literature and elsewhere (A Henne et al., *Construction of environmental DNA libraries in Escherichia coli and screening for the presence of genes conferring utilization of* 4-*hydroxybutyrate,* 65 Applied and Environmental Microbiology 3901-3907, 1999); (S F Brady, *Construction of soil environmental DNA cosmid libraries and screening for clones that produce biologically active small molecules.,* 2 Nature protocols 1297-1305, 2007). Briefly, an environmental sample is taken from a location of interest. In one relevant case, that location may be an area where it is known that microbes capable of oxidizing hydrocarbons grow. Then the DNA of the entire sample is separated from everything else and purified. This DNA contains a mixture of the DNA from many different organisms. This extracted environmental DNA can be cloned into a plasmid (sometimes known as a cosmid or fosmid) in such a way as to be amenable to insertion into a transformable microorganism, such as *E. coli.* Recent advances in the library construction protocol have enabled extremely large and diverse libraries to be constructed. These libraries can be screened under myriad conditions to identify interesting features, after which the genes responsible can be extracted and further studied. In this particular case, these libraries can be tested for ethane monooxygenase activity using the selection methods described above. Additionally, one may add to the screening strain a plasmid or chromosomal genetic element or series of genetic elements that express a known ethane oxidizing enzyme complex. Then, the environmental DNA library can be screened in this strain in order to identify genetic elements that may enable or improve the desired activity, in this case, that of an ethane monooxygenase. An example of a genetically encoded element that could improve function may be a protein-folding chaperone (T Furuya et al., *The mycobacterial binuclear iron monooxygenases require a specific chaperonin-like protein for functional expression in a heterologous host,* 280 1-BBS Journal 817-826, 2013) or a protein that assists in properly assembling the metal centers in a metalloenzyme.

Example 27. Functional Expression of Methane Monooxygenase in *C. glutamicum*

This example describes the expression of a functional monooxygenase in *Corynebacterium glutamicum.*

Construction of Plasmid pNH238

Plasmid pBZ21 (SEQ ID NO: 17) was constructed in the following manner two fragments were generated using PCR to amplify a 6.4 kb fragment from pBZ13 (SEQ ID NO: 15) with primers oBZ095 (SEQ ID NO: 74) and oBZ096 (SEQ ID NO: 75) and a second fragment (6.8 kb) from pDG6 (SEQ ID NO: 22) with primers oBZ090 (SEQ ID NO: 76) and oBZ094 (SEQ ID NO:77). These fragments were isolated and combined using Gibson assembly. The resulting DNA was transformed into electrocompetent *E. coli* and transformants were selected on LB agar supplemented with spectinomycin (100 μg/mL). Correct colonies were identified by colony PCR and tested to confirm monooxygenase activity. This plasmid was isolated and used as a template for PCR amplification with primers oNH600b (SEQ ID NO: 78) and oNH6O1s (SEQ ID NO: 79). The resulting reaction was treated with DpnI restriction enzyme to remove the plasmid template. PCR amplification was used to generate a second DNA fragment, with pDG6 (SEQ ID NO: 22) as the template, and using primers oNH602b (SEQ ID NO: 80) and oNH603 (SEQ ID NO: 81). Both fragments were isolated, assembled with Gibson assembly, and transformed into electrocompetent *E. coli.* Transformants were selected on LB agar plates supplemented with spectinomycin (100 μg/mL) and kanamycin (50 μg/mL). Correct colonies were identified by colony PCR. The plasmids were isolated and transformed into *E. coli* strain ER2925, a dam-dcm-strain. These colonies were used to isolate pNH238 DNA (SEQ ID NO: 46) without dam or dcm methylation for efficient transformation into *C. glutamicum*. The *C. glutamicum* strain NRRL B-3330 was made electrocompetent according to the method of van der Rest (van der Rest et al., A heat shock following electroporation induces highly efficient transformation of *Corynebacterium glutamicum* with xenogeneic plasmidDNA, Appl. Microbiol. Biotechnol., Vol 52(4), 1999). Transformants were selected on LBHIS agar plates supplemented with kanamycin (20 μg/mL).

A single colony (named NH686) was inoculated into LB supplemented with sorbitol (20 mM) and kanamycin (20 μg/mL). The control strain, *C. glutamicum* NRRL B-3330, was inoculated into LB supplemented with sorbitol (20 mM). Both strains were placed at 30° C., shaking at 220 rpm. After 16 hours, linL of the culture was added to 9 mL of LB supplemented with sorbitol (20 mM), L-arabinose (1 M), and $FeSO_4$ (80 μM). Strain NH687 containing the pNH238 plasmid was also supplemented with kanamycin. These strains were placed at 30° C., 220 rpm, for 6 hours. The cultures were then centrifuged at 4 krpm for 5 mM. The cultures were washed once in 10 mL PBS and 800 μL was pipetted into a microcentrifuge tube and pelleted. These pellets were resuspended in 250 μL of PBS supplemented with coumarin (11 mM), sorbitol (0.1 M), L-arabinose (1 M), and $FeSO_4$ (80 μM). All tubes were incubated at 30° C., shaking at 220 rpm. A functional monooxygenase will hydroxylate coumarin to umbelliferone, which can be measured by fluorescence. After 42 hours, the tubes were removed and centrifuged. 150 μL of the supernatant was pipetted into a clear-bottom plate and the fluorescence was read on a plate reader. The excitation wavelength was 360 nm and the emission wavelength was 460 nm. The background fluorescence of the media (lacking any cells) was subtracted from both the control strain and NH687. The fluorescence of NRRL B-3330 was found to be 151, while the fluorescence of the monooxygenase-expressing strain NH687 was 664. This significant increase in fluorescence demonstrates the hydroxylation of the substrate by an active monooxygenase in NH687.

Example 28. Bioconversion of Ethanol to Amino Acids in *C. glutamicum*

Strains of *Corynebacterium glutamicum* have been shown to overproduce glutamate (NRRL B-2784) or lysine (NRRL B-3330). These strains have been tested in our lab and shown to consume ethanol as a sole carbon and energy source. Growth on a modified minimal media with ethanol as the only carbon source may result in the accumulation of glutamate and/or lysine from these strains. Cells can be cultured in a standard rich media, such as BHIS (A Vertes et al., *MINIREVIEW Manipulating Corynebacteria, from Individual Genes to Chromosomes,* 71 7633-7642, 2005), and then transferred into a minimal media formulation, such as CGXII but with ethanol substituted for glucose as the carbon source (A Vertes et al., *MINIREVIEW Manipulating Corynebacteria, from Individual Genes to Chromosomes,* 71 7633-7642, 2005). In another media formulation, *C. glutamicum* strains were grown in a modified M9 medium containing M9 salts, 2 mM $MgSO_4$, 0.2 mM $CaCl_2$, 10 μM $FeSO_4$, R5 trace elements, 4 mg/L biotin, and 1% (v/v) ethanol. The strains were inoculated into this media at incubated at 30° C., shaking at 200 rpm. After 24 hours, the strains grew to an OD600 of 1.5. The cells can be separated from the broth by centrifugation and the amount of glutamate or lysine produced in the broth can be analyzed using standard methods known to one skilled in the art.

Example 29. Bioconversion of Ethane to Amino Acids in *C. glutamicum*

This example describes a strain and method for culturing a strain to produce amino acids from an ethane feedstock in *Corynebacterium glutamicum.*

The strain from above is capable of growth on ethanol as a major or sole carbon source. By expressing an ethane-oxidizing enzyme in this strain, one may construct a strain capable of converting ethane into amino acids, such as glutamate or lysine. Enzymes that may oxidize ethane in *Corynebacterium glutamicum* can be selected from Table 1 and expressed from plasmid(s) or from a chromosomal locus.

This strain may be cultured in a rich media, such as BHIS, and then transferred into sealed serum bottle containing a minimal media with no carbon source, such as CGXII lacking glucose. The sealed bottle can be injected with ethane into the headspace above the media in order to provide a carbon source. Alternatively, a limiting amount of ethanol can be included in the minimal media to condition the cells for growth via the ethanol-assimilation pathway or to provide some carbon for the case in which the ethane-oxidation is functional but not sufficient to support growth. Additionally, the strain may be continuously cultured in a bioreactor, chemostat, or turbidostat to maintain constant growth conditions.

The strains NH686 and NH687 can be tested as above with ethane as the feedstock, injected into the headspace above the culture in a sealed serum bottle, as described elsewhere herein.

Example 30. Functional Expression of Toluene-4-Monooxygenase in *Pichia pastoris*

The monooxygenases described above can be expressed in yeast from plasmids or via chromosomal integrations. The genetic constructs may be assembled using standard promoters and terminators to drive the transcription and translation of the desired polypeptides. Some exemplary promoters that are commonly used include the promoters PADH1, PTEF1, PTEF2, PGAP. Some exemplary terminators include TCYC1, TTEF1, TILV5, TGAP, TAOX I. These genetic constructs can be transformed into the yeast cells using standard methods such as electroporation and chemical transformation, described elsewhere (J M Cregg et al., Recombinant protein expression in *Pichia pastoris.,* 16 MOLECULAR BIOTECHNOLOGY 23-52, 2000). Colonies can be checked for correct genetic signatures using colony PCR methods.

A method for testing a yeast strain for functional monooxygenase enzymes is similar to the method for *E. coli* described above. Briefly, the yeast cells are cultured in a rich media, such as YPD, until the culture reaches an OD600 equal to about 1.5 and then it is washed in minimal media or PBS. To test the strain for activity with naphthalene as a substrate, as an example, the yeast cells are resuspended in 1 mL of PBS with naphthalene added. The culture is then incubated at 30° C., shaking at 220 rpm, for 16 hrs. Then, the culture is centrifuged to separate the cells and the supernatant and cell pellet are assayed with Fast Blue B salt dissolved in water. If the culture changes color, then 1-naphthol has been produced. The color change can be read using a spectrophotometer at 540 nm, and compared to a control strain which does not oxidize naphthalene. The method for testing for methane or ethane oxidation is similar except the naphthalene is omitted, the culture is inoculated into a sterile, sealed serum bottle and the methane or ethane gas is injected into the headspace above the culture. The assay for methanol or ethanol is similar to that described herein.

In one specific example, *Pichia pastoris* strain NH393 was constructed in the following manner and observed to oxidize naphthalene to 1-naphthol when assayed as above. Two plasmids were designed to contain the six genes of the toluene-4-monooxygenase from *Pseudomonas mendocina* KR1, each expressed from its own promoter and terminator pair. These two plasmids (pNH104 expressing tmoA, tmoB, tmoC is SEQ ID NO: 29 and pNH132 expressing tmoD, tmoE, tmoF is SEQ ID NO: 30) were constructed by cloning a standard vector and a fragment that was synthesized by standard DNA synthesis techniques by an outside vendor. These plasmids were digested with restriction enzyme BsaI and transformed into *P. pastoris* (NRRL Y-11430) using standard electroporation techniques (J. Lin-Cereghino et al., Condensed protocol for competent cell preparation and transformation of the methylotrophic yeast *Pichia pastoris*, Biotechniques, vol. 38.1, p. 44-48, 2005). The transformants were selected on YPD supplemented with antibiotics (G418 (Geneticin) at 250μ/mL, nourseothricin at 25μ/mL). These were streaked for single colonies on the same YPD+antibiotics media and checked by colony PCR for proper integration of the desired DNA at the appropriate locus. Strain NH393 was isolated in this way with confirmed integrations of the DNA that expresses the toluene-4-monooxygenase.

This strain was tested for naphthalene oxidation, as described above. When the Fast Blue B reagent was mixed with the cell pellet and mixed, a color change to purple accompanied only the strain expressing the monooxygenase (NH393), but not in the control strain (Y-11430). This indicates the functional expression of this soluble diiron monooxygenase in *P. pastoris*. To our knowledge, this is the first instance of a heterologous soluble diiron monooxygenase enzyme being functionally expressed in a yeast cell.

Example 31. Functional Expression of Methane Monooxygenase in *Pichia pastoris*

This example describes the functional expression of two monooxygenases in the methylotrophic yeast *Pichia pastoris* (also known as *Komagataella phaffii*).

Plasmid Construction

The plasmids pNH166 (SEQ ID NO: 34), pNH167 (SEQ ID NO: 35), pNH172 (SEQ ID NO: 36), pNH173 (SEQ ID NO: 37) were constructed in the following manner. Synthetic DNA was designed to express the six subunits of the monooxygenase and the groES and groEL chaperonin subunits. Plasmids pNH166 and pNH172 encode the monooxygenase from the bacterial strain *Methylocystis* sp LW5 and plasmids pNH167 and pNH173 encode the monooxygenase from the bacterial strain *Solimonas aquatica* (DSM 25927). The DNA was synthesized from a commercial vendor (Gen9). These sequences were digested with restriction enzyme XhoI. Cloning vectors were amplified by PCR to provide sequences at the ends of the linear amplicon corresponding to a homologous sequence at the end of the desired DNA to be inserted. The resulting reaction mix was treated with restriction enzyme DpnI to remove the background plasmid, leaving only the amplified DNA. Both the cloning vectors and the XhoI-digested DNA for insertion were purified using DNA columns (Zymo Research). The inserts were ligated to the cloning vectors using Gibson Assembly (New England Biolabs). The Gibson reaction was purified with a DNA column and transformed into electrocompetent *E. coli* cells. Single colonies of the transformation were isolated and confirmed correct by colony PCR. The resulting plasmids contained the desired insert flanked by sequences that are homologous to a chromosomal region in the host (for integration by homologous recombination). Additionally, the plasmids contain an antibiotic selection marker that can be used to isolate clones of the host strain that have successfully integrated the desired DNA fragment at the intended location.

Strain Construction

The strain MC100-3 (in which both alcohol oxidase genes were deleted, preventing the degradation of methanol) was grown in 5 mL of YPD media, shaking at 220 rpm and 30° C., to an OD of approximately 1.5. The plasmids were digested with the restriction enzyme BsaI to generate a linear fragment for integration. The resulting reaction was purified by DNA column, as above, and eluted in 10 μL. The strain was transformed using standard techniques (J. Lin-Cereghino et al., Condensed protocol for competent cell preparation and transformation of the methylotrophic yeast *Pichia pastoris, Biotechniques, vol.* 38.1, p. 44-48, 2005) Briefly, the culture was centrifuged and washed in sorbitol (1 M) twice and concentrated into 100 μL. From the purified DNA elution, 3 μL was used in an electroporation cuvette, along with the washed cells. Cultures were recovered at 30° C. and 220 rpm for 2 hours before plating on YPD+antibiotic agar plates. For integration cassettes containing a resistance gene for nourseothricin, the YPD plates contained nourseothricin at a concentration of 25 μg/mL. For cassettes containing a gene providing resistance to geneticin (G418), the concentration of G418 in the YPD plates was 500 μg/mL.

Specifically, strain NH461 is MC100-3, which is *Komagataella phaffii* with mutations inactivating both alcohol oxidase enzymes Aox1p and Aox2p, rendering this strain incapable of degrading or consuming methanol. Strain NH509 was constructed by sequentially integrating the DNA cassettes from pNH172 and pNH166. This strain was isolated as a single colony and confirmed by colony PCR to have integrated the desired DNA cassettes into the intended chromosomal locations. A similar procedure was used to generate strain NH510 from pNH173 and pNH167.

Methane Oxidation Assay

Strains NH461, NH509, and NH510 were assayed for methane oxidation, as described herein. Briefly, the strains were separately inoculated into 1 mL of YPD and placed at 30° C. and 220 rpm overnight. The following day, each strain was subcultured using 500 μL of culture into 25 mL of YPD+$FeSO_4$ (80 uM) at 30° C. and 220 rpm for 6 hours. The cultures were centrifuged at 4 krpm for 5 min and resuspended in 10 mL of phosphate buffered saline plus 0.8% glycerol and $FeSO_4$ (80 μM). These cells were pipetted into serum bottles, 5 mL into each bottle, and stoppered and sealed with butyl rubber stoppers. One bottle was injected with 60 mL air into the headspace using a syringe while the other bottle was injected with 60 mL of methane gas. These sealed bottles were incubated upright at 30° C., 220 rpm. After 72 hours of incubation, the bottles were removed from the incubator and sampled for methanol. The method of detection for methanol was described elsewhere herein. A commercially-available kit using an enzymatic assay generates a colorimetric readout that can be calibrated using a standard curve of known methanol concentrations. This assay was performed according to the manufacturer's instructions. The concentration of methanol in the samples was calculated as described above, using the air-injected samples as controls. Using this method, the strains were observed to make the following concentrations of methanol. The strain NH509 produced 20 μM of methanol and NH510 produced 55 μM of methanol, while the control strain NH461 produced almost no methanol (less than 3 μM, within the noise of the assay).

TABLE 18

Bioconversion of methane to methanol in *Pichia pastoris*

| Strain | mmoXYZC | mmoBD-groES/EL | Methanol (uM) |
|---|---|---|---|
| NH461 (MC100-3) | None | None | <3 |
| NH509 | *Methylocystis* | *Methylocystis* | 20 |
| NH510 | *S. aquatica* | *S. aquatica* | 55 |

The functional expression of the monooxygenase is evidenced by the conversion of methane into methanol in these strains.

Example 32. Protein Folding Chaperones Improve Function of sMMO in *P. pastoris*

This example describes the improvement in monooxygenase activity in *P. pastoris* due to the co-expression of a protein-folding chaperone.

The expression of a monooxygenase enzyme complex has been described herein. Briefly, the different enzyme subunits are expressed individually from promoters and followed by terminators. Additionally, one can express other open reading frames from promoters and terminators in the same way. One such additional protein complex is the bacterial groES/groEL protein-folding chaperonin. In the same manner that this chaperonin aids in the activity of the monooxygenase complex in bacteria, adding the groES/groEL open reading frames to a yeast strain will also improve the functionality of the monooxygenase in a yeast cell.

Example 33. Ethanol to Malate in *P. pastoris*

This example describes the conversion of ethanol into malate in an engineered strain of *Pichia pastoris.*

The strain NH038 was constructed to constitutively express a pathway from pyruvate to malate along with a malate transporter to export malate from the cell. The plasmid pNHOO1 (SEQ ID NO: 82) was constructed with 750 bp homology to the HSP82 locus flanking either side of a KanMX gene cassette providing resistance to G418/Geneticin antibiotic. DNA fragments containing the sequences encoding the promoter PTEF2 from *Pichia pastoris*, the coding sequence from the malate transporter from *Schizosaccharyomyces ponibe*, and the terminator TCYC1 from *Saccharoyniyces cerevisiae* were amplified from genomic DNA prepared from their respective strains. These three fragments were added to the pNHOO1 backbone using Gibson cloning to generate pNH010 (SEQ ID NO: 85). Separately, three DNA fragments were amplified by PCR to construct a cassette containing the promoter PGAP from *Pichia pastoris*, the malate dehydrogenase (lacking the last three amino acids which serve as a peroxisomal targeting sequence) from *Saccharomyces cerevisiae*, and the terminator TGCW14 from *Pichia pastoris*. These three fragments were added to the pNHOO1 backbone using Gibson cloning to generate pNHOO9 (SEQ ID NO: 84) Similarly, three DNA fragments were amplified by PCR to construct a cassette containing the promoter PGCW14 from *Pichia pastoris*, the coding sequence of PYC2 from Saccharnmyces *cerevisiae*, and the terminator TA0X1 from *Pichia pastoris*. These three fragments were combined into the backbone from pNHOO1 using Gibson cloning and named pNH003 (SEQ ID NO: 83). Combining these cassettes was also performed using Gibson cloning. The plasmid backbone from pNH010 (SEQ ID NO: 85) was amplified and an insert made by amplifying pNH009 (containing the desired PGAP-MDH3(SKL)-TGCW14 fragment). The subsequent plasmid, pNHO 1 1 (SEQ ID NO: 86), was then digested with NotI restriction enzyme. The DNA fragment encoding PGCW14-PYC2-TA0X1 was amplified from pNHO03 and Gibson cloned into the pNHO1 1 NotI-digested backbone. The resulting plasmid, pNH014 (SEQ ID NO: 57), contained all three cassettes to express the three genes in *Pichia pastoris*: PYC2, MDH3(ASKL), and MAEI. These three genes convert pyruvate into oxaloacetate and then into malate before exporting it from the cell. This plasmid was digested with BsaI in order to linearize the fragment containing the 750 bp homology to the HSP82 locus surrounding the three gene expression cassettes and a KanMX marker. The strain Y-11430 (*Pichia pastoris*) was transformed using standard methods and the recovered cells were plated on YPD+Geneticin (250 μg/mL) for 2 days. Colonies were verified by PCR to contain the desired DNA at the intended locus. A single colony from the transformants was selected for fermentation and named NH038.

Strain NH038 was fermented using a minimal media containing ethanol as the sole carbon source. First the strain was grown to stationary phase overnight in 1 mL of YPD media shaking at 200 rpm at 30° C. From this overnight culture, 20 μL, was subcultured into 1 mL of buffered minimal media containing ethanol (13.4 g/L YNB+metals (Biobasic), 100 mM $KH_2PO_4$ pH 6.0, 0.00004% biotin, 2% ethanol). The culture was placed at 30° C., 200 rpm shaking. After 44 hours, the culture was centrifuged at 16.1 krpm for 2 mM and the supernatant was sampled for HPLC analysis. The HPLC analysis was performed as described above (Example 21), except a standard curve of malate (rather than succinate) samples was generated from commercially available purified malic acid (Sigma Aldrich). HPLC analysis detected 90 mg/L of malic acid in the sample. The same strain was cultured in buffered minimal media containing glucose and HPLC analysis detected 440 mg/L, while in media containing no added carbon source, the culture failed to grow.

Example 34. Ethanol to Secreted Protein in *P. pastoris*

*Pichia pastoris* has long been a model organism for the production of secreted proteins for a range of applications, including therapeutics. *P. pastoris* has the ability to grow on ethanol, as demonstrated in our lab. *P. pastoris* strains capable of protein production can be grown on ethanol as a sole carbon source and the proteins can be separated from the cells and media for relevant applications. Genetic constructs for secreted proteins are well understood, where the DNA sequence encoding the protein of interest is appended to a secretion signal. One common secretion signal is that of the alpha-factor peptide. A strain of *P. pastoris* may be constructed by first cloning the alpha-factor gene fused to another gene of interest (the protein to be secreted). This construct can be used to modify the genome of *P. pastoris* by electrocompetent transformation techniques described elsewhere (J L Cereghino & J M Cregg, Heterologous protein expression in the methylotrophic yeast *Pichia pastoris.,* 24 FEMS microbiology reviews 45-66, 2000). Transformants are selected using antibiotic selections, such as zeocin, nourseothricin, or G418. Colonies are purified by streaking on rich media agar plates containing the antibiotic, and the correct genetic construct is confirmed by colony PCR amplification and sequencing. These strains may be cultured in minimal media containing ethanol as the major or sole carbon and energy source. One such media formulation contains yeast nitrogen base (available commercially from many sources, such as Difco or Sigma Aldrich), biotin (final concentration 0.4 mg/L), and ethanol (final concentration 1% v/v). In an alternative formulation, a buffer can be added to stabilize the pH, such as $KH_2PO_4$ (pH 6.0) at 100 mM final concentration. Strain Y-11430 was inoculated into YPD media and incubated at 30° C., shaking at 200 rpm. After 16 hours, 10 μL of this culture was transferred into 2 mL of the buffered minimal media with 1% ethanol, described above. After 24 hours, this culture had grown to an OD600 of 2.0.

Example 35. Improved Aerobic Growth on Ethanol as a Major or Sole Carbon Source in *S. cerevisiae*

The growth of *S. cerevisiae* on ethanol as a sole carbon source is also possible using an enzyme pathway that converts ethanol into acetyl-CoA, via acetaldehyde. In an analogous manner to the methods described above for *E. coli*, the expression and regulation of the enzymes in this pathway can be synthetically altered using targeted or random strategies. Libraries of genetic variants can be assayed in a growth competition in the same way, using appropriate media and growth conditions for the yeast *S. cerevisiae*. For example, the expression and regulation of the yeast gene ADH2 may be altered to increase the growth rate on ethanol as a major or sole carbon source. ADH2 is the gene that encodes the alcohol dehydrogenase that is responsible for conversion of ethanol into acetaldehyde. Likewise, the genes ALD4 and ALD6 are required for conversion of acetaldehyde to acetate and are activated during growth on ethanol. Altering the expression of any or all of these may improve growth on minimal ethanol media. Furthermore, as described above, random strategies, such as chemical mutagenesis, may also improve growth on ethanol media and may be utilized to identify genes for further improvements.

Example 36. Synthetic Ethanotroph in Yeast

Several yeast strains, including the most commonly used *Saccharomyces cerevisiae* and *Pichia pastoris*, are capable of growth on ethanol under aerobic conditions.

The procedure to convert these strains into synthetic ethanotrophs is conceptually similar to the method for converting a bacterial strain, though it differs in some details, as described below. The monooxygenases shown above in Table 1 can be expressed in yeast from plasmids or via chromosomal integrations. The genetic constructs may be assembled using standard promoters and terminators to drive the transcription and translation of the desired polypeptides. Some exemplary promoters that are commonly used include the promoters PADH1, PTEF1, PTEF2, PGAP. Some exemplary terminators include TCYC1, TTEF1, TILV5, TGAP, TAOX1. These genetic constructs can be transformed into the yeast cells using standard methods such as electroporation and chemical transformation, described elsewhere (J M Cregg et al., *Recombinant protein expression in Pichia pastoris.,* 16 Molecular biotechnology 23-52, 2000). Colonies can be checked for correct genetic signatures using colony PCR methods.

A method for testing a yeast strain for successful, functional ethane-oxidizing enzymes is similar to the method for *E. coli* described above. Briefly, the yeast cells are cultured in a rich media, such as YPD, and then washed in minimal media with ethanol as the major or sole carbon source. The cells may be grown or passaged in minimal ethanol media to adapt them to this mode of growth. The minimal ethanol media contains everything needed for the yeast cells to grow, with ethanol as the only source of carbon. The next step is to wash the cells with minimal media lacking any carbon source at least once, and then to resuspend the cells in this minimal, no-carbon media in a serum bottle, plug the top with a stopper and inject ethane into the headspace above the liquid. This ethane provides the major or sole carbon source for the cells, if they are capable of converting it to ethanol, via the monooxygenase enzyme complex being expressed. This sealed bottle can be incubated for a prolonged time period to allow the ethane to dissolve into the media and for the cells to consume the ethane and grow. Growth can be measured either by an increase in optical density of the culture, relative to a control into which no ethane has been injected, or by counting the colony forming units for both the experiment and control.

Related experiments involve the targeting of the monooxygenase subunits to various subcompartments of the yeast cell, such as the peroxisome, the endoplasmic reticulum, and the mitochondria. Targeting tags for each have been studied and published in the literature. For targeting to the peroxisome, a serine-lysine-leucine tripeptide (SKL) is genetically encoded at the C-terminus of each polypeptide subunit. For targeting to the endoplasmic reticulum, a lysine-aspartate-glutamate-leucine tetrapeptide (KDEL) is genetically encoded at the C-terminus of each polypeptide subunit. For targeting to the mitochondrial matrix, there are many published tags (F Hard et al., *Mitochondrial protein inport,* 988 Biochimica et biophysica acta 1-45, 1989), but the most common is the tag from the Su9 FO ATPase subunit.

As described in herein, it may be preferable to grow the strains in a competition with ethane as the major or sole carbon source, or it may yield more reliable results to feed a limiting amount of ethanol plus an excess of ethane. A growth advantage is realized by a cell with a functional monooxygenase in either case, a situation which will ultimately result in those cells coming to occupy the largest fraction of the culture's population.

Example 37. Ethane to Protein in Yeast this Example Describes a Strain of Yeast Capable of Converting Ethane into a Commercial Product The strains of *P. pastoris* described above may be combined to generate a single strain of *P. pastoris* capable of converting ethane into a secreted protein.

The methods to combine these two genetic elements into a single strain are well known to anyone skilled in the art. The DNA can be designed and assembled using standard techniques and integrated into the host genome by transformation and antibiotic selection, as described above. Similar methods can be used for *S. cerevisiae* or other well-studied yeast, as well.

Any yeast strain that is capable of growing on ethane is itself a source of single cell protein, and can be sold as such. Single cell protein is used as a nutrient source for fishmeal and even as a source of protein in food for people.

All references cited herein are incorporated by reference as if each had been individually incorporated by reference in its entirety. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A method for producing diiron monooxygenase, comprising:

a) culturing a synthetic microorganism comprising:

(i) at least one synthetic polynucleotide comprising at least one monooxygenase coding region encoding a diiron monooxygenase comprising SEQ ID NO: 10, wherein the diiron monooxygenase comprises one or more subunits and (ii) at least one protein folding chaperone coding region encoding a protein folding chaperone, each linked to at least one promoter, under suitable culture conditions and for a sufficient period of time to produce the diiron monooxygenase;

b) lysing the cells, and optionally, purifying the diiron monooxygenase to produce a lysate or purified diiron monooxygenase.

2. The method of claim 1, wherein the diiron monooxygenase comprises a subunit having a sequence at least 90% identical to SEQ ID NO: 10.

3. The method of claim 1, wherein the lysate or purified diiron monooxygenase is subsequently incubated with a substrate and hydrogen peroxide.

4. The method of claim 1, wherein the lysate or purified diiron monooxygenase is subsequently incubated with a substrate, oxygen, and NADH.

5. The method of claim 3, wherein the substrate is methane.

6. The method of claim 1, wherein the microorganism is *E. coli*.

7. The method of claim 1, wherein the diiron monooxygenase is used to produce a chemical.

8. The method of claim 7, wherein the chemical is one or more of methanol, formaldehyde, formate, carbon dioxide, and derivatives thereof.

9. The method of claim 8, wherein the chemical is one or more of methanol or formaldehyde.

10. The method of claim 1, wherein the at least one protein folding chaperone comprises groES/groEL.

11. The method of claim 1, wherein the at least one synthetic polynucleotide comprises a polynucleotide having SEQ ID NO: 9.

12. The method of claim 3, wherein the substrate is methane.

13. The method of claim 1, wherein the protein folding chaperone coding region comprises a sequence set forth in any one of SEQ ID NO: 63, SEQ ID NO: 65, SEQ ID NO: 67, or SEQ ID NO: 69.

* * * * *